United States Patent
Kai et al.

(10) Patent No.: US 9,212,130 B2
(45) Date of Patent: Dec. 15, 2015

(54) HETEROCYCLIC DERIVATIVE AND PHARMACEUTICAL COMPOSITION COMPRISING THE SAME

(75) Inventors: Hiroyuki Kai, Toyonaka (JP); Takeshi Endoh, Toyonaka (JP); Sae Jikihara, Toyonaka (JP); Tohru Horiguchi, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 13/816,085

(22) PCT Filed: Aug. 9, 2011

(86) PCT No.: PCT/JP2011/068097
§ 371 (c)(1),
(2), (4) Date: Feb. 8, 2013

(87) PCT Pub. No.: WO2012/020742
PCT Pub. Date: Feb. 16, 2012

(65) Prior Publication Data
US 2013/0225596 A1    Aug. 29, 2013

(30) Foreign Application Priority Data

Aug. 10, 2010  (JP) .................................. 2010-179177
Mar. 31, 2011  (JP) .................................. 2011-076986

(51) Int. Cl.
*A61K 31/505*  (2006.01)
*A61K 31/497*  (2006.01)
(Continued)

(52) U.S. Cl.
CPC ............. *C07C 233/75* (2013.01); *C07C 217/80* (2013.01); *C07C 217/84* (2013.01); *C07C 217/92* (2013.01); *C07C 233/25* (2013.01); *C07D 211/72* (2013.01); *C07D 213/69* (2013.01); *C07D 213/74* (2013.01); *C07D 213/80* (2013.01); *C07D 213/82* (2013.01); *C07D 215/22* (2013.01);
(Continued)

(58) Field of Classification Search
CPC .. C07C 233/75; C07C 217/84; C07C 217/80; C07D 401/14; C07D 239/84; C07D 213/74; C07D 211/72; C07D 237/04; C07D 412/04; C07D 413/12; C07D 409/12; C07D 409/06; C07D 277/28; C07D 405/06; A61K 31/505; A61K 31/497; A61K 31/44; A61K 31/16; A61K 31/50; A61K 31/135; A61K 31/501; A61K 31/425; A61K 31/517
USPC ............ 514/252.05, 252.18, 266.4, 352, 646, 514/629, 247, 648, 252.01, 272, 365, 514/266.24; 544/295, 292, 239, 238, 321, 544/287; 546/312, 221, 315; 548/205; 564/431, 221, 315
See application file for complete search history.

(56) References Cited

U.S. PATENT DOCUMENTS 3,598,815 A    8/1971  Gilles
4,021,249 A    5/1977  Noguchi et al.
(Continued)

FOREIGN PATENT DOCUMENTS

EP    0 005 911 A1    12/1979
EP    0 547 461 A1    6/1993
(Continued)

OTHER PUBLICATIONS

Abstract of Okano, Natsuko et al., "Preparation of 2-phenylaminopyrimidinones, intermediates as pesticides and herbicides in agriculture", Chem. Abstracts Service, Columbus, OH (1999); STN Accession No. 1999-672770.
(Continued)

*Primary Examiner* — James O Wilson
*Assistant Examiner* — Ebenezer O Sackey
(74) *Attorney, Agent, or Firm* — Finnegan, Henderson, Farabow, Garrett & Dunner LLP

(57) ABSTRACT

The present invention provides novel compounds having a $P2X_3$ and/or $P2X_{2/3}$ receptor antagonistic effect.
A pharmaceutical composition having a $P2X_3$ and/or $P2X_{2/3}$ receptor antagonistic effect comprising a compound of the formula (I):

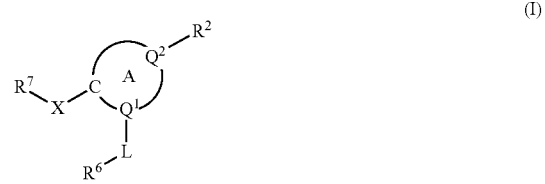

(I)

wherein
ring A is substituted or unsubstituted 5 to 7-membered cycloalkane, substituted or unsubstituted 5 to 7-membered cycloalkene or the like;
C is a carbon atom;
—X— is —N($R^{16}$)— or the like;
$R^{16}$ is hydrogen, substituted or unsubstituted alkyl or the like;
$R^7$ is substituted or unsubstituted 5- or 6-membered heteroaryl, substituted or unsubstituted 6 to 10 membered aryl;
$Q^1$ and $Q^2$ are each independently a carbon atom or a nitrogen atom;
-L- is —O—, —S— or the like;
$R^6$ is substituted or unsubstituted cycloalkyl, substituted or unsubstituted cycloalkenyl or the like;
$R^2$ is hydrogen, hydroxy or the like,
or its pharmaceutically acceptable salt or a solvate thereof.

34 Claims, No Drawings

(51) Int. Cl.

| | |
|---|---|
| *A61K 31/44* | (2006.01) |
| *A61K 31/135* | (2006.01) |
| *A61K 31/425* | (2006.01) |
| *C07C 233/75* | (2006.01) |
| *C07C 217/84* | (2006.01) |
| *C07C 217/80* | (2006.01) |
| *C07D 401/14* | (2006.01) |
| *C07D 239/84* | (2006.01) |
| *C07D 211/72* | (2006.01) |
| *C07D 237/04* | (2006.01) |
| *C07C 217/92* | (2006.01) |
| *C07D 213/74* | (2006.01) |
| *C07D 213/80* | (2006.01) |
| *C07D 213/82* | (2006.01) |
| *C07D 215/22* | (2006.01) |
| *C07D 217/24* | (2006.01) |
| *C07D 231/38* | (2006.01) |
| *C07D 233/96* | (2006.01) |
| *C07D 235/30* | (2006.01) |
| *C07D 237/32* | (2006.01) |
| *C07D 239/42* | (2006.01) |
| *C07D 239/47* | (2006.01) |
| *C07D 239/54* | (2006.01) |
| *C07D 239/95* | (2006.01) |
| *C07D 239/96* | (2006.01) |
| *C07D 241/20* | (2006.01) |
| *C07D 255/02* | (2006.01) |
| *C07D 261/12* | (2006.01) |
| *C07D 263/32* | (2006.01) |
| *C07D 263/34* | (2006.01) |
| *C07D 263/48* | (2006.01) |
| *C07D 265/10* | (2006.01) |
| *C07D 265/26* | (2006.01) |
| *C07D 265/36* | (2006.01) |
| *C07D 277/20* | (2006.01) |
| *C07D 277/34* | (2006.01) |
| *C07D 277/38* | (2006.01) |
| *C07D 401/12* | (2006.01) |
| *C07D 405/12* | (2006.01) |
| *C07D 405/14* | (2006.01) |
| *C07D 417/12* | (2006.01) |
| *C07D 417/14* | (2006.01) |
| *C07D 277/28* | (2006.01) |
| *C07D 405/06* | (2006.01) |
| *C07D 409/06* | (2006.01) |
| *C07D 409/12* | (2006.01) |
| *C07D 413/12* | (2006.01) |
| *C07D 407/06* | (2006.01) |
| *C07C 233/25* | (2006.01) |
| *C07D 215/56* | (2006.01) |
| *C07D 217/22* | (2006.01) |
| *C07D 233/88* | (2006.01) |
| *C07D 237/20* | (2006.01) |
| *C07D 239/48* | (2006.01) |
| *C07D 239/545* | (2006.01) |
| *C07D 239/557* | (2006.01) |
| *C07D 239/78* | (2006.01) |
| *C07D 265/06* | (2006.01) |
| *C07D 277/42* | (2006.01) |
| *C07D 213/69* | (2006.01) |

(52) U.S. Cl.
CPC ........... *C07D 215/56* (2013.01); *C07D 217/22* (2013.01); *C07D 217/24* (2013.01); *C07D 231/38* (2013.01); *C07D 233/88* (2013.01); *C07D 233/96* (2013.01); *C07D 235/30* (2013.01); *C07D 237/04* (2013.01); *C07D 237/20* (2013.01); *C07D 237/32* (2013.01); *C07D 239/42* (2013.01); *C07D 239/47* (2013.01); *C07D 239/48* (2013.01); *C07D 239/54* (2013.01); *C07D 239/545* (2013.01); *C07D 239/557* (2013.01); *C07D 239/78* (2013.01); *C07D 239/84* (2013.01); *C07D 239/95* (2013.01); *C07D 239/96* (2013.01); *C07D 241/20* (2013.01); *C07D 255/02* (2013.01); *C07D 261/12* (2013.01); *C07D 263/32* (2013.01); *C07D 263/34* (2013.01); *C07D 263/48* (2013.01); *C07D 265/06* (2013.01); *C07D 265/10* (2013.01); *C07D 265/26* (2013.01); *C07D 265/36* (2013.01); *C07D 277/20* (2013.01); *C07D 277/28* (2013.01); *C07D 277/34* (2013.01); *C07D 277/38* (2013.01); *C07D 277/42* (2013.01); *C07D 401/12* (2013.01); *C07D 401/14* (2013.01); *C07D 405/06* (2013.01); *C07D 405/12* (2013.01); *C07D 405/14* (2013.01); *C07D 407/06* (2013.01); *C07D 409/06* (2013.01); *C07D 409/12* (2013.01); *C07D 413/12* (2013.01); *C07D 417/12* (2013.01); *C07D 417/14* (2013.01); *C07C 2101/14* (2013.01)

(56) References Cited

U.S. PATENT DOCUMENTS

| | | |
|---|---|---|
| 4,127,718 A | 11/1978 | Illy et al. |
| 4,156,002 A | 5/1979 | Brown et al. |
| 4,158,724 A | 6/1979 | Illy et al. |
| 4,254,122 A | 3/1981 | Brown |
| 4,317,911 A | 3/1982 | Rasberger et al. |
| 4,518,688 A | 5/1985 | Leppard et al. |
| 5,232,924 A | 8/1993 | Watanabe et al. |
| 5,389,599 A | 2/1995 | Schallner et al. |
| 6,177,437 B1 | 1/2001 | Wright |
| 7,745,451 B2 | 6/2010 | Kelly et al. |
| 7,858,632 B2 | 12/2010 | Broka et al. |
| 2002/0049320 A1 | 4/2002 | Gopalsamy et al. |
| 2007/0037974 A1 | 2/2007 | Brotherton-Pleiss et al. |
| 2007/0049534 A1 | 3/2007 | Dillon et al. |
| 2007/0049609 A1 | 3/2007 | Broka et al. |
| 2007/0049610 A1 | 3/2007 | Dillon et al. |
| 2007/0049758 A1 | 3/2007 | Dillon et al. |
| 2009/0099195 A1 | 4/2009 | Bayrakdarian et al. |
| 2009/0270369 A1 | 10/2009 | Ozaki et al. |
| 2010/0317676 A1 | 12/2010 | Kelly et al. |
| 2011/0077242 A1 | 3/2011 | Broka et al. |

FOREIGN PATENT DOCUMENTS

| | | |
|---|---|---|
| EP | 2 399 910 A1 | 12/2011 |
| JP | 57-144269 | 9/1982 |
| JP | 11-189577 | 7/1999 |
| JP | 2000-72757 | 3/2000 |
| JP | 62-156110 | 7/2000 |
| JP | 2006528640 | 2/2005 |
| JP | 2007-526268 | 9/2007 |
| JP | 2008-546639 | 12/2008 |
| JP | 2009-007258 | 1/2009 |
| JP | 2010-526138 | 7/2010 |
| JP | 2010523667 | 7/2010 |
| RU | 2057754 | 4/1996 |
| SU | 867303 | 9/1981 |
| WO | WO 99/52881 A1 | 10/1999 |
| WO | WO-00/39101 | 7/2000 |
| WO | WO 00/51990 | 9/2000 |
| WO | WO-01/55093 | 8/2001 |
| WO | WO 02/094767 A2 | 11/2002 |

(56) References Cited

FOREIGN PATENT DOCUMENTS

| WO | WO-2004/054617 | 7/2004 |
|---|---|---|
| WO | WO 2005/009980 A1 | 2/2005 |
| WO | WO 2005/095359 A1 | 10/2005 |
| WO | WO-2006/074057 | 7/2006 |
| WO | WO 2006/102112 A2 | 9/2006 |
| WO | WO 2006/104713 A1 | 10/2006 |
| WO | WO 2006/104715 A1 | 10/2006 |
| WO | WO 2006/119502 A2 | 11/2006 |
| WO | WO 2006/119504 | 11/2006 |
| WO | WO 2007/079163 A2 | 7/2007 |
| WO | WO 2007/079214 A2 | 7/2007 |
| WO | WO 2008/005538 | 1/2008 |
| WO | WO 2008/016522 A2 | 2/2008 |
| WO | WO-2008/089051 | 7/2008 |
| WO | WO 2008/089051 A1 | 7/2008 |
| WO | WO 2008/136756 A1 | 11/2008 |
| WO | WO 2009/058653 A1 | 5/2009 |
| WO | WO 2010/051188 A1 | 5/2010 |
| WO | WO 2008/127591 A2 | 7/2010 |
| WO | WO 2010/092966 | 8/2010 |
| WO | WO 2012/016182 | 2/2011 |
| WO | WO 2012/020749 | 2/2012 |
| WO | WO 2012/135800 | 10/2012 |

OTHER PUBLICATIONS

Abstract of Fukuchi, T et al., "Novel 2-aminopyrimidinone derivatives, useful as insecticide and acaricide", Thomson Scientific, London, GB (May 15, 2001); STN Accession No. 2001-468100.

Abstract of Fukuchi, T et al., "2-anilino-4(3H)-pyrimidinone derivatives, pesticidally/herbicidally active, useful in agriculture/horticulture and their preparation", Thomson Scientific, London, GB (2003); STN Accession No. 2003-318151.

Abstract of Fukuchi, T et al., "A novel 2-substituted amoni-5,6-dihydro-4(3H)-pyrimidinone derivative", Thomson Scientific, London, GB (2001); STN Accession No. 2001-491646.

Ji-Zhen, Li et al., "Polymer Supported Synthesis of Multi-substituted Pyrimidine-4-one Derivatives via Pbf-activated Thiourea", Chem. Research in Chinese Universities, vol. 27, No. 2, (2011) pp. 221-223.

English Abstract of WO 9952881 A1, (via Espacenet), no date.

Supplementary European Search Report for European Application No. 11816406, mailed Oct. 20, 2014.

Akteries et al., "Reactions of Carbonyl Diisocyanate with Amides and Acids," Chem. Ber., vol. 119, pp. 669-682 (1986).

Bernatowicz, et al., 1H-Pyrazole-1-carboxamidine Hydrochloride: An Attractive Reagent for Guanylation of Amines and Its Application to Peptide Synthesis, J. Org. Chem., vol. 57, pp. 2497-2502, (1992). CAS RN 857972-98-6 (entered into STN Aug. 3, 2005).

Dräger, et al., "A new reagent and its polymer-supported variant for the amidination of amines", Tetrahedron Letters: vol. 43, pp. 1401-1403, (2002).

English-language International Search Report from the Japanese Patent Office for International Application No. PCT/JP2010/051920 mailed Mar. 30, 2010.

English-language International Search Report for International Application No. PCT/JP2011/068113 from the Japanese Patent Office mailed Nov. 1, 2011.

Esayan, et al., Synthesis and sulfuric acid hydrolysis γ-chiorocretylbenzyl (alkyl) isocyanurates, Armyanskii Khimicheskii Zhurnal, vol. 28, No. 4, pp. 332-337, (1975).

Gopalsamy et al., "Combinatorial Synthesis of Heterocycles: Solid-Phase Synthesis of 6-Amino-2,4-Dioxo-3,4-Dihydro-1,3,5-Triazine Derivatives." J. Comb. Chem., vol. 3, pp. 278-283 (2001).

Han, Jun, "Advances in Characterization of Pharmaceutical Hydrates," Trends in Bio/Pharmaceutical Industry, pp. 25-29, Mar. 2008.

Knotz, "1-Chloromethylisatin, an excellent reagent for the identification of carboxylic acids and NH-acid compounds", Scientia Pharmaceutica, vol. 38, No. 4, pp. 227-233, (1970).

Lerchova, et al., "Antioxidants and Stabilizers, L. Transformation of the 1,3,5-Tris(4-hydroxy-3,5-di-tert-butylbenzyl)cyanuric acid into Akylperoxycyclohexadienones, their Properties and Effects on the Oxidation of Tetralin and Polypropylene", Angewandte Makromolekulare Chemie, vol. 39, No. 1, pp. 107-118, (1974).

Notification of Transmittal of Translation of the International Preliminary Report on Patentability, International Preliminary Report on Patentability, and Translation of the Written Opinion of the International Searching Authority, for International Patent Application No. PCT/JP2010/051920, mailed Sep. 22, 2011 (14 pages).

Notification of Transmittal of Translation of the International Preliminary Report on Patentability, International Preliminary Report on Patentability, and Translation of the Written Opinion of the International Searching Authority, for International Patent Application No. PCT/JP2011/068097, mailed Mar. 21, 2013 (10 pages).

Notification of Transmittal of Translation of the International Preliminary Report on Patentability, International Preliminary Report on Patentability, and Translation of the Written Opinion of the International Searching Authority, for International Patent Application No. PCT/JP2011/068113, mailed Mar. 21, 2013 (15 pages).

Pecchi, et al., "Identification and structure-activity relationship of 2-morpholino 6-(3-hydroxyphenyl) pyrimidines, a class of potent and selective PI3 kinase inhibitors", Bioorganic & Medicinal Chemistry Letters, vol. 20, No. 23, pp. 6895-6898, (2010).

Schriof-Grégore, et al., "Preparation of $N$-alkyl-$N^1$-carboalkoxy guanidines: unexpected effective trans-alkoxylation transforming the 2,2,2-trichloroethoxycarbonyl into various carbamates", Tetrahedron Letters, vol. 48, pp. 2357-2359. (2007).

Shao, et al., "Strapped porphyrin rosettes based on the melamine-cyanuric acid motif. Self-assembly and supramolecular recognition", Tetrahedron, vol. 60, No. 41, pp. 9155-9162, (2004).

Simov et al., "Triazines and Other 6-Membered Rings," Chemical Abstracts, Heterocyclic Compounds, vol. 67, pp. 10246 (1987).

Somogyi, L et al., "Cyclisierungsreaktionen von mono-und disubstituierten Biguaniden mit Phenylisothiocyanat," Chem. Ber., vol. 100, pp. 1975-1982 (1967).

Supplementary European Search Report for European Application No. 10741243, mailed Sep. 13, 2012.

Suyama et al., "The Reaction of 3-Cyano-2-Methyl-1-Phenylisothiourea with Isocyanate, Isothiocyanate and Carbodimide," Nippon Kagaku Kaishi, No. 9, pp. 845-848 (1996).

Vippagunta, Sudha R., "Crystalline Solids," Advanced Drug Delivery Reviews 48 (2001) pp. 3-26.

Zuen, et al., "Crystalline furanic polyisocyanates", Polymer Bulletin 26, vol. 26, No. 4, pp. 383-390, (1991).

Office Action dated Apr. 2, 2013 in U.S. Appl. No. 13/201,209.

Office Action dated Dec. 4, 2012 in U.S. Appl. No. 13/201,209.

English-language International Search Report for International Application No. PCT/JP2011/068097 from the Japanese Patent Office mailed Nov. 15, 2011.

Kennedy, "P2X Receptors: Targets for Novel Analgesics?", The Neuroscientist, vol. 11, No. 4, pp. 345-356, (2005).

Cockayne, et al., "$P2X_2$ knockout mice and $P2X_2/P2X_3$ double knockout mice reveal a role for the $P2X_2$ receptor subunit in mediating multiple sensory effects of ATP", J. Physiol., vol. 567, No. 2, pp. 621-639, (2005).

Shieh, et al., "P2X receptor ligands and pain", Expert Opinion Ther. Patents, vol. 16, No. 8, pp. 1113-1127, (2006).

North, "$P2X_3$ receptors and peripheral pain mechanisms", Symposium Report, J. Physiol., vol. 554, No. 2, pp. 301-308, (2003).

Kennedy, et al., "Topical Review, Crossing the pain barrier: P2 receptors as targets for novel analgesics", J. Physiol., vol. 553, No. 3, pp. 683-694, (2003).

Gever, et al., "Pharmacology of P2X channels", Pflugers Arch—Eur J Physiol., vol. 452, pp. 513-537, (2006).

Jarvis, et al., "A-317491, a novel potent and selective non-nucleotide antagonist of $P2X_3$ and $P2X_{2/3}$ receptors, reduces chronic inflammatory and neuropathic pain in the rat", PNAS, vol. 99, No. 26, pp. 17179-17184, (Dec. 24, 2002).

Balboni, et al., "Triazine Compounds as Antagonists at Bv8-Prokineticin Receptors", J. Med. Chem., vol. 51, No. 23, pp. 7635-7639, (2008).

(56) References Cited

OTHER PUBLICATIONS

Carter et al., "Identification and SAR of novel diaminopyrimidines. Part 1: The discovery of RO-4, a dual $P2X_3/P2X_{2/3}$ antagonist for the treatment of pain", Bioorganic & Medicinal Chemistry Letters, vol. 19, pp. 1628-1631, (2009).

Adriaensen et al., "Functional Morphology of Pulmonary Neuroepithelial Bodies: Extremely Complex Airway Receptors", The Anatomical Record Part A, vol. 270A, pp. 25-40 (2003).

Basoglu, MD, et al., "Effects of Aerosolized Adenosine 5'-Triphosphate vs Adenosine 5'-Monophosphate on Dyspnea and Airway Caliber in Healthy Nonsmokers and Patients with Asthma", Chest, vol. 128, No. 4, pp. 1905-1909 (2005).

Brouns et al., "Intraepithelial Vagal Sensory Nerve Terminals in Rat Pulmonary Neuroepithelial Bodies Express P2X3 Receptors", Am. J. Respir. Cell Mol. Biol., vol. 23, pp. 52-61 (2000).

English Abstract of JP 11-189577 (1999), (Patent Abstracts of Japan).
English Abstract of JP 2009-7258 (2009), (Patent Abstracts of Japan).
English Abstract of WO 01/55093 (2001), (via WIPO Patentscope).
English Abstract of WO 04/054617 (2004), (via WIPO Patentscope).
English Abstract of WO 10/092966 (2010), (via WIPO Patentscope).
English Abstract of WO 12/020749 (2012), (via WIPO Patentscope).
International Search Report from the Japanese Patent Office for International Application No. PCT/JP2013/052991 mailed Mar. 12, 2013.
Kennedy et al., "Crossing the pain barrier: P2 receptors as targets for novel analgesics", J. Physiology, vol. 553, No. 3, pp. 683-694 (2003).
Notification of Transmittal of Translation of the International Preliminary Report on Patentability (PCT/IB/338); English-language translation of International Preliminary Report on Patentability (PCT/IB/373) issued Aug. 12, 2014, and Written Opinion from The International Searching Authority (PCT/ISA/237) mailed Mar. 12, 2013, for International Application No. PCT/JP2013/052991.
Office Action dated Nov. 7, 2014 in U.S. Appl. No. 13/201,209.
Office Action dated Feb. 26, 2015 in U.S. Appl. No. 13/814,346.

HETEROCYCLIC DERIVATIVE AND PHARMACEUTICAL COMPOSITION COMPRISING THE SAME

TECHNICAL FIELD

The invention relates to a compound useful for the treatment of diseases or conditions associated with P2X receptor, specifically to $P2X_3$ and/or $P2X_{2/3}$ receptor, and a pharmaceutical composition comprising such compound.

BACKGROUND ART

Adenosine triphosphate (ATP) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. ATP thus released mediates various extracellular signal transductions through an ATP receptor (Non-Patent Document 4, Non-Patent Document 5).

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel (Non-Patent Document 6).

ATP is known to cause pain, and studies with $P2X_3$ knockout and knockdown methodologies have shown that $P2X_3$ receptor mediates transmission of chronic pain. $P2X_3$ receptors are expressed in a specific manner on peripheral sensory nerve to form a homo-complex or hetero-complex with $P2X_2$ ($P2X_{2/3}$) (Non-Patent Document 1).

Later, the compound A-317491 was reported as a specific antagonist to $P2X_3$ and $P2X_{2/3}$ receptors. A-317491 is tri-substituted-N-[(1S)-1,2,3,4-tetrahydro-1-naphthalenyl]benzamide derivative represented by the formula:

[Chemical Formula 1]

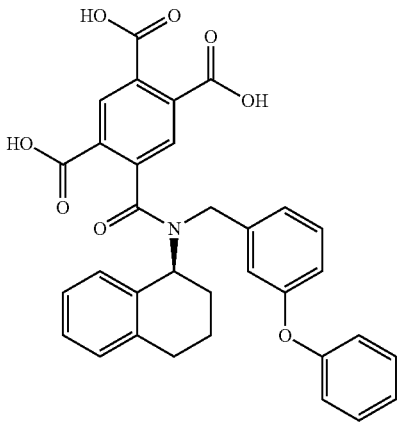

(Patent Document 1). It was reported to exhibit an antagonist effect to $P2X_3$ and $P2X_{2/3}$ receptors and analgesic action in neuropathic pain model and inflammatory pain model (Non-Patent Document 7). This indicates that pain sensation is transmitted via $P2X_3$ or $P2X_{2/3}$ receptor and that a compound having an $P2X_3$ or $P2X_{2/3}$ receptor antagonistic effect is useful as an analgesic. Also, compounds that exhibit $P2X_3$ or $P2X_{2/3}$ receptor antagonistic effect are described in Patent Documents 2-7.

Additionally, it was recently reported that vesical reflex was strongly reduced in $P2X_3$ knockout mouse (Non-Patent Document 2), suggesting that a compound having $P2X_3$ antagonistic effect is useful in the treatment of diseases caused by overactive bladder.

Patent Documents 8, 9, 10 and 11 disclose compounds having similar structure to the compounds of the present invention but they do not disclose analgesic effect and $P2X_3$ or $P2X_{2/3}$ receptor antagonistic effect. Non-Patent Document 8 discloses compounds having similar structure to the compounds of the present invention and having analgesic effect, but it does not discloses $P2X_3$ or $P2X_{2/3}$ receptor antagonistic effect. Patent Documents 12 and 13 disclose compounds having $P2X_3$ receptor antagonistic effect but the structures are different with those of the compounds of the present invention.

PRIOR ART

Patent Document

[Patent Document 1] WO02/094767
[Patent Document 2] WO2005/095359
[Patent Document 3] US20070037974
[Patent Document 4] US20070049758
[Patent Document 5] US20070049610
[Patent Document 6] US20070049609
[Patent Document 7] US20070049534
[Patent Document 8] JP12-072757A
[Patent Document 9] WO2006/104713
[Patent Document 10] WO2006/104715
[Patent Document 11] WO2006/102112
[Patent Document 12] WO2010/051188
[Patent Document 13] WO2010/092966

Non-Patent Document

[Non-Patent Document 1] Neuroscientist 11 (2005) pp. 345-356
[Non-Patent Document 2] J. Physiol. 567.2 (2005) pp. 621-639
[Non-Patent Document 3] Expert Opin. Ther. Patens (2006) 16(8), p. 113-1127
[Non-Patent Document 4] J. Physiology (2003), 554(2), p. 301-308
[Non-Patent Document 5] J. Physiology (2003), 553(3), p. 683-694
[Non-Patent Document 6] Pflungars Arch Eur J physiol (2006), p. 452, 513-537
[Non-Patent Document 7] PNAS (2002), 99(26), p. 17179-17184
[Non-Patent Document 8] Journal of Medicinal Chemistry (2008), 51(23), p. 7635-7639

SUMMARY OF THE INVENTION

Problems to be Solved by the Invention

The present invention provides a novel compound or a pharmaceutical composition having a $P2X_3$ and/or $P2X_{2/3}$ receptor antagonistic effect or a pharmaceutical composition having the effect.

Means for Solving the Problem

During studies to solve the problems described above, the inventors have discovered novel compounds that hind specifically to P2X₃ anchor P2X_{2/3} receptor and exhibit an antagonistic effect, or pharmaceutical compositions. The present invention was completed based on these findings.

The present invention relates to the followings:

(1α)

A pharmaceutical composition having a P2X₃ and/or P2X_{2/3} receptor antagonistic effect comprising the compound of the formula (I):

[Chemical Formula 2]

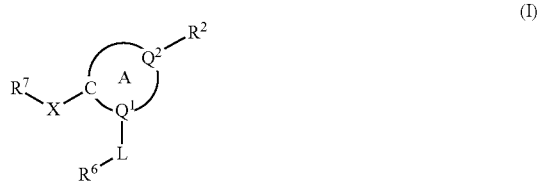

(I)

wherein ring A is substituted or unsubstituted 5 to 7-membered cycloalkane, substituted or unsubstituted 5 to 7-membered cycloalkene, a substituted or unsubstituted 5 to 7-membered nitrogen-containing non-aromatic heterocyclic ring, a benzene ring or a substituted or unsubstituted 5- or 6-membered aromatic heterocyclic ring, or a fused ring consisting of two rings selected from substituted or unsubstituted 5 to 7-membered cycloalkane, substituted or unsubstituted 5 to 7-membered cycloalkene, a substituted or unsubstituted 5 to 7-membered nitrogen-containing non-aromatic heterocyclic ring, a benzene ring, and a substituted or unsubstituted 5- or 6-membered aromatic heterocyclic ring, provided that a compound wherein ring A is a triazine ring is excluded;

C is a carbon atom;

—X— is —N(R¹⁶)—, —O—, —S—, or —(CR^{16a}R^{16b})—;

R¹⁶ is hydrogen, substituted or unsubstituted alkyl, substituted or unsubstituted alkenyl, substituted or unsubstituted alkynyl, or substituted or unsubstituted acyl;

R^{16a} and R^{16b} are each independently hydrogen, halogen, hydroxy, substituted or unsubstituted alkyl, substituted or unsubstituted alkenyl, substituted or unsubstituted alkenyl, substituted or unsubstituted alkyloxy, substituted or unsubstituted alkynyloxy, or substituted or unsubstituted alkenyloxy;

R⁷ is substituted or unsubstituted 5- or 6-membered heteroaryl or substituted or unsubstituted 6 to 10-membered aryl;

Q¹ and Q² are each independently a carbon atom or a nitrogen atom;

when Q¹ is a carbon atom, -L- is —O—, —S—, —N(R⁸)— or —(CR^{9c}R^{9d})n¹-;

when Q¹ is a nitrogen atom, -L- is —(CR^{9a}R^{9b})n¹-;

R⁸ is hydrogen, substituted or unsubstituted alkyl, substituted or unsubstituted alkenyl, substituted or unsubstituted alkenyl, or substituted or unsubstituted acyl;

R^{9a}, R^{9b}, R^{9c} and R^{9d} are each independently, hydrogen, halogen, hydroxy, substituted or unsubstituted alkyl, substituted or unsubstituted alkenyl, substituted or unsubstituted alkynyl, substituted or unsubstituted substituted or unsubstituted alkynyloxy, or substituted or unsubstituted alkenyloxy, or R^{9c} and R^{9d} attached to the same carbon atom, and/or R^{9a} and R^{9b} attached to the same carbon atom are taken together to form oxo thioxo;

n¹ is an integer of 1 to 4;

R⁶ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

R² is hydrogen, hydroxy, halogen, cyano, substituted or unsubstituted substituted or unsubstituted alkenyl, substituted or unsubstituted alkenyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino;

provided that

[Chemical Formula 3]

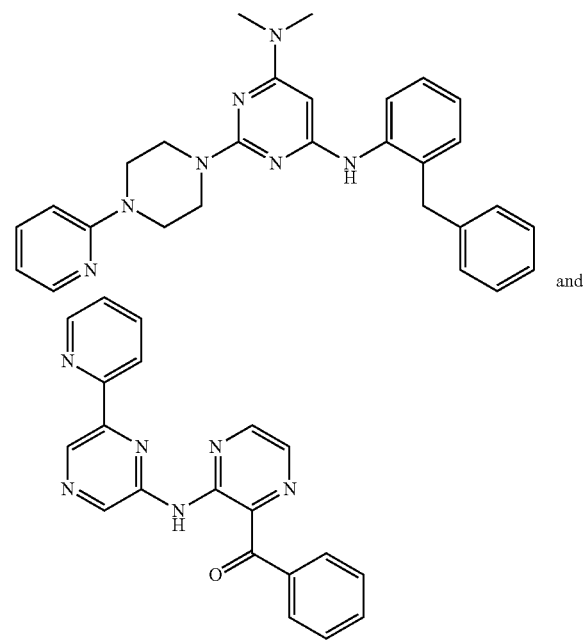

and are excluded, or its pharmaceutically acceptable salt or a solvate thereof.

(2α)

The pharmaceutical composition having a P2X₃ and/or P2X_{2/3} receptor antagonistic effect according to the above (1α) comprising the compound wherein ring A is a substituted or unsubstituted cyclohexane ring, a substituted or unsubstituted cyclohexadiene ring, a substituted or unsubstituted cyclohexene ring, a substituted or unsubstituted benzene ring, a substituted or unsubstituted pyridine ring, a substituted or unsubstituted dihydropyridine ring, a substituted or unsubstituted tetrahydropyridine ring, a substituted or unsubstituted pyrimidine ring, a substituted or unsubstituted dihydropyrimidine ring, a substituted or unsubstituted tetrahydropyrimidine ring, a substituted or unsubstituted hexahydropyrimidine ring, a substituted or unsubstituted piperidine ring, a substituted or unsubstituted piperazine ring, a substituted or unsubstituted pyrazine ring, a substituted or unsubstituted dihydropyrazine ring, a substituted or unsubstituted tetrahydropyrazine ring, a substituted or unsubstituted pyridazine ring, a substituted or unsubstituted dihydropyridazine ring, a substituted or unsubstituted tetrahydropyridazine ring, a substituted or unsubstituted indene ring, a substituted or unsubstituted benzofuran ring, a substituted or unsubstituted benzofuran ring, a substituted or unsubstituted benzo(b)thiophene ring, a substituted or unsubstituted benzo(c)thiophene ring, a substituted or unsubstituted indoline ring, a substituted or unsubstituted indole ring, a substituted or unsubstituted benzimidazole ring, a substituted or unsubstituted cyclopenta[b]pyridine ring, a substituted or unsubstituted 1H-indazole ring, a substituted or unsubstituted benzisoxazole ring, a substituted or unsubstituted benzoxazole ring, a substituted or unsubstituted 2,1-benzisoxazole ring, a substituted or unsubstituted benzothiazole ring, a substituted car unsubstituted naphthalene ring, a substituted or unsubstituted 1,2,3,4-tetrahydronaphthalene ring, a substituted or unsubstituted 3H-2-benzopyran ring, to substituted or unsubstituted quinoline ring, a substituted or unsubstituted isoquinoline ring, a substituted or unsubstituted quinazoline ring, a substituted or unsubstituted quinoxaline ring, a substituted or unsubstituted 1,8-naphthyridine ring, a substituted or unsubstituted 1,7-naphthyridine ring, a substituted or unsubstituted 1,6-naphthyridine ring, a substituted or unsubstituted 1,5-naphthyridine ring, a substituted or unsubstituted 2H-1,3-benzoxazine ring, a substituted or unsubstituted 2H-1,4-benzoxazine ring, a substituted or unsubstituted 1H-2,3-benzoxazine ring, a substituted or unsubstituted 4H-3,1-benzoxazine ring, or a substituted or unsubstituted 4H-1,4-benzoxazine ring, or its pharmaceutically acceptable salt or a solvate thereof.

(3α)

The pharmaceutical composition having a $P2X_3$ and/or $P2X_{2/3}$ receptor antagonistic effect according to the above (1α) or (2α) comprising the compound wherein ring A is a substituted or unsubstituted benzene ring, a substituted or unsubstituted dihydropyridine ring, a substituted or unsubstituted dihydropyrimidine ring, a substituted or unsubstituted tetrahydropyrimidine ring, a substituted or unsubstituted oxazole ring, a substituted or unsubstituted pyridazine ring, or a substituted or unsubstituted pyrazole ring, or its pharmaceutically acceptable salt or a solvate thereof.

(4α)

The pharmaceutical composition having a $P2X_3$ and/or $P2X_{2/3}$ receptor antagonistic effect according to the above (1α) or (2α) comprising the compound wherein ring A is a substituted or unsubstituted indene ring, a substituted or unsubstituted benzofuran ring, a substituted or unsubstituted isobenzofuran ring, a substituted or unsubstituted benzo(b)thiophene ring, a substituted or unsubstituted benzo(c)thiophene ring, a substituted or unsubstituted indoline ring, a substituted or unsubstituted indole ring, a substituted or unsubstituted benzimidazole ring, a substituted or unsubstituted cyclopenta[b]pyridine ring, a substituted or unsubstituted 1H-indazole ring, a substituted or unsubstituted benzisoxazole ring, a substituted or unsubstituted benzoxazole ring, a substituted or unsubstituted 2,1-benzisoxazole ring, a substituted or unsubstituted benzothiazole ring, a substituted or unsubstituted naphthalene ring, a substituted or unsubstituted 1,2,3,4-tetrahydronaphthalene ring, a substituted or unsubstituted 3H-2-benzopyran ring, a substituted or unsubstituted quinoline ring, a substituted or unsubstituted isoquinoline ring, a substituted or unsubstituted quinazoline ring, a substituted or unsubstituted quinoxaline ring, a substituted or unsubstituted 1,8-naphthyridine ring, a substituted or unsubstituted 1,7-naphthyridine ring, a substituted or unsubstituted 1,6-naphthyridine ring, a substituted or unsubstituted 1,5-naphthyridine ring, a substituted or unsubstituted 2H-1,3-benzoxazine ring, a substituted or unsubstituted 2H-1,4-benzoxazine ring, a substituted or unsubstituted 1H-2,3-benzoxazine ring, a substituted or unsubstituted 4H-3,1-benzoxazine ring, or a substituted or unsubstituted 4H-1,4-benzoxazine ring, or its pharmaceutically acceptable salt or a solvate thereof.

(5α)

The pharmaceutical composition having a $P2X_3$ and/or $P2X_{2/3}$ receptor antagonistic effect according to any one of the above (1α) to (4α) comprising the compound wherein ring A is a ring optionally substituted with oxo or thioxo, or its pharmaceutically acceptable salt or a solvate thereof.

(6α)

The pharmaceutical composition having a $P2X_3$ and/or $P2X_{2/3}$ is receptor antagonistic effect according to any one of the above (1α) to (5α) comprising the compound of —X— is —N($R^{16}$)—; and $R^{16}$ is hydrogen, substituted or unsubstituted substituted or unsubstituted alkenyl, substituted or unsubstituted alkynyl, or substituted or unsubstituted acyl, or its pharmaceutically acceptable salt or a solvate thereof.

(7α)

The pharmaceutical composition having a $P2X_3$ and/or $P2X_{2/3}$ receptor antagonistic effect according to any one of the above (1α) to (6α) comprising the compound wherein —X— is —NH—; $R^7$ is substituted or unsubstituted 6-membered heteroaryl or substituted or unsubstituted phenyl; -L- is —($CR^{9a}R^{9b}$)—; and wherein $R^{9a}$ and $R^{9b}$ are as defined in the above (1α), or its pharmaceutically acceptable salt or a solvate thereof.

(8α)

The pharmaceutical composition having a $P2X_3$ and/or $P2X_{2/3}$ receptor antagonistic effect according to any one of the above (1α) to (7α) comprising the compound wherein $Q^2$ is a carbon atom; and
$R^2$ is a group of the formula: —NH—C(=O)—($CR^{8a}R^{8b}$)n-$R^9$;
wherein n is an integer of 0 to 4; $R^{8a}$ and $R^{8b}$ are each independently hydrogen, halogen, hydroxy, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or
a group of the formula: —($CR^{8a}R^{8b}$)m-$R^9$;
wherein m is an integer of 1 to 6; and $R^{8a}$, $R^{8b}$ and $R^9$ are as defined above,
or its pharmaceutically acceptable salt or a solvate thereof.

(9α)

The pharmaceutical composition having a $P2X_3$ and/or $P2X_{2/3}$ is receptor antagonistic effect according to any one of the above (1α) to (7α) comprising the compound wherein $Q^2$ is a nitrogen atom; $R^2$ is C1-C6 alkyl or a group of the formula: —$(CR^{8a}R^{8b})_m$-$R^9$; and $R^{8a}$, $R^{8b}$, m and $R^9$ are as defined in the above (8α), or its pharmaceutically acceptable salt or a solvate thereof.

(10α)

The pharmaceutical composition having a $P2X_3$ and/or $P2X_{2/3}$ receptor antagonistic effect, according to the above (1α) comprising the compound of the formula:

[Chemical Formula 4]

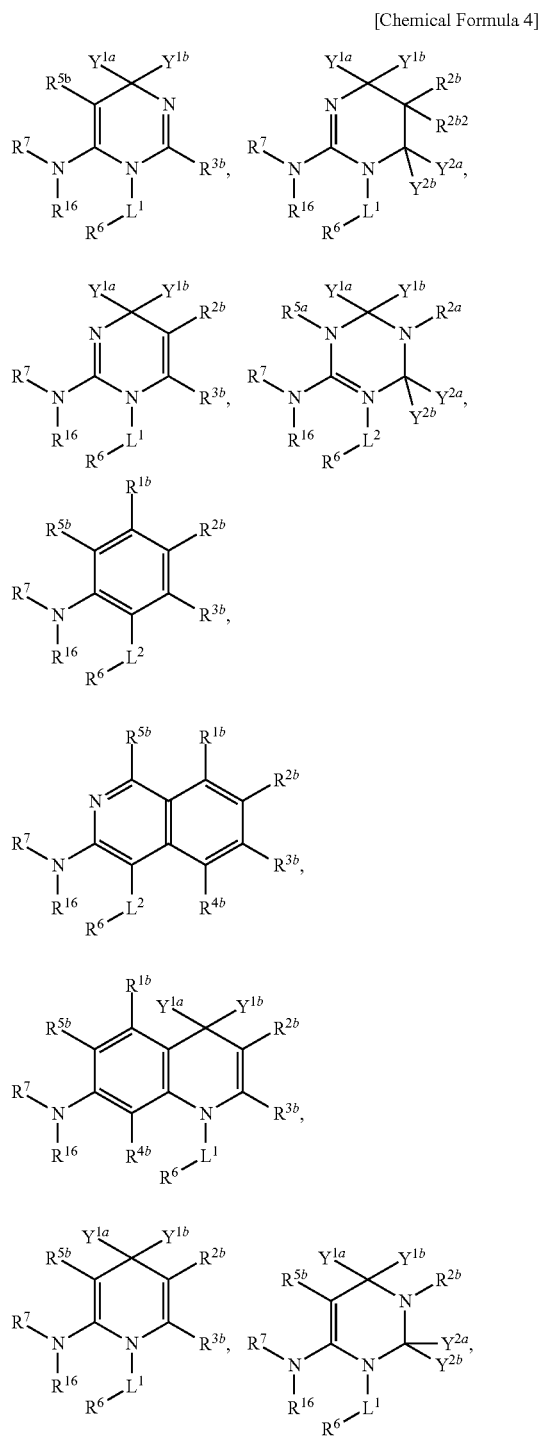

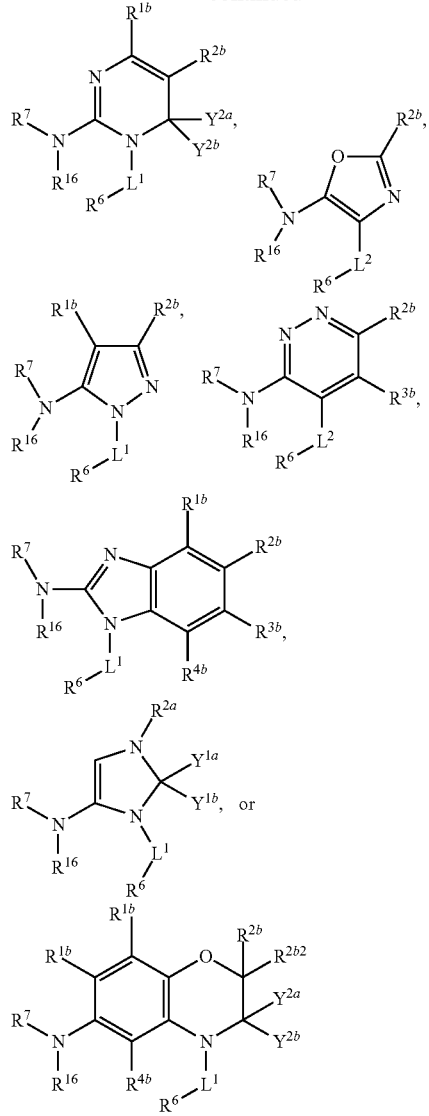

wherein
$Y^{1a}$, $Y^{1b}$, $Y^{2a}$, $Y^{2b}$, $R^{1b}$, $R^{2b}$, $R^{2b2}$, $R^{3b}$, $R^{4b}$ and $R^{5b}$ are each independently hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino or $Y^{1a}$ and $Y^{1b}$, and/or $Y^{2a}$ and $Y^{2b}$ are taken together to form oxo thioxo;

$R^{2a}$ and $R^{5a}$ are each independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, or substituted or unsubstituted sulfamoyl, $R^7$ is a group of the formula:

[Chemical Formula 5]

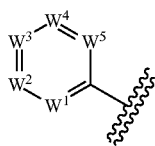

wherein
=$W^1$-$W^2$=$W^3$-$W^4$=$W^5$- is a group selected from the following (a) to (h):
(a): =C(H)—C($R^{10a}$)=C($R^{10b}$)—C($R^{10c}$)=C(H)—;
(b): =N—C($R^{10a}$)=C($R^{10b}$)—C($R^{10c}$)=C(H)—;
(c): =C(H)—N=C($R^{10b}$)—C($R^{10c}$)=C(H)—;
(d): =C(H)—C($R^{10a}$)=N—C($R^{10c}$)=C(H)—;
(e): =C(H)—C($R^{10a}$)=C($R^{10b}$)—N=C(H)—;
(f): =N—C($R^{10a}$)=C($R^{10b}$)—C($R^{10c}$)=N—;
(g): =C(H)—C($R^{10a}$)=N—C($R^{10c}$)=C(H)—; and
(h): =C(H)—N=C($R^{10b}$)—N=C(H)—;

$R^{10a}$, $R^{10b}$ and $R^{10c}$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring;

$R^{16}$ is hydrogen, substituted or unsubstituted acyl, substituted or unsubstituted alkyl, substituted or unsubstituted alkenyl, or substituted or unsubstituted alkynyl;

$L^1$ is —$CR^{9a}R^{9b}$—;

$L^2$ is —$CR^{9c}R^{9d}$—;

$R^{9a}$, $R^{9b}$, $R^{9c}$ and $R^{9d}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy; and $R^6$ is as defined in the above (1α), or its pharmaceutically acceptable salt or a solvate thereof.

(11α)

The pharmaceutical composition having a $P2X_3$ and/or $P2X_{2/3}$ receptor antagonistic effect according to the above (10α) comprising the compound of the formula:

[Chemical Formula 6]

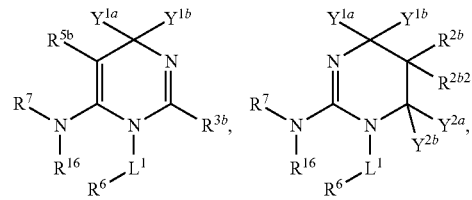

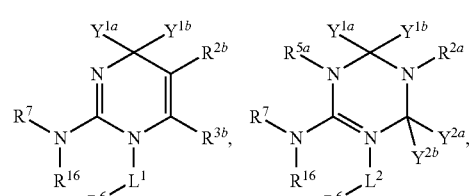

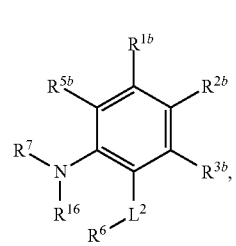

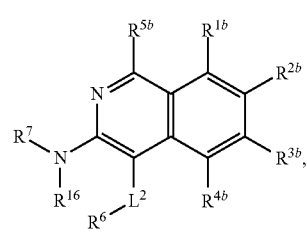

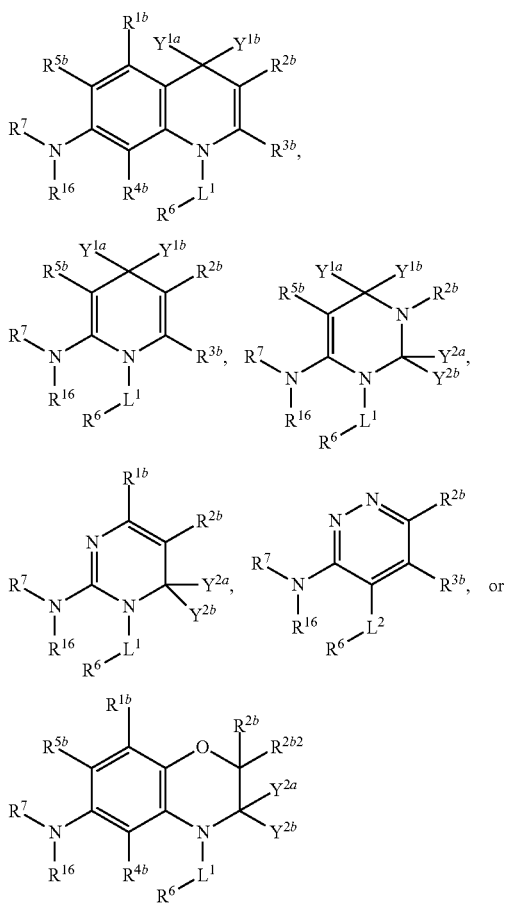

wherein $Y^{1a}, Y^{1b}, Y^{2a}, Y^{2b}, R^{1b}, R^{2a}, R^{2b}, R^{2b2}, R^{3b}, R^{4b}, R^{5a}, R^{5b}, R^6, R^7, R^{16}, L^1,$ and $L^2$ are as defined in the above (10α), or its pharmaceutically acceptable salt or a solvate thereof.
(12α)

The pharmaceutical composition having a P2X$_3$ and/or P2X$_{2/3}$ receptor antagonistic effect according to the above (10α) comprising the compound of the formula:

[Chemical Formula 7]

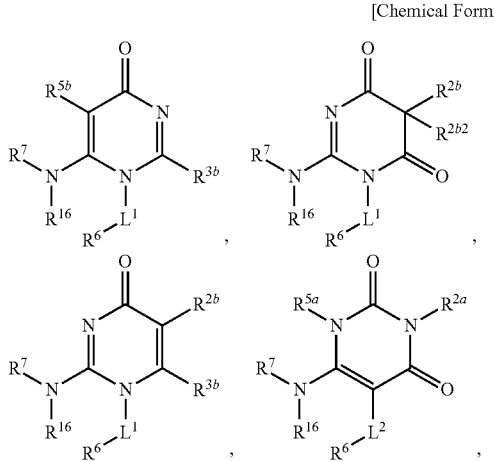

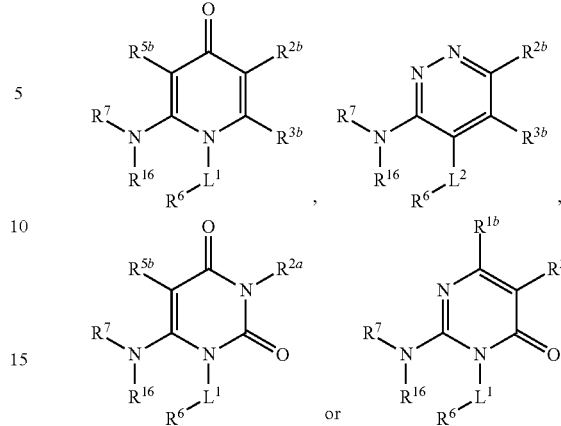

wherein $R^{2a}, R^{2b}, R^{2b2}, R^{3b}, R^{5a}, R^{5b}, R^6, R^7, R^{16}, L^1$ and $L^2$ are as defined in the above (10α), or its pharmaceutically acceptable salt or a solvate thereof.
(13α)

The pharmaceutical composition having a P2X$_3$ and/or P2X$_{2/3}$ receptor antagonistic effect according to any one of the above (1α) to (12α) comprising the compound wherein $R^6$ is a group of the formula:

[Chemcial Formula 8]

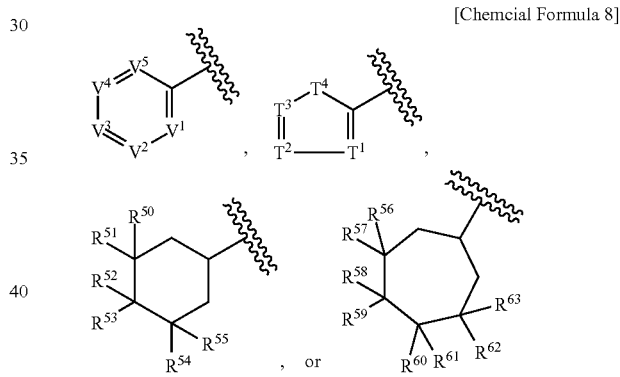

wherein $=V^1-V^2=V^3-V^4=V^5-$ is a group selected from the following (i) to (p):
(i): $=C(H)-C(R^A)=C(R^B)-C(R^C)=C(H)-$;
(j): $=N-C(R^A)=C(R^B)-C(R^C)=C(H)-$;
(k): $=C(H)-N=C(R^B)-C(R^C)=C(H)-$;
(l): $=C(H)-C(R^A)=N-C(R^C)=C(H)-$;
(m): $=C(H)-C(R^A)=C(R^B)-N=C(H)-$;
(n): $=N-C(R^A)=C(R^B)-C(R^C)=N-$;
(o): $=C(H)-C(R^A)=N-C(R^C)=C(H)-$; and
(p): $=C(H)-N=C(R^B)-N=C(H)-$;

$R^A, R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or $R^A$ and $R^B$, $R^B$ and $R^C$ together with ring atoms to which they are attached form a non-aromatic carbocyclic ring, a non-aromatic heterocyclic ring, an aromatic carbocyclic ring, or an aromatic heterocyclic ring;

=$T^1$-$T^2$=$T^3$-$T^4$- is a group selected from the following (q) to (t):

(q): =C(H)—C($R^D$)=C($R^E$)—S—;
(r): =C(H)—C($R^D$)=C($R^E$)—O—;
(s): =N—C($R^D$)=C($R^E$)—S—; and
(t): =N—C($R^D$)=C($R^E$)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring; and $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or its pharmaceutically acceptable salt or a solvate thereof.

(13A)

The pharmaceutical composition having a $P2X_3$ and/or $P2X_{2/3}$ receptor antagonistic effect according to any one of the above (1α) to (12α) comprising the compound wherein $R^6$ is

[Chemcial Formula 9]

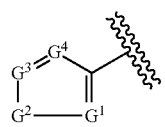

wherein
=$G^1$-$G^2$-$G^3$=$G^4$- is a group selected from the following (u) to (x):

(u): =C(H)—S—C($R^F$)—C(H)—;
(v): =C(H)—O—C($R^F$)—C(H)—;
(w): =C(H)—S—C($R^F$)=N—; and
(x): =C(H)—O—C($R^F$)=N—;

$R^F$ is hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy, or its pharmaceutically acceptable salt or a solvate thereof.

(14A)

A compound of the formula (I):

[Chemical Formula 10]

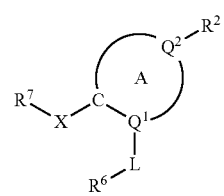

(I)

wherein ring A is a substituted or unsubstituted cyclohexane ring, a substituted or unsubstituted cyclohexene ring, a substituted or unsubstituted 6-membered nitrogen-containing non-aromatic heterocyclic ring, a benzene ring or a substituted or unsubstituted 6-membered aromatic heterocyclic ring, or a fused ring wherein any of the above ring is fused with one ring selected from substituted or unsubstituted 5 to 7-membered cycloalkane, substituted or unsubstituted 5 to 7-membered cycloalkene, a substituted or unsubstituted 5 to 7-membered nitrogen-containing non-aromatic heterocyclic ring, a benzene ring and a substituted or unsubstituted 5- or 6-membered aromatic heterocyclic ring, provided that a compound wherein ring A is a triazine ring is excluded;

C is a carbon atom;

—X— is —N($R^{16}$);

$R^{16}$ is hydrogen, substituted or unsubstituted alkyl, substituted or unsubstituted alkenyl, substituted or unsubstituted alkynyl or substituted or unsubstituted acyl;

$R^7$ is a group of the formula:

[Chemical Formula 11]

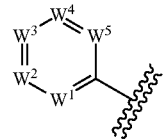

wherein
=$W^1$-$W^2$=$W^3$-$W^4$=$W^5$- is a group selected from the following (a) to (h):

(a): =C(H)—C($R^{10a}$)=C($R^{10b}$)—C($R^{10c}$)=C(H)—;
(b): =N—C($R^{10a}$)=C($R^{10b}$)—C($R^{10c}$)=C(H)—;
(c): =C(H)—N=C($R^{10b}$)—C($R^{10c}$)=C(H)—;
(d): =C(H)—C($R^{10a}$)=N—C($R^{10c}$)=C(H)—;

(e): =C(H)—C($R^{10a}$)=C($R^{10b}$)—N=C(H)—;
(f): =N—C($R^{10a}$)=C($R^{10b}$)—C($R^{10c}$)=N—;
(g): =C(H)—C($R^{10a}$)=N—C($R^{10c}$)=C(H)—; and
(h): =C(H)—N=C($R^{10b}$)—N=C(H)—;

$R^{10a}$, $R^{10b}$ and $R^{10c}$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring;

provided that groups of (a) to (h) have at least one substituent; wherein "groups of (a) to (h) have at least one substituent" means at least one of $R^{10a}$, $R^{10b}$ and $R^{10c}$ is not hydrogen in the groups of (a), (b) and (f), at least one of $R^{10b}$ and $R^{10c}$ is not hydrogen in the group of (c), at least one of $R^{10a}$ and $R^{10c}$ is not hydrogen in the groups of (d) and (g), at least one of $R^{10a}$ and $R^{10b}$ is not hydrogen in the group of (e), and $R^{10b}$ is not hydrogen in the group of (h);

$Q^1$ and $Q^2$ are each independently a carbon atom or a nitrogen atom;

when $Q^1$ is a carbon atom, -L- is —C$R^{9a}R^{9b}$—;
when $Q^1$ is a nitrogen atom, -L- is —C$R^{9c}R^{9d}$—;

$R^{9a}$, $R^{9b}$, $R^{9c}$ and $R^{9d}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy; and $R^6$ is a group of the formula:

[Chemical Formula 12]

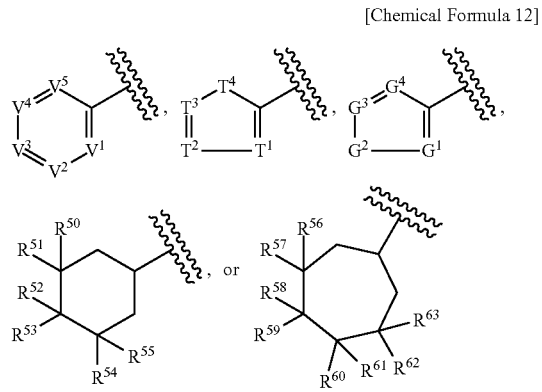

wherein =$V^1$-$V^2$=$V^3$-$V^4$-$V^5$- is a group selected from the following (i) to (p):
(i): =C(H)—C($R^A$)=C($R^B$)—C($R^C$)=C(H)—;
(j): =N—C($R^A$)=C($R^B$)—C($R^C$)=C(H)—;
(k): =C(H)—N=C($R^B$)—C($R^C$)=C(H)—;
(l): =C(H)—C($R^A$)=N—C($R^C$)=C(H)—;
(m): =C(H)—C($R^A$)=C($R^B$)—N=C(H)—;
(n): =N—C($R^A$)=C($R^B$)—C($R^C$)=N—;
(o): =C(H)—C($R^A$)=N—C($R^C$)=C(H)—; and
(p): =C(H)—N=C($R^B$)—N=C(H)—;

$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkenyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring, provided that groups of (i) to (p) have at least one substituent; wherein "groups of (i) to (p) have at least one substituent" means at least one of $R^A$, $R^B$ and $R^C$ is not hydrogen in the groups of (i), (j) and (n), at least one of $R^B$ and $R^C$ is not hydrogen in the group of (k), at least one of $R^A$ and $R^C$ is not hydrogen in the groups of (l) and (o), at least one of $R^A$ and $R^B$ is not hydrogen in the group of (m), and $R^B$ is not hydrogen in the group of (p);

=$T^1$-$T^2$=$T^3$-$T^4$- is a group selected from the following; (q) to (t):
(q): =C(H)—C($R^D$)=C($R^E$)—S—;
(r): =C(H)—C($R^D$)=C($R^E$)—O—;
(s): =N—C($R^D$)=C($R^E$)—S—; and
(t): =N—C($R^D$)=C($R^E$)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

$G^1$-$G^2$-$G^3$=$G^4$- is a group selected from the following (u) to (x):
(u): =C(H)—S—C($R^F$)—C(H)—;
(v): =C(H)—O—C($R^F$)—C(H)—;
(w): =C(H)—S—C($R^F$)=N—; and
(x): =C(H)—O—C($R^F$)=N—;

$R^F$ is hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy;

$R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy;

$R^2$ is hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, provided that
(i) a compound wherein

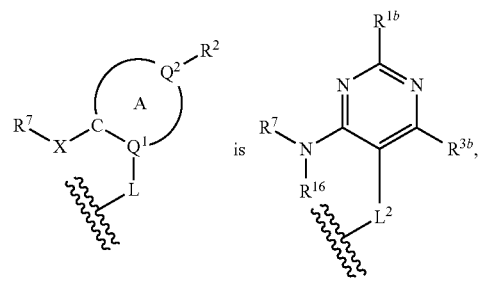

[Chemical Formula 13]

$R^{16}$ is hydrogen, and
(α) $R^{1b}$ is amino substituted with substituted or unsubstituted phenyl, and $R^{3b}$ is methyl, or
(β) $R^{1b}$ is methylthio, and $R^{3b}$ is chloro,
(ii) a compound wherein

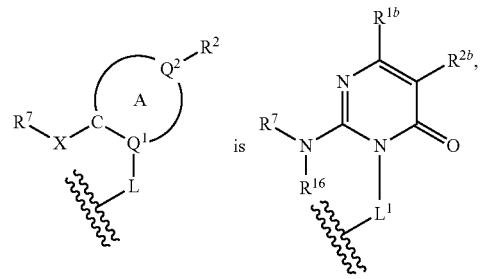

[Chemical Formula 14]

$R^{16}$ is hydrogen, and
(α) $R^{1b}$ is unsubstituted alkyl, and $R^{2b}$ is substituted or unsubstituted arylmethyl or substituted or unsubstituted heteroarylmethyl, or
(β) $R^{1b}$ is trifluoromethyl, and $R^{2b}$ is hydrogen,
(iv) a compound wherein

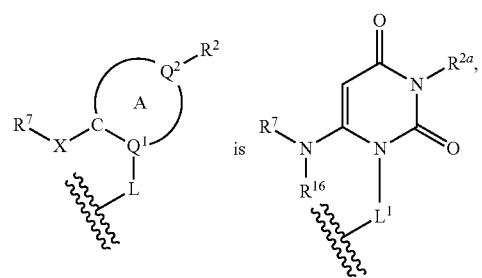

[Chemical Formula 15]

$R^{16}$ is hydrogen, and
(α) $R^{2a}$ is hydrogen, and $R^7$ is phenyl substituted with n-octyl, or
(β) $R^{2a}$ is methyl, and $R^6$ is phenyl substituted with methylsulfonyl, and
(v) a compound wherein
$R^7$ is phenyl substituted with —C(=O)CH(Me)CH$_2$C(=O)OMe,
(vi) a compound wherein
ring A is a benzene ring, and $R^6$ is 2,6-di-tert-butyl-4-hydroxyphenyl, and (vii)
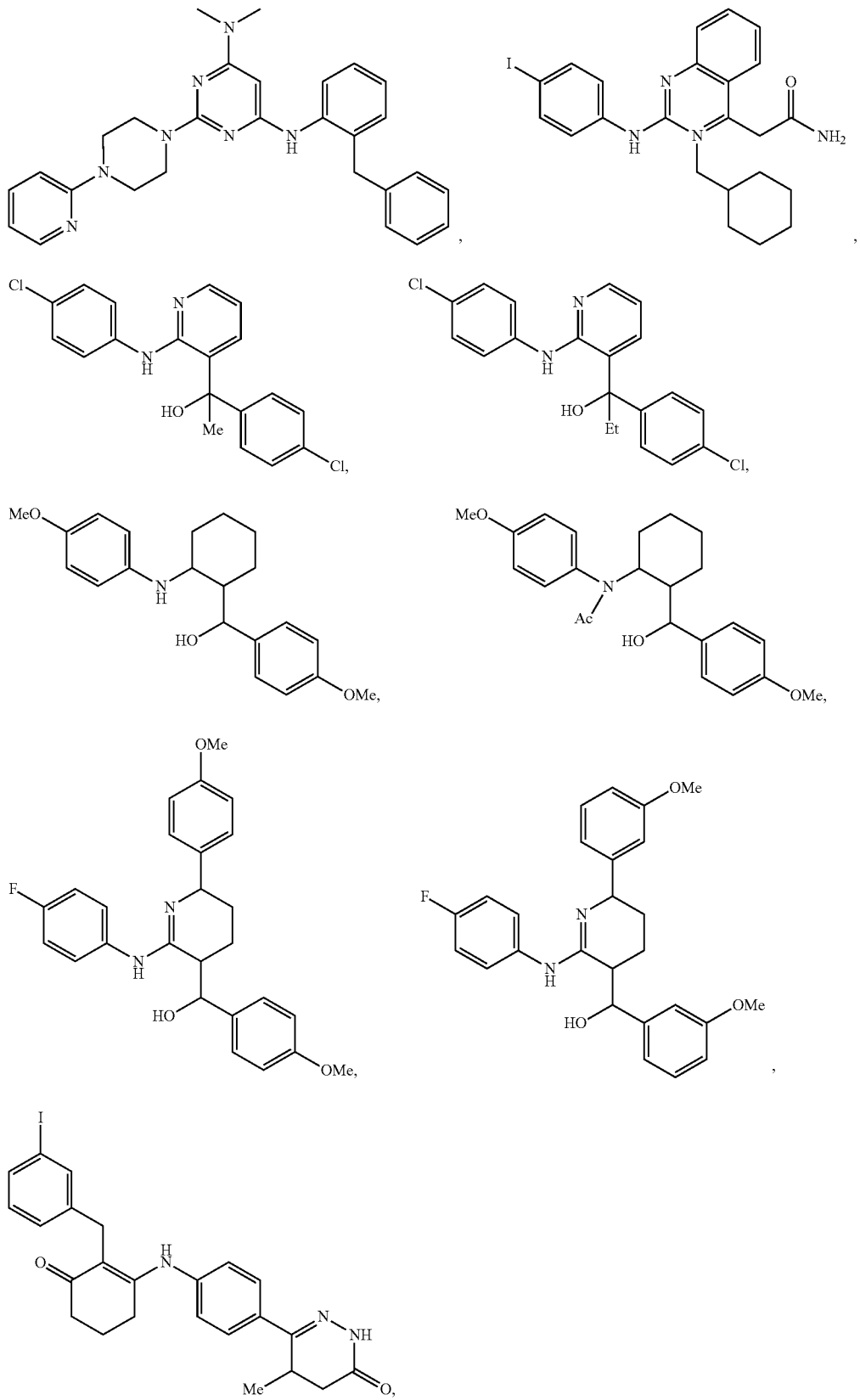

-continued
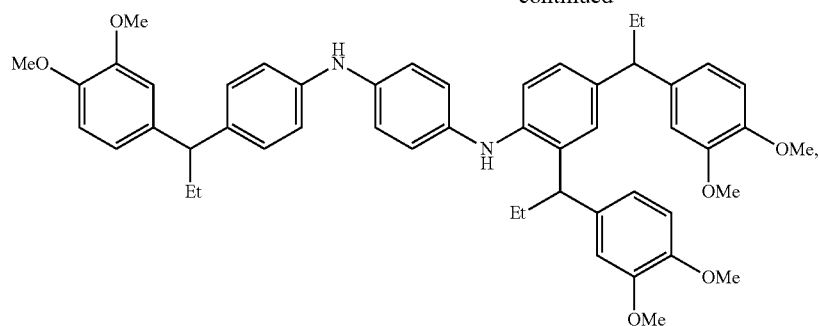
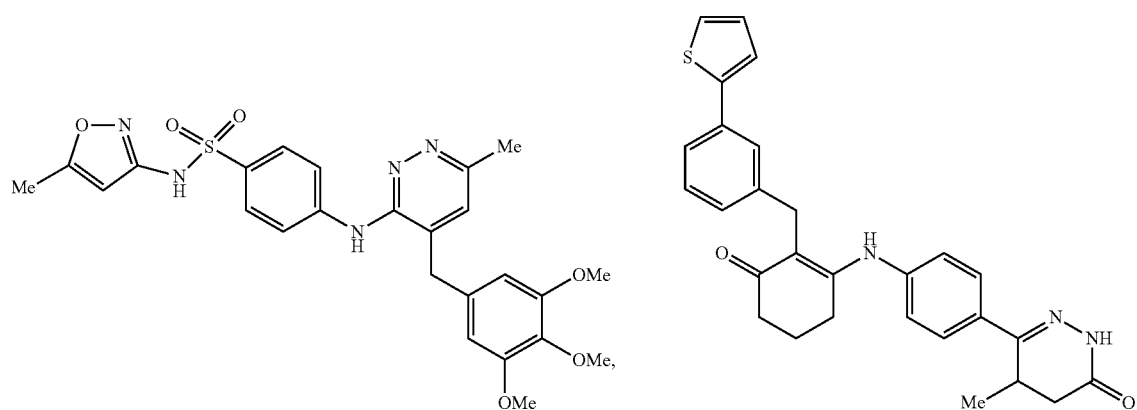
[Chemical Formula 17]
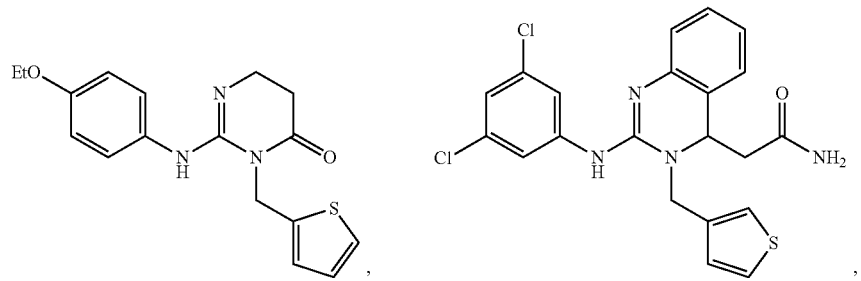
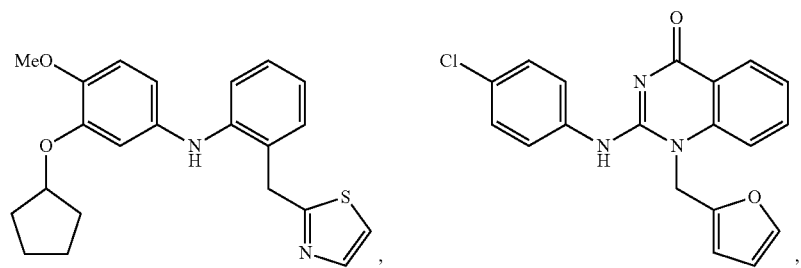
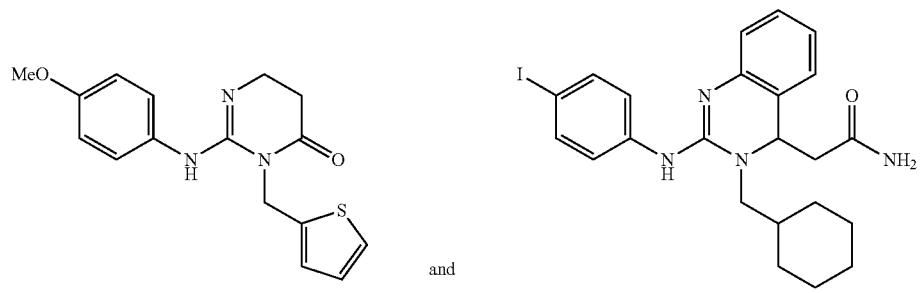
and wherein Me is methyl, Et is ethyl, Ac is acetyl,
are excluded,
or its pharmaceutically acceptable salt or a solvate thereof.
(14α) A compound of the formula (I):

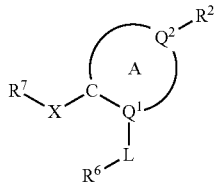

(I)

wherein
ring A is a substituted or unsubstituted cyclohexane ring, a substituted or unsubstituted cyclohexene ring, a substituted or unsubstituted 6-membered nitrogen-containing non-aromatic heterocyclic ring, a benzene ring, or a substituted or unsubstituted 6-membered aromatic heterocyclic ring, or
a fused ring wherein any of the above ring is fused with one ring selected from substituted or unsubstituted 5 to 7-membered cycloalkane, substituted or unsubstituted 5 to 7-membered cycloalkene, substituted or unsubstituted 5 to 7-membered nitrogen containing non-aromatic, heterocyclic ring, a benzene ring, and a substituted or unsubstituted 5 or 6-membered aromatic heterocyclic ring, provided that a compound wherein ring A is a triazine ring is excluded;
C is a carbon atom;
—X— is —N($R^{16}$)—;
$R^{16}$ is hydrogen, substituted or unsubstituted alkyl, substituted or unsubstituted alkenyl, or substituted or unsubstituted alkynyl, or substituted or unsubstituted acyl;
$R^7$ is a group of the formula:

[Chemical Formula 19]

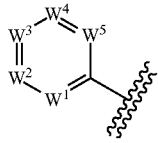

wherein
=$W^1$-$W^2$=$W^3$-$W^4$=$W^5$- is a group selected from the following (a) to (h):
(a): =C(H)—C($R^{10a}$)=C($R^{10b}$)—C($R^{10c}$)=C(H)—;
(b): =N—C($R^{10a}$)=C($R^{10b}$)—C($R^{10c}$)=C(H)—;
(c): =C(H)—N=C($R^{10b}$)—C($R^{10c}$)=C(H)—;
(d): =C(H)—C($R^{10a}$)=N—C($R^{10c}$)=C(H)—;
(e): =C(H)—C($R^{10a}$)=C($R^{10b}$)—N=C(H)—;
(f): =N—C($R^{10a}$)=C($R^{10b}$)—C($R^{10c}$)=N—;
(g): =C(H)—C($R^{10a}$)=N—C($R^{10c}$)=C(H)—; and
(h): =C(H)—N=C($R^{10b}$)—N=C(H)—;
$R^{10a}$, $R^{10b}$ and $R^{10c}$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic, heterocyclyloxy, substituted or unsubstituted aryloxy or substituted or unsubstituted heteroaryloxy; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, provided that groups of (a) to (h) have at least one substituent: wherein "groups of (a) to (h) have at least one substituent" means at least one of $R^{10a}$, $R^{10b}$ and $R^{10c}$ is not hydrogen in the groups of (a), (b) and (f), at least one of $R^{10b}$ and $R^{10c}$ is not hydrogen in the group of (c), at least one of $R^{10a}$ and $R^{10c}$ is not hydrogen in the groups of (d) and (g), at least one of $R^{10a}$ and $R^{10b}$ is not hydrogen in the group of (e), and $R^{10b}$ is not hydrogen in the group of (h);
$Q^1$ and $Q^2$ are each independently a carbon atom or a nitrogen atom;
when $Q^1$ is a carbon atom, -L- is —C$R^{9a}R^{9b}$—;
when $Q^1$ is a nitrogen atom, -L- is —C$R^{9c}R^{9d}$—;
$R^{9a}$, $R^{9b}$, $R^{9c}$ and $R^{9d}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy; and
$R^6$ is

[Chemical Formula 20]

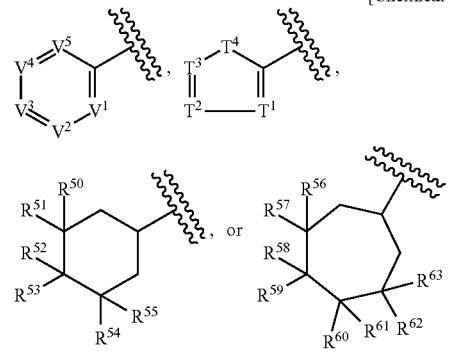

wherein =$V^1$-$V^2$=$V^3$-$V^4$=$V^5$- is a group selected from the following (i) to (p):
(i): =C(H)—C($R^A$)=C($R^B$)—C($R^C$)=C(H)—;
(j): =N—C($R^A$)=C($R^B$)—C($R^C$)=C(H)—;
(k): =C(H)—N=C($R^B$)—C($R^C$)=C(H)—;
(l): =C(H)—C($R^A$)=N—C($R^C$)=C(H)—;
(m): =C(H)—C($R^A$)=C($R^B$)—N=C(H)—;
(n): =N—C($R^A$)=C($R^B$)—C($R^C$)=N—;
(o): =C(H)—C($R^A$)=N—C($R^C$)=C(H)—; and
(p): =C(H)—N=C($R^B$)—N=C(H)—;
$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted tar unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring, provided that groups of (i) to (p) have at least one substituent wherein "provided that groups of (i) to (p) have at least one substituent" means at least one of $R^A$, $R^B$ and $R^C$ is not hydrogen in the groups of (i), (j) and (n), at least one of $R^B$ and $R^C$ is not hydrogen in the group of (k), at least one of $R^A$ and $R^C$ is not hydrogen in the groups of (l) and (o), at least one of $R^A$ and $R^B$ is not hydrogen in the group of (m), and $R^B$ is not hydrogen in the group of (p);

=$T^1$-$T^2$=$T^3$-$T^4$- is a group selected from the following (q) to (t):
(q): =C(H)—C($R^D$)=C($R^E$)—S—;
(r): =C(H)—C($R^D$)=C($R^E$)—O—;
(s): =N—C($R^D$)=C($R^E$)—S—; and
(t): =N—C($R^D$)=C($R^E$)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

$R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy;

$R^2$ is hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, provided that (i) a compound wherein

[Chemical Formula 21]

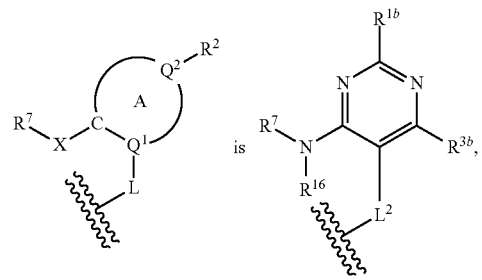

$R^{16}$ is hydrogen, and (α) $R^{1b}$ is amino substituted with substituted or unsubstituted phenyl, and $R^{3b}$ is methyl, or (β) $R^{1b}$ is methylthio, and $R^{3b}$ is chloro, (ii) a compound wherein

[Chemical Formula 22]

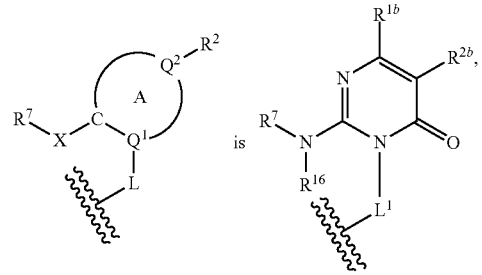

$R^{16}$ is hydrogen, and (α) $R^{1b}$ is unsubstituted alkyl, and $R^{2b}$ is substituted or unsubstituted arylmethyl or substituted or unsubstituted heteroarylmethyl, or (β) $R^{1b}$ is trifluoromethyl, and $R^{2b}$ is hydrogen, (iv) a compound wherein

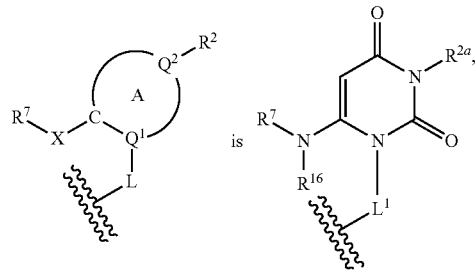

[Chemical Formula 23]

is $R^{16}$ is hydrogen, and
(α) $R^{2a}$ is hydrogen, and $R^7$ is phenyl substituted with n-octyl, or
(β) $R^{2a}$ is methyl, and $R^6$ is phenyl substituted with methylsulfonyl, and (v) a compound wherein
$R^7$ is phenyl substituted with —C(=O)CH(Me)CH$_2$C(=O)OMe, (vi) a compound wherein
ring A is a benzene ring, and $R^6$ is 2,6-di-tert-butyl-4-hydroxyphenyl, and (vii)

[Chemical Formula 24]

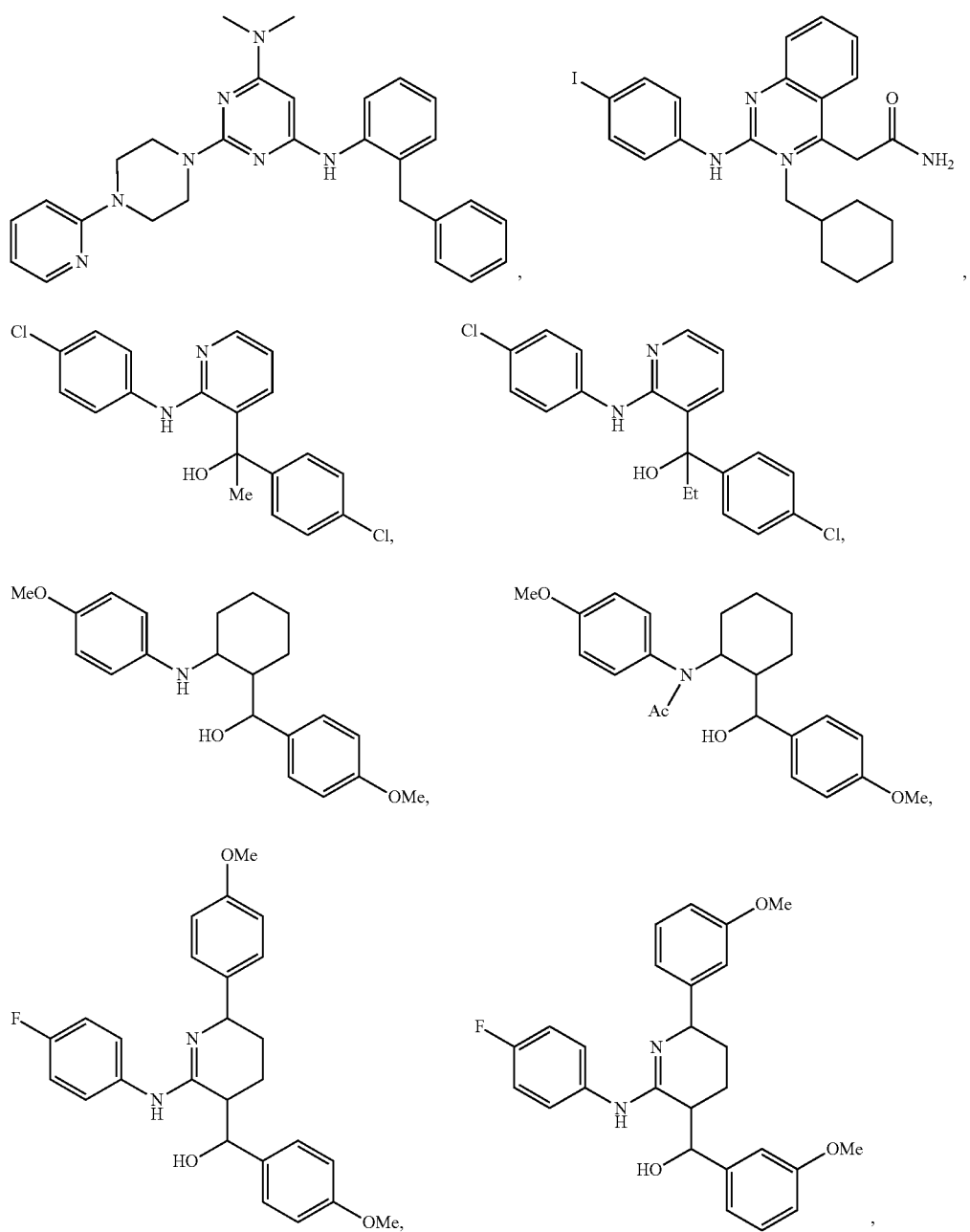

-continued
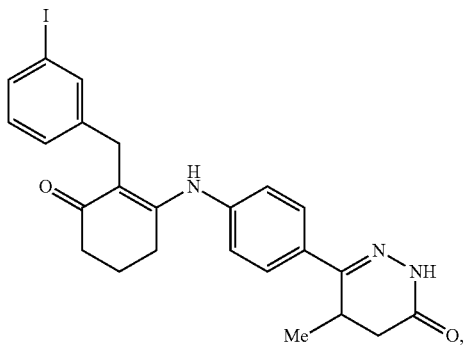
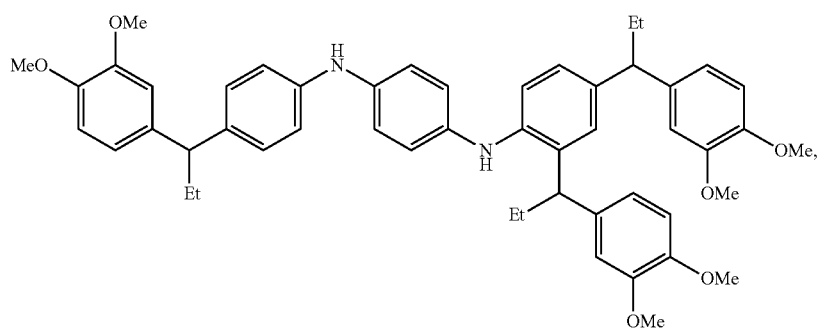
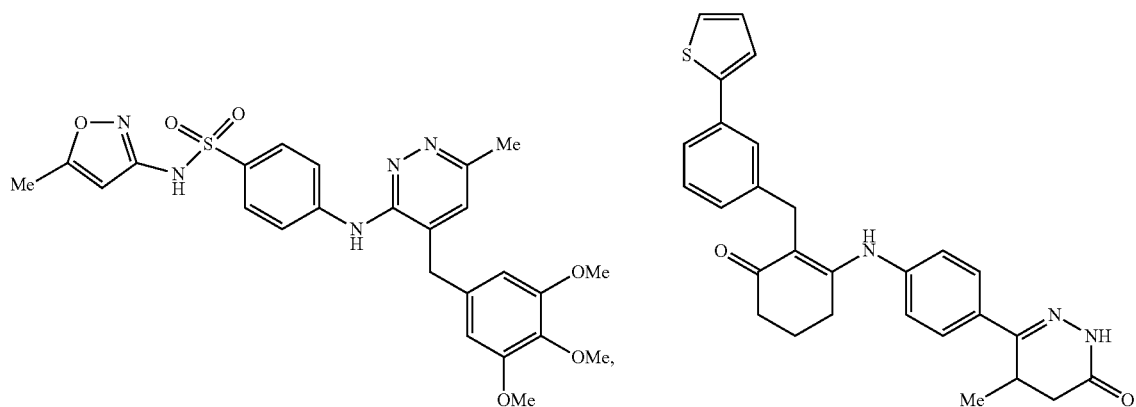
[Chemical Formula 25]
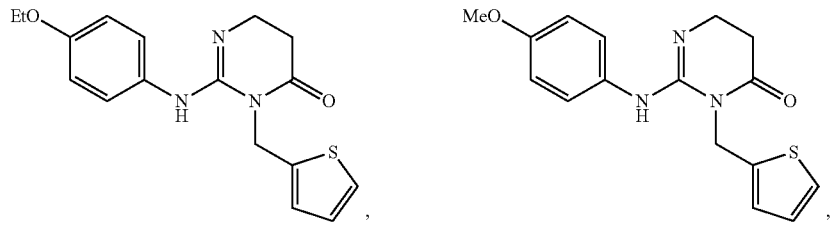
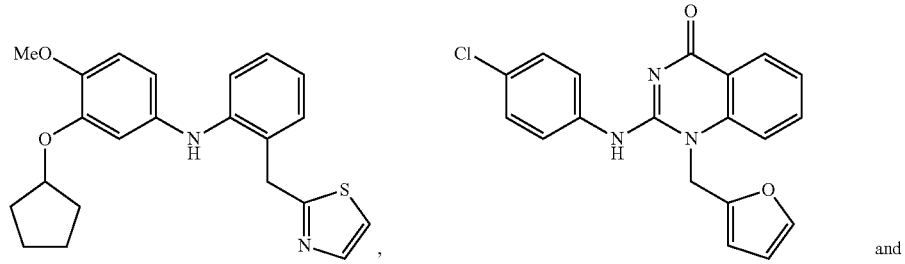
and

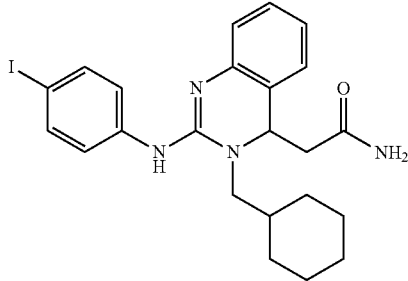
wherein Me is methyl, Et is ethyl, and Ac is acetyl, are excluded,
or its pharmaceutically acceptable salt or a solvate thereof.
(15α)
The compound according to the above (14A) (14α) wherein the compound is
[Chemical Formula 26]
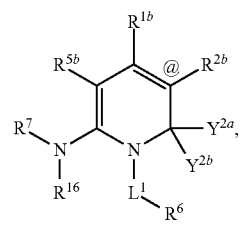 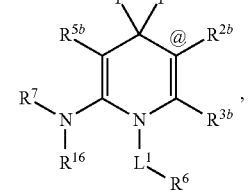
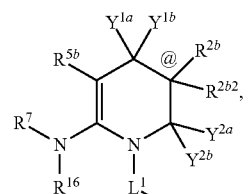 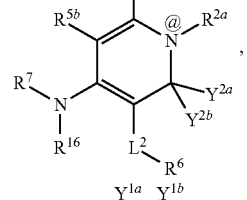
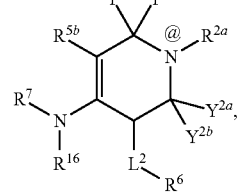 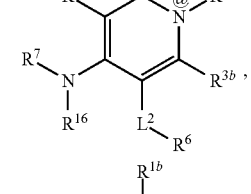
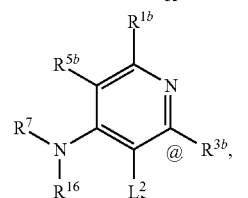 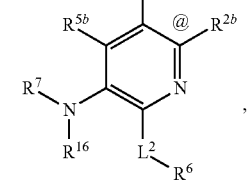
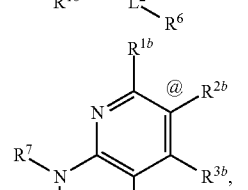 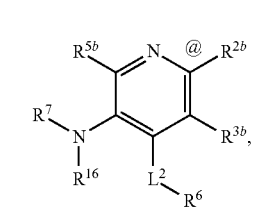
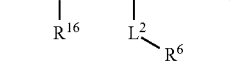
-continued
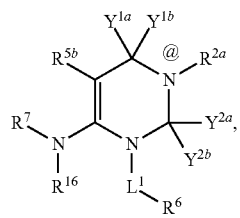 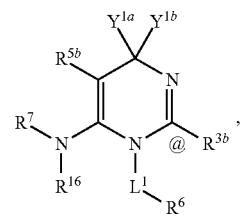
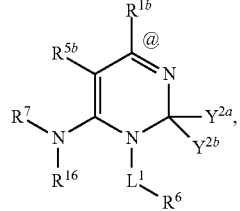 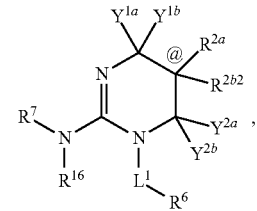
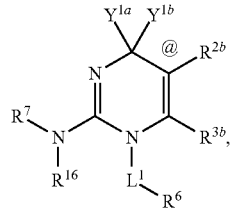 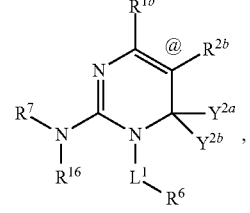
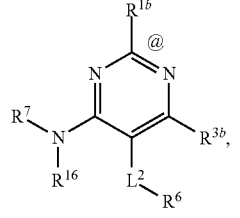 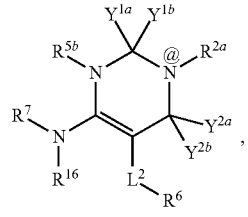
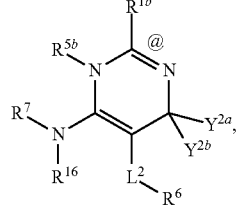 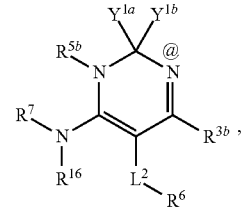
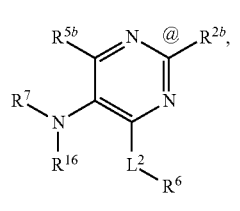 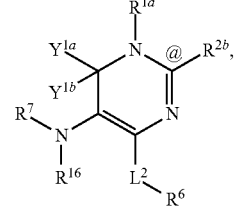

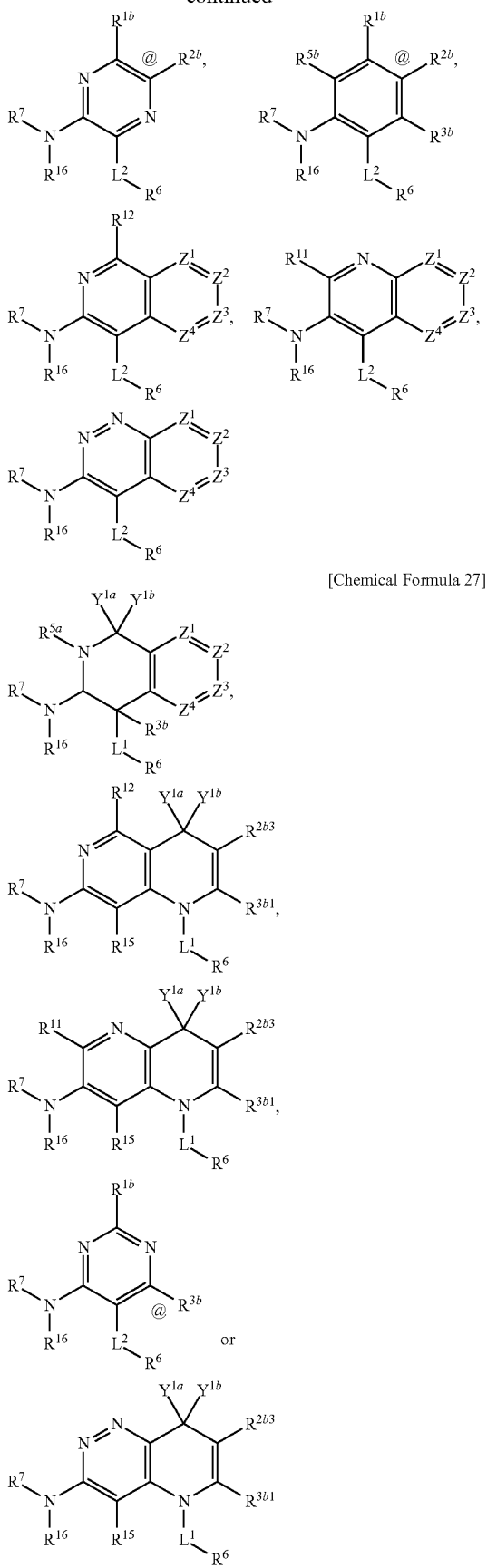

[Chemical Formula 27]

wherein $Y^{1a}, Y^{1b}, Y^{2a}, Y^{2b}, R^{1b}, R^{2b}, R^{2b2}, R^{3b}, R^{5b}, R^{11}, R^{12}$ and $R^{15}$ are each independently hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl or substituted or unsubstituted amino, or $Y^{1a}$ and $Y^{1b}$, and/or $Y^{2a}$ and $Y^{2b}$ are taken together to form oxo or thioxo;

$R^{2a}$ and $R^{5a}$ are each independently hydrogen, substituted or unsubstituted substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl or substituted or unsubstituted sulfamoyl;

-$L^1$- is —$CR^{9c}R^{9d}$—;

-$L^2$- is —$CR^{9a}R^{9b}$—;

-$Z^1=Z^2-Z^3=Z^4$- is a group selected from the following (u) to (y):

(u): —N=C($R^{2b3}$)—C($R^{3b1}$)=C($R^{4b}$)—;
(v): —C($R^{1b1}$)=N—C($R^{3b1}$)=C($R^{4b}$)—;
(w): —(R^{1b1})=C($R^{2b3}$)—N=C($R^{4b}$)—;
(x): —C($R^{1b1}$)=C($R^{2b3}$)—C($R^{3b1}$)=N—; and
(y): —C($R^{1b1}$)=C($R^{2b3}$)—C($R^{3b1}$)=C($R^{4b}$)—;

one of $R^{2b3}$ and $R^{3b1}$ is hydroxy, halogen, cyano, substituted or unsubstituted substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, and the other is hydrogen;

$R^{1b1}$ or $R^{4b}$ is each independently hydrogen, halogen, or substituted or unsubstituted alkyl;

$R^6$, $R^7$, $R^{16}$, $R^{9a}$, $R^{9b}$, $R^{9c}$ and $R^{9d}$ are as defined in the above (14α), or its pharmaceutically acceptable salt or a solvate thereof.

In the above formulas, when ring A is a monocyclic ring, the ring atom $Q^2$ in ring A is the atom with @ mark attached to $R^{1b}$, $R^{2a}$, $R^{2b}$, $R^{2b2}$, $R^{3b}$ etc., and when ring A is a fused ring, the ring atom $Q^2$ in ring A is the atom attached to one of $R^{2b3}$ and $R^{3b1}$, (16α)

The compound according to the above (14A) or (14α) wherein the compound is

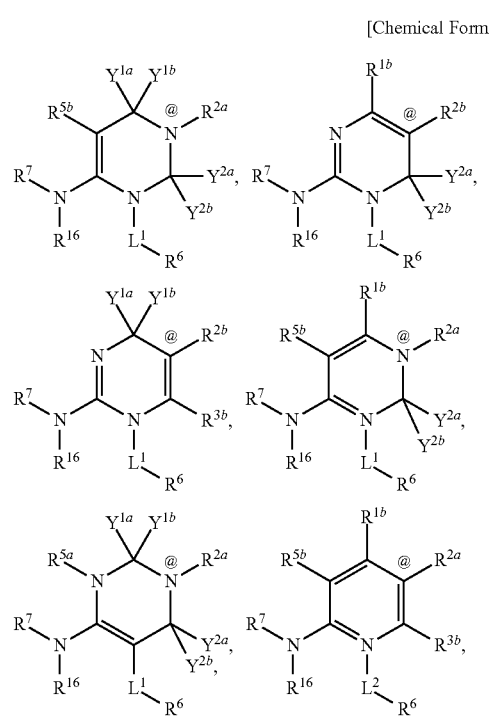

[Chemical Formula 28]

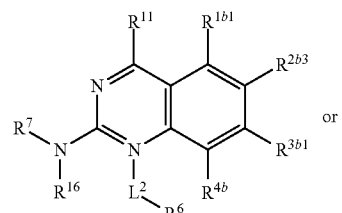

or

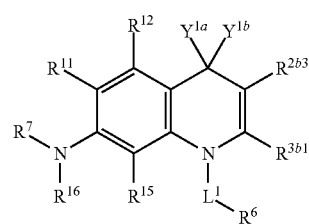

wherein $R^6$, $R^7$ and $R^{16}$ are as defined in the above (14α);

$L^1$, $L^2$, $Y^{1a}$, $Y^{1b}$, $Y^{2a}$, $Y^{2b}$, $R^{1b}$, $R^{2a}$, $R^{2b}$, $R^{2b3}$, $R^{3b}$, $R^{3b1}$, $R^{4b}$, $R^{5a}$, $R^{5b}$, $R^{11}$, $R^{12}$ and $R^{15}$ are as defined in the above (15α), or its pharmaceutically acceptable salt or a solvate thereof.

In the above formulas, when ring A is a monocyclic ring, the ring atom $Q^2$ in ring A is the atom with @ mark attached to $R^{2a}$ and $R^{2b}$, and when ring A is a fused ring, the ring atom $Q^2$ in ring A is the atom attached to one of $R^{2b3}$ and $R^{3b1}$.

(17α)

The compound according to the above (14A) or (14α) wherein the compound is

[Chemical Formula 29]

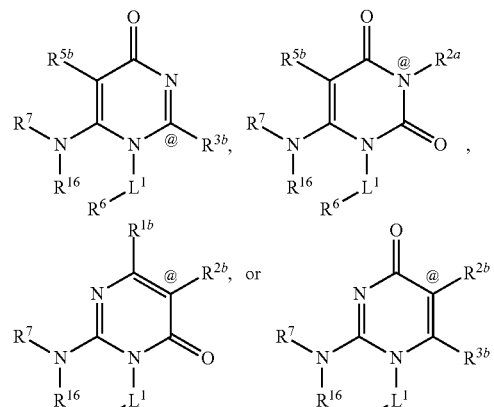

wherein $R^6$, $R^7$ and $R^{16}$ are as defined in the above (14α);

$L^1$, $R^{1b}$, $R^{2a}$, $R^{2b}$, $R^{3b}$ and $R^{5b}$ are as defined in the above (15α), or its pharmaceutically acceptable salt or a solvate thereof.

In the above formulas, the ring atom $Q^2$ in ring A is the atom with @ mark attached to $R^{2a}$, $R^{2b}$ and $R^{3b}$.

(17A)

The compound according to the above (14A) or (14α) wherein the compound is

[Chemical Formula 30]

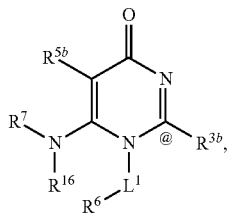

wherein $R^6$, $R^7$ and $R^{16}$ are as defined in the above (14α);
$L^1$, $R^{3b}$ and $R^{5b}$ are as defined in the above (15α),
or its pharmaceutically acceptable salt or a solvate thereof,
In the above formula, the ring atom $Q^2$ in ring A is the carbon atom with @ mark attached to $R^{3b}$.

(17B)

The compound according to the above (14A) or (14α) wherein the compound is

[Chemical Formula 31]

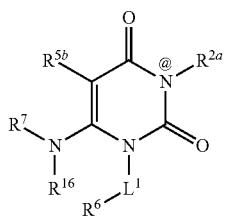

wherein $R^6$, $R^7$ and $R^{16}$ are as defined in the above (14α);
$L^1$, $R^{2a}$ and $R^{5b}$ are as defined in the above (15α),
or its pharmaceutically acceptable salt or a solvate thereof.
In the above formula, the ring atom $Q^2$ in ring A is the nitrogen atom with @ mark attached to $R^{2a}$.

(17C)

The compound according to the above (14A) or (14α) wherein the compound is

[Chemical Formula 32]

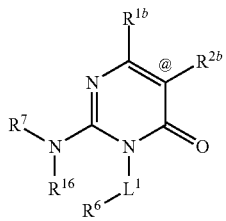

wherein $R^6$, $R^7$ and $R^{16}$ are as defined in the above (14α);
$L^1$, $R^{1b}$ and $R^{2b}$ are as defined in the above (15α),
or its pharmaceutically acceptable salt ore solvate thereof.
In the above formula, the ring atom $Q^2$ in ring A is the carbon atom with @ mark attached to $R^{2b}$.

(17D)

The compound according to the above (14A) or (14α) wherein the compound is

[Chemical Formula 33]

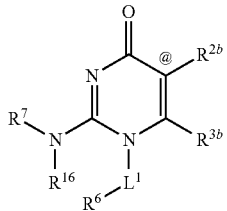

wherein $R^6$, $R^7$, and $R^{16}$ are as defined in the above (14α);
$L^1$, $R^{2b}$ and $R^{3b}$ are as defined in the above (15α),
or its pharmaceutically acceptable salt or a solvate thereof.
In the above formula, the ring atom $Q^2$ in ring A is the carbon atom with @ mark attached to $R^{2b}$.

(18α)

The compound according to any one of the above (14A), (14α) to (17α) and (17A) to (17D) wherein $R^{10a}$ and $R^{10c}$ are each independently hydrogen, halogen, or haloalkyl;
$R^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyloxy, provided that at least one of $R^{10a}$ and $R^{10c}$ is halogen or haloalkyl in the groups of (d) and (g); or
$R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring,
or its pharmaceutically acceptable salt or a solvate thereof.

(19α)

The compound according to any one of the above (14A), (14α) to (17α), (17A) to (17D) and (18α), wherein ring A or the ring corresponding to ring A is a ring optionally substituted with oxo or thioxo, or its pharmaceutically acceptable salt or a solvate thereof.

(20α)

The compound according to the above (15α) or (16α), wherein $Y^{1a}$ and $Y^{1b}$, and $Y^{2a}$ and $Y^{2b}$ are each independently taken together to form oxo, or its pharmaceutically acceptable salt or a solvate thereof.

(21α)

The compound according to any one of the above (14A), (14α) to (17α), (17A) to (17D) and (18α) to (20α), wherein $R^{16}$ is hydrogen, or its pharmaceutically acceptable salt or a solvate thereof.

(22α)

The compound according to any one of the above (14A), (14α) to (17α), (17A) to (17D) and (18α) to (21α), wherein $Q^2$ or the atom corresponding to $Q^2$ is a carbon atom; and
$R^2$, $R^{2b}$, or $R^{2b2}$ is
a group of the formula: $-NH-C(=O)-(CR^{8a}R^{8b})n-R^9$;
n is an integer of 0 to 4; $R^{8a}$ and $R^{8b}$ are each independently hydrogen, halogen, hydroxy, or substituted or unsubstituted alkyl; $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or a group of the formula: —$(CR^{8a}R^{8b})_m$-$R^9$;

m is an integer of 1 to 6; and $R^{8a}$, $R^{8b}$ and $R^9$ are as defined above.

(23α)

The compound according to any one of the above (14A), (14α) to (17α), (17A) to (17D) and (18α) to (21α), wherein $Q^2$ or the atom corresponding to $Q^2$ is a nitrogen atom; and $R^2$ or $R^{2a}$ is C1-C6 alkyl or a group of the formula: —$(CR^{8a}R^{8b})_m$-$R^9$; and in and $R^9$ are as defined in the above (22α), or its pharmaceutically acceptable salt or a solvate thereof.

(24α)

A compound of the formula (II):

[Chemical Formula 34]

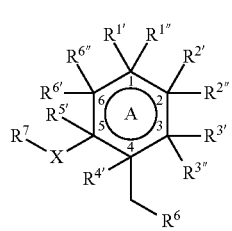

(II)

wherein
ring A is a ring of the formula:

[Chemical Formula 35]

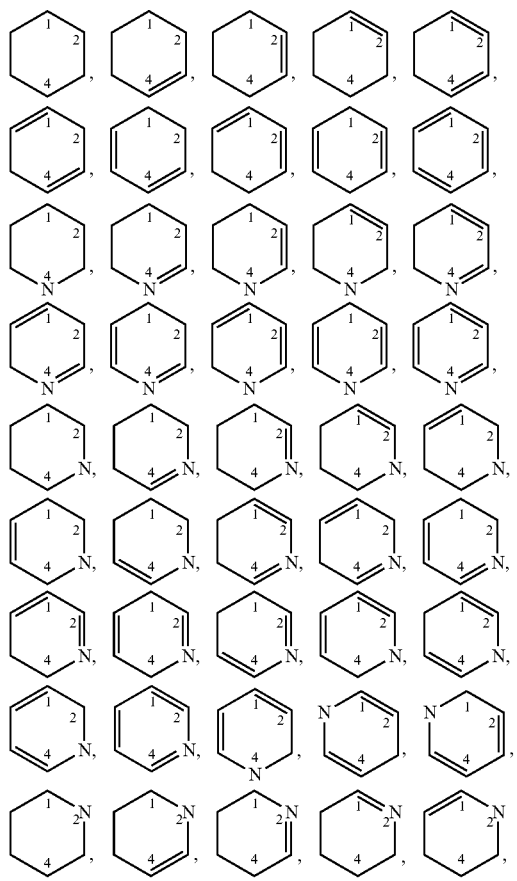

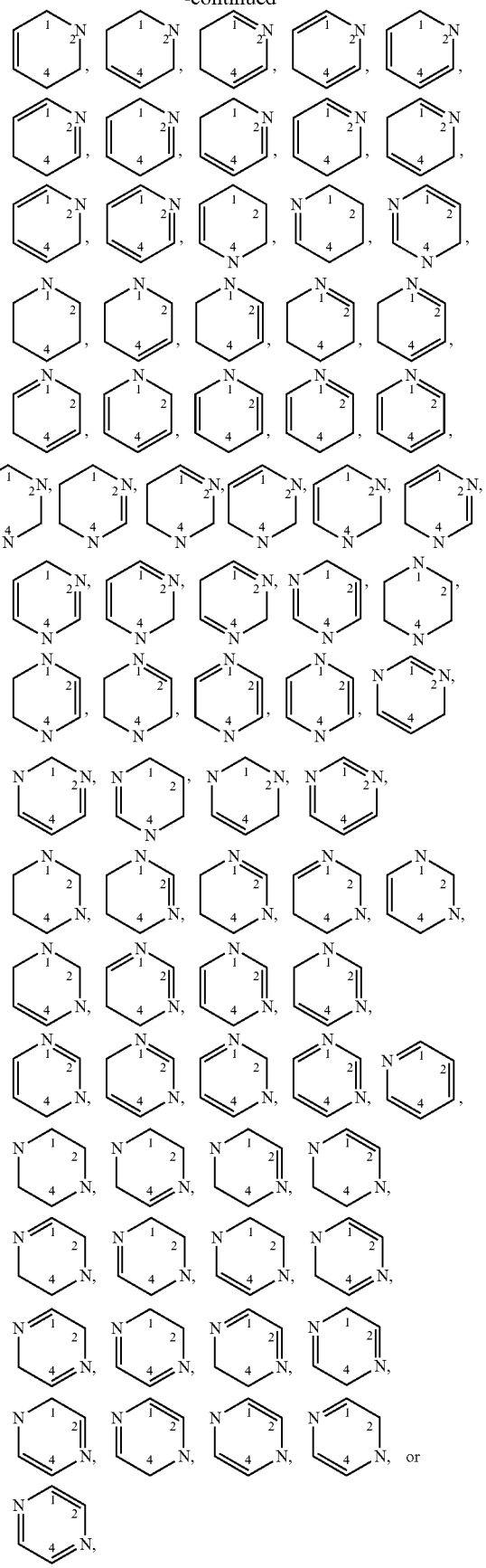

wherein the numbers in the ring correspond to the numbers in the ring A of the above formula (II);

$R^{1'}$, $R^{1''}$, $R^{3'}$, $R^{3''}$, $R^{4'}$, $R^{5'}$, $R^{6'}$ or $R^{6''}$ is each independently hydrogen or halogen; or $R^{1'}$ and $R^{1''}$, $R^{3'}$ and $R^{3''}$ and/or $R^{6'}$ and $R^{6''}$ are taken together to form oxo;

$R^{2''}$ is hydrogen;

when a ring atom which hinds to $R^{2'}$ is a carbon atom, then $R^{2''}$ is a group of the formula: —NH—C(=O)—$(CR^{8a}R^{8b})$n-$R^9$;

n is an integer of 0 to 4; $R^{8a}$ and $R^{8b}$ are each independently hydrogen, halogen, hydroxy, or substituted or unsubstituted alkyl; and $R^9$ is hydroxy, carboxy, suite, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or a group of the formula: —$(CR^{8a}R^{8b})$m-$R^9$;

m is an integer of 1 to 6; and $R^{8a}$, $R^{8b}$ and $R^9$ are as defined above;

when a ring atom attached to $R^{2'}$ is a nitrogen atom, then $R^{2'}$ is C1-C6 alkyl or a group of the formula; —$(CR^{8a}R^{8b})$m-$R^9$; m is an integer of 1 to 6; and $R^{8a}$, $R^{8b}$ and $R^9$ are as defined above;

$R^{4'}$ is hydrogen;

$R^6$ is a group of the formula:

[Chemical Formula 36]

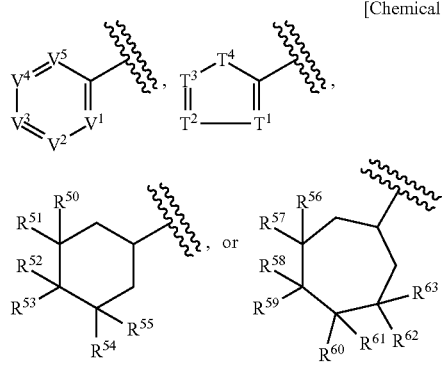

wherein =$V^1$-$V^2$=$V^3$-$V^4$=$V^5$- is a group selected from the following (i) to (p):

(i): =C(H)—C($R^A$)=C($R^B$)—C($R^C$)=C(H)—;
(j): =N—C($R^A$)=C($R^B$)—C($R^C$)=C(H)—;
(k): =C(H)—N=C($R^B$)—C($R^C$)=C(H)—;
(l): =C(H)—C($R^A$)=N—C($R^C$)=C(H)—;
(m): =C(H)—C($R^A$)=C($R^B$)—N=C(H)—;
(n): =N—C($R^A$)=C($R^B$)—C($R^C$)=N—;
(o): =C(H)—C($R^A$)=N—C($R^C$)=C(H)—; and
(p): =C(H)—N=C($R^B$)—N=C(H)—;

$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfa enoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring, provided that groups of (i) to (p) have at least one substituent; wherein "groups of (i) to (p) have at least one substituent" means at least one of $R^A$, $R^B$ and $R^C$ is not hydrogen in the groups of (i), (j) and (n), at least one of $R^B$ and $R^C$ is not hydrogen in the group of (k), at least one of $R^A$ and $R^C$ is not hydrogen in the groups of (l) and (o), at least one of $R^A$ and $R^C$ is not hydrogen in the group of (m), and $R^B$ is not hydrogen in the group of (p);

=$T^1$-$T^2$=$T^3$-$T^4$- is a group selected from the following (q) to (t):

(q): =C(H)—C($R^D$)=C($R^E$)—S—;
(r): =C(H)—C($R^D$)=C($R^E$)—O—;
(s): =N—C($R^D$)=C($R^E$)—S—; and
(t): =N—C($R^D$)=C($R^E$)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring; and $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy;

—X— is —NH— or —$CH_2$—; and $R^7$ is a group of the formula:

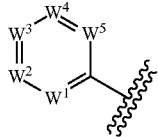

[Chemical Formula 37]

wherein $=W^1-W^2=W^3-W^4=W^5-$ is
(a): $=C(H)-C(R^{10a})=C(R^{10b})-C(R^{10c})=C(H)-$;
(b): $=N-C(R^{10a})=C(R^{10b})-C(R^{10c})=C(H)-$;
(c): $=C(H)-N=C(R^{10b})-C(R^{10c})=C(H)-$;
(d): $=C(H)-C(R^{10a})=N-C(R^{10c})=C(H)-$;
(e): $=C(H)-C(R^{10a})=C(R^{10b})-N=C(H)-$;
(f): $=N-C(R^{10a})=C(R^{10b})-C(R^{10c})=N-$;
(g): $=C(H)-C(R^{10a})=N-C(R^{10c})=C(H)-$; and
(h): $=C(H)-N=C(R^{10b})-N=C(H)-$;
$R^{10a}$ and $R^{10c}$ are each independently hydrogen, halogen, or haloalkyl; and
$R^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyloxy, provided that at least one of $R^{10a}$ and $R^{10c}$ is halogen or haloalkyl in groups of (d) and (g); or
$R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring; provided that
(i) when a ring atom attached to $R^{1''}$, $R^{2''}$, $R^{3''}$, $R^{4'}$, $R^{5'}$, or $R^{6''}$ is a nitrogen atom, then $R^{1''}$, $R^{2''}$, $R^{3''}$, $R^{4'}$, $R^{5'}$, or $R^{6''}$ is absent, respectively;
(ii) when a ring atom attached to $R^{1'}$ and $R^{1''}$ is a nitrogen atom, and a bond between the 1-position and the 6-position or a bond between the 1-position and the 2-position is a double bond, then $R^{1'}$ and $R^{1''}$ are absent;
when a ring atom attached to $R^{2'}$ and $R^{2''}$ is a nitrogen atom, and a bond between the 1-position and the 2-position or a bond between the 2-position and the 3-position is a double bond, then $R^{2'}$ and $R^{2''}$ are absent;
when a ring atom attached to $R^{3'}$ and $R^{3''}$ is a nitrogen atom, and a bond between the 2-position and the 3-position or a bond between the 3-position and the 4-position is a double bond, then $R^{3'}$ and $R^{3''}$ are absent; when a ring atom attached to $R^{6'}$ and $R^{6''}$ is a nitrogen atom, and a bond between the 5-position and the 6-position or a bond between the 6-position and the 1-position is a double bond, then $R^{6'}$ and $R^{6''}$ are absent; and
(iii) when a ring atom attached to $R^{1'}$ and $R^{1''}$ is a carbon atom, and a bond between the 1-position and the 6-position or a bond between the 1-position and the 2-position is a double bond, then $R^{1''}$ is absent;
when a ring atom attached to $R^{2'}$ and $R^{2''}$ is a carbon atom, and a bond between the 1-position and the 2-position or a bond between the 2-position and the 3-position is a double bond, then $R^{2'}$ is absent;
when a ring atom attached to $R^{3'}$ and $R^{3''}$ is a carbon atom, and a bond between the 2-position and the 3-position or a bond between the 3-position and the 4-position is a double bond, then $R^{3'}$ is absent;
when a ring atom attached to $R^{4'}$ is a carbon atom, and a bond between the 3-position and the 4-position or a bond between the 4-position and the 5-position is a double bond, then $R^{4'}$ is absent;

when a ring atom attached to $R^{5'}$ is a carbon atom, and a bond between the 4-position and the 5-position or a bond between the 5-position and the 6-position is a double bond, then $R^{5'}$ is absent;
when a ring atom attached to $R^{6'}$ and $R^{6''}$ is a carbon atom, and a bond between the 5-position and the 6-position or a bond between the 6-position and the 1-position is a double bond, then $R^{6''}$ is absent,
or its pharmaceutically acceptable salt or a solvate thereof.

(25α)

The compound according to above (24α), wherein the compound is

[Chemical Formula 38]

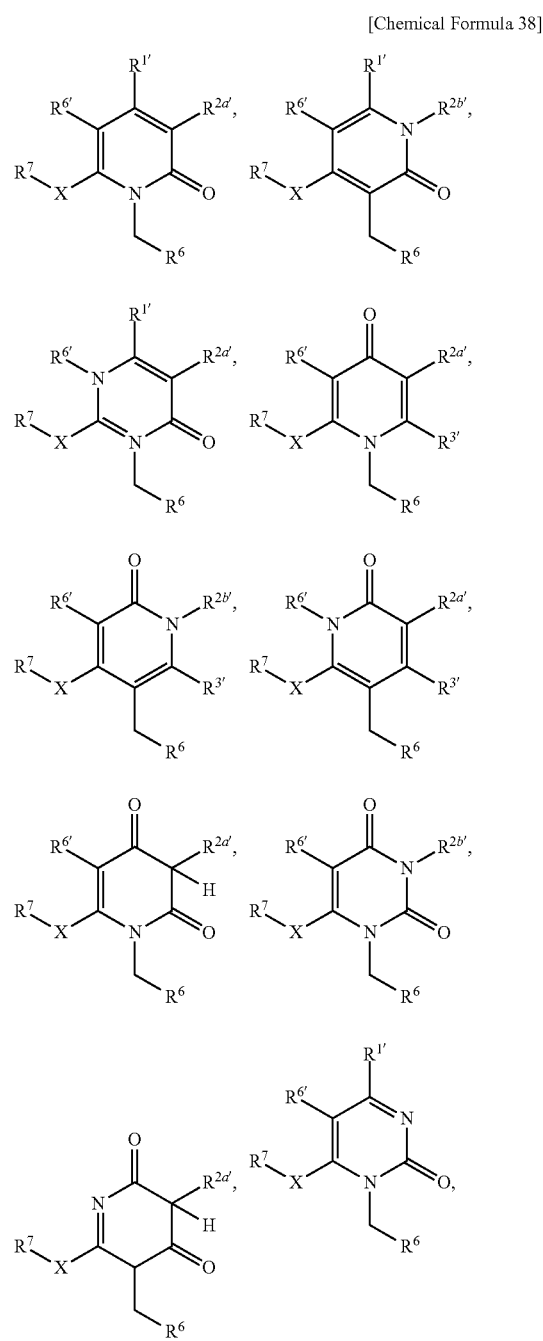

-continued

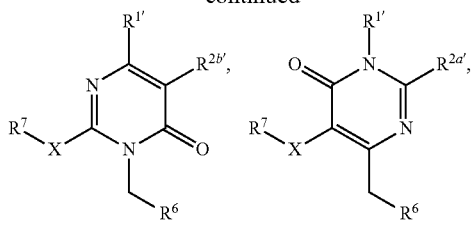
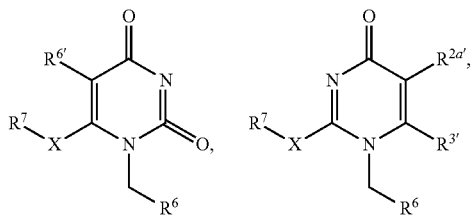
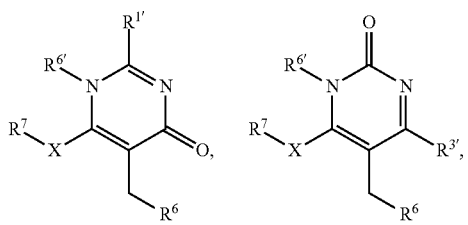
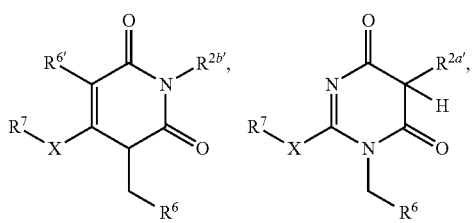
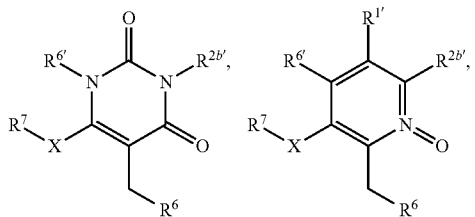
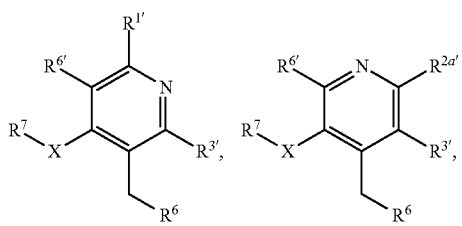
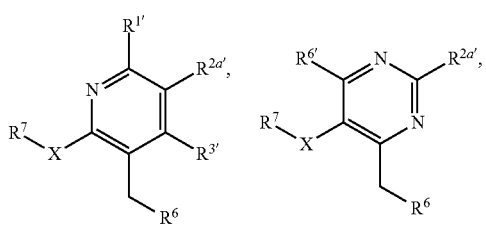

-continued

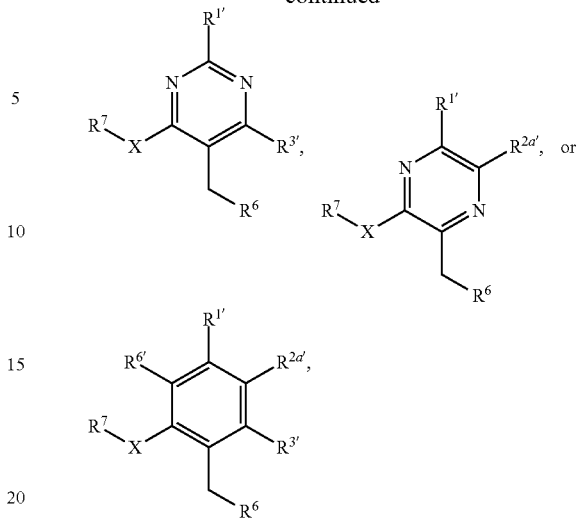

wherein
$R^6$ is as defined in the above (24α);
$R^{1'}$, $R^{3'}$ and $R^{6'}$ are each independently hydrogen or halogen;
$R^{2a'}$ is a group of the formula: $-NH-C(=O)-(CR^{8a}R^{8b})_n-R^9$;
n is an integer of 0 to 4; $R^{8a}$ and $R^{8b}$ are each independently hydrogen, halogen, hydroxy, or substituted or unsubstituted alkyl; $R^9$ is hydroxy, carboxy, sulk, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl; or
a group of the formula: $-(CR^{8a}R^{8b})_m-R^9$;
m is an integer of 1 to 6; and $R^{8a}$, $R^{8b}$ and $R^9$ are as defined above;
$R^{2b'}$ is C1-C6 alkyl or a group of the formula: $-(CR^{8a}R^{8b})_m-R^9$; m is an integer of 1 to 6; and $R^{8a}$, $R^{8b}$ and $R^9$ are as defined above;
—X— is —NH— or —CH$_2$—; and
$R^7$ is a group of the formula:

[Chemical Formula 39]

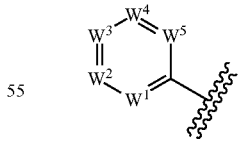

wherein $=W^1-W^2=W^3-W^4=W^5-$ is
(a): $=C(H)-C(R^{10a})=C(R^{10b})-C(R^{10c})=C(H)-$;
(b): $=N-C(R^{10a})=C(R^{10b})-C(R^{10c})=C(H)-$;
(c): $=C(H)-N=C(R^{10b})-C(R^{10c})=C(H)-$;
(d): $=C(H)-C(R^{10a})=N-C(R^{10c})=C(H)-$;
(e): $=C(H)-C(R^{10a})=C(R^{10b})-N=C(H)-$;
(f): $=N-C(R^{10a})=C(R^{10b})-C(R^{10c})=N-$;
(g): $=C(H)-C(R^{10a})=N-C(R^{10c})=C(H)-$; and
(h): $=C(H)-N=C(R^{10b})-N=C(H)-$;

$R^{10a}$ and $R^{10c}$ are each independently hydrogen, halogen, or haloalkyl; and $R^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyloxy, or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, provided that at least one of $R^{10a}$ and $R^{10c}$ is halogen or haloalkyl in groups of (d) and (g), or its pharmaceutically acceptable salt or a solvate thereof.

(26α) A compound of the formula (III):

[Chemical Formula 40]

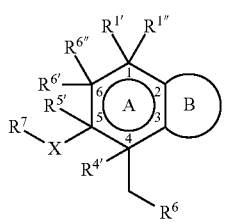

(III)

wherein a ring of the formula:

[Chemical Formula 41]

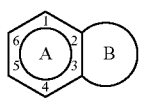

is a ring selected from the following rings wherein the numbers out of the ring correspond to the numbers in the ring A of the formula (III):

[Chemical Formula 42]

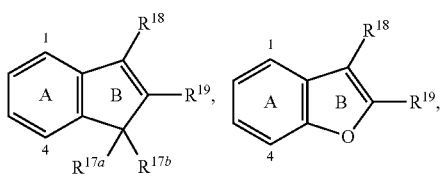

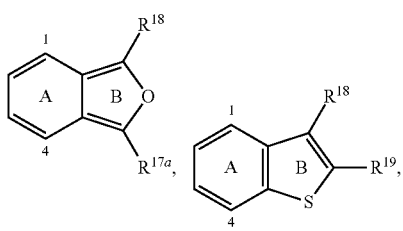

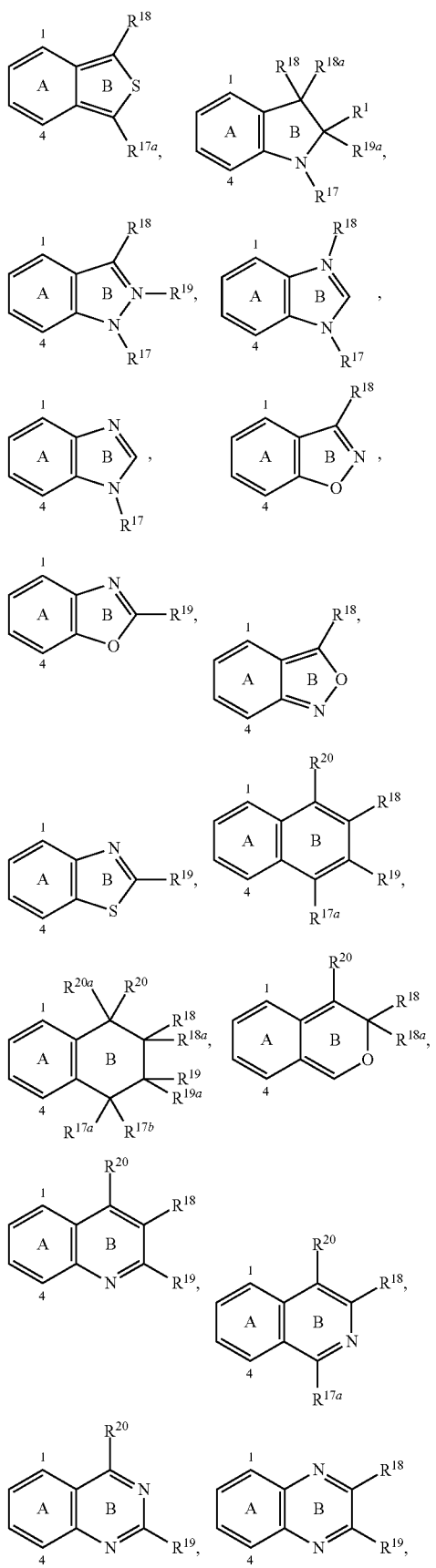

-continued

[Chemical structures shown]

wherein $R^{17a}$, $R^{17b}$, $R^{18a}$, $R^{19a}$ and $R^{20a}$ are each independently hydrogen, halogen, substituted or unsubstituted alkyl; or $R^{17a}$ and $R^{17b}$, $R^{18}$ and $R^{18a}$, $R^{19}$ and $R^{19a}$, or/and $R^{20}$ and $R^{20a}$ are taken together to form oxo or thioxo;

$R^{17}$ is hydrogen, halogen, substituted or unsubstituted acyl or substituted or unsubstituted alkyl;

$R^{18}$, $R^{19}$ and $R^{20}$ are each independently hydrogen, a group of the formula: —NH—C(=O)—$(CR^{8a}R^{8b})$n-$R^9$;

n is an integer of 0 to 4; $R^{8a}$ and $R^{8b}$ are each independently hydrogen, halogen, hydroxy, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or
a group of the formula: —$(CR^{8a}R^{8b})$m-$R^9$;
m is an integer of 1 to 6; and $R^{8a}$, $R^{8b}$ and $R^9$ are as defined above;

$R^{1'}$, $R^{1''}$, $R^{5'}$, $R^{6'}$ and $R^{6''}$ are each independently hydrogen or halogen; or $R^{1'}$ and $R^{1''}$ are taken together to form oxo;

$R^{4'}$ is hydrogen;

$R^6$ is a group of the formula:

[Chemical Formula 36]

[Chemical structures shown]

wherein =$V^1$-$V^2$=$V^3$-$V^4$=$V^5$- is a group selected from the following (i) to (p):

(i): =C(H)—C($R^A$)=C($R^B$)—C($R^C$)=C(H)—;
(j): =N—C($R^A$)=C($R^B$)—C($R^C$)=C(H)—;
(k): =C(H)—N=C($R^B$)—C($R^C$)=C(H)—;
(l): =C(H)—C($R^A$)=N—C($R^C$)=C(H)—;
(m): =C(H)—C($R^A$)=C($R^B$)—N=C(H)—;
(n): =N—C($R^A$)=C($R^B$)—C($R^C$)=N—;
(o): =C(H)—C($R^A$)=N—C($R^C$)=C(H)—; and
(p): =C(H)—N=C($R^B$)—N=C(H)—;

$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; oar $R^A$ and $R^B$, oar $R^B$ and $R^C$ together with ring atoms to which they are attached form a non-aromatic carbocyclic ring, a non-aromatic heterocyclic ring, an aromatic carbocyclic ring, or an aromatic heterocyclic ring, provided that groups of (i) to (p) have at least one substituent, wherein "groups of (i) to (p) have at least one substituent" means at least one of $R^A$, $R^B$ and $R^C$ is not hydrogen in the groups of (i), (j) and (n), at least one of $R^B$ and $R^C$ is not hydrogen in the group of (k), at least one of $R^A$ and $R^C$ is not hydrogen in the groups of (l) and (o), at least one of $R^A$ and $R^B$ is not hydrogen in the group of (m), $R^B$ is not hydrogen in the group of (p);

=$T^1$-$T^2$=$T^3$-$T^4$- is a group selected from the following (q) to (t):

(q): =C(H)—C($R^D$)=C($R^E$)—S—;
(r): =C(H)—C($R^D$)=C($R^E$)—O—;

(s): =N—C(R$^D$)=C(R$^E$)—S—; and
(t): =N—C(R$^D$)=C(R$^E$)—O—;
R$^D$ and R$^E$ are each independently hydrogen, halogen, hydroxy, cyano, nitro, substituted or unsubstituted alkyl, substituted or unsubstituted alkenyl, substituted or unsubstituted alkenyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or R$^A$ and R$^B$, or R$^B$ and R$^C$ together with ring atoms to which they are attached form a non-aromatic carbocyclic ring, a non-aromatic heterocyclic ring, an aromatic carbocyclic ring, or an aromatic heterocyclic ring;

R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, and R$^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy;

—X— is —NH— or —CH$_2$—; and
R$^7$ is a group of the formula:

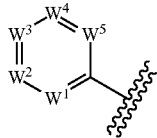

[Chemical Formula 44]

wherein =W$^1$-W$^2$=W$^3$-W$^4$=W$^5$- is
(a): =C(H)—C(R$^{10a}$)=C(R$^{10b}$)—C(R$^{10c}$)=C(H)—;
(b): =N—C(R$^{10a}$)=C(R$^{10b}$)—C(R$^{10c}$)=C(H)—;
(c): =C(H)—N=C(R$^{10b}$)—C(R$^{10c}$)=C(H)—;
(d): =C(H)—C(R$^{10a}$)=N—C(R$^{10c}$)=C(H)—;
(e): =C(H)—C(R$^{10a}$)=C(R$^{10b}$)—N=C(H)—;
(f): =N—C(R$^{10a}$)=C(R$^{10b}$)—C(R$^{10c}$)=N—;
(g): =C(H)—C(R$^{10a}$)=N—C(R$^{10c}$)=C(H)—; and
(h): =C(H)—N=C(R$^{10b}$)—N=C(H)—;
R$^{10a}$ and R$^{10c}$ are each independently hydrogen, halogen, or haloalkyl; and
R$^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyloxy, provided that at least one of R$^{10a}$ and R$^{10c}$ is halogen or haloalkyl in groups of (d) and (g); or
R$^{10a}$ and R$^{10b}$, or R$^{10b}$ and R$^{10c}$ together with ring atoms to which they are attached form a non-aromatic carbocyclic ring, a non-aromatic heterocyclic ring, an aromatic carbocyclic ring, or an aromatic heterocyclic ring; provided that
(i) when a ring atom attached to R$^{1''}$, R$^{4'}$, R$^{5'}$, or R$^{6''}$ is a nitrogen atom, then R$^{1''}$, R$^{4'}$, R$^{5'}$, or R$^{6''}$ is absent, respectively;
(ii) when a ring atom attached to R$^{1'}$ and R$^{1''}$ is a nitrogen atom, and a bond between the 1-position and the 6-position or a bond between the 1-position and the 2-position is a double bond, then R$^{1'}$ and R$^{1''}$ are absent;
when a ring atom attached to R$^{6'}$ and R$^{6''}$ is a nitrogen atom, and a bond between the 5-position and the 6-position or a bond between the 6-position and the 1-position is a double bond, then R$^{6'}$ and R$^{6''}$ are absent; and
(iii) when a ring atom attached to R$^{1'}$ and R$^{1''}$ is a carbon atom, and a bond between the 1-position and the 6-position or a bond between the 1-position and the 2-position is a double bond, then R$^{1''}$ is absent;
when a ring atom attached to R$^{4'}$ is a carbon atom, and a bond between the 3-position and the 4-position or a bond between the 4-position and the 5-position is a double bond, then R$^{4'}$ is absent;
when a ring atom attached to R$^{5'}$ is a carbon atom, and a bond between the 4-position and the 5-position or a bond between the 5-position and the 6-position is a double bond, then R$^{5'}$ is absent;
when a ring atom attached to R$^{6'}$ and R$^{6''}$ is a carbon atom, and a bond between the 5-position and the 6-position or a bond between the 6-position and the 1-position is a double bond, then R$^{6'}$ is absent,
or its pharmaceutically acceptable salt or a solvate thereof.

(27α)
A compound of the formula:

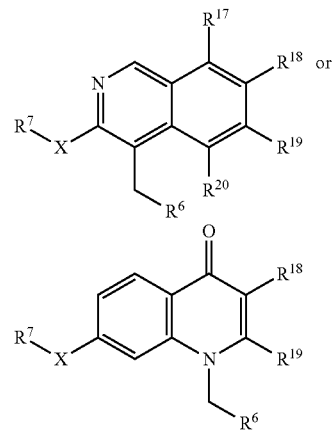

[Chemical Formula 45]

wherein
R$^{17}$, R$^{19}$ and R$^{20}$ are each independently hydrogen or halogen;
R$^{18}$ is hydrogen,
a group of the formula: —NH—C(=O)—(CR$^{8a}$R$^{8b}$)n-R$^9$;
n is an integer of 0 to 4; R$^{8a}$ and R$^{8b}$ are each independently hydrogen, halogen, hydroxy, or substituted or unsubstituted alkyl; and R$^9$ is hydroxy, carboxy, sulfo, cyano, a substituted or unsubstituted nonaromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or a group of the formula: —(CR$^{8a}$R$^{8b}$)m-R$^9$;

m is an integer of 1 to 6; and R$^{8a}$, R$^{8b}$ and R$^9$ are as defined above;

R$^6$ is a group of the formula:

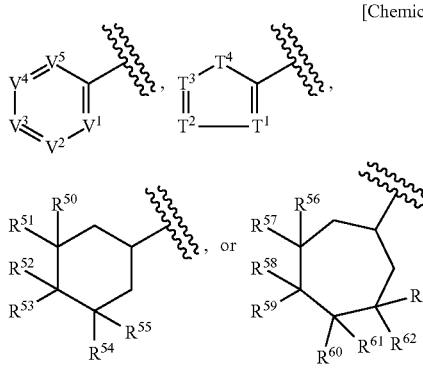
[Chemical Formula 46]

wherein =V$^1$-V$^2$=V$^3$-V$^4$=V$^5$- is a group selected from the following (i) to (p):
(i): =C(H)—C(R$^A$)=C(R$^B$)—C(R$^C$)=C(H)—;
(j): =N—C(R$^A$)=C(R$^B$)—C(R$^C$)=C(H)—;
(k): =C(H)—N=C(R$^B$)—C(R$^C$)=C(H)—;
(l): =C(H)—C(R$^A$)=N—C(R$^C$)=C(H)—;
(m): =C(H)—C(R$^A$)=C(R$^B$)—N=C(H)—;
(n): =N—C(R$^A$)=C(R$^B$)—C(R$^C$)=N—;
(o): =C(H)—C(R$^A$)=N—C(R$^C$)=C(H)—; and
(p): =C(H)—N=C(R$^B$)—N=C(H)—;

R$^A$, R$^B$ and R$^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; R$^A$ and R$^B$, or R$^B$ and R$^C$ together with ring atoms to which they are attached form a non-aromatic carbocyclic ring, a non-aromatic heterocyclic ring, an aromatic carbocyclic ring, or an aromatic heterocyclic ring; provided that groups of (i) to (p) have at least one substituent; wherein "groups of (i) to (p) have at least one substituent" means at least one of R$^A$, R$^B$ and R$^C$ is not hydrogen in the groups of (i), (j) and (n), at least one of R$^B$ and R$^C$ is not hydrogen in the group of (k), at least one of R$^A$ and R$^C$ is not hydrogen in the groups of (l) and (o), at least one of R$^A$ and R$^B$ is not, hydrogen in the group of (m), and R$^B$ is not hydrogen in the group of (p);

=T$^1$-T$^2$=T$^3$-T$^4$- is a group selected from the following (q) to (t):
(q): =C(H)—C(R$^D$)=C(R$^E$)—S—;
(r): =C(H)—C(R$^D$)=C(R$^E$)—O—;
(s): =N—C(R$^D$)=C(R$^E$)—S—; and
(t): =N—C(R$^D$)=C(R$^E$)—O—;

R$^D$ and R$^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or R$^A$ and R$^B$, R$^B$ and R$^C$ together with ring atoms to which they are attached form a non-aromatic carbocyclic ring, a non-aromatic heterocyclic ring, an aromatic carbocyclic ring, or an aromatic heterocyclic ring;

R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, and R$^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkenyloxy;

—X— is —NH— or —CH$_2$—; and

R$^7$ is a group of the formula:

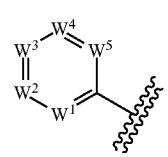
[Chemical Formula 47]

wherein =W$^1$-W$^2$=W$^3$-W$^4$=W$^5$- is
(a): =C(H)—C(R$^{10a}$)=C(R$^{10b}$)—C(R$^{10c}$)=C(H)—;
(b): =N—C(R$^{10a}$)=C(R$^{10b}$)—C(R$^{10c}$)=C(H)—;
(c): =C(H)—N=C(R$^{10b}$)—C(R$^{10c}$)=C(H)—;
(d): =C(H)—C(R$^{10a}$)=N—C(R$^{10c}$)=C(H)—;
(e): =C(H)—C(R$^{10a}$)=C(R$^{10b}$)—N=C(H)—;
(f): =N—C(R$^{10a}$)=C(R$^{10b}$)—C(R$^{10c}$)=N—;
(g): =C(H)—C(R$^{10a}$)=N—C(R$^{10c}$)=C(H)—; and
(h): =C(H)—N=C(R$^{10b}$)—N=C(H)—;

R$^{10a}$ and R$^{10c}$ are each independently hydrogen, halogen, or haloalkyl; and R$^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyloxy, provided that at least one of $R^{10a}$ and $R^{10c}$ is halogen or haloalkyl in groups of (d) and (g); or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic, ring, or an aromatic heterocyclic ring, or its pharmaceutically acceptable salt or a solvate thereof.

(28α)

The compound according to any one of the above (24α) to (27α), wherein n is 1 to 3, and $R^9$ is hydroxy, carboxy, cyano, substituted or unsubstituted alkyloxy, substituted or unsubstituted alkyloxycarbonyl, substituted or unsubstituted carbamoyl, substituted or unsubstituted sulfamoyl, or substituted or unsubstituted amino, or its pharmaceutically acceptable salt or a solvate thereof (29α)

The compound according to any one of the above (26α) to (28α), wherein $R^{18}$ is a group of the formula: —NH—C(=O)—$(CR^{8a}R^{8b})$n-$R^9$; n is an integer of 0 to 4; $R^{8a}$ and $R^{8b}$ are each independently hydrogen, halogen, hydroxy, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or its pharmaceutically acceptable salt or a solvate thereof.

(30α)

The compound according to any one of the above (14α) to (17α), (17A) to (17D) and (18α) to (29α), wherein $R^A$, $R^B$, $R^C$, $R^D$, $R^E$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, alkyl, or alkyloxy, or its pharmaceutically acceptable salt or a solvate thereof.

(31α)

The compound according to the above (30α), wherein $R^6$ is phenyl, thienyl, cyclohexyl, or cycloheptyl; and $R^A$, $R^B$, $R^C$, $R^D$, $R^E$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, alkyl, or alkyloxy, or its pharmaceutically acceptable salt or a solvate thereof.

(32α)

The compound according to any one of the above (24α) to (31α), wherein —X— is —NH—, or its pharmaceutically acceptable salt or a solvate thereof.

(32A)

The compound according to any one of the above (14α) to (17α), (17A) to (17D), (18α) to (29α) and (32α), wherein $R^6$ is a group of the formula:

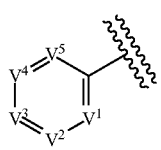

[Chemical Formula 48]

wherein =$V^1V^2$=$V^3$-$V^4$=$V^5$- is a group selected from the following (i) to (p):

(i): =C(H)—C($R^A$)=C($R^B$)—C($R^C$)=C(H)—;
(j): =N—C($R^A$)=C($R^B$)—C($R^C$)=C(H)—;
(k): =C(H)—N=C($R^B$)—C($R^C$)=C(H)—;
(l): =C(H)—C($R^A$)=N—C($R^C$)=C(H)—;
(m): =C(H)—C($R^A$)=C($R^B$)—N=C(H)—;
(n): =N—C($R^A$)=C($R^B$)—C($R^C$)=N—;
(o): =C(H)—C($R^A$)=N—C($R^C$)=C(H)—; and
(p): =C(H)—N=C($R^B$)—N=C(H)—;

$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted nonaromatic heterocyclyloxy, substituted or unsubstituted aryloxy or substituted or unsubstituted heteroaryloxy; $R^A$ and $R^B$, or $R^B$ and $R^C$ together with ring atoms to which they are attached form a now aromatic carbocyclic ring, a non-aromatic heterocyclic ring, an aromatic carbocyclic ring, or an aromatic heterocyclic ring, provided that groups of (i) to (p) have at least one substituent; wherein "groups of (i) to (p) have at least one substituent" means at least one of $R^A$, $R^B$ and $R^C$ is not hydrogen in the groups of (i), (j) and (n), at least one of $R^B$ and $R^C$ is not hydrogen in the group of (k), at least one of $R^A$ and $R^C$ is not hydrogen in the groups of (l) and (o), at least one of $R^A$ and $R^B$ is not hydrogen in the group of (m), and $R^B$ is not hydrogen in the group of (p);

or its pharmaceutically acceptable salt or a solvate thereof.

(32B)

The compound according to the above (32A) wherein $R^A$, $R^B$ and $R^C$ are each independently hydrogen, halogen, alkyl, or alkyloxy, or its pharmaceutically acceptable salt or a solvate thereof.

(32C)

The compound according to the above (32A) or (32B) wherein $R^6$ is phenyl, or its pharmaceutically acceptable salt or a solvate thereof.

(32D)

The compound according to any one of the above (14α) to (17α), (17A) to (17D), (18α) to (29α) and (32α) wherein $R^6$ is a group of the formula:

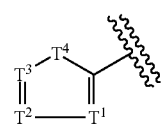

[Chemical Formula 49]

=$T^1$-$T^2$=$T^3$-$T^4$- is a group selected from the following (q) to (t):

(q): =C(H)—C($R^D$)=C($R^E$)—S—;
(r): =C(H)—C($R^D$)=C($R^E$)—O—;
(s): =N—C($R^D$)=C($R^E$)—S—; and
(t): =N—C($R^D$)=C($R^E$)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted qtr unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring, or its pharmaceutically acceptable salt or a solvate thereof.

(32E)
The compound according to the above (32D) wherein $R^D$ and $R^E$ are each independently hydrogen, halogen, alkyl, or alkyloxy, or its pharmaceutically acceptable salt or a solvate thereof.

(32F)
The compound according to the above (32D) or (32E) wherein $R^6$ is thienyl, or its pharmaceutically acceptable salt or a solvate thereof.

(32G)
The compound according to any one of the above (14α) to (17α), (17A) to (17D), (18α) to (29α) and (32α) wherein $R^6$ is a group of the formula;

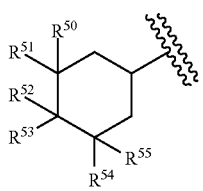

[Chemical Formula 50]

wherein $R^{50}$, $R^{51}$, $R^{52}$, $R^{53}$, $R^{54}$, and $R^{55}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or its pharmaceutically acceptable salt or a solvate thereof.

(32H)
The compound according to the above (32G) wherein $R^{50}$, $R^{51}$, $R^{52}$, $R^{53}$, $R^{54}$, and $R^{55}$ are each independently hydrogen, halogen, alkyl, or alkyloxy, or its pharmaceutically acceptable salt or a solvate thereof.

(32I)
The compound according to the above (32G) or (32H) wherein $R^6$ is cyclohexyl, or its pharmaceutically acceptable salt or a solvate thereof.

(32J)
The compound according to any one of the above (14α) to (17α), (17A) to (17D), (18α) to (29α) and (32α) wherein $R^6$ is a group of the formula:

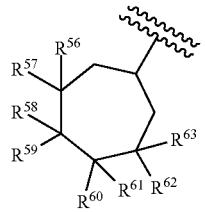

[Chemical Formula 51]

wherein $R^{56}$, $R^{57}$, $R^{58}$, $R^{59}$, $R^{60}$, $R^{61}$, $R^{62}$, and $R^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or its pharmaceutically acceptable salt or a solvate thereof.

(32K)
The compound according to the above (32J) wherein $R^{56}$, $R^{57}$, $R^{58}$, $R^{59}$, $R^{60}$, $R^{61}$, $R^{62}$, and $R^{63}$ are each independently hydrogen, halogen, alkyl, or alkyloxy, or its pharmaceutically acceptable salt or a solvate thereof.

(32L)
The compound according to the above (32J) or (32K) wherein $R^6$ is cycloheptyl, or its pharmaceutically acceptable salt or a solvate thereof.

(32M)
The compound according to any one of the above (14A), (15α) to (17α), (17A) to (17D) and (18α) to (23α) wherein $R^6$ is a group of the formula:

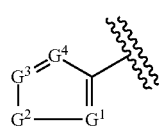

[Chemical Formula 52]

wherein
$=G^1\text{-}G^2\text{-}G^3\text{=}G^4\text{-}$ is a group selected from the following (u) to (x):
(u): =C(H)—S—C($R^F$)—C(H)—;
(v): =C(H)—O—C($R^V$)—C(H)—;
(w): =C(H)—S—C($R^F$)=N—; and
(x): =C(H)—O—C($R^F$)=N—;
$R^F$ is hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy,
or its pharmaceutically acceptable salt or a solvate thereof.
(32N)
The compound according to the above (32M) wherein $R^F$ is hydrogen, halogen, alkyl, or alkyloxy, or its pharmaceutically acceptable salt or a solvate thereof.
(32O)
The compound according to the above (32M) (32N) wherein $R^6$ is thienyl, or its pharmaceutically acceptable salt or a solvate thereof.
(33α)
The compound according to any one of the above (14A), (14α) to (17α), (17A) to (17D), (18α) to (32α) and (32A) to (32O) wherein $R^7$ is a group of the formula:

[Chemical Formula 53]

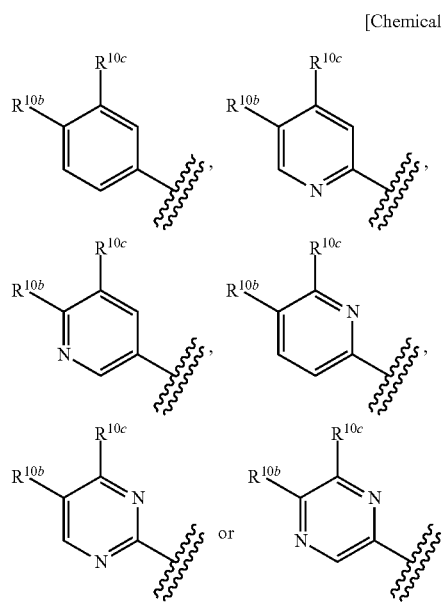

wherein $R^{10b}$ is substituted or unsubstituted alkyl, substituted or unsubstituted alkyloxy, substituted or unsubstituted aryloxy, substituted or unsubstituted heteroaryloxy, substituted or unsubstituted nitrogen-containing non-aromatic heterocyclyloxy; and $R^{10c}$ is hydrogen, halogen, or haloalkyl; or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring,
or its pharmaceutically acceptable salt or a solvate thereof.
(34α)
The compound according to any one of the above (14A), (14α) to (17α), (17A) to (17D), (18α) to (32α), (32A) to (32O) and (33α) wherein $R^7$ is a group of the formula:

[Chemical Formula 54]

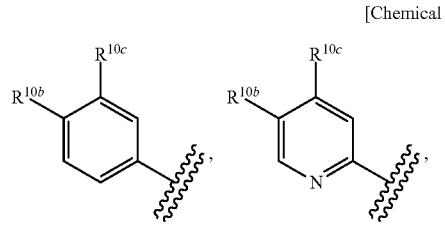

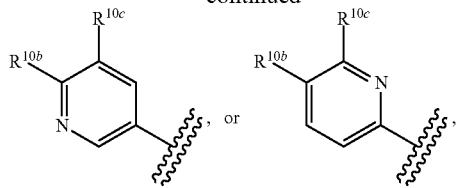

$R^{10b}$ and $R^{10c}$ are as defined in the above (33α), or its pharmaceutically acceptable salt or a solvate thereof.
(35α)
A pharmaceutical composition comprising the compound according to any one of the above (14A), (14α) to (17α), (17A) to (17D), (18α) to (32α), (32A) to (32O), (33α) and (34α), or its pharmaceutically acceptable salt or a solvate thereof.
(36α)
The pharmaceutical composition according to the above (35α), which has a $P2X_3$ and/or $P2X_{2/3}$ receptor antagonistic effect.
(37α)
A compound according to any one of the above (14α) to (17α), (17A) to (17D), (18α) (32α), (32A) to (32L), (33α) and (34α), or its pharmaceutically acceptable salt, or a solvate thereof for use in a method for treating and/or preventing a disease related to $P2X_3$ and/or $P2X_{2/3}$ receptor.
(38α)
A method for treating and/or preventing a disease related to $P2X_3$ and/or $P2X_{2/3}$ receptor comprising administering the compound according to any one of the above (14α) to (17α), (17A) to (17D), (18α) to (32α), (32A) to (32L), (33α) and (34α), or its pharmaceutically acceptable salt, or a solvate thereof.

Furthermore, the present invention relates to
(1)
A pharmaceutical composition having a $P2X_3$ and/or $P2X_{2/3}$ receptor antagonistic effect comprising a compound of the formula (I):

[Chemical Formula 55]

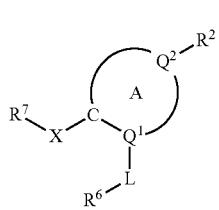

(I)

wherein
ring A is substituted or unsubstituted 5 to 7-membered cycloalkane, substituted or unsubstituted 5 to 7-membered cycloalkene, a substituted or unsubstituted 5 to 7-membered nitrogen containing non-aromatic heterocyclic ring, a benzene ring or a substituted or unsubstituted 5- or 6-membered aromatic heterocyclic ring, or a fused ring consisting of two rings selected from substituted or unsubstituted 5 to 7-membered cycloalkane, substituted or unsubstituted 5 to 7-membered cycloalkene, a substituted or unsubstituted 5 to 7-membered nitrogen-containing non-aromatic heterocyclic ring, a benzene ring, and a substituted or unsubstituted 5- or 6-membered aromatic heterocyclic ring, provided that a compound wherein ring A is a triazine ring is excluded;

C is a carbon atom;

—X— is —N(R$^{16}$)—, —O—, —S—, or —(CR$^{16a}$R$^{16b}$)—;

R$^{16}$ is hydrogen, substituted or unsubstituted alkyl, substituted or unsubstituted alkenyl, substituted or unsubstituted alkynyl, or substituted or unsubstituted acyl;

R$^{16a}$ and R$^{16b}$ are each independently hydrogen, halogen, hydroxy, substituted or unsubstituted substituted or unsubstituted alkenyl, substituted or unsubstituted alkynyl, substituted or unsubstituted alkyloxy, substituted or unsubstituted alkynyloxy, or substituted or unsubstituted alkenyloxy;

R$^7$ is substituted or unsubstituted 5- or 6-membered heteroaryl or substituted or unsubstituted 6- to 10-membered aryl;

Q$^1$ and Q$^2$ are each independently a carbon atom or a nitrogen atom;

when Q$^1$ is a carbon atom, -L- is —O—, —S—, —N(R$^8$)— or —(CR$^{9c}$R$^{9d}$)n$^1$-;

when Q$^1$ is a nitrogen atom, -L- is —(CR$^{9a}$R$^{9b}$)n$^1$-;

R$^8$ is hydrogen, substituted or unsubstituted alkyl, substituted or unsubstituted alkenyl, substituted or unsubstituted alkynyl, or substituted or unsubstituted acyl;

R$^{9a}$, R$^{9b}$, R$^{9c}$ and R$^{9d}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy or R$^{9c}$ and R$^{9d}$, and/or R$^{9a}$ and R$^{9b}$ are taken together to form oxo or thioxo;

n$^1$ is an integer of 1 to 4;

R$^6$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; and R$^2$ is hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, provided that

[Chemical Formula 56]

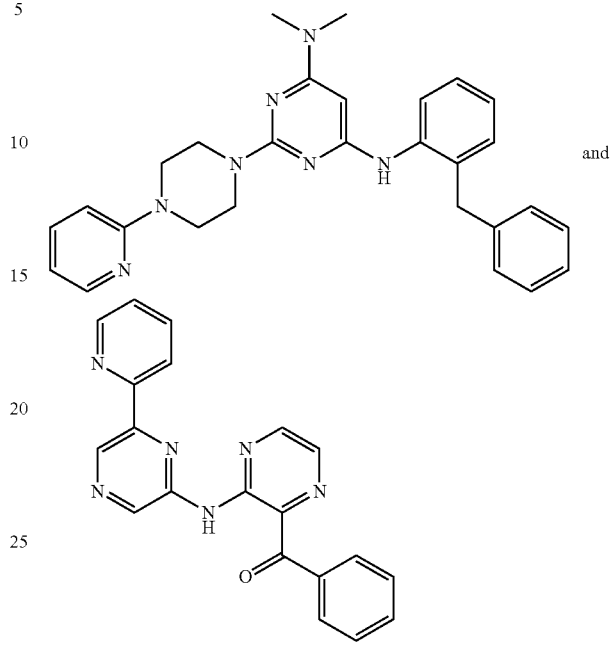

and are excluded, or its pharmaceutically acceptable salt or a solvate thereof as an active ingredient.

More specifically, the present invention relates to the following (2) to (38).

(2)

The pharmaceutical composition having a P2X$_3$ and/or P2X$_{2/3}$ receptor antagonistic effect according to the above (1) comprising the compound wherein ring A is a substituted or unsubstituted cyclohexane ring, a substituted or unsubstituted cyclohexadiene ring, a substituted or unsubstituted cyclohexene ring, a substituted or unsubstituted benzene ring, a substituted or unsubstituted pyridine ring, a substituted or unsubstituted dihydropyridine ring, a substituted or unsubstituted tetrahydropyridine ring, a substituted or unsubstituted pyrimidine ring, a substituted or unsubstituted dihydropyrimidine ring, a substituted or unsubstituted tetrahydropyrimidine ring, a substituted or unsubstituted hexahydropyrimidine ring, a substituted or unsubstituted piperidine ring, a substituted or unsubstituted piperazine ring, a substituted or unsubstituted pyrazine ring, a substituted or unsubstituted dihydropyrazine ring, a substituted or unsubstituted tetrahydropyrazine ring, a substituted or unsubstituted indene ring, a substituted or unsubstituted benzofuran ring, a substituted or unsubstituted benzofuran ring, a substituted or unsubstituted benzo(b)thiophene ring, a substituted or unsubstituted benzo(c)thiophene ring, a substituted or unsubstituted indoline ring, a substituted or unsubstituted indole ring, a substituted or unsubstituted benzimidazole ring, a substituted or unsubstituted cyclopenta[b]pyridine ring, a substituted or unsubstituted 1H-indazole ring, a substituted or unsubstituted benzisoxazole ring, a substituted or unsubstituted benzoxazole ring, a substituted or unsubstituted 2,1-benzisoxazole ring, a substituted or unsubstituted benzothiazole ring, a substituted or unsubstituted naphthalene ring, a substituted or unsubstituted 1,2,3,4-tetrahydronaphthalene ring, a substituted or unsubstituted 3H-2-benzopyran ring, a substituted or unsubstituted quinoline ring, a substituted or unsubstituted isoquinoline ring, a substituted or unsubstituted quinazoline ring, a substituted or unsubstituted quinoxaline ring, a substituted or unsubstituted 1,8-naphthyridine ring, a substituted or unsubstituted 1,7-naphthyridine ring, a substituted or unsubstituted 1,6-naphthyridine ring, a substituted or unsubstituted 1,5-naphthyridine ring, a substituted or unsubstituted 2H-1,3-benzoxazine ring, a substituted or unsubstituted 2H-1,4-benzoxazine ring, a substituted or unsubstituted 1H-2,3-benzoxazine ring, a substituted or unsubstituted 4H-3,1-benzoxazine ring, or a substituted or unsubstituted 4H-1,4-benzoxazine ring, or its pharmaceutically acceptable salt or a solvate thereof as an active ingredient.

(3)

The pharmaceutical composition having a $P2X_3$ and/or $P2X_{2/3}$ receptor antagonistic effect according to the above (1) or (2) comprising the compound wherein ring A is a substituted or unsubstituted benzene ring, a substituted or unsubstituted dihydropyridine ring, a substituted or unsubstituted dihydropyrimidine ring, a substituted or unsubstituted tetrahydropyrimidine ring, a substituted or unsubstituted oxazole ring, or a substituted or unsubstituted pyrazole ring, or its pharmaceutically acceptable salt or a solvate thereof as an active ingredient.

(4)

The pharmaceutical composition having a $P2X_3$ and/or $P2X_{2/3}$ receptor antagonistic effect according to the above (1) or (2) comprising the compound wherein ring A is a substituted or unsubstituted indene ring, a substituted or unsubstituted benzofuran ring, a substituted or unsubstituted isobenzofuran ring, a substituted or unsubstituted benzo(b)thiophene ring, a substituted or unsubstituted benzo(c)thiophene ring, a substituted or unsubstituted indoline ring, a substituted or unsubstituted indole ring, a substituted or unsubstituted benzimidazole ring, a substituted or unsubstituted cyclopenta[b]pyridine ring, a substituted or unsubstituted 1H-indazole ring, a substituted or unsubstituted benzisoxazole ring, a substituted or unsubstituted benzoxazole ring, a substituted or unsubstituted 2,1-benzisoxazole ring, a substituted or unsubstituted benzothiazole ring, a substituted or unsubstituted naphthalene ring, a substituted or unsubstituted 1,2,3,4-tetrahydronaphthalene ring, a substituted or unsubstituted 3H-2-benzopyran ring, a substituted or unsubstituted quinoline ring, a substituted or unsubstituted isoquinoline ring, a substituted or unsubstituted quinazoline ring, a substituted or unsubstituted quinoxaline ring, a substituted or unsubstituted 1,8-naphthyridine ring, a substituted or unsubstituted 1,7-naphthyridine ring, a substituted or unsubstituted 1,6-naphthyridine ring, a substituted or unsubstituted 1,5-naphthyridine ring, a substituted or unsubstituted 2H-1,3-benzoxazine ring, a substituted or unsubstituted 2H-1,4-benzoxazine ring, a substituted or unsubstituted 1H-2,3-benzoxazine ring, a substituted or unsubstituted 4H-3,1-benzoxazine ring, or a substituted or unsubstituted 4H-1,4-benzoxazine ring, or its pharmaceutically acceptable salt or a solvate thereof as an active ingredient.

(5)

The pharmaceutical composition having a $P2X_3$ and/or $P2X_{2/3}$ receptor antagonistic effect according to any one of the above (1) to (4) comprising the compound wherein ring A is a ring optionally substituted with oxo or thioxo, or its pharmaceutically acceptable salt or a solvate thereof as an active ingredient.

(6)

The pharmaceutical composition having a $P2X_3$ and/or $P2X_{2/3}$ receptor antagonistic effect according to any one of the above (1) to (5) comprising the compound wherein —X— is —$N(R^{16})$—; and $R^{16}$ is hydrogen, substituted or unsubstituted alkyl, substituted or unsubstituted alkenyl, substituted or unsubstituted alkynyl, or substituted or unsubstituted acyl, or its pharmaceutically acceptable salt or a solvate thereof as an active ingredient.

(7)

The pharmaceutical composition having a $P2X_3$ and/or $P2X_{2/3}$ receptor antagonistic effect according to any one of the above (1) to (6) comprising the compound wherein —X— is —NH—; $R^7$ is substituted or unsubstituted 6-membered heteroaryl or substituted or unsubstituted phenyl; and -L- is —$(CR^{9a}R^{9b})$—, or its pharmaceutically acceptable salt or a solvate thereof as an active ingredient.

(8)

The pharmaceutical composition having a $P2X_3$ and/or $P2X_{2/3}$ receptor antagonistic effect according to any one of the above (1) to (7) comprising the compound wherein $Q^2$ is a carbon atom; $R^2$ is a group of the formula: —NH—C(=O)—$(CR^{8a}R^{8b})$n-$R^9$, wherein n is an integer of 0 to 4; $R^{8a}$ and $R^{8b}$ are each independently hydrogen, halogen, hydroxy, or substituted or unsubstituted alkyl; $R^9$ is hydroxy, carboxy, sulfo, tetrazolyl, a substituted or unsubstituted non-aromatic heterocyclic group, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl substituted or unsubstituted amino, or substituted or unsubstituted guanidyl, or a group of the formula: —$(CR^{8a}R^{8b})$m-$R^9$, wherein m is an integer of 1 to 6; $R^{8a}$, $R^{8b}$ and $R^9$ are as defined above, or its pharmaceutically acceptable salt or a solvate thereof as an active ingredient.

(9)

The pharmaceutical composition having a $P2X_3$ and/or $P2X_{2/3}$ receptor antagonistic effect according to any one of the above (1) to (7) comprising the compound wherein $Q^2$ is a nitrogen atom; $R^2$ is C1-C6 alkyl or a group of the formula: —$(CR^{8a}R^{8b})$m-$R^9$, $R^{8a}$, $R^{8b}$, m and $R^9$ are as defined in the above (8), or its pharmaceutically acceptable salt or a solvate thereof as an active ingredient.

(10)

The pharmaceutical composition having a $P2X_3$ and/or $P2X_{2/3}$ receptor antagonistic effect according to the above (1) comprising the compound of the formula:

[Chemical Formula 57]

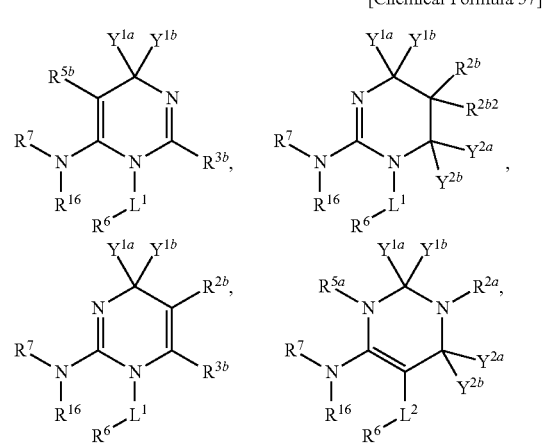

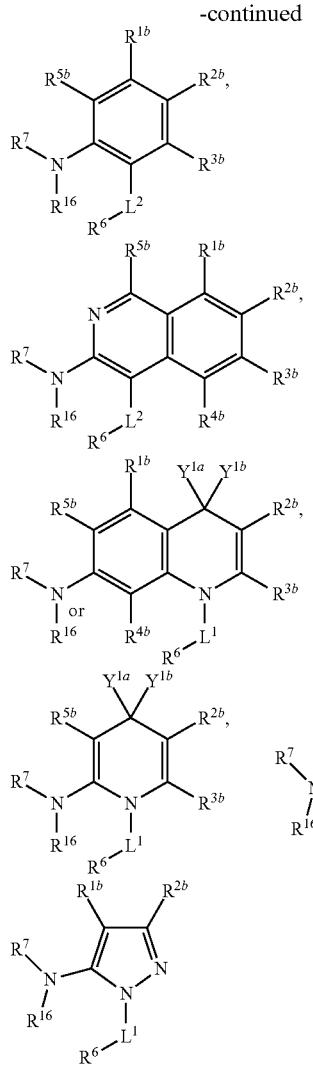
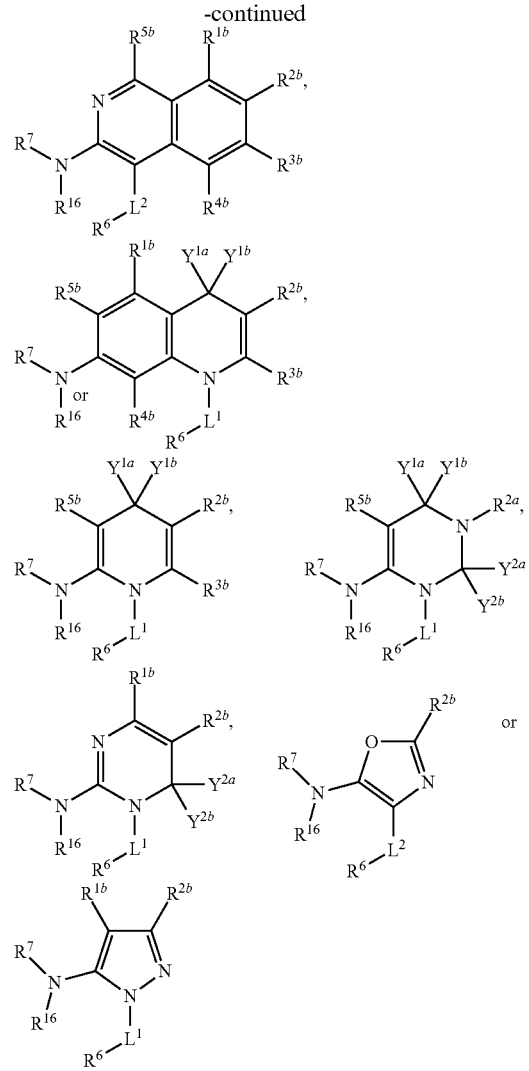
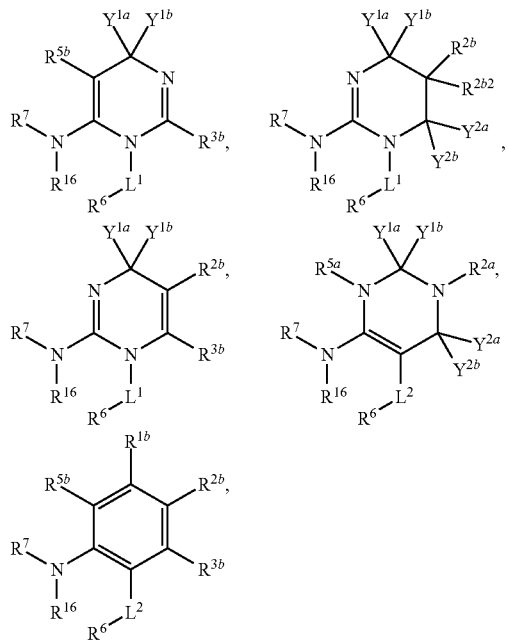

[Chemical Formula 58]

wherein
Y$^{1a}$, Y$^{1b}$, Y$^{2a}$, Y$^{2b}$, R$^{1b}$, R$^{2b}$, R$^{2b2}$, R$^{3b}$, R$^{4b}$ and R$^{5b}$ are each independently hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl or substituted or unsubstituted amino, or $Y^{1a}$ and $Y^{1b}$, and/or $Y^{2a}$ and $Y^{2b}$ are taken together to form oxo or thioxo;

$R^{2a}$ and $R^{5a}$ are each independently hydrogen, substituted or unsubstituted alkyl, substituted or unsubstituted alkenyl, substituted or unsubstituted alkenyl, substituted or unsubstituted cycloalkyl, substituted or unsubstituted cycloalkenyl, a substituted or unsubstituted non aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, or substituted or unsubstituted sulfamoyl;

$R^7$ is a group of the formula (A):

[Chemical Formula 59]

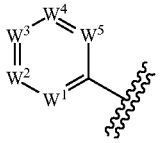

(A)

wherein $=W^1-W^2=W^3-W^4=W^5-$ is a group selected from the following (a) to (h):

(a): $=C(H)-C(R^{10a})=C(R^{10b})-C(R^{10c})=C(H)-$;
(b): $=N-C(R^{10a})=C(R^{10b})-C(R^{10c})=C(H)-$;
(c): $=C(H)-N=C(R^{10b})-C(R^{10c})=C(H)-$;
(d): $=C(H)-C(R^{10a})=N-C(R^{10c})=C(H)-$;
(e): $=C(H)-C(R^{10a})=C(R^{10b})-N=C(H)-$;
(f): $=N-C(R^{10a})=C(R^{10b})-C(R^{10c})=N-$;
(g): $=C(H)-C(R^{10a})=N-C(R^{10c})=C(H)-$; and
(h): $=C(H)-N=C(R^{10b})-N=C(H)-$;

$R^{10a}$, $R^{10b}$ and $R^{10c}$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring;

$R^{16}$ is hydrogen, substituted or unsubstituted acyl, substituted or unsubstituted alkyl, substituted or unsubstituted alkenyl, or substituted or unsubstituted alkynyl;

$L^1$ is $-CR^{9a}R^{9b}-$;
$L^2$ is $-CR^{9a}R^{9d}-$;
$R^{9a}$, $R^{9b}$, $R^{9c}$ and $R^{9d}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy; and $R^6$ is as defined in the above (1), or its pharmaceutically acceptable salt or a solvate thereof as an active ingredient.

(11)
The pharmaceutical composition having a $P2X_3$ and/or $P2X_{2/3}$ receptor antagonistic effect according to the above (10) comprising the compound of the formula:

[Chemical Formula 60]

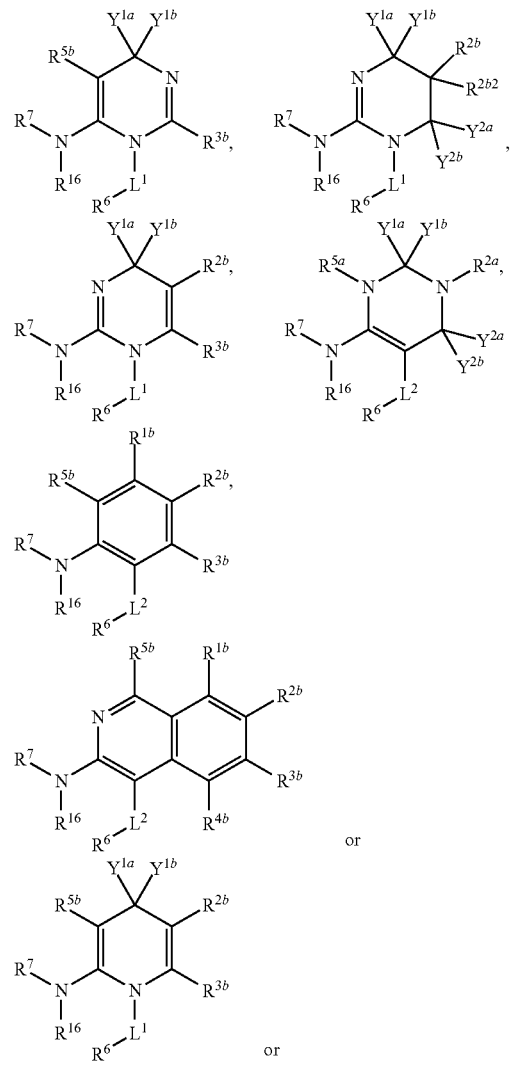

or

-continued

[Chemical Formula 61]

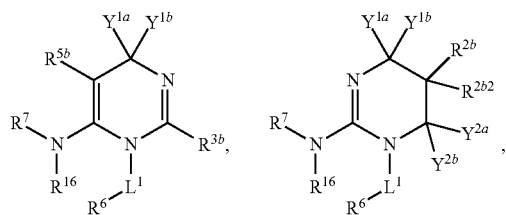

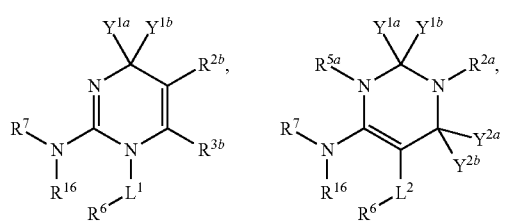

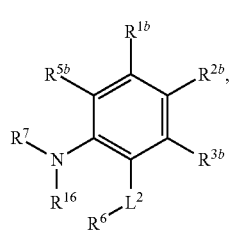

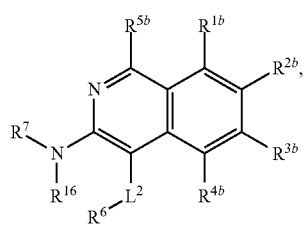

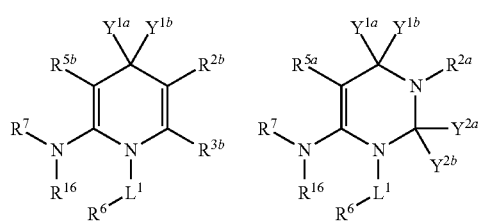

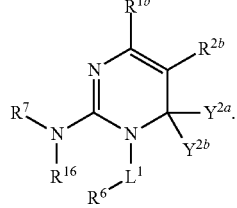

wherein $Y^{1a}, Y^{1b}, Y^{2a}, Y^{2b}, R^{1b}, R^{2a}, R^{2b}, R^{2b2}, R^{3b}, R^{4b}, R^{5b}, R^6, R^7, R^{16}, L^1$ and $L^2$ are as defined in the above (10), or its pharmaceutically acceptable salt or a solvate thereof as an active ingredient.

(12)

The pharmaceutical composition having a P2X$_3$ and/or P2X$_{2/3}$ receptor antagonistic effect according to the above (10) comprising the compound of the formula:

[Chemical Formula 62]

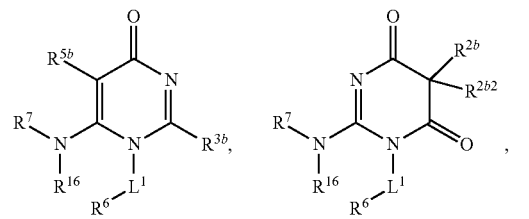

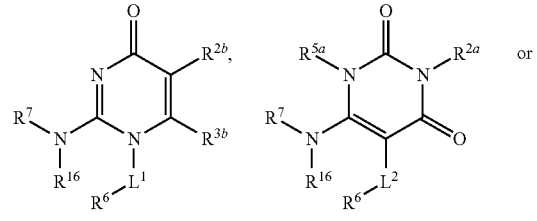

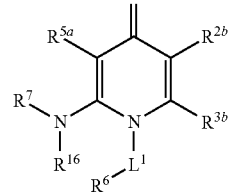

or

[Chemical Formula 63]

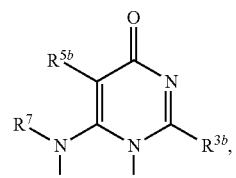

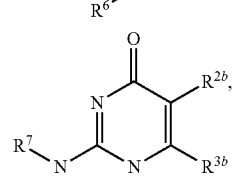

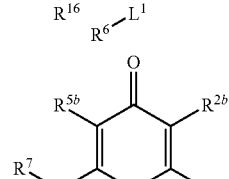

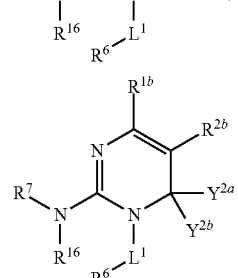

wherein $R^{2a}, R^{2b}, R^{2b2}, R^{3b}, R^{5b}, R^6, R^7, R^{16}, L^1$ and $L^2$ are as defined in the above (10), or its pharmaceutically acceptable salt or a solvate thereof as an active ingredient,

(13)
The pharmaceutical composition having a P2X$_3$ and/or P2X$_{2/3}$ receptor antagonistic effect according to any one of the above (1) to (12) comprising the compound wherein R$^6$ is a group of the formula:

[Chemical Formula 64]

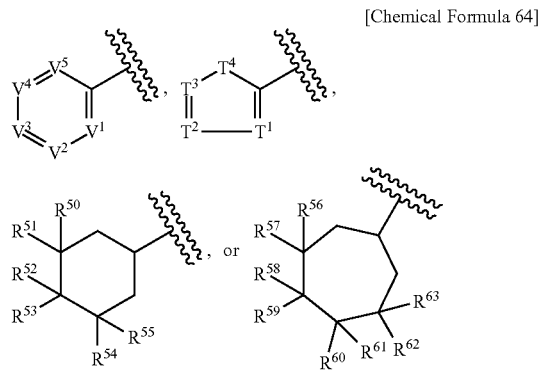

wherein =V$^1$-V$^2$=V$^3$-V$^4$=V$^5$- is a group selected from the following (i) to (p):
(i): =C(H)—C(R$^A$)=C(R$^B$)—C(R$^C$)=C(H)—;
(j): =N—C(R$^A$)=C(R$^B$)—C(R$^C$)=C(H)—;
(k): =C(H)—N=C(R$^B$)—C(R$^C$)=C(H)—;
(l): =C(H)—C(R$^A$)=N—C(R$^C$)=C(H)—;
(m): =C(H)—C(R$^A$)=C(R$^B$)—N=C(H)—;
(n): =N—C(R$^A$)=C(R$^B$)—C(R$^C$)=N—;
(o): =C(H)—C(R$^A$)=N—C(R$^C$)=C(H)—; and
(p): =C(H)—N=C(R$^B$)—N=C(H)—;
R$^A$, R$^B$ and R$^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or R$^A$ and R$^B$, or R$^B$ and R$^C$ together with ring atoms to which they are attached form a non-aromatic carbocyclic ring, a non-aromatic heterocyclic ring, an aromatic carbocyclic ring, or an aromatic heterocyclic ring;
=T$^1$-T$^2$=T$^3$-T$^4$- is a group selected from the following (q) to (t):
(q): =C(H)—C(R$^D$)=C(R$^E$)—S—;
(r): =C(H)—C(R$^D$)=C(R$^E$)—O—;
(s): =N—C(R$^D$)=C(R$^E$)—S—; and
(t): =N—C(R$^D$)=C(R$^E$)—O—;
R$^D$ and R$^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted car unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or R$^A$ and R$^B$, or R$^B$ and R$^C$ together with ring atoms to which they are attached form a non-aromatic carbocyclic ring, a non-aromatic heterocyclic ring, an aromatic carbocyclic ring, or an aromatic heterocyclic ring;
R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, and R$^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxyl, or its pharmaceutically acceptable salt or a solvate thereof as an active ingredient.

(14)
A compound of the formula (I):

[Chemical Formula 65]

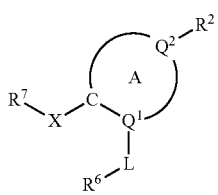

(I)

wherein
ring A is a substituted or unsubstituted cyclohexane ring, a substituted or unsubstituted cyclohexene ring, a substituted or unsubstituted 6-membered nitrogen-containing non-aromatic heterocyclic ring, a benzene ring or a substituted or unsubstituted 6-membered aromatic heterocyclic ring or a fused ring wherein any of the above ring is fused with one ring selected from substituted or unsubstituted 5 to 7-membered cycloalkane, substituted or unsubstituted 5 to 7-membered cycloalkene, a substituted or unsubstituted 5 to 7-membered nitrogen-containing non-aromatic heterocyclic ring, a benzene, ring and a substituted or unsubstituted 5- or 6-membered aromatic heterocyclic ring, provided that a compound wherein ring A is a triazine ring is excluded;
C is a carbon atom;
—X— is —N(R$^{16}$)—;
R$^{16}$ is hydrogen, substituted or unsubstituted alkyl, substituted or unsubstituted alkenyl, or substituted or unsubstituted alkynyl, or substituted or unsubstituted acyl;

$R^7$ is a group of the formula. (A):

[Chemical Formula 66]

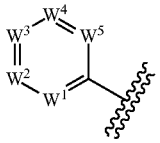

(A)

wherein =$W^1$-$W^2$=$W^3$-$W^4$=$W^5$- is a group selected from the following (a) to (h):

(a): =C(H)—C($R^{10a}$)=C($R^{10b}$)—C($R^{10c}$)=C(H)—;
(b): =N—C($R^{10a}$)=C($R^{10b}$)—C($R^{10c}$)=C(H)—;
(c): =C(H)—N=C($R^{10b}$)—C($R^{10c}$)=C(H)—;
(d): =C(H)—C($R^{10a}$)=N—C($R^{10c}$)=C(H)—;
(e): =C(H)—C($R^{10a}$)=C($R^{10b}$)—N=C(H)—;
(f): =N—C($R^{10a}$)=C($R^{10b}$)—C($R^{10c}$)=N—;
(g): =C(H)—C($R^{10a}$)=N—C($R^{10c}$)=C(H)—; and
(h): =C(H)—N=C($R^{10b}$)—N=C(H)—;

$R^{10a}$, $R^{10b}$ and $R^{10c}$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy Or substituted or unsubstituted heteroaryloxy; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, provided that at least one of $R^{10a}$, $R^{10b}$ and $R^{10c}$ is not hydrogen in each group of (a) to (h);

$Q^1$ and $Q^2$ are each independently a carbon atom or a nitrogen atom;

when $Q^1$ is a carbon atom, -L- is —$CR^{9a}R^{9b}$—;

when $Q^1$ is a nitrogen atom, -L- is —$CR^{9c}R^{9d}$—;

$R^{9a}$, $R^{9b}$, $R^{9c}$ and $R^{9d}$ are each independently hydrogen, halogen, hydroxy, substituted or unsubstituted alkyl, substituted or unsubstituted alkenyl, substituted or unsubstituted alkyloxy, substituted or unsubstituted alkynyloxy or substituted or unsubstituted alkenyloxy;

$R^6$ is a group of the formula:

[Chemical Formula 67]

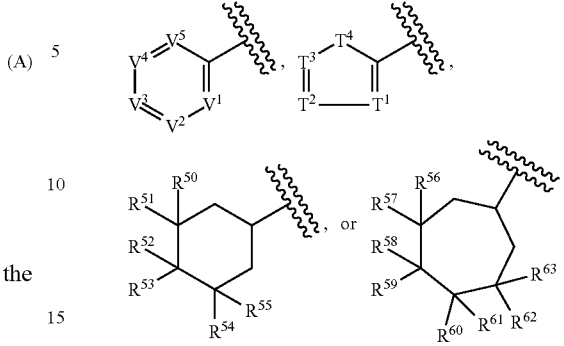

wherein =$V^1$-$V^2$=$V^3$-$V^4$=$V^5$- is a group selected from the following (i) to (p):

(i): =C(H)—C($R^A$)=C($R^B$)—C($R^C$)=C(H)—;
(j): =N—C($R^A$)=C($R^B$)—C($R^C$)=C(H)—;
(k): =C(H)—N=C($R^B$)—C($R^C$)=C(H)—;
(l): =C(H)—C($R^A$)=N—C($R^C$)=C(H)—;
(m): =C(H)—C($R^A$)=C($R^B$)—N=C(H)—;
(n): =N—C($R^A$)=C($R^B$)—C($R^C$)=N—;
(o): =C(H)—C($R^A$)=N—C($R^C$)=C(H)—; and
(p): =C(H)—N=C($R^B$)—N=C(H)—;

$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted tar unsubstituted aryloxy, or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

=$T^1$-$T^2$=$T^3$-$T^4$- is a group selected from the following (q) to (t):

(q): =C(H)—C($R^D$)=C($R^E$)—S—;
(r): =C(H)—C($R^D$)=C($R^E$)—O—;
(s): =N—C($R^D$)=C($R^E$)—S—; and
(t): =N—C($R^D$)=C($R^E$)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

$R^{50}, R^{51}, R^{52}, R^{53}, R^{54}, R^{55}, R^{56}, R^{57}, R^{58}, R^{59}, R^{60}, R^{61}, R^{62}$, and $R^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy;

$R^2$ is hydrogen, hydroxy, halogen, cyano, substituted or unsubstituted substituted or unsubstituted alkenyl, substituted or unsubstituted alkynyl, substituted or unsubstituted alkyloxy, substituted or unsubstituted alkenyloxy, substituted or unsubstituted alkynyloxy, substituted, or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, provided that (i) a compound wherein

[Chemical Formula 68]

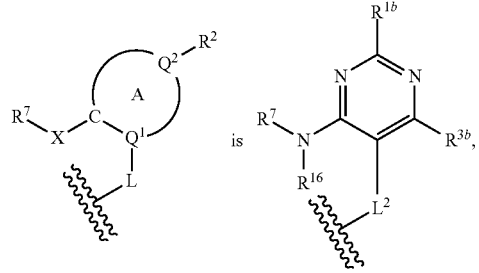

$R^{16}$ is hydrogen, and (α) $R^{1b}$ is amino substituted with substituted or unsubstituted phenyl, and $R^{3b}$ is methyl, or (β) $R^{1b}$ is methylthio, and $R^{3b}$ is chloro, (ii) a compound wherein

[Chemical Formula 69]

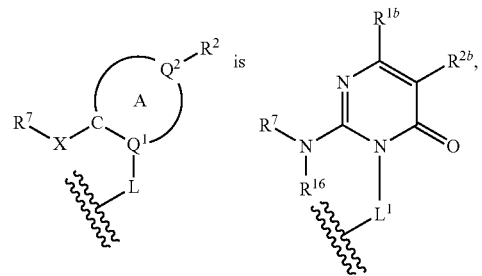

$R^{16}$ is hydrogen, and (α) $R^{1b}$ is unsubstituted alkyl, and $R^{2b}$ is substituted or unsubstituted arylmethyl or substituted or unsubstituted heteroarylmethyl or (β) $R^{1b}$ is trifluoromethyl, and $R^{2b}$ is hydrogen, (iv) a compound wherein

[Chemical Formula 70]

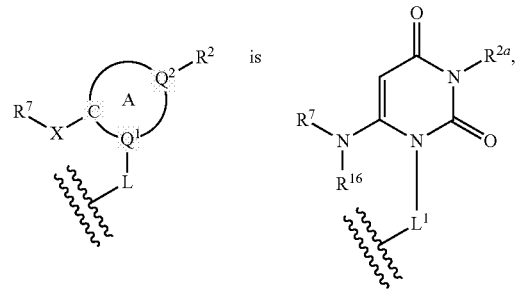

$R^{16}$ is hydrogen, and (α) $R^{2a}$ is hydrogen, and $R^7$ is phenyl substituted with n-octyl, or (β) $R^{2a}$ is methyl, and $R^6$ is phenyl substituted with methylsulfonyl, (v) a compound wherein $R^6$ is phenyl substituted with —C(=O)CH(Me)CH$_2$C(=O)OMe, and (vi)

[Chemical Formula 71]
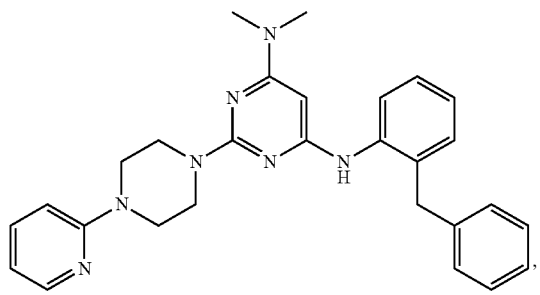
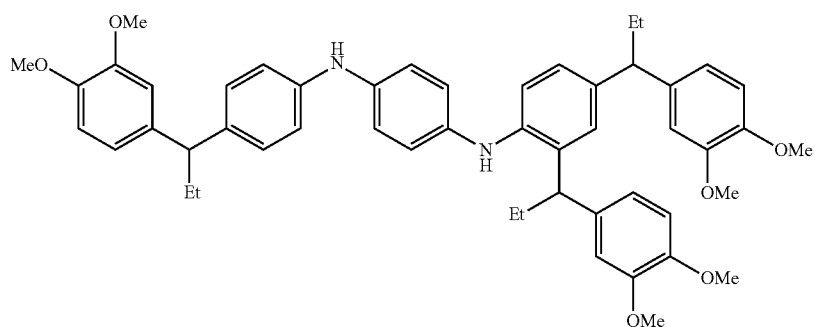
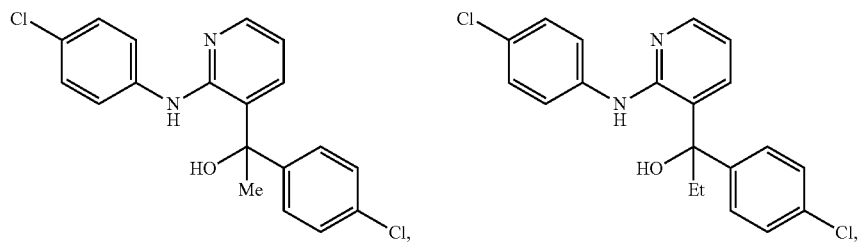
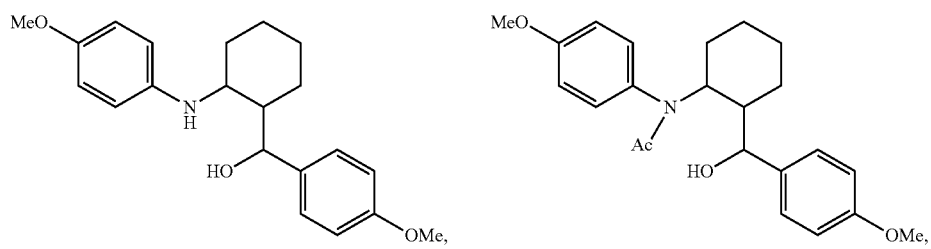
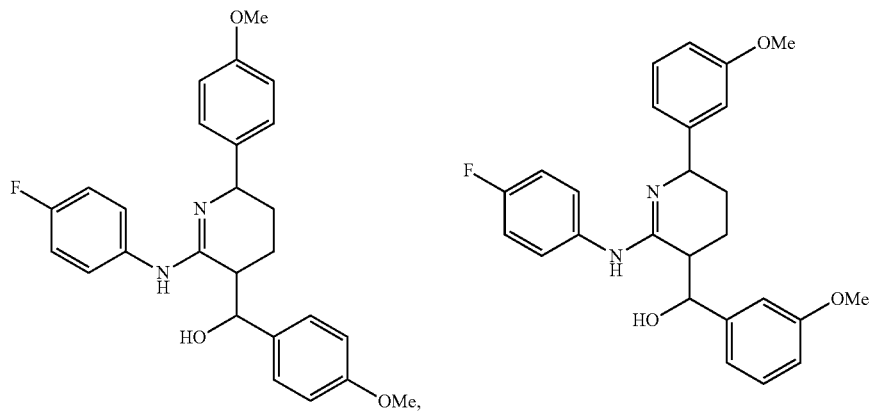
and

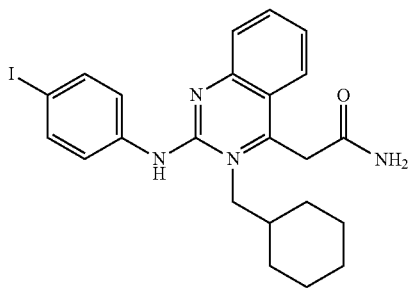
are excluded,
or its pharmaceutically acceptable salt or a solvate thereof.
(15)
The compound according to the above (14) wherein the compound is
[Chemical Formula 72]
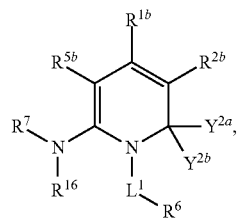 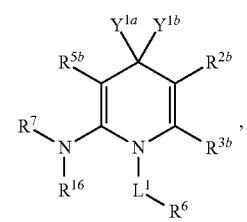
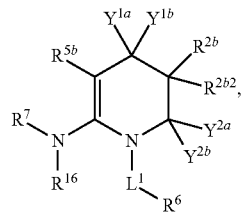 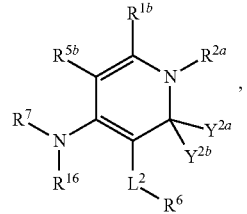
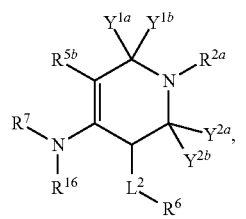 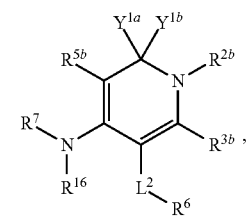
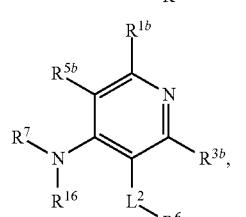 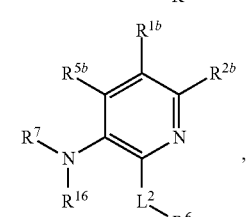
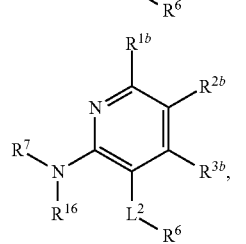 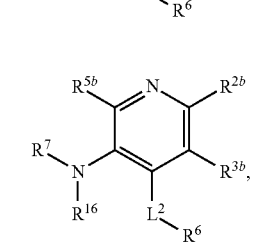
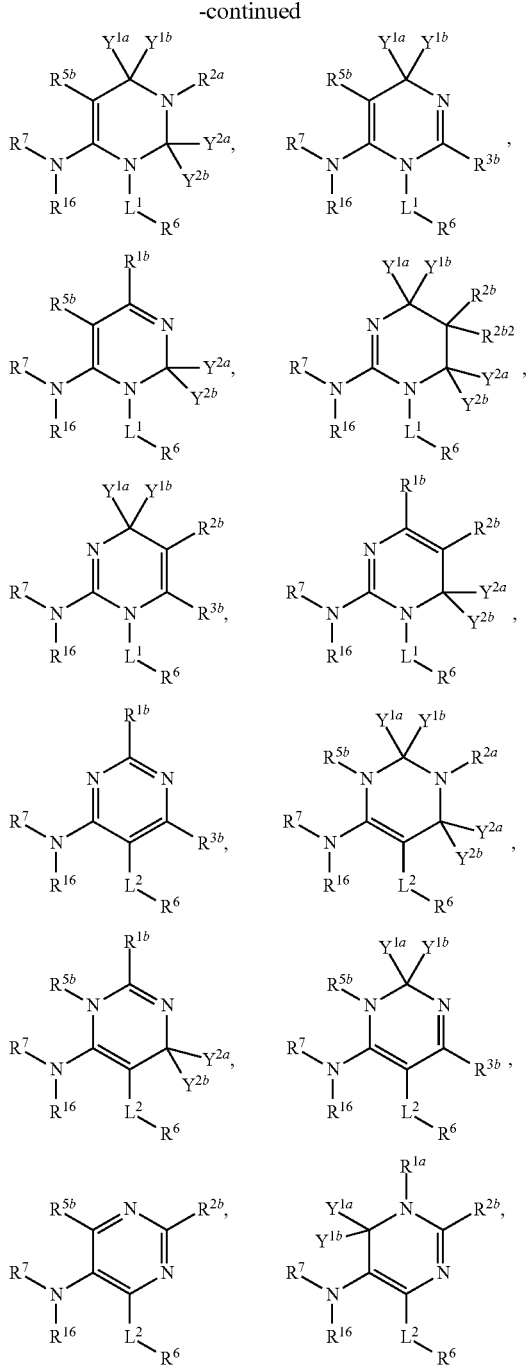

-continued

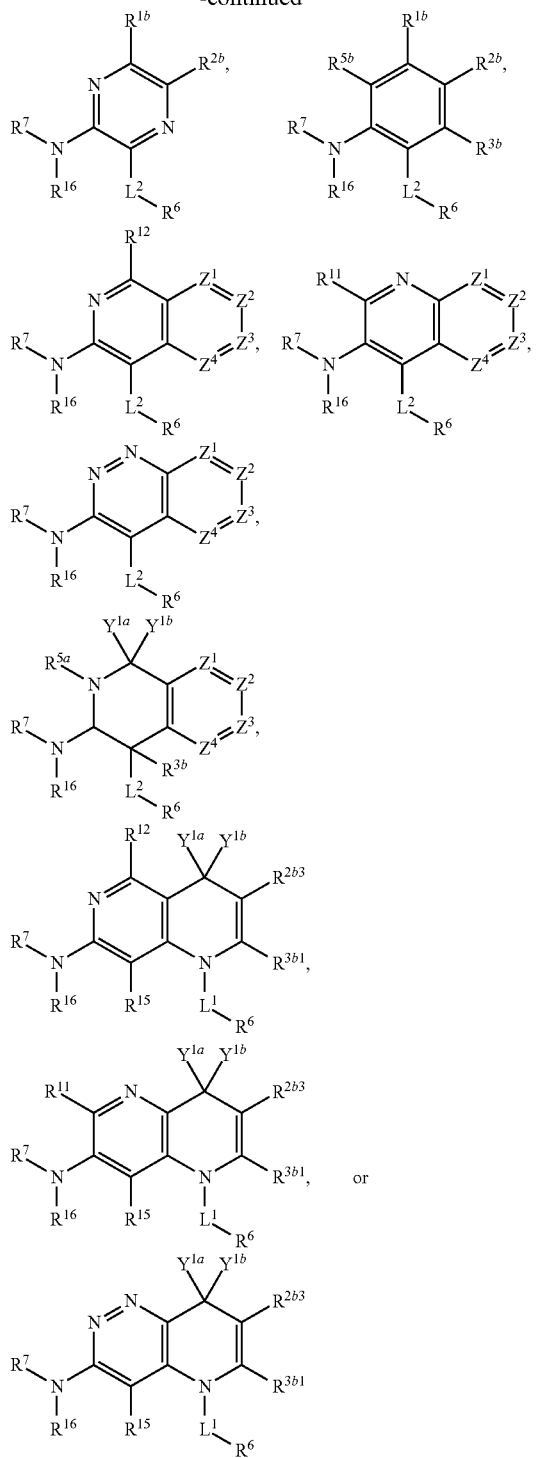

wherein
$Y^{1a}, Y^{1b}, Y^{2a}, Y^{2b}, R^{1b}, R^{2b}, R^{2b2}, R^{3b}, R^{5b}, R^{11}, R^{12}$ and $R^{15}$ are each independently hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, or $Y^{1a}$ and $Y^{1b}$, and/or $Y^{2a}$ and $Y^{2b}$ are taken together to form oxo or thioxo;

$R^{2a}$ and $R^{5a}$ are each independently hydrogen, substituted or unsubstituted substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, or substituted or unsubstituted sulfamoyl;

-$L^1$- is —$CR^{9c}R^{9d}$—;
-$L^2$- is —$CR^{9a}R^{9b}$—;
-$Z^1=Z^2-Z^3=Z^4$- is a group selected from the following (u) to (y):
(u): —N=C($R^{2b3}$)—C($R^{3b1}$)=C($R^{4b}$)—;
(v): —C($R^{1b1}$)=N—C($R^{3b1}$)=C($R^{4b}$)—;
(w): —($R^{1b1}$)=C($R^{2b3}$)—N=C($R^{4b}$)—;
(x): —C($R^{1b1}$)=C($R^{2b3}$)—C($R^{3b1}$)=N—; and
(y): —C($R^{1b1}$)=C($R^{2b3}$)—C($R^{3b1}$)=C($R^{4b}$)—;

one of $R^{2b3}$ and $R^{3b1}$ is hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, aryl, substituted or unsubstituted heteroaryl, substituted or unsubstituted cycloalkyloxy, substituted or unsubstituted cycloalkenyloxy, substituted or unsubstituted non-aromatic heterocyclyloxy substituted or unsubstituted aryloxy, substituted or unsubstituted heteroaryloxy, substituted or unsubstituted cycloalkylthio substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, and the other is hydrogen;

$R^{1b1}$ and $R^{4b}$ are each independently hydrogen, halogen, or substituted or unsubstituted alkyl;

$R^6, R^7, R^{16}, R^{9a}, R^{9b}, R^{9c}$ and $R^{9d}$ are as defined in the above (14), or its pharmaceutically acceptable salt or a solvate thereof.

(16)
The compound according to the above (14) wherein the compound is

[Chemical Formula 73]

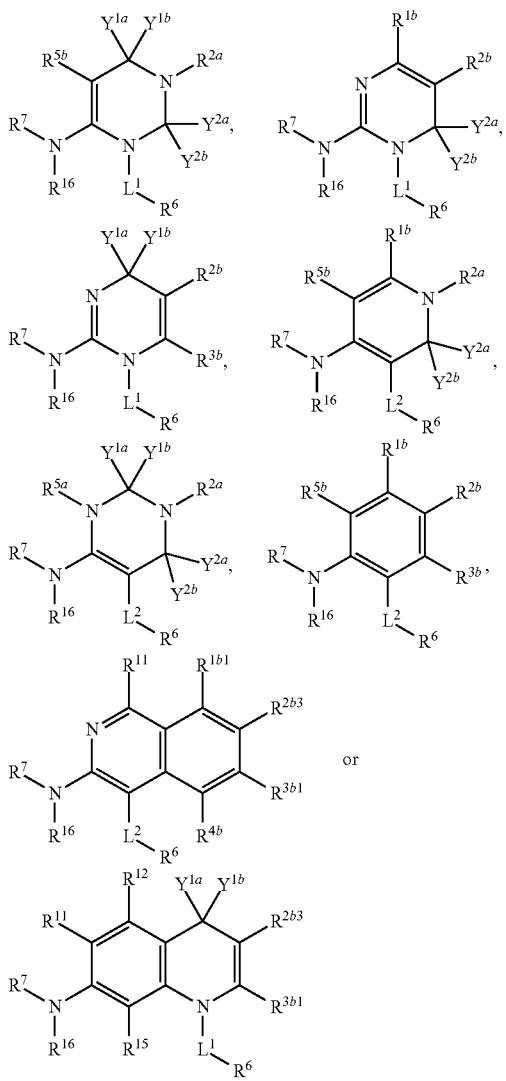

wherein $R^6$, $R^7$ and $R^{16}$ are as defined in the above (14); and $L^1, L^2, Y^{1a}, Y^{1b}, Y^{2a}, Y^{2b}, R^{1b}, R^{2a}, R^{2b}, R^{2b3}, R^{3b}, R^{3b1}, R^{4b}, R^{5a}, R^{5b}, R^{11}, R^{12}$ and $R^{15}$ are as defined in the above (15), or its pharmaceutically acceptable salt or a solvate thereof.

(17)
The compound according to the above (14) wherein the compound is

[Chemical Formula 74]

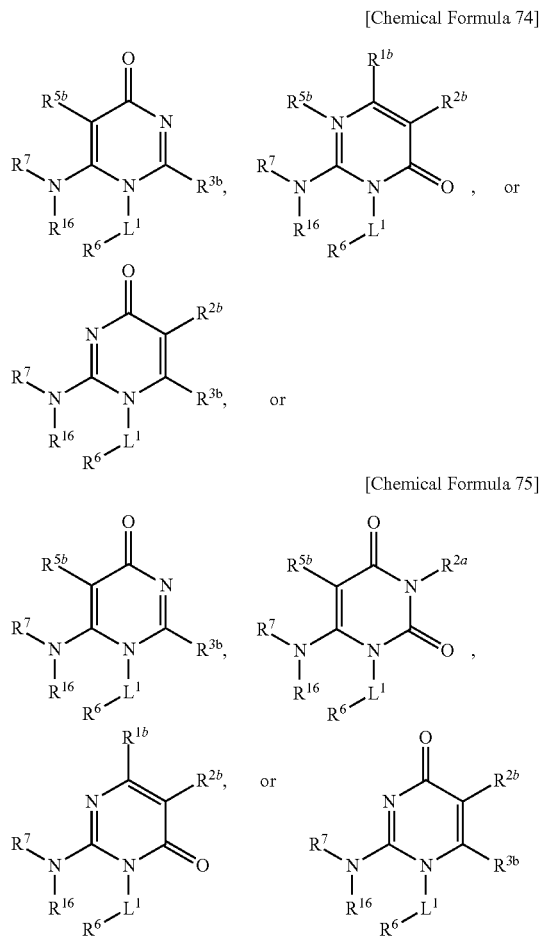

wherein $R^6$, $R^7$ and $R^{16}$ are as defined in the above (14);
$L^1, R1^b, R^{2b}, R^{3b}$ and $R^{5b}$ are as defined in the above (15), its pharmaceutically acceptable salt or a solvate thereof.

(18)
The compound according to any one of the above (14) to (17) wherein $R^{10a}$ and $R^{10c}$ are each independently hydrogen, halogen, or haloalkyl;

$R^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyl; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, provided that at least one of $R^{10a}$, $R^{10b}$ and $R^{10c}$ is not hydrogen in each group of (a) to (h), or its pharmaceutically acceptable salt or a solvate thereof.

(19)
The compound according to any one of the above (14) to (18) wherein ring A is a ring optionally substituted with oxo or thioxo, or its pharmaceutically acceptable salt or a solvate thereof.

(20)

The compound according to the above (15) or (16) wherein $Y^{1a}$ and $Y^{1b}$, $Y^{2a}$ and $Y^{2b}$, and $Y^{3a}$ and $Y^{3b}$ are each independently taken together to form oxo, or its pharmaceutically acceptable salt or a solvate thereof.

(21)

The compound according to any one of the above (14) to (20) wherein —X— is —NH—, or its pharmaceutically acceptable salt or a solvate thereof.

(22)

The compound according to any one of the above (14) to (21) wherein $Q^2$ is a carbon atom; $R^2$ is
a group of the formula: —NH—C(=O)—$CR^{8a}R^{8b}$)n-$R^9$, n is an integer of 0 to 4; $R^{8a}$ and
$R^{8b}$ are each independently hydrogen, halogen, hydroxy, or substituted or unsubstituted alkyl; $R^9$ is hydroxy, carboxy, sulfo, tetrazolyl, a substituted or unsubstituted non-aromatic heterocyclic group, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or
a group of the formula: —($CR^{8a}R^{8b}$)m-$R^9$, m is an integer of 1 to 6; and $R^{8a}$, $R^{8b}$ and $R^9$ are as defined above.

(23)

The compound according to any one of the above (14) to (22) wherein $Q^2$ is a nitrogen atom; $R^2$ is C1-C6 alkyl or a group of the formula: —($CR^{8a}R^{8b}$)m-$R^9$, m and $R^9$ are as defined in the above (22), or its pharmaceutically acceptable salt or a solvate thereof.

(24)

A compound of the formula (II):

[Chemical Formula 76]

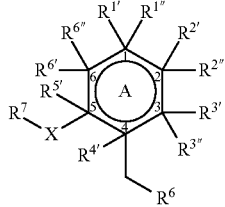

(II)

wherein ring A is a ring of the formula:

[Chemical Formula 77]

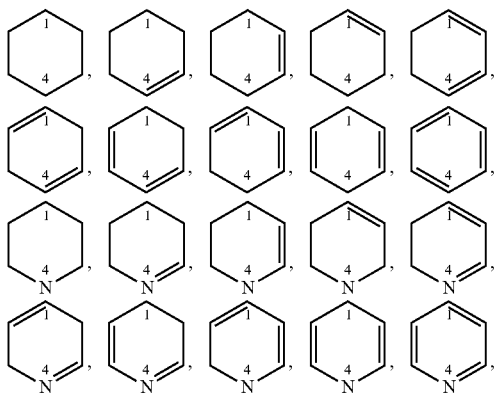

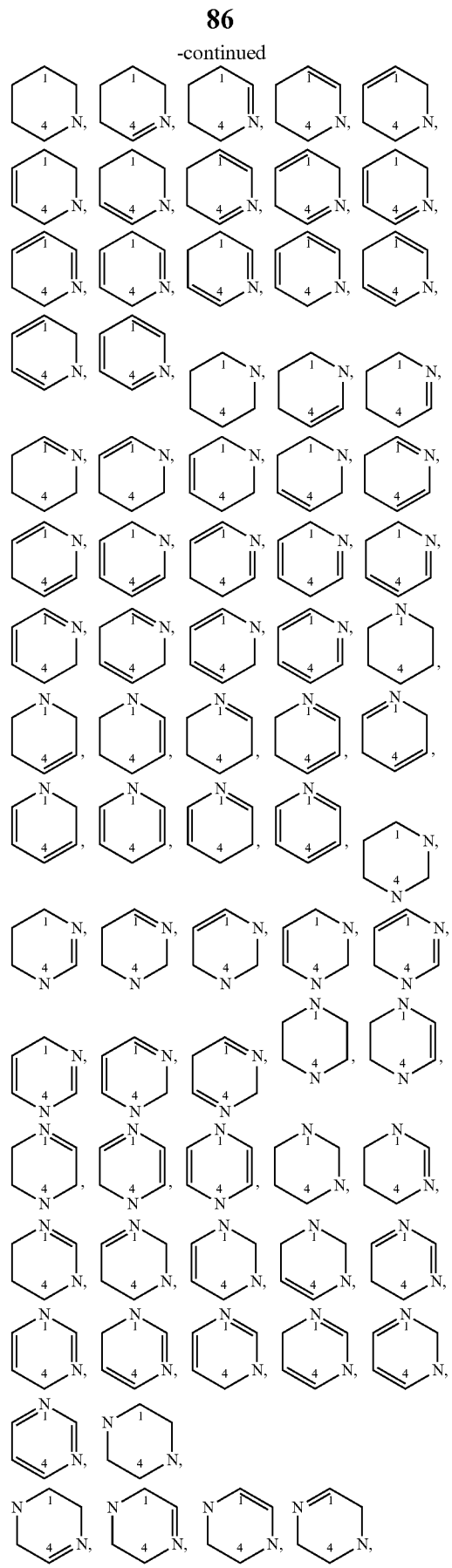

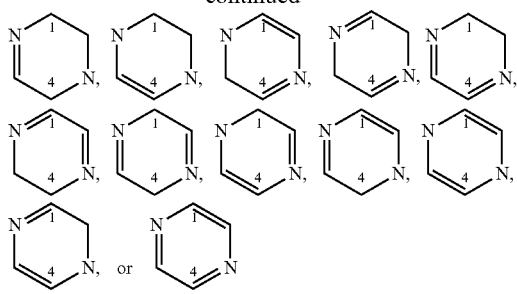

wherein the numbers in the ring correspond to the numbers in ring A of the above formula (II);

$R^{1'}$, $R^{1''}$, $R^{3'}$, $R^{3''}$, $R^{4'}$, $R^{5'}$, $R^{6'}$ and $R^{6''}$ are each independently hydrogen or halogen; or $R^{1'}$ and $R^{1''}$, and/or $R^{3'}$ and $R^{3''}$ are taken together to form oxo;

$R^{2''}$ is hydrogen;

when a ring atom attached to $R^{2'}$ is a carbon atom, then $R^{2'}$ is a group of the formula: —NH—C(═O)—$(CR^{8a}R^{8b})$n-$R^9$ wherein n is an integer of 0 to 4; $R^{8a}$ and $R^{8b}$ are each independently hydrogen, halogen, hydroxy, or substituted or unsubstituted alkyl; $R^9$ is hydroxy, carboxy, sulfo, tetrazolyl, a substituted or unsubstituted non-aromatic heterocyclic group, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or a group of the formula; —$(CR^{8a}R^{8b})$m-$R^9$ wherein in is an integer of 1 to 6; and $R^{8a}$, $R^{8b}$ and $R^9$ are as defined above;

when a ring atom attached to $R^{2'}$ is a nitrogen atom, then $R^{2'}$ is C1-C6 alkyl or a group of the formula: —$(CR^{8a}R^{8b})$m-$R^9$ wherein in is an integer of 1 to 6; $R^{8a}$, $R^{8b}$ and $R^9$ are as defined above;

$R^{4'}$ is hydrogen;

$R^6$ is a group of the formula

[Chemical Formula 78]

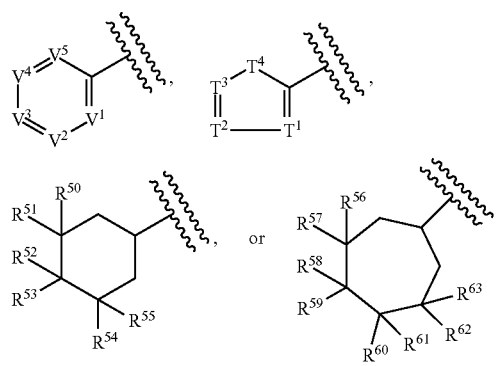

wherein =$V^1$-$V^2$=$V^3$-$V^4$=$V^5$- is a group selected from the following (i) to (p):

(i): ═C(H)—C($R^A$)═C($R^B$)—C($R^C$)═C(H)—;
(j): ═N—C($R^A$)═C($R^B$)—C($R^C$)═C(H)—;
(k): ═C(H)—N═C($R^B$)—C($R^C$)═C(H)—;
(l): ═C(H)—C($R^A$)═N—C($R^C$)═C(H)—;
(m): ═C(H)—C($R^A$)═C($R^B$)—N═C(H)—;
(n): ═N—C($R^A$)═C($R^B$)—C($R^C$)═N—;
(o): ═C(H)—C($R^A$)═N—C($R^C$)═C(H)—; and
(p): ═C(H)—N═C($R^B$)—N═C(H)—;

$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

=$T^1$-$T^2$=$T^3$-$T^4$- is a group selected from the following (q) to (t):

(q): ═C(H)—C($R^D$)═C($R^E$)—S—;
(r): ═C(H)—C($R^D$)═C($R^E$)—O—;
(s): ═N—C($R^D$)═C($R^E$)—S—; and
(t): ═N—C($R^D$)═C($R^E$)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

$R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, hydroxy, cyano, substituted or unsubstituted substituted or unsubstituted alkenyl, substituted or unsubstituted alkynyl, substituted or unsubstituted alkyloxy, substituted or unsubstituted alkenyloxy, or substituted or unsubstituted alkynyloxy;

—X— is —NH— or —CH$_2$—; and $R^7$ is a group of the formula:

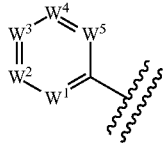

[Chemical Formula 79]

wherein $=W^1-W^2=W^3-W^4=W^5-$ is
$=C(H)-C(R^{10a})=C(R^{10b})-C(R^{10c})=C(H)-;$
$=N-C(R^{10a})=C(R^{10b})-C(R^{10c})=C(H)-;$
$=C(H)-N=C(R^{10b})-C(R^{10c})=C(H)-;$
$=C(H)-C(R^{10a})=N-C(R^{10c})=C(H)-;$
$=C(H)-C(R^{10a})=C(R^{10b})-N=C(H)-;$
$=N-C(R^{10a})=C(R^{10b})-C(R^{10c})=N-;$
$=C(H)-C(R^{10a})=N-C(R^{10c})=C(H)-;$ and
$=C(H)-N=C(R^{10b})-N=C(H)-;$ $R^{10a}$ and $R^{10c}$ are each independently hydrogen, halogen, or haloalkyl;

$R^{10b}$ is substituted or unsubstituted alkyl, substituted or unsubstituted alkyloxy, substituted or unsubstituted aryloxy, substituted or unsubstituted heteroaryloxy, or a substituted or unsubstituted nitrogen-containing non-aromatic heterocyclic group; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring;

provided that (i) when a ring atom attached to $R^{1''}$, $R^{2''}$, $R^{3''}$, $R^{4'}$, $R^{5'}$, or $R^{6''}$ is a nitrogen atom, then $R^{1''}$, $R^{2''}$, $R^{3''}$, $R^{4'}$, $R^{5'}$, or $R^{6''}$ is absent, respectively;

(ii) when a ring atom attached to $R^{1'}$ and $R^{1''}$ is a nitrogen atom, and a bond between the 1-position and the 6-position or a bond between the 1-position and the 2-position is a double bond, then $R^{1'}$ and $R^{1''}$ are absent;

when a ring atom attached to $R^{2'}$ and $R^{2''}$ is a nitrogen atom, and a bond between the 1-position and the 2-position or a bond between the 2-position and the 3-position is a double bond, then $R^{2'}$ and $R^{2''}$ are absent;

when a ring atom attached to $R^{3'}$ and $R^{3''}$ is a nitrogen atom, and a bond between the 2-position and the 3-position or a bond, between the 3-position and the 4-position is a double bond, then $R^{3'}$ and $R^{3''}$ are absent;

when a ring atom attached to $R^{6'}$ and $R^{6''}$ is a nitrogen atom, and a bond between the 5-position and the 6-position or a bond between the 6-position and the 1-position is a double bond, then $R^{6'}$ and $R^{6''}$ are absent; and (iii) when a ring atom attached to $R^{1'}$ and $R^{1''}$ is a carbon atom, and a bond between the 1-position and the 6-position or a bond between the 1-position and the 2-position is a double bond, then $R^{1''}$ is absent;

when a ring atom attached to $R^{2'}$ and $R^{2''}$ is a carbon atom, and a bond between the 1-position and the 2-position or a bond between the 2-position and the 3-position is a double bond, $R^{2''}$ is absent;

when a ring atom attached to $R^{3'}$ and $R^{3''}$ is a carbon atom, and a bond between the 2-position and the 3-position or a bond between the 3-position and the 4-position is a double bond, then $R^{3''}$ is absent;

when a ring atom attached to $R^{4'}$ is a carbon atom, and a bond between the 3-position and the 4-position or a bond between the 4-position and the 5-position is a double bond, then $R^{4'}$ is absent;

when a ring atom attached to $R^{5'}$ is a carbon atom, and a bond between the 4-position and the 5-position or a bond between the 5-position and the 6-position is a double bond, then $R^{5'}$ is absent;

when a ring atom attached to $R^{6'}$ and $R^{6''}$ is a carbon atom, and a bond between the 5-position and the 6-position or a bond between the 6-position and the 1-position is a double bond, then $R^{6''}$ is absent, or its pharmaceutically acceptable salt or a solvate thereof.

(25)

The compound according to the above (24) wherein the compound is

[Chemical Formula 80]

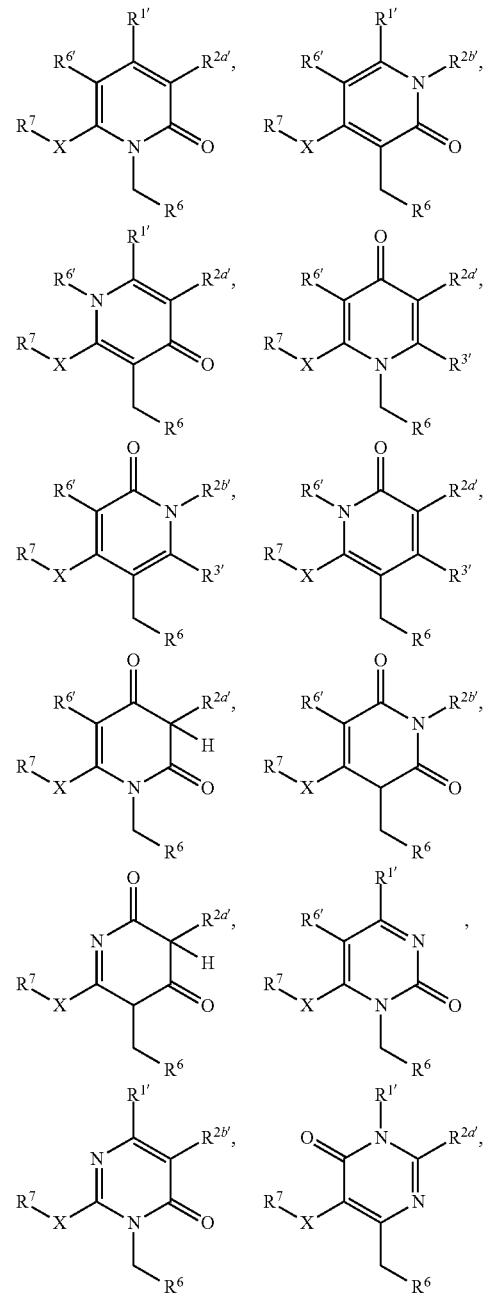

-continued

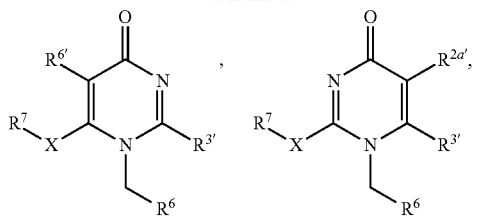
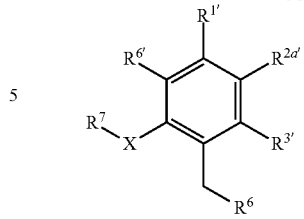

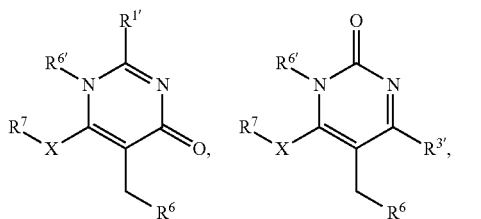

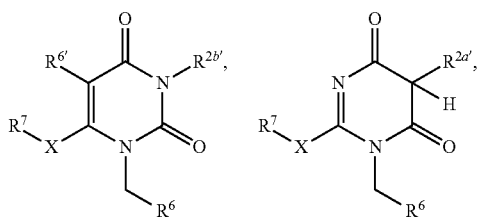

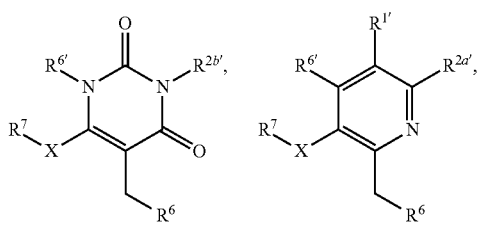

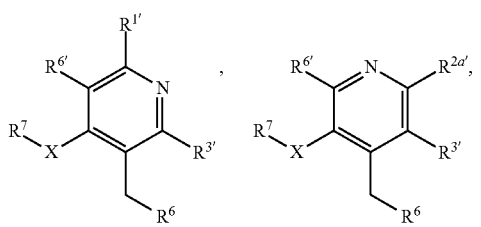

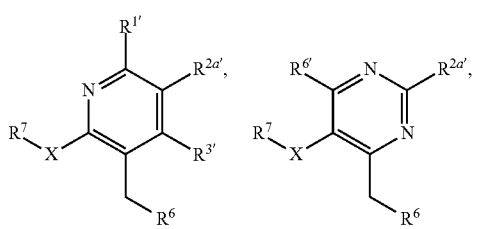

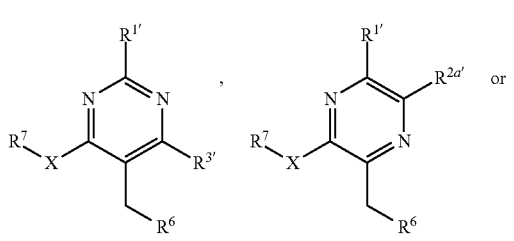

-continued

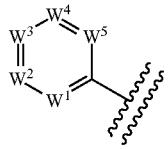

wherein $R^6$ is as defined in the above (24);

$R^{1'}$ and $R^{3'}$ are each independently hydrogen or halogen;

$R^{2a'}$ is a group of the formula: —NH—C(=O)—$(CR^{8a}R^{8b})$n-$R^9$ wherein n is an integer of 0 to 4; $R^{8a}$ and $R^{8b}$ are each independently hydrogen, halogen, hydroxy, or substituted or unsubstituted alkyl; $R^9$ is hydroxy, carboxy, sulfo, tetrazolyl, a substituted or unsubstituted non-aromatic heterocyclic group, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or a group of the formula: —$(CR^{8a}R^{8b})$m-$R^9$ wherein m is an integer of 1 to 6; $R^{8a}$, $R^{8b}$ and $R^9$ are as defined above;

$R^{2b'}$ is C1-C6 alkyl or a group of the formula: —$(CR^{8a}R^{8b})$m-$R^9$ wherein in is an integer of 1 to 6; $R^{8a}$, $R^{8b}$ and $R^9$ are as defined above;

—X— is —NH— or —CH$_2$—;

$R^7$ is a group of the formula:

[Chemical Formula 81]

wherein =$W^1$-$W^2$=$W^3$-$W^4$=$W^5$- is

=C(H)—C($R^{10a}$)=C($R^{10b}$)—C($R^{10c}$)=C(H)—;

=N—C($R^{10a}$)=C($R^{10b}$)—C($R^{10c}$)=C(H)—;

=C(H)—N=C($R^{10b}$)—C($R^{10c}$)=C(H)—;

=C(H)—C($R^{10a}$)=N—C($R^{10c}$)=C(H)—;

=C(H)—C($R^{10a}$)=C($R^{10b}$)—N=C(H)—;

=N—C($R^{10a}$)=C($R^{10b}$)—C($R^{10c}$)=N—;

=C(H)—C($R^{10a}$)=N—C($R^{10c}$)=C(H)—; and

=C(H)—N=C($R^{10b}$)—N=C(H)—;

$R^{10a}$ and $R^{10c}$ are each independently hydrogen, halogen, or haloalkyl;

$R^{10b}$ is substituted or unsubstituted alkyl, substituted or unsubstituted alkyloxy, substituted or unsubstituted aryloxy, substituted or unsubstituted heteroaryloxy, or a substituted or unsubstituted nitrogen-containing non-aromatic heterocyclic group; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, or its pharmaceutically acceptable salt or a solvate thereof.

(26) A compound of the formula (III):
[Chemical Formula 82]
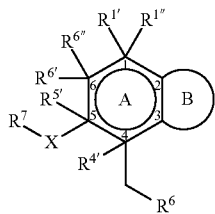
(III)
wherein the ring of the formula:
[Chemical Formula 83]
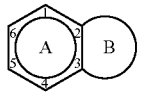
is a ring selected from the following rings wherein the numbers out of the ring correspond to the number in ring A of the above formula (III):
[Chemical Formula 84]
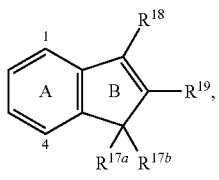
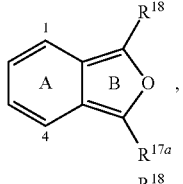
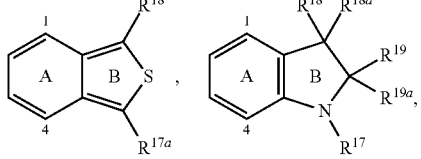
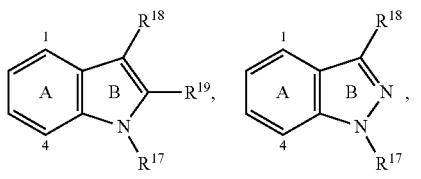
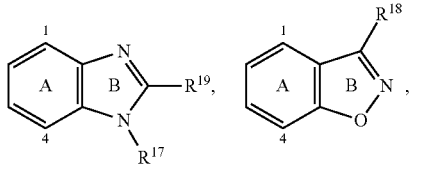
-continued
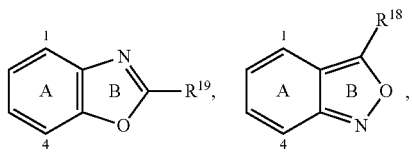
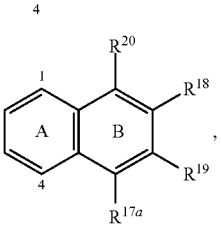
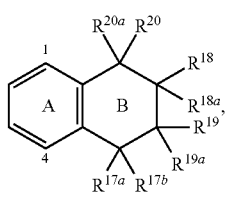
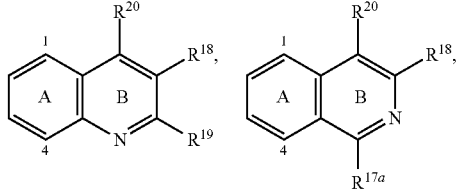
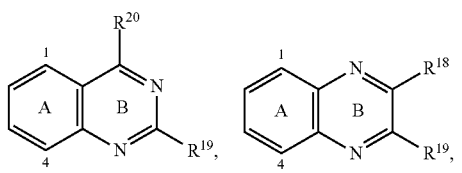
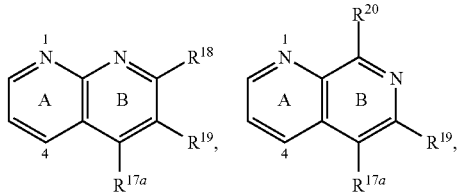
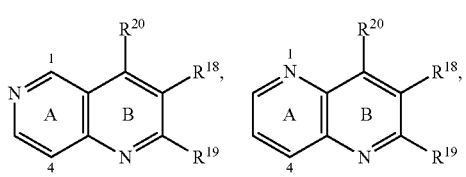
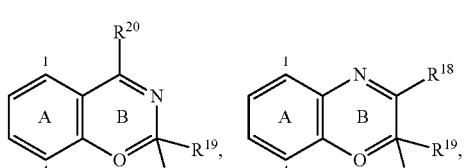
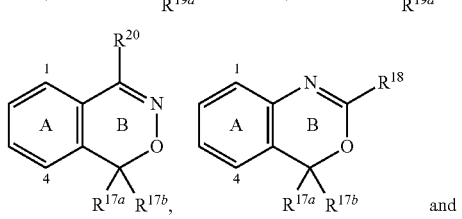
and -continued

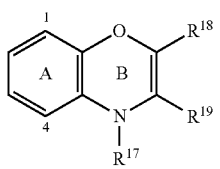

wherein $R^{17a}$, $R^{17b}$, $R^{18a}$, $R^{19a}$ and $R^{20}$ are each independently hydrogen, halogen, substituted or unsubstituted alkyl; or $R^{17a}$ and $R^{17b}$, $R^{18}$ and $R^{18a}$, $R^{19}$ and $R^{19a}$, or/and $R^{20}$ and $R^{20a}$ are taken together to form oxo or thioxo;

$R^{17}$ is hydrogen, halogen, substituted or unsubstituted acyl or substituted or unsubstituted alkyl;

$R^{18}$ and $R^{19}$ are each independently hydrogen, a group of the formula: —NH—C(=O)—(CR$^{8a}$R$^{8b}$)n-R$^9$ wherein n is an integer of 0 to 4; $R^{8a}$ and $R^{8b}$ are each independently hydrogen, halogen, hydroxy, or substituted or unsubstituted alkyl; $R^9$ is hydroxy, carboxy, sulfo, tetrazolyl, a substituted or unsubstituted non-aromatic heterocyclic group, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or a group of the formula: —(CR$^{8a}$R$^{8b}$)m-R$^9$ wherein m is an integer of 1 to 6; $R^{8a}$, $R^{8b}$ and $R^9$ are as defined above;

$R^{1'}$, $R^{1''}$, $R^{5'}$, $R^{6'}$ and $R^{6''}$ are each independently hydrogen or halogen; or $R^{1'}$ and $R^{1''}$ are taken together to form oxo;

$R^{4'}$ is hydrogen;

$R^6$ is a group of the formula

[Chemical Formula 85]

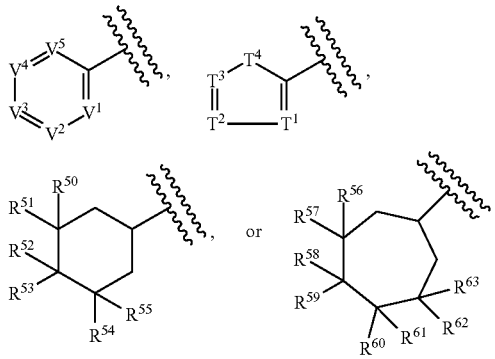

wherein =V$^1$-V$^2$=V$^3$-V$^4$=V$^5$- is a group selected from the following (i) to (p):
(i): =C(H)—C(R$^A$)=C(R$^B$)—C(R$^C$)=C(H)—;
(j): =N—C(R$^A$)=C(R$^B$)—C(R$^C$)=C(H)—;
(k): =C(H)—N=C(R$^B$)—C(R$^C$)=C(H)—;
(l): =C(H)—C(R$^A$)=N—C(R$^C$)=C(H)—;
(m): =C(H)—C(R$^A$)=C(R$^B$)—N=C(H)—;
(n): =N—C(R$^A$)=C(R$^B$)—C(R$^C$)=N—;
(o): =C(H)—C(R$^A$)=N—C(R$^C$)=C(H)—; and
(p): =C(H)—N=C(R$^B$)—N=C(H)—;

$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted oar unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

=T$^1$-T$^2$=T$^3$-T$^4$- is a group selected from the following (q) to (t):
(q): =C(H)—C(R$^D$)=C(R$^E$)—S—;
(r): =C(H)—C(R$^D$)=C(R$^E$)—O—;
(s): =N—C(R$^D$)=C(R$^E$)—S—; and
(t): =N—C(R$^D$)=C(R$^E$)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

$R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, hydroxy, cyano, substituted or unsubstituted substituted or unsubstituted alkenyl, substituted or unsubstituted alkynyl, substituted or unsubstituted alkyloxy, substituted or unsubstituted alkenyloxy, or substituted or unsubstituted alkynyloxy;

—X— is —NH— or —CH$_2$—;

$R^7$ is a group of the formula:

[Chemical Formula 86]

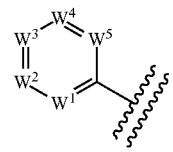

wherein =W$^1$-W$^2$=W$^3$-W$^4$=W$^5$- is
=C(H)—C(R$^{10a}$)=C(R$^{10b}$)—C(R$^{10c}$)=C(H)—;
=N—C(R$^{10a}$)=C(R$^{10b}$)—C(R$^{10c}$)=C(H)—;

=C(H)—N=C(R$^{10b}$)—C(R$^{10c}$)=C(H)—;
=C(H)—C(R$^{10a}$)=N—C(R$^{10c}$)=C(H)—;
=C(H)—C(R$^{10a}$)=C(R$^{10b}$)—N=C(H)—;
=N—C(R$^{10a}$)=C(R$^{10b}$)—C(R$^{10c}$)=N—;
=C(H)—C(R$^{10a}$)=N—C(R$^{10c}$)=C(H)—; and
=C(H)—N=C(R$^{10b}$)—N=C(H)—;

R$^{10a}$ and R$^{10c}$ are each independently hydrogen, halogen, or haloalkyl;

R$^{10b}$ is substituted or unsubstituted alkyl, substituted or unsubstituted alkyloxy, substituted or unsubstituted aryloxy, substituted or unsubstituted heteroaryloxy, or a substituted or unsubstituted nitrogen-containing non-aromatic heterocyclic group; or R$^{10a}$ and R$^{10b}$, or R$^{10b}$ and R$^{10c}$ together with ring atoms to which they are attached form a non-aromatic carbocyclic ring, a non-aromatic heterocyclic ring, an aromatic carbocyclic ring, or an aromatic heterocyclic ring;

provided that (i) when a ring atom attached to R$^{1''}$, R$^{4'}$, R$^{5'}$, or R$^{6''}$ is a nitrogen atom, then R$^{1''}$, R$^{4'}$, R$^{5'}$, or R$^{6''}$ is absent, respectively;

(ii) when a ring atom attached to R$^{1'}$ and R$^{1''}$ is a nitrogen atom, and a bond between the 1-position and the 6-position or a bond between the 1-position and the 2-position is a double bond, then R$^{1'}$ and R$^{1''}$ are absent;

when a ring atom attached to R$^{6'}$ and R$^{6''}$ is a nitrogen atom, and a bond between the 5-position and the 6-position or a bond between the 6-position and the 1-position is a double bond, then R$^{6'}$ and R$^{6''}$ are absent; and (iii) when a ring atom attached to R$^{1'}$ and R$^{1''}$ is a carbon atom, a bond between the 1-position and the 6-position or a bond between the 1-position and the 2-position is a double bond, then R$^{1''}$ is absent;

when a ring atom attached to R$^{4'}$ is a carbon atom, and a bond between the 3-position and the 4-position or a bond between the 4-position and the 5-position is a double bond, then R$^{4'}$ is absent;

when a ring atom attached to R$^{5'}$ is a carbon atom, and a bond between the 4-position and the 5-position or a bond between the 5-position and the 6-position is a double bond, then R$^{5'}$ is absent;

when a ring atom attached to R$^{6'}$ and R$^{6''}$ is a carbon atom, and a bond between the 5-position and the 6-position or a bond between the 6-position and the 1-position is a double bond, then R$^{6''}$ is absent, or its pharmaceutically acceptable salt or a solvate thereof.

(27)
A compound of the formula:

[Chemical Formula 87]

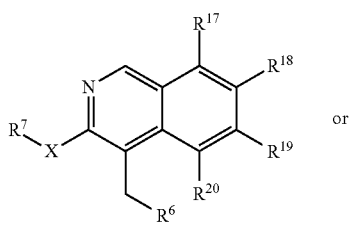

or

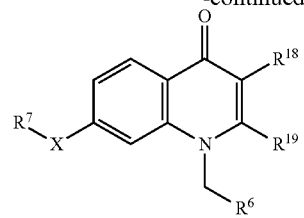

-continued wherein
R$^{17}$, R$^{19}$ and R$^{20}$ are each independently hydrogen or halogen;
R$^{18}$ is hydrogen,
a group of the formula: —NH—C(=O)—(CR$^{8a}$R$^{8b}$)n-R$^9$ wherein n is an integer of 0 to 4; R$^{8a}$ and R$^{8b}$ are each independently hydrogen, halogen, hydroxy, or substituted or unsubstituted alkyl; R$^9$ is hydroxy, carboxy, sulfo, tetrazolyl, a substituted or unsubstituted non-aromatic heterocyclic group, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or a group of the formula: —(CR$^{8a}$R$^{8b}$)m-R$^9$ wherein m is an integer of 1 to 6; R$^{8a}$, R$^{8b}$ and R$^9$ are as defined above;
R$^6$ is

[Chemical Formula 88]

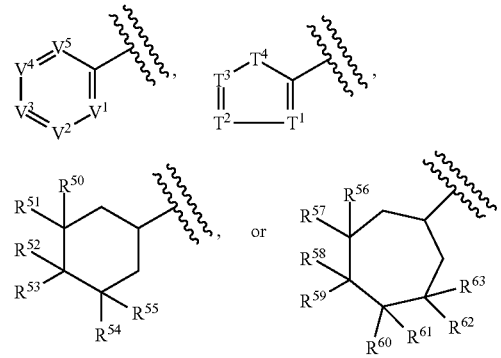

wherein =V$^1$-V$^2$=V$^3$-V$^4$=V$^5$- is a group selected from the following (i) to (p):
(i): =C(H)—C(R$^A$)=C(R$^B$)—C(R$^C$)=C(H)—;
(j): =N—C(R$^A$)=C(R$^B$)—C(R$^C$)=C(H)—;
(k): =C(H)—N=C(R$^B$)—C(R$^C$)=C(H)—;
(l): =C(H)—C(R$^A$)=N—C(R$^C$)=C(H)—;
(m): =C(H)—C(R$^A$)=C(R$^B$)—N=C(H)—;
(n): =N—C(R$^A$)=C(R$^B$)—C(R$^C$)=N—;
(o): =C(H)—C(R$^A$)=N—C(R$^C$)=C(H)—; and
(p): =C(H)—N=C(R$^B$)—N=C(H)—;
R$^A$, R$^B$ and R$^C$ are each independently hydrogen, halogen, hydroxy, cyano, nitro, substituted or unsubstituted alkyl, substituted or unsubstituted alkenyl, substituted qtr unsubstituted alkynyl, substituted or unsubstituted alkyloxy, substituted or unsubstituted, alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy- or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

$=T^1-T^2=T^3-T^4-$ is a group selected from the following (q) to (t):

(q): $=C(H)-C(R^D)=C(R^E)-S-$;
(r): $=C(H)-C(R^D)=C(R^E)-O-$;
(s): $=N-C(R^D)=C(R^E)-S-$; and
(t): $=N-C(R^D)=C(R^E)-O-$;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring;

$R^{50}, R^{51}, R^{52}, R^{53}, R^{54}, R^{55}, R^{56}, R^{57}, R^{58}, R^{59}, R^{60}, R^{61}, R^{62}$, and $R^{63}$ are each independently hydrogen, halogen, hydroxy, cyano, substituted or unsubstituted substituted or unsubstituted alkenyl, substituted or unsubstituted alkynyl, substituted or unsubstituted alkyloxy, substituted or unsubstituted alkenyloxy, or substituted or unsubstituted alkynyloxy;

$-X-$ is $-NH-$ or $-CH_2-$;

$R^7$ is a group of the formula:

[Chemical Formula 89]

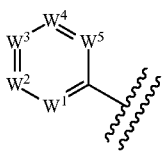

wherein $=W^1-W^2=W^3-W^4=W^5-$ is
$=C(H)-C(R^{10a})=C(R^{10b})-C(R^{10c})=C(H)-$;
$=N-C(R^{10a})=C(R^{10b})-C(R^{10c})=C(H)-$;
$=C(H)-N=C(R^{10b})-C(R^{10c})=C(H)-$;
$=C(H)-C(R^{10a})=N-C(R^{10c})=C(H)-$;
$=C(H)-C(R^{10a})=C(R^{10b})-N=C(H)-$;
$=N-C(R^{10a})=C(R^{10b})-C(R^{10c})=N-$;
$=C(H)-C(R^{10a})=N-C(R^{10c})=C(H)-$; and
$=C(H)-N=C(R^{10b})-N=C(H)-$;

$R^{10a}$ and $R^{10c}$ are each independently hydrogen, halogen, or haloalkyl;

$R^{10b}$ is substituted or unsubstituted alkyl, substituted or unsubstituted alkyloxy, substituted or unsubstituted aryloxy, substituted or unsubstituted heteroaryloxy, or a substituted or unsubstituted nitrogen-containing non-aromatic heterocyclic group; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, or its pharmaceutically acceptable salt or a solvate thereof.

(28)

The compound according to any one of the above (24) to (27) wherein n is an integer of 1 to 3, and $R^9$ is hydroxy, carboxy, substituted or unsubstituted alkyloxycarbonyl, substituted or unsubstituted carbamoyl, substituted or unsubstituted sulfamoyl, or substituted or unsubstituted amino, or its pharmaceutically acceptable salt or a solvate thereof.

(29)

The compound according to any one of the above (26) to (28) wherein $R^{18}$ is a group of the formula; $-NH-C(=O)-(CR^{8a}R^{8b})n-R^9$ wherein n is an integer of 0 to 4; $R^{8a}$ and $R^{8b}$ are each independently hydrogen, halogen, hydroxy, or substituted or unsubstituted alkyl; and $R^9$ is hydroxy, carboxy, sulfo, tetrazolyl, a substituted or unsubstituted non-aromatic heterocyclic group, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, or its pharmaceutically acceptable salt or a solvate thereof.

(30)

The compound according to any one of the above (24) to (29) wherein $R^A, R^B, R^C, R^D, R^E, R^{50}, R^{51}, R^{52}, R^{53}, R^{54}, R^{55}, R^{56}, R^{57}, R^{58}, R^{59}, R^{60}, R^{61}, R^{62}$, and $R^{63}$ are each independently hydrogen, halogen, alkyl, or alkyloxy, or its pharmaceutically acceptable salt or a solvate thereof.

(31)

The compound according to the above (30) wherein $R^6$ is phenyl, thienyl, cyclohexyl, cycloheptyl: $R^A, R^B, R^C, R^D, R^E, R^{50}, R^{51}, R^{52}, R^{53}, R^{54}, R^{55}, R^{56}, R^{57}, R^{58}, R^{59}, R^{60}, R^{61}, R^{62}$, and $R^{63}$ are each independently hydrogen, halogen, alkyl, or alkyloxy, or its pharmaceutically acceptable salt or a solvate thereof.

(32)

The compound according to any one of the above (24) to (31) wherein $-X-$ is $-NH-$, or its pharmaceutically acceptable salt or a solvate thereof.

(33)

The compound according to any one of the above (14) to (23) and (24) to (32) wherein $R^7$ is a group of the formula:

[Chemical Formula 90]

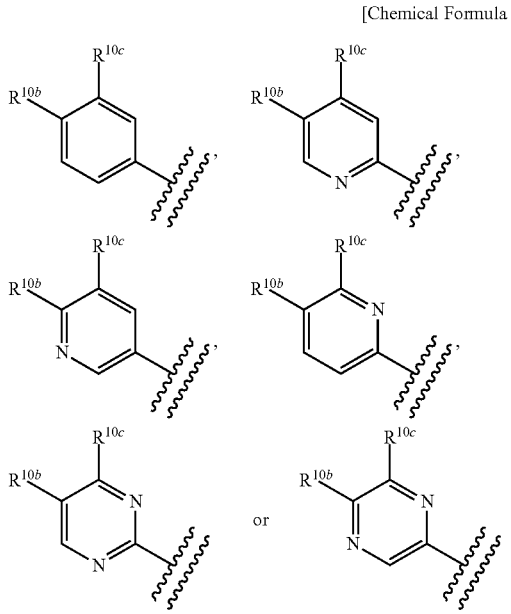

or the formula:

[Chemical Formula 91]

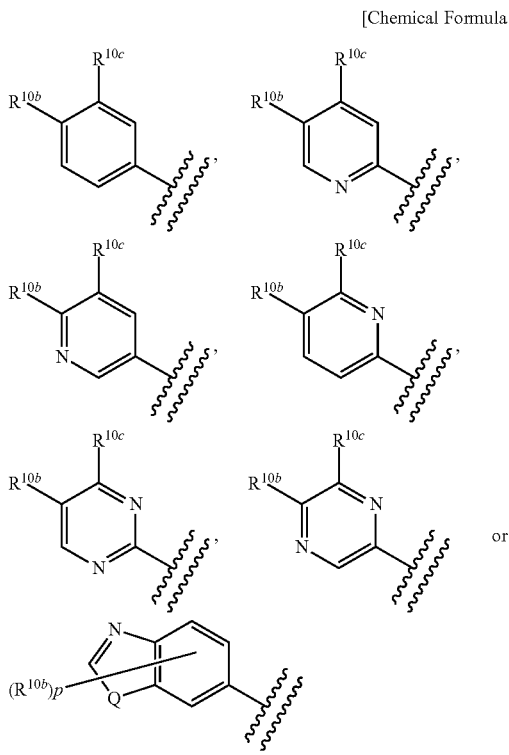

wherein Q is an oxygen atom or a nitrogen atom; p is an integer of 0 to 3; $R^{10b}$ is substituted or unsubstituted alkyl, substituted or unsubstituted alkyloxy, substituted or unsubstituted aryloxy, substituted or unsubstituted heteroaryloxy, or a substituted or unsubstituted nitrogen-containing non-aromatic heterocyclic group; $R^{10c}$ is hydrogen, halogen, or haloalkyl; or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, or its pharmaceutically acceptable salt or a solvate thereof.

In the above (33), preferable "heteroaryl" in "heteroaryloxy" for $R^{10b}$ is thiazole, isothiazole, oxazole, isoxazole, pyrazole, imidazole, triazole, furan, thiophen, thiadiazole, oxadiazole, pyridine, pyrimidine, pyrazine, pyridazine, triazine or benzoxazole.

(34)

The compound according to any one of the above (14) to (23) and (24) to (33) wherein $R^7$ is a group of the formula:

[Chemical Formula 92]

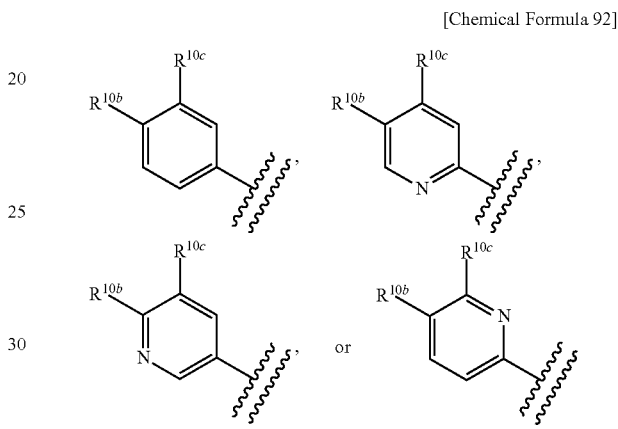

or the formula:

[Chemical Formula 93]

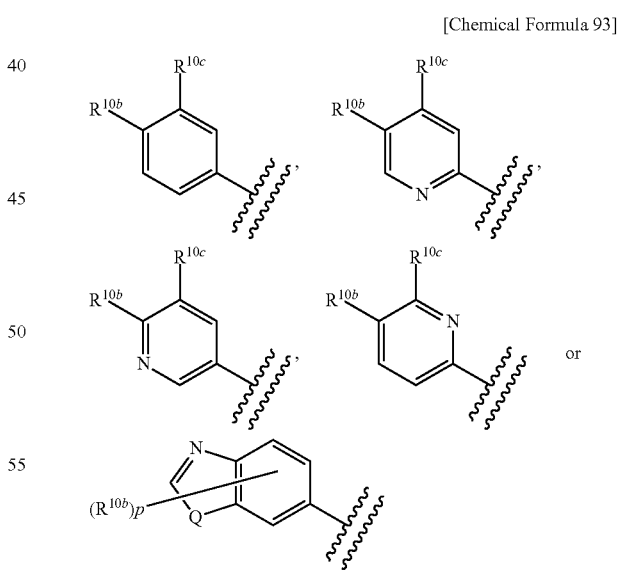

wherein Q, p, $R^{10b}$ and $R^{10c}$ are as defined in the above (33), or its pharmaceutically acceptable salt or a solvate thereof.

(35)

A pharmaceutical composition comprising the compound according to any one of the above (14) to (34), or its pharmaceutically acceptable salt or a solvate thereof.

(36)

A pharmaceutical composition according to the above (35), which as a P2X$_3$ and/or P2X$_{2/3}$ receptor antagonistic effect.

(37)

A method for treating and/or preventing a disease related to P2X$_3$ and/or P2X$_{2/3}$ receptor comprising administering the compound according to any one of the above (14) to (34), or its pharmaceutically acceptable salt or a solvate thereof, (38)

A compound according to any one of the above (14) to (34), or its pharmaceutically acceptable salt, or a solvate thereof for use in a method for treating and/or preventing a disease related to P2X$_3$ and/or P2X$_{2/3}$ receptor.

Effect of the Invention

The compound of the invention has an antagonistic effect on P2X$_3$ and/or P2X$_{2/3}$ receptor and is useful in the treatment of diseases or conditions associated with a P2X$_3$ and/or P2X$_{2/3}$ receptor, especially chronic pain, overactive bladder, etc.

MODE FOR CARRYING OUT THE INVENTION

The terms used in this description are explained below. The meanings of the terms are as follows unless otherwise specified:

The term "halogen" means fluoro, chloro, bromo and iodo.

The halogen moiety in said "haloalkyl" and "haloalkyloxy" is as defined above for "halogen".

The term "alkyl" includes straight-chain or branched-chain monovalent hydrocarbon groups having a carbon number of 1 to 15, as one embodiment 1 to 10, and as another embodiment 1 to 6. Examples of "alkyl" include methyl, ethyl, n-propyl, isopropyl, n-butyl, isobutyl, sec butyl, tert-butyl, n-pentyl, isopentyl, neopentyl, n-hexyl, isohexyl, n-heptyl, isoheptyl, n-octyl, isooctyl, n-nonyl, n-decyl, n-undecanyl, dodecenyl, and tridecenyl.

The alkyl moiety in said "haloalkyl", "alkylamino", "alkylimino", "alkylsulfonyl", "alkylsulfamoyl", "alkylcarbamoyl", "arylalkyl", and "arylalkylamino" is as defined above for "alkyl".

The term "alkyloxy" includes alkyloxy groups in which the alkyl moiety is as defined above "alkyl". Examples of "alkyloxy" include methoxy, ethoxy, propoxy, isopropoxy, butoxy, isobutoxy, sec-butoxy, tert-butoxy, pentyloxy, isopentyloxy, neopentyloxy, and hexyloxy.

The alkyloxy moiety in said "haloalkyloxy" and "alkyloxyimino" is as defined above for "alkyloxy".

Examples of "alkylthio" include methylthio, ethylthio, propylthio, isopropylthio, butylthio, isobutylthio, sec-butylthio, tert-butylthio, pentylthio, isopentylthio, neopentylthio, and hexylthio.

Examples of "alkyloxycarbonyl" include methyloxycarbonyl, ethyloxycarbonyl, n-propyloxycarbonyl, isopropyloxycarbonyl, n-butyloxycarbonyl, and tert-butyloxycarbonyl, n-pentyloxycarbonyl.

Examples of "alkylcarbamoyl" include mono- or dialkylcarbamoyl groups such as methylcarbamoyl, ethylcarbamoyl, n-propylcarbamoyl, isopropylcarbamoyl, cyclopropylcarbamoyl, n-butylcarbamoyl, dimethylcarbamoyl, diethylcarbamoyl, and dipropylcarbamoyl groups.

The term "alkenyl" includes linear or branched alkenyl having at least one double bond at any position and having a carbon number of 2 to 15, as one embodiment 2 to 10, and as another embodiment 2 to 6. Examples of "alkenyl" include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, and tridecenyl.

The alkenyl moiety in said "alkenyloxy", "alkenylthio", "alkenyloxycarbonyl" and "alkenylcarbamoyl" is as defined above for "alkenyl".

The term "alkynyl" includes linear or branched alkynyl having a carbon number of 2 to 15, as one embodiment 2 to 10, and as another embodiment 2 to 6. Examples of "alkynyl" include ethynyl, propynyl, butynyl, pentynyl, hexynyl, heptynyl, octynyl, nonyl, and decynyl. These have at least one triple bond at any position and may further have a double bond.

The alkynyl moiety in said "alkynyloxy", "alkynylthio", "alkynyloxycarbonyl" and "alkenylcarbamoyl" is as defined above for "alkynyl".

The term "acyl" includes groups of R—C(=O)—. Examples of R include above-mentioned "alkyl", "alkenyl", and "alkynyl" and after-mentioned "cycloalkyl", "cycloalkenyl", "non-aromatic heterocyclic group", "aryl", and "heteroaryl".

The "acyl" moiety in said "acylamino" and "acylimino" is as defined above for "acyl".

The term "cycloalkane" includes monocyclic or polycyclic saturated carbocycles having a carbon number of 3 to 10. Examples of monocyclic cycloalkanes include cyclopropane, cyclobutane, cyclopentane, cyclohexane, cycloheptane, cyclooctane, cyclononane, and cyclodecane. As one embodiment, the cycloalkane is C3 to C8 cycloalkane. As another embodiment, the cycloalkane is C3 to C7 cycloalkane. Examples of polycyclic cycloalkanes include norbornane and decahydronaphthalene.

The term "cycloalkyl" includes monovalent groups derived from the aforementioned "cycloalkane". Examples of monocyclic cycloalkyls include cyclopropyl, cyclobutyl, cyclopentyl, cyclohexyl, cycloheptyl, cyclooctyl, cyclononyl, and cyclodecyl. Examples of polycyclic cycloalkyls include norbornyl, decahydronaphthalene-5-yl, and decahydronaphthalene-6-yl. As one embodiment, the cycloalkyl is C3 to C8 cycloalkyl. As another embodiment, the cycloalkyl is C3 to C7 cycloalkyl.

Examples of "cycloalkyl" in $R^2$ include cyclopentyl, cyclohexyl, cycloheptyl, and cyclooctyl.

Examples of "cycloalkyl" in $R^6$ include cyclopentyl, cyclohexyl, cycloheptyl, and cyclooctyl.

The "cycloalkyl" moiety in said "cycloalkyloxycarbonyl" is as defined above for "cycloalkyl".

The term "cycloalkanediyl" includes divalent groups derived from the aforementioned "cycloalkane". Examples of monocyclic cycloalkanediyls include cyclopropanediyl, cyclobutanediyl, cyclopentanediyl, cyclohexanediyl, cycloheptanediyl, cyclooctanediyl, cyclononanediyl, and cyclodecanediyl. Examples of polycyclic cycloalkanediyls include norbornanediyl.

The term "cycloalkene" includes non-aromatic monocyclic oar polycyclic rings having at least one carbon-carbon double bond and having a carbon number of 3 to 10. Examples of monocyclic cycloalkenes include cyclopentene and cyclohexene. As one embodiment, the monocyclic cycloalkene is C3 to C8 cycloalkene. As another embodiment, the monocyclic cycloalkene is C3 to C7 cycloalkene. Examples of polycyclic cycloalkenes included norbornene and indene.

The term "cycloalkenyl" includes monovalent groups derived from the aforementioned "cycloalkene". Examples of monocyclic cycloalkenyls include cyclopentenyl and cyclohexenyl. As one embodiment, the monocyclic cycloalkenyl is C3 to C8 cycloalkyl. As another embodiment, the monocyclic cycloalkenyl is C3 to C7 cycloalkyl. Examples of polycyclic cycloalkenyls include norbornenyl, indene-1-yl, indene-2-yl, and indene-3-yl.

The "cycloalkenyl" moiety in said "cycloalkenyloxycarbonyl" is as defined above for "cycloalkenyl".

The term "cycloalkenediyl" includes divalent groups derived from the aforementioned "cycloalkene". Examples of monocyclic cycloalkenediyls include cyclopentenediyl and cyclohexenediyl. Examples of polycyclic cycloalkenediyls include norbornenediyl.

The term "aromatic carbocyclic ring" includes monocyclic or fused-ring aromatic hydrocarbon rings. Examples of "aromatic carbocyclic ring" include benzene rings, naphthalene rings, anthracene rings, and phenanthrene rings.

The term "aryl" means a monovalent group derived from the aforementioned "aromatic carbocyclic ring". Examples of "aryl" include phenyl, 1-naphthyl, 2-naphthyl, anthryl, and phenanthryl.

The "aryl" moiety in said "aryloxy", "arylthio", and "aryloxycarbonyl" is as defined above for "aryl".

The term "aromatic carbocyclediyl" includes divalent groups derived from the aforementioned "aromatic carbocyclic ring". Examples of "aromatic carbocyclediyl" include 1,2-phenylene, 1,3-phenylene, 1,4-phenylene, and 1,2-naphthylene.

The term "heterocyclic ring" includes
5- to 7-membered rings having at least one atom selected from nitrogen atom, oxygen atom, and/or sulfur atom in the ring;
rings fused at least two rings independently selected from the above-mentioned rings; and
aromatic or non-aromatic fused rings derived from rings fused 5- to 7-membered rings having at least one nitrogen atom, oxygen atom, and/or sulfur atom in the ring to at least one of the aforementioned "aromatic carbocyclic ring", the aforementioned "cycloalkane", and the aforementioned "cycloalkene".

Examples of "heterocyclic ring" include
monocyclic non-aromatic heterocyclic rings such as pyrroline, pyrrolidine, piperidine, piperazine, morpholine, thiomorphone, tetrahydropyran, dihydropyridine, dihydropyridazine, dioxane, oxathiolane, thiane, dihydroimidazole, tetrahydrofuran, tetrahydropyran, tetrahydrothiazole, tetrahydropyridazine, tetrahydroisothiazole, triazepine, dihydrotriazepine, and tetrahydrotriazepine;
monocyclic aromatic heterocyclic rings such as pyrrole, pyrazine, pyrazole, tetrazole, furan, thiophene, pyridine, imidazole, triazole, tetrazole, triazine, pyridazine, pyrimidine, isoxazole, thiazole, isothiazole, thiadiazole, oxazole, and oxadiazole; and fused heterocyclic rings such as indole, isoindole, indazole, indolidine, indoline, isoindoline, quinoline, isoquinoline, cinnoline, phthalazine, quinazoline, naphthyridine, quinoxaline, purine, pteridine, benzopyran, benzimidazole, benzisoxazole, benzoxazole, benzoxadiazole, benzoisothiazole, benzothiazole, benzothiadiazole, benzofuran, isobenzofuran, benzothiophene, benzotriazole, imidazopyridine, triazolopyridine, imidazothiazole, pyrazinopyridazine, benzimidazole, benzodioxane, tetrahydroquinoline, and tetrahydrobenzothiophene.

The term "heterocyclic group" includes monovalent groups derived from the aforementioned "heterocyclic ring".

Examples of "heterocyclic group" include
monocyclic non-aromatic heterocyclyls such as pyrrolinyl, pyrrolidine, pyrrolidinyl, imidazolinyl, imidazolidinyl, pyrazolinyl, pyrazolidinyl, piperidino, piperidyl, piperazino, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, dihydroimidazolyl, tetrahydrofuryl, tetrahydropyranyl, tetrahydrothiazolinyl, tetrahydropyridazinyl, tetrahydroisothiazolinyl, triazepinyl, dihydrotriazepinyl, and tetrahydrotriazepinyl;
monocyclic aromatic heterocyclyls such as pyrrolyl, pyrazinyl, pyrazolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl, and oxadiazolyl; and
fused heterocyclyls such as indolyl, isoindolyl, indazolyl, indolizinyl, isoindolinyl, quinolyl, isoquinolyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolinyl, benzodioxanyl, tetrahydroquinoline, and tetrahydrobenzothienyl.

The term "heterocyclediyl" includes divalent groups derived from the aforementioned "heterocyclic ring".

Examples of "heterocyclediyl" include
monocyclic non-aromatic heterocyclediyls such as pyrrolinediyl, pyrrolidinediyl, imidazolidinediyl, pyrazolinediyl, pyrazolidinediyl, piperidinediyl, piperazinediyl, morpholinediyl, thiomorpholinediyl, tetrahydropyrandiyl, dihydropyridinediyl, dihydropyridazinediyl, dihydropyrazinediyl, dioxanediyl, oxathiolanediyl, thianediyl, dihydroimidazolediyl, tetrahydrofurandiyl, tetrahydropyrandiyl, tetrahydrothiazolediyl, tetrahydropyridazinediyl, tetrahydroisothiazolediyl, triazepinediyl, dihydrotriazepinediyl, and tetrahydrotriazepinediyl;
monocyclic aromatic heterocyclediyls such as pyrrolediyl, pyrazinediyl, pyrazolediyl, tetrazolediyl, furandiyl, thiophenediyl, pyridinediyl, imidazolediyl, triazolediyl, tetrazolediyl, triazinediyl, pyridazinediyl, pyrimidinediyl, pyrazinediyl, isooxazolediyl, thiazolediyl, isothiazolediyl, thindiazolediyl, oxazolediyl, and oxadiazolediyl; and
fused heterocyclediyls such as indolediyl, isoindolediyl, indazolediyl, indolinediyl, isoquinolinediyl, cinnolinediyl, quinazolinediyl, naphthyridinediyl, quinoxalinediyl, purinediyl, pteridinediyl, benzopyrandiyl, benzimidazolediyl, benzisoxazolediyl, berizoxazolediyl, benzoxadiazolediyl, benzisothiazolediyl, benzothiazolediyl, benzothiadiazolediyl, benzofurandiyl, isobenzofurandiyl, benzothiophenediyl, benzotriazolechyl, imidazopyridinediyl, triazolopyridinediyl, imidazothiazolediyl, pyrazinopyridazinediyl, benzimidazolinediyl, benzodioxanediyl, tetrahydroquinolinediyl, and tetrahydrobenzothiophenediyl.

The term "non-aromatic carbocyclic ring" includes the aforementioned "cycloalkane", the aforementioned "cycloalkene", and rings fused the aforementioned "cycloalkane" or the aforementioned "cycloalkene" to the aforementioned "aromatic carbocyclic ring". Examples of fused rings include indene.

The term "non-aromatic carbocyclic group" includes monovalent groups derived from the aforementioned "non-aromatic carbocyclic ring". Examples of "non-aromatic carbocyclic group" include cyclopropyl, cyclobutyl, cyclopentyl, cyclohexyl, cycloheptyl, cyclooctyl, cyclononyl, cyclodecyl, cyclopentenyl, cyclohexenyl, norbornyl, tetrahydronaphthalene-5-yl, tetrahydronaphthalene-6-yl, norbornenyl, indene-1-yl, indene-2-yl, and indene-3-yl.

The "non-aromatic carbocyclic ring" moiety in said "non-aromatic carbocyclyloxy", "non-aromatic carbocyclylthio", and "non-aromatic carbocyclyloxycarbonyl" is as defined above for "non-aromatic carbocyclic ring".

The term "aromatic heterocyclic ring" includes aromatic rings in the aforementioned "heterocyclic ring".

"Aromatic heterocyclic ring" includes 5- to 7-membered aromatic rings having at least one nitrogen atom, oxygen atom, and/or sulfur atom in the ring;

aromatic rings fused at least two rings independently selected from the above-mentioned rings; and aromatic rings fused 5- to 7-membered aromatic rings having at least one nitrogen atom, oxygen atom, and/or sulfur atom in the rings to at least one of the aforementioned "aromatic carbocyclic ring".

Examples of "aromatic heterocyclic ring" include monocyclic aromatic heterocyclic rings such as pyrazine, pyrazole, tetrazole, furan, thiophene, pyridine, imidazole, triazole, triazine, pyridazine, pyrimidine, pyrazine, isoxazole, thiazole, isothiazole, thiadiazole, oxazole, and oxadiazole; and fused aromatic heterocyclic rings such as indole, isoindole, indazole, indolidine, quinoline, isoquinoline, cinnoline, phthalazine, quinazoline, naphthyldine, quinoxaline, purine, pteridine, benzimidazole, benzisooxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, and benzimidazoline.

The term "heteroaryl" includes monovalent groups derived from the aforementioned "aromatic heterocyclic ring". "Heteroaryl" includes 5- to 7-membered aromatic cyclic groups having at least one nitrogen atom, oxygen atom, and/or sulfur atom in the ring;

fused aromatic cyclic groups fused at least two rings independently selected from the above-mentioned cyclic groups; and aromatic cyclic groups fused 5- to 7-membered aromatic rings having at least one nitrogen atom, oxygen atom, and/or sulfur atom in the ring to at least one of the aforementioned "aromatic carbocyclic ring".

Examples of "heteroaryl" include monocyclic heteroaryls such as pyrrolyl, pyrazinyl, pyrazolyl, indolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl, and oxadiazolyl; and fused heteroaryls such as isoindolyl, indazolyl, indolizinyl, isoindolinyl, quinolyl, isoquinolyl, phthalazinyl, quinazolinyl, naphthyridinyl, quinoxalinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, and benzimidazolinyl.

Examples of "heteroaryl" in $R^2$ include pyridyl.

Examples of "heteroaryl" in $R^7$ include pyridyl, pyrimidyl, benzofuryl, benzothienyl, indolyl, benzoisoxazolyl, and benzothiazolyl.

The "heteroaryl" moiety in said "heteroaryloxy", "heteroarylthio", and "heteroaryloxycarbonyl" is as defined above for "heteroaryl".

The term "non-aromatic heterocyclic ring" includes non-aromatic rings in the aforementioned "heterocyclic ring".

"Non-aromatic heterocyclic ring" includes 5- to 7-membered non-aromatic rings having at least one nitrogen atom, oxygen atom, and/or sulfur atom in the ring;

non-aromatic rings fused at least two rings independently selected from the above-mentioned cyclic groups;

rings fused 5- to 7-membered aromatic rings having at least one nitrogen atom, oxygen atom, and/or sulfur atom in the ring to at least one of the aforementioned "cycloalkane" and the aforementioned "cycloalkane"; and rings fused 5- to 7-membered non-aromatic heterocyclic rings having at least one nitrogen atom, oxygen atom, and/or sulfur atom in the ring to at least one of the aforementioned "aromatic carbocyclic ring" and "non-aromatic carbocyclic ring".

Examples of non-aromatic heterocyclic rings include monocyclic non-aromatic heterocyclic rings such as pyrroline, pyrrolidine, imidazoline, imidazolidine, pyrazoline, pyrazolidine, piperidine, piperazine, morpholine, thiomorpholine, thiomorpholine, tetrahydropyran, dihydropyridine, dihydropyridazine, dihydropyrazine, dioxane, oxathiolane, thiane, dihydroimidazole, tetrahydrofuran, tetrahydropyran, tetrahydrothiazoline, tetrahydroisothiazoline, tetrahydropyridazine, triazepine, dihydrotriazepine, and tetrahydrotriazepine; and fused non-aromatic heteroaromatic rings such as indoline, isoindoline, benzopyran, benzodioxane, tetrahydroquinoline, benzo[d]oxazole-2(3H)-one, and tetrahydrobenzothiophene.

The term "non-aromatic heterocyclic group" includes monovalent groups derived from the aforementioned "non-aromatic heterocyclic ring".

Examples of "non-aromatic heterocyclic group" include monocyclic non-aromatic heterocyclyls such as pyrrolinyl, pyrrolidino, pyrrolidinyl, imidazolidinyl, pyrazolinyl, pyrazolidinyl, piperidine, piperidyl, piperazine, piperadinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, dihydroimidazolyl, tetrahydrofuryl, tetrahydropyranyl, tetrahydrothiazolinyl, tetrahydropyridazinyl, tetrahydroisothiazolinyl, triazepinyl, dihydrotriazepinyl, and tetrahydrotriazepinyl; and fused heterocyclyls such as benzodioxane, tetrahydroquinoline, benzo[d]oxazole-2(3H)-one, and tetrahydrobenzothiophene.

The "non-aromatic heterocyclic ring" moiety in said "non-aromatic heterocyclyloxy", "non-aromatic heterocyclylthio", and "non-aromatic heterocyclyloxycarbonyl" is as defined above for "non-aromatic heterocyclic ring".

The term "nitrogen-containing non-aromatic heterocyclic ring" includes 4- to 7-membered non-aromatic rings that contain at least one nitrogen atom in the ring and may further contain, in the ring, any one or more atoms selected from oxygen atom and sulfur atom; and rings fused two or more of the above-mentioned rings. Examples of "nitrogen-containing non-aromatic heterocyclic ring" include pyrroline, pyrrolidine, pyrrolidine, piperidine, piperazine, morpholine, and thiomorpholine.

The term "nitrogen-containing non-aromatic heterocyclic group" includes groups derived from 4- to 7-membered non-aromatic rings that contain at least one nitrogen atom in the ring and may further contain, in the ring, any one or more atoms selected from oxygen atom and sulfur atom; and rings fused two or more of the above-mentioned rings. Examples of "nitrogen-containing non-aromatic heterocyclic group" include pyrrolinyl, pyrrolidino, pyrrolidinyl, piperidino, piperidyl, piperazino, piperadinyl, morpholinyl, morpholino, and thiomorpholino.

Examples of the substituents of the "substituted alkyl", "substituted alkenyl", "substituted alkynyl", "substituted alkyloxy", "substituted alkenyloxy", "substituted alkynyloxy", "substituted alkylthio", "substituted alkenylthio", "substituted alkynylthio", "substituted alkyloxycarbonyl", "substituted alkenyloxycarbonyl", "substituted alkynyloxycarbonyl", "substituted alkylcarbamoyl", "substituted alkenylcarbamoyl", and "substituted alkynylcarbamoyl" include, but not limited to, one or more identical or different substituents selected from the group consisting of the following:

hydroxy, carboxy, halogen (F, Cl, Br, I), haloalkyloxy (for example, $CF_3O$), cycloalkyl (for example, cyclopropyl), cycloalkenyl (for example, cyclopropenyl), alkyloxy (for example, methoxy, ethoxy, propoxy, and butoxy), alkenyloxy (for example, vinyloxy and allyloxy), alkyloxycarbonyl (for example, methoxycarbonyl, ethoxycarbonyl, and tert-butoxycarbonyl), nitro, nitroso, amino, alkylamino (for example, methylamino, ethylamino, and dimethylamino), acylamino (for example, acetylamine and benzoylamino), arylalkylamino (for example, benzylamino and tritylamino), hydroxyamino, imino, hydroxyimino, alkylimino (for example, methylimino, ethylimino, and dimethylimino), alkyloxyimino (for example, methoxyimino and ethoxyimino), acylimino (for example, acetylimino and benzoylimino), azide, aryl (for example, phenyl), arylalkyl (for example, benzyl and phenylethyl), arylalkyloxy (for example, benzyloxy), a non-aromatic heterocyclic group (for example, pyrrolinyl, piperidyl, piperazino, pyrrolidino, dioxanyl, tetrahydropyranyl, morpholinyl, and morpholino), heteroaryl (for example, furyl, thienyl, pyridyl, isoxazolyl, thiazolyl, thiadiazolyl, oxazolyl, oxadiazolyl, tetrazolyl, indolyl, and benzofuryl), heteroarylalkyl (pyridylmethyl and pyridylethyl), non-aromatic heterocyclyloxy (for example, pyrrolinyloxy, piperidyloxy, piperazinooxy, pyrrolidinooxy, pyrrolidinyloxy, dioxanyloxy, tetrahydropyranyloxy, morpholinyloxy, and morpholinooxy), cyano, isocyano, isocyanato, thiocyanate, isothiocyanato, mercapto, alkylthio (for example, methylthio), alkylsulfonyl (for example, methanesulfonyl and ethanesulfonyl), carbamoyl, alkylcarbamoyl (for example, methylcarbamoyl, ethylcarbamoyl, and dimethylcarbamoyl), sulfamoyl, alkylsulfamoyl, acyl (for example, formyl and acetyl), acyloxy (for example, formyloxy), thioformyl, thiocarboxy, dithiocarboxy, thiocarbamoyl, sulfino, sulfo, hydrazine, azide, ureido, amidino, guanidino, phthalimide, trialkylsilyl (for example, trimethylsilyl), and oxo.

Examples of the substituents of the "substituted alkyl" in $R^{2a}$ include hydroxy: carboxy; alkyloxycarbonyl; alkenyloxycarbonyl; alkynyloxycarbonyl; alkylcarbamoyl; hydroxyalkylcarbamoyl; a non-aromatic heterocyclic group; a now aromatic heterocyclic group substituted with alkyl; non-aromatic cyclyloxy; unsubstituted aryl; aryl substituted with halogen, alkyl, haloalkyl, or trihaloalkyl; unsubstituted heteroaryl; and heteroaryl substituted with alkyl, haloalkyl, or trihaloalkyl.

Examples of the substituents of the "substituted alkyl" in $R^{2a}$ include hydroxy, carboxy, methyloxycarbonyl, hydroxyethylcarbamoyl, dihydrodiisopropylcarbamoyl, dimethyldioxanyl, tetrahydropyranyloxy, phenyl, methylphenyl, chlorophenyl, and trifluorophenyl.

Examples of the substituents of the "substituted alkyl" in $R^{2b}$ include aryl, heteroaryl, alkyloxycarbonyl, alkenyloxycarbonyl, and alkynyloxycarbonyl.

Examples of the substituents of the "substituted alkyl" in $R^{2b}$ include aryl and alkyloxycarbonyl.

Examples of the substituents of the "substituted alkyl" in $R^{2b}$ include phenyl and ethyloxycarbonyl.

Examples of the substituents of the "substituted alkenyl" in $R^{2b}$ include carboxy, alkyloxycarbonyl, alkenyloxycarbonyl, and alkynyloxycarbonyl.

Examples of the substituents of the "substituted alkenyl" in $R^{2b}$ include carboxy and alkyloxycarbonyl.

Examples of the substituents of the "substituted alkenyl" in $R^{2b}$ include carboxy and ethyloxycarbonyl.

Examples of the substituents of the "substituted alkylthio" in $R^{2b}$ include haloaryl.

Examples of the substituents of the "substituted alkylthio" in $R^{2b}$ include halophenyl.

Examples of the substituents of the "substituted alkylthio" $R^{2b}$ include chlorophenyl.

The substituents of the "substituted acyl" are selected from the group consisting of the substituents of the aforementioned "substituted alkyl", the aforementioned "alkyl", the aforementioned "alkenyl", and the aforementioned "alkenyl". In particular, when R of acyl (R—C(=O)—) is "cycloalkyl", "cycloalkenyl", "a non-aromatic heterocyclic group", "aryl", or "heteroaryl", examples of the substituents of the rings include alkyl (for example, methyl, ethyl, isopropyl, and tert-butyl), haloalkyl (for example, $CF_3$, $CH_2CF_3$, and $CH_2CCl_3$), alkenyl, alkenyl (for example, ethynyl), alkyloxy (for example, methoxy, ethoxy, and isopropyloxy), and halogen (for example, fluoro and chloro).

Examples of the substituents of the "substituted carbamoyl" or "substituted sulfamoyl" include, but not limited to, one or more identical or different substituents selected from the group consisting of the following:

hydroxy, carboxy, halogen (F, Cl, Br, I), alkyl (for example, methyl and ethyl), alkenyl (for example, vinyl), alkynyl (for example, ethynyl), cycloalkyl (for example, cyclopropyl), cycloalkenyl (for example, cyclopropenyl), alkyloxycarbonyl (for example, methoxycarbonyl, ethoxycarbonyl, and tert-butoxycarbonyl), carboxyalkyl (for example, carboxyethyl), alkyloxyalkyl (for example, methoxypropyl), cyanoalkyl (for example, cyanoethyl), alkyloxycarbonylalkyl (for example, methoxycarbonylethyl), amino, alkylamino (for example, methylamino, ethylamino, and dimethylamino), acylamino (for example, formylamino, acetylamino, and benzoylamino), arylalkylamino (for example, benzylamino and tritylamino), hydroxyamino, hydroxyalkyl (for example, hydroxymethyl, hydroxyethyl, and hydroxypropyl), alkyloxycarbonylamino (for example, tert-butyloxycarbonylamino), aryl (for example, phenyl), substituted aryl (for example, phenyl or the like substituted with halogen, alkyloxy, or the like), heteroaryl (for example, benzothiazole), substituted heteroaryl (for example, heteroaryl substituted with alkyl), a non-aromatic heterocyclic group (for example, tetrahydropyranyl), cyano, isocyano, isocyanato, thiocyanato, isothiocyanato and acyl (for example, formyl and acetyl).

Examples of the substituents of the "substituted alkylcarbamoyl" in $R^{2b}$ include hydroxy, carboxy, cyano, alkyloxy, and alkyloxycarbonyl.

Examples of the substituents of the "substituted alkylcarbamoyl" in $R^{2b}$ include hydroxy.

Examples of the substituents of the "substituted amino" include, but not limited to, one or more identical or different substituents selected from the group consisting of the following:

alkyl (for example, methyl, ethyl, isopropyl, and tert-butyl), haloalkyl(for example, $CF_3$, $CH_2CF_3$, and $CH_2CCl_3$), hydroxyalkyl (for example, hydroxyethyl and —$C(CH_3)_2$ $CH_2OH$), carboxyalkyl (for example, carboxymethyl and carboxyethyl), alkylaminoalkyl (for example, dimethylaminoalkyl), non-aromatic heterocyclylalkyl (for example, tetrahydropyranylmethyl), alkenyl (for example, vinyl), alkynyl (for example, ethynyl), cycloalkyl (for example, cyclopropyl), cycloalkenyl (for example, cyclopropenyl), alkyloxy (for example, methoxy, ethoxy, propoxy, and butoxy), haloalkyloxy (for example, $CF_3O$), alkenyloxy (for example, vinyloxy and allyloxy), carbamoyl, alkylcarbamoyl (for example, methylcarbamoyl, ethylcarbamoyl, and dimethylcarbamoyl, carbamoylalkyl (for example, carbamoylmethyl), alkylcarbamoylalkyl (for example, methylcarbamoylmethyl), sulfamoyl, alkylsulfamoyl (for example, methylsulfamoyl), alkylsulfamoylalkyl (for example, methylsulfamoylmethyl), sulfamoylalkyl (for example, sulfamoylmethyl), non-aromatic cyclylcarbamoyl (for example, tetrahydropyranylcarbamoyl), alkylsulfonyl (for example, methanesulfonyl and ethanesulfonyl), alkyloxycarbonyl (for example, methoxycarbonyl, ethoxycarbonyl, propoxycarbonyl, and tert-butyloxycarbonyl), amino, alkylamino (for example, methylamino, ethylamino, and dimethylamino), acylamino (for example, acetylamino and benzoylamino), arylalkylamino (for example, benzylamino and tritylamino), hydroxyamino, imino, hydroxyimino, alkylimino (for example, methylimino, ethylimino, and dimethylimino), alkyloxyimino (for example, methoxyimino and ethoxyimino), acylimino (for example, acetylimino and benzoylimino), aryl (for example, phenyl), arylalkyl (for example, benzyl), aryloxy (for example, phenoxy), a arylalkyloxycarbonyl (for example, benzyloxycarbonyl), a non-aromatic heterocyclic group (for example, pyrrolinyl, pyrrolidino, piperidino, piperidyl, piperazino, piperadinyl, morpholinyl, and morpholino), heteroaryl (for example, pyridyl, thienyl, thiazolyl, and furyl), heteroarylalkyl (for example, pyridylmethyl, thienylmethyl, thiazolylmethyl, and furylmethyl), non-aromatic heterocyclyloxy (for example, piperazinooxy and piperidinooxy), heteroaryloxy (for example, pyridyloxy), hydroxy, halogen (F, Cl, Br, I), cyano, acyl (for example, formyl and acetyl) and substituted acyl (for example, acyl substituted with hydroxy, alkyl, alkyloxy, alkylcarbonyloxy, alkyloxycarbonyl, acyl, oxo, or cyano).

Examples of the substituents of the "substituted amino" in $R^{2b}$ include alkyl, alkenyl, alkynyl, carboxyalkyl, carboxyalkenyl, carboxyalkynyl, substituted or unsubstituted acyl, carboxycarbonyl, arylalkyl, arylalkenyl, arylalkynyl, arylalkyloxycarbonyl, hydroxyalkyl, hydroxyalkenyl, hydroxyalkenyl, dialkylaminoalkyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl, alkyloxycarbonyl, alkenyloxycarbonyl, alkynyloxycarbonyl, carbamoyl, alkylcarbamoyl, alkenylcarbamoyl, alkynylcarbamoyl, non-aromatic heterocyclylcarbamoyl, alkylsulfonyl, alkenylsulfonyl, and alkynylsulfonyl.

Examples of the substituents of the "substituted amino" in $R^{2b}$ include alkyl, carboxyalkyl, arylalkyl, arylalkyloxycarbonyl, hydroxyalkyl, dialkylaminoalkyl, non-aromatic heterocyclylalkyl, carboxycarbonyl, carboxyalkylcarbonyl, alkyloxycarbonyl, non-aromatic heterocyclylalkylcarbonyl, alkyl non-aromatic heterocyclylcarbonyl, non-aromatic heterocyclylcarbonyl, formyl, acetyl, alkylcarbonyl, heteroarylcarbonyl, alkyloxyheteroarylcarbonyl, alkyloxyalkylcarbonyl, cyanoalkylcarbonyl, alkylcarbamoyl, non-aromatic heterocyclylcarbamoyl, alkylcarbonyloxyalkylcarbonyl, hydroxyalkylcarbonyl, alkylcarbonyl non-aromatic heterocyclylcarbonyl, oxo non-aromatic heterocyclylcarbonyl, and alkylsulfonyl.

Examples of the substituents of the "substituted amino" in $R^{2b}$ include methyl, ethyl, isopropyl, carboxymethyl, benzyl, benzyloxycarbonyl, hydroxyethyl, dimethylaminoethyl, isopropyl, hydroxyisopropyl, tetrahydropyranylmethyl, hydroxypropyl, carboxycarbonyl, carboxyethylcarbonyl, ethyloxycarbonyl, tert-butyloxycarbonyl, tetrahydropyranylmethylcarbonyl, methyldioxanylcarbonyl, tetrahydropyranylcarbonyl, morpholinylcarbonyl, formyl, acetyl, propylcarbonyl, isopropylcarbonyl, methyloxypyridylcarbonyl, methyloxyethylcarbonyl, methyloxymethylcarbonyl, cyanoisopropylcarbonyl, ethylcarbamoyl, tetrahydropyranylcarbamoyl, methanesulfonyl, acetyloxypropylcarbonyl, hydroxyethylcarbonyl, hydroxyisopropylcarbonyl, oxodihydropyridylcarbonyl, and acetylpiperidinylcarbanyl, Examples of the substituents of the "substituted cycloalkyl", "substituted cycloalkenyl", "substituted aryl", "substituted heterocyclic group", "substituted heteroaryl", "substituted non-aromatic carbocyclic group", "substituted non-aromatic heterocyclic group", and "substituted nitrogen-containing non-aromatic heterocyclic group" include, but not limited to, one or more identical or different substituents selected from the group consisting of the following:

alkyl (for example, methyl, ethyl, isopropyl, and tert-butyl), haloalkyl (for example, $CF_3$, $CH_2CF_3$, and $CH_2CCl_3$), haloalkyloxy (for example, $CF_3O$ and $CHCF_2O$), alkenyl (for example, vinyl), alkynyl (for example, ethynyl), cycloalkyl (for example, cyclopropyl), cycloalkenyl (for example, cyclopropenyl), alkyloxy (for example, methoxy, ethoxy, propoxy, and butoxy), alkenyloxy (for example, vinyloxy and allyloxy), alkyloxycarbonyl (for example, methoxycarbonyl, ethoxycarbonyl, and tert-butoxycarbonyl), nitro, nitroso, amino, alkylamino (for example, methylamino, ethylamino, and dimethylamino), acylamino (for example, acetylamino and benzoylamino), arylalkylamino (for example, benzylamino and tritylamino), hydroxyamino, imino, hydroxyimino, alkylimino (for example, methylimino, ethylimino, and dimethylimino), alkyloxyimino (for example, methoxyimino and ethoxyimino), acylimino (for example, acetylimino and benzoylimino), azide, aryl (for example, phenyl), arylalkyl (for example, benzyl), unsubstituted aryloxy (for example, phenoxy), aryloxy substituted with one or more identical or different substituents selected from the following Substituent Group Z, unsubstituted aryloxy (for example, phenoxy), aryloxy substituted with one or more identical or different substituents selected from the following Substituent Group Z, arylalkyloxy (for example, benzyloxy), a non-aromatic heterocyclic group (for example, pyrrolinyl, pyrrolidino, piperidino, piperidyl, piperazine, piperadinyl, morpholinyl, and morpholino), heteroaryl (for example, pyridyl, thienyl, thiazolyl, and furyl), heteroarylalkyl (for example, pyridylmethyl, thienylmethyl, thiazolylmethyl, and furylmethyl), non-aromatic heterocyclyloxy (for example, piperazinooxy and piperidinooxy), unsubstituted heteroaryloxy (for example, pyridyloxy), heteroaryloxy substituted with one or more identical or different substituents selected from the following Substituent Group Z, cyano, isocyano, isocyanato, thiocyanato, isothiocyanato, mercapto, alkylthio (for example, methylthio), alkylsulfonyl (for example, methanesulfonyl and ethanesulfonyl), substituted or unsubstituted carbamoyl (for example, carbamoyl and N-methyl-N-methoxycarbamoyl), substituted or unsubstituted alkylcarbamoyl (for example, methylcarbamoyl, ethylcarbamoyl, dimethylcarbamoyl, hydroxyethylcarbamoyl, trifluoromethylcarbamoyl, and trifluoroethylcarbamoyl), sulfamoyl, alkylsulfamoyl, hydroxy, carboxy, halogen (F, Cl, Br, I), acyl (for example, formyl and acetyl), formyloxy, thioformyl, thiocarboxy, dithiocarboxy, thiocarbamoyl, sulfino, hydrazino, aside, ureido, amidino, guanidine, phthalimide and oxo.

Substituent group Z includes hydroxy, carboxy, cyano, nitro, halogen, alkyl, alkenyl, alkynyl, alkyloxy, alkenyloxy, alkynyloxy, alkylthio, alkenylthio, alkynylthio, acyl, alkyloxycarbonyl, alkenyloxycarbonyl, alkynyloxycarbonyl, carbamoyl, amino, sulfamoyl, methylsulfonyl, methylsulfinyl, cycloalkyl, cycloalkenyl, a non-aromatic heterocyclic group, aryl, heteroaryl, cycloalkyloxy, cycloalkenyloxy, non-aromatic heterocyclyloxy, aryloxy, and heteroaryloxy.

In the formula —($CR^{8a}R^{8b}$)m-$R^9$ in $R^2$, m is preferably 1 to 3.

When ring A is,

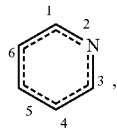

the formula represents

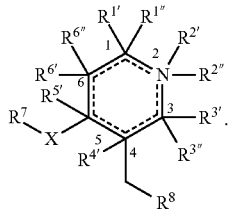

When ring A is a fused ring, ring A includes compounds in which one ring is substituted with —X—$R^7$ and -L-$R^6$, and the other ring is substituted with $R^2$, and compounds in which one ring is substituted with —X—$R^7$, and the other ring is substituted with -L-$R^6$ and $R^2$. Examples of ring A include

[Chemical Formula 94]

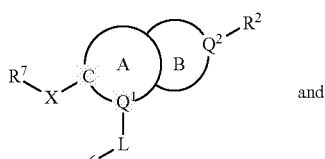

and

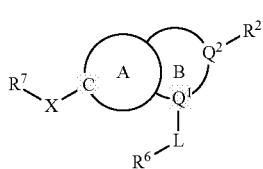

wherein
ring B is substituted or unsubstituted 5- to 7-membered cycloalkane, substituted or unsubstituted 5- to 7-membered cycloalkene, a substituted or unsubstituted 5- to 7-membered nitrogen-containing non-aromatic heterocyclic ring, benzene rings, or a substituted or unsubstituted 5- or 8-membered aromatic heterocyclic ring, and other symbols are as defined above.

One embodiment of the compounds of the present invention or the compositions of the present invention is described below.

In the compounds of the formula (IV):

[Chemical Formula 95]

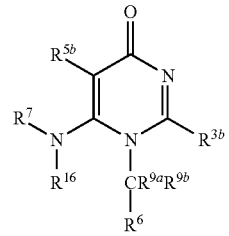

(IV)

the embodiments of the following (IV-A) to (IV-N) are described below:

(IV-A)
Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{3b}$ and $R^{5b}$ are each independently hydrogen, nitro, halogen, hydroxy, carboxy, substituted or unsubstituted alkyl, substituted or unsubstituted acyl, substituted or unsubstituted alkyloxy substituted or unsubstituted alkenyloxy, substituted or unsubstituted alkynyloxy, substituted or unsubstituted cycloalkyloxy, substituted or unsubstituted cycloalkenyl, substituted or unsubstituted non-aromatic heterocyclyloxy, substituted or unsubstituted aryloxy, substituted or unsubstituted heteroaryloxy, substituted or unsubstituted alkylthio, substituted or unsubstituted alkenylthio, substituted or unsubstituted alkynylthio, substituted or unsubstituted cycloalkylthio, substituted or unsubstituted cycloalkenylthio, a substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted sulfamoyl or substituted or unsubstituted amino;

$R^6$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

$R^7$ is substituted or unsubstituted aryl or substituted or unsubstituted heteroaryl;

$R^{9a}$ and $R^{9b}$ are each independently hydrogen, halogen, hydroxy, substituted or unsubstituted alkyl, substituted or unsubstituted alkenyl, substituted or unsubstituted alkenyl, substituted or unsubstituted alkyloxy, substituted or unsubstituted alkynyloxy, car substituted or unsubstituted alkenyloxy, or may be taken together to form oxo or thioxo; and $R^{16}$ is hydrogen, substituted or unsubstituted acyl, substituted or unsubstituted alkyl, substituted or unsubstituted alkenyl, or substituted or unsubstituted alkynyl.

(IV-B)

Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{3b}$ and $R^{5b}$ each independently hydrogen; unsubstituted alkyl; alkyl substituted with one or more substituents selected from Substituent Group B (Substituent Group B; halogen, hydroxy, substituted or unsubstituted alkyloxy, substituted or unsubstituted alkenyloxy, substituted or unsubstituted alkynyloxyl, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; alkynyl substituted with one or more substituents selected from Substituent Group B; unsubstituted amino; amino substituted with substituent(s) selected from Substituent Group A (Substituent Group A; alkyl, alkenyl, alkenyl, carboxyalkyl, carboxyalkenyl, carboxyalkynyl, substituted or unsubstituted acyl, carboxycarbonyl, arylalkyl, arylalkenyl, arylalkynyl, arylalkyloxycarbonyl, hydroxyalkyl, hydroxyalkenyl, hydroxyalkynyl, dialkylaminoalkyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl, alkyloxycarbonyl, alkenyloxycarbonyl, alkylnyloxycarbonyl, carbamoyl, alkylcarbamoyl, alkenylcarbamoyl, alkynylcarbamoyl, non-aromatic heterocyclylcarbamoyl, alkylsulfonyl, alkenylsulfonyl, and alkynylsulfonyl); unsubstituted carbamoyl; or carbamoyl substituted with substituents) selected from Substituent Group A;

$R^6$ is substituted or unsubstituted cycloalkyl, substituted or unsubstituted aryl, or substituted or unsubstituted heteroaryl;

$R^7$ is substituted or unsubstituted aryl or substituted or unsubstituted heteroaryl;

$R^{9a}$ and $R^{9b}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, substituted or unsubstituted alkenyloxy, or may be taken together to form oxo or thioxo; and $R^{16}$ is hydrogen, substituted or unsubstituted acyl, substituted or unsubstituted substituted or unsubstituted alkenyl, and substituted or unsubstituted alkynyl, (IV-C1)

Compounds of the aforementioned (IV-A) or (IV-B), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is a group of the formula:

[Chemical Formula 96]

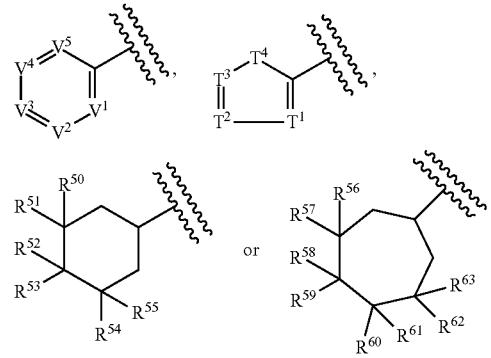

wherein
$=V^1-V^2=V^3-V^4=V^5-$ is a group selected from the following (i) to (p):

(i): $=C(H)-C(R^A)=C(R^B)-C(R^C)=C(H)-$;
(j): $=N-C(R^A)=C(R^B)-C(R^C)=C(H)-$;
(k): $=C(H)-N=C(R^B)-C(R^C)=C(H)-$;
(l): $=C(H)-C(R^A)=N-C(R^C)=C(H)-$;
(m): $=C(H)-C(R^A)=C(R^B)-N=C(H)-$;
(n): $=N-C(R^A)=C(R^B)-C(R^C)=N-$;
(o): $=C(H)-C(R^A)=N-C(R^C)=C(H)-$; and
(p): $=C(H)-N=C(R^B)-N=C(H)-$;

$R^A$, $R^B$, and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy, or $R^A$ and $R^B$, or $R^B$ and $R^C$ together with the ring atoms to which they are attached form a non-aromatic carbocyclic ring, a non-aromatic heterocyclic ring, an aromatic carbocyclic ring, or an aromatic heterocyclic ring, provided that the groups of (i) to (p) have at least one substituent; wherein "the groups of (i) to (p) have at least one substituent" means that at least one of $R^A$, $R^B$, and $R^C$ is not hydrogen in the groups of (i), (j) and (n); at least one of $R^B$ and $R^C$ is not hydrogen in the group of (k); at least one of $R^A$ and $R^C$ is not hydrogen in the groups of (l) and (o); at least one of $R^A$ and $R^B$ is not hydrogen in the group of (m); and $R^B$ is not hydrogen in the group of (p);

=T$^1$-T$^2$=T$^3$-T$^4$- is a group selected from the following (q) to (t);
(q): =C(H)—C(R$^D$)=C(R$^E$)—S—;
(r): =C(H)—C(R$^D$)=C(R$^E$)—O—;
(s): =N—C(R$^D$)=C(R$^E$)—S—; and
(t): =N—C(R$^D$)=C(R$^E$)—O—;

R$^D$ and R$^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy, or R$^A$ and R$^B$, or R$^B$ and R$^C$ together with the ring atoms to which they are attached form a non-aromatic carbocyclic ring, a non-aromatic heterocyclic ring, an aromatic carbocyclic ring, or an aromatic heterocyclic ring;

R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, and R$^{63}$ are each independently hydrogen, halogen, hydroxy, cyano, substituted or unsubstituted substituted or unsubstituted alkenyl, substituted or unsubstituted alkynyl, substituted or unsubstituted alkyloxy, substituted or unsubstituted alkenyloxy, or substituted or unsubstituted alkynyloxy (In this description, the substituent defined above as R$^6$ is referred to as R$^{6A}$); and R$^7$ is a group of the formula (A):

[Chemical Formula 97]

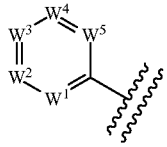

(A)

wherein
=W$^1$-W$^2$=W$^3$-W$^4$=W$^5$- is a group selected from the following (a) to (h):
(a): =C(H)—C(R$^{10a}$)=C(R$^{10b}$)—C(R$^{10c}$)=C(H)—;
(b): =N—C(R$^{10a}$)=C(R$^{10b}$)—C(R$^{10c}$)=C(H)—;
(c): =C(H)—N=C(R$^{10b}$)—C(R$^{10c}$)=C(H)—;
(d): =C(H)—C(R$^{10a}$)=N—C(R$^{10c}$)=C(H)—;
(e): =C(H)—C(R$^{10a}$)=C(R$^{10b}$)—N=C(H)—;
(f): =N—C(R$^{10a}$)=C(R$^{10b}$)—C(R$^{10c}$)=N—;
(g): =C(H)—C(R$^{10a}$)=N—C(R$^{10c}$)=C(H)—; and
(h): =C(H)—N=C(R$^{10b}$)—N=C(H)—;

R$^{10a}$, R$^{10b}$ and R$^{10c}$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy, or R$^{10a}$ and R$^{10b}$, or R$^{10b}$ and R$^{10c}$ together with the ring atoms to which they are attached form a non-aromatic carbocyclic ring, non-aromatic heterocyclic ring, aromatic carbocyclic ring, or aromatic heterocyclic ring, provided that the groups of (a) to (h) have at least one substituent; wherein "the groups of (a) to (h) have at least one substituent" means that at least one of R$^{10a}$, R$^{10b}$, and R$^{10c}$ is not hydrogen in the groups of (a), (b) and (f); at least one of R$^{10b}$ and R$^{10c}$ is not hydrogen in the group of (c); at least one of R$^{10a}$ and R$^{10c}$ is not hydrogen in the groups of (d) and (g); at least one of R$^{10a}$ and R$^{10b}$ is not hydrogen in the group of (e); and R$^{10b}$ is not hydrogen in the group of (h) (In this description, the substituent defined above as R$^7$ is referred to as R$^{7A}$.

(IV-C2)

Compounds of the aforementioned (IV-A) to (IV-C1), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein R$^6$ is a group of the formula:

[Chemical Formula 98]

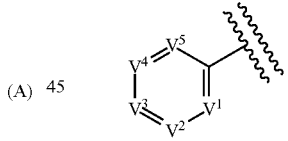

wherein
=V$^1$-V$^2$=V$^3$-V$^4$=V$^5$- is a group selected from the following (i) to (p):
(i): =C(H)—C(R$^A$)=C(R$^B$)—C(R$^C$)=C(H)—;
(j): =N—C(R$^A$)=C(R$^B$)—C(R$^C$)=C(H)—;
(k): =C(H)—N=C(R$^B$)—C(R$^C$)=C(H)—;
(l): =C(H)—C(R$^A$)=N—C(R$^C$)=C(H)—;
(m): =C(H)—C(R$^A$)=C(R$^B$)—N=C(H)—;
(n): =N—C(R$^A$)=C(R$^B$)—C(R$^C$)=N—;
(o): =C(H)—C(R$^A$)=N—C(R$^C$)=C(H)—; and
(p): =C(H)—N=C(R$^B$)—N=C(H)—;

R$^A$, R$^B$ and R$^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy, or $R^A$ and $R^B$, or $R^B$ and $R^C$ together with the ring atoms to which, they are attached form a non-aromatic carbocyclic ring, non-aromatic heterocyclic ring, aromatic carbocyclic ring, or aromatic heterocyclic ring, provided that the groups of (i) to (p) have at least one substituent; wherein "the groups of (i) to (p) have at least one substituent" means that at least one of $R^A$, $R^B$, and $R^C$ is not hydrogen in the groups of (i), (j) and (n); at least one of $R^B$ and $R^C$ is not hydrogen in the group of (k); at least one of $R^A$ and $R^C$ is not hydrogen in the groups of (l) and (o); at least one of $R^A$ and $R^B$ is not hydrogen in the group of (m); and $R^B$ is not hydrogen in the group of (p). (In this description, the substituent defined, above as $R^6$ is referred to as $R^{6B}$.)

(IV-C3)

Compounds of the aforementioned (IV-A) to (IV-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is a group of the formula:

[Chemical Formula 99]

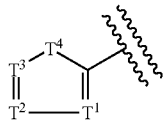

wherein
=$T^1$-$T^2$=$T^3$-$T^4$- is a group selected from the following (q) to (t):
(q): =C(H)—C($R^D$)=C($R^E$)—S—;
(r): =C(H)—C($R^D$)=C($R^E$)—O—;
(s): =N—C($R^D$)=C($R^E$)—S—; and
(t): =N—C($R^D$)=C($R^E$)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl substituted or unsubstituted alkenyloxycarbonyl, substituted or unsubstituted alkynyloxycarbonyl, substituted or unsubstituted carbamoyl substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy, or $R^A$ and $R^B$, or $R^B$ and $R^C$ together with the ring atoms to which they are attached form a non-aromatic carbocyclic ring, non-aromatic heterocyclic ring, aromatic carbocyclic ring, or aromatic heterocyclic ring (In this description, the substituent defined above as $R^6$ is referred to as $R^{6C}$.)

(IV-C4)

Compounds of the aforementioned (IV-A) to (IV-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is a group of the formula:

[Chemical Formula 100]

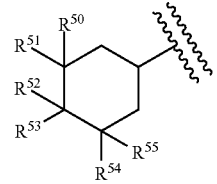

wherein $R^{50}$, $R^{51}$, $R^{52}$, $R^{53}$, $R^{54}$, and $R^{55}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy (In this description, the substituent defined above as $R^6$ is referred to as $R^{6D}$.)

(IV-C5)

Compounds of the aforementioned (IV-A) to (IV-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is a group of the formula:

[Chemical Formula 101]

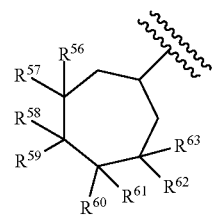

wherein $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy (In this description, the substituent defined above as $R^6$ is referred to as $R^{6E}$.)

(IV-C6)

Compounds of the aforementioned (IV-A) or (IV-B), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is a group of the formula:

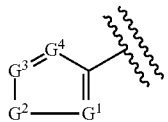
[Chemical Formula 102]

wherein
=$G^1$-$G^2$-$G^3$=$G^4$- is a group selected from the following (u) to (x):
(u): =C(H)—S—C($R^F$)—C(H)—;
(v): =C(H)—O—C($R^F$)—C(H)—;
(w): =C(H)—S—C($R^F$)=N—; and
(x): =C(H)—O—C($R^F$)=N—;
$R^F$ is hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy (In this description, the substituent defined above as $R^6$ is referred to as $R^{6F}$); and $R^7$ is $R^{7A}$.
(IV-D)

Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{3b}$ and $R^{5b}$ are each independently hydrogen; unsubstituted alkyl; alkyl substituted with one or more substituents selected from Substituent Group B (Substituent Group B; halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl substituted or unsubstituted alkenyloxycarbonyl, substituted or unsubstituted alkynyloxycarbonyl substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; alkynyl substituted with one or more substituents selected from Substituent Group B; unsubstituted amino; amino substituted with one or more substituents selected from Substituent Group A (Substituent Group A; alkyl, alkenyl, alkynyl, carboxyalkyl, carboxyalkenyl, carboxyalkynyl, substituted or unsubstituted acyl, carboxycarbonyl, arylalkyl, arylalkenyl, arylalkynyl, arylalkyloxycarbonyl, hydroxyalkyl, hydroxyalkenyl, hydroxyalkynyl, dialkylaminoalkyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl, alkyloxycarbonyl, alkenyloxycarbonyl, alkynyloxycarbonyl, carbamoyl, alkylcarbamoyl, alkenylcarbamoyl, alkynylcarbamoyl, non-aromatic heterocyclylcarbamoyl, alkylsulfonyl, alkenylsulfonyl, and alkynylsulfonyl); unsubstituted carbamoyl; or carbamoyl substituted with substituent(s) selected from Substituent Group A;
$R^6$ is aryl optionally substituted with one or more substituents selected from Substituent Group C (Substituent Group C; halogen, hydroxy, alkyl, alkenyl, alkynyl, haloalkyl, cycloalkylalkyl, alkyloxy, alkenyloxy, alkynyloxy, cycloalkyloxy, cycloalkyl, and a non-aromatic heterocyclic group); heteroaryl optionally substituted with one or more substituents selected from Substituent Group C or cycloalkyl optionally substituted with one or more substituents selected from Substituent Group C;
$R^7$ is aryl optionally substituted with one or more substituents selected from Substituent Group D (Substituent Group D; halogen, carboxy, alkyl, alkenyl, alkynyl, alkyloxy, alkenyloxy, alkynyloxy, cycloalkyl, cycloalkenyl, and cycloalkynyl); or heteroaryl optionally substituted with one or more substituents selected from Substituent Group D; and
$R^{9a}$, $R^{9b}$, and $R^{16}$ are hydrogen.
The "heteroaryl" in $R^7$ is preferably thiazolyl, isothiazolyl, oxazolyl, isoxazolyl, pyrazolyl, imidazolyl, triazolyl, furyl, thienyl, thiadiazolyl, oxadiazolyl, pyridyl, pyrimidyl, pyrazinyl, pyridazinyl, triazinyl, benzothiazolyl, or benzoxazolyl.
(IV-E)

Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^{3b}$ and $R^{5b}$ are each independently hydrogen; unsubstituted alkyl; alkyl substituted with one or more substituents selected from Substituent Group B (Substituent Group B; halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; alkynyl substituted with one or more substituents selected from Substituent Group B; unsubstituted amino; amino substituted with substituent (a) selected from Substituent Group A (Substituent Group A; alkyl, alkenyl, carboxyalkyl, carboxyalkenyl, carboxyalkynyl, substituted or unsubstituted acyl, carboxycarbonyl, arylalkyl, arylalkenyl, arylalkynyl, arylalkyloxycarbonyl, hydroxyalkyl, hydroxyalkenyl, hydroxyalkynyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl, alkyloxycarbonyl, alkenyloxycarbonyl, alkynyloxycarbonyl, carbamoyl, alkylcarbamoyl, alkenylcarbamoyl, alkynylcarbamoyl, non-aromatic heterocyclylcarbamoyl, alkylsulfonyl, alkenylsulfonyl, and alkynylsulfonyl); unsubstituted carbamoyl; or carbamoyl substituted with substituent(s) selected from Substituent Group A;

$R^6$ is aryl optionally substituted with one or more substituents selected from Substituent Group C (Substituent Group C; halogen, hydroxy, allyl, alkenyl, alkynyl, haloalkyl, cycloalkylalkyl, alkyloxy, alkenyloxy, alkynyloxy, cycloalkyloxy, cycloalkyl, and a non-aromatic heterocyclic group); heteroaryl optionally substituted with one or more substituents selected from Substituent Group C; or cycloalkyl optionally substituted with one or more substituents selected from Substituent Group C;

$R^7$ is aryl optionally substituted with one or more substituents selected from Substituent Group E (Substituent Group E; halogen, carboxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, cycloalkynyl, substituted or unsubstituted nitrogen-containing non-aromatic heterocyclyloxy, substituted or unsubstituted aryloxy, and substituted or unsubstituted heteroaryloxy); or heteroaryl optionally substituted with one or more substituents selected from Substituent Group E; and $R^{9a}$, $R^{9b}$, and $R^{16}$ are hydrogen.

The "heteroaryl" in $R^7$ is preferably thiazolyl, isothiazolyl, oxazolyl, isoxazolyl, pyrazolyl, imidazolyl, triazolyl, thienyl, thiadiazolyl, oxadiazolyl, pyridyl, pyrimidyl, pyrazinyl, pyridazinyl, triazinyl, benzothiazolyl, or benzoxazolyl.

(IV-F)

Compounds of the aforementioned (IV-E), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^7$ is aryl optionally substituted with one or more substituents selected from Substituent Group F (Substituent Group F; halogen, substituted or unsubstituted alkyl, substituted or unsubstituted alkyloxy, a substituted or unsubstituted nitrogen-containing non-aromatic heterocyclyloxy, substituted or unsubstituted aryloxy, and substituted or unsubstituted heteroaryloxy); or heteroaryl optionally substituted with one or more substituents selected from Substituent Group F.

(IV-G)

Compounds of the aforementioned (IV-E), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^7$ is aryl optionally substituted with one or more substituents selected from Substituent Group G (Substituent Group G halogen, alkyl, haloalkyl, alkyloxy, nitrogen-containing non-aromatic heterocyclyloxy optionally substituted with substituent(s) selected from Substituent Group H (Substituent Group H; halogen, carboxy, oxo, alkyl, alkyloxycarbonyl), aryloxy optionally substituted with substituent(s) selected from Substituent Group H; and heteroaryloxy optionally substituted with substituent(s) selected from Substituent Group H); or heteroaryl optionally substituted with one or more substituents selected from Substituent Group G.

(IV-H)

Compounds of the aforementioned (IV-D), pharmaceutically acceptable salts or solvates thereof, or pharmaceutical compositions comprising the above-mentioned compounds, salts, or solvates and having a. P2X$_3$ and/or P2X$_{2/3}$ is receptor antagonistic effect, wherein $R^7$ is $R^{7A}$ wherein $R^{10a}$, $R^{10b}$, and $R^{10c}$ are each independently a hydrogen atom or a substituent selected from Substituent Group D, provided that the groups of (a) to (h) have at least one substituent.

(IV-I)

Compounds of the aforementioned (IV-E), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group E, provided that the groups of (a) to (h) have at least one substituent.

(IV-J)

Compounds of the aforementioned (IV-F), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group F, provided that the groups of (a) to (h) have at least one substituent.

(IV-K)

Compounds of the aforementioned (IV-G), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group G, provided that the groups of (a) to (h) have at least one substituent.

(IV-L1)

Compounds of the aforementioned (IV-D) to (IV-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^6$ is $R^{6A}$, i.e., $R^A$, $R^B$, $R^C$, $R^D$, $R^E$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently a hydrogen atom or a substituent selected from Substituent Group C, provided that the groups of (i) to (p) have at least one substituent.

(IV-L2)

Compounds of the aforementioned (IV-D) to (IV-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect,
wherein R$^6$ is R$^{6B}$, i.e., R$^A$, R$^B$, and R$^C$ are each independently a hydrogen atom or a substituent selected from Substituent Group C, wherein the groups of (i) to (p) have at least one substituent.

(IV-L3)
Compounds of the aforementioned (IV-D) to (IV-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect,
wherein R$^6$ is R$^{6C}$, R$^D$ and R$^E$ are each independently a hydrogen atom or a substituent selected from Substituent Group C.

(IV-L4)
Compounds of the aforementioned (IV-D) to (IV-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect,
wherein R$^6$ is R$^{6D}$, i.e., R$^{50}$, R$^{51}$, R$^{52}$, R$^{53}$, R$^{54}$, and R$^{55}$ are each independently a hydrogen atom or a substituent selected from Substituent Group C.

(IV-L5)
Compounds of the aforementioned (IV-D) to (IV-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect,
wherein R$^6$ is R$^{6E}$, i.e., R$^{56}$, R$^{57}$, R$^{58}$, R$^{59}$, R$^{60}$, R$^{61}$, R$^{62}$, and R$^{63}$ are each independently a hydrogen atom or a substituent selected from Substituent Group C.

(IV-L6)
Compounds of the aforementioned (IV-D) (IV-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect,
wherein R$^6$ is R$^{6F}$, i.e., R$^F$ is a hydrogen atom or a substituent selected from Substituent Group C.

(IV-M1)
Compounds of the aforementioned (IV-A), (IV-B), (IV-C1) to (IV-C6), (IV-D) to (IV-K), and (IV-L1) to (IV-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect,
wherein R$^{3b}$ is
a group of the formula: —NH—C(=O)—(CR$^{8a}$R$^{8b}$)n-R$^9$ wherein n is an integer of 0 to 4; R$^{8a}$ and R$^{8b}$ are each independently hydrogen, halogen, hydroxy, or substituted or unsubstituted alkyl; and R$^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl or
a group of the formula: —(CR$^{8a}$R$^{8b}$)m-R$^9$ wherein m is an integer of 1 to 6; R$^{8a}$, R$^{8b}$, and R$^9$ are as defined above.

(IV-M2)
Compounds of the aforementioned (IV-A), (IV-B), (IV-C1) to (IV-C6), (IV-D) to (IV-K), and (IV-L1) to (IV-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect,
wherein R$^{3b}$ is
a group of the formula: —NH—C(=O)—(CR$^{8a}$R$^{8b}$)n-R$^{9A}$ wherein n is an integer of 0 to 4; R$^{8a}$ and R$^{8b}$ are each independently hydrogen, halogen, hydroxy, or substituted or unsubstituted alkyl; and R$^{9A}$ is hydroxy, carboxy, cyano, a substituted or unsubstituted non-aromatic heterocyclic group, substituted or unsubstituted alkyloxy, substituted or unsubstituted alkyloxycarbonyl, substituted or unsubstituted carbamoyl, substituted or unsubstituted sulfamoyl, or substituted or unsubstituted amino or
a group of the formula: —(CR$^{8a}$R$^{8b}$)m-R$^{9A}$ wherein m is an integer of 1 to 6; R$^{8a}$, R$^{8b}$, and R$^{9A}$ are as defined above.

(IV-M3)
Compounds of the aforementioned (IV-A), (IV-B), (IV-C1) to (IV-C6), (IV-D) to (IV-K), and (IV-L1) to (IV-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein R$^{3b}$ is a group of the formula: —NH—C(=O)—(CR$^{8a}$R$^{8b}$)n-R$^9$ wherein n is an integer of 0 to 4; R$^{8a}$ and R$^{8b}$ are each independently hydrogen, halogen, hydroxy, or substituted or unsubstituted alkyl; and R$^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl.

(IV-M4)
Compounds of the aforementioned (IV-A), (IV-B), (IV-C1) to (IV-C6), (IV-D) to (IV-K), and (IV-L1) to (IV-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein R$^{3b}$ is a group of the formula: —NH—C(=O)—(CR$^{8a}$R$^{8b}$)n-R$^{9A}$ wherein n is an integer of 0 to 4; R$^{8a}$ and R$^{8b}$ are each independently hydrogen, halogen, hydroxy, or substituted or unsubstituted alkyl; and R$^{9A}$ is hydroxy, carboxy, cyano, a substituted or unsubstituted non-aromatic heterocyclic group, substituted or unsubstituted alkyloxy, substituted or unsubstituted alkyloxycarbonyl, substituted or unsubstituted carbamoyl, substituted or unsubstituted sulfamoyl, or substituted or unsubstituted amino.

(IV-M5)
Compounds of the aforementioned (IV-A), (IV-B), (IV-C1) to (IV-C6), (IV-D) to (IV-K), and (IV-L1) to (IV-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein R$^{8b}$ is a group of the formula: —(CR$^{8a}$R$^{8b}$)m-R$^9$ wherein m is an integer of 1 to 6; R$^{8a}$ and R$^{8b}$ are each independently hydrogen, halogen, hydroxy, or substituted or unsubstituted alkyl; and R$^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl.

(IV-M6)

Compounds of the aforementioned (IV-A)), (IV-B), (IV-C1) to (IV-C6), (IV-D) to (IV-K), and (IV-L1) to (IV-L6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{3b}$ is a group of the formula: $—(CR^{8a}R^{8b})m-R^{9A}$
  wherein m is an integer of 1 to 6; $R^{8a}$ and $R^{8b}$ are each independently hydrogen, halogen, hydroxy, or substituted or unsubstituted alkyl; and $R^{9A}$ is hydroxy, carboxy, cyano, a substituted or unsubstituted non-aromatic heterocyclic group, substituted or unsubstituted alkyloxy, substituted or unsubstituted alkyloxycarbonyl, substituted or unsubstituted carbamoyl, substituted or unsubstituted sulfamoyl, or substituted or unsubstituted amino.

(IV-N)

Compounds of the aforementioned (IV-A), (IV-B), (IV-C1) to (IV-C6), (IV-D) to (IV-K), (IV-L1) to (IV-L6), and (IV-M1) to (IV-M6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{5b}$ is hydrogen; and $R^{9a}$, $R^{9b}$, and $R^{16}$ are hydrogen.

Another embodiment of the compounds of the present invention or the compositions of the present invention is described below.

In the compounds of the formula (V):

[Chemical Formula 103]

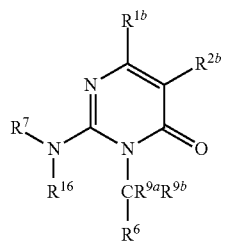

(V)

embodiments of the following (V-A) to (V-O) are described below:

(V-A)

Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{1b}$ and $R^{2b}$ are each independently hydrogen, nitro, halogen, hydroxy, carboxy, substituted or unsubstituted alkyl, substituted or unsubstituted acyl, substituted or unsubstituted alkyloxy, substituted or unsubstituted alkenyloxy, substituted or unsubstituted alkynyloxy, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted alkylthio, substituted or unsubstituted alkenylthio, substituted or unsubstituted alkynylthio, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted sulfamoyl, or substituted or unsubstituted amino;

$R^6$ is substituted or unsubstituted cycloalkyl substituted or unsubstituted cycloalkenyl, a substituted or unsubstituted non-aromatic heterocyclic group, substituted or unsubstituted aryl or substituted or unsubstituted heteroaryl;

$R^7$ is substituted or unsubstituted aryl or substituted or unsubstituted heteroaryl:

$R^{9a}$ and $R^{9b}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, substituted or unsubstituted alkenyloxy, or $R^{9a}$ and $R^{9b}$ may be taken together to form oxo or thioxo;

$R^{16}$ is hydrogen, substituted or unsubstituted acyl, substituted or unsubstituted alkyl, substituted or unsubstituted alkenyl, or substituted or unsubstituted alkynyl.

(V-B)

Compounds of the aforementioned, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{1b}$ and $R^{2b}$ are each independently hydrogen; unsubstituted alkyl; alkyl substituted with one or more substituents selected from Substituent Group B (Substituent Group B; halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted, alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted, heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; alkynyl substituted with one or more substituents selected from Substituent Group B; unsubstituted amino; amino substituted with substituent(s) selected from Substituent Group A (Substituent Group A; alkyl, alkenyl, alkynyl, carboxyalkyl, carboxyalkenyl, carboxyalkynyl, substituted or unsubstituted acyl, carboxycarbonyl, arylalkyl, arylalkenyl, arylalkynyl, arylalkyloxycarbonyl, hydroxyalkyl, hydroxyalkenyl, hydroxyalkynyl, dialkylaminoalkyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl, alkyloxycarbonyl, alkenyloxycarbonyl, alkynyloxycarbonyl, carbamoyl, alkylcarbamoyl, alkenylcarbamoyl, alkynylcarbamoyl, non-aromatic heterocyclylcarbamoyl, alkylsulfonyl, alkenylsulfonyl, and alkynylsulfonyl); unsubstituted carbamoyl; or carbamoyl substituted with substituent(s) selected from Substituent Group A;

$R^6$ is substituted or unsubstituted cycloalkyl, substituted or unsubstituted aryl, or substituted or unsubstituted heteroaryl;

$R^7$ is substituted or unsubstituted aryl or substituted or unsubstituted heteroaryl;

$R^{9a}$ and $R^{9b}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy, or $R^{9a}$ and $R^{9b}$ may be taken together to form oxo or thioxo; and $R^{16}$ is hydrogen, substituted or unsubstituted acyl, substituted or unsubstituted alkyl, substituted or unsubstituted alkenyl, or substituted or unsubstituted alkynyl.

(V-C1)
Compounds of the aforementioned (V-A) or (V-B), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^6$ is $R^{6A}$; and $R^7$ is $R^{7A}$.

(V-C2)
Compounds of the aforementioned (V-A) to (V-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6B}$.

(V-C3)
Compounds of the aforementioned (V-A) to (V-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6C}$.

(V-C4)
Compounds of the aforementioned (V-A) to (V-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6D}$.

(V-C5)
Compounds of the aforementioned (V-A) to (V-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6E}$.

(V-C6)
Compounds of the aforementioned (V-A) (V-B), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^6$ is $R^{6F}$; and $R^7$ is $R^{7A}$.

(V-D)
Compounds of the aforementioned pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^{1b}$ and $R^{2b}$ are each independently hydrogen; unsubstituted alkyl; alkyl substituted with one or more substituents selected from Substituent Group B (Substituent Group B; halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkenyl; alkenyl substituted with one or more substituents selected from Substituent Group B; unsubstituted amino; amino substituted with substituent(s) selected from Substituent Group A (Substituent Group A; alkyl, alkenyl, alkenyl, carboxyalkyl, carboxyalkenyl, carboxyalkynyl, substituted or unsubstituted acyl, carboxycarbonyl, arylalkyl, arylalkenyl, arylalkynyl, arylalkyloxycarbonyl, hydroxyalkyl, hydroxyalkenyl, hydroxyalkynyl, dialkylaminoalkyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl, alkyloxycarbonyl, alkenyloxycarbonyl, alkynyloxycarbonyl, carbamoyl, alkylcarbamoyl, alkenylcarbamoyl, alkynylcarbamoyl, non-aromatic heterocyclylcarbamoyl, alkylsulfonyl, alkenylsulfonyl, and alkynylsulfonyl); unsubstituted carbamoyl; or carbamoyl substituted with substituent(s) selected from Substituent Group A;

$R^6$ is aryl optionally substituted with one or more substituents selected from Substituent Group C (Substituent Group C; halogen, hydroxy, alkyl, alkenyl, alkynyl, haloalkyl, cycloalkylalkyl, alkyloxy, alkenyloxy, alkynyloxy, cycloalkyloxy, cycloalkyl, and a non-aromatic heterocyclic group); heteroaryl optionally substituted with one or more substituents selected from Substituent Group C; and cycloalkyl optionally substituted with one or more substituents selected from Substituent Group C;

$R^7$ is aryl optionally substituted with one or more substituents selected from Substituent Group (Substituent Group B; halogen, carboxy, alkyl, alkenyl, alkynyl, alkyloxy, alkenyloxy, alkynyloxy, cycloalkyl, cycloalkenyl, and cycloalkynyl); or heteroaryl optionally substituted with one or more substituents selected from Substituent Group B; and $R^{9a}$, $R^{9b}$, and $R^{16}$ are hydrogen.

The "heteroaryl" in $R^7$ is preferably thiazolyl, isothiazolyl, oxazolyl, isoxazolyl, pyrazolyl, imidazolyl, triazolyl, furyl, thienyl, thiadiazolyl, oxadiazolyl, pyridyl, pyrimidyl, pyrazinyl, pyridazinyl, triazinyl, benzothiazolyl, or benzoxazolyl.

(V-E)

$R^{1b}$ and $R^{2b}$ are each independently hydrogen; unsubstituted alkyl; alkyl substituted with one or more substituents selected from Substituent Group B (Substituent Group B; halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; alkynyl substituted with substituent(s) selected from Substituent Group B; unsubstituted amino; amino substituted with substituent(s) selected from Substituent Group A (Substituent Group A; alkyl, alkenyl, alkynyl, carboxyalkyl, carboxyalkenyl, carboxyalkynyl, substituted or unsubstituted acyl, carboxycarbonyl, arylalkyl, arylalkenyl, arylalkynyl, arylalkyloxycarbonyl, hydroxyalkyl, hydroxyalkenyl, hydroxyalkynyl, dialkylaminoalkyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl, alkyloxycarbonyl, alkenyloxycarbonyl, alkynyloxycarbonyl, carbamoyl, alkylcarbamoyl, alkenylcarbamoyl, alkynylcarbamoyl, non-aromatic heterocyclylcarbamoyl, alkylsulfonyl, alkenylsulfonyl, and alkynylsulfonyl); unsubstituted carbamoyl; or carbamoyl substituted with substituent(s) selected from Substituent Group A;

$R^6$ is aryl optionally substituted with one or more substituents selected from Substituent Group C (Substituent Group C; halogen, hydroxy, alkyl, alkenyl, alkynyl, haloalkyl, cycloalkylalkyl, alkyloxy, alkenyloxy, alkynyloxy, cycloalkyloxy, cycloalkyl, and a non-aromatic heterocyclic group); heteroaryl optionally substituted with one or more substituents selected from Substituent Group C; or cycloalkyl optionally substituted with one or more substituents selected from Substituent Group C;

$R^7$ is aryl optionally substituted with one or more substituents selected from Substituent Group E (Substituent Group E; halogen, carboxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, cycloalkynyl, a substituted or unsubstituted nitrogen-containing non-aromatic heterocyclyloxy, substituted or unsubstituted aryloxy, and substituted or unsubstituted heteroaryloxy); or heteroaryl optionally substituted with one or more substituents selected from Substituent Group E; and $R^{9a}$, $R^{9b}$, and $R^{16}$ are hydrogen.

The "heteroaryl" $R^7$ is preferably thiazolyl, isothiazolyl, oxazolyl, isoxazolyl, pyrazolyl, imidazolyl, triazolyl, furyl, thienyl, thiadiazolyl, oxadiazolyl, pyridyl, pyrimidyl, pyrazinyl, pyridazinyl, triazinyl, benzothiazolyl, or benzoxazolyl.

(V-F)

Compounds of the aforementioned (V-E), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is aryl optionally substituted with one or more substituents selected from Substituent Group F (Substituent Group F; halogen, substituted or unsubstituted alkyl, substituted or unsubstituted alkyloxy, a substituted or unsubstituted nitrogen-containing non-aromatic heterocyclyloxy, substituted or unsubstituted aryloxy, and substituted or unsubstituted heteroaryloxy); or heteroaryl optionally substituted with one or more substituents selected from Substituent Group F.

(V-G)

Compounds of the aforementioned (V-E), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is aryl optionally substituted with one or more substituents selected from Substituent Group G (Substituent Group G; halogen, alkyl, haloalkyl, alkyloxy, nitrogen-containing non-aromatic heterocyclyloxy optionally substituted with substituent(s) selected from Substituent. Group H (Substituent Group H; halogen, carboxy, oxo, alkyl, and alkyloxycarbonyl), aryloxy optionally substituted with substituent(s) selected from Substituent. Group H, and heteroaryloxy optionally substituted with substituent(s) selected from Substituent Group H); or heteroaryl optionally substituted with one or more substituents selected from Substituent Group G.

(V-H)

Compounds of the aforementioned (V-D), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group D, provided that the groups of (a) to (h) have at least one substituent.

(V-I)

Compounds of the aforementioned (V-E), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group E, provided that the groups of (a) to (h) have at least one substituent.

(V-J)

Compounds of the aforementioned (V-F), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group F, provided that the groups of (a) to (h) have at least one substituent.

(V-K)

Compounds of the aforementioned (V-G), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group G, provided that the groups of (a) to (h) have at least one substituent.

(V-L1)

Compounds of the aforementioned (V-D) to (V-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6A}$, i.e., $R^A$, $R^B$, $R^C$, $R^D$, $R^E$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently a hydrogen atom or a substituent selected from Substituent Group C, provided that the groups of (i) to (p) have at least one substituent.

(V-L2)

Compounds of the aforementioned (V-D) to (V-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6B}$, i.e., $R^A$, $R^B$, and $R^C$ are each independently a hydrogen atom or a substituent selected from Substituent Group C, provided that the groups of (i) to (p) have at least one substituent.

(V-L3)

Compounds of the aforementioned (V-D) to (V-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6C}$, i.e., $R^D$ and $R^E$ are each independently a hydrogen atom or a substituent selected from Substituent Group C.

(V-L4)

Compounds of the aforementioned (V-D) to (V-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6D}$, i.e., $R^{50}$, $R^{51}$, $R^{52}$, $R^{53}$, $R^{54}$, and $R^{55}$ are each independently hydrogen atom or a substituent selected from Substituent Group C.

(V-L5)

Compounds of the aforementioned (V-D) to (V-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6E}$, i.e., $R^{56}$, $R^{57}$, $R^{58}$, $R^{59}$, $R^{60}$, $R^{61}$, $R^{62}$, and $R^{63}$ are each independently a hydrogen atom or a substituent selected from Substituent Group C.

(V-L6)

Compounds of the aforementioned (V-D) to (V-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6F}$, i.e., $R^F$ is a hydrogen atom or a substituent selected from Substituent Group C.

(V-M1)

Compounds of the aforementioned (V-A), (V-B), (V-C1) to (V-C6), (V-D) to (V-K), or (V-L1) to (V-L6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2b}$ is a group of the formula: —NH—C(=O)—$(CR^{8a}R^{8b})$n-$R^9$ wherein n is an integer of 0 to 4; $R^{8a}$ and $R^{8b}$ are each independently hydrogen, halogen, hydroxy, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl or a group of the formula: —$(CR^{8a}R^{8b})$m-$R^9$ wherein m is an integer of 1 to 6; and $R^{8a}$, $R^{8b}$, and $R^9$ are as defined above.

(V-M2)

Compounds of the aforementioned (V-A), (V-B), (V-C1) to (V-C6), (V-D) to (V-K), or (V-L1) to (V-L6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2b}$ is a group of the formula: —NH—C(=O)—$(CR^{8a}R^{8b})$n-$R^{9A}$ wherein n is an integer of 0 to 4; $R^{8a}$ and $R^{8b}$ are each independently hydrogen, halogen, hydroxy, or substituted or unsubstituted alkyl; and $R^{9A}$ is hydroxy, carboxy, cyano, a substituted or unsubstituted non-aromatic heterocyclic group, substituted or unsubstituted alkyloxy, substituted or unsubstituted alkyloxycarbonyl, substituted or unsubstituted carbamoyl, substituted or unsubstituted sulfamoyl, substituted or unsubstituted amino or a group of the formula: —$(CR^{8a}R^{8b})$m-$R^{9A}$ wherein m is an integer of 1 to 6; and $R^{8a}$, $R^{8b}$, and $R^{9A}$ are as defined above.

(V-M3)

Compounds of the aforementioned (V-A), (V-B), (V-C1) to (V-C6), (V-D) to (V-K), or (V-L1) to (V-L6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2b}$ is a group of the formula: —NH—C(=O)—$(CR^{8a}R^{8b})$n-$R^9$ wherein n is an integer of 0 to 4; $R^{8a}$ and $R^{8b}$ are each independently hydrogen, halogen, hydroxy, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl.

(V-M4)

Compounds of the aforementioned (V-A), (V-B), (V-C1) to (V-C6), (V-D) to (V-K), or (V-L1) to (V-L6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2b}$ is a group of the formula: —NH—C(=O)—(CR$^{8a}$R$^{8b}$)n-R$^{9A}$ wherein n is an integer of 0 to 4; R$^{8a}$ and R$^{8b}$ are each independently hydrogen, halogen, hydroxy, or substituted or unsubstituted alkyl; and R$^{9A}$ is hydroxy, carboxy, cyano, a substituted or unsubstituted non-aromatic heterocyclic group, substituted or unsubstituted alkyloxy, substituted or unsubstituted alkyloxycarbonyl, substituted or unsubstituted carbamoyl, substituted or unsubstituted sulfamoyl, or substituted or unsubstituted amino.

(V-M5)

Compounds of the aforementioned (V-A), (V-B), (V-C1) to (V-C6), (V-D) to (V-K), or (V-L1) to (V-L6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2b}$ is a group of the formula: —(CR$^{8a}$R$^{8b}$)m-R$^9$ wherein m is an integer of 1 to 6; R$^{8a}$ and R$^{8b}$ are each independently hydrogen, halogen, hydroxy, or substituted or unsubstituted alkyl; and R$^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl.

(V-M6)

Compounds of the aforementioned (V-A), (V-B), (V-C1) to (V-C6), (V-D) to (V-K), or (V-L1) to (V-L6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2b}$ is a group of the formula: —(CR$^{8a}$R$^{8b}$)m-R$^{9A}$ wherein in is an integer of 1 to 6; R$^{8a}$ and R$^{8b}$ are each independently hydrogen, halogen, hydroxy, or substituted or unsubstituted alkyl; and R$^{9A}$ is hydroxy, carboxy, cyano, a substituted or unsubstituted non-aromatic heterocyclic group, substituted or unsubstituted alkyloxy, substituted or unsubstituted alkyloxycarbonyl, substituted or unsubstituted carbamoyl, substituted or unsubstituted sulfamoyl, or substituted or unsubstituted amino.

(V-N)

Compounds of the aforementioned (V-A), (V-B), (V-C1) to (V-C6), (V-D) to (V-K), or (V-L1) to (V-L6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2b}$ is unsubstituted alkyl; alkyl substituted with one or more substituents selected from Substituent Group J (Substituent Group J; hydroxy, carboxy, substituted or unsubstituted alkyloxycarbonyl, substituted or unsubstituted alkenyloxycarbonyl, substituted or unsubstituted alkynyloxycarbonyl, substituted or unsubstituted heteroaryloxycarbonyl, substituted or unsubstituted carbamoyl, substituted or unsubstituted amino, substituted or unsubstituted sulfamoyl, a substituted or unsubstituted non-aromatic heterocyclic group, substituted or unsubstituted aryl, and substituted or unsubstituted heteroaryl); alkenyl substituted with one or more substituents selected from Substituent Group J; or alkynyl substituted with one or more substituents selected from Substituent Group J.

(V-O)

Compounds of the aforementioned (V-A), (V-B), (V-C1) to (V-C5), (V-D) to (V-K), (V-L1) to (V-L6), (V-M1) to (V-M6), or (V-N), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{1b}$ is hydrogen or unsubstituted alkyl.

Another embodiment of the compounds of the present invention or the compositions of the present invention is described below.

In the compounds of the formula (VI):

[Chemical Formula 104]

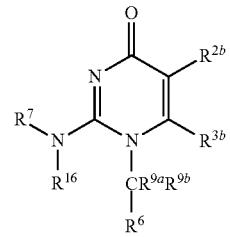

(VI)

embodiments of the following (VI-A) to (VI-O) are described below:

(VI-A)

Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{3b}$ and $R^{2b}$ are each independently hydrogen, nitro, halogen, hydroxy, carboxy, substituted or unsubstituted alkyl, substituted or unsubstituted acyl, substituted or unsubstituted alkyloxy, substituted or unsubstituted alkenyloxy, substituted or unsubstituted alkynyloxy, substituted or unsubstituted cycloalkyloxy, substituted or unsubstituted cycloalkenyl, substituted or unsubstituted non-aromatic heterocyclyloxy, substituted or unsubstituted aryloxy, substituted or unsubstituted heteroaryloxy, substituted or unsubstituted alkylthio, substituted or unsubstituted alkenylthio, substituted or unsubstituted alkynylthio, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted sulfamoyl, or substituted or unsubstituted amino;

R$^6$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

R⁷ is substituted or unsubstituted aryl or substituted or unsubstituted heteroaryl, R⁹ᵃ and R⁹ᵇ are each independently hydrogen, halogen, hydroxy, substituted or unsubstituted alkyl, substituted or unsubstituted, alkenyl, substituted or unsubstituted alkynyl, substituted or unsubstituted alkyloxy, substituted or unsubstituted alkynyloxy, or substituted or unsubstituted alkenyloxy, or R⁹ᵃ and R⁹ᵇ may be taken together to form oxo or thioxo; and R¹⁶ is hydrogen, substituted or unsubstituted acyl, substituted or unsubstituted alkyl, substituted or unsubstituted alkenyl, substituted or unsubstituted alkynyl.

(VI-B)

Compounds, pharmaceutically acceptable salts or solvates thereof, or pharmaceutical compositions comprising the above-mentioned compounds, salts, or solvates and having a P2X₃ and/or P2X₂/₃ receptor antagonistic effect, wherein R³ᵇ and R²ᵇ are each independently hydrogen; unsubstituted alkyl; alkyl substituted with one or more substituents selected from Substituent Group B (Substituent Group B: halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; alkynyl substituted with one or more substituents selected from Substituent Group B; unsubstituted amino; amino substituted with substituent(s) selected from Substituent Group A (Substituent Group A: alkyl, alkenyl, alkynyl, carboxyalkyl, carboxyalkenyl, carboxyalkynyl, substituted or unsubstituted acyl, carboxycarbonyl, arylalkyl, arylalkynyl, arylalkyloxycarbonyl, hydroxyalkyl, hydroxyalkenyl, hydroxyalkynyl, dialkylaminoalkyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl, alkyloxycarbonyl, alkenyloxycarbonyl, alkynyloxycarbonyl, carbamoyl, alkylcarbamoyl, alkenylcarbamoyl, alkynylcarbamoyl, non-aromatic heterocyclylcarbamoyl, alkylsulfonyl, alkenylsulfonyl and alkynylsulfonyl); unsubstituted carbamoyl; or carbamoyl substituted with substituent(s) selected from Substituent Group A;

R⁶ is substituted or unsubstituted cycloalkyl, substituted or unsubstituted aryl, or substituted or unsubstituted heteroaryl;

R⁷ is substituted or unsubstituted aryl or substituted or unsubstituted heteroaryl;

R⁹ᵃ and R⁹ᵇ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy, or R⁹ᵃ and R⁹ᵇ may be taken together to form oxo or thioxo; and R¹⁶ is hydrogen, substituted or unsubstituted acyl, substituted or unsubstituted alkyl, substituted or unsubstituted alkenyl, or substituted or unsubstituted alkynyl.

(VI-C1)

Compounds of the aforementioned (VI-A) or (VI-B), pharmaceutically acceptable salts or solvates thereof, or pharmaceutical compositions comprising the above-mentioned compounds, salts, or solvates and having a P2X₃ and/or P2X₂/₃ receptor antagonistic effect, wherein R⁶ is R⁶ᴬ; and R⁷ is R⁷ᴬ.

Compounds of the aforementioned (VI-A) to (VI-C1), pharmaceutically acceptable salts or solvates thereof, or pharmaceutical compositions comprising the above-mentioned compounds, salts, or solvates and having a P2X₃ and/or P2X₂/₃ receptor antagonistic effect, wherein R⁶ is R⁶ᴮ.

(VI-C3)

Compounds of the aforementioned (VI-A) to (VI-C1), pharmaceutically acceptable salts or solvates thereof, or pharmaceutical compositions comprising the above-mentioned compounds, salts, or solvates and having a P2X₃ and/or P2X₂/₃ receptor antagonistic effect, wherein R⁶ is R⁶ᶜ.

(VI-C4)

Compounds of the aforementioned (VI-A) to (VI-C1), pharmaceutically acceptable salts or solvates thereof, or pharmaceutical compositions comprising the above-mentioned compounds, salts, or solvates and having a P2X₃ and/or P2X₂/₃ receptor antagonistic effect, wherein R⁶ is R⁶ᴰ.

(VI-C5)

Compounds of the aforementioned (VI)-A) to (VI-C1), pharmaceutically acceptable salts or solvates thereof, or pharmaceutical compositions comprising the above-mentioned compounds, salts, or solvates and having a P2X₃ and/or P2X₂/₃ receptor antagonistic effect, wherein R⁶ is R⁶ᴱ.

(VI-C6)

Compounds of the aforementioned (VI-A) or (VI-B), pharmaceutically acceptable salts or solvates thereof, or pharmaceutical compositions comprising the above-mentioned compounds, salts, or solvates and having a P2X₃ and/or P2X₂/₃ receptor antagonistic effect, wherein R⁶ is R⁶ᶠ; and R⁷ is R⁷ᴬ.

(VI-D)

Compounds, pharmaceutically acceptable salts or solvates thereof, or pharmaceutical compositions comprising the above-mentioned compounds, salts, or solvates and having a P2X₃ and/or P2X₂/₃ receptor antagonistic effect, wherein R³ᵇ and R²ᵇ are each independently hydrogen; unsubstituted alkyl; alkyl substituted with one or more substituents selected from Substituent Group B (Substituent Group B halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; alkynyl substituted with one or more substituents selected from Substituent Group B; unsubstituted amino; amino substituted with substituent(s) selected from Substituent Group A (Substituent Group A: alkyl, alkenyl, alkynyl, carboxyalkyl, carboxyalkenyl, carboxyalkynyl, substituted or unsubstituted acyl, carboxycarbonyl, arylalkyl, arylalkenyl, arylalkynyl, arylalkyloxycarbonyl, hydroxyalkyl, hydroxyalkenyl, hydroxyalkynyl, dialkylaminoalkyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl, alkyloxycarbonyl, alkenyloxycarbonyl, alkynyloxycarbonyl, carbamoyl, alkylcarbamoyl, alkenylcarbamoyl, alkynylcarbamoyl, nor-aromatic heterocyclylcarbamoyl, alkylsulfonyl, alkenylsulfonyl and alkynylsulfonyl); unsubstituted carbamoyl; or carbamoyl substituted with substituents) selected from Substituent Group A;

$R^6$ is aryl optionally substituted with one or more substituents selected from Substituent Group C (Substituent Group C: halogen, hydroxy, alkyl, alkenyl, alkynyl, haloalkyl, cycloalkylalkyl, alkyloxy, alkenyloxy, alkynyloxy, cycloalkyloxy, cycloalkyl, and a non-aromatic heterocyclic group), heteroaryl optionally substituted with one or more substituents selected from Substituent Group C, or cycloalkyl optionally substituted with one or more substituents selected from Substituent Group C;

$R^7$ is aryl optionally substituted with one or more substituents selected from Substituent Group D (Substituent Group D: halogen, carboxy, alkyl, alkenyl, alkynyl, alkyloxy, alkenyloxy, alkynyloxy, cycloalkyl, cycloalkenyl, and cycloalkynyl) or heteroaryl optionally substituted with one or more substituents selected from Substituent Group D; and $R^{9a}$, $R^{9b}$, and $R^{16}$ are hydrogen.

Preferred examples of "heteroaryl" in $R^7$ include thiazolyl, isothiazolyl, oxazolyl, isoxazolyl, pyrazolyl, imidazolyl, triazolyl, furyl, thienyl, thiadiazolyl, oxadiazolyl, pyridyl, pyrimidyl, pyrazinyl, pyridazinyl, triazinyl, benzothiazolyl, and benzoxazolyl.

(VI-E)

Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{3b}$ and $R^{2b}$ are each independently hydrogen; unsubstituted alkyl; alkyl substituted with one or more substituents selected from Substituent Group B (Substituent Group B: halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; alkynyl substituted with one or more substituents selected from Substituent. Group B; unsubstituted amino; amino substituted with substituent(s) selected from Substituent Group A (Substituent Group A: alkyl, alkenyl, alkenyl, carboxyalkyl, carboxyalkenyl, carboxyalkynyl, substituted or unsubstituted acyl, carboxycarbonyl, arylalkyl, arylalkenyl, arylalkynyl, arylalkyloxycarbonyl, hydroxyalkyl, hydroxyalkenyl, hydroxyalkynyl, dialkylaminoalkyl, cycloalkylalkyl, cycloalkylalkenyl, cycloalkylalkynyl, non-aromatic heterocyclylalkyl, non-aromatic heterocyclylalkenyl, non-aromatic heterocyclylalkynyl alkyloxycarbonyl, alkenyloxycarbonyl, alkynyloxycarbonyl, carbamoyl, alkylcarbamoyl, alkenylcarbamoyl, alkynylcarbamoyl, non-aromatic heterocyclylcarbamoyl, alkylsulfonyl, alkenylsulfonyl and alkynylsulfonyl); unsubstituted carbamoyl; or carbamoyl substituted with substituent(s) selected from Substituent Group A;

$R^6$ is aryl optionally substituted with one or more substituents selected from Substituent Group C (Substituent Group C halogen, hydroxy, alkenyl, alkenyl, haloalkyl, cycloalkylalkyl, alkyloxy, alkenyloxy, alkynyloxy, cycloalkyloxy, cycloalkyl, and a nonaromatic heterocyclic group), heteroaryl optionally substituted with one or more substituents selected from Substituent Group C, or cycloalkyl optionally substituted with one or more substituents selected from Substituent Group C;

$R^7$ is aryl optionally substituted with one or more substituents selected from Substituent Group E (Substituent Group E: halogen, carboxy, substituted or unsubstituted alkyl, substituted or unsubstituted alkenyl, substituted or unsubstituted alkenyl, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, cycloalkynyl, a substituted or unsubstituted nitrogen-containing non-aromatic heterocyclyloxy, substituted or unsubstituted aryloxy, and substituted or unsubstituted heteroaryloxy) or heteroaryl optionally substituted with one or more substituents selected from Substituent Group E; and $R^{9a}$, $R^{9b}$, and $R^{16}$ are hydrogen.

Preferred examples of "heteroaryl" in $R^7$ include thiazolyl, isothiazolyl, oxazolyl, isoxazolyl, pyrazolyl, imidazolyl, triazolyl, furyl, thienyl, thiadiazolyl, oxadiazolyl, pyridyl, pyrimidyl, pyrazinyl, pyridazinyl, triazinyl, benzothiazolyl, and benzoxazolyl.

(VI-F)

Compounds of the aforementioned (VI-E), pharmaceutically acceptable salts or solvates thereof, or pharmaceutical compositions comprising the above-mentioned compounds, salts, or solvates and having a $P2X_3$ and/or $P2X_{2/3}$ is receptor antagonistic effect, wherein $R^7$ is aryl optionally substituted with one or more substituents selected from Substituent Group F (Substituent Group F: halogen, substituted or unsubstituted alkyl, substituted or unsubstituted alkyloxy, a substituted or unsubstituted nitrogen-containing non-aromatic heterocyclyloxy, substituted or unsubstituted aryloxy, and substituted or unsubstituted heteroaryloxy) or heteroaryl optionally substituted with one or more substituents selected from Substituent Group F.

(VI-G)

Compounds of the aforementioned (VI-E), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^7$ is aryl optionally substituted with one or more substituents selected from Substituent Group G (Substituent Group G: halogen, alkyl, haloalkyl, alkyloxy, nitrogen-containing non-aromatic heterocyclyloxy optionally substituted with substituent(s) selected from Substituent Group H (Substituent Group H: halogen, carboxy, oxo, alkyl, and alkyloxycarbonyl), aryloxy optionally substituted with substituent(s) selected from Substituent Group H, and heteroaryloxy optionally substituted with substituent(s) selected from Substituent Group H) or heteroaryl optionally substituted with one or more substituents selected from Substituent Group G.

(VI-H)

Compounds of the aforementioned (VI-D), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group D, provided that the groups of (a) to (h) have at least one substituent.

(VI-I)

Compounds of the aforementioned (VI-E), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group E, provided that the groups of (a) to (h) have at least one substituent.

(VI-J)

Compounds of the aforementioned (VI-F), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect.

wherein $R^7$ is $R^{7A}$ wherein $R^{10a}$, $R^{10b}$, and $R^{10c}$ are each independently a hydrogen atom or a substituent selected from Substituent Group F, provided that the groups of (a) to (h) have at least one substituent.

(VI-K)

Compounds of the aforementioned (VI-G), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group G, provided that the groups of (a) to (h) have at least one substituent.

(VI-L1)

Compounds of the aforementioned (VI-D) to (VI-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^6$ is $R^{6A}$, i.e., $R^A$, $R^B$, $R^C$, $R^D$, $R^E$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently a hydrogen atom or a substituent selected from Substituent Group C, provided that the groups of (i) to (p) have at least one substituent.

(VI-L2)

Compounds of the aforementioned (VI-D) to (VI-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^6$ is $R^{6B}$, i.e., $R^A$, $R^B$, and $R^C$ are each independently a hydrogen atom or a substituent selected from Substituent Group C, provided that the groups of (i) to (p) have at least one substituent.

(VI-L3)

Compounds of the aforementioned (VI-D) to (VI-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^6$ is $R^{6C}$, i.e., $R^D$ and $R^E$ are each independently a hydrogen atom or a substituent selected from Substituent Group C.

(VI-L4)

Compounds of the aforementioned (VI-D) to (VI-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^6$ is $R^{6D}$, i.e., $R^{50}$, $R^{51}$, $R^{52}$, $R^{53}$, $R^{54}$, and $R^{55}$ are each independently a hydrogen atom or a substituent selected from Substituent Group C.

(VI-L5)

Compounds of the aforementioned (VI-D) to (VI-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^6$ is $R^{6E}$, i.e., $R^{56}$, $R^{57}$, $R^{58}$, $R^{59}$, $R^{60}$, $R^{61}$, $R^{62}$, and $R^{63}$ are each independently a hydrogen atom or a substituent selected from Substituent Group C.

(VI-L6)

Compounds of the aforementioned (VI-D) to (VI-K), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein $R^6$ is $R^{6F}$, i.e., $R^F$ are each independently a hydrogen atom or a substituent selected from Substituent Group C.

(VI-M1)

Compounds of the aforementioned (VI-A), (VI-B), (VI-C1) to (VI-C6), (VI-D) to (VI-K), and (VI-L1) to (VI-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein one of $R^{2b}$ and $R^{3b}$ a group of the formula: $-\text{NH}-\text{C}(=\text{O})-(\text{CR}^{8a}\text{R}^{8b})\text{n-R}^9$ wherein n is an integer from 0 to 4;

$R^{8a}$ and $R^{8b}$ are each independently hydrogen, halogen, hydroxyl, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl or a group of the formula: —(CR$^{8a}$R$^{8b}$)m-R$^9$ wherein m is an integer from 1 to 6; and R$^{8a}$, R$^{8b}$, and R$^9$ are as defined above and the other of R$^{2b}$ and R$^{3b}$ is hydrogen.

(VI-M2)

Compounds of the aforementioned (VI-A), (VI-B), (VI-C1) to (VI-C6), (VI-D) to (VI-K), and (VI-L1) to (VI-L6), pharmaceutically acceptable salts or solvates thereof, or pharmaceutical compositions comprising the above-mentioned compounds, salts, or solvates and having a P2X$_3$ and/or P2X$_{2/3}$ is receptor antagonistic effect, wherein one of R$^{2b}$ and R$^{3b}$ is a group of the formula: —NH—C(=O)—(CR$^{8a}$R$^{8b}$)n-R$^{9A}$ wherein n is an integer from 0 to 4;

R$^{8a}$ and R$^{8b}$ are each independently hydrogen, halogen, hydroxyl, or substituted or unsubstituted alkyl; and R$^9$ is hydroxy, carboxy, cyano, a substituted or unsubstituted non-aromatic heterocyclic group, substituted or unsubstituted alkyloxy, substituted or unsubstituted alkyloxycarbonyl, substituted or unsubstituted carbamoyl, substituted or unsubstituted sulfamoyl, or substituted or unsubstituted amino or a group of the formula: —(CR$^{8a}$R$^{8b}$)m-R$^{9A}$ wherein m is an integer from 1 to 6; and R$^{8a}$, R$^{8b}$, and R$^{9A}$ are as defined above and the other of R$^{2b}$ and R$^{3b}$ is hydrogen.

(VI-M3)

Compounds of the aforementioned (VI-A), (VI-B), (VI-C1) to (VI-C6), (VI-D) to (VI-K), and (VI-L1) to (VI-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein one of R$^{2b}$ and R$^{3b}$ is a group of the formula: —NH—C(=O)—(CR$^{8a}$R$^{8b}$)n-R$^9$ wherein n is an integer from 0 to 4; R$^{8a}$ and R$^{8b}$ are each independently hydrogen, halogen, hydroxy, or substituted or unsubstituted alkyl; and R$^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl and the other of R$^{2b}$ and R$^{3b}$ is hydrogen.

(VI-M4)

Compounds of the aforementioned (VI-A), (VI-B), (VI-C1) to (VI-C6), (VI-D) to (VI-K), and (VI-L1) to (VI-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein one of R$^{2b}$ and R$^{3b}$ is a group of the formula: —NH—C(=O)—(CR$^{8a}$R$^{8b}$) n-R$^{9A}$ wherein n is an integer from 0 to 4; R$^{8a}$ and R$^{8b}$ are each independently hydrogen, halogen, hydroxyl, or substituted or unsubstituted alkyl; and R$^{9A}$ is hydroxy, carboxy, cyano, a substituted or unsubstituted non-aromatic heterocyclic group, substituted or unsubstituted alkyloxy, substituted or unsubstituted alkyloxycarbonyl, substituted or unsubstituted carbamoyl, substituted or unsubstituted sulfamoyl, or substituted or unsubstituted amino and the other of R$^{2b}$ and R$^{3b}$ is hydrogen.

(VI-M5)

Compounds of the aforementioned (VI-A), (VI-B), (VI-C1) to (VI-C6), (VI-D) to (VI-K), and (VI-L1) to (VI-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein one of R$^{2b}$ and R$^{3b}$ is a group of the formula: —(CR$^{8a}$R$^{8b}$)m-R$^9$ wherein m is an integer from 1 to 6; R$^{8a}$ and R$^{8b}$ are each independently hydrogen, halogen, hydroxyl, or substituted or unsubstituted alkyl; and R$^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl and the other of R$^{2b}$ and R$^{3b}$ is hydrogen.

(VI-M6)

Compounds of the aforementioned (VI-A), (VI-B), (VI-C1) to (VI-C6), (VI-D) to (VI-K), and, (VI-L1) to (VI-L6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein one of R$^{2b}$ and R$^{3b}$ is a group of the formula: —(CR$^{8a}$R$^{8b}$)m-R$^{9A}$ wherein m is an integer from 1 to 6; R$^{8a}$ and R$^{8b}$ are each independently hydrogen, halogen, hydroxyl, or substituted or unsubstituted alkyl; and R$^{9A}$ is hydroxy, carboxy, cyano, a substituted or unsubstituted non-aromatic heterocyclic group, substituted or unsubstituted alkyloxy, substituted or unsubstituted alkyloxycarbonyl, substituted or unsubstituted carbamoyl, substituted or unsubstituted sulfamoyl, or substituted or unsubstituted amino and other of R$^{2b}$ and R$^{3b}$ is hydrogen, (VI-N)

Compounds of the aforementioned (VI-A), (VI-B), (VI-C1) to (VI-C6), (VI-D) to (VI-K), (VI-L1) to (VI-L6), and (VI-M1) to (VI-M6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein R$^{3b}$ is hydrogen.

(VI-O)

Compounds of the aforementioned (VI-A), (VI-B), (VI-C1) to (VI-C6), (VI-D) (VI-K), (VI-L1) to (VI-L6), and (VI-M1) to (VI-M6), pharmaceutically acceptable salts or solvates thereof, or pharmaceutical compositions comprising the above-mentioned compounds, salts, or solvates and having a P2X$_3$ and/or P2X$_{2/3}$ receptor antagonistic effect, wherein R$^{2b}$ is hydrogen.

Another embodiment of the compounds of the present invention or the compositions of the present invention is described below.

In the compounds of the formula (X):

[Chemical Formula 105]

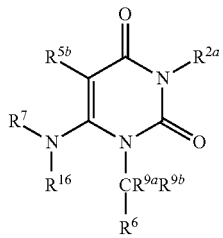

(X)

embodiments of the following (X-A) to (X-N) are described below:

(X-A)

Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{5b}$ is hydrogen, hydroxy, halogen, cyano, substituted or unsubstituted alkyl, substituted or unsubstituted alkenyl, substituted or unsubstituted alkenyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino;

$R^{2a}$ is hydrogen, substituted or unsubstituted alkyl, substituted or unsubstituted alkenyl, substituted or unsubstituted alkenyl, substituted or unsubstituted cycloalkyl, substituted or unsubstituted cycloalkenyl, a substituted or unsubstituted non-aromatic, heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, or substituted or unsubstituted sulfamoyl;

$R^6$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

$R^7$ is substituted or unsubstituted aryl or substituted or unsubstituted heteroaryl;

$R^{9a}$ and $R^{9b}$ are each independently hydrogen, halogen, hydroxy, substituted or unsubstituted alkyl, substituted or unsubstituted alkenyl, substituted or unsubstituted alkenyl, substituted or unsubstituted alkyloxy, substituted or unsubstituted alkynyloxy, substituted or unsubstituted alkenyloxy, or $R^{9a}$ and $R^{9b}$ may be taken together to form oxo or thioxo; and $R^{16}$ is hydrogen, substituted or unsubstituted acyl, substituted or unsubstituted alkyl, substituted or unsubstituted alkenyl, or substituted or unsubstituted alkynyl.

(X-B)

Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2a}$ and $R^{5b}$ are each independently hydrogen; unsubstituted alkyl; alkyl substituted with one or more substituents selected from Substituent Group B (Substituent Group B halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocycly-loxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; or alkenyl substituted with one or more substituents selected from Substituent Group B;

$R^6$ is substituted or unsubstituted cycloalkyl, substituted or unsubstituted aryl, or substituted or unsubstituted heteroaryl;

$R^7$ is substituted or unsubstituted aryl or substituted or unsubstituted heteroaryl;

$R^{9a}$ and $R^{9b}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, substituted or unsubstituted alkenyloxy, or $R^{9a}$ and $R^{9b}$ may be taken together to form oxo or thioxo; and $R^{16}$ is hydrogen, substituted or unsubstituted acyl, substituted or unsubstituted alkyl, substituted or unsubstituted alkenyl, or substituted or unsubstituted alkenyl.

(X-C1)
Compounds of the aforementioned (X-A) or (X-B), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^6$ is $R^{6A}$; and $R^7$ is $R^{7A}$.

(X-C2)
Compounds of the aforementioned (X-A) (X-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^6$ is $R^{6B}$.

(X-C3)
Compounds of the aforementioned (X-A) to (X-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^6$ is $R^{6C}$.

(X-C4)
Compounds of the aforementioned (X-A) to (X-C1), pharmaceutically-acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^6$ is $R^{6D}$.

(X-C5)
Compounds of the aforementioned (X-A) to (X-C1), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^6$ is $R^{6E}$.

(X-C6)
Compounds of the aforementioned (X-A) or (X-B) pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^6$ is $R^{6F}$; and $R^7$ is $R^{7A}$.

(X-D)
Compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect,
wherein $R^{2a}$ and $R^{5b}$ are each independently hydrogen; unsubstituted alkyl; alkyl substituted with one or more substituents selected from Substituent Group B (Substituent Group B halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; or alkynyl substituted with one or more substituents selected from Substituent Group B;

$R^6$ is aryl optionally substituted with one or more substituents selected from Substituent Group C (Substituent Group C halogen, hydroxy, alkyl, alkenyl, alkynyl, haloalkyl, cycloalkylalkyl, alkyloxy, alkenyloxy, alkynyloxy, cycloalkyloxy, cycloalkyl, and a non-aromatic heterocyclic group), heteroaryl optionally substituted with one or more substituents selected from Substituent. Group C, or cycloalkyl optionally substituted with one or more substituents selected from Substituent Group C;

$R^7$ is aryl optionally substituted with one or more substituents selected from Substituent Group D (Substituent Group D: halogen, carboxy, alkyl, alkenyl, alkynyl, alkyloxy, alkenyloxy, alkynyloxy, cycloalkyl, cycloalkenyl, and cycloalkynyl) or heteroaryl optionally substituted with one or more substituents selected from Substituent Group D; and $R^{9a}$, $R^{9b}$, and $R^{16}$ are hydrogen.

Preferred examples of "heteroaryl" in $R^7$ include thiazolyl, isothiazolyl, oxazolyl, isoxazolyl, pyrazolyl, imidazolyl, triazolyl, furyl, thienyl, thiadiazolyl, oxadiazolyl, pyridyl, pyrimidyl, pyrazinyl, pyridazinyl, triazinyl, benzothiazolyl, and benzoxazolyl.

(X-E)
A pharmaceutical composition having a $P2X_3$ and/or $P2X_{2/3}$ receptor antagonistic effect and comprising a compound consisting of:
$R^{2a}$ and $R^{5b}$ are each independently hydrogen; unsubstituted alkyl; alkyl substituted with one or more substituents selected from Substituent Group B (Substituent Group B: halogen, hydroxy, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted carbamoyl, substituted or unsubstituted amino, substituted or unsubstituted sulfamoyl, cyano, nitro, substituted or unsubstituted cycloalkyl, substituted or unsubstituted cycloalkenyl, a substituted or unsubstituted non-aromatic heterocyclic group, substituted or unsubstituted aryl, and substituted or unsubstituted heteroaryl); unsubstituted alkenyl; alkenyl substituted with one or more substituents selected from Substituent Group B; unsubstituted alkynyl; nor alkynyl substituted with one or more substituents selected from Substituent Group B;

$R^6$ is aryl optionally substituted with one or more substituents selected from Substituent Group C (Substituent Group C; halogen, hydroxy, alkyl, alkenyl, alkynyl, haloalkyl, cycloalkylalkyl, alkyloxy, alkenyloxy, alkynyloxy, cycloalkyloxy, cycloalkyl, and a non-aromatic heterocyclic group), heteroaryl optionally substituted with one or more substituents selected from Substituent Group C, or cycloalkyl optionally substituted with one or more substituents selected from Substituent Group C;

$R^7$ is aryl optionally substituted with one or more substituents selected from Substituent Group E (Substituent Group E: halogen, carboxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, cycloalkynyl, substituted or unsubstituted nitrogen-containing non-aromatic heterocyclyloxy, substituted or unsubstituted aryloxy, and substituted or unsubstituted heteroaryloxy) or heteroaryl optionally substituted with one or more substituents selected from Substituent Group E; and $R^{9a}$, $R^{9b}$, and $R^{16}$ are hydrogen.

Preferred examples of "heteroaryl" in $R^7$ include thiazolyl, isothiazolyl, oxazolyl, isoxazolyl, pyrazolyl, imidazolyl, triazolyl, furyl, thienyl, thiadiazolyl, oxadiazolyl, pyridyl, pyrimidyl, pyrazinyl, pyridazinyl, triazinyl, benzothiazolyl, and benzoxazolyl.

(X-F)

Compounds of the aforementioned (X-E), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is aryl optionally substituted with one or more substituents selected from Substituent Group F (Substituent Group F: halogen, substituted or unsubstituted alkyl, substituted or unsubstituted alkyloxy, a substituted or unsubstituted nitrogen-containing non-aromatic heterocyclyloxy, substituted or unsubstituted aryloxy, and substituted or unsubstituted heteroaryloxy) or heteroaryl optionally substituted with one or more substituents selected from Substituent Group F.

(X-G)

Compounds of the aforementioned (X-E), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is aryl optionally substituted with one or more substituents selected from Substituent Group G (Substituent Group G: halogen, alkyl, haloalkyl, alkyloxy, nitrogen-containing non-aromatic heterocyclyloxy optionally substituted with substituent(s) selected from Substituent Group H (Substituent Group H: halogen, carboxy, oxo, alkyl, and alkyloxycarbonyl), aryloxy optionally substituted with substituent(s) selected from Substituent Group H, and heteroaryloxy optionally substituted with substituent(s) selected from Substituent Group H) or heteroaryl optionally substituted with one or more substituents selected from Substituent Group G.

(X-H)

Compounds of the aforementioned (X-D), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group D, provided that the groups of (a) to (h) have at least one substituent, (X-I)

Compounds of the aforementioned (X-E), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group E, provided that the groups of (a) to (h) have at least one substituent.

(X-J)

Compounds of the aforementioned (X-F), pharmaceutically acceptable salts or solvates thereof, or pharmaceutical compositions comprising the above-mentioned compounds, salts, or solvates and having a $P2X_3$ and/or $P2X_{2/3}$ is receptor antagonistic effect, wherein $R^7$ is $R^{7A}$ wherein $R^{10a}$, $R^{10b}$, and $R^{10c}$ are each independently a hydrogen atom or a substituent selected from Substituent Group F, provided that the groups of (a) to (h) have at least one substituent.

(X-K)

Compounds of the aforementioned (X-G), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^7$ is $R^{7A}$ wherein $R^{10a}$, $R^{10b}$, and $R^{10c}$ are each independently a hydrogen atom or a substituent selected from Substituent Group G, provided that the groups of (a) to (h) have at least one substituent.

(X-L1)

Compounds of the aforementioned (X-D) to (X-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6A}$, i.e., $R^A$, $R^B$, $R^C$, $R^D$, $R^E$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently a hydrogen atom or a substituent selected from Substituent Group C, provided that the groups of (i) to (p) have at least one substituent.

(X-L2)

Compounds of the aforementioned (X-D) to (X-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect.

wherein $R^6$ is $R^{6B}$, i.e., $R^A$, $R^B$ and $R^C$ are each independently a hydrogen atom or a substituent selected from Substituent Group C, provided that the groups of (i) to (p) have at least one substituent.

(X-L3)

Compounds of the aforementioned (X-D) to (X-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6C}$, i.e., $R^D$ and $R^E$ are each independently a hydrogen atom or a substituent selected from Substituent Group C.

(X-L4)

Compounds of the aforementioned (X-D) to (X-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6D}$, i.e., $R^{50}$, $R^{51}$, $R^{52}$, $R^{53}$, $R^{54}$ and $R^{55}$ are each independently a hydrogen atom or a substituent selected from Substituent Group C.

(X-L5)

Compounds of the aforementioned (X-D) to (X-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6E}$, i.e., $R^{56}$, $R^{57}$, $R^{58}$, $R^{59}$, $R^{60}$, $R^{61}$, $R^{62}$, and $R^{63}$ are each independently a hydrogen atom or a substituent selected from Substituent Group C.

(X-L6)

Compounds of the aforementioned (X-D) to (X-K), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^6$ is $R^{6F}$, i.e., $R^F$ is a hydrogen atom or a substituent selected from Substituent Group C.

(X-M1)

Compounds of the aforementioned (X-A), (X-B), (X-C1) to (X-C6), (X-D) to (X-K), and (X-L1) to (X-L6), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2a}$ is a group of the formula: —$(CR^{8a}R^{8b})m-R^9$ wherein in is an integer from 1 to 6; $R^{8a}$ and $R^{8b}$ are each independently hydrogen, halogen, hydroxy, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl.

(X-M2)

Compounds of the aforementioned (X-A), (X-B), (X-C1) to (X-C6), (X-D) to (X-K), and (X-L1) to (X-L5), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{2a}$ is a group of the formula: —$(CR^{8a}R^{8b})m-R^{9A}$ wherein in is an integer from 1 to 6; $R^{8a}$ and $R^{8b}$ are each independently hydrogen, halogen, hydroxy, or substituted or unsubstituted alkyl; and $R^{9A}$ is hydroxy, carboxy, cyano, a substituted or unsubstituted non-aromatic heterocyclic group, substituted or unsubstituted alkyloxy, substituted or unsubstituted alkoxycarbonyl, substituted or unsubstituted carbamoyl, substituted or unsubstituted sulfamoyl, or substituted or unsubstituted amino.

(X-N)

Compounds of the aforementioned (X-A), (X-B), (X-C1) to (X-C6), (X-D) to (X-K), (X-L1) to (X-L6), and (X-M1) to (V-M2), pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein $R^{5b}$ is hydrogen.

Another embodiment of the compounds of the present invention or the compositions of the present invention is described below.

Compounds of the following formula, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect:

[Chemical Formula 106]

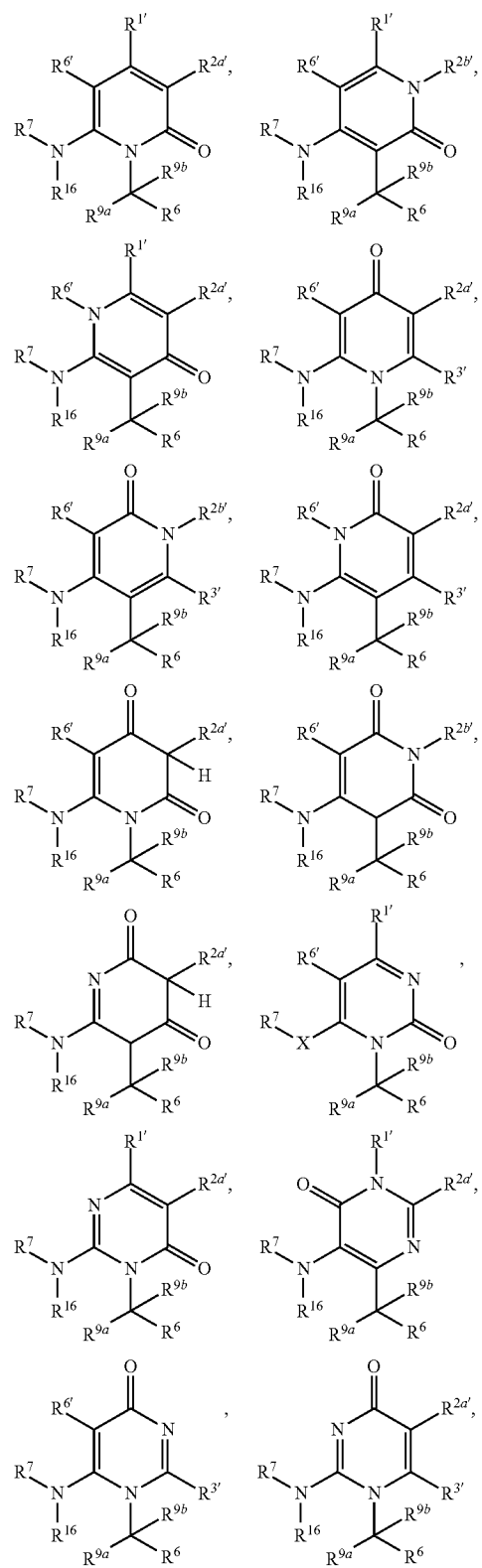

153
-continued

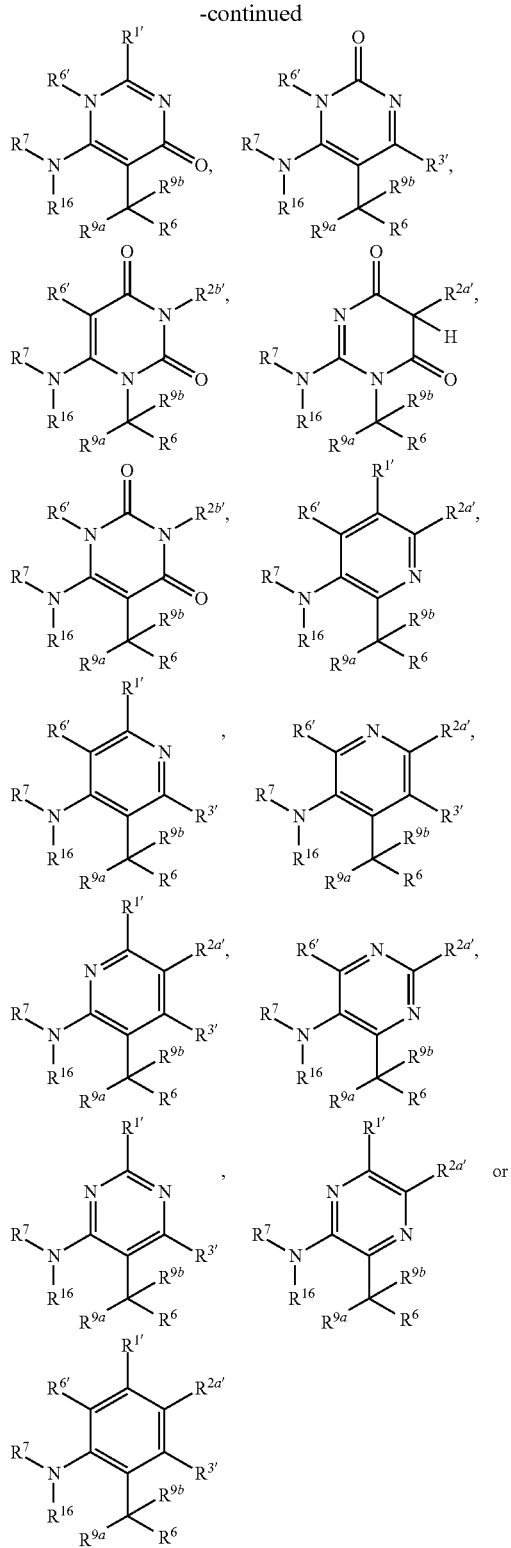

which has substituents defined in the aforementioned (IV-A) to (IV-N), (V-A) to (V-O), (VI-A) to (VI-O), and (X-A) to (X-N), i.e., $R^{9a}$, $R^{9b}$, and $R^{16}$ correspond respectively to $R^{9a}$, $R^{9b}$, and $R^{16}$ in the formula (IV); $R^{1'}$ corresponds to $R^{1b}$ in the formula (V); $R^{6'}$ corresponds to $R^{5b}$ in the formula (X); $R^{3'}$ corresponds to $R^{2b}$ in the formula (IV); $R^{2a'}$ corresponds to

154

$R^{2b}$ in the formula (V); $R^{2b'}$ corresponds to $R^{2a}$ in the formula (X), preferably C1-C6 alkyl or a group of the formula: —$(CR^{8a}R^{8b})m-R^9$ (wherein m is an integer from 1 to 6; and $R^{8a}$, $R^{8b}$, and $R^9$ are hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl); $R^6$ is $R^{64}$, i.e., $R^A$, $R^B$, $R^C$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently a hydrogen atom or a substituent selected from Substituent Group C, provided that the groups of (i) to (p) have at least one substituent; wherein "the groups of (i) to (p) have at least one substituent" means that at least one of $R^A$, $R^B$, and $R^C$ is not hydrogen in the groups of (i), (j), and (n); at least one of $R^B$ and $R^C$ is not hydrogen in the group of (k); at least one of $R^A$ and $R^C$ is not hydrogen in the groups of (l) and (o); at least one of $R^A$ and $R^B$ is not hydrogen in the group of (m); and $R^B$ is not hydrogen in the group of (p); $R^7$ is $R^{7A}$ wherein $R^{10a}$, $R^{10b}$ and $R^{10c}$ are each independently a hydrogen atom or a substituent selected from Substituent Group E, provided that the groups of (a) to (h) have at least one substituent; wherein "the groups of (a) to (h) have at least one substituent" means that at least one of $R^{10a}$, $R^{10b}$, and $R^{10c}$ is not hydrogen in the groups of (a), (b), and (f); at least one of $R^{10b}$ and $R^{10c}$ is not hydrogen in the group of (c); at least one of $R^{10a}$ and $R^{10c}$ is not hydrogen in the groups of (d) and (g); at least one of $R^{10a}$ and $R^{10b}$ is not hydrogen in the group of (e); and $R^{10b}$ is not hydrogen in the group of (h).

Another embodiment of the compounds of the present invention or the compositions of the present invention is described below.

Compounds of the following formula, pharmaceutically acceptable salts or solvates thereof, or pharmaceutical compositions comprising the above-mentioned compounds, salts, or solvates and having a P2X$_3$ and/or P2X$_{2/3}$ receptor antagonistic effect:

[Chemical Formula 107]

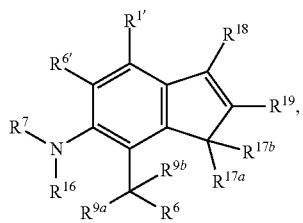

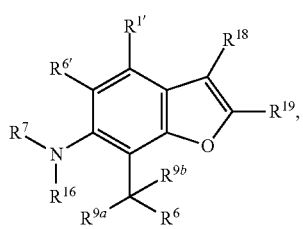

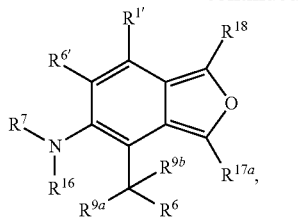
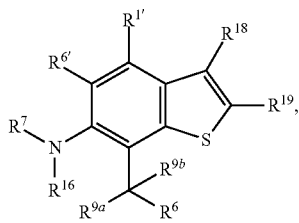
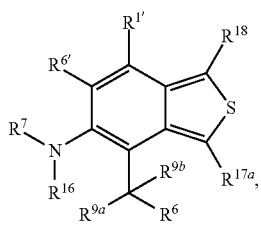
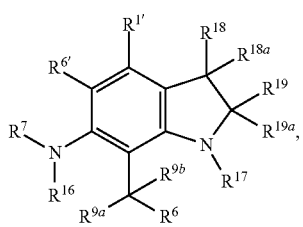
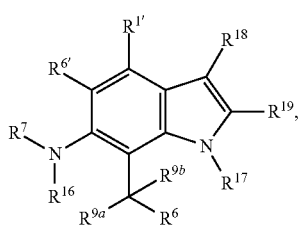
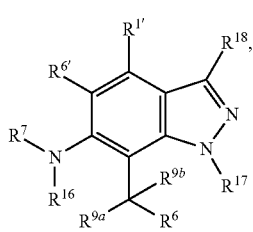
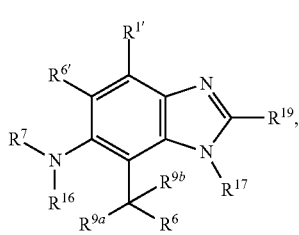
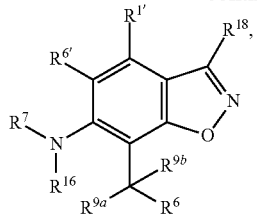
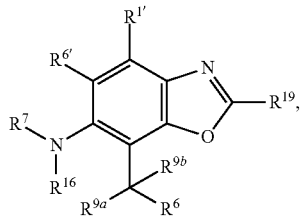
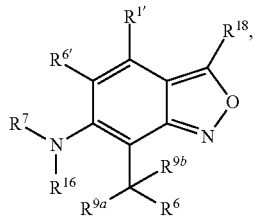
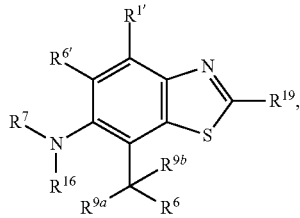
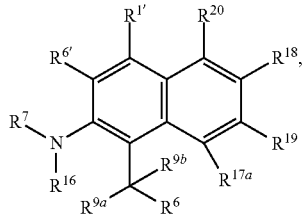
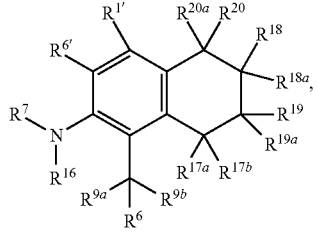
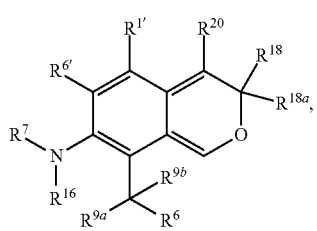

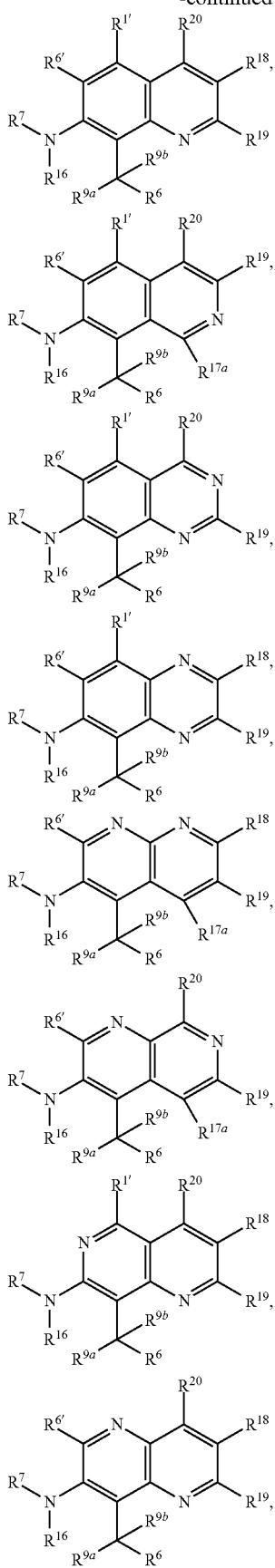
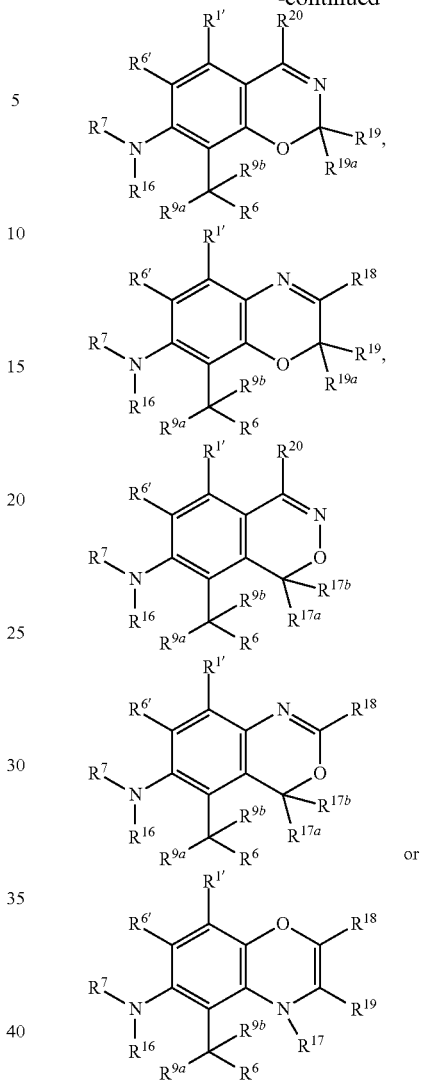

wherein $R^{17a}$, $R^{17b}$, $R^{18a}$, $R^{19a}$, and $R^{20a}$ are each independently hydrogen, halogen, or substituted or unsubstituted alkyl; or $R^{17a}$ and $R^{17b}$, $R^{18a}$ and $R^{18b}$, $R^{19a}$ and $R^{19b}$, and/or $R^{20a}$ and $R^{20b}$ may be taken together to form oxo thioxo;

$R^{17}$ is hydrogen, halogen, substituted or unsubstituted acyl, or substituted or unsubstituted alkyl; and which has substituents defined in the aforementioned (IV-A) to (IV-N), (V-A) to (V-O), and (VI-A) to (VI-O), i.e., $R^{1'}$ corresponds to $R^{1b}$ in the formula (V); $R^{6'}$ corresponds to $R^{5b}$ in the formula (IV);

$R^{9a}$, $R^{9b}$, and $R^{16}$ correspond respectively to $R^{9a}$, $R^{9b}$, and $R^{16}$ in the formula (IV); $R^{18}$, $R^{19}$, and $R^{20}$ correspond to $R^{2b}$ in the formula (V); $R^6$ is $R^{64}$, i.e., $R^A$, $R^B$, $R^C$, $R^{50}$, $R^{51}$, $R^{52}$, $R^{53}$, $R^{54}$, $R^{55}$, $R^{56}$, $R^{57}$, $R^{58}$, $R^{58}$, $R^{59}$, $R^{60}$, $R^{61}$, $R^{62}$, and $R^{63}$ are each independently a hydrogen atom or a substituent selected from Substituent Group C, provided that the groups of (i) to (p) have at least one substituent; wherein "the groups of (i) to (p) have at least one substituent" means that at least one of $R^A$, $R^B$, and $R^C$ is not hydrogen in the groups of (i), (j), and (n); at least one of $R^B$ and $R^C$ is not hydrogen in the group of (k); at least one of $R^A$ and $R^C$ is not hydrogen in the groups of (l) and (o); at least one of $R^A$ and $R^B$ is not hydrogen in the group of (m); and $R^B$ is not hydrogen in the group of (p); $R^7$ is $R^{7A}$ wherein $R^{10a}$, $R^{10b}$, and $R^{10c}$ are each independently a hydrogen atom or a substituent selected from Substituent Group E, provided that the groups of (a) to (h) have at least one substituent; wherein "the groups of (a) to (h) have at least one substituent" means that at least one of $R^{10a}$, $R^{10b}$, and $R^{10c}$ is not hydrogen in the groups (a), (b), and (f); at least one of $R^{10b}$ and $R^{10c}$ is not hydrogen in the group of (c); at least one of $R^{10a}$ and $R^{10c}$ is not hydrogen in the groups of (d) and (g); at least one of $R^{10a}$ and $R^{10b}$ is not hydrogen in the group of (e); and $R^{10b}$ is not hydrogen in the group of (h).

Further in the aforementioned compound, compounds, pharmaceutically acceptable salts or solvates thereof, or pharmaceutical compositions comprising the above-mentioned compounds, salts, or solvates and having a $P2X_3$ and/or $P2X_{2/3}$ receptor antagonistic effect, wherein one of $R^{18}$ and $R^{19}$ is hydrogen and the other is a group of the formula: —NH—C(=O)—$(CR^{8a}R^{8b})$n-$R^9$ wherein n is an integer from 0 to 4; $R^{8a}$ and $R^{8b}$ are each independently hydrogen, halogen, hydroxy, or substituted or unsubstituted alkyl; and $R^9$ is hydroxy, carboxy, sulfo, cyano, substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl or a group of the formula: —$(CR^{8a}R^{8b})$m-$R^9$ wherein in is an integer from 1 to 6; and $R^{8a}$, $R^{8b}$, and $R^9$ are as defined above.

A general synthesis method for the compound of the present invention is shown below. The starting materials and reaction reagents used for synthesis are either commercially available or that can be manufactured using commercially available compounds according to a widely known method in the art.

Compounds of the present invention of the formulas (I) to (VI) may be manufactured by the following synthesis routes:

A compound of the present invention of the formula (I) (hereinafter compounds of other formulas may be abbreviated similarly) may be manufactured by, for example, the following synthesis route:

[Method A]

[Chemical Formula 108]

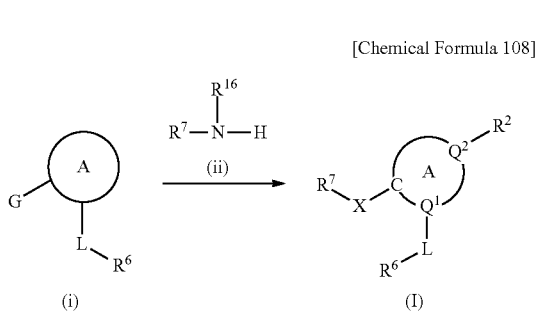

wherein G represents a leaving group such as halogen, substituted or unsubstituted alkylthio, substituted or unsubstituted alkylsulfinyl, or substituted or unsubstituted alkylsulfonyl; and the other symbols are as defined in the above (1α)

In other words, the compound of the present invention of the formula (I) may be manufactured by reacting Compound (i) with Compound (ii) in the absence of solvent or in an appropriate solvent in the presence of a palladium catalyst and a base or an acid if necessary.

In this reaction, the amount of Compound (ii) to be used may be one or more equivalents and preferably 1 to 5 equivalents relative to 1 equivalent of Compound (i).

Examples of a base appropriate for use include metal hydroxide (e.g., sodium hydroxide, potassium hydroxide, tripotassium phosphate, etc.), metal hydride (e.g., sodium hydride, lithium hydride, etc.), metal carboxylate (e.g., sodium carbonate, potassium carbonate, cesium carbonate, etc.), and metal alkoxide (e.g., sodium methoxide, sodium ethoxide, potassium t-butoxide, etc.), and the amount thereof to be used may be one or more equivalents and preferably 1 to 5 equivalents relative to 1 equivalent of Compound (i).

Examples of an acid appropriate for use include acetic acid and phosphoric acid, and the amount thereof to be used may be one or more equivalents and preferably 1 to 5 equivalents relative to 1 equivalent of Compound (i).

Examples of a palladium catalyst appropriate for use include tris (dibenzylideneacetone) dipalladium(0), palladium acetate(II), dichlorobis (triphenylphosphine) palladium (II), and tetrakis(triphenylphosphine) palladium(II), and the amount thereof to be used may be 0.001 equivalent or more and preferably 0.01 to 1 equivalent relative to 1 equivalent of Compound (i).

Examples of solvent appropriate for use include alcohols (e.g., t-butanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, water, and mixed solvents thereof.

The reaction temperature is between −10 and 250° C., under microwave irradiation as necessary, and preferably between 0 and 200° C. The reaction time may be between 10 minutes and 80 hours, which varies depending on the compound.

The obtained desired compound of the formula (I) may be purified as necessary by a conventional method (e.g., column chromatography, recrystallization, etc.).

[Method B]

[Chemical Formula 109]

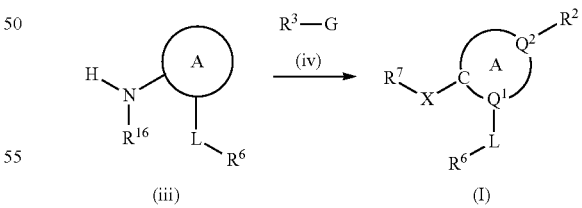

wherein the symbols are as defined in Method A.

In other words, the compound of the present invention of the formula (I) may be manufactured by reacting Compound (iii) with Compound (iv) in the absence of solvent or in an appropriate solvent, if necessary, in the presence of a palladium catalyst and a base or an acid.

In this reaction, the amount of Compound (iii) to be used may be one or more equivalents and preferably 1 to 5 equivalents relative to 1 equivalent of Compound (iv).

Examples of a base appropriate for use include metal hydroxide (e.g., sodium hydroxide, potassium hydroxide, tripotassium phosphate, etc.), metal hydride (e.g., sodium hydride, lithium hydride, etc.), metal carboxylate (e.g., sodium carbonate, potassium carbonate, cesium carbonate, etc.), and metal alkoxide (e.g., sodium methoxide, sodium ethoxide, potassium t-butoxide, etc.), and the amount thereof to be used may be one or more equivalents and preferably 1 to 5 equivalents relative to 1 equivalent of Compound (iii).

Examples of a palladium catalyst appropriate for use include tris (dibenzylideneacetone) dipalladium(0), palladium acetate(II), dichlorobis (triphenylphosphine) palladium (II), and tetrakis (triphenylphosphine) palladium(II), and the amount thereof to be used may be 0.001 equivalent or more and preferably 0.01 to 1 equivalent relative to 1 equivalent of Compound (iii).

Examples of a solvent appropriate for use include alcohols (e.g., t-butanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, water, and mixed solvents thereof.

The reaction temperature is between −10 and 250° C. under microwave irradiation as necessary, and preferably between 0 and 200° C. The reaction time may be between 10 minutes and 80 hours, which varies depending on the compound.

The obtained desired compound of the formula (I) may be purified as necessary by a conventional method (e.g., column chromatography, recrystallization, etc.).

[Method C]

[Chemical Formula 110]

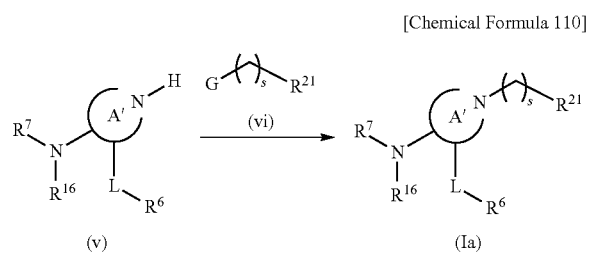

wherein A' is a nitrogen-containing heterocyclic ring; $R^{21}$ is a substituent selected from Substituent Group B; s is an integer from 1 to 4; and the other symbols are as defined in Method A.

In other words, the compound of the present invention of the formula (Ia) may be manufactured by reacting Compound (v) with Compound (vi) in an appropriate solvent in the presence of a base.

In this reaction, the amount of Compound (vi) to be used may be one or more equivalents and preferably 1 to 5 equivalents relative to 1 equivalent of Compound (v).

Examples of a base appropriate for use include metal hydroxide (e.g., sodium hydroxide, potassium hydroxide, tripotassium phosphate, etc.), metal hydride (e.g., sodium hydride, lithium hydride, etc.), metal carboxylate (e.g., sodium carbonate, potassium carbonate, cesium carbonate, etc.), metal alkoxide (e.g., sodium methoxide, sodium ethoxide, potassium t-butoxide, etc.), and metal alkyl (e.g., butyllithium, etc.), and the amount thereof to be used may be one or more equivalents and preferably 1 to 5 equivalents relative to 1 equivalent of Compound (v).

Examples of a solvent appropriate for use include alcohols (e.g., t-butanol, isopropanol, etc), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, water, and mixed solvents thereof.

The reaction temperature is between −10 and 250° C., under microwave irradiation as necessary, and preferably between 0 and 200° C. The reaction time may be between 10 minutes and 80 hours, which varies depending on the compound.

The obtained desired Compound (Ia) may be purified as necessary by a conventional method (e.g., column chromatography, recrystallization, etc.).

[Method D]

[Chemical Formula 111]

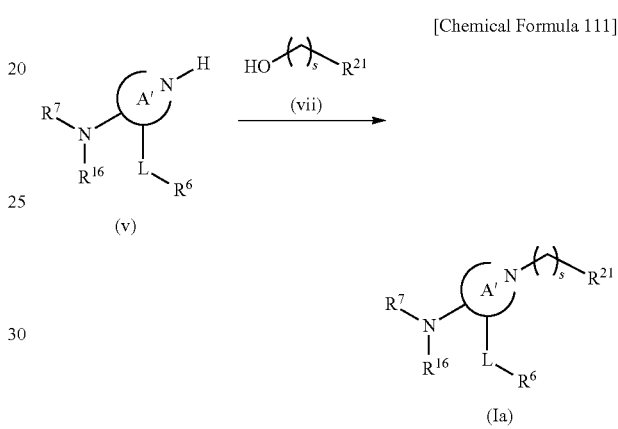

wherein the symbols are as defined in Method C.

In other words, the compound of the present invention of the formula (Ia) may be manufactured by subjecting Compound (v) and Compound (vii) to condensation reaction, such as Mitsunobu reaction.

In this reaction, the amount of Compound (vii) to be used may be one or more equivalents and preferably 1 to 5 equivalents relative to 1 equivalent of Compound (v).

Examples of alkylphosphines appropriate for use include triphenylphosphine and tributylphosphine, and the amount thereof to be used may be one or more equivalents and preferably 1 to 5 equivalents relative to 1 equivalent of Compound (v).

Examples of azodicarboxylates appropriate for use include diethyl azodicarboxylate and di-2-methoxyethyl azodicarboxylate, and the amount thereof to be used may be one or more equivalents and preferably 1 to 5 equivalents relative to 1 equivalent of Compound (v).

Examples of a solvent appropriate for use include aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), and mixed solvents thereof.

The reaction temperature is between −10 and 200° C. and preferably between 0 and 120° C. The reaction time may be between 10 minutes and 80 hours, which varies depending on the compound.

The obtained desired Compound (Ia) may be purified as necessary by a conventional method (e.g., column chromatography, recrystallization, etc.).

[Method E]

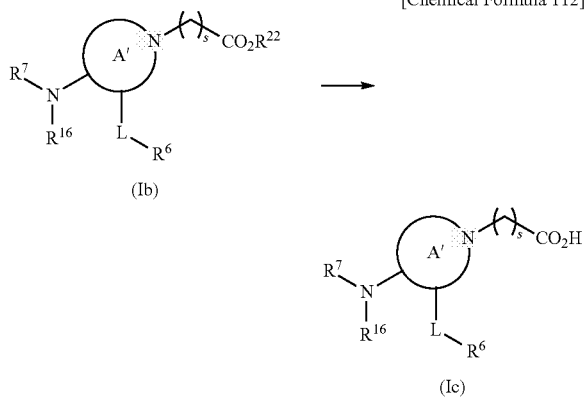

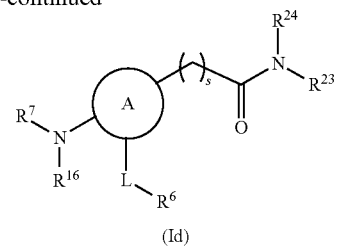

wherein $R^{22}$ is substituted or unsubstituted alkyl; and the other symbols are as defined in Method C.

In other words, the compound of the present invention of the formula (Ic) may be manufactured by subjecting Compound (Ib) obtained by Method A, Method B, Method C, or Method D to hydrolysis in the presence of a base or an acid.

Examples of a base appropriate for use include metal hydroxide (e.g., sodium hydroxide, potassium hydroxide, lithium hydroxide, etc.) and metal carboxylate (e.g., sodium carbonate, potassium carbonate, cesium carbonate, etc.), and the amount thereof to be used may be one or more equivalents and preferably 1 to 5 equivalents relative to 1 equivalent, of Compound (Ib).

Examples of an acid appropriate for use include hydrochloric acid, trifluoroacetic acid, and para-toluenesulfonic acid, and the amount thereof to be used may be one or more equivalents and preferably 1 to 5 equivalents relative to 1 equivalent of Compound (Ib).

Examples of a solvent appropriate for use include alcohols (e.g., methanol, ethanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, water, and mixed solvents thereof.

The reaction temperature is between −10 and 200° C. and preferably between 0 to 120° C. The reaction time may be between 10 minutes and 80 hours, which varies depending on the compound.

The obtained desired Compound (Ic) may be purified as necessary by a conventional method (e.g., column chromatography, recrystallization, etc.).

[Method F]

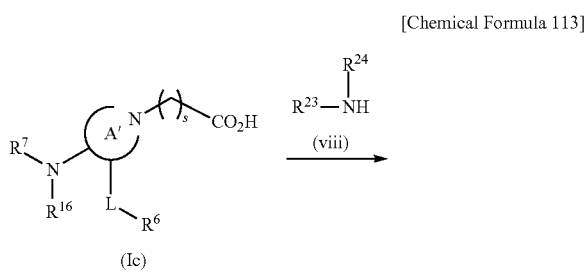

wherein $R^{23}$ and $R^{24}$ are each independently hydrogen, substituted or unsubstituted alkyl, substituted or unsubstituted arylalkyl, substituted or unsubstituted heteroarylalkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, or substituted or unsubstituted acyl; and the other symbols are as defined in Method C.

In other words, the compound of the present, invention of the formula (Id) may be manufactured by subjecting Compound (Ic) obtained by Method E and Compound (viii) to condensation in an appropriate solvent.

Examples of a condensation agents appropriate for use include condensation agents such as 1-hydroxybenzotriazole or HOAt, 1-ethyl-3-(3-dimethylaminopropyl) carbodiimide hydrochloride, HATU, and PyBOp, and bases such as triethylamine and diisopropylethylamine, and the amount thereof to be used may be one or more equivalents and preferably 1 to 5 equivalents relative to 1 equivalent of Compound (Ic).

Examples of a solvent appropriate for use include aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane etc.), N,N-dimethylformamide, DMSO, NMP, and mixed solvents thereof.

The reaction temperature is between −10 and 200° C. and preferably between 0 and 120° C. The reaction time may be between 10 minutes and 80 hours, which varies depending on the compound.

The obtained desired Compound (Id) may be purified as necessary by a conventional method (e.g., column chromatography, recrystallization, etc.).

[Method G]

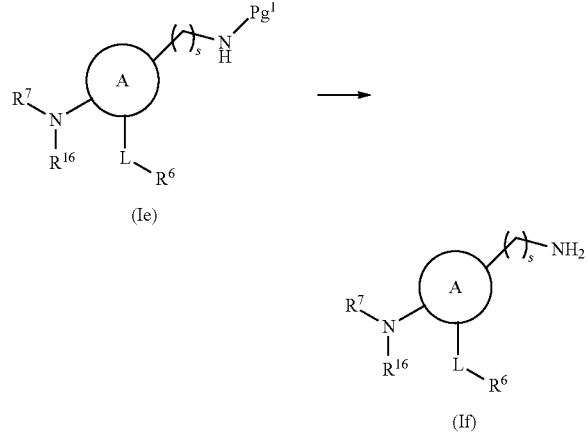

wherein $Pg^1$ is an appropriate protecting group for an amino group; and the other symbols are as defined in Method C.

In other words, the compound of the present invention of the formula (If) may be manufactured by subjecting Compound (Ie) obtained by Method A, Method B, Method C, or Method D to de-protection in an appropriate solvent in the presence of an acid.

Examples of an acid appropriate for use include hydrochloric acid, trifluoroacetic acid, and para-toluenesulfonic acid, and the amount thereof to be used may be 0.01 equivalent or more and preferably 0.5 to 3 equivalents relative to 1 equivalent of Compound (Ie).

Examples of a solvent appropriate for use include alcohols (e.g., methanol, ethanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane, etc.), water, and mixed solvents thereof.

The reaction temperature is between −10 and 200° C. and preferably between 0 and 120° C. The reaction time may be between 10 minutes and 80 hours, which varies depending on the compound.

The obtained desired Compound (If) may be purified as necessary by a conventional method (e.g., column chromatography, recrystallization, etc.) or salt formation.

[Method H]

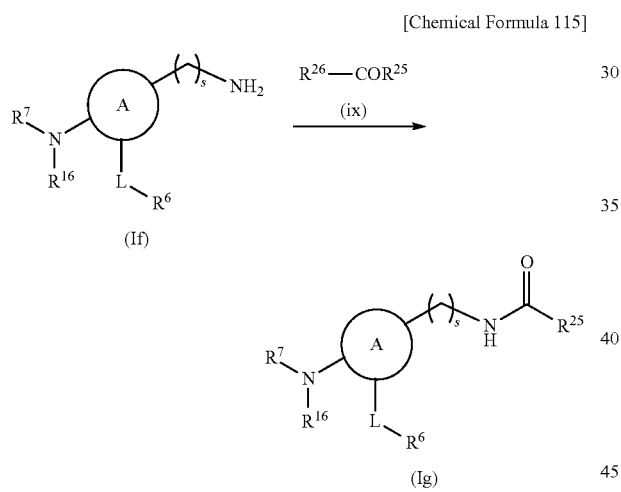

wherein $R^{25}$ is substituted or unsubstituted alkyl, substituted or unsubstituted arylalkyl, substituted or unsubstituted heteroarylalkyl, substituted or unsubstituted alkenyl, substituted or unsubstituted alkenyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, or substituted or unsubstituted acyl; $R^{26}$ is hydroxy or halogen; and the other symbols are as defined in Method C.

In other words, the compound of the present invention of the formula (Ig) may be manufactured by reacting Compound (If) obtained by Method G with Compound (ix) in an appropriate solvent in the presence of a base or a condensation agent.

Examples of a base appropriate for use include triethylamine, diisopropylethylamine, and pyridine, and the amount thereof to be used may be one or more equivalents and preferably 1 to 5 equivalents relative to 1 equivalent of Compound (If).

Examples of a condensation agents appropriate for use include condensation agents such as 1-hydroxybenzotriazole car HOAt, 1-ethyl-3-(3-dimethylaminopropyl) carbodiimide hydrochloride, HATU, and PyBOp, and bases such as triethylamine and diisopropylethylamine, and the amount thereof to be used may be one or more equivalents and preferably 1 to 5 equivalents relative to 1 equivalent of Compound (If).

Examples of a solvent appropriate for use include halogenated hydrocarbons (e.g., dichloromethane, chloroform, etc.), aromatic hydrocarbons (e.g., toluene, benzene, xylene, etc), saturated hydrocarbons (e.g., cyclohexane, hexane, etc.), ethers (e.g., tetrahydrofuran, diethyl ether, dioxane, dimethoxyethane, etc.), N,N-dimethylformamide, DMSO, NMP, and mixed solvents thereof.

The reaction temperature is between −10 and 200° C. and preferably between 0 and 120° C. The reaction time may be between 10 minutes and 80 hours, which varies depending on the compound.

The obtained desired Compound (Ig) may be purified as necessary by a conventional method (e.g., column chromatography, recrystallization, etc.).

[Method I]

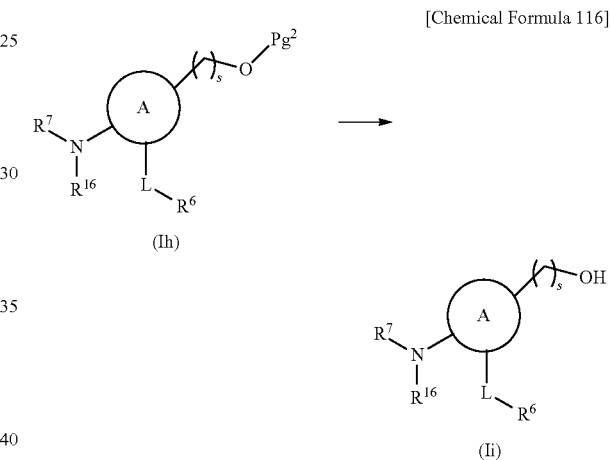

wherein $Pg^2$ is an appropriate protecting group for a hydroxy group; and the other symbols are as defined in Method C.

In other words, the compound of the present invention of the formula (Ii) may be manufactured by subjecting Compound (Ih) obtained by Method A, Method B, Method C, or Method D to deprotection in an appropriate solvent in the presence of an acid.

Examples of an acid appropriate for use include hydrochloric acid, trifluoroacetic acid, and para-toluenesulfonic acid, and the amount thereof to be used may be 0.01 equivalent or more and preferably 0.5 to 3 equivalents relative to 1 equivalent of Compound (Ih).

Examples of a solvent appropriate for use include alcohols (e.g., methanol, ethanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane, etc.), water, and mixed solvents thereof.

The reaction temperature is between −10 and 200° C. and preferably between 0 and 120° C. The reaction time may be between 10 minutes and 80 hours, which varies depending on the compound.

The obtained desired Compound (Ii) may be purified as necessary by a conventional method (e.g., column chromatography, recrystallization, etc.).

The compounds of the present invention (I) are not limited to a specific isomer but include all possible isomers and racemates. For example, they include a tautomer as shown below.

[Chemical Formula 117]

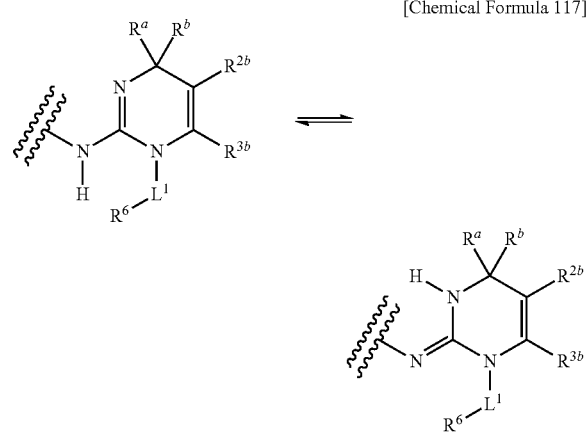

In addition, one or more hydrogen atoms, carbon atoms or other atoms of the compound of the formula (I) can be replaced by an isotope of the hydrogen atom, carbon atom or other atoms. Compounds of the formula (I) include all radio-labeled forms of compounds of the formula (I). The "radio-labeled," "radiolabeled form" and the like of the compound of the formula (I) are encompassed by the present invention and useful as a research and/or diagnostic tool in metabolism pharmacokinetic studies and in binding assays. It is also useful for a medicament.

Examples of isotopes that can be incorporated into the compound of the formula (I) of the invention include isotopes of hydrogen, carbon, nitrogen, oxygen, phosphorous, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$, respectively. Radiolabeled compounds of the present invention can be prepared by methods known in the art. For example, tritiated compounds of formula (I) can be prepared by introducing tritium into the particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in *Isotopes in the Physical and Biomedical Sciences, Vol. 1, Labeled Compounds (Part A)* Chapter 6, (1987). $^{14}C$-labeled compounds can be prepared by employing starting materials having a $^{14}C$ carbon.

The compounds of the above formula (I) or its salt can be converted into hydrate or solvate thereof by known methods. Examples of suitable solvates are solvate with acetone, 2-butanol, 2-propanol, ethanol, ethyl acetate, tetrahydrofuran, diethyl ether or the like. For example, it includes a non-toxic and water-soluble hydrate or solvate such as a solvate with ethanol.

As pharmaceutically acceptable salt of the compound of the formula (I), examples include salts with alkaline metals (e.g. lithium, sodium and potassium), alkaline earth metals (e.g. calcium and barium), magnesium, transition metal (e.g. zinc and iron), ammonia, organic bases (e.g. trimethylamine, triethylamine, dicyclohexylamine, ethanolamine, diethanolamine, triethanolamine, meglumine, diethanolamine, ethylenediamine, pyridine, picoline, quinoline), and amino acids, and salts with inorganic acids (e.g. hydrochloric acid, sulfuric acid, nitric acid, carbonic acid, hydrobromic acid, phosphoric acid and hydroiodic acid) and organic acids (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic, acid and ethanesulfonic acid). Especially preferable are salts with hydrochloric acid, sulfuric acid, phosphoric acid, tartaric acid, or methanesulfonic acid. These salts may be formed by usual methods.

The compound of the formula (I) or its pharmaceutically acceptable salt may form solvate such as hydrate, and/or crystalline polymorphism, and the present invention also includes such various kinds of solvate and crystalline polymorphism. The "solvate" includes a compound of the formula (I) which coordinate arbitrary number of solvent molecules such as water molecules. The compound of the formula (I) or its pharmaceutically acceptable salt can adhere water or form hydrate by absorbing water molecules after leaving in the atmosphere. Moreover, the compound of the formula (I) or its pharmaceutically acceptable salt can form the crystalline polymorphism by recrystallization.

The compound of the formula (I) of the present invention or its pharmaceutically acceptable salt may form prodrug, and the present invention also includes such various kinds of prodrug. Prodrug is a derivative of the compound of the present invention having a group which can be chemically or metabolically decomposed and the one which becomes a pharmaceutically active compound of the present invention by solvolysis or physiological conditions in vivo. Prodrug includes a compound which converts into the compound of the formula (I) by enzymatical oxidation, reduction, hydrolysis or the like under physiological conditions in a living body, and a compound which converts into the compound of the formula (I) by hydrolyzing by stomach acid or the like. The method of selecting suitable prodrug derivatives and the method of manufacturing them are disclosed in Design of Prodrugs, Elsevier, and Amsterdam 1985. Prodrug itself may possess the activity.

When the compound of the formula (I) or its pharmaceutically acceptable salt has a hydroxy group, examples of the prodrug includes acyloxy derivatives and sulfonyloxy derivatives which can be manufactured by reacting a compound having a hydroxy group with a suitable acid halide, suitable acid anhydride, suitable sulfonyl chloride, suitable sulfonylanhydride and mixed anhydride. For example, $CH_3COO-$, $C_2H_5COO-$, t-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3$—O-$PhSO_3-$, $PhSO_3-$, and p-$CH_3PhSO_3-$ are exemplified.

The compound of the formula (I) has an antagonistic effect on $P2X_3$ and/or $P2X_{2/3}$ receptor, and therefore, is useful as a therapeutic agent for diseases associated with a $P2X_3$ and/or $P2X_{2/3}$ receptor, Since $P2X_3$ and/or $P2X_{2/3}$ receptor is believed to associate with pain and diseases in urinary system (Nature 407, 26, 1011-1015 (2000), Nature, Vol. 407, No. 26, 1015-1017 (2000), Nan-Patent Document 1, Non-Patent Document 2, etc), the compound of the invention is useful in the treatment, alleviation of symptoms or prevention of diseases, such as for example, pain associated with rheumatoid arthritis, pain associated with osteoarthritis, headache, migraine, orofacial pain, toothache, glossagra, pain associated with temporomandibular arthrosis, trigeminal neuralgia, shoulder pain, pain associated with hernia of intervertebral disk, pain associated with cervical spondylosis deformans, pain associated with spinal canal stenosis, pain associated with thoracic outlet syndrome, pain associated with traumatic brachial plexus injury syndrome, pain associated with shoulder-hand syndrome, pain associated with whiplash injury, chest pain, abdominal pain, colic pain, pain associated with cholelithiasis, pain associated with pancreatitis, pain associated with urinary calculosis, pain associated with irritable bowel syndrome, lumbar backache, sciatica, pain associated with bone fracture, pain associated with osteoporosis, joint pain, pain associated with gout, pain associated with cauda equina syndrome, pain associated with ankylosing spondylitis, sore muscle, pain associated with painful spasm, pain associated with myofascial pain syndrome, pain associated with fibromyalgia syndrome, complex regional pain syndrome, pain associated with arteriosclerosis obliterans, pain associated with Buerger's disease, pain associated with Raynaud's phenomenon, pain associated with zoster, causalgic pain, pain associated with entrapment neuropathy, pain associated with carpal canal syndrome, pain associated with diabetes, pain associated with Guillain-Barre syndrome, pain associated with Hansen's disease, pain associated with drug therapy, pain associated with radiation therapy, pain associated with cord injury, pain associated with syringomyelia, pain associated with stroke, thalamic pain, pain associated with deafferentation, sympathetically-maintained pain, ABC syndrome, multiple sclerosis, pain associated with skin disease, cancer pain, postoperative pain, pain associated with injury, pain associated with gangrene, pain associated with somatoform disorder, pain associated with somatization disorder, pain associated with depression, pain associated with Parkinson's disease, knee joint pain, pain associated with arthritis, neuropathic pain such as menstrual pain, intermenstrual pain, labor pain, etc., inflammatory pain, nociceptive pain, psychogenic pain, overactive bladder, incontinence, pollakiuria, urinary urgency, cystatrophia, prostatic hypertrophy, prostatitis, prostate pain, detrusor hyperreflesxia, urination disorder, nervous pollakiuria, chronic prostatitis, chronic cystitis, etc.

The compound of the present invention can be a drug with reduced side-effect such as effect on motor function because it has a high affinity for ATP receptor, especially $P2X_3$ receptor, and also has high subtype selectivity and high selectivity for other receptors. Also, the compound of the present invention is advantageous because of its high stability, high oral absorption, high solubility, good bioavailability, low clearance, long half-life, prolonged duration, and/or low activity of hepatic enzyme inhibition etc.

In another embodiment, the present invention provides a pharmaceutical composition comprising an effective amount of the compound of the present invention, in combination with a pharmaceutically acceptable carrier.

For use of the compound of the present invention as a medicament, a pharmaceutical composition can be prepared according to conventional methods, using pharmaceutically acceptable carriers well-known in the art, such as excipients, binders, disintegrants, lubricants, colourants, flavors, surfactants, etc.

For the pharmaceutical composition of the present invention to be administered in the treatment of mammals including human, an appropriate unit dosage form may be selected depending on the purpose of the treatment and the route of administration. Specifically, such unit dosage form includes oral formulations such as tablet, coated tablet, powder, granule, capsule, liquid, pill, suspension, emulsion, etc., and parenteral formulations such as injectable solution, suppository, ointment, patch, aerosol, etc. Such unit dosage from can be formulated according to methods well-known in the art.

The amount of the present compound in a formulation can vary depending on its dosage form, route for administration, dosing regimen, etc.

Means for administration of the present pharmaceutical composition may be selected depending on dosage form, patient's age, sex, body weight, severity of the disease, and other factors, etc., and route for administration can be selected from various routes such as oral, subcutaneous, transdermal, rectal, intranasal, buccal, etc.

Dose of the present compound in the present pharmaceutical composition can be determined depending on the choice of route for administration, patient's age, sex, body weight, severity of the disease, the compound to be administered, and other factors, etc., and can be generally from 0.05 to 1000 mg/kg/day, preferably from 0.1 to 10 mg/kg/day, for oral administration to adults. For parenteral administration, dose can vary widely depending on its route but generally from 0.005 to 100 mg/kg/day, preferably from 0.01 to 1 mg/kg/day. Such pharmaceutical composition of the present invention may be administered once a day or in several times at a divided dosage in a day.

In some embodiments of the present compounds, there is provided compounds of the following formula (VI) having the following groups are provided:

[Chemical Formula 118]

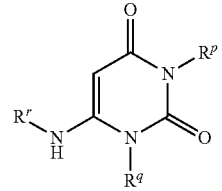

(VII)

TABLE 1

| | Rp |
|---|---|
| Rp1 | 4-Cl—Bn |
| Rp2 | CH$_2$CONHCH(CH$_2$OH)$_2$ |
| Rp3 | CH$_2$CONH(CH$_2$)$_2$OH |
| Rp4 | CH$_2$CHMeCOOH |
| Rp5 | CH$_2$CH(CH$_2$OH)$_2$ |
| Rp6 | CH(Me)CH(Me)COOH |
| Rp7 | CH$_2$C(Me)$_2$COOH |
| Rp8 | (CH$_2$)$_2$COOH |
| Rp9 | (CH$_2$)$_2$CONHMe |
| Rp10 | (CH$_2$)$_3$COOH |
| Rp11 | (CH$_2$)$_3$CONHMe |

TABLE 2

| | Rq |
|---|---|
| Rq1 | 4-Me—PhCH2 |
| Rq2 | 4-Et—PhCH2 |
| Rq3 | 4-Vinyl-PhCH2 |
| Rq4 | 4-F—PhCH2 |
| Rq5 | 4-Cl—PhCH2 |
| Rq6 | 4-Br—PhCH2 |
| Rq7 | c-Hexylmethyl |
| Rq8 | c-Heptylmethyl |

TABLE 3

| Rr | Rr |
|---|---|
| Rr1 | 4-PrO—Ph |
| Rr2 | 4-i-PrO—Ph |
| Rr3 | 4-c-BuO—Ph |
| Rr4 | 4-s-BuO—Ph |
| Rr5 | 4-c-PrCH$_2$O—Ph |
| Rr6 | 4-PhO—Ph |
| Rr7 | 4-(6-Me-3-Pyridyl)O—Ph |
| Rr8 | 4-(3-Me-4-Pyridyl)O—Ph |
| Rr9 | 4-Piperidino-Ph |
| Rr10 | 3-F-4-i-PrO—Ph |
| Rr11 | 3-Cl-4-EtO—Ph |
| Rr12 | 3-Cl-4-PrO—Ph |
| Rr13 | 3-Cl-4-i-PrO—Ph |
| Rr14 | 3-Cl-4-s-BuO—Ph |
| Rr15 | 3-Br-4-i-PrO—Ph |
| Rr16 | 3-Me-4-i-PrO—Ph |
| Rr17 | 3-Me-4-i-Bu—Ph |
| Rr18 | 3-Cl-4-i-Bu—Ph |
| Rr19 | 3-Et-4-i-PrO—Ph |
| Rr20 | 3-Vinyl-4-i-PrO—Ph |

In the above tables, Me is methyl, Et is ethyl, Pr is propyl, i-Pr is isopropyl, cPr is cyclopropyl, s-Bu is sec-butyl, c-Bu is cyclobutyl, Ph is phenyl, Bn is benzyl, and THP is tetrahydropyranyl.

The combination of Rp, Rq and Rr, i.e., (Rp, Rq, Rr), is any one of the following combinations:
(Rp1,Rq1,Rr1),(Rp1,Rq1,Rr2),(Rp1,Rq1,Rr3),(Rp1,Rq1,Rr4),(Rp1,Rq1,Rr5),(Rp1,Rq1,Rr6),(Rp1,Rq1,Rr7),(Rp1,Rq1,Rr8),(Rp1,Rq1,Rr9),(Rp1,Rq1,Rr10),(Rp1,Rq1,Rr11),(Rp1,Rq1,Rr12),(Rp1,Rq1,Rr13),(Rp1,Rq1,Rr14),(Rp1,Rq1,Rr15),(Rp1,Rq1,Rr16),(Rp1,Rq1,Rr17),(Rp1,Rq1,Rr18),(Rp1,Rq1,Rr19),(Rp1,Rr20),(Rp1,Rq2,Rr1),(Rp1,Rq2,Rr2),(Rp1,Rq2,Rr3),(Rp1,Rq2,Rr4),(Rp1,Rq2,Rr5),(Rp1,Rq2,Rr6),(Rp1,Rq2,Rr7),(Rp1,Rq2,Rr8),(Rp1,Rq2,Rr9),(Rp1,Rq2,Rr10),(Rp1,Rq2,Rr11),(Rp1,Rq2,Rr12),(Rp1,Rq2,Rr13),(Rp1,Rq2,Rr14),(Rp1,Rq2,Rr15),(Rp1,Rq2,Rr16),(Rp1,Rq2,Rr17),(Rp1,Rq2,Rr18),(Rp1,Rq2,Rr19),(Rp1,Rq2,Rr20),(Rp1,Rq3,Rr1),(Rp1,Rq3,Rr2),(Rp1,Rq3,Rr3),(Rp1,Rq3,Rr15),(Rp1,Rq3,Rr5),(Rp1,Rq3,Rr6),(Rp1,Rq3,Rr7),(Rp1,Rq3,Rr8),(Rp1,Rq3,Rr9),(Rp1,Rq3,Rr10),(Rp1,Rq3,Rr11),(Rp1,Rq3,Rr12),(Rp1,Rq3,Rr13),(Rp1,Rq3,Rr14),(Rp1,Rq3,Rr15),(Rp1,Rq3,Rr16),(Rp1,Rq3,Rr17),(Rp1,Rq3,Rr18),(Rp1,Rq3,Rr19),(Rp1,Rq3,Rr20),(Rp1,Rq4,Rr1),(Rp1,Rq4,Rr2),(Rp1,Rq4,Rr3),(Rp1,Rq4,Rr4),(Rp1,Rr5),(Rp1,Rq4,Rr6),(Rp1,Rq4,Rr7),(Rp1,Rr8),(Rp1,Rq4,Rr9),(Rp1,Rq4,Rr10),(Rp1,Rq4,Rr11),(Rp1,Rq4,Rr12),(Rp1,Rq4,Rr13),(Rp1,Rq1,Rr14),(Rp1,Rq4,Rr15),(Rp1,Rq4,Rr16),(Rp1,Rr17),(Rp1,Rq14,Rr18),(Rp1,Rq4,Rr19),(Rp1,Rq4,Rr20),(Rp1,Rq5,Rr1),(Rp1,Rq5,Rr2),(Rp1,Rq5,Rr3),(Rp1,Rq5,Rr11),(Rp1,Rq5,Rr5),(Rp1,Rq5,Rr6),(Rp1,Rq5,Rr7),(Rp1,Rq5,Rr8),(Rp1,Rq5,Rr9),(Rp1,Rq5,Rr10),(Rp1,Rq5,Rr11),(Rp1,Rq5,Rr12),(Rp1,Rq5,Rr13),(Rp1,Rq5,Rr14),(Rp1,Rq5,Rr15),(Rp1,Rq5,Rr16),(Rp1,Rq5,Rr17),(Rp1,Rq5,Rr18),(Rp1,Rq5,Rr19),(Rp1,Rq5, Rr20),(Rp1,Rq6,Rr1),(Rp1,Rq6,Rr2),(Rp1,Rq6,Rr3),(Rp1,Rq6,Rr4),(Rp1,Rq6,Rr5),(Rp1,Rq6,Rr6),(Rp1,Rq16,Rr7),(Rp1,Rq6,Rr8),(Rp1,Rq6,Rr9),(Rp1,Rq6,Rr10),     Rp1,Rq6,Rr11),(Rp1,Rq6,Rr12),(Rp1,Rq6,Rr13),(Rp1,Rq6,Rr14),(Rp1,Rq6,Rr15),(Rp1,Rq6,Rr16),(Rp1,Rq6,Rr17),(Rp1,Rq6,Rr18),(Rp1,Rq6,Rr19),(Rp1,Rq6,Rr20),(Rp1,Rq7,Rr1),(Rp1,Rq7,Rr2),(Rp1,Rq7,Rr3),(Rp1,Rq7,Rr4),(Rp1,Rq7,Rr5),(Rp1,Rq7,Rr6),(Rp1,Rq7,Rr7),(Rp1,Rq7,Rr8),(Rp1,Rq7,Rr9),(Rp1,Rq7,Rr10),(Rp1,Rq7,Rr11),(Rp1,Rq7,Rr12),(Rp1,Rq7,Rr13),(Rp1,Rq7,Rr14),(Rp1,Rq7,Rr15),(Rp1,Rq7,Rr16),(Rp1,Rq7,Rr17),(Rp1,Rq7,Rr18),(Rp1,Rq7,Rr9),(Rp1,Rq7,Rr20),(Rp1,Rq8,Rr1),(Rp1,Rq8,Rr2),(Rp1,Rq8,Rr3),(Rp1,Rq8,Rr4),(Rp1,Rq8,Rr5),(Rp1,Rq8,Rr6),(Rp1,Rq8,Rr7),(Rp1,Rq8,Rr8),(Rp1,Rq8,Rr9),(Rp1,Rq8,Rr10),(Rp1,Rq8,Rr11),(Rp1,Rq8,Rr12),(Rp1,Rq8,Rr13),(Rp1,Rq8,Rr14),(Rp1,Rq8,Rr5),(Rp1,Rq8,Rr16),(Rp1,Rq8,Rr17),(Rp1,Rq8,Rr18),(Rp1,Rq8,Rr19),(Rp1,Rq8,Rr20),(Rp2,Rq1,Rr1),(Rp2,Rq1,Rr2),(Rp2,Rq1,Rr3),(Rp2,Rq1,Rr4),(Rp2,Rq1,Rr5),(Rp2,Rq1,Rr6),(Rp2,Rq1,Rr7),(Rp1,Rq1,Rr8),(Rp2,Rq1,Rr9),(Rp3,Rq1,Rr10),(Rp2,Rq1,Rr11),(Rp2,Rq1,Rr12),(Rp2,Rq1,Rr13),(Rp2,Rq1,Rr14),(Rp2,Rq1,Rr15),(Rp2,Rq1,Rr16),(Rp2,Rq1,Rr17),(Rp2,Rq1,Rr18),(142,Rq1,Rr19),(Rp2,Rq1,Rr20),(Rp2,Rq2,Rr1),(Rp2,Rq2,Rr2),(Rp2,Rq2,Rr3),(Rp2,Rq2,Rr4),(Rp2,Rq2,Rr5),(Rp2,Rq2,Rr6),(Rp2,Rq2,Rr7),(Rp2,Rq2,Rr8),(Rp2,Rq2,Rr9),(Rp2,Rq2,Rr10),(Rp2,Rq2,Rr11),(Rp2,Rq2,Rr12),(Rp2,Rq2,Rr13),(Rp2,Rq2,Rr14),(Rp2,Rq2,Rr15),(Rp2,Rq2,Rr10),(Rp2,Rq2,Rr17),(Rp2,Rq2,Rr18),(Rp2,Rq2,Rr19),(Rp2,Rq2,Rr20),(Rp2,Rq3,Rr1),(Rp2,Rq3,Rr2),(Rp2,Rq3,Rr3),(Rp2,Rq3,Rr4),(Rp2,Rq3,Rr5),(Rp2,Rq3,Rr6),(Rp2,Rq3,Rr7),(Rp2,Rq3,Rr8),(Rp2,Rq3,Rr9),(Rp2,Rq3,Rr10),(Rp2,Rq3,Rr11),(Rp2,Rq3,Rr12),(Rp2,Rq3,Rr13),(Rp2,Rq3,Rr14),(Rp2,Rq3,Rr15),(Rp2,Rq3,Rr16),(Rp2,Rq3,Rr17),(Rp2,Rq3,Rr18),(Rp2,Rq3,Rr19),(Rp2,Rq3,Rr20),(Rp2,Rq4,Rr1),(Rp2,Rq4,Rr2),(Rp2,Rq4,Rr3),(Rp2,Rq4,Rr4),(Rp2,Rq4,Rr5),(Rp2,Rq4,Rr6),(Rp2,Rq4,Rr7),(Rp2,Rq4,Rr8),(Rp2,Rq4,Rr9),(Rp2,Rq4,Rr1),(Rp2,Rq4,Rr1),(Rp2,Rq4,Rr12),(Rp2,Rq4,Rr13),(Rp2,Rq4,Rr14),(Rp2,Rq4,Rr15),(Rp2,Rq4,Rr16),(Rp2,Rq4,Rr17),(Rp2,Rq4,Rr18),(Rp2,Rq4,Rr19),(Rp2,Rq4,Rr20),(Rp2,Rq5,Rr1),(Rp2,Rq5,Rr2),(Rp2,Rq5,Rr3),(Rp2,Rq5,Rr4),(Rp2,Rq5,Rr5),(Rp2,Rq5,Rr6),(Rp2,Rq5,Rr7),(Rp2,Rq5,Rr8),(Rp2,Rq5,Rr9),(Rp2,Rq5,Rr10),(Rp2,Rq5,Rr11),(Rp2,Rq5,Rr10),(Rp2,Rq5,Rr13),(Rp2,Rq5,Rr14),(Rp2,Rq5,Rr15),(Rp2,Rq5,Rr16),(Rp2,Rq5,Rr17),(Rp2,Rq5,Rr18),(Rp2,Rq5,Rr19),(Rp2,Rq5,Rr20),(Rp2,Rq6,Rr1),(Rp2,Rq6,Rr2),(Rp2,Rq6,Rr3),(Rp2,Rq6,Rr4),(Rp2,Rq6,Rr5),(Rp2,Rq6,Rr6),(Rp2,Rq6,Rr7),(Rp2,Rq6,Rr8),(Rp2,Rq6,Rr9),(Rp2,Rq6,Rr10),(Rp2,Rq6,Rr11),(Rp2,Rq6,Rr12),(Rp2,Rq6,Rr13),(Rp2,Rq6,Rr14),(Rp2,Rq6,Rr15),(Rp2,Rq6,Rr16),(Rp2,Rq6,Rr17),(Rp2,Rq6,Rr18),(Rp2,Rq6,Rr19),(Rp2,Rq6,Rr20),(Rp2,Rq7,Rr1),(Rp2,Rq7,Rr2),(Rp2,Rq7,Rr3),(Rp2,Rq7,Rr4),(Rp2,Rq7,Rr5),(Rp2,Rq7,Rr6),(Rp2,Rq7,Rr7),(Rp2,Rq7,Rr8),(Rp2,Rq7,Rr9),(Rp2,Rq7,Rr10),(Rp2,Rq7,Rr11),(Rp2,Rq7,Rr12),(Rp2,Rq7,Rr13),(Rp2,Rq7,Rr14),(Rp2,Rq7,Rr15),(Rp2,Rq7,Rr16),(Rp2,Rq7,Rr17),(Rp2,Rq7,Rr18),(Rp2,Rq7,Rr19),(Rp2,Rq7,Rr20),(Rp2,Rq8,Rr1),(Rp2,Rq8,Rr2),(Rp2,Rq8,Rr3),(Rp2,Rq8,Rr4),(Rp2,Rq8,Rr5),(Rp2,Rq8,Rr6),(Rp2,Rq8,Rr7),(Rp2,Rq8,Rr8),(Rp2,Rq8,Rr9),(Rp2,Rq8,Rr10),(Rp2,Rq8,Rr1   (Rp2,Rq8,Rr12),(Rp2,Rq8,Rr13),(Rp2,Rq8,Rr14),(Rp2,Rq8,Rr15),(Rp2,Rq8,Rr16),(Rp2,Rq8,Rr17),(Rp2,Rq8,Rr18),(Rp2,Rq8,Rr19),(Rp2,Rq5,Rr20),(Rp3,Rq1,Rr1),(Rp3,Rq1,Rr2),(Rp3,Rq1,Rr3),(Rp3,Rq1,Rr5),Rr6),(Rp3,Rq1,Rr7),(Rp3,Rq1,Rr8),(Rp3,Rq1,Rr9),(Rp1,Rq1,Rr10),(Rp3,Rq1,Rr11),(Rp3,Rq1,Rr12),(Rp3,Rq1,Rr13),(Rp3,Rq1,Rr14),(Rp3,Rq1,Rr15),(Rp3,Rq1,Rr16),(Rp3,Rq1,Rr17),(Rp3,Rq1,Rr18),(Rp3,Rq1,Rr19),(Rp3,Rq1,Rr20),(Rp3,Rq2,Rr1),(Rp3,Rq2,Rr2),(Rp3,Rq2,Rr3),(Rp3,Rq2,Rr4),(Rp3,Rq2,Rr5),(Rp3,Rq2,Rr6),(Rp3,Rq2,Rr7),(Rp3,Rq2,Rr8),(Rp3,Rq2,Rr9),(Rp3,Rq2,Rr10),(Rp3,Rq2,Rr11),(Rp3,Rq2,Rr10),(Rp3,Rq2,Rr13),(Rp3,Rq2,Rr14),(Rp3,Rq2,Rr15),(Rp3,Rq2,Rr16),(Rp3,Rq2,Rr17),(Rp3,Rq2,Rr18),(Rp3,Rq2,Rr19),(Rp3,Rq2,Rr20),(Rp3,Rq3,Rr1),(Rp3,Rq3,Rr2),(Rp3,Rq3,Rr3),(Rp3,Rq3,Rr4),(Rp3,Rq3,Rr5),(Rp3,Rq3,Rr6),(Rp3,Rq3,Rr7),(Rp3,Rq3,Rr8),(Rp3,Rq3,Rr9),(Rp3,Rq3,Rr10),(Rp3,Rq3,Rr11),(Rp3,Rq3,Rr12),(Rp3,Rq3,Rr13),(Rp3,Rq3,Rr14),(Rp3,Rq3,Rr15),(Rp3,Rq3,Rr16), (Rp3,Rq3,Rr17),(Rp3,Rq3,Rr18),(Rp3,Rq3,Rr19),(Rp3,Rq3,Rr20),(Rp3,Rq4,Rr1),(Rp3,Rq4,Rr2),(Rp3,Rq4,Rr3),(Rp3,Rq4,Rr4),(Rp3,Rq4,Rr5),(Rp3,Rq4,Rr6),(Rp3,Rq4,Rr7),(Rp3,Rq4,Rr8),(Rp3,Rq4,Rr9),(Rp3,Rq4,Rr10),(Rp3,Rq4,Rr11),(Rp3,Rq4,Rr12),(Rp3,Rq4,Rr13),(Rp3,Rq4,Rr14),(Rp3,Rq4,Rr15),(Rp3,Rq4,Rr16),(Rp3,Rq4,Rr17),(Rp3,Rq4,Rr18),(Rp3,Rq4,Rr19),(Rp3,Rq4,Rr20),(Rp3,Rq5,Rr2),(Rp3,Rq5,Rr3),(Rp3,Rq5,Rr4),(Rp3,Rq5,Rr5),(Rp3,Rq5,Rr6),(Rp3,Rq5,Rr7),(Rp3,Rq5,Rr8),(Rp3,Rq5,Rr9),(Rp3,Rq5,Rr10),(Rp3,Rq5,Rr11),(Rp3,Rq5,Rr12),(Rp3,Rq5,Rr13),(Rp3,Rq5,Rr14),(Rp3,Rq5,Rr15),(Rp3,Rq5,Rr16),(Rp3,Rq5,Rr17),(Rp3,Rq5,Rr1,(Rp3,Rq5,Rr19),(Rp3,Rq5,Rr20),(Rp3,Rq6,Rr1),(Rp3,Rq6,Rr2),(Rp3,Rq6,Rr3),(Rp3,Rq6,Rr4),(Rp3,Rq6,Rr5),(Rp3,Rq6,Rr6),(Rp3,Rq6,Rr7),(Rp3,Rq6,Rr8),(Rp3,Rq6,Rr9),(Rp3,Rq6,Rr10),(Rp3,Rq6,Rr11),(Rp3,Rq6,Rr12),(Rp3,Rq6,Rr13),(Rp3,Rq6,Rr14),(Rp3,Rq6,Rr15),(Rp3,Rq6,Rr16),(Rp3,Rq6,Rr17),(Rp3,Rq8,Rr18),(Rp3,Rq6,Rr19),(Rp3,Rq6,Rr20),(Rp3,Rq7,Rr1),(Rp3,Rq7,Rr2),(Rp3,Rq7,Rr3),(Rp3,Rq7,Rr4),(Rp3,Rq7,Rr5),(Rp3,Rq7,Rr6),(Rp3,Rq7,Rr7),(Rp3,Rq7,Rr8),(Rp3,Rq7,Rr9),(Rp3,Rq7,Rr10),(Rp3,Rq7,Rr11),(Rp3,Rq7,Rr12),(Rp3,Rq7,Rr13),(Rp3,Rq7,Rr14),(Rp3,Rq7,Rr15),(Rp3,Rq7,Rr16),(Rp3,Rq7,Rr17),(Rp3,Rq7,Rr18),(Rp3,Rq7,Rr19),(Rp3,Rq7,Rr20),(Rp3,Rq8,Rr1),(Rp3,Rq8,Rr2),(Rp3,Rq8,Rr3),(Rp3,Rq8,Rr4),(Rp3,Rq8,Rr5),(Rp3,Rq8,Rr6),(Rp3,Rq8,Rr7),(Rp3,Rq8,Rr8),(Rp3,Rq8,Rr9),(Rp3,Rq8,Rr10),(Rp3,Rq8,Rr11),(Rp3,Rq8,Rr12),(Rp3,Rq8,Rr13),(Rp3,Rq8,Rr14),(Rp3,Rq8,Rr15),(Rp3,Rq8,Rr16),(Rp3,Rq8,Rr17),(Rp3,Rq8,Rr18),(Rp3,Rq8,Rr19),(Rp3,Rq8,Rr20),(Rp4,Rq1,Rr1),(Rp4,Rq1,Rr2),(Rp4,Rq1,Rr3),(Rp4,Rq1,Rr4),(Rp4,Rq1,Rr5),(Rp4,Rq1,Rr6),(Rp4,Rq1,Rr7),(Rp4,Rq1,Rr8),(Rp4,Rq1,Rr9),(Rp4,Rq1,Rr10),(Rp4,Rq1,Rr11),(Rp4,Rq1,Rr12),(Rp4,Rq1,Rr13),(Rp4,Rq1,Rr14),(Rp4,Rq1,Rr15),(Rp4,Rq1,Rr16),(Rp4,Rq1,Rr17),(Rp4,Rq1,Rr18),(Rp4,Rq1,Rr19),(Rp4,Rq1,Rr20),(Rp4,Rq2,Rr1),(Rp4,Rq2,Rr2),(Rp4,Rq2,Rr3),(Rp4,Rq2,Rr4),(Rp4,Rq2,Rr5),(Rp4,Rq2,Rr3),(Rp4,Rq2,Rr7),(Rp4,Rq2,Rr8),(Rp4,Rq2,Rr9),(Rp4,Rq2,Rr10),(Rp4,Rq2,Rr11),(Rp4,Rq2,Rr2),(Rp4,Rq2,Rr13),(Rp4,Rq2,Rr14),(Rp4,Rq2,Rr15),(Rp4,Rq2,Rr16),(Rp4,Rq2,Rr17),Rp4,Rq2,Rr18),(Rp4,Rq2,Rr19),(Rp4,Rq2,Rr20),(Rp4,Rq3,Rr1),(Rp4,Rq3,Rr2),(Rp4,Rq3,Rr3),(Rp4,Rq3,Rr4),(Rp4,Rq3,Rr5),(Rp4,Rq3,Rr6),(Rp4,Rq3,Rr7),(Rp4,Rq3,Rr8),(Rp4,Rq3,Rr9),(Rp4,Rq3,Rr10),(Rp4,Rq3,Rr11),(Rp4,Rq3,Rr12),(Rp4,Rq3,Rr13),(Rp4,Rq3,Rr14),(Rp4,Rq3,Rr15),(Rp4,Rq3,Rr16),(Rp4,Rq3,Rr17),(Rp4,Rq3,Rr18),(Rp4,Rq3,Rr19),(Rp4,Rq3,Rr20),(Rp4,Rq4,Rr1),(Rp4,Rq4,Rr2),(Rp4,Rq4,Rr3),(Rp4,Rq4,Rr4),(Rp4,Rq4,Rr5),(Rp4,Rq4,Rr6),(Rp4,Rq4,Rr7),(Rp4,Rq4,Rr8),(Rp4,Rq4,Rr9),(Rp4,Rq1,Rr10),(Rp4,Rq4,Rr11),(Rp4,Rq4,Rr12),(Rp4,Rq4,Rr13),(Rp4,Rq4,Rr14),(Rp4,Rq4,Rr15),(Rp4,Rq4,Rr16),(Rp4,Rq4,Rr17),(Rp4,Rq4,Rr18),(Rp4,Rq4,Rr19),(Rp4,Rq4,Rr20),(Rp4,Rq5,Rr1),(Rp4,Rq5,Rr2),(Rp4,Rq5,Rr3),(Rp4,Rq5,Rr4),(Rp4,Rq5,Rr5),(Rp4,Rq5,Rr6),(Rp4,Rq5,Rr7),(Rp4,Rq5,Rr8),(Rp4,Rq5,Rr9),(Rp4,Rq5,Rr10),(Rp4,Rq5,Rr11),(Rp4,Rq5,Rr12),(Rp4,Rq5,Rr13),(Rp4,Rq5,Rr14),(Rp4,Rq5,Rr15),(Rp4,Rq5,Rr16),(Rp4,Rq5,Rr17),(Rp4,Rq5,Rr18),(Rp4,Rq5,Rr19),(Rp4,Rq5,Rr20),(Rp4,Rq6,Rr1),(Rp4,Rq6,Rr2),(Rp4,Rq6,Rr3),(Rp4,Rq6,Rr4),(Rp4,Rq6,Rr5),(Rp4,Rq6,Rr6),(Rp4,Rq6,Rr7),(Rp4,Rq6,Rr8),(Rp4,Rq6,Rr9),(Rp4,Rq6,Rr10),(Rp4,Rq6,Rr11),(Rp4,Rq6,Rr12),(Rp4,Rq6,Rr13),(Rp4,Rq6,Rr14),(Rp4,Rq8,Rr15),(Rp4,Rq6,Rr16),(Rp4,Rq6,Rr17),(Rp4,Rq6,Rr18),(Rp4,Rq6,Rr19),(Rp4,Rq6,Rr20),(Rp4,Rq7,Rr1),(Rp4,Rq7,Rr2),(Rp4,Rq7,Rr3),(Rp4,Rq7,Rr4),(Rp4,Rq7,Rr5),(Rp4,Rq7,Rr6),(Rp4,Rq7,Rr7),(Rp4,Rq7,Rr8),(Rp4,Rq7,Rr9),(Rp4,Rq7,Rr10),(Rp4,Rq7,Rr11),(Rp4,Rq7,Rr12),(Rp4,Rq7,Rr13),(Rp4,Rq7,Rr14),(Rp4,Rq7,Rr15),(Rp4,Rq7,Rr16),(Rp4,Rq7,Rr17),(Rp4,Rq7,Rr18),(Rp4,Rq7,Rr19),(Rp4,Rq7,Rr20),(Rp4,Rq8,Rr1),(Rp4,Rq8,Rr2),(Rp4,Rq8,Rr3),(Rp4,Rq8,Rr4),(Rp4,Rq8,Rr5),(Rp4,Rq8,Rr6),(Rp4,Rq8, Rr7),(Rp4,Rq8,Rr8),(Rp4,Rq8,Rr9),(Rp4,Rq8,Rr10),(Rp4,Rq8,Rr11),(Rp4,Rq8,Rr12),(Rp4,Rq8,Rr13),(Rp4,Rq8,Rr14),(Rp4,Rq8,Rr15),(Rp4,Rq8,Rr16),(Rp4,Rq8,Rr7),(Rp4,Rq8,Rr18),(Rp4,Rq8,Rr19),(Rp4,Rq8,Rr20),(Rp5,Rq1,Rr1),(Rp5,Rq1,Rr2),(Rp5,Rq1,Rr3),(Rp5,Rq1,Rr4),(Rp5,Rq1,Rr5),(Rp5,Rq1,Rr6),(Rp5,Rq1,Rr7),(Rp5,Rq1,Rr8),(Rp5,Rq1,Rr9),(Rp5,Rq1,Rr10),(Rp5,Rq1,Rr11),(Rp5,Rq1,Rr12),(Rp5,Rq1,Rr13),(Rp5,Rq1,Rr14),(Rp5,Rq1,Rr15),(Rp5,Rq1,Rr6),(Rp5,Rq1,Rr17),(Rp5,Rq1,Rr18),(Rp5,Rq1,Rr19),(Rp5,Rq1,Rr20),(Rp5,Rq2,Rr1),(Rp5,Rq2,Rr2),(Rp5,Rq2,Rr3),(Rp5,Rq2,Rr4),(Rp5,Rq2,Rr5),(Rp5,Rq2,Rr6),(Rp5,Rq2,Rr7),(Rp5,Rq2,Rr8),(Rp5,Rq2,Rr9),(Rp5,Rq2,Rr1),(Rp5,Rq2,Rr11),(Rp5,Rq2,Rr12),(Rp5,Rq2,Rr13),(Rp5,Rq2,Rr14),(Rp5,Rq2,Rr15),(Rp5,Rq2,Rr16),(Rp5,Rq2,Rr17),(Rp5,Rq2,Rr18),(Rp5,Rq2,Rr19),(Rp5,Rq2,Rr20),(Rp5,Rq3,Rr1),(Rp5,Rq3,Rr2),(Rp5,Rq3,Rr3),(Rp5,Rq3,Rr4),(Rp5,Rq3,Rr5),(Rp5,Rq3,Rr6),(Rp5,Rq3,Rr7),(Rp5,Rq3,Rr8),(Rp5,Rq3,Rr9),(Rp5,Rq3,Rr10),(Rp5,Rq3,Rr11),(Rp5,Rq3,Rr12),(Rp5,Rq3,Rr3),(Rp5,Rq3,Rr14),(Rp5,Rq3,Rr15),(Rp5,Rq3,Rr16),(Rp5,Rq3,Rr17),(Rp5,Rq3,Rr18),(Rp5,Rq3,Rr19),(Rp5,Rq3,Rr20),(Rp5,Rq4,Rr1),(Rp5,Rq4,Rr2),(Rp5,Rq4,Rr3),(Rp5,Rq4,(Rp5,Rq4,Rr5),(Rp5,Rq4,Rr6),(Rp5,Rq4,Rr7),(Rp5,Rq4,Rr8),(Rp5,Rq4,Rr9),(Rp5,Rq4,Rr10),(Rp5,Rq1,Rr11),(Rp5,Rq4,Rr12),(Rp5,Rq4,Rr13),(Rp5,Rq4,Rr14),(Rp5,Rq1,Rr15),(Rp5,Rq4,Rr1(Rp5,Rq4,Rr17),(Rp5,Rq4,Rr18),(Rp5,Rq4,Rr19),(Rp5,Rq4,Rr20), Rp5,Rq5,Rr1),(Rp5,Rq5,Rr2),(Rp5,Rq5,Rr3),(Rp5,Rq5,Rr4),(Rp5,Rq5,Rr5),(Rp5,Rq5,Rr6),(Rp5,Rq5,Rr7),(Rp5,Rq5,Rr8),(Rp5,Rq5,Rr9),(Rp5,Rq5,Rr10),(Rp5,Rq5,Rr11),(Rp5,Rq5,Rr12),(Rp5,Rq5,Rr13),(Rp5,Rq5,Rr14),(Rp5,Rq5,Rr15),(Rp5,Rq5,Rr16),(Rp5,Rq5,Rr17),(Rp5,Rq5,Rr18),(Rp5,Rq5,Rr19),(Rp5,Rq5,Rr20),(Rp5,Rq6,Rr1),(Rp5,Rq6,Rr2),(Rp5,Rq3,Rr3),(Rp5,Rq6,Rr4),(Rp5,Rq6,Rr5),(Rp5,Rq6,Rr6),(Rp5,Rq6,Rr7),(Rp5,Rq6,Rr8),(Rp5,Rq6,Rr9),(Rp5,Rq6,Rr10),(Rp5,Rq6,Rr11),(Rp5,Rq6,Rr12),(Rp5,Rq6,Rr13),(Rp5,Rq6,Rr14),(Rp5,Rq6,Rr15),(Rp5,Rq6,Rr16),(Rp5,Rq6,Rr7),(Rp5,Rq6,Rr18),(Rp5,Rq6,Rr19),(Rp5,Rq6,Rr20),(Rp5,Rq7,Rr1),(Rp5,Rq7,Rr2),(Rp5,Rq7,Rr3),(Rp5,Rq7,Rr4),(Rp5,Rq7,Rr5),(Rp5,Rq7,Rr6),(Rp5,Rq7,Rr7),(Rp5,Rq7,Rr8),(Rp5,Rq7,Rr9),(Rp5,Rq7,Rr10),(Rp5,Rq7,Rr11),(Rp5,Rq7,Rr12),(Rp5,Rq7,Rr13),(Rp5,Rq7,Rr14),(Rp5,Rq7,Rr15),(Rp5,Rq7,Rr16),(Rp5,Rq7,Rr17),(Rp5,Rq7,Rr18),(Rp5,Rq7,Rr19),(Rp5,Rq1,Rr20),(Rp5,Rq8,Rr1),(Rp5,Rq8,Rr2),(Rp5,Rq8,Rr3),(Rp5,Rq8,Rr4),(Rp5,Rq8,Rr5),(Rp5,Rq8,Rr6),(Rp5,Rq8,Rr7),(Rp5,Rq8,Rr8),(Rp5,Rq8,Rr9),(Rp5,Rq8,Rr10),(Rp5,Rq8,Rr11),(Rp5,Rq8,Rr12),(Rp5,Rq8,Rr13),(Rp5,Rq8,Rr14),(Rp5,Rq8,Rr15),(Rp5,Rq8,Rr16),(Rp5,Rq8,Rr17),(Rp5,Rq8,Rr18),(Rp5,Rq8,Rr19),(Rp5,Rq8,Rr20),(Rp6,Rq1,Rr1),(Rp6,Rq1,Rr2),(Rp6,Rq1,Rr3),(Rp6,Rq1,Rr4),(Rp6,Rq1,Rr5),(Rp6,Rq1,Rr6),(Rp6,Rq1,Rr7),(Rp6,Rq1,Rr8),(Rp6,Rq1,Rr9),(Rp6,Rq1,Rr10),(Rp6,Rq1,Rr11),(Rp6,Rq1,Rr1),(Rp6,Rq1,Rr13),(Rp6,Rq1,Rr14),(Rp6,Rq1,Rr15),(Rp6,Rq1,Rr16),(Rp6,Rq1,Rr17),(Rp6,Rq1,Rr18),(Rp6,Rq1,Rr19),(Rp6,Rq1,Rr20),(Rp6,Rq2,Rr1),(Rp6,Rq2,Rr2),(Rp6,Rq2,Rr3),(Rp6,Rq2,Rr4),(Rp6,Rq2,Rr5),(Rp6,Rq2,Rr6),(Rp6,Rq2,Rr7),(Rp6,Rq2,Rr8),(Rp6,Rq2,Rr9),(Rp6,Rq2,Rr10),(Rp6,Rq2,Rr1),(Rp6,Rq2,Rr12),(Rp6,Rq2,Rr13),(Rp6,Rq2,Rr14),(Rp6,Rq2,Rr15),(Rp6,Rq2,Rr16),(Rp6,Rq2,Rr17),(Rp6,Rq2,Rr18),(Rp6,Rq2,Rr19),(Rp6,Rq2,Rr20),(Rp6,Rq3,Rr1),(Rp6,Rq3,Rr2),(Rp3,Rq3,Rr3),(Rp6,Rq3,Rr4),(Rp6,Rq3,Rr5),(Rp6, Rq3,Rr6),(Rp6,Rq3,Rr7),(Rp6,Rq3,Rr8),(Rp6,Rq3,Rr9), (Rp6,Rq3,Rr10),(Rp6,Rq3,Rr11),(Rp6,Rq3,Rr12),(Rp6, Rq3,Rr13),(Rp6,Rq3,Rr14),(Rp6,Rq3,Rr15),(Rp6,Rq3, Rr16),(Rp6,Rq3,Rr17),(Rp6,Rq3,Rr18),(Rp6,Rq3,Rr19), (Rp6,Rq3,Rr20),(Rp6,Rq4,Rr1),(Rp6,Rq5,Rr2),(Rp6,Rq1, Rr3),(Rp6,Rq1,Rr4),(Rp6,Rq4,Rr5),(Rp6,Rq4,Rr6),(Rp6, Rq4,Rr7),(Rp6,Rq4,Rr8),(Rp6,Rq4,Rr9),(Rp6,Rq4,Rr10), (Rp6,Rq4,Rr11),(Rp6,Rq4,Rr12),(Rp6,Rq1,Rr13),(Rp6, Rq4,Rr14),(Rp6,Rq4,Rr15),(Rp6,Rq1,Rr16),(Rp6,Rq4, Rr17),(Rp6,Rq4,Rr18),(Rp6,Rq4,Rr19),(Rp6,Rq4,Rr20), (Rp6,Rq5,Rr1),(Rp6,Rq5,Rr2),(Rp6,Rq5,Rr3),(Rp6,Rq5, Rr4),(Rp6,Rq5,Rr5),(Rp6,Rq5,Rr6),(Rp6,Rq5,Rr7),(Rp6, Rq5,Rr8),(Rp6,Rq5,Rr9),(Rp6,Rq5,Rr10),(Rp6,Rq5,Rr11), (Rp6,Rq5,Rr12),(Rp6, Rq5,Rr13),(Rp6,Rq5,Rr14),(Rp6, Rq5,Rr15),(Rp6,Rq5,Rr16),(Rp6,Rq5,Rr17),(Rp6,Rq5, Rr18),(Rp6,Rq5,Rr19),(Rp6,Rq5,Rr20),(Rp6,Rq6,Rr1), (Rp6,Rq6,Rr2),(Rp6,Rq6,Rr3),(Rp6,Rq6,Rr4),(Rp6,Rq6, Rr5),(Rp6,Rq6,Rr6),(Rp6,Rq6,Rr7),(Rp6,Rq6,Rr8),(Rp6, Rq6,Rr9),(Rp6,Rq6,Rr10),(Rp6,Rq6,Rr11),(Rp6,Rq6, Rr12),(Rp6,Rq6,Rr13),(Rp6,Rq6,Rr14),(Rp6,Rq6,Rr15), (Rp6,Rq6,Rr16),(Rp6,Rq6,Rr17),(Rp6,Rq6,Rr18),(Rp6, Rq6,Rr19),(Rp6,Rq6,Rr20),(Rp6,Rq7,Rr1),(Rp6,Rq7,Rr2), (Rp6,Rq7,Rr3),(Rp6,Rq7,Rr4),(Rp6,Rq7,Rr5),(Rp6,Rq7, Rr6),(Rp6,Rq7,Rr8),(Rp6,Rq7,Rr9),(Rp6,Rq7,Rr10),(Rp6, Rq7,Rr11),(Rp6,Rq7,Rr12),(Rp6,Rq7,Rr13),(Rp6,Rq7, Rr14),(Rp6,Rq7,Rr15),(Rp6,Rq7,Rr16),(Rp6,Rq7,Rr17), (Rp6,Rq7,Rr18),(Rp6,Rq7,Rr19),(Rp6, Rq7,Rr20),(Rp6, Rq8,Rr1),(Rp6,Rq8,Rr2),(Rp6,Rq8,Rr3),(Rp6,Rq8,Rr4), (Rp6,Rq8,Rr5),(Rp6,Rq8,Rr6),(Rp6,Rq8,Rr7),(Rp6,Rq8, Rr8),(Rp6,Rq8,Rr9),(Rp6,Rq8,Rr10),(Rp6,Rq8,Rr11), (Rp6,Rq8,Rr12),(Rp6,Rq8,Rr13),(Rp6,Rq8,Rr14),(Rp6, Rq8,Rr15),(Rp6,Rq8,Rr16),(Rp6,Rq8,Rr17),(Rp6,Rq8, Rr18),(Rp6,Rq8,Rr19),(Rp6,Rq8,Rr20),(Rp7,Rq1,Rr1), (Rp1,Rq1,Rr2),(Rp7,Rq1,Rr3),(Rp7,Rq1,Rr4),(Rp7,Rq1, Rr5),(Rp7,Rq1,Rr6),(Rp7,Rq1,Rr7),(Rp7,Rq1,Rr8),(Rp7, Rq1,Rr9),(Rp7,Rq1,Rr10),(Rp7,Rq1,Rr11),(Rp7,Rq1, Rr12),(Rp7,Rq1,Rr13),(Rp7,Rq1,Rr14),(Rp7,Rq1,Rr15), (Rp7,Rq1,Rr10),(Rp7,Rq1,Rr17),(Rp7,Rq1,Rr18),(Rp7, Rq1,Rr19),(Rp7,Rq1,Rr20),(Rp7,Rq2,Rr1),(Rp7,Rq2,Rr2), (Rp7,Rq2,Rr3),(Rp7,Rq2,Rr4),(Rp7,Rq2,Rr5),(Rp7,Rq2, Rr6),(Rp7,Rq2,Rr7),(Rp7,Rq2,Rr8),(Rp7,Rq2,Rr9),(Rp7, Rq2,Rr10),(Rp7,Rq2,Rr11),(Rp7,Rq2,Rr12),(Rp7,Rq2, Rr13),(Rp7,Rq2,Rr14),(Rp7,Rq2,Rr15),(Rp7,Rq2,Rr16), (Rp7,Rq2,Rr17),(Rp7,Rq2,Rr18),(Rp7,Rq2,Rr19),(Rp7, Rq2,Rr20),(Rp7,Rq3,Rr1),(Rp7,Rq3,Rr2),(Rp7,Rq3,Rr3), (Rp7,Rq3,Rr4),(Rp7,Rq3,Rr5),(Rp7,Rq3,Rr6),(Rp3,Rq3, Rr7),(Rp7,Rq3,Rr8),(Rp7,Rq3,Rr9),(Rp7,Rq3,Rr10),(Rp7, Rq3,Rr11),(Rp7,Rq3,Rr12),(Rp7,Rq3,Rr13),(Rp1,Rq3, Rr14),(Rp7,Rq3,Rr15),(Rp7,Rq3,Rr16),(Rp7,Rq3,Rr17), (Rp7,Rq3,Rr18),(Rp7,Rq3,Rr19),(Rp7,Rq8,Rr20),(Rp7, Rq4,Rr1),(Rp7,Rq4,Rr2),(Rp7,Rq4,Rr3),(Rp7,Rq4,Rr4), (Rp7,Rq4,Rr5),(Rp7,Rq4,Rr6),(Rp7,Rq4,Rr7),(Rp7,Rq4, Rr8),(Rp7,Rq4,Rr9),(Rp7,Rq4,Rr10),(Rp7,Rq4,Rr11), (Rp7,Rq4,Rr12),(Rp7,Rq4,Rr13),(Rp7,Rq4,Rr14),(Rp7, Rq4,Rr15),(Rp7,Rq4,Rr16),(Rp7,Rq4,Rr17),(Rp7,Rq4, Rr18),(Rp7,Rq4,Rr19),(Rp7,Rq4,Rr20),(Rp7,Rq5,Rr1), (Rp7,Rq5,Rr2),(Rp7,Rq5,Rr3),(Rp7,Rq5,Rr4),(Rp7,Rq5, Rr5),(Rp7,Rq5,Rr6),(Rp7,Rq5,Rr7),(Rp7,Rq5,Rr8),(Rp7, Rq5,Rr9),(Rp7,Rq5,Rr10),(Rp7,Rq5,Rr11),(Rp7,Rq5, Rr12),(Rp7,Rq5,Rr13),(Rp7,Rq5,Rr14),(Rp7,Rq5,Rr15), (Rp7,Rq5,Rr16),(Rp7,Rq5,Rr17),(Rp7,Rq5,Rr18),(Rp7, Rq5,Rr19),(Rp7,Rq5,Rr20),(Rp7,Rq6,Rr1),(Rp7,Rq6,Rr2), Rr3),(Rp7,Rq6,Rr4),(Rp7,Rq6,Rr5),(Rp7,Rq6,Rr6),(Rp7, Rq6,Rr7),(Rp7,Rq6,Rr8),(Rp7,Rq6,Rr9),(Rp7,Rq6,Rr10), (Rp7,Rq6,Rr11),(Rp7,Rq6,Rr12),(Rp7,Rq6,Rr13),(Rp7, Rq6,Rr14),(Rp7,Rq6,Rr15),(Rp7,Rq6,Rr16),(Rp7,Rq6, Rr17),(Rp7,Rq6,Rr18),(Rp7,Rq6,Rr19),(Rp7,Rq6,Rr20), (Rp7,Rq7,Rr1),(Rp7,Rq7,Rr2),(Rp7,Rq7,Rr3),(Rp7,Rq7, Rr4),(Rp7,Rq7,Rr5),(Rp7,Rq7,Rr8),(Rp7,Rq7,Rr7),(Rp7, Rq7,Rr8),(Rp7,Rq7,Rr9),(Rp7,Rq7,Rr10),(Rp7,Rq7,Rr11), (Rp7,Rq7,Rr12),(Rp7,Rq7,Rr13),(Rp7,Rq7,Rr14),(Rp7, Rq7,Rr15),(Rp7,Rq7,Rr16),(Rp7,Rq7,Rr17),(Rp7,Rq7, Rr18),(Rp7,Rq7,Rr19),(Rp7,Rq7,Rr20),(Rp7,Rq8,Rr1), (Rp7,Rq8,Rr2),(Rp7,Rq8,Rr3),(Rp7,Rq8,Rr4),(Rp7,Rq8, Rr5),(Rp7,Rq8,Rr6),(Rp7,Rq8,Rr7),(Rp7,Rq8,Rr8),(Rp7, Rq8,Rr9),(Rp7,Rq8,Rr10),(Rp7,Rq8,Rr11),(Rp7,Rq8, Rr12),(Rp7,Rq8,Rr13),(Rp7,Rq8,Rr1),(Rp7,Rq8,Rr15), (Rp7,Rq8,Rr16),(Rp7,Rq8,Rr17),(Rp7,Rq8,Rr18),(Rp7, Rq8,Rr19),(Rp7,Rq8,Rr20),(Rp8,Rq8,Rr1),(Rp8,Rq1,Rr2), (Rp8,Rq1,Rr3),(Rp8,Rq1,Rr4),(Rp8,Rq1,Rr5),(Rp8,Rq1, Rr6),(Rp8,Rq1,Rr7),(Rp8,Rq1,Rr8),(Rp8,Rq1,Rr9),(Rp8, Rq1,Rr10),(Rp8,Rq1,Rr11),(Rp8,Rq1,Rr12),(Rp8,Rq1, Rr13),(Rp8,Rq1,Rr11),(Rp8,Rq1,Rr15),(Rp8,Rq1,Rr16), (Rp8,Rq1,Rr17),(Rp8,Rq1,Rr18),(Rp8,Rq1,Rr19),(Rp8, Rq1,Rr20),(Rp8,Rq2,Rr1),(Rp8,Rq2,Rr2),(Rp8,Rq2,Rr3), (Rp8,Rq2,Rr11),(Rp8,Rq2,Rr5),(Rp8,Rq2,Rr6),(Rp8,Rq2, Rr7),(Rp8,Rq2,Rr8),(Rp8,Rq2,Rr9),(Rp8,Rq2,Rr10),(Rp8, Rq2,Rr11),(Rp8,Rq2,Rr12),(Rp8,Rq2,Rr13),(Rp8,Rq2, Rr14),(Rp8,Rq2,Rr15),(Rp8,Rq2,Rr16),(Rp8,Rq2,Rr17), (Rp8,Rq2,Rr18),(Rp8,Rq2,Rr19),(Rp8,Rq2,Rr20),(Rp8, Rq3,Rr1),(Rp8,Rq3,Rr2),(Rp8,Rq3,Rr3),(Rp8,Rq3,Rr4), (Rp8,Rq3,Rr5),(Rp8,Rq3,Rr6),(Rp8,Rq3,Rr7),(Rp8,Rq3, Rr8),(Rp8,Rq3,Rr9),(Rp8,Rq3,Rr10),(Rp8,Rq3,Rr11), (Rp8,Rq3,Rr12),(Rp8,Rq3,Rr13),(Rp8,Rq3,Rr14),(Rp8, Rq3,Rr15),(Rp8,Rq3,Rr16),(Rp8,Rq3,Rr17),(Rp8,Rq3, Rr18),(Rp8,Rq3,Rr19),(Rp8,Rq3,Rr20),(Rp8,Rq4,Rr1), (Rp8,Rq4,Rr2),(Rp8,Rq4,Rr3),(Rp8,Rq4,Rr4),(Rp8,Rq4, Rr5),(Rp8,Rq4,Rr6),(Rp8,Rq4,Rr7),(Rp8,Rq4,Rr8),(Rp8, Rq4,Rr9),(Rp8,Rq4,Rr10),(Rp8,Rq4,Rr11),(Rp8,Rq4, Rr12),(Rp8,Rq4,Rr13),(Rp8,Rq4,Rr14),(Rp8,Rq4,Rr15), (Rp8,Rq4,Rr16),(Rp8,Rq4,Rr17),(Rp8,Rq4,Rr18),(Rp8, Rq4,Rr19),(Rp8,Rq4,Rr20),(Rp8,Rq5,Rr1),(Rp8,Rq5,Rr2), (Rp8,Rq5,Rr3),(Rp8,Rq5,Rr4),(Rp8,Rq5,Rr5),(Rp8,Rq5, Rr6),(Rp8,Rq5,Rr7),(Rp8,Rq5,Rr8),(Rp8,Rq5,Rr9),(Rp8, Rq5,Rr10),(Rp8,Rq5,Rr11),(Rp8,Rq5,Rr12),(Rp8,Rq5, Rr13),(Rp8,Rq5,Rr14),(Rp8,Rq5,Rr15),(Rp8,Rq5,Rr16), (Rp8,Rq5,Rr17),(Rp8,Rq5,Rr18),(Rp8,Rq5,Rr19),(Rp8, Rq5,Rr20),(Rp8,Rq6,Rr1),(Rp8,Rq6,Rr2),(Rp8,Rq6,Rr3), (Rp8,Rq6,Rr4),(Rp8,Rq6,Rr5),(Rp8,Rq6,Rr6),(Rp8,Rq6, Rr7),(Rp8,Rq6,Rr8),(Rp8,Rq6,Rr9),(Rp8,Rq6,Rr10),(Rp8, Rq6,Rr12),(Rp8,Rq6,Rr13),(Rp8,Rq6,Rr14),(Rp8,Rq6, Rr15),(Rp8,Rq6,Rr16),(Rp8,Rq6,Rr17),(Rp8,Rq6,Rr18), (Rp8,Rq6,Rr19),(Rp8,Rq6,Rr20),(Rp8,Rq7,Rr1),(Rp8,Rq7, Rr2),(Rp8,Rq7,Rr3),(Rp8,Rq7,Rr4),(Rp8,Rq7,Rr5),(Rp8, Rq7,Rr6),(Rp8,Rq7,Rr7),(Rp8,Rq7,Rr8),(Rp8,Rq7,Rr9), (Rp8,Rq7,Rr10),(Rp8,Rq7,Rr11),(Rp8,Rq7,Rr12),(Rp8, Rq7,Rr13),(Rp8,Rq7,Rr14),(Rp8,Rq7,Rr15),(Rp8,Rq7, Rr16),(Rp8,Rq7,Rr17),(Rp8,Rq7,Rr18),(Rp8,Rq7,Rr19), (Rp8,Rq7,Rr20),(Rp8,Rq8,Rr1),(Rp8,Rq8,Rr2),(Rp8,Rq8, Rr3),(Rp8,Rq8,Rr4),(Rp8,Rq8,Rr5),(Rp8,Rq8,Rr6),(Rp8, Rq8,Rr7),(Rp8,Rq8,Rr8),(Rp8,Rq8,Rr9),(Rp8,Rq8,Rr10), (Rp8,Rq8,Rr11),(Rp8,Rq8,Rr12),(Rp8,Rq8,Rr13),(Rp8, Rq8,Rr14),(Rp8,Rq8,Rr15),(Rp8,Rq8,Rr16),(Rp8,Rq8, Rr17),(Rp8,Rq8,Rr18),(Rp8,Rq8,Rr19),(Rp8,Rq8,Rr20), (Rp9,Rq1,Rr1),(Rp9,Rq1,Rr2),(Rp9,Rq1,Rr3),(Rp9,Rq1, Rr4),(Rp9,Rq1,Rr5),(Rp9,Rq1,Rr6),(Rp9,Rq1,Rr7),(Rp9, Rq1,Rr8),(Rp9,Rq1,Rr9),(Rp9,Rq1,Rr10),(Rp9,Rq1,Rr11), (Rp9,Rq1,Rr12),(Rp9,Rq1,Rr13),(Rp9,Rq1,Rr14),(Rp9, Rq1,Rr15),(Rp9,Rq1,Rr16),(Rp9,Rq1,Rr17),(Rp9,Rq1, Rr18),(Rp9,Rq1,Rr19),(Rp9,Rq1,Rr20),(Rp9,Rq2,Rr1), (Rp9,Rq2,Rr2),(Rp9,Rq2,Rr3),(Rp9,Rq2,Rr4),(Rp9,Rq2, Rr5),(Rp9,Rq2,Rr6),(Rp9,Rq2,Rr7),(Rp9,Rq2,Rr8),(Rp9, Rq2,Rr9),(Rp9,Rq2,Rr10),(Rp9,Rq2,Rr11),(Rp9,Rq2, Rr12),(Rp9,Rq2,Rr13),(Rp9,Rq2,Rr14),(Rp9,Rq2,Rr15), (Rp9,Rq2,Rr16),(Rp9,Rq2,Rr17),(Rp9,Rq2,Rr18),(Rp9,
Rq2,Rr19),(Rp9,Rq2,Rr20),(Rp9,Rq3,Rr1),(Rp9,Rq3,Rr2),
(Rp9,Rq3,Rr3),(Rp9,Rq3,Rr11),(Rp9,Rq3,Rr5),(Rp9,Rq3,
Rr6),(Rp9,Rq3,Rr7),(Rp9,Rq3,Rr8),(Rp9,Rq3,Rr9),(Rp9,
Rq3,Rr10),(Rp9,Rq3,Rr11),(Rp9,Rq3,Rr12),(Rp9,Rq3,
Rr13),(Rp9,Rq3,Rr14),(Rp9,Rq3,Rr15),(Rp9,Rq3,Rr16),
(Rp9,Rq3,Rr17),(Rp9,Rq3,Rr18),(Rp9,Rq3,Rr19 Rq3,
Rr20),(Rp9,Rq3,Rr1),(Rp9,Rq4,Rr2),(Rp9,Rq4,Rr3),(Rp9,
Rq4,Rr4),(Rp9,Rq4,Rr5),(Rp9,Rq4,Rr6),(Rp9,Rq4,Rr7),
(Rp9,Rq4,Rr8),(Rp9,Rq4,Rr9),(Rp9,Rq1,Rr10),(Rp9,Rq1,
Rr11),(Rp9,Rq4,Rr12),(Rp9,Rq1,Rr13),(Rp9,Rq4,Rr14),
(Rp9,Rq4,Rr15),(Rp9,Rq4,Rr16),(Rp9,Rq4,Rr17),(Rp9,
Rq4,Rr18),(Rp9,Rq1,Rr19),(Rp9,Rq1,Rr20),(Rp9,Rq5,
Rr1),(Rp9,Rq5,Rr2),(Rp9,Rq5,Rr3),(Rp9,Rq5,Rr4),(Rp9,
Rq15,Rr5),(Rp9,Rq5,Rr6),(Rp9,Rq5,Rr7),(Rp9,Rq5,Rr8),
(Rp9,Rq5,Rr9),(Rp9,Rq5,Rr10),(Rp9,Rq5,Rr11),(Rp9,Rq5,
Rr12),(Rp9,Rq5,Rr13),(Rp9,Rq5,Rr14),(Rp9,Rq5,Rr15),
(Rp9,Rq5,Rr16),(Rp9,Rq5,Rr17),(Rp9,Rq5,Rr18),(Rp9,
Rq5,Rr19),(Rp9,Rq5,Rr20),(Rp9,Rq6,Rr1),(Rp9,Rq6,Rr2),
(Rp9,Rq6,Rr3),(Rp9,Rq6,Rr4),(Rp9,Rq6,Rr5),(Rp9,Rq6,
Rr6),(Rp9,Rq6,Rr7),(Rp9,Rq6,Rr8),(Rp9,Rq6,Rr9),(Rp9,
Rq6,Rr10),(Rp9,Rq6,Rr11),(Rp9,Rq6,Rr12),(Rp9,Rq6,
Rr13),(Rp9,Rq3,Rr14),(Rp9,Rq6,Rr15),(Rp9,Rq6,Rr16),
(Rp9,Rq6,Rr17),(Rp9,Rq6,Rr18),(Rp9,Rq6,Rr19),(Rp9,
Rq6,Rr20),(Rp9,Rq7,Rr1),(Rp9,Rq7,Rr2),(Rp9,Rq7,Rr3),
(Rp9,Rq7,Rr4),(Rp9,Rq7,Rr5),(Rp9,Rq7,Rr6),(Rp9,Rq7,
Rr7),(Rp9,Rq7,Rr8),(Rp9,Rq7,Rr9),(Rp9,Rq7,Rr10),(Rp9,
Rq7,Rr11),(Rp9,Rq7,Rr12),(Rp9,Rq7,Rr13),(Rp9,Rq7,
Rr14),(Rp9,Rq7,Rr15),(Rp9,Rq7,Rr16),(Rp9,Rq7,Rr17),
(Rp9,Rq7,Rr18),(Rp9,Rq7,Rr19),(Rp9,Rq7,Rr20),(Rp9,
Rq8,Rr1),(Rp9,Rq8,Rr2),(Rp9,Rq8,Rr3),(Rp9,Rq8,Rr4),
(Rp9,Rq8,Rr5),(Rp9,Rq8,Rr6),(Rp9,Rq8,Rr7),(Rp9,Rq8,
Rr8),(Rp9,Rq8,Rr9),(Rp9,Rq8,Rr10),(Rp9,Rq8,Rr11),
(Rp9,Rq8,Rr12),(Rp9,Rq8,Rr13),(Rp9,Rq8,Rr14),(Rp9,
Rq8,Rr15),(Rp9,Rq8,Rr16),(Rp9,Rq8,Rr17),(Rp9,Rq8,
Rr18),(Rp9,Rq8,Rr19),(Rp9,Rq8,Rr20),(Rp10,Rq1,Rr1),
(Rp10,Rq1,Rr2),(Rp10,Rq1,Rr3),(Rp10,Rq1,Rr4),(Rp10,
Rq1,Rr5),(Rp10,Rq1,Rr6),(Rp10,Rq1,Rr7),(Rp10,Rq1,
Rr8),(Rp10,Rq1,Rr9),(Rp10,Rq1,Rr0),(Rp10,Rq1,Rr11),
(Rp10,Rq1,Rr12),(Rp10,Rq1,Rr13),(Rp10,Rq1,Rr14),
(Rp10,Rq1,Rr15),(Rp10,Rq1,Rr16),(Rp10,Rq1,Rr17),
(Rp10,Rq1,Rr8),(Rp10,Rq1,Rr19),(Rp10,Rq1,Rr20),(Rp10,
Rq2,Rr1),(Rp10,Rq2,Rr2),(Rp10,Rq2,Rr3),(Rp10,Rq2,
Rr4),(Rp10,Rq2,Rr5),(Rp10,Rq2,Rr6),(Rp10,Rq2,Rr7),
(Rp10,Rq2,Rr8),(Rp10,Rq2,Rr9),(Rp10,Rq2,Rr10),(Rp10,
Rq2,Rr1),(Rp10,Rq2,Rr12),(Rp0,Rq2,Rr13),(Rp10,Rq2,
Rr14),(Rp10,Rq2,Rr15),(Rp10,Rq2,Rr16),(Rp10,Rq2,
Rr17),(Rp10,Rq2,Rr18),(Rp10,Rq2,Rr19),(Rp10,Rq2,
Rr20),(Rp10,Rq2,Rr1),(Rp10,Rq3,Rr2),(Rp10,Rq3,Rr3),
(Rp10,Rq3,Rr4),(Rp10,Rq3,Rr5),(Rp10,Rq3,Rr6),(Rp10,
Rq3,Rr7),(Rp10,Rq3,Rr8),(Rp10,Rq3,Rr9),(Rp10,Rq3,
Rr10),(Rp10,Rq3,Rr11),(Rp10,Rq3,Rr12),(Rp10,Rq3,
Rr13),(Rp10,Rq3,Rr14),(Rp10,Rq3,Rr15),(Rp10,Rq4,
Rr16),(Rp10,Rq3,Rr7),(Rp10,Rq3,Rr18),(Rp10,Rq3,Rr19),
(Rp10,Rq3,Rr20),(Rp10,Rq4,Rr1),(Rp10,Rq1,Rr2),(Rp10,
Rq1,Rr3),(Rp10,Rq4,Rr4),(Rp10,Rq4,Rr5),(Rp10,Rq4,
Rr6),(Rp10,Rq4,Rr7),(Rp10,Rq4,Rr8),(Rp10,Rq5,Rr9),
(Rp10,Rq4,Rr10),(Rp10,Rq4,Rr11),(Rp10,Rq44,Rr12),
(Rp10,Rq4,Rr13),(Rp10,Rq4,Rr14),(Rp10,Rq4,Rr15),
(Rp10,Rq4,Rr16),(Rp10,Rq1,Rr17),(Rp10,Rq4,Rr18),
(Rp10,Rq4,Rr19),(Rp10,Rq4,Rr20),(Rp10,Rq5,Rr1),(Rp10,
Rq5,Rr2),(Rp10,Rq5,Rr3),(Rp10,Rq5,Rr4),(Rp10,Rq5,
Rr5),(Rp10,Rq5,Rr6),(Rp10,Rq5,Rr7),(Rp10,Rq5,Rr8),
(Rp10,Rq5,Rr9),(Rp10,Rq5,Rr10),(Rp10,Rq5,Rr11),(Rp10,
Rq5,Rr12),(Rp10,Rq5,Rr13),(Rp10,Rq5,Rr14),(Rp10,Rq5,
Rr15),(Rp10,Rq5,Rr16),(Rp10,Rq5,Rr17),(Rp10,Rq5,
Rr18),(Rp10,Rq5,Rr19),(Rp10,Rq5,Rr20),(Rp10,Rq6,
Rr10),(Rp10,Rq6,Rr2),(Rp10,Rq6,Rr3),(Rp10,Rq6,Rr4),
(Rp10,Rq6,Rr5),(Rp10,Rq6,Rr6),(Rp10,Rq6,Rr7),(Rp10,
Rq6,Rr8),(Rp10,Rq6,Rr9),(Rp10,Rq6,Rr10),(Rp10,Rq6,
Rr11),(Rp10,Rq6,Rr12),(Rp10,Rq6,Rr13),(Rp10,Rq6,
Rr14),(Rp10,Rq6,Rr15),(Rp10,Rq6,Rr1.6),(Rp10,Rq6,
Rr17),(Rp10,Rq6,Rr18),(Rp10,Rq6,Rr19),(Rp10,Rq6,
Rr20),(Rp10,Rq7,Rr1),(Rp10,Rq7,Rr2),(Rp10,Rq7,Rr3),
(Rp10,Rq7,Rr4),(Rp10,Rq7,Rr5),(Rp10,Rq7,Rr3),(Rp10,
Rq7,Rr7),(Rp10,Rq7,Rr8),(Rp10,Rq7,Rr9),(Rp10,Rq7,
Rr10),(Rp10,Rq7,Rr11),(Rp10,Rq7,Rr12),(Rp10,Rq7,
Rr13),(Rp10,Rq7,Rr14),(Rp10,Rq7,Rr15),(Rp10,Rq7,
Rr16),(Rp10,Rq7,Rr17),(Rp10,Rq7,Rr18),(Rp10,Rq7,Rr9),
(Rp10,Rq7,Rr20),(Rp10,Rq8,Rr1),(Rp10,Rq8,Rr2),(Rp10,
Rq8,Rr3),(Rp10,Rq8,Rr4),(Rp10,Rq8,Rr5),(Rp10,Rq8,
Rr6),(Rp10,Rq8,Rr7),(Rp10,Rq8,Rr8),(Rp10,Rq8,Rr9),
(Rp10,Rq8,Rr10),(Rp10,Rq8,Rr11),(Rp10,Rq8,Rr12),
(Rp10,Rq8,Rr13),(Rp10,Rq8,Rr14),(Rp10,Rq8,Rr15),
(Rp10,Rq8,Rr16),(Rp10,Rq8,Rr17),(Rp10,Rq8,Rr18),
(Rp10,Rq8,Rr19),(Rp10,Rq8,Rr20),(Rp11,Rq1,Rr1),(Rp11,
Rq1,Rr2),(Rp11,Rq1,Rr3),(Rp11,Rq1,Rr4),(Rp11,Rq1,
Rr5),(Rp11,Rq1,Rr6),(Rp11,Rq1,Rr7),(Rp11,Rq1,Rr8),
(Rp11,Rq1,Rr9),(Rp11,Rq1,Rr10),(Rp11,Rq1,Rr11),(Rp11,
Rq1,Rr12),(Rp11,Rq1,Rr13),(Rp11,Rq1,Rr14),(Rp11,Rq1,
Rr15),(Rp11,Rq1,Rr16),(Rp11,Rq1,Rr17),(Rp11,Rq1,
Rr18),(Rp11,Rq1,Rr19),(Rp11,Rq1,Rr20),(Rp11,Rq2,
Rr1),(Rp11,Rq2,Rr2),(Rp11,Rq2,Rr3),(Rp11,Rq2,Rr4),
(Rp11,Rq2,Rr5),(Rp11,Rq2,Rr6),(Rp11,Rq2,Rr7),(Rp11,
Rq2,Rr8),(Rp11,Rq2,Rr9),(Rp11,Rq2,Rr10),(Rp11,Rq2,
Rr11),(Rp11,Rq2,Rr12),(Rp11,Rq2,Rr13),(Rp11,Rq2,
Rr14),(Rp11,Rq2,Rr15),(Rp11,Rq2,Rr16),(Rp11,Rq2,
Rr17),(Rp11,Rq2,Rr18),(Rp11,Rq2,Rr19),(Rp11,Rq2,
Rr20),(Rp11,Rq1,Rr1),(Rp11,Rq3,Rr2),(Rp11,Rq3,Rr3),
(Rp11,Rq3,Rr4),(Rp11,Rq3,Rr5),(Rp11,Rq3,Rr6),(Rp11,
Rq3,Rr7),(Rp11,Rq3,Rr8),(Rp11,Rq3,Rr9),(Rp11,Rq3,
Rr10),(Rp11,Rq3,Rr11),(Rp11,Rq3,Rr12),(Rp11,Rq3,
Rr13),(Rp11,Rq3,Rr14),(Rp11,Rq3,Rr15),(Rp11,Rq3,
Rr16),(Rp11,Rq3,Rr17),(Rp11,Rq1,Rr18),(Rp11,Rq1,
Rr19),(Rp11,Rq3,Rr20),(Rp11,Rq1,Rr1),(Rp11,Rq4,Rr2),
(Rp11,Rq4,Rr3),(Rp11,Rq4,Rr4),(Rp11,Rq4,Rr5),(Rp11,
Rq4,Rr6),(Rp1,Rq4,Rr7),(Rp11,Rq21,Rr8),(Rp11,Rq4,
Rr9),(Rp11,Rq4,Rr10),(Rp11,Rq4,Rr11),(Rp11,Rq4,Rr12),
(Rp11,Rq4,Rr13),(Rp11,Rq4,Rr14),(Rp11,Rq4,Rr15),
(Rp11,Rq4,Rr16),(Rp11,Rq4,Rr17),(Rp11,Rq4,Rr18),
(Rp11,Rq4,Rr19),(Rp11,Rq4,Rr20),(Rp11,Rq5,Rr1),(Rp11,
Rq5,Rr2),(Rp11,Rq5,Rr3),(Rp11,Rq5,Rr4),(Rp11,Rq5,
Rr5),(Rp11,Rq5,Rr6),(Rp11,Rq5,Rr7),(Rp11,Rq5,Rr8),
(Rp11,Rq5,Rr9),(Rp11,Rq5,Rr10),(Rp11,Rq5,Rr11),(Rp11,
Rq5,Rr12),(Rp11,Rq5,Rr13),(Rp11,Rq5,Rr14),(Rp11,Rq5,
Rr15),(Rp11,Rq5, Rr16),(Rp11,Rq5,Rr17),(Rp11,Rq5,
Rr18),(Rp11,Rq11,Rr19),(Rp11,Rq5,Rr20),(Rp11,Rq9,
Rr1),(Rp11,Rq8,Rr2),(Rp11,Rq6,Rr3),(Rp11,Rq8,Rr4),
(Rp11,Rq6,Rr5),(Rp11,Rq6,Rr6),(Rp11,Rq6,Rr7),(Rp11,
Rq6,Rr8),(Rp11,Rq6,Rr9),(Rp11,Rq6,Rr10),(Rp11,Rq6,
Rr11),(Rp11,Rq6,Rr12),(Rp11,Rq6,Rr13),(Rp11,Rq5,
Rr14),(Rp11,Rq6,Rr15),(Rp11,Rq6,Rr16),(Rp11,Rq6,
Rr17),(Rp11,Rq6,Rr18),(Rp11,Rq6,Rr19),(Rp11,Rq6,
Rr20),(Rp11,Rq7,Rr1),(Rp11,Rq7,Rr2),(Rp11,Rq7,Rr3),
(Rp11,Rq7,Rr1),(Rp11,Rq7,Rr5),(Rp11,Rq7,Rr6),(Rp11,
Rq7,Rr7),(Rp11,Rq7,Rr8),(Rp11,Rq7,Rr9),(Rp11,Rq7,
Rr10),(Rp11,Rq7,Rr11),(Rp11,Rq7,Rr12),(Rp11,Rq7,
Rr13),(Rp11,Rq7,Rr14),(Rp11,Rq7,Rr15),(Rp11,Rq7,
Rr16),(Rp11,Rq7,Rr17),(Rp11,Rq7,Rr18),(Rp11,Rq7,
Rr19),(Rp11,Rq7,Rr20),(Rp11,Rq8,Rr1),(Rp11,Rq8,Rr2),
(Rp11,Rq8,Rr3),(Rp11,Rq8,Rr4),(Rp11,Rq8,Rr5),(Rp11,
Rq8,Rr6),(Rp11,Rq8,Rr7),(Rp11,Rq8,Rr8),(Rp11,Rq8,
Rr9),(Rp11,Rq8,Rr10),(Rp11,Rq8,Rr11),(Rp11,Rq8,Rr12),
(Rp11,Rq8,Rr13),(Rp11,Rq8,Rr11),(Rp11,Rq8,Rr15), (Rp11,Rq8,Rr16),(Rp11,Rq8,Rr17),(Rp11,Rq8,Rr18), (Rp11,Rq8,Rr19),(Rp11,Rq8,Rr20)

In some embodiments of the present compounds, there is provided compounds of the following formula (VIII) and the formula (IX) having the following groups:

[Chemical Formula 119]

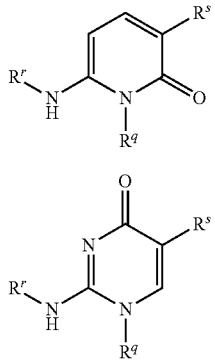

(VIII)

(IX)

TABLE 4

| Rs | |
|---|---|
| Rs1 | 4-Cl—Bn |
| Rs2 | CH2CONHCH(CH2OH)2 |
| Rs3 | CH2CONH(CH2)2OH |
| Rs4 | CH2CHMeCOOH—S |
| Rs5 | CH2CH(CH2OH)2 |
| Rs6 | CH2C(Me)2COOH |
| Rs7 | (CH2)3COOH |
| Rs8 | CONH(CH2)2OH |
| Rs9 | CON(Me)(CH2)2OH |
| Rs10 | CONHCH(CH2OH)2 |
| Rs11 | CONHCH(Me)COOH |
| Rs12 | NH(CH2)3OH |
| Rs13 | NHCO(CH2)2COOH |
| Rs14 | NHCOCH2-4-THP |
| Rs15 | NHCO-4-THP |

TABLE 5

| Rq | |
|---|---|
| Rq1 | 4-Me—PhCH2 |
| Rq2 | 4-Et—PhCH2 |
| Rq3 | 4-Vinyl-PhCH2 |
| Rq4 | 4-F—PhCH2 |
| Rq5 | 4-Cl—PhCH2 |
| Rq6 | 4-Br—PhCH2 |
| Rq7 | c-Hexylmethyl |
| Rq8 | c-Heptylmethyl |

TABLE 6

| Rr | Rr |
|---|---|
| Rr1 | 4-PrO—Ph |
| Rr2 | 4-i-PrO—Ph |
| Rr3 | 4-c-BuO—Ph |
| Rr4 | 4-s-BuO—Ph |
| Rr5 | 4-c-PrCH$_2$O—Ph |
| Rr6 | 4-PhO—Ph |
| Rr7 | 4-(6-Me-3-Pyridyl)O—Ph |
| Rr8 | 4-(3-Me-4-Pyridyl)O—Ph |
| Rr9 | 4-Piperidino-Ph |

TABLE 6-continued

| Rr | Rr |
|---|---|
| Rr10 | 3-F-4-i-PrO—Ph |
| Rr11 | 3-Cl-4-EtO—Ph |
| Rr12 | 3-Cl-4-PrO—Ph |
| Rr13 | 3-Cl-4-i-PrO—Ph |
| Rr14 | 3-Cl-4-s-BuO—Ph |
| Rr15 | 3-Br-4-i-PrO—Ph |
| Rr16 | 3-Me-4-i-PrO—Ph |
| Rr17 | 3-Me-4-Bu—Ph |
| Rr18 | 3-Cl-4-i-Bu—Ph |
| Rr19 | 3-Et-4-i-PrO—Ph |
| Rr20 | 3-Vinyl-4-i-PrO—Ph |

The combination of Rs, Rq and Rr, i.e., (Rs, Rq, Rr), is any one of the following combinations:
(Rs1,Rq1,Rr2),(Rs1,Rq1,Rr3),(Rs1,Rq1,Rr4),(Rs1,Rq1,Rr5),(Rs1,Rq1,Rr6),(Rs1,Rq1,Rr7),(Rs1,Rq1,Rr8),(Rs1,Rq1,Rr9),(Rs1,Rq1,Rr10),(Rs1,Rq1,Rr11),(Rs1,Rq1,Rr12),(Rs1,Rq1,Rr13),(Rs1,Rq1,Rr14),(Rs1,Rq1,Rr15),(Rs1,Rq1,Rr16),(Rs1,Rq1,Rr17),(Rs1,Rq1,Rr18),(Rs1,Rq1,Rr19),(Rs1,Rq1,Rr20),(Rs1,Rq2,Rr1),(Rs1,Rq2,Rr2),(Rs1,Rq2,Rr3),(Rs1,Rq2,Rr4),(Rs1,Rq2,Rr5),(Rs1,Rq2,Rr6),(Rs1,Rq2,Rr7),(Rs1,Rq2,Rr8),(Rs1,Rq2,Rr9),(Rs1,Rq2,Rr10),(Rs1,Rq2,Rr11),(Rs1,Rq2,Rr12),(Rs1,Rq2,Rr13),(Rs1,Rq2,Rr14),(Rs1,Rq2,Rr15),(Rs1,Rq2,Rr16),(Rs1,Rq2,Rr17),(Rs1,Rq2,Rr18),(Rs1,Rq2,Rr19),(Rs1,Rq2,Rr20),(Rs1,Rq3,Rr1),(Rs1,Rq3,Rr2),(Rs1,Rq3,Rr3),(Rs1,Rq3,Rr4),(Rs1,Rq3,Rr5),(Rs1,Rq3,Rr6),(Rs1,Rq3,Rr7),(Rs1,Rq3,Rr8),(Rs1,Rq3,Rr9),(Rs1,Rq3,Rr10),(Rs1,Rq3,Rr11),(Rs1,Rq3,Rr12),(Rs1,Rq3,Rr13),(Rs1,Rq3,Rr14),(Rs1,Rq3,Rr15),(Rs1,Rq3,Rr16),(Rs1,Rq3,Rr17),(Rs1,Rq3,Rr18),(Rs1,Rq3,Rr19),(Rs1,Rq3,Rr20),(Rs1,Rq1,Rr1),(Rs1,Rq4,Rr2),(Rs1,Rq4,Rr3),(Rs1,Rq4,Rr4),(Rs1,Rq4,Rr5),(Rs1,Rq4,Rr6),(Rs1,Rq4,Rr7),(Rs1,Rq4,Rr8),(Rs1,Rq4,Rr9),(Rs1,Rq4,Rr10),(Rs1,Rq4,Rr11),(Rs1,Rq4,Rr12),(Rs1,Rq4,Rr3),(Rs1,Rq4,Rr14),(Rs1,Rq4,Rr15),(Rs1,Rq4,Rr16),(Rs1,Rq4,Rr17),(Rs1,Rq4,Rr18),(Rs1,Rq1,Rr19),(Rs1,Rq4,Rr20),(Rs1,Rq5,Rr1),(Rs1,Rq5,Rr2),(Rs1,Rq5,Rr3),(Rs1,Rq5,Rr4),(Rs1,Rq5,Rr11),(Rs1,Rq5,Rr6),(Rs1,Rq5,Rr7),(Rs1,Rq5,Rr8),(Rs1,Rq5,Rr9),(Rs1,Rq5,Rr10),(Rs1,Rq5,Rr11),(Rs1,Rq5,Rr2),(Rs1,Rq5,Rr13),(Rs1,Rq5,Rr14),(Rs1,Rq5,Rr11,Rq5,Rr16),(Rs1,Rq5,Rr17),(Rs1,Rq5,Rr18),(Rs1,Rq5,Rr9),(Rs1,Rq5,Rr20),(Rs1,Rq6,Rr1),(Rs1,Rq6,Rr2),(Rs1,Rq6,Rr3),(Rs1,Rq6,Rr1),(Rs1,Rq6,Rr5),(Rs1,Rq6,Rr6),(Rs1,Rq6,Rr7),(Rs1,Rq6,Rr8),(Rs1,Rq6,Rr9),(Rs1,Rq6,Rr10),(Rs1,Rq6,Rr11),(Rs1,Rq6,Rr12),(Rs1,Rq6,Rr13),(Rs1,Rq6,Rr14),(Rs1,Rq6,Rr15),(Rs1,Rq6,Rr16),(Rs1,Rq6,Rr17),(Rs1,Rq6,Rr18),(Rs1,Rq6,Rr19),(Rs1,Rq6,Rr20),(Rs1,Rq7,Rr1), (Its 1,Rq7,Rr2),(Rs1,Rq7,Rr3),(Rs1,Rq7,Rr4),(Rs1,Rq7,Rr5),(Rs1,Rq7,Rr6),(Rs1,Rq7,Rr7),(Rs1,Rq7,Rr8),(Rs1,Rq7,Rr9),(Rs1,Rq7,Rr10),(Rs1,Rq7,Rr11),(Rs1,Rq7,Rr12),(Rs1,Rq7,Rr13),(Rs1,Rq7,Rr14),(Rs1,Rq7,Rr15),(Rs1,Rq7,Rr16),(Rs1,Rq7,Rr17),(Rs1,Rq7,Rr18),(Rs1,Rq7,Rr19),(Rs1,Rq7,Rr20),(Rs1,Rq8,Rr1),(Rs1,Rq8,Rr2),(Rs1,Rq8,Rr3),(Rs1,Rq8,Rr4),(Rs1,Rq8,Rr5),(Rs1,Rq8,Rr6),(Rs1,Rq8,Rr7),(Rs1,Rq8,Rr8),(Rs1,Rq8,Rr9),(Rs1,Rq8,Rr10),(Rs1,Rq8,Rr11),(Rs1,Rq8,Rr12),(Rs1,Rq8,Rr13),(Rs1,Rq8,Rr14),(Rs1,Rq8,Rr15),(Rs1,Rq8,Rr10,(Rs1,Rq8,Rr17),(Rs1,Rq8,Rr18),(Rs1,Rq8,Rr19),(Rs1,Rq8,Rr20),(Rs2,Rq8,Rr1),(Rs2,Rq1,Rr2),(Rs2,Rq1,Rr3),(Rs2,Rq1,Rr4),(Rs2,Rq1,Rr5),(Rs2,Rq1,Rr6),(Rs2,Rq1,Rr7),(Rs2,Rq1,Rr8),(Rs2,Rq1,Rr9),(Rs2,Rq1,Rr10),(Rs2,Rq1,Rr11),(Rs2,Rq1,Rr12),(Rs2,Rq1,Rr13),(Rs2,Rq1,Rr14),(Rs2,Rq1,Rr15),(Rs2,Rq1,Rr16), (1182,Rq1,Rr17),(Rs2,Rq1,Rr18),(Rs2,Rq1,Rr19),(Rs2,Rq1,Rr20),(Rs2,Rq2,Rr1),(Rs2,Rq2,Rr2),(Rs2,Rq2,Rr3),(Rs2,Rq2,Rr4),(Rs2, Rq2,Rr5),(Rs2,Rq2,Rr6),(Rs2,Rq2,Rr7),(Rs2,Rq2,Rr8), (Rs2,Rq2,Rr9),(Rs2,Rq2,Rr10),(Rs2,Rq2,Rr11),(Rs2,Rq2, Rr12),(Rs2,Rq2,Rr13),(Rs2,Rq2,Rr14),(Rs2,Rq2,Rr15), (Rs2,Rq2,Rr16),(Rs2,Rq2,Rr17),(Rs2,Rq2,Rr18),(Rs2,Rq2, Rr19),(Rs2,Rq2,Rr20),(Rs2,Rq3,Rr1),(Rs2,Rq3,Rr2),(Rs2, Rq3,Rr3),(Rs2,Rq3,Rr4),(Rs2,Rq3,Rr5),(Rs2,Rq3,Rr6), (Rs2,Rq3,Rr7),(Rs2,Rq3,Rr8),(Rs2,Rq3,Rr9),(Rs2,Rq3, Rr10),(Rs2,Rq3,Rr11),(Rs2,Rq3,Rr12),(Rs2,Rq3,Rr13), (Rs2,Rq3,Rr14),(Rs2,Rq3,Rr15),(Rs2,Rq3,Rr16),(Rs2,Rq3, Rr17),(Rs2,Rq3,Rr18),(Rs2,Rq3,Rr19),(Rs2,Rq3,Rr20), (Rs2,Rq4,Rr1),(Rs2,Rq4,Rr2),(Rs2,Rq4,Rr3),(Rs2,Rq4, Rr4),(Rs2,Rq4,Rr5),(Rs2,Rq4,Rr6),(Rs2,Rq4,Rr7),(Rs2, Rq4,Rr8),(Rs2,Rq1,Rr9),(Rs2,Rq4,Rr10),(Rs2,Rq4,Rr11), (Rs2,Rq4,Rr12),(Rs2,Rq1,Rr13),(Rs2,Rq4,Rr14),(Rs2,Rq4, Rr15),(Rs2,Rq4,Rr16),(Rs2,Rq4,Rr17),(Rs2,Rq1,Rr18), (Rs2,Rq4,Rr19),(Rs2,Rq4,Rr20),(Rs2,Rq5,Rr1),(Rs2,Rq5, Rr2),(Rs2, Rq5,Rr3),(Rs2,Rq5,Rr4),(Rs2,Rq5,Rr5),(Rs2, Rq5,Rr6),Rs2,Rq5,Rr7),(Rs2,Rq5,Rr8),(Rs2,Rq5,Rr9), (Rs2,Rq5,Rr10),(Rs2,Rq5,Rr11),(Rs2,Rq5,Rr12),(Rs2,Rq5, Rr13),(Rs2,Rq5,Rr14),(Rs2,Rq5,Rr15),(Rs2,Rq5,Rr16), (Rs2,Rq5,Rr17),(Rs2,Rq5,Rr18),(Rs2,Rq5,Rr19),(Rs2,Rq5, Rr20),(Rs2,Rq6,Rr1),(Rs2,Rq6,Rr2),(Rs2,Rq6,Rr3),(Rs2, Rq6,Rr4),(Rs2,Rq6,Rr5),(Rs2,Rq6,Rr6),(Rs2,Rq6,Rr7), (Rs2,Rq6,Rr8),(Rs2,Rq6,Rr9),(Rs2,Rq6,Rr10),(Rs2,Rq6, Rr11),(Rs2,Rq6,Rr12),(Rs2,Rq6,Rr13),(Rs2,Rq6,Rr14), (Rs2,Rq6,Rr15),(Rs2,Rq6,Rr16),(Rs2,Rq6,Rr17),(Rs2,Rq6, Rr18),(Rs2,Rq1,Rr19),(Rs2,Rq6,Rr20),(Rs2,Rq7,Rr1), (Rs2,Rq7,Rr2),(Rs2,Rq7,Rr3),(Rs2,Rq7,Rr4),(Rs2,Rq7, Rr5),(Rs2,Rq7,Rr6),(Rs2,Rq7,Rr7),(Rs2,Rq7,Rr8),(Rs2, Rq7,Rr9),(Rs2,Rq7,Rr10),(Rs2,Rq7,Rr11),(Rs2,Rq7,Rr12), (Rs2,Rq7,Rr13),(Rs2,Rq7,Rr14),(Rs2,Rq7,Rr15),(Rs2,Rq7, Rr16),(Rs2,Rq7,Rr17),(Rs2,Rq7,Rr18),(Rs2,Rq7,Rr19), (Rs2,Rq7,Rr20),(Rs2,Rq8,Rr1),(Rs2,Rq8,Rr2),(Rs2,Rq8, Rr3),(Rs2,Rq8,Rr4),(Rs2,Rq8,Rr5),(Rs2,Rq8,Rr6),(Rs2, Rq8,Rr7),(Rs2,Rq8,Rr8),(Rs2,Rq8,Rr9),(Rs2,Rq8,Rr10), (Rs2,Rq8,Rr11),(Rs2,Rq8,Rr12),(Rs2,Rq8,Rr13),(Rs2,Rq8, Rr14),(Rs2,Rq8,Rr15),(Rs2,Rq8,Rr16),(Rs2,Rq8,Rr17), (Rs2,Rq8,Rr18),(Rs2,Rq8,Rr19),(Rs2,Rq8,Rr20),(Rs3,Rq1, Rr1),(Rs3,Rq1,Rr2),(Rs3,Rq1,Rr3),(Rs3,Rq1,Rr4),Rs3, Rq1,Rr5),(Rs3,Rq1,Rr6),(Rs3,Rq1,Rr7),(Rs3,Rq1,Rr8), (Rs3,Rq1,Rr9),(Rs3,Rq1, Rr10),(Rs3,Rq1,Rr11),(Rs3,Rq1, Rr12),(Rs3,Rq1,Rr13),(Rs3,Rq1,Rr14),(Rs3,Rq1,Rr15), (Rs3,Rq1,Rr16),(Rs3,Rq1,Rr17),(Rs3,Rq1,Rr18),(Rs3,Rq1, Rr19),(Rs1,Rr20),(Rs3,Rq2,Rr1),(Rs3,Rq2,Rr2),(Rs3,Rq2, Rr3),(Rs3,Rq2,Rr4),(Rs3,Rq2,Rr5),(Rs3,Rq2,Rr6),(Rs3, Rq2,Rr7),(Rs3,Rq2,Rr8),(Rs3,Rq2,Rr9),(Rs3,Rq2,Rr10), (Rs3,Rq2,Rr11),(Rs3,Rq2,Rr12),(Rs3,Rq2, Rr13),(Rs3, Rq2,Rr14),(Rs3,Rq2,Rr15),(Rs3,Rq2,Rr16),(Rs3,Rq2, Rr17),(Rs3,Rq2,Rr18),(Rs3,Rq2,Rr19),(Rs3,Rq2,Rr20), (Rs3,Rq3,Rr1),(Rs3,Rq3,Rr2),(Rs3,Rq3,Rr3),(Rs3,Rq3, Rr4),(Rs3,Rq3,Rr5),(Rs3,Rq3,Rr6),(Rs3,Rq3,Rr7),(Rs3, Rq3,Rr8),(Rs3,Rq3,Rr9),(Rs3,Rq3,Rr10),(Rs3,Rq3,Rr11), (Rs3,Rq3,Rr12),(Rs3,Rq3,Rr13),(Rs3,Rq3,Rr14),(Rs3,Rq3, Rr15),(Rs3,Rq3,Rr16),(Rs3,Rq3,Rr17),(Rs3,Rq3,Rr18), (Rs3,Rq3,Rr19),(Rs3,Rq3,Rr20),(Rs3,Rq4,Rr1),(Rs3,Rq4, Rr2),(Rs3,Rq4,Rr3),(Rs3,Rq4,Rr4),(Rs3,Rq4,Rr5),(Rs3, Rq4,Rr6),(Rs3,Rq4,Rr7),(Rs3,Rq4,Rr8),(Rs3,Rq4,Rr9), (Rs3,Rq4,Rr10),(Rs3,Rq4,Rr11),(Rs3,Rq4, Rr12),(Rs3, Rq4,Rr13),(Rs3,Rq4, Rr14),(Rs3,Rq4,Rr15),(Rs3,Rq4, Rr16),(Rs3,Rq4,Rr17),(Rs3,Rq4,Rr18),(Rs3,Rq4,Rr19), (Rs3,Rq4,Rr20),(Rs3,Rq5,Rr1),(Rs3,Rq5,Rr2),(Rs3,Rq5, Rr3),(Rs3,Rq5,Rr4),(Rs3,Rq5,Rr5),(Rs3,Rq5,Rr6),(Rs3, Rq5,Rr7),(Rs3,Rq5,Rr8),(Rs3,Rq5,Rr9),(Rs3,Rq5,Rr10), (Rs3,Rq5,Rr11),(Rs3,Rq5,Rr12),(Rs3,Rq5,Rr13),(Rs3,Rq5, Rr14),(Rs3,Rq5,Rr15),(Rs3,Rq5,Rr16),(Rs3,Rq5,Rr17), (Rs3,Rq5,Rr18),(Rs3,Rq5,Rr19),(Rs3,Rq5,Rr20),(Rs3,Rq6, Rr1),(Rs3,Rq6,Rr2),(Rs3,Rq6,Rr3),(Rs3,Rq6,Rr4),(Rs3, Rq6,Rr5),(Rs3,Rq6,Rr6),(Rs3,Rq6, Rr7),(Rs3,Rq6,Rr8), (Rs3,Rq6,Rr9),(Rs3,Rq6,Rr10),(Rs3,Rq6,Rr11),(Rs3,Rq6, Rr2),(Rs3,Rq6,Rr13),(Rs3,Rq6,Rr14),(Rs3,Rq6,Rr15), (Rs3,Rq6,Rr16),(Rs3,Rq6,Rr17),(Rs3,Rq6,Rr18),(Rs3,Rq6, Rr19),(Rs3,Rq6,Rr20),(Rs3,Rq7,Rr1),(Rs3,Rq7,Rr2),(Rs3, Rq7,Rr3),(Rs3,Rq7,Rr4),(Rs3,Rq7,Rr5),(Rs3,Rq7,Rr6), (Rs3,Rq7,Rr7),Rs3,Rq7,Rr8),(Rs3,Rq7,Rr9),(Rs3,Rq7, Rr10),(Rs3,Rq7,Rr11),(Rs3,Rq7,Rr2),(Rs3,Rq7,Rr13), (Rs3,Rq7,Rr14),(Rs3,Rq7,Rr15),(Rs3,Rq7,Rr16),(Rs3,Rq7, Rr17),(Rs3,Rq7,Rr18),(Rs3,Rq7,Rr19),(Rs3,Rq7,Rr20), (Rs3,Rq8,Rr1),(Rs3,Rq8,Rr2),(Rs3,Rq8,Rr3),(Rs3,Rq8, Rr4),(Rs3,Rq8,Rr5),(Rs3,Rq8,Rr6),(Rs3,Rq8,Rr7),(Rs3, Rq8,Rr8),(Rs3,Rq8,Rr9),(Rs3,Rq8,Rr10),(Rs3,Rq8,Rr11), (Rs3,Rq8,Rr12),(Rs3,Rq8,Rr13),(Rs3,Rq8,Rr14),(Rs3,Rq8, Rr15),(Rs3,Rq8,Rr16),(Rs3,Rq8,Rr17),(Rs3,Rq8,Rr18), (Rs3,Rq8,Rr19),(Rs3,Rq8,Rr20),(Rs4,Rq1,Rr1),(Rs4,Rq1, Rr2),(Rs4,Rq1,Rr3),(Rs4,Rq1,Rr4),(Rs4,Rq1,Rr5),(Rs4, Rq1,Rr6),(Rs4,Rq1,Rr7),(Rs4,Rq1,Rr8),(Rs4,Rq1,Rr9), (Rs4,Rq1,Rr10),(Rs4,Rq1,Rr11),(Rs4,Rq1,Rr12),(Rs4,Rq1, Rr13),(Rs4,Rq1,Rr14),(Rs4,Rq1,Rr15),(Rs4,Rq1,Rr16), (Rs4,Rq1,Rr17),(Rs4,Rq1,Rr18),(Rs4,Rq1,Rr19),(Rs4,Rq1, Rr20),(Rs4, Rq2,Rr1),(Rs4,Rq2,Rr2),(Rs4,Rq2,Rr3),(Rs4, Rq2,Rr4),(Rs4,Rq2,Rr5),(Rs4,Rq2,Rr6),(Rs4,Rq2,Rr7), (Rs1,Rq2,Rr8),(Rs4,Rq2,Rr9),(Rs4,Rq2,Rr10),(Rs4,Rq2, Rr11),(Rs4,Rq2,Rr12),(Rs4,Rq2,Rr13),(Rs4,Rq2,Rr14), (Rs4,Rq2,Rr15),(Rs4,Rq2,Rr16),(Rs4,Rq2,Rr17),(Rs1,Rq2, Rr18),(Rs4,Rq2,Rr19),(Rs4,Rq2,Rr20),(Rs4,Rq3,Rr1), (Rs4,Rq3,Rr2),(Rs4,Rq3,Rr3),(Rs4,Rq3,Rr4),(Rs4,Rq3, Rr5),(Rs4,Rq3,Rr6),(Rs4,Rq3,Rr7),(Rs4,Rq3,Rr8),(Rs4, Rq3,Rr9),(Rs4,Rq3,Rr10),(Rs4,Rq3,Rr11),(Rs4,Rq3,Rr12), (Rs4,Rq3,Rr13),(Rs4,Rq3,Rr14),(Rs4,Rq3,Rr15),(Rs4,Rq3, Rr16),(Rs4,Rq3,Rr17),(Rs1,Rq3,Rr18),(Rs4,Rq3,Rr19), (Rs4,Rq3,Rr20),(Rs4,Rq4,Rr1),(Rs4,Rq1,Rr2),(Rs4,Rq4, Rr3),(Rs4,Rq4,Rr4),(Rs4,Rq4,Rr5),(Rs4,Rq4,Rr6),(Rs4, Rq4,Rr7),(Rs1,Rq4,Rr8),(Rs4,Rq4,Rr9),(Rs1,Rq4,Rr10), (Rs4,Rq4,Rr11),(Rs4,Rq4,Rr12),(Rs4,Rq4,Rr13),(Rs4,Rq4, Rr14),(Rs4,Rq4,Rr15),(Rs4,Rq4,Rr16),(Rs1,Rq4,Rr17), (Rs4,Rq4,Rr18),(Rs4,Rq4,Rr19),(Rs4,Rq4,Rr20),(Rs4,Rq5, Rr1),(Rs4,Rq5,Rr2),(Rs4,Rq5,Rr3),(Rs4,Rq5,Rr4),(Rs4, Rq5,Rr5),(Rs4,Rq5,Rr6),(Rs4,Rq5,Rr7),(Rs4,Rq5,Rr8), (Rs4,Rq5,Rr9),(Rs4,Rq5,Rr10),(Rs4,Rq5,Rr11),(Rs4,Rq5, Rr12),(Rs4,Rq5,Rr13),(Rs1,Rq5,Rr14),(Rs4,Rq5,Rr15), (Rs4,Rq5,Rr16),(Rs4,Rq5,Rr17),(Rs4,Rq5,Rr18),(Rs4,Rq5, Rr19),(Rs4,Rq5,Rr20),(Rs1,Rq6,Rr1),(Rs4,Rq6,Rr2),(Rs4, Rq6,Rr3),(Rs4,Rq6,Rr4),(Rs4,Rq6,Rr5),(Rs4,Rq6,Rr6), (Rs4,Rq6,Rr7),(Rs1,Rq6,Rr8),(Rs4,Rq6,Rr9),(Rs4,Rq6, Rr10),(Rs4,Rq6,Rr11),(Rs4,Rq6,Rr12),(Rs4,Rq6,Rr13), (Rs4,Rq6,Rr14),(Rs4,Rq6,Rr15),(Rs4,Rq6,Rr16),(Rs4,Rq6, Rr17),(Rs4,Rq6,Rr18),(Rs4,Rq6,Rr19),(Rs4,Rq6,Rr20), (Rs4,Rq7,Rr1),(Rs4,Rq7,Rr2),(Rs4,Rq7,Rr3),(Rs4,Rq7, Rr4),(Rs4,Rq7,Rr5),(Rs4,Rq7,Rr6),(Rs4,Rq7,Rr7),(Rs4, Rq7,Rr8),(Rs4,Rq7,Rr9),(Rs4,Rq7,Rr10),(Rs4,Rq7,Rr11), (Rs6,Rq7,Rr12),(Rs4,Rq7,Rr13),(Rs4,Rq7,Rr14),(Rs4,Rq7, Rr15),(Rs4,Rq7,Rr16),(Rs4,Rq7,Rr17),(Rs4,Rq7,Rr18), (Rs4,Rq7,Rr19),(Rs4,Rq7,Rr20),(Rs4,Rq8,Rr1),(Rs4,Rq8, Rr2),(Rs4,Rq8,Rr3),(Rs4,Rq8,Rr4),(Rs4,Rq8,Rr5),(Rs4, Rq8,Rr6),(Rs4,Rq8,Rr7),(Rs4,Rq8,Rr8),(Rs4,Rq8,Rr9), (Rs4,Rq8,Rr10),(Rs4,Rq8,Rr11),(Rs4,Rq8,Rr12),(Rs4,Rq8, Rr13),(Rs4,Rq8,Rr14),(Rs4,Rq8,Rr15),(Rs4,Rq8,Rr16), (Rs4,Rq8,Rr17),(Rs4,Rq8,Rr18),(Rs4,Rq8,Rr19),(Rs4,Rq8, Rr20),(Rs5,Rq1,Rr1),(Rs5,Rq1,Rr2),(Rs5,Rq1,Rr3),(Rs5, Rq1,Rr4),(Rs5,Rq1,Rr5),(Rs5,Rq1,Rr6),(Rs5,Rq1,Rr7), (Rs5,Rq1,Rr8),(Rs5,Rq1,Rr9),(Rs5,Rq1,Rr10),(Rs5,Rq1, Rr11),(Rs5,Rq3,Rr12),(Rs5,Rq1,Rr13),(Rs5,Rq1,Rr14), (Rs5,Rq1,Rr15),(Rs5,Rq1,Rr16),(Rs5,Rq1,Rr17),(Rs5,Rq1, Rr18),(Rs5,Rq1,Rr19),(Rs5,Rq1,Rr20),(Rs5,Rq2,Rr1), (Rs5,Rq2,Rr2),(Rs5,Rq2,Rr3),(Rs5,Rq2,Rr4),(Rs5,Rq2, Rr5),(Rs5,Rq2,Rr6),(Rs5,Rq2,Rr7),(Rs5,Rq2,Rr8),(Rs5,Rq2,Rr9),(Rs5,Rq2,Rr10),(Rs5,Rq2,Rr11),(Rs5,Rq2,Rr12),(Rs5,Rq2,Rr13),(Rs5,Rq2,Rr14),(Rs5,Rq2,Rr15),(Rs5,Rq2,Rr16),(Rs5,Rq2,Rr17),(Rs5,Rq2,Rr18),(Rs5,Rq2,Rr19),(Rs5,Rq2,Rr20),(Rs5,Rq3,Rr1),(Rs5,Rq3,Rr2),(Rs5,Rq3,Rr3),(Rs5,Rq3,Rr4),(Rs5,Rq3,Rr5),(Rs5,Rq3,Rr6),(Rs5,Rq3,Rr7),(Rs5,Rq3,Rr8),(Rs5,Rq3,Rr9),(Rs5,Rq3,Rr10),(Rs5,Rq3,Rr11),(Rs5,Rq3,Rr12),(Rs5,Rq3,Rr13),(Rs5,Rq3,Rr14),(Rs5,Rq3,Rr15),(Rs5,Rq3,Rr16),(Rs5,Rq3,Rr17),(Rs5,Rq3,Rr18),(Rs5,Rq3,Rr19),(Rs5,Rq3,Rr20),(Rs5,Rq4,Rr1),(Rs5,Rq4,Rr2),(Rs5,Rq4,Rr3),(Rs5,Rq4,Rr4),(Rs5,Rq4,Rr5),(Rs5,Rq4,Rr6),(Rs5,Rq4,Rr7),(Rs5,Rq4,Rr8),(Rs5,Rq4,Rr9),(Rs5,Rq4,Rr10),(Rs5,Rq4,Rr11),(Rs5,Rq4,Rr12),(Rs5,Rq4,Rr13),(Rs5,Rq4,Rr14),(Rs5,Rq4,Rr15),(Rs5,Rq4,Rr16),(Rs5,Rq4,Rr17),(Rs5,Rq4,Rr18),(Rs5,Rs4,Rr19),(Rs5,Rq4,Rr20),(Rs5,Rq5,Rr1),(Rs5,Rq5,Rr2),(Rs5,Rq5,Rr3),(Rs5,Rq5,Rr4),(Rs5,Rq5,Rr5),(Rs5,Rq5,Rr6),(Rs5,Rq5,Rr7),(Rs5,Rq5,Rr8),(Rs5,Rq5,Rr9),(Rs5,Rq5,Rr10),(Rs5,Rq5,Rr11),(Rs5,Rq5,Rr12),(Rs5,Rq5,Rr13),(Rs5,Rq5,Rr14),(Rs5,Rq5,Rr15),(Rs5,Rq5,Rr16),(Rs5,Rq5,Rr17),(Rs5,Rq5,Rr18),(Rs5,Rq5,Rr19),(Rs5,Rq5,Rr20),(Rs5,Rq6,Rr1),(Rs5,Rq6,Rr2),(Rs5,Rq6,Rr3),(Rs5,Rq6,Rr4),(Rs5,Rq6,Rr5),(Rs5,Rq6,Rr6),(Rs5,Rq6,Rr7),(Rs5,Rq6,Rr8),(Rs5,Rq6,Rr9),(Rs5,Rq6,Rr10),(Rs5,Rq6,Rr11),(Rs5,Rq6,Rr12),(Rs5,Rq6,Rr13),(Rs5,Rq6,Rr14),(Rs5,Rq6,Rr15),(Rs5,Rq6,Rr16),(Rs5,Rq6,Rr17),(Rs5,Rq6,Rr18),(Rs5,Rq6,Rr19),(Rs5,Rq6,Rr20),(Rs5,Rq7,Rr1),(Rs5,Rq7,Rr2),(Rs5,Rq7,Rr3),(Rs5,Rq7,Rr4),(Rs5,Rq7,Rr5),(Rs5,Rq7,Rr6),(Rs5,Rq7,Rr7),(Rs5,Rq7,Rr8),(Rs5,Rq7,Rr9),(Rs5,Rq7,Rr10),(Rs5,Rq7,Rr11),(Rs5,Rq7,Rr12),(Rs5,Rq7,Rr13),(Rs5,Rq7,Rr14),(Rs5,Rq7,Rr15),(Rs5,Rq7,Rr16),(Rs5,Rq7,Rr17),(Rs5,Rq7,Rr18),(Rs5,Rq7,Rr19),(Rs5,Rq7,Rr20),(Rs5,Rq8,Rr1),(Rs5,Rq8,Rr2),(Rs5,Rq8,Rr3),(Rs5,Rq8,Rr4),(Rs5,Rq8,Rr5),(Rs5,Rq8,Rr6),(Rs5,Rq8,Rr7),(Rs5,Rq8,Rr8),(Rs5,Rq8,Rr9),(Rs5,Rq8,Rr10),(Rs5,Rq8,Rr11),(Rs5,Rq8,Rr12),(Rs5,Rq8,Rr13),(Rs5,Rq8,Rr14),(Rs5,Rq8,Rr15),(Rs5,Rq8,Rr16),(Rs5,Rq8,Rr17),(Rs5,Rq8,Rr18),(Rs5,Rq8,Rr19),(Rs5,Rq8,Rr20),(Rs6,Rq1,Rr1),(Rs6,Rq1,Rr2),(Rs6,Rq1,Rr3),(Rs6,Rq1,Rr4),(Rs6,Rq1,Rr5),(Rs6,Rq1,Rr6),(Rs6,Rq1,Rr7),(Rs6,Rq1,Rr8),(Rs6,Rq1,Rr9),(Rs6,Rq1,Rr10),(Rs6,Rq1,Rr11),(Rs6,Rq1,Rr12),(Rs6,Rq1,Rr13),(Rs6,Rq1,Rr14),(Rs6,Rq1,Rr15),(Rs6,Rq1,Rr16),(Rs6,Rq1,Rr17),(Rs6,Rq1,Rr18),(Rs6,Rq1,Rr19),(Rs6,Rq1,Rr20),(Rs6,Rq2,Rr1),(Rs6,Rq2,Rr2),(Rs6,Rq2,Rr3),(Rs6,Rq2,Rr4),(Rs6,Rq2,Rr5),(Rs6,Rq2,Rr6),(Rs6,Rq2,Rr7),(Rs6,Rq2,Rr8),(Rs6,Rq2,Rr9),(Rs6,Rq2,Rr10),(Rs6,Rq2,Rr11),(Rs6,Rq2,Rr12),(Rs6,Rq2,Rr13),(Rs6,Rq2,Rr14),(Rs3,Rq2,Rr15),(Rs6,Rq2,Rr16),(Rs6,Rq2,Rr17),(Rs6,Rq2,Rr18),(Rs6,Rq2,Rr19),(Rs6,Rq2,Rr20),(Rs6,Rq3,Rr1),(Rs6,Rq3,Rr2),(Rs6,Rq3,Rr3),(Rs6,Rq3,Rr4),(Rs6,Rq3,Rr5),(Rs6,Rq3,Rr6),(Rs6,Rq3,Rr7),(Rs6,Rq3,Rr8),(Rs6,Rq3,Rr9),(Rs6,Rq3,Rr10),(Rs6,Rq3,Rr11),(Rs6,Rq3,Rr12),(Rs6,Rq3,Rr13),(Rs6,Rq3,Rr14),(Rs6,Rq3,Rr15),(Rs6,Rq3,Rr16),(Rs6,Rq3,Rr17),(Rs6,Rq3,Rr18),(Rs6,Rq3,Rr19),(Rs6,Rq3,Rr20),(Rs6,Rq4,Rr1),(Rs6,Rq4,Rr2),(Rs6,Rq4,Rr3),(Rs6,Rq4,Rr4),(Rs6,Rq4,Rr5),(Rs6,Rq4,Rr6),(Rs6,Rq4,Rr7),(Rs6,Rq4,Rr8),(Rs6,Rq4,Rr9),(Rs6,Rq4,Rr10),(Rs6,Rq4,Rr11),(Rs6,Rq4,Rr12),(Rs6,Rq4,Rr13),(Rs6,Rq4,Rr14),(Rs6,Rq4,Rr15),(Rs6,Rq4,Rr16),(Rs6,Rq4,Rr17),(Rs6,Rq4,Rr18),(Rs6,Rq4,Rr19),(Rs6,Rq4,Rr20),(Rs6,Rq5,Rr1),(Rs6,Rq5,Rr2),(Rs6,Rq5,Rr3),(Rs6,Rq5,Rr4),(Rs6,Rq5,Rr5),(Rs6,Rq5,Rr6),(Rs6,Rq5,Rr7),(Rs6,Rq5,Rr8),(Rs6,Rq5,Rr9),(Rs6,Rq5,Rr10),(Rs6,Rq5,Rr11),(Rs6,Rq5,Rr12),(Rs6,Rq5,Rr13),(Rs6,Rq5,Rr14),(Rs6,Rq5,Rr15),(Rs6,Rq5,Rr16),(Rs6,Rq5,Rr17),(Rs6,Rq5,Rr18),(Rs6,Rq5,Rr19),(Rs6,Rq5,Rr20),(Rs6,Rq6,Rr1),(Rs6,Rq6,Rr2),(Rs6,Rq6,Rr3),(Rs6,Rq6,Rr4),(Rs6,Rq6,Rr5),(Rs6,Rq6,Rr6),(Rs6,Rq6,Rr7),(Rs6,Rq6,Rr8),(Rs6,Rq6,Rr9),(Rs6,Rq6,Rr10),(Rs6,Rq6,Rr11),(Rs6,Rq6,Rr12),(Rs6,Rq6,Rr13),(Rs6,Rq6,Rr14),(Rs6,Rq6,Rr15),(Rs6,Rq6,Rr16),(Rs6,Rq6,Rr17),(Rs3,Rq6,Rr18),(Rs6,Rq6,Rr19),(Rs6,Rq6,Rr20),(Rs6,Rq7,Rr1),(Rs6,Rq7,Rr2),(Rs6,Rq7,Rr3),(Rs6,Rq7,Rr4),(Rs6,Rq7,Rr5),(Rs6,Rq7,Rr6),(Rs6,Rq7,Rr7),(Rs6,Rq7,Rr8),(Rs3,Rq7,Rr9),(Rs6,Rq7,Rr10),(Rs6,Rq7,Rr11),(Rs6,Rq7,Rr12),(Rs6,Rq7,Rr13),(Rs6,Rq7,Rr14),(Rs6,Rq7,Rr15),(Rs6,Rq7,Rr16),(Rs6,Rq7,Rr17),(Rs6,Rq7,Rr18),(Rs6,Rq7,Rr19),(Rs6,Rq7,Rr20),(Rs6,Rq8,Rs1),(Rs6,Rq8,Rr2),(Rs6,Rq8,Rr3),(Rs6,Rq8,Rr4),(Rs6,Rq8,Rr5),(Rs6,Rq8,Rr8),(Rs6,Rq8,Rr7),(Rs6,Rq8,Rr8),(Rs6,Rq8,Rr9),(Rs6,Rq8,Rr10),(Rs6,Rq8,Rr11),(Rs6,Rq8,Rr12),(Rs6,Rq8,Rr13),(Rs6,Rq8,Rr14),(Rs6,Rq8,Rr15),(Rs6,Rq8,Rr16),(Rs6,Rq8,Rr7),(Rs6,Rq8,Rr18),(Rs6,Rq8,Rr19),(Rs6,Rq8,Rr20),(Rs7,Rq1,Rr1),(Rs7,Rq1,Rr2),(Rs7,Rq1,Rr3),(Rs7,Rq1,Rr4),(Rs7,Rq1,Rr5),(Rs7,Rq1,Rr6),(Rs7,Rq1,Rr7),(Rs7,Rq1,Rr8),(Rs7,Rq1,Rr9),(Rs7,Rq1,Rr10),(Rs7,Rq1,Rr11),(Rs7,Rq1,Rr12),(Rs7,Rq1,Rr3),(Rs7,Rq1,Rr14),(Rs7,Rq1,Rr15),(Rs7,Rq1,Rr16),(Rs7,Rq1,Rr7),(Rs7,Rq1,Rr18),(Rs7,Rq1,Rr19),(Rs7,Rq1,Rr20),(Rs7,Rq2,Rr1),(Rs7,Rq2,Rr2),(Rs7,Rq2,Rr3),(Rs7,Rq2,Rr4),(Rs7,Rq2,Rr5),(Rs7,Rq2,Rr6),(Rs7,Rq2,Rr7),(Rs7,Rq2,Rr8),(Rs7,Rq2,Rr9),(Rs7,Rq2,Rr10),(Rs7,Rq2,Rr11),(Rs7,Rq2,Rr12),(Rs7,Rq2,Rr13),(Rs7,Rq2,Rr1),(Rs7,Rq2,Rr15),(Rs7,Rq2,Rr16),(Rs7,Rq2,Rr17),(Rs7,Rq2,Rr18),(Rs7,Rq2,Rr19),(Rs7,Rq2,Rr20),(Rs7,Rq3,Rr1),(Rs7,Rq3,Rr2),(Rs7,Rq3,Rr3),(Rs7,Rq3,Rr4),(Rs7,Rq3,Rr5),(Rs7,Rq3,Rr6),(Rs7,Rq3,Rr7),(Rs7,Rq3,Rr8),(Rs7,Rq3,Rr9),(Rs7,Rq3,Rr10),(Rs7,Rq3,Rr11),(Rs7,Rq3,Rr12),(Rs7,Rq3,Rr13),(Rs7,Rq3,Rr14),(Rs7,Rq3,Rr15),(Rs7,Rq3,Rr16),(Rs7,Rq3,Rr17),(Rs7,Rq3,Rr18),(Rs7,Rq3,Rr19),(Rs7,Rq3,Rr20),(Rs7,Rq4,Rr1),(Rs7,Rq4,Rr2),(Rs7,Rq4,Rr3),(Rs7,Rq4,Rr4),(Rs7,Rq4,Rr5),(Rs7,Rq4,Rr6),(Rs7,Rq4,Rr7),(Rs7,Rq4,Rr8),(Rs7,Rq4,Rr9),(Rs7,Rq4,Rr10),(Rs7,Rq4,Rr11),(Rs7,Rq4,Rr12),(Rs7,Rq4,Rr13),(Rs7,Rq4,Rr14),(Rs7,Rq4,Rr15),(Rs7,Rq4,Rr16),(Rs7,Rq4,Rr17),(Rs7,Rq4,Rr18),(Rs7,Rq4,Rr19),(Rs7,Rq4,Rr20),(Rs7,Rq5,Rr1),(Rs7,Rq5,Rr2),(Rs7,Rq5,Rr3),(Rs7,Rq5,Rr4),(Rs7,Rq5,Rr5),(Rs7,Rq5,Rr6),(Rs7,Rq5,Rr7),(Rs7,Rq5,Rr8),(Rs7,Rq5,Rr9),(Rs7,Rq5,Rr10),(Rs7,Rq5,Rr11),(Rs7,Rq5,Rr12),(Rs7,Rq5,Rr13),(Rs7,Rq5,Rr14),(Rs7,Rq5,Rr15),(Rs7,Rq5,Rr16),(Rs7,Rq5,Rr17),(Rs7,Rq5,Rr18),(Rs7,Rq5,Rr19),(Rs7,Rq5,Rr20),(Rs7,Rq6,Rr1),(Rs7,Rq6,Rr2),(Rs7,Rq6,Rr3),(Rs7,Rq6,Rr4),(Rs7,Rq6,Rr5),(Rs7,Rq6,Rr6),(Rs7,Rq6,Rr7),(Rs7,Rq6,Rr8),(Rs7,Rq6,Rr9),(Rs7,Rq6,Rr10),(Rs7,Rq6,Rr11),(Rs7,Rq6,Rr12),(Rs7,Rq6,Rr13),(Rs7,Rq6,Rr14),(Rs7,Rq6,Rr15),(Rs7,Rq6,Rr16),(Rs7,Rq6,Rr17),(Rs7,Rq6,Rr18),(Rs7,Rq6,Rr19),(Rs7,Rq6,Rr20),(Rs7,Rq7,Rr1),(Rs7,Rq7,Rr2),(Rs7,Rq7,Rr3),(Rs7,Rq7,Rr4),(Rs7,Rq7,Rr5),(Rs7,Rq7,Rr6),(Rs7,Rq7,Rr7),(Rs7,Rq7,Rr8),(Rs7,Rq7,Rr9),(Rs7,Rq7,Rr10),(Rs7,Rq7,Rr11),(Rs7,Rq7,Rr12),(Rs7,Rq7,Rr13),(Rs7,Rq7,Rr14),(Rs7,Rq7,Rr15),(Rs7,Rq7,Rr16),(Rs7,Rq7,Rr7),(Rs7,Rq7,Rr18),(Rs7,Rq7,Rr19),(Rs7,Rq7,Rr20),(Rs7,Rq8,Rr1),(Rs7,Rq8,Rr2),(Rs7,Rq8,Rr3),(Rs7,Rq8,Rr4),(Rs7,Rq8,Rr5),(Rs7,Rq8,Rr6),(Rs7,Rq8,Rr7),(Rs7,Rq8,Rr8),(Rs7,Rq8,Rr9),(Rs7,Rq8,Rr10),(Rs7,Rq8,Rr11),(Rs7,Rq8,Rr12),(Rs7,Rq8,Rr13),(Rs7,Rq8,Rr14),(Rs7,Rq8,Rr15),(Rs7,Rq4,Rr16),(Rs7,Rq8,Rr17),(Rs7,Rq8,Rr18),(Rs7,Rq8,Rr19),(Rs7,Rq8,Rr20),(Rs8,Rq1,Rr1),(Rs8,Rq1,Rr2),(Rs8,Rq1,Rr3),(Rs8,Rq1,Rr4),(Rs8,Rq1,Rr5),(Rs8,Rq1,Rr6),(Rs8,Rq1,Rr7),(Rs8,Rq1,Rr8),(Rs8,Rq1,Rr9),(Rs8,Rq1,Rr10),(Rs8,Rq1,Rr11),(Rs8,Rq1,Rr12),(Rs8,Rq1,Rr13),(Rs8,Rq1,Rr14),(Rs8,Rq1,Rr15),(Rs8,Rq1,Rr16),(Rs8,Rq1,Rr17),(Rs8,Rq1,Rr18),(Rs8,Rq1,Rr19),(Rs8,Rq1,Rr20),(Rs8,Rq2,Rr1),(Rs8,Rq2,Rr2),(Rs8,Rq2,Rr3),(Rs8,Rq2,Rr4),(Rs8,Rq2,Rr5),(Rs8,Rq2,Rr6), (Rs8,Rq2,Rr7),(Rs8,Rq2,Rr8),(Rs8,Rq2,Rr9),(Rs8,Rq2,Rr10),(Rs8,Rq2,Rr11),(Rs8,Rq2,Rr12),(Rs8,Rq2,Rr13),(Rs8,Rq2,Rr14),(Rs8,Rq2,Rr15),(Rs8,Rq2,Rr18),(Rs8,Rq2,Rr17),(Rs8,Rq2,Rr18),(Rs8,Rq2,Rr19),(Rs8,Rq2,Rr20),(Rs8,Rq3,Rr1),(Rs8,Rq3,Rr2),(Rs8,Rq3,Rr3),(Rs8,Rq3,Rr4),(Rs8,Rq3,Rr5),(Rs8,Rq3,Rr6),(Rs8,Rq3,Rr7),(Rs8,Rq3,Rr8),(Rs8,Rq3,Rr9),(Rs8,Rq3,Rr10),(Rs8,Rq3,Rr11),(Rs8,Rq3,Rr1 (Rs8,Rq3,Rr13),(Rs8,Rq3,Rr14),(Rs8,Rq3,Rr15),(Rs8,Rq3,Rr16),(Rs8,Rq3,Rr17),(Rs8,Rq3,Rr18),(Rs8,Rq3,Rr19),(Rs8,Rq3,Rr20),(Rs8,Rq4,Rr1),(Rs8,Rq4,Rr2),(Rs8,Rq4,Rr3),(Rs8,Rq4,Rr4),(Rs8,Rq4,Rr5),(Rs8,Rq4,Rr6),(Rs8,Rq4,Rr7),(Rs8,Rq4,Rr8),(Rs8,Rq4,Rr9),(Rs8,Rq4,Rr10),(Rs8,Rq4,Rr11),(Rs8,Rq4,Rr12),(Rs8,Rq4,Rr13),(Rs8,Rq4,Rr14),(Rs8,Rq4,Rr15),(Rs8,Rq1,Rr16),(Rs8,Rq4,Rr17),(Rs8,Rq4,Rr18),(Rs8,Rq4,Rr19),(Rs8,Rq4,Rr20),(Rs8,Rq5,Rr1),(Rs8,Rq5,Rr2),(Rs8,Rq5,Rr3),(Rs8,Rq5,Rr4),(Rs8,Rq5,Rr5),(Rs8,Rq5,Rr6),(Rs8,Rq5,Rr7),(Rs8,Rq5,Rr8),(Rs8,Rq5,Rr9),(Rs8,Rq5,Rr10),(Rs8,Rq5,Rr11),(Rs8,Rq5,Rr12),(Rs8,Rq5,Rr13),(Rs8,Rq5,Rr14),(Rs8,Rq5,Rr15),(Rs8,Rq5,Rr16),(Rs8,Rq5,Rr17),(Rs8,Rq5,Rr18),(Rs8,Rq5,Rr19),(Rs8,Rq5,Rr20),(Rs8,Rq6,Rr1),(Rs8,Rq6,Rr2),(Rs8,Rq6,Rr3),(Rs8,Rq6,Rr4),(Rs8,Rq6,Rr5),(Rs8,Rq6,Rr6),(Rs8,Rq6,Rr7),(Rs8,Rq6,Rr8),(Rs8,Rq8,Rr9),(Rs8,Rq6,Rr10),(Rs8,Rq6,Rr11),(Rs8,Rq6,Rr12),(Rs8,Rq6,Rr13),(Rs8,Rq6,Rr14),(Rs8,Rq6,Rr15),(Rs8,Rq6,Rr16),(Rs8,Rq6,Rr17),(Rs8,Rq6,Rr18),(Rs8,Rq8,Rr19),(Rs8,Rq8,Rr20),(Rs8,Rq7,Rr1),(Rs8,Rq7,Rr2),(Rs8,Rq7,Rr3),(Rs8,Rq7,Rr4),(Rs8,Rq7,Rr5),(Rs8,Rq7,Rr6),(Rs8,Rq7,Rr7),(Rs8,Rq7,Rr8),(Rs8,Rq7,Rr9),(Rs8,Rq7,Rr10),(Rs8,Rq7,Rr11),(Rs8,Rq7,Rr12),(Rs8,Rq7,Rr13),(Rs8,Rq7,Rr14),(Rs8,Rq7,Rr15),(Rs8,Rq7,Rr16),(Rs8,Rq7,Rr17),(Rs8,Rq7,Rr18),(Rs8,Rq7,Rr19),(Rs8,Rq7,Rr20),(Rs8,Rq8,Rr1),(Rs8,Rq8,Rr2),(Rs8,Rq8,Rr3),(Rs8,Rq8,Rr4),(Rs8,Rq8,Rr5),(Rs8,Rq8,Rr6),(Rs8,Rq8,Rr7),(Rs8,Rq8,Rr8),(Rs8,Rq8,Rr9),(Rs8,Rq8,Rr10),(Rs8,Rq8,Rr11),(Rs8,Rq8,Rr12),(Rs8,Rq8,Rr13),(Rs8,Rq8,Rr14),(Rs8,Rq8,Rr15),(Rs8,Rq8,Rr16),(Rs8,Rq8,Rr17),(Rs8,Rq8,Rr18),(Rs8,Rq8,Rr19),(Rs8,Rq8,Rr20),(Rs9,Rq1,Rr1),(Rs9,Rq1,Rr2),(Rs9,Rq1,Rr3),(Rs9,Rq1,Rr4),(Rs9,Rq1,Rr5),(Rs9,Rq1,Rr6),(Rs9,Rq1,Rr7),(Rs9,Rq1,Rr8),(Rs9,Rq1,Rr9),(Rs9,Rq1,Rr10), (Rs9,Rq1,Rr11),(Rs9,Rq1,Rr12),(Rs9,Rq1,Rr13),(Rs9,Rq1,Rr14),(Rs9,Rq1,Rr15),(Rs9,Rq1,Rr16),(Rs9,Rq1,Rr17),(Rs9,Rq1,Rr18),(Rs9,Rq1,Rs19),(Rs9,Rq1,Rr20),(Rs9,Rq2,Rr1),(Rs9,Rq2,Rr2),(Rs9,Rq2,Rr3),(Rs9,Rq2,Rr4),(Rs9,Rq2,Rr5),(Rs9,Rq2,Rr6),(Rs9,Rq2,Rr7),(Rs9,Rq2,Rr8),(Rs9,Rq2,Rr9),(Rs9,Rq2,Rr10),(Rs9,Rq2,Rr11),(Rs9,Rq2,Rr12),(Rs9,Rq2,Rr13),(Rs9,Rq2,Rr14),(Rs9,Rq2,Rr15),(Rs9,Rq2,Rr16),(Rs9,Rq2,Rr17),(Rs9,Rq2,Rr18),(Rs9,Rq2,Rr19),(Rs9,Rq2,Rr20),(Rs9,Rq3,Rr1),(Rs9,Rq3,Rr2),(Rs9,Rq3,Rr3),(Rs9,Rq3,Rr4),(Rs9,Rq3,Rr5),(Rs9,Rq3,Rr6),(Rs9,Rq3,Rr7),(Rs9,Rq3,Rr8),(Rs9,Rq3,Rr9),(Rs9,Rq3,Rr10),(Rs9,Rq3,Rr11),(Rs9,Rq3,Rr12),(Rs9,Rq3,Rr13),(Rs9,Rq3,Rr14),(Rs9,Rq3,Rr15),(Rs9,Rq3,Rr16),(Rs9,Rq3,Rr17),(Rs9,Rq3,Rr18),(Rs9,Rq3,Rr19),(Rs9,Rq3,Rr20),(Rs9, Rq4,Rr1),(Rs9, Rq4,Rr2),(Rs9,Rq4,Rr3),(Rs9,Rq4,Rr4),(Rs9,Rq4,Rr5),(Rs9,Rq4,Rr6),(Rs9,Rq4 (Rs9,Rq4,Rr8),(Rs9,Rq4,Rr9),(Rs9,Rq4,Rr10),(Rs9,Rq4,Rr11),(Rs9,Rq4,Rr12),(Rs9,Rq4,Rr13),(Rs9,Rq4,Rr14),(Rs9,Rq4,Rr15),(Rs9,Rq4,Rr16),(Rs9,Rq4,Rr17),(Rs9,Rq4,Rr18),(Rs9,Rq4,Rr19),(Rs9,Rq4,Rr20),(Rs9,Rq5,Rr1),(Rs9,Rq5,Rr2),(Rs9, Rq5,Rr3),(Rs9,Rq5,Rr4),(Rs9,Rq5,Rr5),(Rs9,Rq5,Rr6),(Rs9,Rq5,Rr7),(Rs9, Rq5,Rr8),(Rs9,Rq5,Rr9),(Rs9,Rq5,Rr10),(Rs9,Rq5,Rr11),(Rs9,Rq5,Rr12),(Rs9,Rq5,Rr13),(Rs9,Rq5,Rr14),(Rs9,Rq5,Rr15),(Rs9,Rq5,Rr16),(Rs9,Rq5,Rr17),(Rs9,Rq5,Rr18),(Rs9,Rq5,Rr19),(Rs9,Rq5,Rr20),(Rs9,Rq6,Rr1),(Rs9,Rq6,Rr2),(Rs9,Rq6,Rr3),(Rs9,Rq6,Rr4),(Rs9,Rq6,Rr5),(Rs9,Rq6,Rr6),(Rs9,Rq6,Rr7),(Rs9,Rq6,Rr8),(Rs9,Rq6,Rr9),(Rs9,Rq6,Rr10),(Rs9,Rq6,Rr11),(Rs9,Rq6,Rr12),(Rs9,Rq6,Rr13),(Rs9,Rq6,Rr14),(Rs9,Rq6,Rr15),(Rs9,Rq6,Rr16),(Rs9,Rq6,Rr17),(Rs9,Rq6,Rr18),(Rs9,Rq6,Rr9),(Rs9,Rq6,Rr20),(Rs9,Rq7,Rr1),(Rs9,Rq7,Rr2),(Rs9,Rq7,Rr3),(Rs9,Rq7,Rr4),(Rs9,Rq7,Rr5),(Rs9,Rq7,Rr8),(Rs9,Rq7,Rr7),(Rs9,Rq7,Rr8),(Rs9,Rq7,Rr9),(Rs9,Rq7,Rr10),(Rs9,Rq7,Rr11),(Rs9,Rq7,Rr12),(Rs9,Rq7,Rr13),(Rs9,Rq7,Rr14),(Rs9,Rq7,Rr15),(Rs9,Rq7,Rr16),(Rs9,Rq7,Rr17),(Rs9,Rq7,Rr18),(Rs9,Rq7,Rr19),(Rs9,Rq7,Rr20),(Rs9,Rq8,Rr1),(Rs9,Rq8,Rr2),(Rs9,Rq8,Rr3),(Rs9,Rq8,Rr4),(Rs9,Rq8,Rr5),(Rs9,Rq8,Rr6),(Rs9,Rq8,Rr7),(Rs9,Rq8,Rr8),(Rs9,Rq8,Rr9),(Rs9,Rq8,Rr10),(Rs9,Rq8,Rr1),(Rs9,Rq8,Rr12),(Rs9,Rq8,Rr13),(Rs9,Rq8,Rr14),(Rs9,Rq8,Rr15),(Rs9,Rq8,Rr16),(Rs9,Rq8,Rr17),(Rs9,Rq8,Rr18),(Rs9,Rq8,Rr19),(Rs9,Rq8,Rr20),(Rs1),(Rs10,Rq1,Rr1),(Rs10,Rq1,Rr2),(Rs10,Rq1,Rr3),(Rs10,Rq1,Rr4),(Rs10,Rq1,Rr5),(Rs10,Rq1,Rr6),(Rs10,Rq1,Rr7),(Rs10,Rq1,Rr8),(Rs10,Rq1,Rr9),(Rs10,Rq1,Rr10),(Rs10,Rq1,Rr11),(Rs10,Rq1,Rr12),(Rs10,Rq1,Rr13),(Rs10,Rq1,Rr14),(Rs10,Rq1,Rr15),(Rs10,Rq1,Rr16),(Rs10,Rq1,Rr17),(Rs10,Rq1,Rr18),(Rs10,Rq1,Rr19),(Rs10,Rq1,Rr20),(Rs10,Rq2,Rr1),(Rs10,Rq2,Rr2),(Rs10, Rq2,Rr3),(Rs10,Rq2,Rr4),(Rs10,Rq2,Rr5),(Rs10,Rq2,Rr6),(Rs10,Rq2,Rr7),(Rs10,Rq2,Rr8),(Rs10,Rq2,Rr9),(Rs10,Rq2,Rr10),(Rs10,Rq2,Rr11),(Rs10,Rq2,Rr12),(Rs10,Rq2,Rr13),(Rs10,Rq2,Rr14),(Rs10,Rq2,Rr15),(Rs10,Rq2,Rr16),(Rs10,Rq2,Rr17),(Rs10,Rq2,Rr18),(Rs10,Rq2,Rr19),(Rs10,Rq2,Rr20),(Rs10,Rq3,Rr1),(Rs10,Rq3,Rr2),(Rs10,Rq3,Rr3),(Rs10,Rq3,Rr4),(Rs10,Rq3,Rr5),(Rs10,Rq3,Rr6),(Rs10,Rq3,Rr7),(Rs10,Rq3,Rr8),(Rs10,Rq3,Rr9),(Rs10,Rq3,Rr10),(Rs10,Rq3,Rr1),(Rs10,Rq3,Rr12),(Rs10,Rq3,Rr13),(Rs10,Rq3,Rr14),(Rs10,Rq3,Rr15),(Rs10,Rq3,Rr16),(Rs10,Rq3,Rr17),(Rs10,Rq3,Rr18),(Rs10,Rq3,Rr19),(Rs10,Rq3,Rr20),(Rs10,Rq4,Rr1),(Rs10,Rq4,Rr2),(Rs10,Rq4,Rr3),(Rs10,Rq4,Rr4),(Rs10,Rq4,Rr5),(Rs10,Rq4,Rr6),(Rs10,Rq1,Rr7),(Rs10,Rq4,Rr8),(Rs10,Rq4, Rr9),(Rs10,Rq4,Rr10),(Rs10,Rq4,Rr11),(Rs10,Rq4,Rr12),(Rs10,Rq4,Rr13),(Rs10,Rq4,Rr14),(Rs10,Rq4,Rr15),(Rs10,Rq4,Rr16),(Rs10,Rq4,Rr17),(Rs10,Rq4,Rr18),(Rs10,Rq4,Rr19),(Rs10,Rq4,Rr20),(Rs10,Rq5,Rr1),(Rs10,Rq5,Rr2),(Rs10,Rq5,Rr3),(Rs10,Rq5,Rr4),(Rs10,Rq5,Rr5),(Rs10,Rq5,Rr6),(Rs10,Rq5,Rr7),(Rs10,Rq5,Rr8),(Rs10,Rq5,Rr9),(Rs10,Rq5,Rr10),(Rs10,Rq5,Rr11),(Rs10,Rq5,Rr12),(Rs10,Rq5,Rr13),(Rs10,Rq5,Rr14),(Rs10,Rq6,Rr15),(Rs10,Rq5,Rr16),(Rs10,Rq5,Rr17),(Rs10,Rq5,Rr18),(Rs10,Rq5,Rr19),(Rs10,Rq5,Rr20),(Rs10,Rq6,Rr1),(Rs10,Rq6,Rr2),(Rs10,Rq6,Rr3),(Rs10,Rq6,Rr4),(Rs10,Rq6,Rr5),(Rs10,Rq6,Rr6),(Rs10,Rq6,Rr7),(Rs10,Rq6,Rr7),(Rs10,Rq6,Rr8),(Rs10,Rq6,Rr9),(Rs10,Rq6,Rr10),(Rs10,Rq6,Rr11),(Rs10,Rq6,Rr12),(Rs10,Rq6,Rr13),(Rs10,Rq6,Rr14),(Rs10,Rq6,Rr15),(Rs10,Rq6,Rr16),(Rs10,Rq6,Rr17),(Rs10,Rq6,Rr18),(Rs10,Rq6,Rr19),(Rs10,Rq6,Rr20),(Rs10,Rq7,Rr1),(Rs10,Rq7,Rr2),(Rs10,Rq7,Rr3),(Rs10,Rq7,Rr4),(Rs10,Rq7,Rr5),(Rs10,Rq7,Rr6),(Rs10,Rq7,Rr7),(Rs10,Rq7,Rr8),(Rs10,Rq7,Rr9),(Rs10,Rq7,Rr10),(Rs10,Rq7,Rr11),(Rs10,Rq7,Rr12),(Rs10,Rq7,Rr13),(Rs10,Rq7,Rr14),(Rs10,Rq7,Rr15),(Rs10,Rq7,Rr16),(Rs10,Rq7,Rr17),(Rs10,Rq7,Rr18),(Rs10,Rq7,Rr19),(Rs10,Rq7,Rr20),(Rs10,Rq8,Rr1),(Rs10,Rq8,Rr2),(Rs10,Rq8,Rr3),(Rs10,Rq8,Rr4),(Rs10,Rq8,Rr5),(Rs10,Rq8,Rr6),(Rs10,Rq8,Rr7),(Rs10,Rq8,Rr8),(Rs10,Rq8,Rr9),(Rs10,Rq8,Rr10),(Rs10,Rq8,Rr11),(Rs10,Rq8,Rr12),(Rs10,Rq8,Rr13),(Rs10,Rq8,Rr14),(Rs10,Rq8,Rr15),(Rs10,Rq8,Rr16),(Rs10,Rq8,Rr17),(Rs10,Rq8,Rr18),(Rs10,Rq8,Rr19),(Rs10,Rq8,Rr20),(Rs11,Rq1,Rr1),(Rs11,Rq1,Rr2),(Rs11,Rq1,Rr3),(Rs11,Rq1,Rr4),(Rs11,Rq1,Rr6),(Rs11,Rq1,Rr6),(Rs11,Rq1,Rr7),(Rs11,Rq1,Rr8),(Rs11,Rq1,Rr9),(Rs11,Rq1,Rr10),(Rs11,Rq1,Rr11),(Rs11,Rq1,Rr12),(Rs11,Rq1, Rr13),(Rs11,Rq1,Rr14),(Rs11,Rq1,Rr15),(Rs11,Rq1,Rr16),
(Rs11,Rq1,Rr17),(Rs11,Rq1,Rr18),(Rs11,Rq1,Rr19),
(Rs11,Rq1,Rr20),(Rs11,Rq2,Rr1),(Rs11,Rq2,Rr2),(Rs11,
Rq2,Rr3),(Rs11,Rq2,Rr4),(Rs11,Rq2,Rr5),(Rs11,Rq2,Rr6),
(Rs11,Rq2,Rr7),(Rs11,Rq2,Rr8),(Rs11,Rq2,Rr9),(Rs11,
Rq2,Rr10),(Rs11,Rq2,Rr11),(Rs11,Rq2,Rr12),(Rs1,Rq2,
Rr13),(Rs11,Rq2,Rr14),(Rs11,Rq2,Rr15),(Rs11,Rq2,Rr16),
(Rs11,Rq2,Rr17),(Rs11,Rq2,Rr18),(Rs11,Rq2,Rr19),
(Rs11,Rq2,Rr20),(Rs11,Rq3,Rr1),(Rs11,Rq3,Rr2),(Rs11,
Rq3,Rr3),(Rs11,Rq3,Rr4),(Rs11,Rq3,Rr5),(Rs11,Rq3,Rr6),
(Rs11,Rq3,Rr7),(Rs11,Rq3,Rr8),(Rs11,Rq3,Rr9),(Rs11,
Rq3,Rr10),(Rs11,Rq3,Rr11),(Rs11,Rq3,Rr12),(Rs11,Rq3,
Rr13),(Rs11,Rq3,Rr14),(Rs11,Rq3,Rr15),(Rs11,Rq3,Rr16),
(Rs11,Rq3,Rr17),(Rs11,Rq3,Rr18),(Rs11,Rq3,Rr19),
(Rs11,Rq3,Rr20),(Rs11,Rq4,Rr1),(Rs11,Rq4,Rr2),(Rs11,
Rq4,Rr3),(Rs11,Rq4,Rr4),(Rs11,Rq4,Rr5),(Rs11,Rq4,Rr6),
(Rs11,Rq4,Rr7),(Rs11,Rq4,Rr8),(Rs11,Rq4,Rr9),(Rs11,
Rq4,Rr10),(Rs11,Rq4,Rr11),(Rs11,Rq4,Rr12),(Rs11,Rq4,
Rr13),(Rs11,Rq4,Rr14),(Rs11,Rq4,Rr15),(Rs11,Rq4,Rr16),
(Rs11,Rq4,Rr17),(Rs11,Rq4,Rr18),(Rs11,Rq4,Rr19),
(Rs11,Rq4,Rr20),(Rs11,Rq5,Rr1),(Rs11,Rq5,Rr2),(Rs11,
Rq5,Rr3),(Rs11,Rq5,Rr4),(Rs11,Rq5,Rr5),(Rs11,Rq5,Rr6),
(Rs11,Rq5,Rr7),(Rs11,Rq5,Rr8),(Rs11,Rq5,Rr9),(Rs11,
Rq5,Rr10),(Rs11,Rq5,Rr11),(Rs11,Rq5,Rr12),(Rs11,Rq5,
Rr13),(Rs11,Rq5,Rr14),(Rs11,Rq5,Rr15),(Rs11,Rq5,Rr16),
(Rs11,Rq5,Rr17),(Rs11,Rq5,Rr18),(Rs11,Rq5,Rr19),
(Rs11,Rq5,Rr20),(Rs11,Rq6,Rr1),(Rs11,Rq6,Rr2),(Rs11,
Rq6,Rr3),(Rs11,Rq6,Rr4),(Rs11,Rq6,Rr5),(Rs11,Rq6,
Rr6),(Rs11,Rq6,Rr7),(Rs11,Rq6,Rr8),(Rs11,Rq6,Rr9),
(Rs11,Rq6,Rr10),(Rs11,Rq6,Rr11),(Rs11,Rq6,Rr12),
(Rs11,Rq6,Rr13),(Rs11,Rq6,Rr14),(Rs11,Rq6,Rr16),
(Rs11,Rq6,Rr16),(Rs11,Rq6,Rr17),(Rs11,Rq6,Rr18),
(Rs11,Rq6,Rr19),(Rs11,Rq6,Rr20),(Rs1,Rq7,Rr1),(Rs11,
Rq7,Rr2),(Rs11,Rq7,Rr3),(Rs11,Rq7,Rr4),(Rs11,Rq7,Rr5),
(Rs11,Rq7,Rr6),(Rs11,Rq7,Rr7),(Rs11,Rq7,Rr8),(Rs11,
Rq7,Rr9),(Rs11,Rq7,Rr10),(Rs11,Rq7,Rr11),(Rs11,Rq7,
Rr12),(Rs11,Rq7,Rr13),(Rs11,Rq7,Rr14),(Rs11,Rq7,Rr15),
(Rs11,Rq7,Rr16),(Rs11,Rq7,Rr17),(Rs11,Rq7,Rr18),
(Rs11,Rq7,Rr19),(Rs11,Rq7,Rr20),(Rs11,Rq8,Rr1),(Rs11,
Rq8,Rr2),(Rs11,Rq8,Rr3),(Rs11,Rq8,Rr4),(Rs11,Rq8,Rr5),
(Rs11,Rq8,Rr6),(Rs11,Rq8,Rr7),(Rs11,Rq8,Rr8),(Rs11,
Rq8,Rr9),(Rs11,Rq8,Rr10),(Rs11,Rq8,Rr11),(Rs11,Rq8,
Rr12),(Rs11,Rq8,Rr13),(Rs11,Rq8,Rr14),(Rs11,Rq8,Rr15),
(Rs11,Rq8,Rr16),(Rs11,Rq8,Rr17),(Rs11,Rq8,Rr18),
(Rs11,Rq8,Rr19),(Rs11,Rq8,Rr20),(Rs12,Rq1,Rr1),(Rs12,
Rq1,Rr2),(Rs12,Rq1,Rr3),(Rs12,Rq1,Rr4),(Rs12,Rq1,Rr5),
(Rs12,Rq1,Rr6),(Rs12,Rq1,Rr7),(Rs12,Rq1,Rr8),(Rs12,
Rq1,Rr9),(Rs12,Rq1,Rr10),(Rs12,Rq11,Rr11),(Rs12,Rq1,
Rr12),(Rs12,Rq1,Rr13),(Rs12,Rq1,Rr14),(Rs12,Rq1,Rr15),
(Rs12,Rq1,Rr16),(Rs12,Rq1,Rr17),(Rs12,Rq1,Rr18),
(Rs12,Rq1,Rr19),(Rs12,Rq1,Rr20),(Rs12,Rq2,Rr1),(Rs12,
Rq2,Rr2),(Rs12,Rq2,Rr3),(Rs12,Rq2,Rr4),(Rs12,Rq2,Rr5),
(Rs12,Rq2,Rr6),(Rs12,Rq2,Rr7),(Rs12,Rq2,Rr8),(Rs12,
Rq2,Rr9),(Rs12,Rq2,Rr10),(Rs12,Rq2,Rr11),(Rs12,Rq2,
Rr12),(Rs12,Rq2,Rr13),(Rs12,Rq2,Rr14),(Rs12,Rq2,Rr15),
(Rs12,Rq2,Rr16),(Rs12,Rq2,Rr17),(Rs12,Rq2,Rr18),
(Rs12,Rq2,Rr19),(Rs12,Rq2,Rr20),(Rs12,Rq3,Rr1),(Rs12,
Rq3,Rr2),(Rs12,Rq3,Rr3),(Rs12,Rq3,Rr4),(Rs12,Rq3,Rr5),
(Rs12,Rq3,Rr6),(Rs12,Rq3,Rr7),(Rs12,Rq3,Rr8),(Rs12,
Rq3,Rr9),(Rs12,Rq3,Rr10),(Rs12,Rq3,Rr11),(Rs12,Rq3,
Rr12),(Rs12,Rq3,Rr13),(Rs12,Rq3,Rr14),(Rs12,Rq3,Rr15),
(Rs12,Rq3,Rr16),(Rs12,Rq3,Rr17),(Rs12,Rq3,Rr18),
(Rs12,Rq3,Rr19),(Rs12,Rq3,Rr20),(Rs12,Rq4,Rr1),(Rs12,
Rq4,Rr2),(Rs12,Rq4,Rr3),(Rs12,Rq4,Rr4),(Rs12,Rq4,Rr5),
(Rs12,Rq4,Rr6),(Rs12,Rq4,Rr7),(Rs12,Rq4,Rr8),(Rs12,
Rq4,Rr9),(Rs12,Rq4,Rr10),(Rs12,Rq4,Rr11),(Rs12,Rq4,
Rr12),(Rs12,Rq4,Rr13),(Rs2,Rq4,Rr14),(Rs12,Rq4,Rr15),
(Rs12,Rq4,Rr16),(Rs12,Rq4,Rr17),(Rs12,Rq4,Rr18),
(Rs12,Rq4,Rr19),(Rs12,Rq4,Rr20),(Rs12,Rq5,Rr1),(Rs12,
Rq5,Rr2),(Rs12,Rq5,Rr3),(Rs12,Rq5,Rr4),(Rs12,Rq5,Rr5),
(Rs12,Rq5,Rr6),(Rs12,Rq5,Rr7),(Rs12,Rq5,Rr8),(Rs12,
Rq5,Rr9),(Rs12,Rq5,Rr10),(Rs12,Rq5,Rr11),(Rs12,Rq5,
Rr12),(Rs12,Rq5,Rr13),(Rs12,Rq5,Rr14),(Rs12,Rq5,Rr15),
(Rs12,Rq5,Rr16),(Rs12,Rq5,Rr17),(Rs12,Rq5,Rr18),
(Rs12,Rq5,Rr19),(Rs12,Rq5,Rr20),(Rs12,Rq5,Rr1),(Rs12,
Rq6,Rr2),(Rs12,Rq6,Rr3),(Rs12,Rq6,Rr4),(Rs12,Rq6,Rr5),
(Rs12,Rq6,Rr6),(Rs12,Rq6,Rr7),(Rs12,Rq6,Rr8),(Rs12,
Rq6,Rr9),(Rs12,Rq6,Rr10),(Rs12,Rq6,Rr1),(Rs12,Rq6,
Rr12),(Rs12,Rq6,Rr13),(Rs12,Rq6,Rr14),(Rs12,Rq6,
Rr15),(Rs12,Rq6,Rr16),(Rs12,Rq6,Rr17),(Rs12,Rq6,Rr18),
(Rs12,Rq6,Rr19),(Rs12,Rq6,Rr20),(Rs12,Rq7,Rr1),(Rs12,
Rq7,Rr2),(Rs12,Rq7,Rr3),(Rs12,Rq7,Rr4),(Rs12,Rq7,Rr5),
(Rs12,Rq7,Rr6),(Rs12,Rq7,Rr7),(Rs12,Rq7,Rr8),(Rs12,
Rq7,Rr9),(Rs12,Rq7,Rr10),(Rs12,Rq7,Rr11),(Rs12,Rq7,
Rr12),(Rs12,Rq7,Rr13),(Rs12,Rq7,Rr14),(Rs12,Rq7,Rr15),
(Rs12,Rq7,Rr16),(Rs12,Rq7,Rr17),(Rs12,Rq7,Rr18),
(Rs12,Rq7,Rr19),(Rs12,Rq7,Rr20),(Rs12,Rq8,Rr1),(Rs12,
Rq8,Rr2),(Rs12,Rq8,Rr3),(Rs12,Rq8,Rr4),(Rs12,Rq8,Rr5),
(Rs12,Rq8,Rr6),(Rs2,Rq8,Rr7),(Rs12,Rq8,Rr8),(Rs12,Rq8,
Rr9),(Rs12,Rq8,Rr10),(Rs12,Rq8,Rr11),(Rs12,Rq8,Rr12),
(Rs12,Rq8,Rr13),(Rs12,Rq8,Rr14),(Rs12,Rq8,Rr15),
(Rs12,Rq8,Rr16),(Rs12,Rq8,Rr17),(Rs12,Rq8,Rr18),
(Rs12,Rq8,Rr19),(Rs12,Rq8,Rr20),(Rs13,Rq1,Rr1),(Rs13,
Rq1, Rr2),(Rs13,Rq1,Rr3),(Rs13,Rq1,Rr4),(Rs13,Rq1,
Rr5),(Rs13,Rq1,Rr6),(Rs13,Rq1,Rr7),(Rs13,Rq1,Rr8),
(Rs13,Rq1,Rr9),(Rs13,Rq1,Rr10),(Rs13,Rq1,Rr11),(Rs13,
Rq1,Rr12),(Rs13,Rq1,Rr13),(Rs13,Rq1,Rr14),(Rs13,Rq1,
Rr15),(Rs13,Rq1,Rr16),(Rs13,Rq1,Rr17),(Rs13,Rq1,Rr18),
(Rs13,Rq1,Rr19),(Rs13,Rq1,Rr20),(Rs13,Rq2,Rr1),(Rs13,
Rq2,Rr2),(Rs13,Rq2,Rr3),(Rs13,Rq2,Rr4),(Rs13,Rq2,Rr5),
(Rs13,Rq2,Rr6),(Rs13,Rq2,Rr7),(Rs13,Rq2,Rr8),(Rs13,
Rq2,Rr9),(Rs13,Rq2,Rr10),(Rs13,Rq2,Rr11),(Rs13,Rq2,
Rr12),(Rs13,Rq2,Rr13),(Rs13,Rq2,Rr14),(Rs13,Rq2,Rr15),
(Rs13,Rq2,Rr16),(Rs13,Rq2,Rr17),(Rs13,Rq2,Rr18),
(Rs13,Rq2,Rr19),(Rs13,Rq2,Rr20),(Rs13,Rq3,Rr1),(Rs13,
Rq3,Rr2),(Rs13,Rq3,Rr3),(Rs13,Rq3,Rr4),(Rs13,Rq3,Rr5),
(Rs13,Rq3,Rr6),(Rs13,Rq3,Rr7),(Rs13,Rq3,Rr8),(Rs13,
Rq3,Rr9),(Rs13,Rq3,Rr10),(Rs13,Rq3,Rr11),(Rs13,Rq3,
Rr12),(Rs13,Rq3,Rr13),(Rs13,Rq3,Rr4),(Rs13,Rq3,Rr15),
(Rs13,Rq3,Rr16),(Rs13,Rq3,Rr17),(Rs13,Rq3,Rr8),(Rs13,
Rq3,Rr19),(Rs13,Rq3,Rr20),(Rs13,Rq4,Rr1),(Rs13,Rq4,
Rr2),(Rs13,Rq4,Rr3),(Rs13,Rq4,Rr4),(Rs13,Rq4,Rr5),
(Rs13,Rq4,Rr6),(Rs13,Rq4,Rr7),(Rs13,Rq4,Rr8),(Rs13,
Rq4,Rr9),(Rs3,Rq4,Rr10),(Rs13,Rq4,Rr11),(Rs13,Rq4,
Rr12),(Rs13,Rq4,Rr13),(Rs13,Rq4,Rr14),(Rs13,Rq4,Rr15),
(Rs13,Rq4,Rr16),(Rs13,Rq4,Rr17),(Rs13,Rq4,Rr18),
(Rs13,Rq4,Rr19),(Rs13,Rq4,Rr20),(Rs13,Rq5,Rr1),(Rs13,
Rq5,Rr2),(Rs13,Rq5,Rr3),(Rs13,Rq5,Rr4),(Rs13,Rq5,Rr5),
(Rs13,Rq5,Rr6),(Rs13,Rq5,Rr7),(Rs13,Rq5,Rr8),(Rs13,
Rq5,Rr9),(Rs13,Rq5,Rr10),(Rs13,Rq5,Rr1),(Rs13,Rq5,
Rr12),(Rs13,Rq5,Rr13),(Rs13,Rq5,Rr14),(Rs13,Rq5,Rr15),
(Rs13,Rq5,Rr16),(Rs13,Rq5,Rr17),(Rs13,Rq5,Rr18),
(Rs13,Rq5,Rr19),(Rs13,Rq5,Rr20),(Rs13,Rq6,Rr1),(Rs13,
Rq6,Rr2),(Rs13,Rq6,Rr3),(Rs13,Rq6,Rr4),(Rs13,Rq6,Rr5),
(Rs13,Rq6,Rr6),(Rs13,Rq6,Rr7),(Rs13,Rq6,Rr8),(Rs13,
Rq6,Rr9),(Rs13,Rq6,Rr10),(Rs13,Rq6,Rr11),(Rs13,Rq6,
Rr12),(Rs13,Rq6,Rr13),(Rs13,Rq6,Rr14),(Rs13,Rq6,Rr15),
(Rs13,Rq6,Rr16),(Rs13,Rq6,Rr17),(Rs13,Rq6,Rr18),
(Rs13,Rq6,Rr19),(Rs13,Rq6,Rr20),(Rs13,Rq7,Rr1),(Rs13,
Rq7,Rr2),(Rs13,Rq7,Rr3),(Rs13,Rq7,Rr4),(Rs13,Rq7,Rr5),
(Rs13,Rq7,Rr6),(Rs13,Rq7,Rr7),(Rs13,Rq7,Rr8),(Rs13,
Rq7,Rr9),(Rs13,Rq7,Rr10),(Rs13,Rq7,Rr11),(Rs13,Rq7,
Rr12),(Rs13,Rq7,Rr13),(Rs13,Rq7,Rr14),(Rs13,Rq7,Rr15),
(Rs13,Rq7,Rr16),(Rs13,Rq7,Rr7),(Rs13,Rq7,Rr18),(Rs13, Rq7,Rr19),(Rs13,Rq7,Rr20),(Rs13,Rq8,Rr1),(Rs13,Rq8, Rr2),(Rs13,Rq8,Rr3),(Rs13,Rq8,Rr4),(Rs13,Rq8,Rr5), (Rs13,Rq8,Rr6),(Rs13,Rq8,Rr7),(Rs13,Rq8,Rr8),(Rs13, Rq8,Rr9),(Rs13,Rq8,Rr10),(Rs13,Rq8,Rr1),(Rs13,Rq8, Rr12),(Rs13,Rq8,Rr13),(Rs13,Rq8,Rr14),(Rs13,Rq8,Rr15), (Rs13,Rq8,Rr16),(Rs13,Rq8,Rr17),(Rs13,Rq8,Rr18), (Rs13,Rq8,Rr19),(Rs13,Rq8,Rr20),(Rs14,Rq1,Rr1),(Rs14, Rq1,Rr2),(Rs14,Rq1,Rr3),(Rs14,Rq1,Rr4),(Rs14,Rq1,Rr5), (Rs14,Rq1,Rr6),(Rs14,Rq1,Rr7),(Rs14,Rq1,Rr8),(Rs14, Rq1,Rr9),(Rs14,Rq1,Rr10),(Rs14,Rq1,Rr11),(Rs14,Rq1, Rr12),(Rs14,Rq1,Rr13),(Rs14,Rq1,Rr14),(Rs14,Rq1,Rr15), (Rs14,Rq1,Rr16),(Rs14,Rq1,Rr17),(Rs14,Rq1,Rr18), (Rs14,Rq1,Rr19),(Rs14,Rq1,Rr20),(Rs14,Rq2,Rr1),(Rs14, Rq2,Rr2),(Rs14,Rq2,Rr3),(Rs14,Rq2,Rr4),(Rs14,Rq2,Rr5), (Rs14,Rq2,Rr6),(Rs14,Rq2,Rr7),(Rs14,Rq2,Rr8),(Rs14, Rq2,Rr9),(Rs14,Rq2,Rr10),(Rs14,Rq2,Rr11),(Rs14,Rq2, Rr12),(Rs14,Rq2,Rr13),(Rs14,Rq2,Rr14),(Rs14,Rq2,Rr15), (Rs14,Rq2,Rr16),(Rs14,Rq2,Rr17),(Rs14,Rq2,Rr18), (Rs14,Rq2,Rr19),(Rs14,Rq2,Rr20),(Rs14,Rq3,Rr1),(Rs14, Rq3,Rr2),(Rs14,Rq3,Rr3),(Rs14,Rq3,Rr4),(Rs14,Rq3,Rr5), (Rs14,Rq3,Rr6),(Rs14,Rq3,Rr7),(Rs14,Rq3,Rr8),(Rs14, Rq3,Rr9),(Rs14,Rq3,Rr10),(Rs14,Rq3,Rr11),(Rs14,Rq3, Rr12),(Rs14,Rq3,Rr13),(Rs14,Rq3,Rr14),(Rs14,Rq3,Rr15), (Rs14,Rq3,Rr16),(Rs14,Rq3,Rr17),(Rs14,Rq3,Rr18), (Rs14,Rq3,Rr19),(Rs14,Rq3,Rr20),(Rs14,Rq4,Rr1),(Rs14, Rq4,Rr2),(Rs14,Rq4,Rr3),(Rs14,Rq4,Rr4),(Rs14,Rq4,Rr5), (Rs14,Rq4,Rr6),(Rs14,Rq4,Rr7),(Rs14,Rq4,Rr8),(Rs14, Rq4,Rr9),(Rs14,Rq4,Rr10),(Rs14,Rq4,Rr11),(Rs14,Rq4, Rr12),(Rs14,Rq4,Rr13),(Rs14,Rq4,Rr14),(Rs14,Rq4,Rr15), (Rs14,Rq4,Rr16),(Rs14,Rq4,Rr17),(Rs14,Rq4,Rr18), (Rs14,Rq4,Rr19),(Rs14,Rq4,Rr20),(Rs14,Rq5,Rr1),(Rs14, Rq5,Rr2),(Rs14,Rq5,Rr3),(Rs14,Rq5,Rr4),(Rs14,Rq5,Rr5), (Rs14,Rq5,Rr6),(Rs14,Rq5,Rr7),(Rs14,Rq5,Rr8),(Rs14, Rq5,Rr9),(Rs14,Rq5,Rr10),(Rs14,Rq5,Rr11),(Rs14,Rq5, Rr12),(Rs14,Rq5,Rr13),(Rs14,Rq5,Rr14),(Rs14,Rq5,Rr15), (Rs14,Rq5,Rr16),(Rs14,Rq5,Rr17),(Rs14,Rq5,Rr18), (Rs14,Rq5,Rr19),(Rs14,Rq5,Rr20),(Rs14,Rq6,Rr1),(Rs14, Rq6,Rr2),(Rs14,Rq6,Rr3),(Rs14,Rq6,Rr4),(Rs14,Rq6,Rr5), (Rs14,Rq6,Rr6),(Rs14,Rq6,Rr7),(Rs14,Rq6,Rr8),(Rs14, Rq8,Rr9),(Rs14,Rq6,Rr10),(Rs14,Rq6,Rr11),(Rs14,Rq6, Rr12),(Rs14,Rq6,Rr13),(Rs14,Rq6,Rr14),(Rs14,Rq6,Rr15), (Rs14,Rq6,Rr16),(Rs14,Rq6,Rr17),(Rs14,Rq6,Rr18), (Rs14,Rq6,Rr19),(Rs14,Rq6,Rr20),(Rs14,Rq7,Rr1),(Rs14, Rq7,Rr2),(Rs14,Rq7,Rr3),(Rs14,Rq7,Rr4),(Rs14,Rq7,Rr5), (Rs14,Rq7,Rr6),(Rs14,Rq7,Rr7),(Rs1,Rq7,Rr8),(Rs14,Rq7, Rr9),(Rs14,Rq7,Rr10),(Rs14,Rq7,Rr11),(Rs14,Rq7,Rr12), (Rs14,Rq7,Rr13),(Rs14,Rq7,Rr15),(Rs14,Rq7,Rr16), (Rs14,Rq7,Rr16),(Rs14,Rq7,Rr17),(Rs14,Rq7,Rr18), (Rs14,Rq7,Rr19),(Rs14,Rq7,Rr20),(Rs14,Rq8,Rr1),(Rs14, Rq8,Rr2),(Rs14,Rq8,Rr3),(Rs14,Rq8,Rr4),(Rs4,Rq8,Rr5), (Rs14,Rq8,Rr6),(Rs14,Rq8,Rr7),(Rs14,Rq8,Rr8),(Rs14, Rq8,Rr9),(Rs14,Rq8,Rr10),(Rs14,Rq8,Rr11),(Rs14,Rq8, Rr12),(Rs14,Rq8,Rr13),(Rs14,Rq8,Rr14),(Rs14,Rq8,Rr15), (Rs14,Rq8,Rr16),(Rs14,Rq8,Rr17),(Rs14,Rq8,Rr18), (Rs14,Rq8,Rr19),(Rs14,Rq8,Rr20),(Rs15,Rq1,Rr1),(Rs15, Rq1,Rr2),(Rs15,Rq1,Rr3),(Rs15,Rq1,Rr4),(Rs15,Rq1,Rr5), (Rs15,Rq1,Rr6),(Rs15,Rq1,Rr7),(Rs15,Rq1,Rr8),(Rs15, Rq1,Rr9),(Rs15,Rq1,Rr10),(Rs15,Rq1,Rr11),(Rs15,Rq1, Rr12),(Rs15,Rq1,Rr13),(Rs5,Rq1,Rr14),(Rs15,Rq1,Rr15), (Rs15,Rq1,Rr16),(Rs15,Rq1,Rr17),(Rs15,Rq1,Rr18),(Rs1, Rr19),(Rs15,Rq1,Rr20),(Rs15,Rq2,Rr1),(Rs15,Rq2,Rr2), (Rs15,Rq2,Rr3),(Rs15,Rq2,Rr4),(Rs15,Rq2,Rr5),(Rs15, Rq2,Rr6),(Rs15,Rq2,Rr7),(Rs15,Rq2,Rr8),(Rs15,Rq2,Rr9), (Rs15,Rq2,Rr10),(Rs15,Rq2,Rr11),(Rs15,Rq2,Rr12), (Rs15,Rq2,Rr13),(Rs15,Rq2,Rr14),(Rs15,Rq2,Rr15), (Rs15,Rq2,Rr16),(Rs15,Rq2,Rr1),(Rs15,Rq2,Rr18),(Rs15, Rq2,Rr19),(Rs15,Rq2,Rr20),(Rs15,Rq3,Rr1),(Rs15,Rq3, Rr2),(Rs15,Rq3,Rr3),(Rs15,Rq3,Rr4),(Rs15,Rq3,Rr5), (Rs15,Rq3,Rr6),(Rs15,Rq3,Rr7),(Rs15,Rq3,Rr8),(Rs15, Rq3,Rr9),(Rs15,Rq3,Rr10),(Rs15,Rq3,Rr11),(Rs15,Rq3, Rr12),(Rs15,Rq3,Rr13),(Rs15,Rq3,Rr14),(Rs15,Rq3,Rr15), (Rs15,Rq3,Rr16),(Rs15,Rq3,Rr17),(Rs15,Rq3,Rr18), (Rs15,Rq3,Rr19),(Rs15,Rq3,Rr20),(Rs15,Rq4,Rr1),(Rs15, Rq4,Rr2),(Rs15,Rq4,Rr3),(Rs15,Rq4,Rr4),(Rs15,Rq4,Rr5), (Rs15,Rq4,Rr6),(Rs15,Rq4,Rr7),(Rs15,Rq4,Rr8),(Rs15, Rq4,Rr9),(Rs15,Rq4,Rr10),(Rs15,Rq4,Rr11),(Rs15,Rq4, Rr12),(Rs15,Rq4,Rr13),(Rs15,Rq4,Rr14),(Rs15,Rq4,Rr15), (Rs15,Rq4,Rr16),(Rs15,Rq4,Rr17),(Rs15,Rq4,Rr18), (Rs15,Rq4,Rr19),(Rs15,Rq4,Rr20),(Rs15,Rq5,Rr1),(Rs15, Rq5,Rr2),(Rs15,Rq5,Rr3),(Rs15,Rq5,Rr4),(Rs15,Rq5,Rr5), (Rs15,Rq5,Rr6),(Rs15,Rq5,Rr7),(Rs15,Rq5,Rr8),(Rs15, Rq5,Rr9),(Rs15,Rq5,Rr10),(Rs15,Rq5,Rr11),(Rs15,Rq5, Rr12),(Rs15,Rq5,Rr13),(Rs15,Rq5,Rr14),(Rs15,Rq5,Rr15), (Rs15,Rq5,Rr16),(Rs15,Rq5,Rr17),(Rs15,Rq5,Rr18), (Rs15,Rq5,Rr19),(Rs15,Rq5,Rr20),(Rs15,Rq6,Rr1),(Rs15, Rq6,Rr2),(Rs15,Rq6,Rr3),(Rs15,Rq6,Rr4),(Rs15,Rq6,Rr5), (Rs15,Rq6,Rr6),(Rs15,Rq6,Rr7),(Rs15,Rq6,Rr8),(Rs15, Rq6,Rr9),(Rs15,Rq6,Rr10),(Rs15,Rq6,Rr11),(Rs15,Rq6, Rr12),(Rs15,Rq6,Rr13),(Rs15,Rq6,Rr14),(Rs15,Rq6,Rr15), (Rs15,Rq6,Rr16),(Rs15,Rq6,Rr17),(Rs15,Rq6,Rr18), (Rs15,Rq6,Rr19),(Rs15,Rq6,Rr20),(Rs15,Rq7,Rr1),(Rs15, Rq7,Rr2),(Rs15,Rq7,Rr3),(Rs15,Rq7,Rr4),(Rs15,Rq7,Rr5), (Rs15,Rq7,Rr6),(Rs15,Rq7,Rr7),(Rs15,Rq7,Rr8),(Rs15, Rq7,Rr9),(Rs15,Rq7,Rr10),(Rs15,Rq7,Rr11),(Rs15,Rq7, Rr12),(Rs15,Rq7,Rr13),(Rs15,Rq7,Rr14),(Rs15,Rq7,Rr15), (Rs15,Rq7,Rr16),(Rs15,Rq7,Rr17),(Rs15,Rq7,Rr18), (Rs15,Rq7,Rr19),(Rs15,Rq7,Rr20),(Rs15,Rq8,Rr1),(Rs15, Rq8,Rr2),(Rs15,Rq8,Rr3),(Rs15,Rq8,Rr4),(Rs15,Rq8,Rr5), (Rs15,Rq8,Rr6),(Rs15,Rq8,Rr7),(Rs15,Rq8,Rr8),(Rs15, Rq8,Rr9),(Rs15,Rq8,Rr10),(Rs15,Rq8,Rr1),(Rs15,Rq8, Rr12),(Rs15,Rq8,Rr13),(Rs15,Rq8,Rr14),(Rs15,Rq8,Rr15), (Rs15,Rq8,Rr16),(Rs15,Rq8,Rr17),(Rs15,Rq8,Rr18), (Rs15,Rq8,Rr19),(Rs15,Rq8,Rr20).

Following examples illustrate the present invention in more detail, but the present invention is not limited by these examples. The meaning of each abbreviation is as follows:

Me: methyl

Et: ethyl

Bu: butyl

Ac: acetyl

TMS: tetramethylsilane

TMS-Cl: trimethylsilyl chloride

DMSO: dimethyl sulfoxide

DMF: dimethylformamide

THF: tetrahydrofuran

DBU: 1,8-diazabicyclo[5.4.0]undeca-7-ene

NMP: N-methyl-2-pyrrolidone

HOAt: 1-hydroxy-7-azabenzotriazole

HATU: 2-(7-azabenzotriazole-1-yl)-1,1,3,3-tetramethyluronium hexafluorophosphate PyBOP: benztriazole-1-yl-oxytrispyrrolidinophosphonium hexafluorophosphate rt: room temperature

EXAMPLE 1

Preparation of 1-(4-chlorobenzyl)-3-ethylamino-6-(4-isopropoxyphenylamino)benzene (I-071)

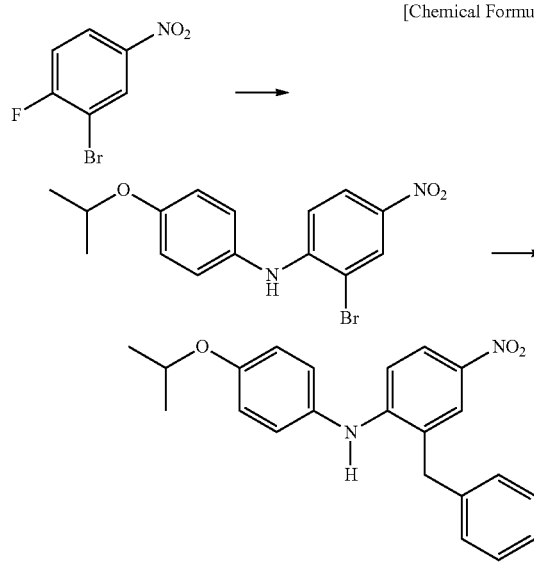

[Chemical Formula 120]

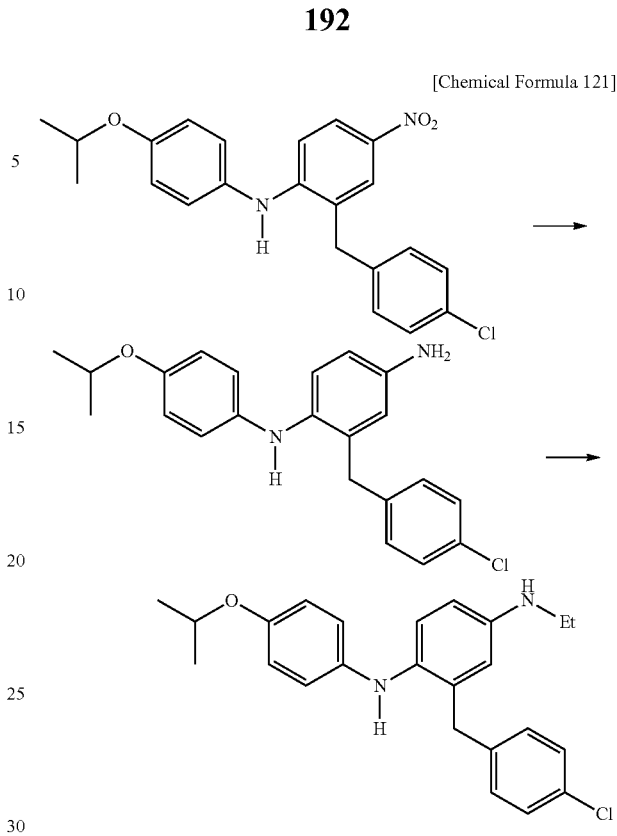

[Chemical Formula 121]

To a mixture of 3-bromo-4-fluoro-1-nitrobenzene (1.0 g, 4.6 mmol) and DMSO (5 mL) were added potassium carbonate (1.01 mg, 7.3 mmol) and 4-isopropoxyaniline (1.03 g, 6.8 mmol), and the resulting mixture was stirred at 100° C. for 0.5 hours. To the reaction mixture was added water (20 mL), and the resulting mixture was extracted with ethyl acetate (30 mL×2). The extract was washed by brine (20 mL) and water, and the organic layer was dried over anhydrous sodium sulphate, and concentrated in vacuo. The resulting residue was purified by silica gel column chromatography (ethyl acetate/hexane). The resulting residue was precipitated by ethyl acetate and hexane to give 3-bromo-4-(4-isopropoxyphenylamino)-1-nitrobenzene (0.55 g, 35%) as orange solid.

1H-NMR (δ ppm TMS/DMSO-d6): 1.28 (6H, d, J=6.0 Hz), 4.61 (1H, sept, J=6.0 Hz), 6.76 (1H, d, J=9.0 Hz), 6.97 (2H, d, J=9.0 Hz), 7.19 (2H, d, J=9.0 Hz), 8.00 (1H, dd, J=8.9 Hz, 2.4 Hz), 8.34 (2H, d, J=2.4 Hz).

To a mixture of 3-bromo-4-(4-isopropoxyphenylamino)-1-nitrobenzene (0.38 g, 1.0 mmol) and THF (1 mL) were added 4-chlorobenzyl zinc chloride (0.5 mol/L THF solution, 3.28 mL, 1.6 mmol), triphenylphosphine (29 mg, 0.11 mmol) and palladium acetate (II) (12.3 mg, 0.06 mmol), and the resulting mixture was heated at reflux for 2 hours. The reaction mixture was concentrated in vacuo. The resulting residue was purified by silica gel column chromatography (ethyl acetate/hexane) to give 1-(4-chlorobenzyl)-3-nitro-6-(4-isopropoxyphenylamino)benzene (235 mg, Yield: 54%) as pale brown amorphous.

1H-NMR (δ ppm TMS/DMSO-d6): 1.27 (6H, d, J=5.7 Hz), 4.07 (2H, s), 4.59 (1H, sept, J=6.0 Hz), 6.82 (1H, d, J=9.3 Hz), 6.96 (2H, d, J=8.7 Hz), 7.12 (2H, d, J=9.0 Hz), 7.30-7.35 (2H, m), 7.36-7.44 (2H, m) 7.78 (1H, d, J=2.7 Hz), 7.92 (1H, dd, J=2.7 Hz, 9.3 Hz), 8.22 (1H, s).

To a mixture of 1-(4-chlorobenzyl)-3-nitro-6-(4-isopropoxyphenylamino)benzene (0.22 g, 0.55 mmol), ethanol (2 mL) and ethyl acetate (2 mL) was added Stannous Chloride hydrate (375 mg, 1.7 mmol), and the resulting mixture was heated at reflux for 3 hours. To the reaction mixture was neutralized by 2 mol/L sodium hydroxide under ice-cooling, and the resulting mixture was extracted with ethyl acetate (50 mL). The extract was washed by saturated aqueous sodium bicarbonate (50 mL) and brine (50 mL), and the organic layer was dried over anhydrous sodium sulphate and concentrated in vacuo. The resulting residue was purified by silica gel column chromatography (ethyl acetate/hexane). The resulting residue was precipitated by diethyl ether and hexane to give 1-(4-chlorobenzyl)-3-amino-6-(4-isopropoxyphenylamino)benzene (93 mg, Yield: 46%) as brown powder.

1H-NMR (δ ppm TMS/DMSO-d6): 1.18 (6H, d, J=6.3 Hz), 3.72 (2H, s), 4.32 (1H, sept, J=6.0 Hz), 4.80 (2H, s), 6.27 (1H, d, J=2.4 Hz), 6.38 (1H, dd, J=2.7 Hz, 8.4 Hz), 6.40-6.50 (2H, m), 6.60-6.70 (2H, m), 6.70 (1H, s), 6.76 (1H, d, J=8.4 Hz), 7.06-7.14 (2H, m), 7.20-7.30 (2H, m).

To a mixture of 1-(4-chlorobenzyl)-3-amino-6-(4-isopropoxyphenylamino)benzene (62 mg, 0.17 mmol) and THF (2 mL) was gradually added trifluoroacetic anhydride (0.029 mL, 0.2 mmol) under ice-cooling, and the resulting mixture was stirred at 0° C. for 1 hour. To the reaction mixture were added potassium tert-butoxide (48 mg, 0.41 mmol) and ethyl iodide (0.016 mL, 0.2 mmol), and the mixture was stirred at 55° C. for 6 hours. Further, 2 mol/L sodium hydroxide (0.1 mL) was added to the mixture, and the resulting mixture was stirred at room temperature for 1 hour. To the reaction mixture was added water (30 and the resulting mixture was extracted with ethyl acetate (30 mL×2). The extract was washed by brine (30 mL), and the organic layer was dried over anhydrous sodium sulphate and concentrated in vacuo. The resulting residue was purified by silica gel column chromatography (ethyl acetate/hexane) to give 1-(4-chlorobenzyl)-3-ethylamino-6-(4-isopropoxyphenylamino)benzene (35 mg, Yield: 52%) as pale yellow oil.

1H-NMP, (δ ppm TMS/DMSO-d6): 1.11 (3H, t, J=6.9 Hz), 1.19 (6H, d, J=5.7 Hz), 2.93 (2H, m), 3.76 (2H, br.s), 4.33 (1H, sept, J=6.0 Hz), 5.2-5.4 (1H, m), 6.20-6.57 (4H, m), 6.58-6.78 (3H, m), 6.78-6.90 (1H, m), 7.07-7.16 (2H, m), 7.21-7.28 (2H, m).

EXAMPLE 2

Preparation of 1-(4-chlorobenzyl)-3-dimethyl-amino-6-(3-fluoro-4-isopropoxyphenylamino)benzene (I-123)

[Chemical Formula 122]

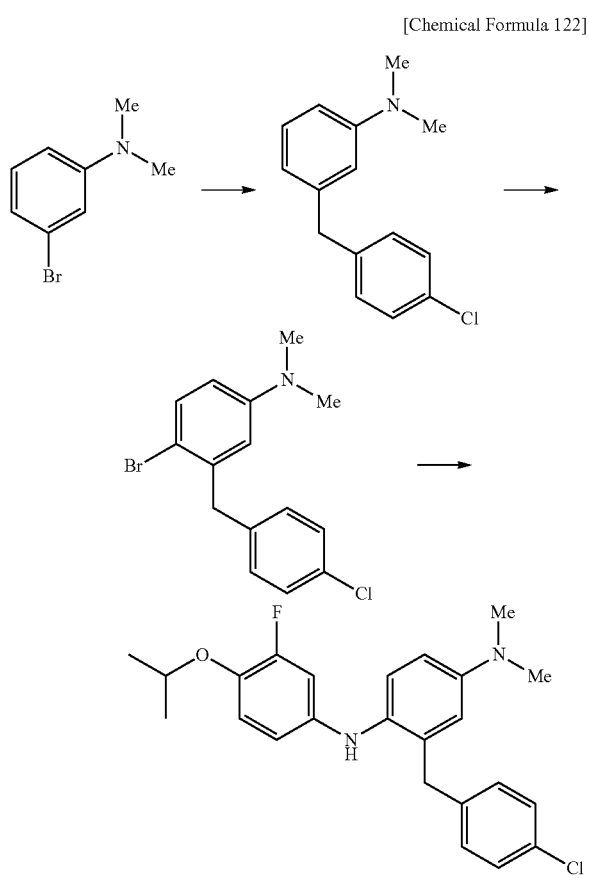

To a mixture of 3-bromo-1-dimethyl-aminobenzene (0.3 g, 1.5 mmol) and THF (3 mL) were added 4-chlorobenzyl zinc chloride (0.5 M THF solution, 6 mL, 3 mmol), triphenylphosphine (39.3 mg, 0.15 mmol) and palladium acetate (II) (17 mg, 0.08 mmol), and the resulting mixture was heated at reflux for 2 hours. To the reaction mixture was added water (200 mL), and the resulting mixture was extracted with ethyl acetate (200 mL). The extract was washed by brine (100 mL), dried over anhydrous magnesium sulfate, and concentrated in vacuo. The resulting residue was purified by silica gel column chromatography (ethyl acetate/hexane) to give 1-(4-chlorobenzyl-3-dimethyl-aminobenzene (0.32 g, Yield: 87%) as colorless oil.

1H-NMR, (δ ppm TMS/CDCl$_3$): 2.89 (6H, s), 3.87 (2H, s), 6.48-6.59 (4H, m), 7.08-7.22 (4H, m).

To a mixture of 1-(4-chlorobenzyl-3-dimethyl-aminobenzene (120 mg, 0.5 mmol) and dichloromethane (3 mL) was added N-bromosuccinimide (104 mg, 0.6 mmol), and the resulting mixture was stirred at room temperature for 1 hour. The reaction mixture was concentrated in vacuo. The resulting residue was purified by silica gel column chromatography (ethyl acetate/hexane) to give 6-bromo-1-(4-chlorobenzyl)-3-dimethyl-aminobenzene (75.6 mg, Yield: 48%) as colorless oil.

1H-NMR (δ ppm TMS/CDCl$_3$): 2.88 (6H, s), 4.02 (2H, s), 6.47-6.49 (2H, m), 7.11 (2H, m), 7.24 (2H, m), 7.35 (1H, m).

A mixture of 6-bromo-1-(4-chlorobenzyl)-3-dimethyl-aminobenzene (67.4 mg, 0.21 mmol), 3-fluoro-4-isopropoxyaniline (38.6 mg, 0.23 mmol), 2-dicyclohexylphosphino-2',6'-diisopropoxybiphenyl (9.7 mg, 0.02 mmol), cesium carbonate (101 mg, 0.31 mmol) and dioxane (3 mL) was added bis(dibenzylideneacetone)palladium(0) (9.5 mg, 0.01 mmol) under nitrogen atmosphere, and the resulting mixture was stirred at 100° C. for 1 hour. The reaction mixture was concentrated in vacuo. The resulting residue was purified by silica gel column chromatography (ethyl acetate/hexane) to give 1-(4-chlorobenzyl)-3-dimethyl-amino-6-(3-fluoro-4-isopropoxyphenylamino)benzene (59 mg, Yield: 69%) as yellow solid.

1H-NMR (δ ppm TMS/CDCl$_3$): 1.34 (6H, d, J=6.2 Hz), 2.96 (6H, s), 3.88 (2H, s), 4.32 (1H, hept, J=6.2 Hz), 4.09 (1H, br.s), 6.27 (1H, m), 6.35 (1H, dd, J=12.9, 2.7 Hz), 6.66 (2H, m), 6.82 (1H, t, J=8.7 Hz), 7.07-7.13 (3H, m), 7.26 (2H, m).

EXAMPLE 3

Preparation of 1-(4-chlorobenzyl)-3-(3-hydroxypropyloxy)-6-(3-fluoro-4 isopropoxyphenylamino)benzene (I-076)

[Chemical Formula 123]

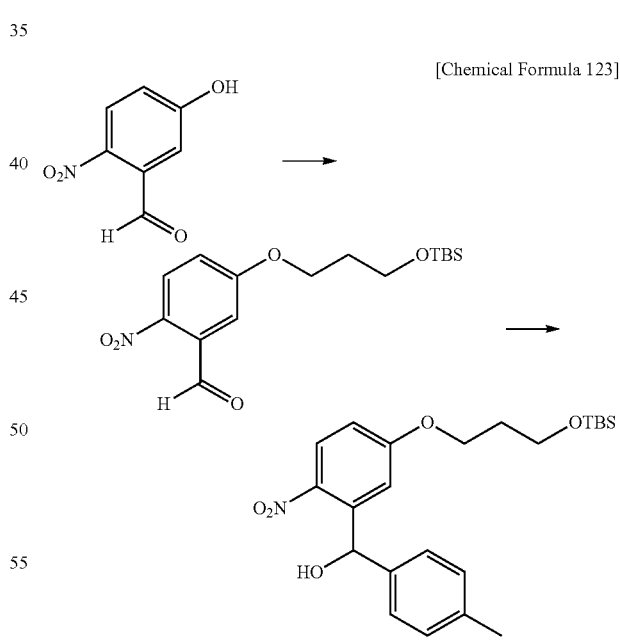

To a mixture of 5-hydroxy-2-nitrobenzaldehyde (3.0 g, 18 mmol) and DMF (10 mL) were added potassium carbonate (3.23 g, 23.3 mmol) and (3-promo-propoxy(t-butyl)dimethyl-silane (5.56 g, 21.5 mmol), and the resulting mixture was stirred at room temperature overnight. To the reaction mixture was added water (200 mL), and the resulting mixture was extracted with ethyl acetate (200 mL×2). The extract was washed by brine (200 mL), dried over anhydrous sodium sulphate, and concentrated in vacuo. The resulting residue was purified by silica gel column chromatography (ethyl acetate/hexane) to give 5-[3-(t-butyldimethylsilanoxy)propyloxy]-2-nitrobenzaldehyde (3.0 g, Yield: 49%) as pale yellow oil.

1H-NMR (δ ppm TMS/DMSO-d6): 0.00 (6H, s), 0.83 (9H, s), 7.92 (2H, q, J=5.7 Hz), 3.73 (2H, t, J=5.7 Hz), 4.21 (2H, t, J=5.7 Hz), 7.22 (1H, d, J=2.7 Hz), 7.33 (1H, d, J=2.7 Hz, 9.0 Hz), 8.16 (1H, d, J=9.0 Hz), 10.25 (1H, s).

To a mixture of 5-[3-(t-butyldimethyl-silanoxy)propyloxy]-2-nitrobenzaldehyde (1.7 g, 5 mmol) and THF (18 mL) was added 4-methylphenylmagnesium bromide (1 mol/L THF solution, 5.26 mL, 5.26 mmol) under ice-cooling, and the resulting mixture was stirred at room temperature for 0.5 hour. To the reaction mixture was added water (200 mL), and the resulting mixture was extracted with ethyl acetate (200 mL×2). The extract was washed by brine (200 mL), dried over anhydrous sodium sulphate, and concentrated in vacuo. The resulting residue was purified by silica gel column chromatography (ethyl acetate/hexane) to give 5-[3-(t-butyl)dimethyl-silanoxypropyloxy]-2-nitro-1-(4-methylphenyl-1-hydroxymethyl)benzene (1.19 g, Yield: 55%) as pale yellow oil.

1H-NMR (δ ppm TMS/DMSO-d6): 0.00 (6H, s), 0.84 (9H, s), 1.92 (2H, q, J=6.3 Hz), 2.24 (3H, s), 3.75 (2H, t, J=6.3 Hz), 4.16 (2H, dt, J=1.2 Hz, 6.3 Hz), 6.12 (1H, s), 6.30 (1H, s), 7.03 (1H, dd, J=2.7 Hz, 9.0 Hz), 7.07 (4H, s), 7.37 (1H, d, J=2.7 Hz), 7.98 (1H, d, J=9.0 Hz).

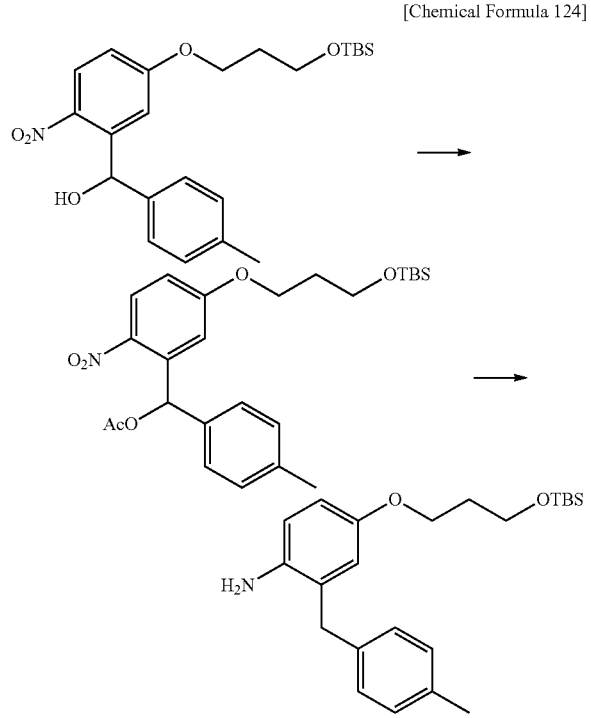

[Chemical Formula 124]

To a mixture of 5-[3-(t-butyl)dimethyl-silanoxypropyloxy]-2-nitro-1-(4-methylphenyl-1-hydroxymethyl-)benzene (156 mg, 0.36 mmol) and pyridine (1.5 mL) were added acetic anhydride (0.068 mL, 0.72 mmol) and 4-dimethylaminopyridine (0.44 mg, 0.004 mmol), and the resulting mixture was stirred at room temperature overnight. To the reaction mixture was added ethyl acetate (50 mL), and the resulting mixture was washed by 2 mol/L aqueous hydrochloric acid (30 mL×2) and brine (50 mL), dried over anhydrous sodium sulphate, and concentrated in vacuo. The crude 5-[3-(t-butyl)dimethyl-silanoxypropyloxy]-2-nitro-1-(4-methylphenyl-1-acetoxymethyl)benzene.

A mixture of the obtained crude product and methanol (2 mL) was hydrogenated by adding 10% Pd/C (34 mg). The insoluble are filtered off, and the filtrate was concentrated in vacuo. The resulting residue was purified by silica gel column chromatography (ethyl acetate/hexane) to give 2-amino-5-[3-(t-butyl)dimethyl-silanoxypropyloxy]-1-(4-methylbenzyl)benzene (54 mg, Yield: 44%) as pale yellow oil.

1H-NMR (δ ppm TMS/DMSO-D6): 0.00 (6H, s), 0.84 (9H, s), 1.79 (2H, q, J=6.3 Hz), 2.25 (3H, s), 3.68 (2H, t, J=6.3 Hz), 3.69 (2H, s), 3.82 (2H, t, J=6.3 Hz), 4.37 (2H, s), 6.42 (1H, m), 6.50-6.54 (2H, m) 7.07 (4H, s).

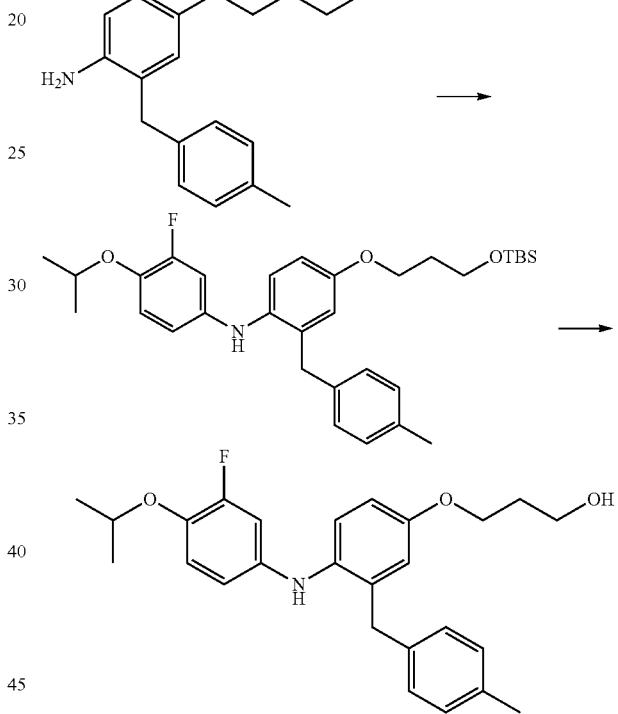

[Chemical Formula 125]

To a mixture of 2-amino-5-[3-(t-butyl)dimethyl-silanoxypropyloxy]-1-(4-methylbenzyl)benzene (54 mg, 0.14 mmol), 4-bromo-2-fluoro-1-isopropoxybenzene (32.6 mg, 0.14 mmol), dicyclohexylphosphino-2',6'-diisopropoxy-1,1'-biphenyl (3.3 mg, 0.007 mmol), potassium t-butoxide (28.3 mg, 0.29 mmol) and toluene (2 mL) was added palladium acetate(II) (1.6 mg, 0.007 mmol) under nitrogen atmosphere, and the resulting mixture was stirred at 100° C. for 1 hour. The reaction mixture was concentrated in vacuo. The resulting residue was purified by silica gel column chromatography (ethyl acetate/hexane) to give 1-(4-chlorobenzyl)-3-[3-(t-butyl)dimethyl-silanoxypropyloxy]-6-(3-fluoro-4-isopropoxy phenylamino)benzene (69 mg, Yield: 92%) as brown oil.

1H-NMR (δ ppm TMS/DMSO-d6): 0.00 (6H, s), 0.84 (9H, s), 1.21 (6H, d, J=6.0 Hz), 1.84 (2H, q, =6.0 Hz), 2.22 (3H, s), 3.70 (2H, t, J=6.0 Hz), 3.80 (2H, s), 3.92 (2H, t, J=6.0 Hz), 4.27 (1H, q, 6.0 Hz), 6.32-6.42 (2H, m), 6.62 (1H, d, J=3.0 Hz), 6.75 (1H, dd, J=2.4 Hz, 8.4 Hz), 6.84-6.94 (1H, m), 6.97-7.08 (5H, m), 7.25 (1H, s).

To a mixture of 1-(4-chlorobenzyl)-3-[3-(t-butyl)dimethyl-silanoxypropyloxy]-6-(3-fluoro-4-isopropoxyphenylamino)benzene (65 mg, 0.12 mmol), acetic acid (0.007 mL, 0.12 mmol) and THF (2 mL) was added tetrabutylammonium fluoride (1.52 mg, 0.29 mmol), and the resulting mixture was stirred at room temperature overnight. To the reaction mixture was added water (20 mL), and the resulting mixture was extracted with ethyl acetate (20 mL×2). The extract was washed by brine (20 mL), dried over anhydrous sodium sulphate, and concentrated in vacuo. The resulting residue was purified by silica gel column chromatography (ethyl acetate/hexane) to give 1-(4-chlorobenzyl)-3-(3-hydroxypropyloxy)-6-(3-fluoro-4-isopropoxyphenylamino)benzene (40 mg, Yield: 78%) as brown oil.

1H-NMR (δ ppm TMS/DMSO-d6): 1.21 (6H, d, J=6.0 Hz), 1.80 (2H, q, J=6.3 Hz), 2.22 (3H, s), 3.51 (2H, dd, J=5.4 Hz, 11.4 Hz), 3.80 (2H, s), 3.92 (2H, t, J=6.3 Hz), 4.27 (1H, q, J=6.3 Hz), 4.50 (1H, t, J=5.1 Hz), 6.30-6.42 (2H, m), 6.63 (1H, d, J=2.1 Hz), 6.75 (1H, dd, J=2.1 Hz, 8.4 Hz), 6.84-6.93 (1H, m), 6.95-7.08 (5H, m), 7.24 (1H, s).

EXAMPLE 4

Preparation of 3-(4-chlorobenzyl)isoxazole-5-one

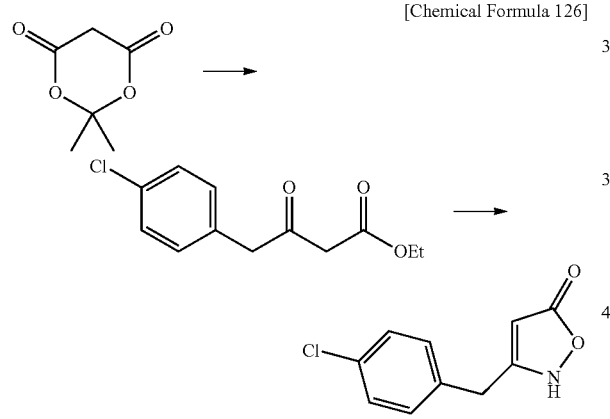

[Chemical Formula 126]

To a mixture of 2,2-dimethyl-1,3-dioxirane-4,6-dion (17.33 g, 120 mmol), pyridine (21.4 mL, 204 mmol) and dichloromethane (150 mL) was added dropwise 2-(4-chlorophenyl)acetyl chloride (25 g, 132 mmol) in dichloromethane (150 mL) under ice-cooling over 20 minutes, and the resulting mixture was stirred at room temperature for 2 hours. To the reaction mixture was added 2 mol/L hydrochloric acid (700 mL), and the resulting mixture was extracted with dichloromethane (500 mL). The extract was washed by water (300 mL×3), dried over anhydrous magnesium sulfate, and concentrated in vacuo. To the resulting residue was added ethanol (200 mL), and the resulting mixture was heated at reflux for 6 hours. The reaction mixture was concentrated in vacuo. The resulting residue was purified by silica gel column chromatography (ethyl acetate/hexane) to give ethyl 4-(4-chlorophenyl)-3-oxo-butanoate (13.62 g, Yield: 47%) as pale orange amorphous, 1H-NMR (δ ppm TMS/CDCl₃): 1.28 (3H, t, J=7.0 Hz), 3.46 (2H, s), 3.82 (2H, s), 4.19 (2H, q, Hz), 7.12-7.20 (2H, m), 7.26-7.34 (2H, m).

A mixture of ethyl 4-(4-chlorophenyl)-3-oxo-butanoate (13.62 g, 56.6 mmol), sodium hydrogencarbonate (9.51 g, 113 mmol), hydroxylamine hydrochloride (4.33 g, 62.3 mmol) and ethanol (56 mL) was heated at reflux for 2 hours. The reaction mixture was concentrated in vacuo. To the resulting residue were added brine (200 mL) and 2 mol/L hydrochloric acid (28.3 mL). The precipitated solid was filtered off, and concentrated in vacuo at 70° C. to give 3-(4-chlorobenzyl)isoxazole-5-one (11.69 g, Yield: 89%) as yellow solid.

1H-NMR (δ ppm TMS/CDCl₃): 3.76 (2H, s), 6.80 (1H, br, s), 7.13-7.37 (5H, m).

EXAMPLE 5

Preparation of 4-(4-chlorobenzyl)-2-benzyloxazole

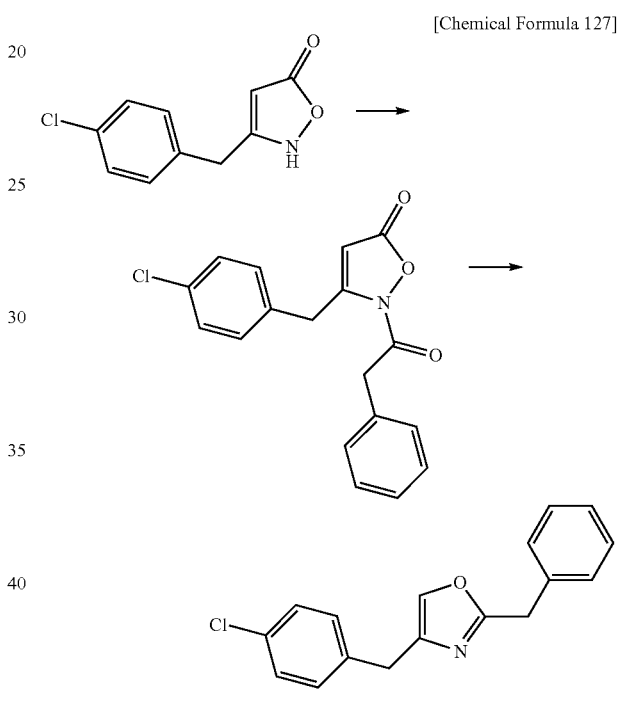

[Chemical Formula 127]

To a mixture of 3-(4-chlorobenzyl)isoxazole-5-one (3 g, 12.2 mmol), diisopropylethylamine (2.13 ml, 12.2 mmol)) and acetonitrile (15 mL) was added dropwise 2-phenylacetyl chloride (1.77 ml 13.4 mmol) in acetonitrile (3 mL) over 5 minutes under ice-cooling, and the resulting mixture was heated at reflux for 3 hours. To the reaction mixture was added water (200 mL), and the mixture was extracted with chloroform (200 mL×2). The extract was dried over anhydrous magnesium sulfate, and concentrated in vacuo. The resulting residue was purified by silica gel column chromatography (ethyl acetate/hexane) to give 3(4-chlorobenzyl)-2-(2-phenylacetyl)isoxazole-5-one (3.47 g, yield: 87%) as colorless oil.

1H-NMR (δ ppm TMS/CDCl₃): 4.04 (2H, s), 4.22 (2H, s), 5.07 (1H, s) 7.14-7.34 (9H, m).

A solution of 3-(4-chlorobenzyl)-2-(2-phenylacetyl)isoxazole-5-one (1.57 g, 4.8 mmol) in acetone (500 mL) was photoirradiated under ice-cooling for 3 hours under nitrogen atmosphere (high-pressure mercury lamp irradiation hv (365 nm)). The reaction mixture was concentrated in vacuo to give 4-(4-chlorobenzyl)-2-benzyloxazole (1.37 g, Yield: 100%) as brown oil.

1H-NMR (δ ppm TMS/CDCl₃): 3.80 (2H, s), 4.07 (2H, s), 7.16-7.29 (10H, m).

EXAMPLE 6

Preparation of 4-(4-chlorobenzyl)-2-benzyl-5-(3-fluoro-4-isopropoxyphenylamino)oxazole (I-070)

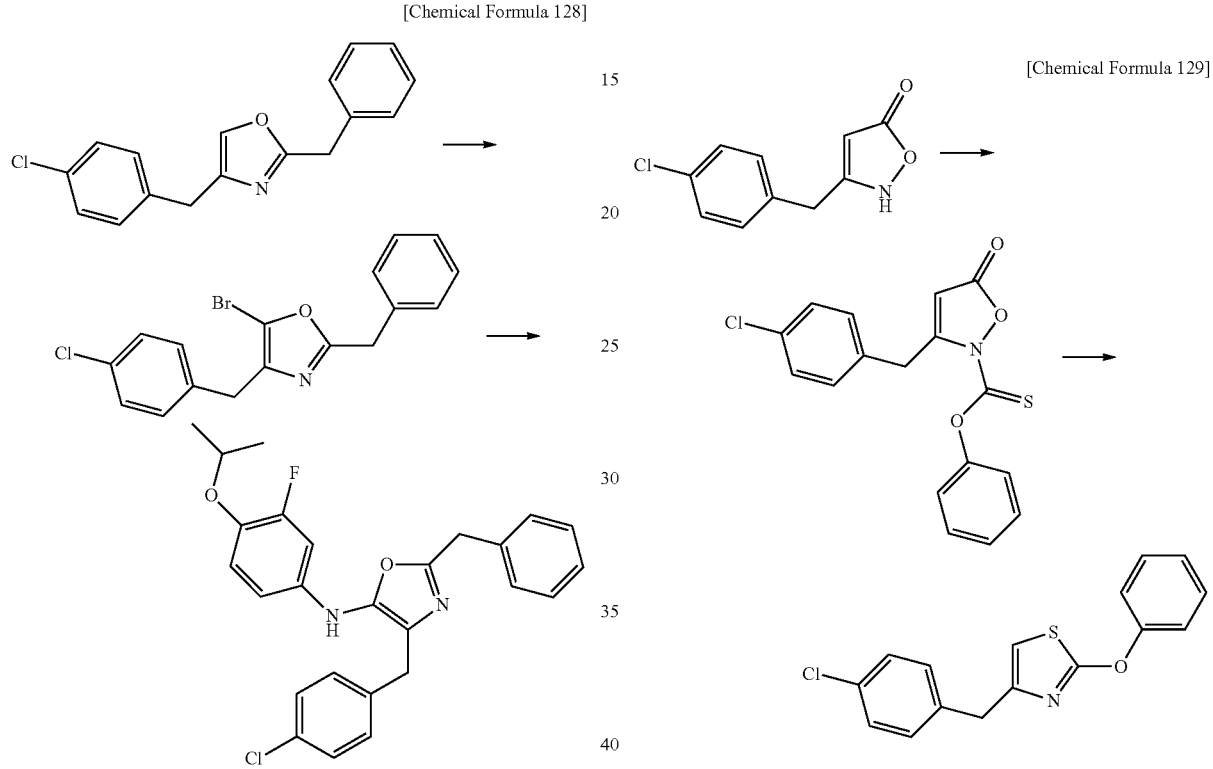

[Chemical Formula 128]

To a mixture of 4-(4-chlorobenzyl)-2-benzyloxazole (623 mg, 2.2 mmol) and chloroform (6 mL) was added N-bromosuccinimide (430 mg, 2.4 mmol), and the resulting mixture was stirred at room temperature for 1 hour and heated at reflux for additional 0.5 hour. The reaction mixture was purified by silica gel column chromatography (ethyl acetate/hexane) to give 5-bromo-4-(4-chlorobenzyl)-2-benzyloxazole (438 mg, Yield: 55%) as yellow oil.

1H-NMR (δ ppm TMS/CDCl₃): 3.74 (2H, s), 4.04 (2H, s), 7.17-7.31 (9H, m).

To a mixture of 5-bromo-4-(4-chlorobenzyl)-2-benzyloxazole (58 mg, 0.16 mmol), 3-fluoro-4-isopropoxyaniline (32.4 mg, 0.19 mmol) and DMF (1 mL) was added potassium carbonate (44 mg, 0.32 mmol), and the resulting mixture was stirred at room temperature for 2 hours. To the mixture was added iced water (200 mL), and the mixture was extracted with ethyl acetate (300 mL). The extract was washed by brine (200 mL), dried over anhydrous sodium sulphate, and concentrated in vacuo. The resulting residue was purified by silica gel column chromatography (ethyl acetate/hexane) and thin layer chromatography (ethyl acetate/hexane) to give 4-(4-chlorobenzyl)-2-benzyl-5-(3-fluoro-4-isopropoxyphenylamino)oxazole (2.2 mg, Yield: 3%) as pale yellow oil.

1H-NMR (δ ppm TMS/CDCl₃): 1.27 (6H, d, J=6.3 Hz), 3.82 (2H, s), 4.26 (1H, hept, J=6.3 Hz), 4.77 (1H, m), 5.54 (1H, m), 6.29-6.40 (2H, m), 6.78 (1H, t, J=8.8 Hz), 7.13-7.47 (10H, m).

EXAMPLE 7

Preparation of 4-(4-chlorobenzyl)-2-phenoxy-thiazole

[Chemical Formula 129]

To a mixture of 3-(4-chlorobenzyl)isoxazole-5-one (1.12 g, 4.5 mmol), diisopropylethylamine (2.38 ml, 13.6 mmol) and toluene (20 mL) was added dropwise a solution of phenoxy-thiocarbonyl chloride (1.88 ml, 13.6 mmol) in toluene (3 mL) over 5 minutes under ice-cooling, and the resulting mixture was stirred at room temperature for 3 hours. To the reaction mixture was added water (200 mL), and the mixture was extracted with ethyl acetate (200 mL×2). The extract was dried over anhydrous magnesium sulfate, and concentrated in vacuo. The resulting residue was purified by silica gel column chromatography (ethyl acetate/hexane) to give 3-(4-chlorobenzyl)-2-(phenoxy-thiocarbonyl)isoxazole-5-one (2.36 g, including ethyl acetate) as colorless oil.

1H-NMR (δ ppm TMS/CDCl₃): 4.42 (2H, s), 5.21 (1H, t, J=1.1 Hz), 7.01-7.47 (9H, m).

A solution of 3-(4-chlorobenzyl)-2-(phenoxy-thiocarbonyl)isoxazole-5-one (1.11 g, 3.2 mmol) in acetone (500 mL) was photoirradiated under ice-cooling for 3 hours under nitrogen atmosphere (high-pressure mercury lamp irradiation hν (365 nm)). The reaction mixture was concentrated in vacuo. The resulting residue was purified by silica gel column chromatography (ethyl acetate/hexane) to give 4-(4-chlorobenzyl)-2-phenoxy-thiazole (707 mg, Yield: 73%) as yellow oil.

1H-NMR (δ ppm TMS/CDCl₃): 3.92 (2H, s), 6.26 (1H, s), 7.20-7.30 (7H, m), 7.38-7.43 (2H, m).

EXAMPLE 8

Preparation of 4-(4-chlorobenzyl)-2-phenoxy-5-(3-fluoro-4-isopropoxyphenylamino)thiazole (I-069)

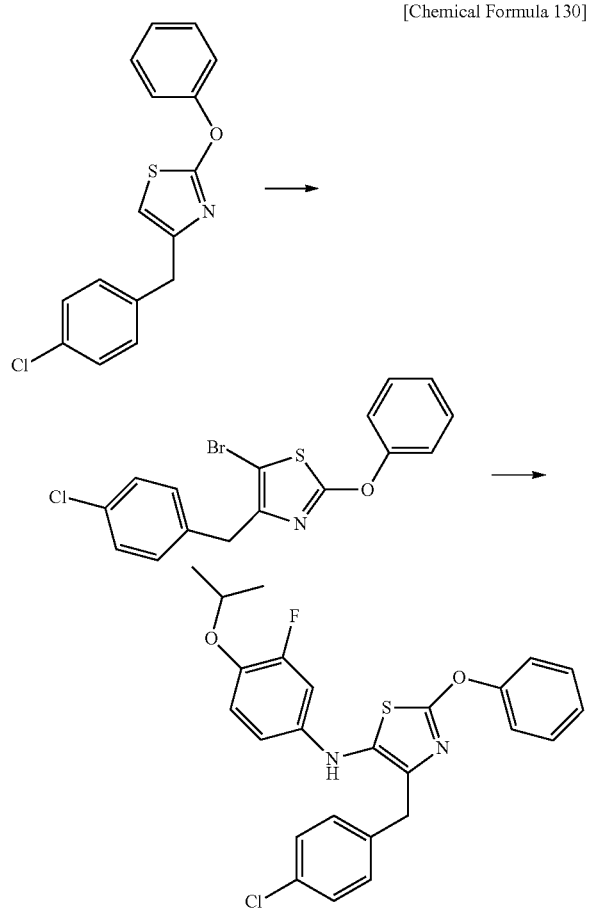

[Chemical Formula 130]

To a mixture of 4-(4-chlorobenzyl)-2-phenoxy-thiazole (679 mg, 2.25 mmol) and chloroform (6 mL) was added N-bromosuccinimide (441 mg, 2.48 mmol), and the resulting mixture was stirred at room temperature for 1 hour. The reaction mixture was concentrated in vacuo. The resulting residue was purified by silica gel column chromatography (ethyl acetate/hexane) to give 5-bromo-4-(4-chlorobenzyl)-2-phenoxy-thiazole (834 mg, Yield: 97%) as yellow oil.

1H-NMR (δ ppm TMS/CDCl₃): 3.90 (2H, s), 7.21-7.29 (7H, m), 7.37-7.43 (2H, m).

To a mixture of 5-bromo-4-(4-chlorobenzyl)-2-phenoxy-thiazole (194 mg, 0.51 mmol), 3-fluoro-4-isopropoxyaniline (103 mg, 0.61 mmol) and DMF (1 mL) was added 60% sodium hydride (24.5 mg, 0.61 mmol), and the resulting mixture was stirred at 80° C. for 1 hour. To the reaction mixture was added iced water (200 mL) and saturated aqueous ammonium chloride (2 mL), and the resulting mixture was extracted with ethyl acetate (200 mL). The extract was washed by brine (200 mL), dried over anhydrous sodium sulphate, and concentrated in vacuo. The resulting residue was purified by silica gel column chromatography (ethyl acetate/hexane) and reversed-phase HPLC to give 4-(4-chlorobenzyl)-2-phenoxy-5-(3-fluoro-4-isopropoxyphenylamino)thiazole (18.3 mg, Yield: 8%) as yellow oil.

1H-NMR (δ ppm TMS/CDCl₃): 1.27 (6H, d, J=6.1 Hz), 4.25 (1H, hept, J=6.1 Hz), 4.53 (1H, br, s), 5.33 (1H, s), 8.24 (1H, dd, J=8.5, 2.7 Hz), 8.32 (1H, dd, J=13.0, 2.7 Hz), 8.48 (1H, s), 8.78 (1H, t, J=8.8 Hz), 7.24-7.44 (9H, m).

EXAMPLE 9

Preparation of 4-(4-chlorobenzyl)-2-dimethyl-amino-5-(3-fluoro-4-isopropoxyphenylamino)-6H-1,3-oxazine-6-one (I-062)

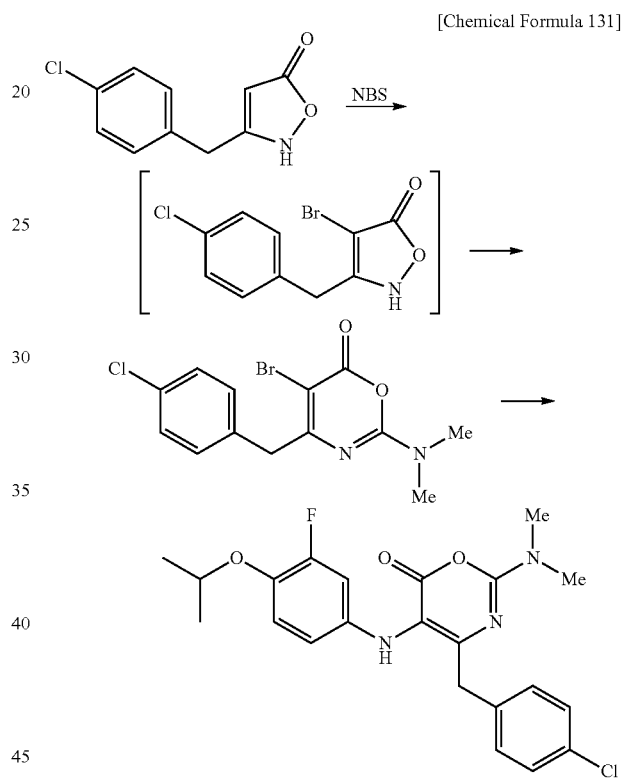

[Chemical Formula 131]

To a mixture of 3-(4-chlorobenzyl)isoxazole-5-one (500 mg, 2.0 mmol) and chloroform (3 mL) was added N-bromosuccinimide (361 mg, 2.0 mmol), and the resulting mixture was stirred at room temperature for 2 hours. To the reaction mixture were added DMF (0.47 ml, 6.1 mmol) and phosphorus oxychloride (0.565 ml, 6.1 mmol), and the resulting mixture was stirred at room temperature for 3 hours. The reaction mixture was poured into water (200 mL), and the mixture was extracted with chloroform (200 mL×2). The extract was dried over anhydrous magnesium sulfate, and concentrated in vacuo. The resulting residue was purified by silica gel column chromatography (ethyl acetate/hexane) to give 4-(4-chlorobenzyl)-2-dimethyl-amino-5-bromo-6H-1,3-oxazine-6-one (283 mg, Yield: 41%) as yellow solid.

1H-NMR (δ ppm TMS/CDCl₃): 3.00 (6H, d, J=3.7 Hz), 3.88 (2H s), 7.25-7.28 (4H, m).

To a mixture of 4-(4-chlorobenzyl)-2-dimethyl-amino-5-bromo-6H-1,3-oxazine-6-one (1.73 mg, 0.5 mmol), 3-fluoro-4-isopropoxyaniline (170 mg, 1.0 mmol) and dioxane (5 mL) was added potassium phosphate (213 mg, 1.0 mmol), and the resulting mixture was stirred at 160° C. for 45 minutes under microwave irradiation. The reaction mixture was poured into water (200 mL), and the resulting mixture was extracted with ethyl acetate (200 mL). The extract was dried over anhydrous magnesium sulfate, and concentrated in vacuo. The resulting residue was purified by silica gel column chromatography (ethyl acetate/hexane) and thin layer chromatography (ethyl acetate/hexane) to give 4-(4-chlorobenzyl)-2-dimethylamino-5-(3-fluoro-4-isopropoxyphenylamino)-6H-1,3-oxazine-6-one (2.8 mg, Yield: 1.3%) as yellow amorphous, 1H-NMR (δ ppm TMS/CDCl$_3$): 1.35 (6H, d, J=6.1 Hz), 3.14 (6H, s), 4.11 (2H, s), 4.44 (1H, hept, 6.1 Hz), 6.89-6.98 (3H, m), 7.22-7.36 (5H, m).

EXAMPLE 10

Preparation of 4-(4-chlorobenzoyl)-3-(3-fluoro-4-isopropoxyphenylamino)-1-hydroxyisoquinoline (I-082) and 3-(4-chlorobenzoyl)(3-fluoro-4-isopropoxyphenyl)amino-1-hydroxyisoquinoline

[Chemical Formula 132]

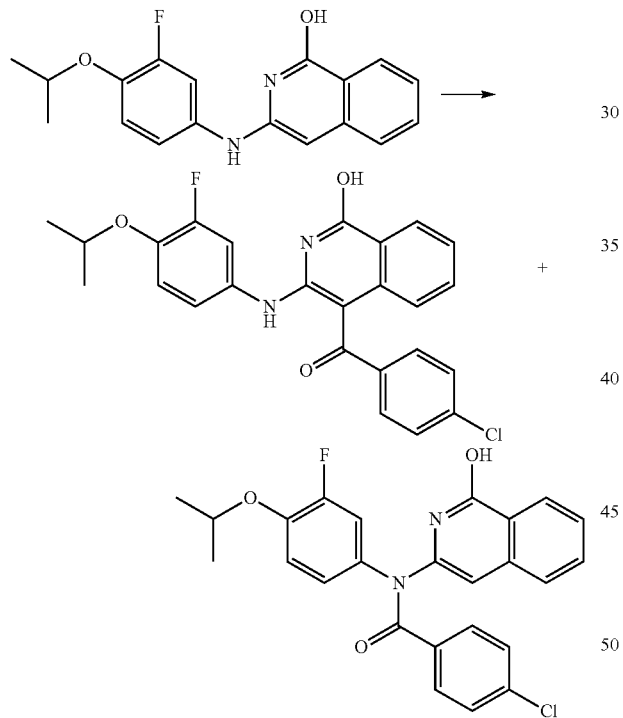

To a mixture of 3-(3-fluoro-4-isopropoxyphenylamino)-1-hydroxyisoquinoline (91 mg, 0.291 mmol) and dioxane (1.5 mL) was added 4-chlorobenzoyl chloride (457 mg, 2.8 mmol), and the resulting mixture was heated at reflux for 3 hours. To the reaction mixture were added iced water (100 mL) and saturated aqueous sodium bicarbonate (30 mL), and the mixture was extracted with ethyl acetate (100 mL). The extract was dried over anhydrous magnesium sulfate, and concentrated in vacuo. The resulting residue was purified by silica gel column chromatography (ethyl acetate/hexane) to give 4-(4-chlorobenzoyl)-3-(3-fluoro-4-isopropoxyphenylamino)-1-hydroxyisoquinoline (75.5 mg, Yield: 58%) as yellow solid, and 3-(4-chlorobenzoyl)(3-fluoro-4-isopropoxyphenyl)amino-1-hydroxyisoquinoline (33.2 mg, Yield: 25%) as colorless solid.

4-(4-chlorobenzoyl)-3-(3-fluoro-4-isopropoxyphenylamino)-1-hydroxyisoquinoline 1H-NMR (δ ppm TMS/CDCl$_3$): 1.43 (6H, d, J=6.1 Hz), 4.60 (1H, hept, J=6.1 Hz), 6.90-7.55 (10H, m), 8.19 (1H, dd, J=7.8, 1.5 Hz), 8.37 (1H, s), 11.5 (1H, s).

3-(4-chlorobenzoyl)(3-fluoro-4-isopropoxyphenyl)amino-1-hydroxyisoquinoline 1H-NMR (δ ppm TMS/CDCl$_3$): 1.30 (6H, d, J=6.1 Hz), 4.46 (1H, hept, J=6.1 Hz), 6.27 (1H, s), 6.83-7.63 (10H, m), 8.19 (1H, d, J=7.6 Hz), 12.3 (1H, s).

EXAMPLE 11

Preparation of 4-(4-chlorobenzyl)-3-(3-fluoro-4-isopropoxyphenylamino)-1-hydroxyisoquinoline (I-118)

[Chemical Formula 133]

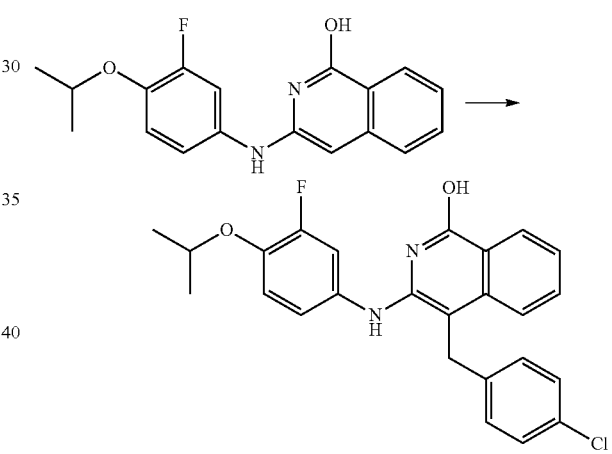

To a mixture of 3-(3-fluoro-4-isopropoxyphenylamino)-1-hydroxyisoquinoline (0.5 g, 1.6 mmol) and dioxane (10 mL) was added 4-chlorobenzyl bromide (1.32 mg, 6.40 mmol), and the resulting mixture was stirred at 160° C. for 0.5 hour under microwave irradiation. To the reaction mixture were added iced water (100 mL) and saturated aqueous sodium bicarbonate (30 mL), and the mixture was extracted with ethyl acetate (100 mL). The extract was dried over anhydrous magnesium sulfate, and concentrated in vacuo. The resulting residue was purified by silica gel column chromatography (ethyl acetate/hexane) to give 4-(4-chlorobenzyl)-3-(3-fluoro-4-isopropoxyphenylamino)-1-hydroxyisoquinoline (0.41 g, Yield: 59%) as yellow solid.

1H-NMR (δ ppm TMS/CDCl$_3$): 1.35 (6H, d, J=6.1 Hz), 4.07 (2H, s), 4.43 (1H, hept, J=6.1 Hz), 5.42 (1H, br.s), 6.63 (1H, m), 6.69 (1H, dd, J=11.3, 2.9 Hz), 6.92 (1H, t, J=8.8 Hz), 7.10 (2H, d, J=8.7 Hz), 7.30 (2H, d, J=8.7 Hz), 7.36 (1H, m), 7.45 (1H, 4, J=7.8 Hz), 7.59 (1H, m), 8.37 (1H, dd, J=8.1, 1.2 Hz), 8.50 (1H, brs. s).

EXAMPLE 12

Preparation of 4-(4-chlorobenzyl)-3-(3-fluoro-4-isopropoxyphenylamino)-1-(2-hydroxyethoxy)isoquinoline (I-162)

[Chemical Formula 134]

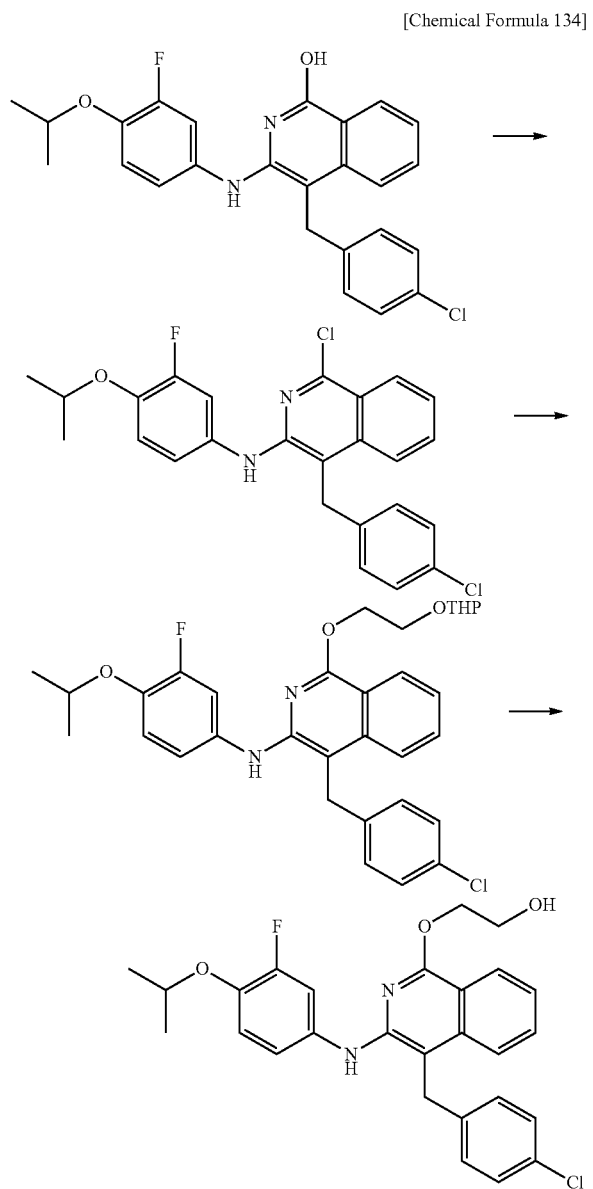

A mixture of 4-(4-chlorobenzyl)-3-(3-fluoro-4-isopropoxyphenylamino)-1-hydroxyisoquinoline (200 mg, 0.46 mmol) and phosphorus oxychloride (2.127 ml, 22.89 mmol) was stirred at 80° C. for 2 hours. The reaction mixture was concentrated in vacuo. The resulting residue was purified by silica gel column chromatography (ethyl acetate/hexane) to give 4-(4-chlorobenzyl)-3-(3-fluoro-4-isopropoxyphenylamino)-1-chloroisoquinoline (160 mg, Yield: 77%) as yellow oil.

1H-NMR (δ ppm TMS/CDCl$_3$): 1.34 (6H, d, J=6.1 Hz), 4.29 (2H, s), 4.41 (1H, hept, J=6.1 Hz), 6.03 (1H, br.s), 6.81-6.93 (2H, m), 7.07 (2H, d, J=8.5 Hz), 7.20 (1H, J=13.3, 2.4 Hz), 7.26 (2H, 4, J=8.5 Hz), 7.44 (1H, m), 7.64 (1H, m), 7.80 (1H, d, J=8.7 Hz), 8.28 (1H, 4, J=8.5 Hz).

To a mixture of 4-(4-chlorobenzyl)-3-(3-fluoro-4-isopropoxyphenylamino)-1-chloroisoquinoline (80 mg, 0.18 mmol), 2-(tetrahydro 2H-pyrane-2-yloxy)ethanol (51 mg, 0.35 mmol) and NMP (2 mL) was added 60% sodium hydride (14 mg, 0.35 mmol), and the resulting mixture was stirred at 150° C. for 0.5 hour under microwave irradiation. To the reaction mixture were added iced water (100 mL) and saturated aqueous ammonium chloride (50 mL), and the mixture was extracted with ethyl acetate (100 mL). The extract was washed by saturated sodium hydrogencarbonate (100 mL) and brine (100 mL), dried over anhydrous magnesium sulfate, and concentrated in vacuo. The resulting residue was purified by silica gel column chromatography (ethyl acetate/hexane) to give 4-(4-chlorobenzyl)-3-(3-fluoro-4-isopropoxyphenylamino)-1-[2-(2-tetrahydro-2H-pyrane-2-yloxy)ethoxy]isoquinoline (52 mg, Yield: 53%) as yellow oil.

1H-NMR (δ ppm TMS/CDCl$_3$): 1.35 (6H, d, J=6.1 Hz), 1.51-1.94 (6H, m), 3.54 (1H, m), 3.92 (2H, m), 4.15 (1H, m), 4.21 (2H, s), 4.41 (1H, hept, J=6.1 Hz), 4.65 (2H, m), 4.77 (1H, m), 5.96 (1H, br.s), 6.75 (1H, m), 6.87 (1H, t, J=8.8 Hz), 7.10 (2H, d, J=8.5 Hz), 7.22-7.32 (4H, era), 7.56 (1H, m), 7.66 (1H, d, J=8.4 Hz), 8.24 (1H, d, J=8.2 Hz).

To a mixture of 4-(4-chlorobenzyl)-3-(3-fluoro-4-isopropoxyphenylamino)-1-[2-(2-tetrahydro-2H-pyrane-2-yloxy)ethoxy]isoquinoline (46 mg, 0.08 mmol) and methanol (3 rat) was added p-toluenesulfonic acid hydrate (23 mg, 0.12 mmol), and the resulting mixture was stirred at room temperature for 1 hour. To the reaction mixture was added saturated aqueous sodium bicarbonate (100 mL), and the mixture was extracted with ethyl acetate (100 mL). The extract was washed by brine (200 mL), dried over anhydrous magnesium sulfate, and concentrated in vacuo. The resulting residue was purified by silica gel column chromatography (ethyl acetate/hexane) to give 4-(4-chlorobenzyl)-3-(3-fluoro-4-isopropoxyphenylamino)-1-(3-hydroxyethoxy)isoquinoline (26 mg, Yield: 69%) as yellow solid.

1H-NMR (δ ppm TMS/CDCl$_3$): 1.38 (6H, d, J=6.4 Hz), 4.08 (2H, m), 4.26 (2H, s), 4.46 (1H, hept, J=6.4 Hz), 4.65 (2H, m), 5.96 (1H, br.s), 6.76 (1H, m), 6.92 (1H, t, J=9.2 Hz), 7.15 (2H, d, J=8.2 Hz), 7.24 (1H, dd, 2.7 Hz), 7.30 (2H, d, J=8.2 Hz), 7.36 (1H, m), 7.63 (1H, m), 7.73 (1H, d, J=8.4 Hz), 8.27 (1H, d, J=8.2 Hz).

EXAMPLE 13

Preparation of 4-(4-chlorobenzoyl)-3-(3-fluoro-4-isopropoxyphenylamino)-1-(2-hydroxyethoxy)isoquinoline (I-110)

[Chemical Formula 135]

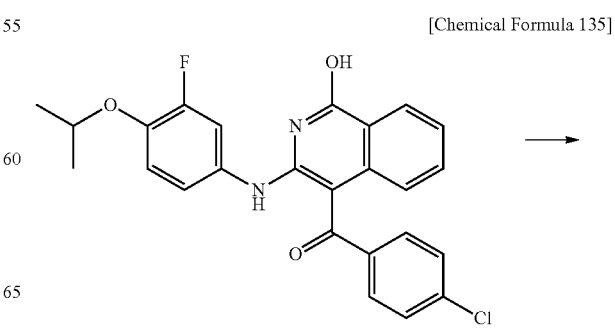

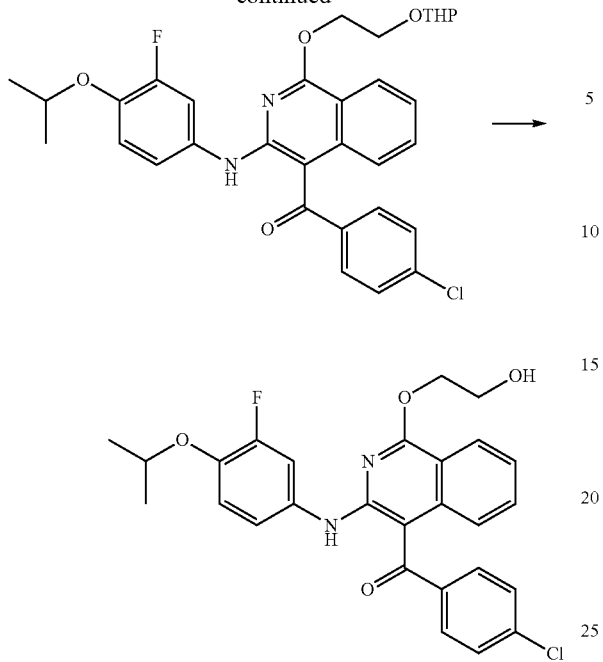

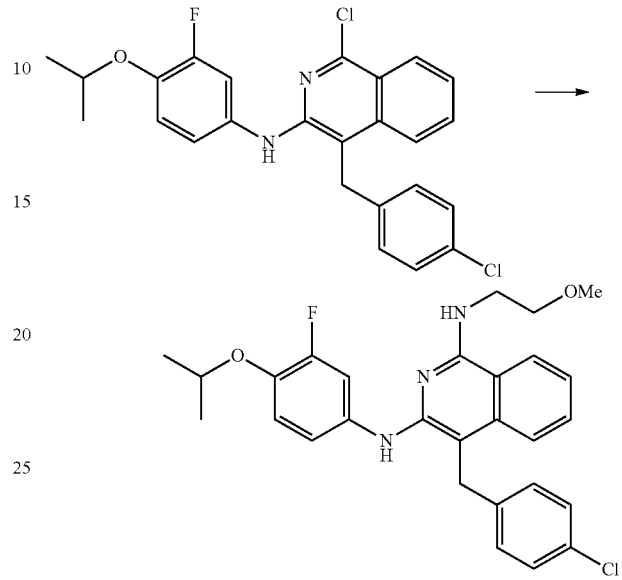

To a mixture of 4-(4-chlorobenzoyl)-3-(3-fluoro-4-isopropoxyphenylamino)-1-hydroxyisoquinoline (37 mg, 0.08 mmol), 2-(tetrahydro-2H-pyrane-2-yloxy)ethanol (14.40 mg, 0.098 mmol), triphenylphosphine (25.8 mg, 0.1 mmol) and dioxane (2 mL) was added di-2-methoxyethylazodicarboxylate (23 mg, 0.1 mmol) under ice cooling, and the resulting mixture was stirred at room temperature for 1 hour. The reaction mixture was concentrated in vacuo. The resulting residue was purified by silica gel column chromatography (ethyl acetate/hexane) to give 4-(4-chlorobenzoyl)-3-(3-fluoro-4-isopropoxyphenylamino)-1-[2-(2-tetrahydro-2H-pyrane-2-yloxy)ethoxy]isoquinoline (36 mg, Yield: 76%) as yellow solid.

1H-NMR (δ ppm TMS/CDCl$_3$): 1.37 (6H, d, J=6.1 Hz), 1.51-1.87 (0H, m), 3.55 (1H, m), 3.88-3.96 (2H, m), 4.17 (1H, m), 4.49 (1H, hept, J=6.1 Hz), 4.88-4.79 (3H, m), 6.92-7.70 (10H, m), 8.13 (1H, m), 10.9 (1H, s).

To a mixture of 4-(4-chlorobenzoyl)-3-(3-fluoro-4-isopropoxyphenylamino)-1-[2-(2-tetrahydro-2H-pyrane-2-yloxy)ethoxy]isoquinoline (31.4 mg, 0.054 mmol), THF (1.5 mL) and methanol (3 mL) was added p-toluenesulfonic acid hydrate (15.5 mg, 0.08 mmol), and the resulting mixture was stirred at room temperature for 1 hour. To the reaction mixture was added saturated aqueous sodium bicarbonate (100 mL), and the mixture was extracted with ethyl acetate (100 mL). The extract was washed by brine (200 mL), dried over anhydrous magnesium sulfate, and concentrated in vacuo to give 4-(4-chlorobenzoyl)-3-(3-fluoro-4-isopropoxyphenylamino)-1-(3-hydroxyethoxy)isoquinoline (25.5 mg, Yield: 95%) as yellow solid.

1H-NMR (δ ppm TMS/CDCl$_3$): 1.37 (6H, d, J=6.1 Hz), 2.02 (1H, t, J=5.9 Hz), 4.07-4.14 (2H, m), 4.50 (1H, hept, J=8.1 Hz), 4.76-4.71 (2H, m), 6.93-7.64 (10H, m), 8.13 (1H, m), 10.8 (1H, s).

EXAMPLE 14

Preparation of 4-(4-chlorobenzyl)-3-(3-fluoro-4-isopropoxyphenylamino)-1-(2-methoxy-ethylamino) isoquinoline (I-160)

[Chemical Formula 136]

To a mixture of 4-(4-chlorobenzyl)-3-(3-fluoro-4-isopropoxyphenylamino)-1-chloroisoquinoline (80 mg, 0.18 mmol), 2-methoxy-ethylamine (15.8 mg, 0.21 mmol), sodium t-butoxide (51 mg, 0.53 mmol), 4,5-bis(diphenylphosphino)-9,9-dimethylxanthene (15.3 mg, 0.026 mmol) and dioxane (3 mL) was added palladium acetate(II) (3.9 mg, 0.018 mmol), and the resulting, mixture was heated at reflux for 1 hour under nitrogen atmosphere. To the reaction mixture were added iced water (100 mL) and saturated aqueous ammonium chloride (50 mL), and the mixture was extracted with ethyl acetate (100 mL). The extract was washed by saturated sodium hydrogencarbonate (100 mL) and brine (100 mL), dried over anhydrous magnesium sulfate, and concentrated in vacuo. The resulting residue was purified by silica gel column chromatography (ethyl acetate/hexane) to give 4-(4-chlorobenzyl)-3-(3-fluoro-4-isopropoxyphenylamino)-1-(2-methoxy-ethylamino)iso quinoline (16.5 mg, Yield: 19%) as yellow oil.

1H-NMR (δ ppm TMS/CDCl$_3$): 1.34 (6H, d, J=6.1 Hz), 3.48 (3H, s), 3.60 (2H, m), 3.77 (2H, m), 4.17 (2H, m), 4.39 (1H, hept, J=6.1 Hz), 5.70 (1H, t, J=5.2 Hz), 5.94 (1H, s), 6.72 (1H, m), 6.86 (1H, t, J=8.7 Hz), 7.12 (2H, J=8.4 Hz), 7.21 (1H, m), 7.24 (2H, d, J=8.4 Hz), 7.41 (1H, dd, J=13.9, 2.4 Hz), 7.49 (1H, m), 7.61 (1H, d, J=8.5 Hz), 7.74 (1H, d, J=8.4 Hz).

EXAMPLE 15

Preparation of 3-(4-chlorobenzyl)-2-(3-chloro-4-isopropoxyphenylamino)-6-trifluoromethylquinazoline-4(3H)-one (I-211)

[Chemical Formula 137]

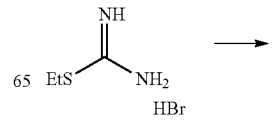

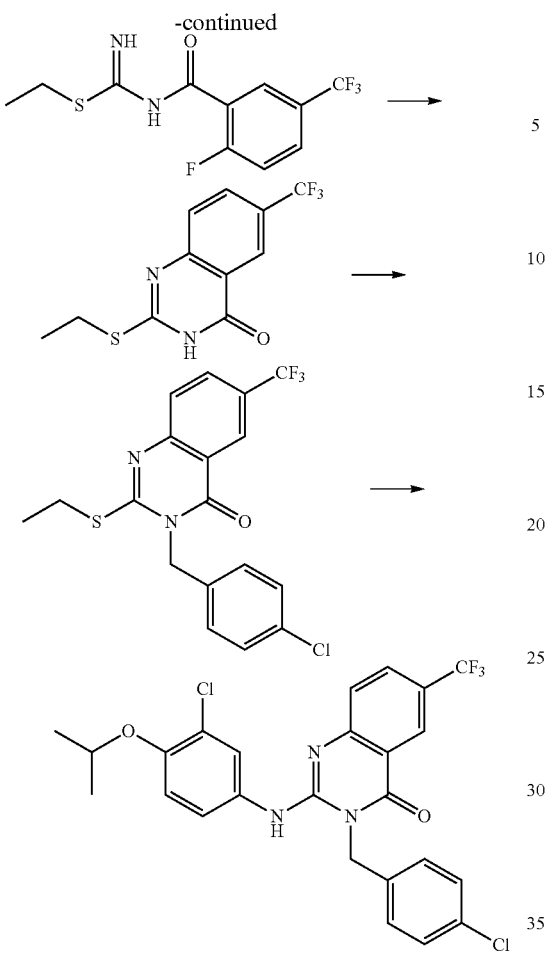

To a mixture of S-ethylisothiourea hydrobromide (0.817 g, 4.41 mmol), triethylamine (0.447 g, 4.41 mmol) and dichloromethane (15 mL) was added 2-fluoro-5-trifluoromethylbenzoyl chloride (0.67 ml, 4.4 mmol) under ice-cooling, and the resulting mixture was stirred at room temperature for 1 hour. The reaction mixture was concentrated in vacuo. The resulting residue was purified by silica gel column chromatography (ethyl acetate/hexane) to give N-(2-fluoro-5-trifluoromethylbenzoyl)-S-ethylthiourea (1.21 g, Yield 93%) as white solid.

1H-NMR (δ ppm TMS/CDCl₃): 1.42 (3H, t, J=7.3 Hz), 3.19 (2H, q, J=7.3 Hz), 7.21 (1H, m), 7.69 (1H, m), 8.42 (1H, dd, J=6.9, 2.4 Hz).

A mixture of N-(2-fluoro-5-trifluoromethylbenzoyl)-S-ethylthiourea (300 mg, 1.02 mmol) and NMP (1.5 mL) was stirred at 170° C. for 0.5 hour under microwave irradiation. The reaction mixture was poured into water (200 mL), and the resulting mixture was extracted with ethyl acetate (200 mL). The extract was dried over anhydrous magnesium sulfate, and concentrated in vacuo. The resulting residue was purified by silica gel column chromatography (ethyl acetate/hexane) to give 2-ethylthio-6-trifluoromethylquinazoline-4(3H)-one (238 mg, Yield: 85%) as white solid.

1H-NMR: (δ ppm TMS/CDCl₃): 1.47 (3H, t, J=7.5 Hz), 3.33 (2H, q, J=7.5 Hz), 7.68 (1H, d, J=8.5 Hz), 7.90 (1H, dd, J=8.6, 1.7 Hz), 8.50 (1H, s), 10.1 (1H, br.s).

To a mixture of 2-ethylthio-6-trifluoromethylquinazoline-4(3H)-one (202 mg, 0.74 nm ml), 4-chlorobenzylbromide (227 mg, 1.11 mmol) and acetonitrile (4 mL) was added potassium carbonate (305 mg, 2.2 mmol), and the resulting;

mixture was heated at reflux for 1 hour. The reaction mixture was filtered off, and the filtrate was concentrated in vacuo. The resulting residue was purified by silica gel column chromatography (ethyl acetate/hexane) to give 3-(4-chlorobenzyl)-2-ethylthio-6-trifluoromethylquinazoline-4(3H)-one (196 mg, Yield: 67%) as white solid.

1H-NMR, (δ ppm TMS/CDCl₃): 1.43 (3H, t, J=7.6 Hz), 3.30 (2H, q, J=7.5 Hz), 5.34 (2H, s), 7.28-7.34 (4H, m) 7.65 (1H, d, J=8.7 Hz), 7.89 (1H, dd, J=87, 2.0 Hz), 8.52 (1H, m).

A mixture of 3-(4-chlorobenzyl)-2-ethylthio-6-trifluoromethylquinazoline-4(3H)-one (80 mg, 0.2 mmol), 3-chloro-4-isopropoxyaniline (448 mg, 2.4 mmol), acetic acid (1.5 mL) and NMP (1.5 mL) was stirred at 150° C. for 1 hour under microwave irradiation. The reaction mixture was poured into water (200 mL), and the resulting mixture was extracted with ethyl acetate (200 mL). The extract was washed by saturated sodium hydrogencarbonate (200 mL) and brine (200 mL), dried over anhydrous magnesium sulfate, and concentrated in vacuo. The resulting residue was purified by silica gel column chromatography (ethyl acetate/hexane) to give 3-(4-chlorobenzyl)-2-(3-chloro-4 isopropoxyphenylamino)-6-trifluoromethylquinazoline-4(3H)-one (57 mg, Yield: 54%) as pale brown amorphous.

1H-NMR (δ ppm TMS/CDCl₃): 1.37 (6H, d, J=6.1 Hz), 4.48 (1H, hept, J=6.1 Hz), 5.30 (2H, s), 6.30 (1H, br.s), 6.90 (1H, d, J=9.0 Hz), 7.08 (1H, br.s), 7.26-7.60 (5H, m), 7.78 (1H, br.s), 8.45 (1H, hr. s).

EXAMPLE 16

Preparation of 1-(4-chlorobenzyl)-2-(3-chloro-4-isopropoxyphenylamine)-6-trifluoromethylquinazoline-4(3H)-one (I-227)

[Chemical Formula 138]

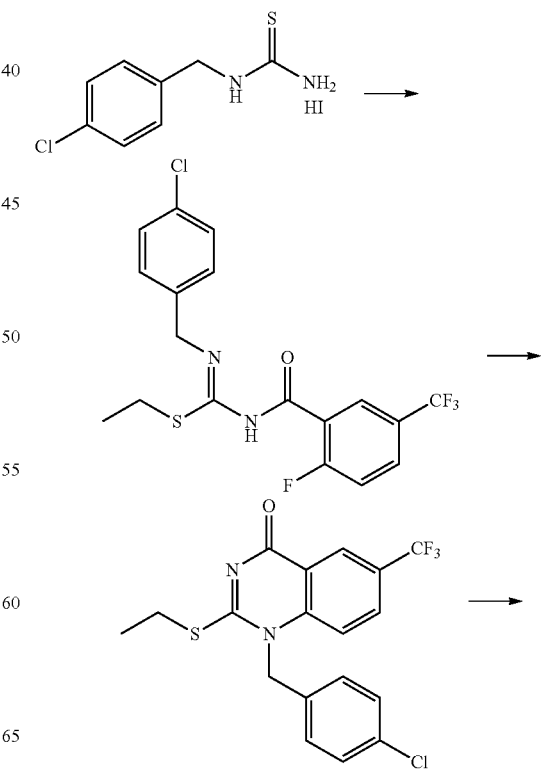

-continued

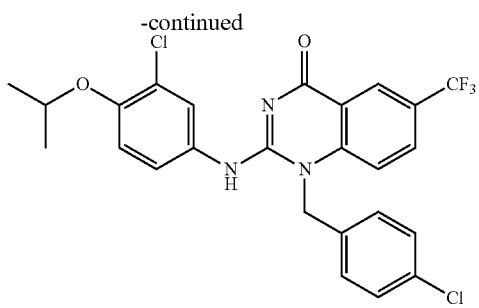

To a mixture of N-(4-chlorobenzyl)thiourea hydroiodic acid (1.57 g, 4.4 mmol), triethylamine (0.61 mL, 4.4 mmol) and dichloromethane (15 mL) was added 2-fluoro-5-trifluoromethylbenzoyl chloride (0.67 ml, 4.4 mmol) under ice-cooling, and the resulting mixture was stirred at room temperature for 1 hour. The reaction mixture was concentrated in vacuo. The resulting residue was purified by silica gel column chromatography (ethyl acetate/hexane) to give N-(4-chlorobenzyl)-N-(2-fluoro-5-trifluoromethylbenzoyl)-S-ethylthiourea (0.58 g, Yield: 30%) as white solid.

1H-NMR (δ ppm TMS/CDCl$_3$): 1.46 (3H, t, J=7.6 Hz), 3.29 (2H, g, J=7.6 Hz), 4.59 (2H, s), 7.22-7.41 (5H, m), 7.73 (1H, m), 8.46 (1H dd, J=6.6, 2.9 Hz), 11.5 (1H, br.s).

A mixture of N-(4-chlorobenzyl)-N'-(2-fluoro-5-trifluoromethylbenzoyl)-S-ethylthiourea (540 mg, 1.29 mmol) and NMP (2.5 mL) was stirred at 170° C. for 0.5 hour under microwave irradiation. The reaction mixture was poured into water (200 mL), and the resulting mixture was extracted with ethyl acetate (200 mL). The extract was dried over anhydrous magnesium sulfate, and concentrated in vacuo. The resulting residue was purified by silica gel column chromatography (ethyl acetate/hexane) to give 1-(4-chlorobenzyl)-2-ethylthio-6-trifluoromethylquinazoline-4(3H)-one (471 mg, Yield: 92%) as white solid.

1H-NMR (δ ppm TMS/CDCl$_3$): 1.42 (3H, t, J=7.5 Hz), 3.37 (2H, d, J=7.5 Hz), 5.46 (2H, s), 7.12 (2H, d, Hz), 7.19 (1H, d, J=8.5 Hz), 7.37 (2H, d, J=8.1 Hz), 7.77 (1H, m), 8.66 (1H, s).

A mixture of 1-(4-chlorobenzyl)-2-ethylthio-6-trifluoromethylquinazoline-4(3H)-one (208 mg, 0.52 mmol), 3-chloro-4-isopropoxyaniline (290 mg, 1.57 mmol) and acetic acid (2 mL) was stirred at 110° C. for 1 hour. The reaction mixture was poured into saturated sodium hydrogencarbonate (200 mL), and the resulting mixture was extracted with ethyl acetate (200 mL). The extract was washed by brine (200 mL), dried over anhydrous magnesium sulfate, and concentrated in vacuo. The resulting residue was purified by silica gel column chromatography (ethyl acetate/hexane) to give 1-(4-chlorobenzyl)-2-(3-chloro-4-isopropoxyphenylamino)-6-trifluoromethylquinazoline-4(3H)-one (258 mg, Yield: 95%) as pale purple amorphous.

1H-NMR (δ ppm TMS/CDCl$_3$): 1.41 (6H, d, J=6.1 Hz), 4.51 (1H, hept, J=6.1 Hz), 5.41 (2H, br.s), 6.72 (1H, dd. J=8.2, 2.9 Hz), 6.93-6.99 (2H, m), 7.07 (1H, d, J=9.3 Hz), 7.25 (2H, d, J=8.4 Hz), 7.35 (2H, d, J=8.4 Hz), 7.72 (1H, dd, J=8.8, 2.9 Hz), 8.07 (1H, br.s), 8.37 (1H, m).

EXAMPLE 17

Preparation of 4-(4-chlorobenzyl)-2-(3-chloro-4-isopropoxyphenylamino)-6-trifluoromethylquinazoline (I-210)

[Chemical Formula 139]

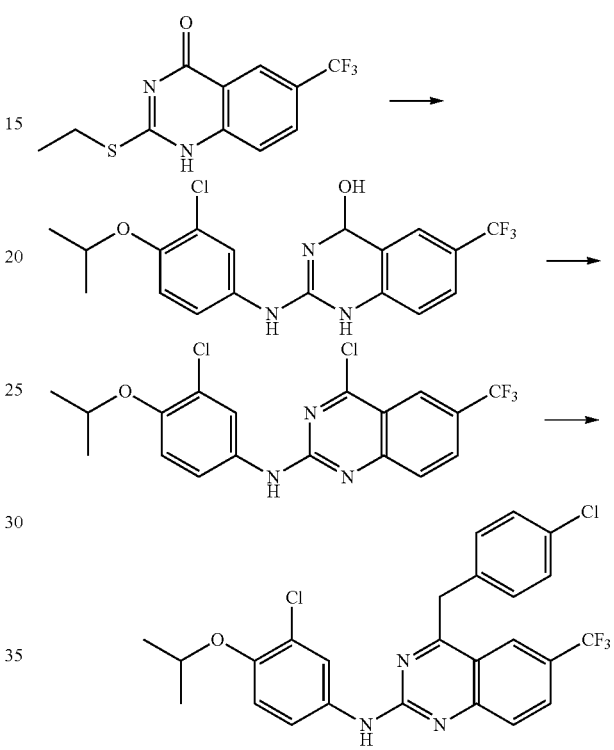

A mixture of 2-ethylthio-6-trifluoromethylquinazoline-4 (3H)-one (300 mg, 1.02 mmol), (3-chloro-4-isopropoxyaniline (568 mg, 3.1 mmol) and NMP (1.5 mL) was stirred at 170° C. for 1 hour under microwave irradiation. The reaction mixture was poured into water (200 mL), and the resulting mixture was extracted with ethyl acetate (200 mL). The extract was dried over anhydrous magnesium sulfate, and concentrated in vacuo. The resulting residue was purified by silica gel column chromatography (ethyl acetate/hexane) to give 2-(3-chloro-4-isopropoxyphenylamino)-6-trifluoromethylquinazoline-4(3H)-one (351 mg, Yield: 86%) as white solid.

1H-NMR (δ ppm TMS/DMSO-d6): 1.30 (6H, d, J=6.0 Hz), 4.61 (1H, hept, J=6.0 Hz), 7.17 (1H, d, J=8.8 Hz), 7.46-7.52 (2H, m), 7.89-7.92 (2H, m), 8.18 (1H, s), 8.87 (1H, br.s), 11.2 (1H, br.s).

A mixture of 2-(3-chloro-4-isopropoxyphenylamino)-6-trifluoromethylquinazoline-4(3H)-one (100 mg, 0.25 mmol) and phosphorus oxychloride (1.2 mL, 12.6 mmol) was stirred at 100° C. for 3 hours. The reaction mixture was concentrated in vacuo to give crude 4-chloro-2-(3-chloro-4-isopropoxyphenylamino)-6-trifluoromethylquinazoline.

To a mixture of the crude 4-chloro-2-(3-chloro-4-isopropoxyphenylamino)-6-trifluoromethylquinazoline and THF (3 mL) were added 4-chlorobenzyl zinc chloride (0.5 mol/L THF solution, 2.5 mL, 1.3 mmol) and triphenylphosphine (6.6 mg, 0.03 mmol), and then palladium acetate(II) (2.8 mg, 0.013 mmol) was added to the mixture under nitrogen atmosphere. The resulting mixture was heated at reflux for 2 hours. To the reaction mixture was added water (200 mL), and the resulting mixture was extracted with ethyl acetate (200 mL). The extract was washed by brine (200 mL), dried over anhydrous magnesium sulfate, and concentrated in vacuo. The resulting residue was purified by reversed-phase HPLC to give 4-(4-chlorobenzyl)-2-(3-chloro-4-isopropoxyphenylamino)-6-trifluoromethylquinazoline (32 mg, Yield: 25%) as yellow amorphous.

1H-NMR, (δ ppm TMS/CDCl$_3$): 1.39 (6H, d, J=6.0 Hz), 4.48 (2H, s), 4.51 (1H, hept, J=6.0 Hz), 6.93 (1H, d, J=8.7 Hz), 7.23-7.33 (4H, m), 7.43-7.52 (2H, m), 7.70-7.97 (3H, m), 8.22 (1H, s).

EXAMPLE 18

Preparation of 4-(4-chlorobenzyl)-2-dimethylamino-5-(4-isopropoxybenzyl)pyridine (I-165)

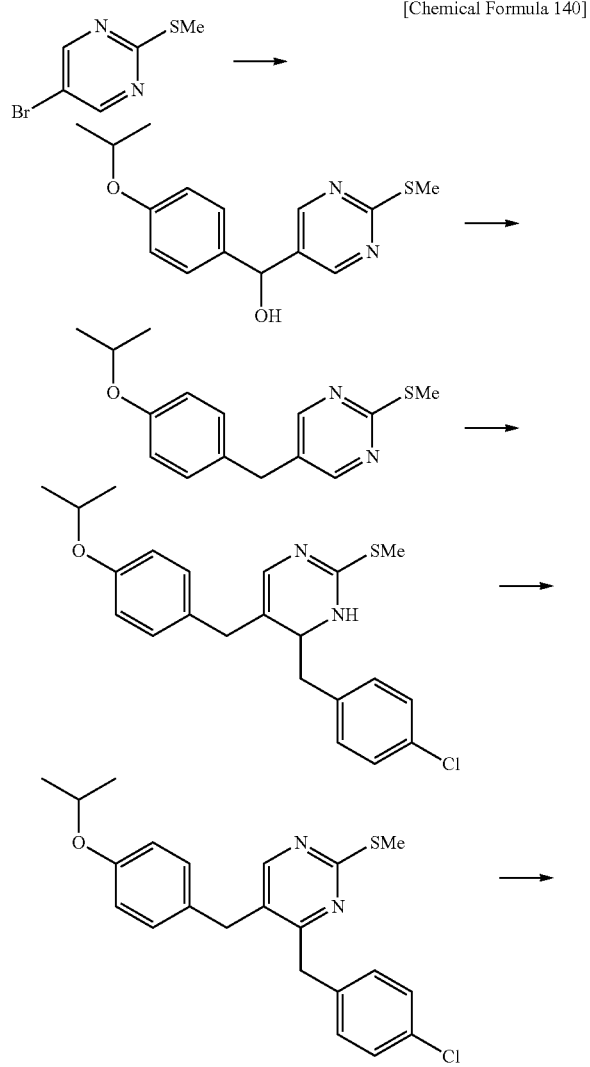

[Chemical Formula 140]

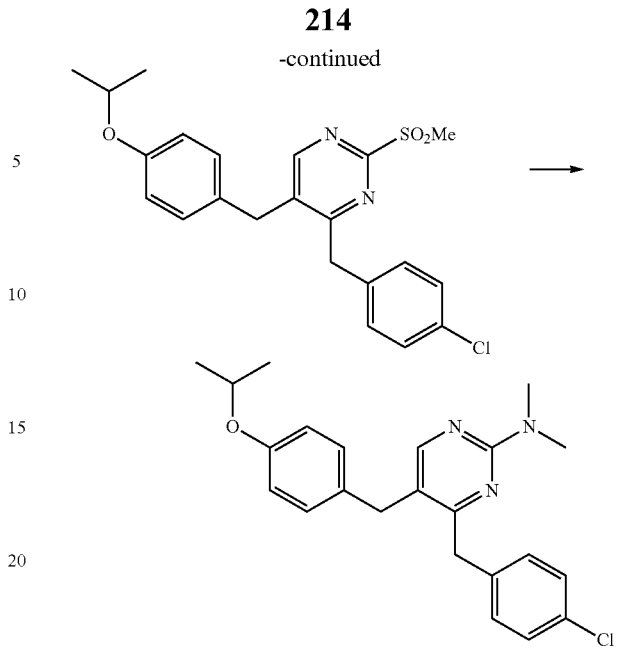

To a mixture of 5-bromo-2-(methylthio)pyridine (7.50 g, 36.6 mmol) and THF (37.5 mL) was added dropwise isopropylmagnesium chloride/lithium chloride (1.3 mol/L in THF, 31.0 ml) at room temperature over 30 minutes, and the resulting mixture was stirred at room temperature for 15 minutes. A solution of 4-isopropoxybenzaldehyde (9.01 g, 54.9 mmol) in THF (37.5 ml) was added gradually at room temperature, and the resulting mixture was stirred at room temperature for 1 hour. The reaction mixture was poured into saturated aqueous ammonium chloride (300 mL), and the mixture was extracted with ethyl acetate (300 mL×3). The extract was dried over anhydrous sodium sulphate, and concentrated in vacuo. The resulting residue was purified by silica gel column chromatography (ethyl acetate/hexane) to give 5-(4-isopropoxy-α-hydroxybenzyl)-2-(methylthio)pyrimidine (4.86 g, Yield: 46%) as orange oil.

1H-NMR (δ ppm TMS/DMSO-d6): 1.23 (6H, d, J=6.1 Hz), 2.50 (3H, s), 4.56 (1H, sept, J=6.0 Hz), 5.70 (1H, d, 3.8 Hz), 6.06 (1H, d, J=4.0 Hz), 6.86 (2H, d, J=8.6 Hz), 7.28 (2H, d, J=8.6 Hz), 8.56 (s, 2H).

To a mixture of 5-(4-isopropoxy-α-hydroxybenzyl)-2-(methylthio)pyrimidine (4.825 g, 16.6 mmol), trifluoroacetic acid (50 mL) and dichloromethane (50 mL) was added gradually triethylsilane (26.4 mL, 166 mmol) at room temperature, and the resulting mixture was stirred at room temperature for 1 hour. The reaction mixture was poured into saturated aqueous sodium bicarbonate (200 mL), and the mixture was extracted with dichloromethane (200 mL×3). The extract was dried over anhydrous sodium sulphate, and concentrated in vacuo. The resulting residue was purified by silica gel column chromatography (ethyl acetate/hexane) to give 5-(4-isopropoxybenzyl)-2-(methylthio)pyrimidine (2.76 g, Yield: 61%) as yellow oil.

1H-NMR (δ ppm TMS/DMSO-d6): 1.22 (6H, d, J=6.1 Hz), 2.50 (3H, s), 3.82 (2H, s), 4.55 (1H, sept, J=6.0 Hz), 6.83 (2H, d, J=8.6 Hz), 7.14 (2H, J=8.6 Hz), 8.53 (2H, s)

To a suspension of magnesium (0.723 g, 29.7 mmol) and diethyl ether (10 mL) was added gradually a solution of 4-chlorobenzylbromide (6.11 g, 29.7 mmol) in diethyl ether (50 mL), and the resulting mixture was stirred at room temperature for 45 minutes to give 4-chlorobenzylmagnesium bromide.

To a mixture of 5-(4-isopropoxybenzyl)-2-(methylthio)pyrimidine (2.72 g, 9.91 mmol) and diethyl ether (50 mL) was added dropwise a solution of the prepared 4-chlorobenzylmagnesium bromide in diethyl ether at room temperature over 20 minutes, and the resulting mixture was stirred at room temperature for 40 minutes. To the reaction mixture was added gradually saturated aqueous ammonium chloride (20 mL). The reaction mixture was poured into water (200 mL), and the mixture was extracted with dichloromethane (200 mL×3). The extract was dried over anhydrous sodium sulphate, and concentrated in vacuo to give crude 4-(4-chlorobenzyl)-5-(4-isopropoxybenzyl)-2-(methylthio)-1,6-dihydro-pyrimidine (6.14 g) as pale yellow oil.

The obtained crude product was dissolved in dichloromethane (100 mL). The solution was added gradually to a suspension of manganese dioxide (18.6 g, 214 mmol) and dichloromethane (100 ml) at room temperature over 40 minutes, and the resulting mixture was stirred at room temperature for 20 minutes. The insoluble were filtered off by using a filter aid such as Celite, and the filtrate was concentrated in vacuo. The resulting residue was purified by silica gel column chromatography (dichloromethane/hexane/diethyl ether) to give 4-(4-chlorobenzyl)-5-(4-isopropoxybenzyl)-2-(methylthio)pyrimidine (3.15 g, Yield: 80%) as colorless oil.

1H-NMR (δ ppm TMS/DMSO-d6): 1.22 (6H, d, J=6.0 Hz), 2.43 (3H, s), 3.89 (2H, s), 3.99 (2H, s), 4.54 (1H, sept, J=6.0 Hz), 6.81 (2H, d, J=8.7 Hz), 7.02 (2H, d, J=8.6 Hz), 7.09 (2H, d, J=8.5 Hz), 7.27 (2H, d, J=8.5 Hz), 8.42 (1H, s).

To a mixture of 4-(4-chlorobenzyl)-5-(4-isopropoxybenzyl)-2-(methylthio)pyrimidine (2.50 g, 6.27 mmol) and dichloromethane (50 mL) was added m-chloroperbenzoic acid (70% wt, (4.63 g, 18.8 mmol) at 0° C., and the resulting mixture was stirred at 0° C. for 40 minutes, Further, m-chloroperbenzoic acid (70% wt, 1.54 g, 6.27 mmol) was added to the mixture, and the mixture was stirred at 0° C. for additional 2 hours. To the reaction mixture was added 10% aqueous sodium thiosulfate (100 mL), and the resulting mixture was extracted with dichloromethane (100 mL×3). The extract was dried over anhydrous sodium sulphate, and concentrated in vacuo. The resulting residue was purified by silica gel column chromatography (ethyl acetate/hexane) to give 4-(4-chlorobenzyl)-5-(4-isopropoxybenzyl)-2-(methanesulfonyl)pyrimidine (2.50 g, Yield: 92%) as yellow oil.

1H-NMR (δ ppm TMS/DMSO-d6): 1.23 (6H, d, J=6.0 Hz), 3.32 (3H, s), 4.09 (2H, s), 4.21 (2H, s), 4.54 (1H, sept, J=6.0 Hz), 6.83 (2H, d, J=8.7 Hz), 7.06 (2H, d, J=8.6 Hz), 7.13 (2H, d, J=8.5 Hz), 7.30 (2H, d, J=8.5 Hz), 8.84 (1H, s).

To a mixture of 4-(4-chlorobenzyl)-5-(4-isopropoxybenzyl)-2-(methanesulfonyl)pyrimidine (80 mg, 0.2 mmol) and dioxane (1 mL) were added dimethylamine hydrochloride (227 mg, 2.8 diisopropylethylamine (0.47 mL, 2.8 mmol) and 4-dimethylaminopyridine (9.1 mg, 0.8 mmol), and the resulting mixture was stirred at 80° C. for 20 hours. The reaction mixture was poured into saturated aqueous sodium bicarbonate (50 mL), and the resulting mixture was extracted with ethyl acetate (50 mL×2). The extract was dried over anhydrous sodium sulphate, and concentrated in vacuo. The resulting residue was purified by silica gel column chromatography (ethyl acetate/hexane/methanol) to give 4-(4-chlorobenzyl)-2-dimethyl-amino-5-(4-isopropoxybenzyl)pyridine (51 mg, Yield: 69%) as pale brown amorphous.

1H-NMR (δ ppm TMS/DMISO-d6): 1.23 (6H, d, J=6.0 Hz), 3.05 (6H, s), 3.74 (2H, s), 3.82 (2H, s), 4.54 (1H, sept, J=6.0 Hz), 6.79 (2H, d, J=8.7 Hz), 6.98 (2H, d, J=8.6 Hz), 7.11 (2H, d, J=8.6 Hz), 7.26 (2H, d, J=8.5 Hz), 8.12 (1H, s).

EXAMPLE 19

Preparation of 4-(4-chlorobenzyl)-2-dimethyl-amino-5-(4-isopropoxyphenylamino)pyrimidine (I-181)

[Chemical Formula 141]

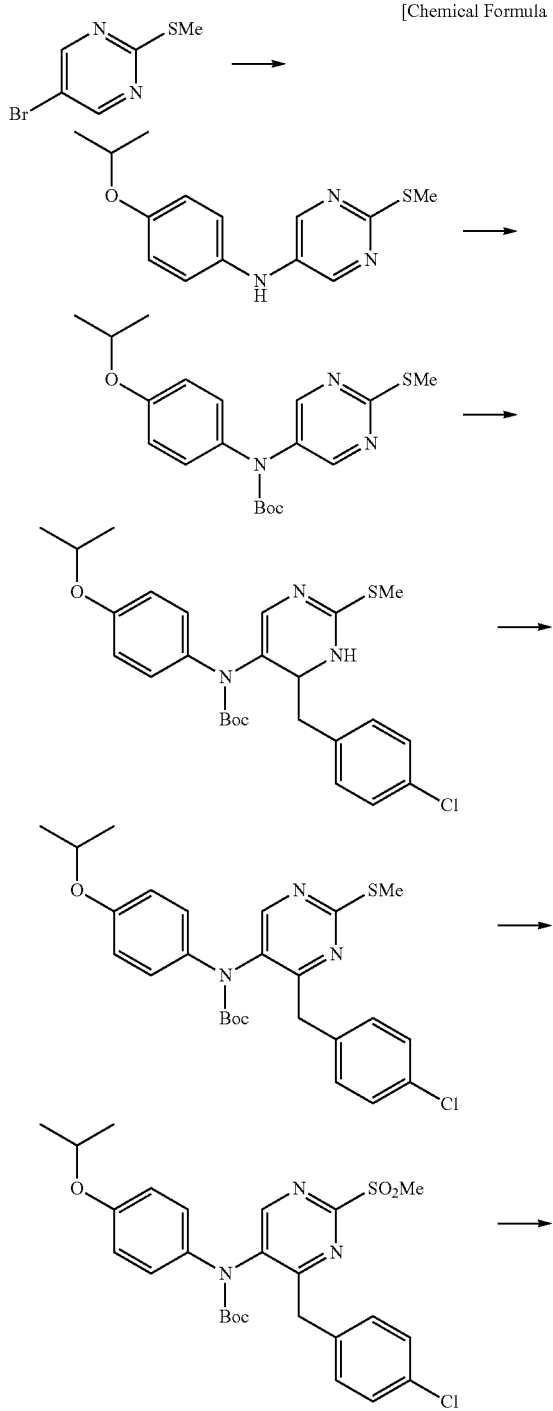

-continued

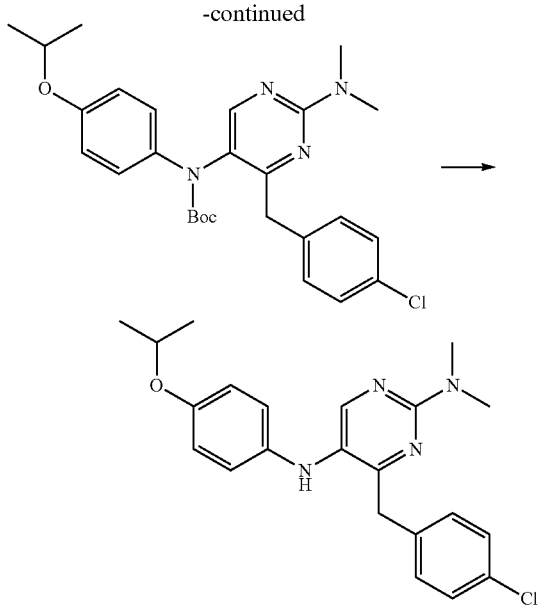

To a mixture of 5-bromo-2-(methylthio)pyrimidine (600 mg, 2.92 mmol), tris(dibenzylideneacetone)(0)-chloroform (303 mg, 0.293 mmol), 4,5-bis(diphenylphosphino)-9,9-dimethylxanthene (169 mg, 0.293 mmol), cesium carbonate (1.91 g, 5.85 mmol) and dioxane (13 mL) was added 4-isopropoxyaniline (531 mg, 3.51 mmol) under nitrogen atmosphere, and the resulting mixture was stirred at 90° C. for 18 hours. The reaction mixture was poured into water (200 mL), and the mixture was extracted with ethyl acetate (100 mL×3). The extract was washed by brine (100 mL), dried over anhydrous magnesium sulfate, and concentrated in vacuo. The resulting residue was purified by silica gel column chromatography (methanol/dichloromethane and ethyl acetate/hexane). The resulting residue was precipitated by dichloromethane and hexane to give 5-(4-isopropoxyphenylamino)-2-(methylthio)pyrimidine (5.24 g, Yield: 65%) as yellow powder.

1H-NMR (DMSO-d6): 1.24 (6H, d, Hz), 2.46 (3H, s), 4.49 (1H, sept, J=6.0 Hz), 6.85 (2H, d, J=9.0 Hz), 7.02 (2H, d, J=9.0 Hz), 8.06 (1H, s), 8.34 (2H, s).

To a mixture of 5-(4-isopropoxyphenylamino)-2-(methylthio)pyrimidine (5.93 g, 21.5 mmol), 4-dimethylaminopyridine (1.32 g, 10.8 mmol) and dichloromethane (400 mL) was added dropwise a solution of di-t-butyl dicarbonate (6.16 g, 28.2 mmol) in dichloromethane (200 mL) at room temperature over 1 hour, and the resulting mixture was stirred at room temperature for 3 hours. Further, to the reaction mixture was added di-t-butyl dicarbonate (6.16 g, 28.2 mmol), and the resulting mixture was stirred at room temperature for 16 hours. The reaction mixture was poured into saturated aqueous sodium bicarbonate (500 mL), and the resulting mixture was extracted with dichloromethane (300 mL×2). The extract was dried over anhydrous sodium sulphate, and concentrated in vacuo. The resulting residue was purified by silica gel column chromatography (ethyl acetate/hexane) to give 5-[4-isopropoxyphenyl(t-butoxycarbonyl)amino]-2-(methylthio)pyrimidine (7.05 g, Yield: 87%) as yellow solid.

1H-NMR (DMSO-d6): 1.25 (6H, d, J=6.0 Hz), 1.38 (OH, s), 2.50 (3H, s), 4.59 (1H, sept, J=6.0 Hz), 6.90 (2H, d, J=9.0 Hz), 7.22 (2H, d, J=9.0 Hz), 8.56 (2H, s)

Preparation of 4-chlorobenzylmagnesium bromide

To a suspension of magnesium (0.77 g, 31.6 mmol) and diethyl ether (10 mL) was added gradually dropwise a solution of 4-chlorobenzylbromide (6.50 g, 31.6 mmol) in diethyl ether (55 mL), and the resulting mixture was stirred at room temperature for 45 minutes to give 4-chlorobenzylmagnesium bromide.

To a mixture of 5-[4-isopropoxyphenyl(t-butoxycarbonyl) amino]-2-(methylthio)pyrimidine (4.00 g, 11 mmol) and diethyl ether (65 mL) was added dropwise a solution of prepared 4-chlorobenzylmagnesium bromide in diethyl ether at room temperature over 20 minutes, and the resulting mixture was stirred at room temperature for 2 hours. To the reaction mixture was added gradually saturated aqueous ammonium chloride (30 mL). The reaction mixture was poured into water (200 mL), and the mixture was extracted with ethyl acetate (200 mL×2). The extract was dried over anhydrous sodium sulphate, and concentrated in vacuo to give crude 4-(4-chlorobenzyl)-5-[4-isopropoxyphenyl(t-butoxycarbonyl) amino]-2-(methylthio)-1,6-dihydro-pyrimidine (7.73 g) as pale yellow oil.

To the mixture of the obtained crude product and THF (120 mL) was added dropwise a solution of 2,3-dichloro-5,6-dicyano-1,4-benzoquinone (2.4 g, 11 mmol) in THF (20 ml) at room temperature over 20 minutes, and the resulting mixture was stirred at room temperature for 25 minutes. To the reaction mixture was added saturated aqueous sodium bicarbonate (30 mL), and the mixture was poured into water (300 ml). The resulting mixture was extracted with ethyl acetate (400 mL×2). The extract was washed by brine (300 mL), dried over anhydrous magnesium sulfate, and concentrated in vacuo. The resulting residue was purified by silica gel column chromatography (methanol/dichloromethane and ethyl acetate/ hexane) to give 4-(4-chlorobenzyl)-5-[4-isopropoxyphenyl (t-butoxycarbonyl)amino]-2-(methylthio)pyrimidine (4.06 g, Yield: 77%) as yellow oil.

1H-NMR (DMSO-d6): 1.24 (6H, d, J=6.0 Hz), 1.29 (9H, s), 2.47 (3H, s), 4.56 (1H, sept, J=6.0 Hz), 6.86 (2H, d, J=9.0 Hz), 7.08-7.15 (4H, m), 7.31 (2H, d J=8.5 Hz), 8.67 (1H, s).

To a mixture of 4-(4-chlorobenzyl)-5-[4-isopropoxyphenyl(t-butoxycarbonyl)amino]-2-(methylthio)pyrimidine (4.06 g, 8.12 mmol) and dichloromethane (80 mL) was added m-chloroperbenzoic acid (70% wt, 4.00 g, 18 mmol) at 0° C. over 10 minutes, and the resulting mixture was stirred at 0° C. for 30 minutes. Further, m-chloroperbenzoic acid (70% wt, 2.00 g, 8.10 mmol) was added to the mixture, and the resulting mixture was stirred at 0° C. for additional 30 minutes, and at room temperature for additional 1 hour. To the reaction mixture was added saturated aqueous sodium bicarbonate (100 mL), and the resulting mixture was extracted with dichloromethane (100 mL×3). The extract was dried over anhydrous sodium sulphate, and concentrated in vacuo. The resulting residue was purified by silica gel column chromatography (ethyl acetate/hexane) to give 4-(4-chlorobenzyl)-5-[4-isopropoxyphenyl(t-butoxycarbonyl)amino]-2-(methanesulfonyl)pyrimidine (3.83 g, Yield: 89%) as white solid.

1H-NMR (DMSO-d6): 1.25 (6H, d, J=6.0 Hz), 1.31 (9H, s), 3.40 (3H, s), 4.04 (2H, s), 4.57 (1H, sept, J=6.0 Hz), 6.88 (2H, d, J=9.0 Hz), 7.09-7.16 (4H, m), 7.33 (2H, d, J=8.5 Hz), 8.67 (1H, s).

To a mixture of 4-(4-chlorobenzyl)-5-[4-isopropoxyphenyl(t-butoxycarbonyl)amino]-2-(methanesulfonyl)pyrimidine (130 mg, 0.24 mmol) and dioxane (2 mL) were added dimethylamine hydrochloride (300 mg, 3.7 mmol), diisopropylethylamine (0.64 mL, 3.7 mmol) and 4-dimethylaminopyridine (12 mg, 0.1 mmol), and the resulting mixture was stirred at 80° C. for 3 hours. The reaction mixture was poured into saturated aqueous sodium bicarbonate (50 mL), and the resulting mixture was extracted with ethyl acetate (50 mL×2). The extract was dried over anhydrous sodium sulphate, and concentrated in vacuo. The resulting residue was purified by silica gel column chromatography (ethyl acetate/hexane/methanol) to give 4-(4-chlorobenzyl)-2-dimethyl-amino-5-[4-isopropoxyphenyl(t-butoxycarbonyl)amino]pyrimidine. The obtained 4-(4-chlorobenzyl)-2-dimethyl-amino-5-[4-isopropoxyphenyl(t-butoxycarbonyl)amino]pyrimidine was dissolved in 4 mol/L hydrogen chloride in dioxane (1 and the resulting mixture was stirred at room temperature for 20 hours. The reaction mixture was concentrated in vacuo. The residue was added to saturated aqueous sodium bicarbonate (50 and the resulting mixture was extracted with ethyl acetate (50 mL×2). The extract was dried over anhydrous sodium sulphate, and concentrated in vacuo. The resulting residue was purified by silica gel column chromatography (ethyl acetate/hexane) to give 4-(4-chlorobenzyl)-2-dimethyl-amino-5-[4-isopropoxyphenylamino]pyrimidine (53 mg, Yield: 55%) as pale brown amorphous.

1H-NMR (δ ppm TMS/DMSO-d6): 1.20 (6H, d, J=6.0 Hz), 3.06 (6H, s), 3.84 (2H, s), 4.37 (1H, sept, J=6.0 Hz), 6.43 (2H, d, J=8.9 Hz), 6.69 (2H, d, J=8.9 Hz), 7.17-7.26 (4H, m), 8.07 (1H, s).

EXAMPLE 20

Preparation of 5-ethyl-2-(3-fluoro-4-isopropoxyphenylamino)-3-(4-methylphenoxy)pyrazine (I-072)

[Chemical Formula 142]

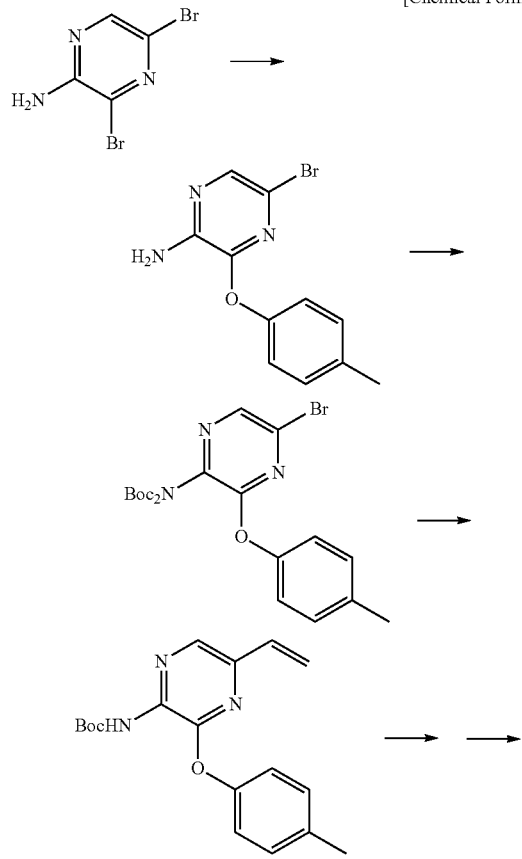

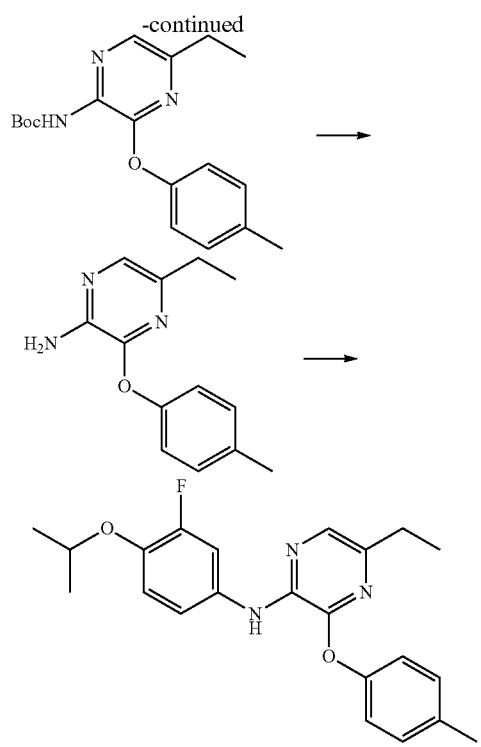

To a mixture of 2-amino-3,5-dibromopyrazine (2.43 g, 9.61 mmol) and THF (60 mL) were added 60% sodium hydride (404 mg, 10.1 mmol) and p-cresol (1.06 mL, 10.1 mmol) under ice-cooling, and the resulting mixture was stirred at 50° C. for 20 hours. To the reaction mixture was added water, and the mixture was extracted with ethyl acetate. The extract was washed by brine, dried over anhydrous sodium sulphate, and concentrated in vacuo. The resulting residue was purified by silica gel column chromatography (ethyl acetate/hexane) to give 5-bromo-2-amino-3-(4-methylphenoxy)pyrazine (1.21 g, Yield: 45%) as colorless solid.

1H-NMR (δ ppm TMS/DMSO-d6): 2.33 (3H, s), 6.83 (2H, s), 7.11 (2H, d, J=8.1 Hz), 7.25 (2H, d, J=8.1 Hz), 7.73 (1H, s).

To a mixture of 5-bromo-2-amino-3-(4-methylphenoxy)pyrazine (427 mg, 1.52 mmol) and THF (5 mL) were added di-t-butyl dicarbonate (0.885 mL, 3.81 mmol) and small amount of 4-dimethylaminopyridine, and the resulting mixture was stirred at room temperature for 20 hours. To the reaction mixture was added water, and the mixture was extracted with ethyl acetate. The extract was washed by brine, dried over anhydrous sodium sulphate, and concentrated in vacuo. The resulting residue was purified by silica gel column chromatography (ethyl acetate/hexane) to give [5-bromo-3-(4-methylphenoxy)-pyrazine-2-yl]dicarbamic acid di-t-butylester (730 mg, Yield: 100%) as colorless oil.

1H-NMR (δ ppm TMS/DMSO-d6): 1.40 (18H, s), 2.33 (3H, s), 7.02 (2H, d, J=8.1 Hz), 7.29 (2H, d, J=8.1 Hz), 8.53 (1H, s).

To a mixture of [5-bromo-3-(4-methylphenoxy)pyrazine-2-yl]dicarbamic acid di-t-butylester (589 mg, 1.23 mmol), THF mL) and DMF (6 mL) were added tributylvinylstannane (1.08 mL, 3.68 mmol), tetrakistriphenylphosphine(0) (71 mg, 0.061 mmol), and lithium chloride (156 mg, 3.68 mmol), and the resulting mixture was heated at reflux for 5 hours. To the reaction mixture was added water, and the mixture was extracted with ethyl acetate. The extract was washed by brine, dried over anhydrous sodium sulphate, and concentrated in vacuo. The resulting residue was purified by silica gel column chromatography (ethyl acetate/hexane) to give [(4-methylphenoxy)-5-vinylpyrazine-2-yl]carbamic acid t-butylester (60 mg, Yield: 15%) as pale yellow solid.

1H-NMR (δ ppm TMS/CDCl3): 1.56 (9H, s), 2.38 (3H, s), 5.27 (1H, d, J=10.6 Hz), 5.89 (1H, d, J=16.9 Hz), 6.58 (1H, dd, J=16.9, 10.6 Hz), 7.08 (2H, d, J=8.1 Hz), 7.21 (2H, d, J=8.1 Hz), 7.53 (1H, s), 7.96 (1H, s), A mixture of [(4-methylphenoxy)-5-vinylpyrazine-2-yl] carbamic acid. t-butylester (59.5 mg, 0.182 mmol) and methanol (1 mL) was hydrogenated under 5% Pd/C. The reaction mixture was filtered off to remove the catalyst. The filtrate was concentrated in vacuo to give [5-ethyl-3-(4-methylphenoxy)pyrazine-2-yl]carbamic acid t-butylester (53 mg, Yield: 89%) as white solid.

1H-NMR (δ ppm TMS/CDCl3): 1.13 (3H, t, J=7.4 Hz), 1.55 (9H, s), 2.37 (3H, s), 2.57 (2H, q, J=7.4 Hz), 7.04 (2H, d, J=8.3 Hz), 7.20 (2H, d, J=8.3 Hz), 7.38 (1H, s), 7.91 (1H, s).

To a mixture of [5-ethyl-3-(4-methylphenoxy-)pyrazine-2-yl]carbamic acid t-butylester (53.2 mg, 0.162 mmol) and chloroform (0.5 mL) was added trifluoroacetic acid (0.25 mL, 3.2 mmol), and the resulting mixture was stirred at room temperature for 4 hours. The reaction mixture was concentrated, and 1 mol/L aqueous sodium hydroxide was added to the residue. The mixture was extracted with ethyl acetate. The extract was washed by brine, dried over anhydrous sodium sulphate, and concentrated in vacuo. The resulting residue was purified by reversed-phase HPLC (0.3% formic acid; acetonitrile) to give 2-amino-5-ethyl-3-(4-methylphenoxy) pyrazine (59 mg, Yield: 50%) as yellow solid.

1H-NMR (δ ppm TMS/DMSO-d6): 1.02 (3H, t, J=7.3 Hz), 2.31 (3H, s), 2.37 (2H, q, J=7.3 Hz), 6.25 (2H, s), 7.06 (2H, d, J=8.1 Hz), 7.21 (2H, d, J=8.1 Hz), 7.49 (1H, s).

To a mixture of 2-amino-5-ethyl-3-(4-methylphenoxy) pyrazine (55.0 mg, 0.240 mmol) and dioxane (1 mL) were added 4-bromo-2-fluoro-1-isopropoxybenzene (61 mg, 0.26 mmol), tris(dibenzylideneacetone)(0) (2.8 mg, 0.0030 mmol), 4,5-bis(diphenylphosphine)-9,9-dimethylxanthene (4.2 mg, 0.0072 mmol) and sodium phenoxide trihydrate (61 mg, 0.36 mmol), and the resulting mixture was heated at reflux for 4 hours. To the reaction mixture was added saturated aqueous sodium bicarbonate, and the mixture was extracted with ethyl acetate. The extract was washed by brine, dried over anhydrous sodium sulphate, and concentrated in vacuo. The resulting residue was purified by reversed-phase HPLC (0.3% formic acid/acetonitrile) to give 5-ethyl-2-(3-fluoro-4-isopropoxyphenylamino)-3-(4-methylphenoxy) pyrazine (17 mg, Yield: 18%) as pale brown solid.

1H-NMR (δ ppm TMS/DMSO-d6): 1.05 (3H, t, J=7.5 Hz), 1.26 (6H, d, J=5.8 Hz), 2.33 (3H, s), 2.44 (2H, q, J=7.5 Hz), 4.45-4.52 (1H, m), 705-7.17 (3H, m), 725 (2H, d, J=8.6 Hz), 7.55-7.61 (1H, m), 7.69 (1H, s), 7.85-7.91 (1H, m), 8.93 (1H, s).

EXAMPLE 21

Preparation of 3-t-butyl-1-(4-chlorobenzyl)-5-(3-fluoro-4-isopropoxyphenylamino)pyrazole (I-050)

[Chemical Formula 143]

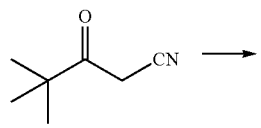

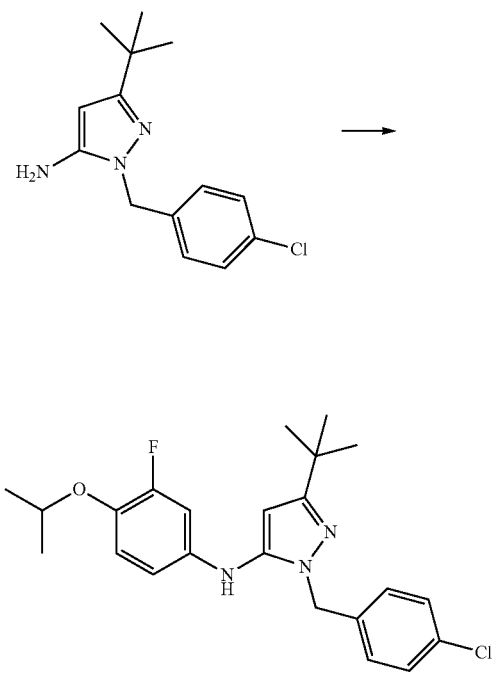

To a mixture of 4-chlorobenzylhydrazine dihydrochloride (166 mg, 0.723 mmol) and ethanol (2 were added triethylamine (0.211 mL, 1.52 mmol) and pivaloylacetonitrile (91.0 mg, 0.723 mmol), and the resulting mixture was heated at reflux for 6 hours. The reaction mixture was concentrated in vacuo. The resulting residue was purified by silica gel column chromatography (ethyl acetate/hexane) to give 5-amino-3-t-butyl-1-(4-chlorobenzyl)pyrazole (144 mg, Yield 76%) as colorless solid.

1H-NMR (δ ppm TMS/DMSO-d6): 1.16 (9H, s), 5.04 (2H, s), 5.10 (2H, s), 5.19 (1H, s), 7.11 (2H, d, J=8.1 Hz), 7.37 (2H, d, J=8.1 Hz).

To a mixture of 5-amino-3-t-butyl-1-(4-chlorobenzyl) pyrazole (50.0 mg, 0.190 mmol) and dioxane (1 mL) were added 4-bromo-2-fluoro-1-isopropoxybenzene (49 mg, 0.21 mmol), tris(dibenzylideneacetone)(0) (2.2 mg, 0.0024 mmol), 4,5-bis(diphenylphosphino)-9,9-dimethylxanthene (3.3 mg, 0.0057 mmol) and sodium phenoxide trihydrate (48 mg, 0.28 mmol), and the resulting mixture was stirred at 170° C. for 30 minutes under microwave irradiation. To the reaction mixture was added saturated aqueous sodium bicarbonate, and the mixture was extracted with ethyl acetate. The extract was washed by brine, dried over anhydrous sodium sulphate, and concentrated in vacuo. The resulting residue was purified by silica gel column chromatography (ethyl acetate/hexane) and reversed-phase HPLC (0.3% formic acid/acetonitrile) to give 3-t-butyl-1-(4-chlorobenzyl)-5-(3-fluoro-4-isopropoxyphenylamino)pyrazole (33 mg, Yield: 42%) as pale yellow solid.

1H-NMR (δ ppm TMS/DMSO-d6): 1.20-1.24 (15H, m), 4.30-4.37 (1H, m), 5.18 (2H, s), 5.92 (1H, s), 6.53-6.65 (2H, m), 6.96 (1H, t, J=9.0 Hz), 7.06 (2H, d, J=8.1 Hz), 7.34 (2H, d, J=8.1 Hz), 7.91 (1H, s).

EXAMPLE 22

Preparation of 6-acetylamino-1-(4-chlorobenzyl)-2-(3-fluoro-4-isopropoxyphenylamino)pyrimidine-4(1H)-one (I-136)

[Chemical Formula 144]

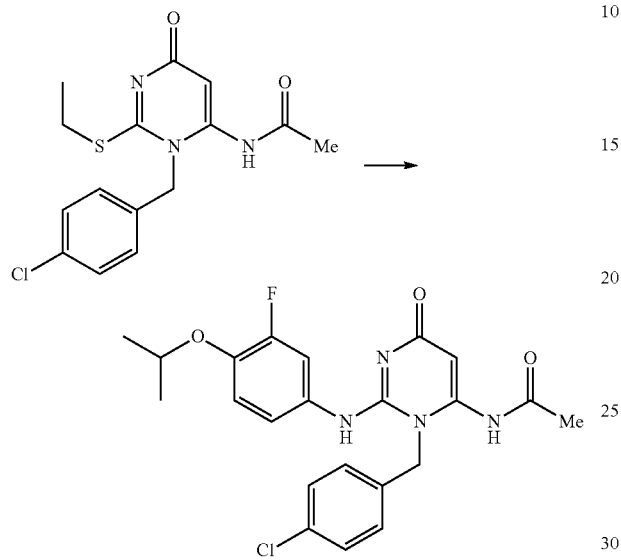

A mixture of 6-acetylamino-1-(4-chlorobenzyl)-2-ethylthiopyrimidine-4(1H)-one (170 mg, 0.5 mmol), 3-fluoro-4-isopropoxyaniline (1.28 mg, 0.75 mmol), t-butanol (3 mL) and acetic acid (0.43 mL) was heated at reflux overnight. The reaction mixture was poured into saturated aqueous sodium bicarbonate (100 mL), and the mixture was extracted with ethyl acetate (100 mL). The extract was washed by saturated aqueous sodium bicarbonate (100 mL) and brine (100 mL), dried over anhydrous sodium sulphate, and concentrated in vacuo. The resulting residue was purified by silica gel column chromatography (methanol/chloroform). The resulting residue was precipitated by ethyl acetate and hexane to give 6-acetylamino-1-(4-chlorobenzyl)-2-(3-fluoro-4-isopropoxyphenylamino)pyrimidine-4(1H)-one (86 mg, Yield: 38%) as white powder.

1H-NMR (δ ppm TMS/DMSO-d6): 1.25 (6H, d, J=5.7 Hz), 1.97 (1.5H, s), 2.01 (1.5H, s), 4.38-4.58 (1H, m), 5.19 (1H, s), 5.22 (1H, 0, 5.42 (0.5H, s), 5.62 (0.5H, s), 6.45 (0.5H, m), 6.66 (0.5H, dd, J=2.4 Hz, 12.6 Hz), 6.93-7.18 (2.5H, m), 7.20-7.34 (1.5H, m), 7.35-7.46 (2H, m), 8.93 (0.5H, s), 9.76 (0.5H, s), 9.95 (0.5H, s), 10.12 (0.5H, s)

EXAMPLE 23

Preparation of 3-benzyl-5-(4-methylbenzyl)-6-(phenylamino)pyrimidine-2,4(1H, 3H)-dion (I-013)

[Chemical Formula 145]

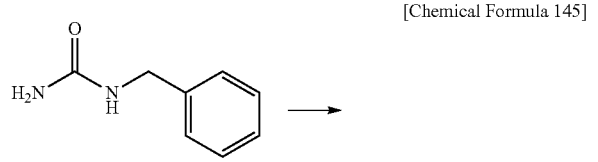

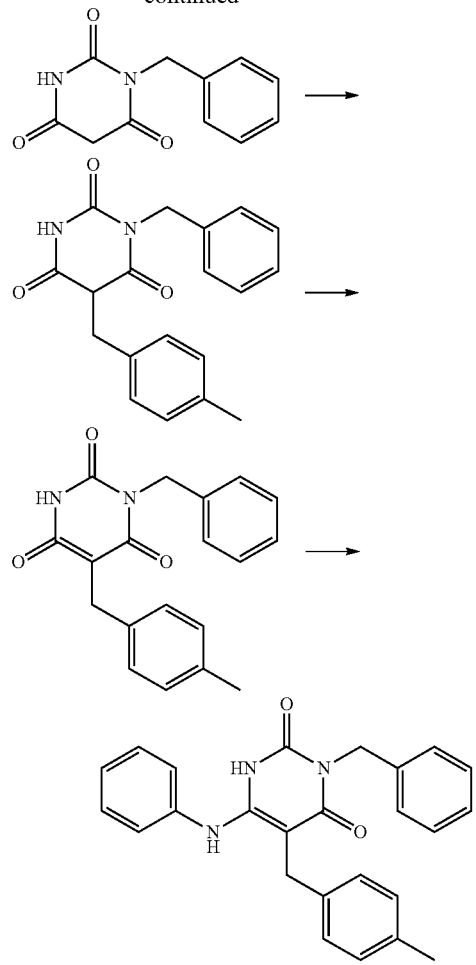

To a mixture of ethyl malonate (5.00 g, 31.2 mmol) and methanol (20 mL) were added 1-benzylurea (4.69 g, 31.2 mmol) and sodium methoxide (1 mol/L methanol solution, 31.2 mL, 31.2 mmol), and the resulting mixture was heated at reflux for 18 hours. The reaction mixture was concentrated, and the water was added to the residue. The insoluble were removed by filtration. To the filtrate was added 2 mol/L hydrochloric acid, and the precipitated solid was filtered off to give 1-benzyl-pyrimidine-2,4,6-trion (2.72 g, Yield: 40%) as colorless solid.

1H-NMR (δ ppm TMS/DMSO-d6): 3.71 (2H, s), 4.88 (2H, s), 7.19-7.38 (5H, m), 11.43 (1H, brs).

To a mixture of 1-benzyl-pyrimidine-2,4,6-trion (2.00 g, 9.17 mmol) and ethanol (20 mL) was added 4-methylbenzaldehyde (1.09 mL, 9.17 mmol), and the resulting mixture was heated at reflux for 1 hour. The precipitated solid was filtered off, and obtained solid was washed by methanol. To the mixture of the obtained solid and ethanol (30 mL) was added sodium borohydride (598 mg, 15.8 mmol), and the resulting mixture was stirred at room temperature for 2 hours. To the mixture were added 2 mol/L hydrochloric acid and methanol, and the precipitated solid was filtered off to give 1-benzyl-5-(4-methylbenzyl)pyrimidine-2,4,6-tiron (2.95 g, Yield: 98%) as colorless solid.

1H-NMR (δ ppm TMS/CDCl3): 2.24 (3H, s), 3.35-3.47 (2H, m), 3.64-3.74 (1H, m), 4.87 (2H, s), 8.80-6.92 (4H, m), 7.18-7.32 (5H, m), 8.98 (1H, brs).

To a mixture of 1-benzyl-5-(4-methylbenzyl)pyrimidine-2,4,6-trion (500 mg, 1.55 mmol) and phosphorus oxychloride (5.5 mL) was added 85% phosphoric acid (1.0 mL), and the resulting mixture was stirred at 100° C. for 3 hours. To the reaction mixture was added iced water, and the precipitated solid was filtered off to give crude 3-benzyl-8-chloro-5-(4-methylbenzyl)pyrimidine-2,4(1H,3H)-dion (874 mg).

1H-NMR (δ ppm TMS/CDCl3): 2.30 (3H, s), 3.78 (2H, s), 5.08 (2H, s), 7.01-7.12 (2H, m), 7.14-7.33 (5H, m), 7.40-7.49 (2H, m), 10.88 (1H, brs).

To a mixture of 3-benzyl-6-chloro-5-(4-methylbenzyl)pyrimidine-2,4(1H,3H)-dion (40.0 mg, 0.117 mmol) and NMP (0.2 int) was added aniline (0.2 mL), and the resulting mixture was stirred at 180° C. for 90 minutes under microwave irradiation. The reaction mixture was purified by eversed-phase HPLC (0.3% formic acid/acetonitrile), 3-benzyl-5-(4-methylbenzyl)-8-(phenylamino)pyrimidine-2,4(1H,3H)-dion (12 mg, Yield: 26%) as pale grey color.

1H-NMR (δ ppm TMS/CDCl3): 2.32 (3H, s), 3.80 (2H, s), 4.98 (2H, s), 6.06 (1H, s), 8.91 (2H, d, J=7.6 Hz), 7.12-7.41 (12H, m), 8.25 (1H, brs).

EXAMPLE 24

Preparation of 5-benzyl-1-(4-chlorobenzyl)-2-(3-chloro-4-isopropoxyphenylamino)pyrimidine-4(1H)-one (I-023)

[Chemical Formula 146]

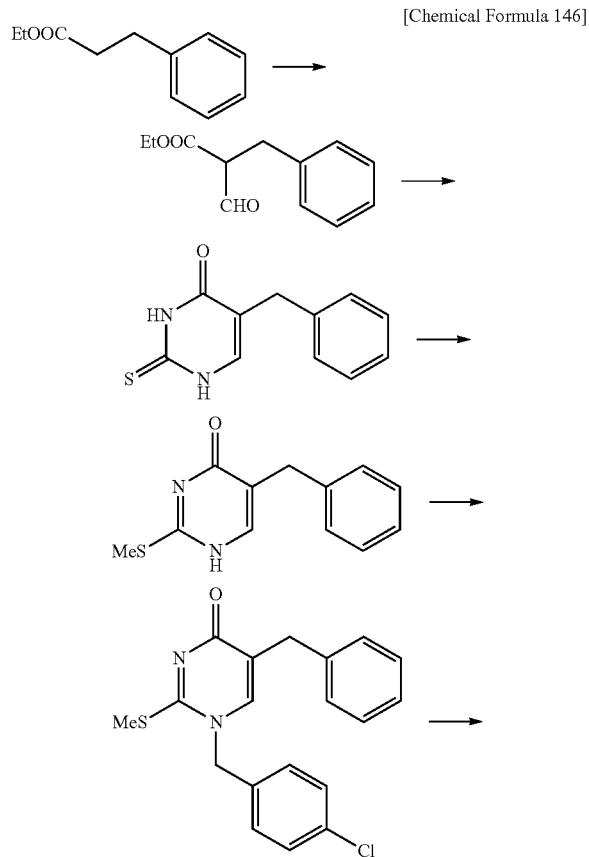

-continued

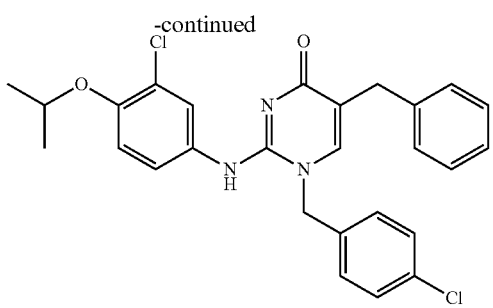

To a mixture of 80% sodium hydride (1.12 g, 28.1 mmol) and dimethoxyethane (50 mL) were added 3-phenylpropanoic acid ethyl ester (5.00 g, 28.1 mmol) and formic acid ethyl (2.27 mL, 28.1 mmol), and the resulting mixture was stirred at room temperature for 18 hours. To the reaction mixture was added water, and the mixture was washed by diethyl ether. To the water layer was added 2 mol/L hydrochloric acid, and the mixture was extracted with ethyl acetate. The extract was washed by brine, dried over anhydrous sodium sulphate, and concentrated in vacuo to give crude 2-formyl-3-phenylpropanoic acid ethyl ester (3.25 g, Yield: 56%).

To a mixture of the crude 2-formyl-3-phenylpropanoic acid ethyl ester (3.25 g, 15.8 mmol) and methanol (15 mL) were added thiourea (1.20 g, 15.8 mmol) and sodium methoxide (1 mol/L methanol solution, 15.8 mL, 15.8 mmol), and the resulting mixture was heated at reflux for 17 hours. The reaction mixture was concentrated, and 2 mmol/L hydrochloric acid was added to the obtained residue. The precipitated solid was filtered off to give crude 5-benzyl-2-tioxo-2,3-dihydro-pyrimidine-4(1H)-one (1.58 g, Yield: 46%).

To a mixture of the crude 5-benzyl-2-thioxo-2,3-dihydropyrimidine-4(1H)-one (500 mg, 2.29 mmol) and ethanol (4.6 mL) were added 1 mol/L aqueous sodium hydroxide (2.3 mL, 2.3 mmol) and methyl iodide (0.14 mL, 2.3 mmol), and the resulting mixture was stirred at 60° C. for 2 hours. To the reaction mixture was added water, and the precipitated solid was filtered off to give 5-benzyl-2-(methylthio)pyrimidine-4 (1H)-one (418 mg, Yield: 79%) as pale yellow solid.

1H-NMR (δ ppm TMS/DMSO-d6): 2.46 (3H, s), 3.62 (2H, s), 7.15-7.31 (6H, m), 7.76 (1H, s).

To a mixture of 5-benzyl-2-(methylthio)pyrimidine-4 (1H)-one (100 mg, 0.430 mmol) and dichloromethane (1 mL) were added diisopropylethylamine (0.083 mL, 0.47 mmol) and 4-chlorobenzylbromide (88 mg, 0.43 mmol) under ice-cooling, and the resulting mixture was stirred at room temperature for 6 hours. The reaction mixture was concentrated, and methanol and water were added to the residue. The precipitated solid was filtered off to give 5-benzyl-1-(4-chlorobenzyl)-2-(methylthio)pyrimidine-4(1H)-one (121 mg, Yield: 79%) as pale brown solid.

1H-NMR (δ ppm TMS/DMSO-d6): 2.43 (3H, s), 3.57 (2H, s), 5.13 (2H, s), 7.16-7.27 (7H, m), 7.47 (2H, d, J=8.52 Hz), 7.82 (1H, s).

A mixture of 5-benzyl-1-(4-chlorobenzyl)-2-(methylthio) pyrimidine-4(1H)-one (120 mg, 0.338 mmol), 3-chloro-4-isopropoxyaniline (94 mg, 0.51 mmol), t-butanol (1.2 mL) and acetic acid (0.29 mL) was heated at reflux overnight. To the reaction mixture was added water, and the mixture was extracted with ethyl acetate. The extract was washed by brine, dried over anhydrous sodium sulphate, and concentrated in vacuo. The resulting residue was purified by silica gel column chromatography (ethyl acetate/hexane) and reversed-phase HPLC (0.3% formic acid/acetonitrile) to give 5-benzyl-1-(4- chlorobenzyl)-2-(3-chloro-4-isopropoxyphenylamino)pyrimidine-4(1H)-one (88 mg, Yield: 53%) as colorless solid.

1H-NMR (δ ppm TMS/CDCl3): 1.37-1.39 (6H, m), 3.58 (2H, s), 4.41-4.53 (1H, m), 4.90 (2H, s), 6.65 (1H, dd, J=8.69, 2.59 Hz), 6.74-6.75 (1H, m), 6.86 (1H, d, J=2.59 Hz), 6.93 (1H, d, J=8.69 Hz), 7.16-7.36 (9H, m), 7.97 (1H, s).

EXAMPLE 25

Preparation of 5-bromo-3-(4-chlorobenzyl)-2-(methylthio)pyrimidine-4(3H)-one

[Chemical Formula 147]

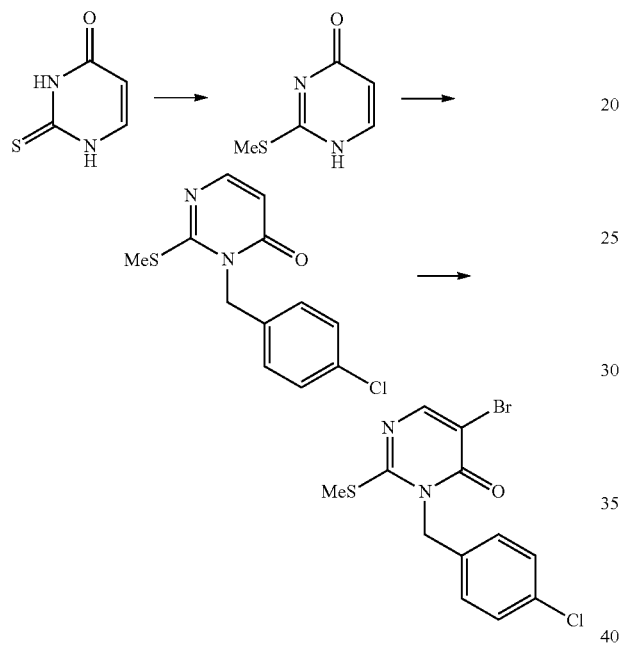

To a mixture of 2-thiouracil (25.0 g, 195 mmol) and ethanol (250 mL) were added 1 mol/L sodium hydroxide (1.07 mL, 215 mmol) and methyl iodide (12.8 mL, 205 mmol), and the resulting mixture was stirred at 60° C. for 7 hours. The reaction mixture was concentrated, and 2 mol/L hydrochloric acid was added to the residue. The precipitated solid was filtered off to give 2-(methylthio)pyrimidine-4(1H)-one (14.6 g, Yield: 53%) as colorless 1H-NMR (δ ppm TMS/DMSO-d6): 2.47 (3H, s), 6.09 (1H, d, J=5.6 Hz), 7.86 (1H, d, J=5.6 Hz), 12.67 (1H, brs).

To a mixture of 2-(methylthio)pyrimidine-4(1H)-one (10.0 g, 70.3 mmol) and DMF (200 mL) were added potassium carbonate (14.6 g, 106 mmol) and 4-chlorobenzylbromide (15.9 g, 77.0 mmol), and the resulting mixture was stirred at room temperature for 20 hours. To the reaction mixture was added water, and the mixture was extracted with chloroform. The extract was washed by brine, dried over anhydrous sodium sulphate, and concentrated in vacuo. The resulting residue was purified by silica gel column chromatography (ethyl acetate/hexane) to give 3-(4-chlorobenzyl)-2-(methylthio)pyrimidine-4(3H)-one (7.3 g, Yield: 39%) as colorless solid.

1H-NMR (δ ppm TMS/DMSO-d6): 2.50 (3H, s), 5.21 (2H, s), 6.28 (1H, d, J=6.3 Hz), 7.25 (2H, d, J=7.8 Hz), 7.40 (2H, d, J=7.8 Hz), 7.90 (1H, d, J=6.3 Hz).

To a mixture of 3-(4-chlorobenzyl)-2-(methylthio)pyrimidine-4(3H)-one (4.00 g, 15.0 mmol) and dichloromethane (40 mL) was added N-bromosuccinimide (5.47 g, 30.7 mmol), and the resulting mixture was stirred at room temperature for 2 hours. The reaction mixture was concentrated in vacuo. The resulting residue was washed by methanol to give 5-bromo-3-(4-chlorobenzyl)-2-(methylthio)pyrimidine-4(3H)-one (3.25 g, Yield: 63%) as colorless solid, 1H-NMR (δ ppm TMS/DMSO-d6): 2.52 (3H, s), 5.25 (2H, s), 7.27 (2H, d, J=8.1 Hz), 7.41 (2H, d, J=8.1 Hz), 8.31 (1H, s).

EXAMPLE 24

Preparation of 2-(3-chloro-4-isopropoxyphenylamino)-3-(4-chlorobenzyl)-5-(2-ethoxycarbonylethenyl) pyrimidine-4(3H)-one (I-132)

[Chemical Formula 148]

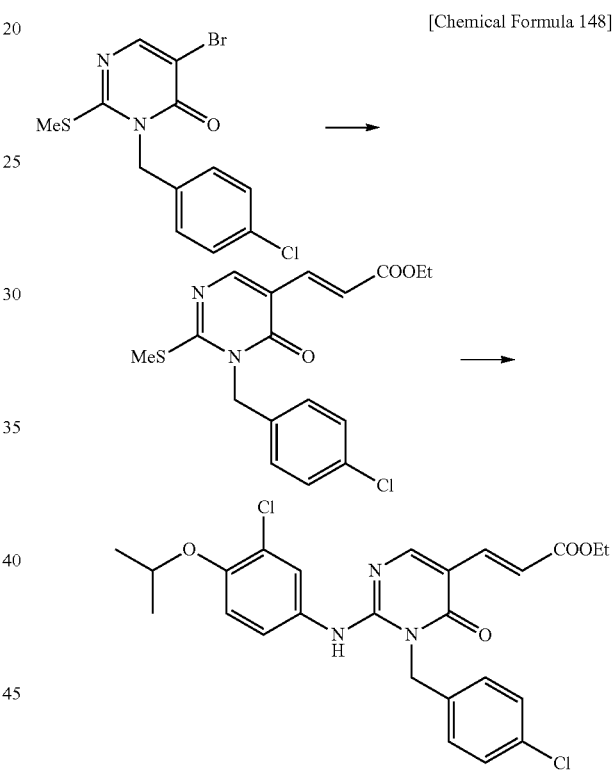

To a mixture of 5-bromo-3-(4-chlorobenzyl)-2-(methylthio)pyrimidine-4(3H)-one (1.00 g, 2.89 mmol) and THF (20 mL) were added (E)-3-(4,4,5,5-tetramethyl-1,3,2-dioxaborolane-2-yl) acrylic acid ethyl ester (981 mg, 4.34 mmol), [1,1'-bis(di-t-butylphosphino)ferrocene]dichloropalladium (II) (189 mg, 0.289 mmol) and 2 mol/L potassium carbonate solution (5.8 mL, 11.6 mmol), and the resulting mixture was heated at reflux for 4 hours. To the reaction mixture was added water, and the mixture was extracted with chloroform. The extract was washed by brine, dried over anhydrous sodium sulphate, and concentrated in vacuo. The resulting residue was washed by ethyl acetate to give 3-(4-chlorobenzyl)-5-(2-ethoxycarbonylethenyl)-2-(methylthio)pyrimidine-4(3H)-one (250 mg, Yield: 24%) as yellow solid.

1H-NMR (δ ppm TMS/DMSO-d6): 1.24 (3H, t, J=6.9 Hz), 2.56 (3H, s), 4.17 (2H, q, J=6.0 Hz), 5.27 (2H, s), 7.03 (1H, d, J=15.9 Hz), 7.28 (2H, d, J=8.1 Hz), 7.41 (2H, d, J=8.1 Hz), 7.50 (1H, d, J=15.9 Hz), 8.38 (1H, s).

A mixture of 3-(4-chlorobenzyl)-5-(2-ethoxycarbonylethenyl)-2-(methylthio) pyrimidine-4(3H)-one (250 mg, 0.685 mmol), 3-chloro-4-isopropoxyaniline (382 mg, 2.06 mmol), t-butanol (5 mL) and acetic acid (0.59 mL) was heated at reflux overnight and purified by reversed-phase HPLC (0.3% formic acid/acetonitrile) to give 2-(3-chloro-4-isopropoxyphenylamino)-3-(4-chlorobenzyl)-5-(2-ethoxycarbonylethenyl) pyrimidine-4(3H)-one (151 mg, Yield: 44%) as pale yellow solid.

1H-NMR (δ ppm TMS/DMSO-d6): 1.18-1.33 (9H, m), 4.08-4.17 (2H, m), 4.55-4.66 (1H, m), 5.38 (2H, s), 6.83 (1H, d, J=16.7 Hz), 7.09-7.50 (8H, m), 8.15 (1H, brs), 9.31 (1H, brs).

EXAMPLE 27

Preparation of 2-(3-chloro-4-isopropoxyphenylamino)-3-(4-chlorobenzyl)-5-(2-hydroxycarbonylethenyl) pyrimidine-4(3H)-one (I-139)

[Chemical Formula 149]

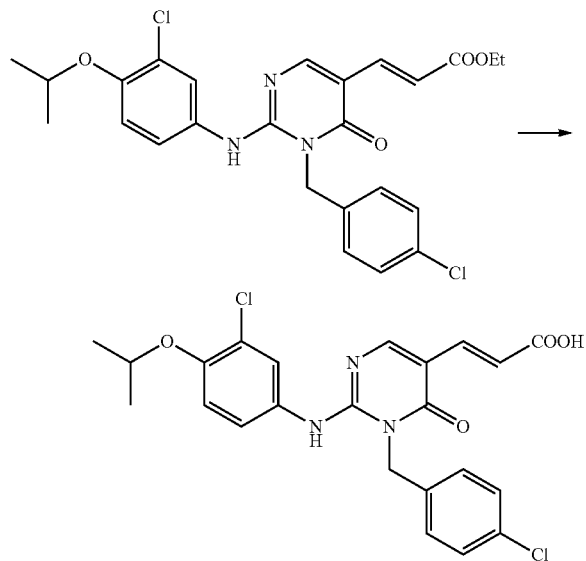

To a mixture of 2-(3-chloro-4-isopropoxyphenylamino)-3-(4-chlorobenzyl)-5-(2-ethoxycarbonylethenyl) pyrimidine-4(3H)-one (25 mg, 0.049 mmol), ethanol (1.5 mL) and THF (0.5 mL) was added 1 mol/L aqueous lithium hydroxide (0.29 mL, 0.29 mmol), and the resulting mixture was stirred at 50° C. overnight. To the reaction mixture was added 2 mol/L hydrochloric acid, and the mixture was extracted with chloroform. The extract was washed by brine, dried over anhydrous sodium sulphate, and concentrated in vacuo. The resulting residue was purified by reversed-phase HPLC (0.3% formic acid/acetonitrile) to give 2-(3-chloro-4-isopropoxyphenylamino)-3-(4-chlorobenzyl)-5-(2-hydroxycarbonylethenyl) pyrimidine-4(3H)-one (14 mg, Yield: 61%) as pale yellow solid.

1H-NMR (δ ppm TMS/DMSO-d6): 1.28 (6H, d, J=5.3 Hz), 4.55-4.65 (1H, m), 5.38 (2H, s), 6.77 (1H, d, J=15.2 Hz), 7.10-7.45 (8H, m), 8.09 (1H, brs).

EXAMPLE 28

Preparation of 2-(3-chloro-4-isopropoxyphenylamino)-3-(4-chlorobenzyl)-5-(2-hydroxycarbonylethyl) pyrimidine-4(3H)-one (I-137)

[Chemical Formula 150]

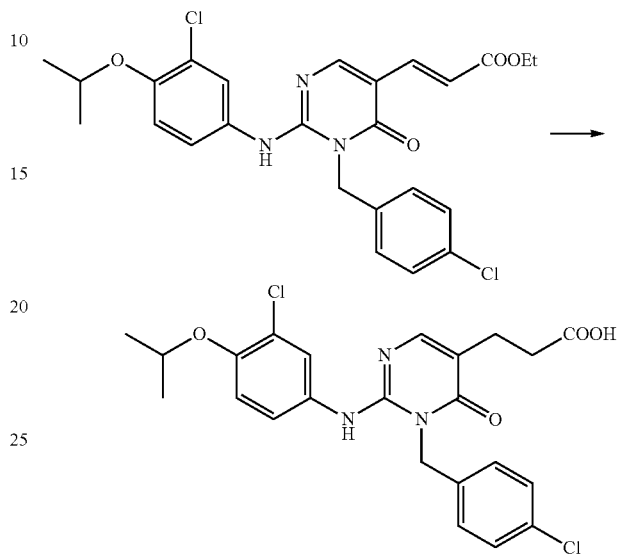

A mixture of 2-(3-chloro-4-isopropoxyphenylamino)-3-(1-chlorobenzyl)-5-(2-ethoxycarbonylethenyl) pyrimidine-4(3H)-one (114 mg, 0.227 mmol), DMF (2 mL) and chloroform (13 mL) was hydrogenated under 5% Pt/C. The reaction mixture was concentrated in vacuo. To a mixture of the obtained residue and ethanol (2 mL) was added aqueous 1 mol/L lithium hydroxide (0.68 mL, 0.68 mmol), and the resulting mixture was stirred at room temperature for 4 hours. To the reaction mixture was added 2 mol/L hydrochloric acid, and the mixture was extracted with chloroform. The extract was washed by brine, dried over anhydrous sodium sulphate, and concentrated in vacuo. The resulting residue was purified by reversed-phase HPLC (0.3% formic acid/acetonitrile) to give 2-(3-chloro-4-isopropoxyphenylamino)-3-(4-chlorobenzyl)-5-(2-hydroxycarbonylethyl) pyrimidine-4(3H)-one (38 mg, Yield: 35%) as pale yellow solid.

1H-NMR (δ ppm TMS/DMSO-d6): 1.27 (6H, d, J=5.8 Hz), 2.38-2.55 (4H, m), 4.50-4.62 (1H, m), 5.39 (2H, s), 7.09 (1H, d, of =8.6 Hz), 7.20-7.60 (6H, m), 8.69 (1H, s),

EXAMPLE 29

Preparation of 2-(3-fluoro-4-isopropoxyphenylamino)-3-(4-chlorobenzyl)-5-(morpholino)pyrimidine-4(3H)-one (I-138)

[Chemical Formula 151]

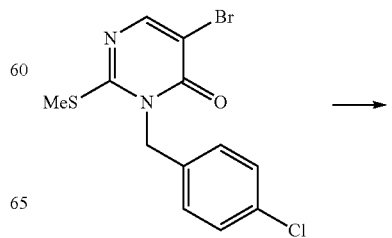

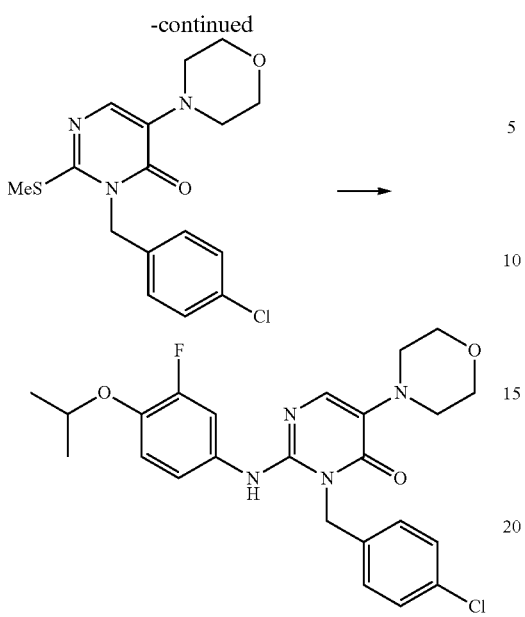

To a mixture of 5-bromo-3-(4-chlorobenzyl)-2-(methylthio)pyrimidine-4(3H)-one (50.0 mg, 0.145 mmol) and dioxane (1 mL) were added morpholine (0.018 mL, 0.20 mmol), tris(dibenzylideneacetone)(0) (13 mg, 0.014 mmol), 4,5-bis(diphenylphosphino)-9,9-dimethylxanthene (25 mg, 0.043 mmol) and cesium carbonate (66 mg, 0.20 mmol), and the resulting mixture was heated at reflux for 15 hours. To the reaction mixture was added water, and the mixture was extracted with chloroform. The extract was washed by brine, dried over anhydrous sodium sulphate, and concentrated in vacuo. The resulting residue was purified by silica gel column chromatography (ethyl acetate/hexane) to give 3-(1-chlorobenzyl)-2-methylthio-5-(morpholino)pyrimidine-4(3H)-one (25 mg, Yield: 49%) as pale yellow solid.

1H-NMR (δ ppm TMS/DMSO-d6): 2.47 (3H, s), 2.98-3.06 (4H, m), 3.67-3.72 (4H, s), 5.20 (2H, s), 7.24 (2H, d, 8.1 Hz), 7.40 (2H, d, J=8.1 Hz), 7.45 (1H, s).

A mixture of 3-(4-chlorobenzyl)-2-methylthio-5-(morpholino)pyrimidine-4(3H)-one (25 mg, 0.071 mmol), 3-fluoro-4-isopropoxyaniline (36 mg, 0.21 mmol), t-butanol (1 mL) and acetic acid (0.061 mL) was heated at reflux overnight and purified by reversed-phase HPLC (0.3% formic acid/acetonitrile) to give 2-(3-fluoro-4-isopropoxyphenylamino)-3-(4-chlorobenzyl)-5-(morpholino)pyrimidine-4(3H)-one (5.5 mg, Yield: 16%) as brown solid.

1H-NMR (δ ppm TMS/DMSO-d6): 1.29 (6H, d, J=5.8 Hz), 3.00-3.07 (4H, m), 3.81-3.87 (4H, m), 4.36-4.44 (1H, m), 5.28 (2H, s), 6.00 (1H, s), 6.64-6.72 (1H, m), 6.79-6.89 (1H, m), 7.07-7.38 (6H, m).

EXAMPLE 30

Preparation of 2-(3-fluoro-4-isopropoxyphenylamino)-3-(4-chlorobenzyl)-5-(tetrahydro-2H-pyrane-4-yl carbonylamino)pyrimidine-4(3H)-one (I-234)

[Chemical Formula 152]

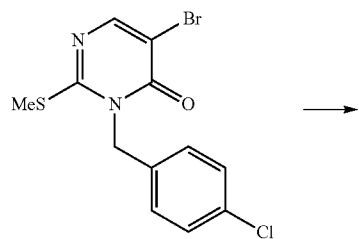

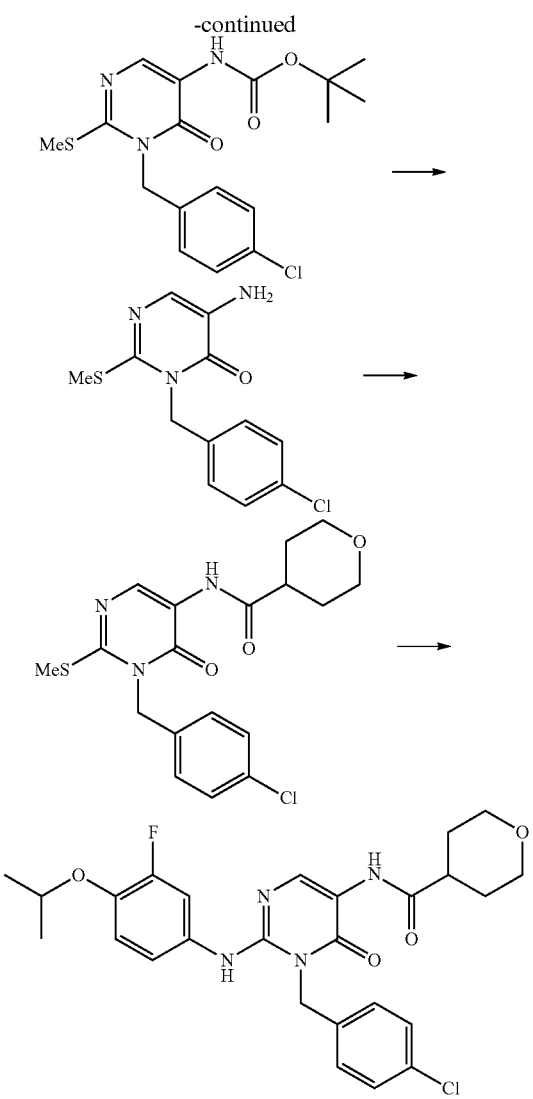

To a mixture of 5-promo-3-(4-chlorobenzyl)-2-(methylthio)pyrimidine-4(3H)-one (1.24 g, 3.59 mmol) and dioxane (15 mL) were added carbamic acid t-butylester (588 mg, 5.02 mmol), tris(dibenzylideneacetone)(0) (329 mg, 0.359 mmol), 4,5-bis(diphenylphosphino)-9,9-dimethylxanthene (623 mg, 1.08 mmol) and cesium carbonate (1.64 g, 5.02 mmol), and the resulting mixture was heated at reflux for 20 hours. To the reaction mixture was added water, and the mixture was extracted with ethyl acetate. The extract was washed by brine, dried over anhydrous sodium sulphate, and concentrated in vacuo. The resulting residue was purified by silica gel column chromatography (ethyl acetate/hexane) to give 5-(t-butoxycarbonyl)amino-3-(4-chlorobenzyl)-2-(methylthio)pyrimidine-4(3H)-one (136 mg, Yield: 10%) as pale yellow solid.

1H-NMR (δ ppm TMS/DMSO-d6): 1.44 (9H, s), 2.50 (3H, s), 5.24 (2H, s), 7.25 (2H, d, J=7.8 Hz), 7.40 (2H, d, J=7.8 Hz), 8.02 (1H, s), 8.26 (1H, s).

To a mixture of 5-(t-butoxycarbonyl)amino-3-(4-chlorobenzyl)-2-(methylthio)pyridine-4(3H)-one (90.0 mg, 0.236 mmol)) and chloroform mL)) was added trifluoroacetic acid (0.36 mL, 4.7 mmol), and the resulting mixture was stirred at room temperature for 20 hours. The reaction mixture was concentrated, and methanol (1 mL), THF (1 mL), water (1 mL) and a small amount of potassium carbonate were added to the residue, and the resulting mixture was stirred at 50° C. for 2 hours. To the reaction mixture was added water, and the mixture was extracted with ethyl acetate. The extract was washed by brine, dried over anhydrous sodium sulphate, and concentrated in vacuo to give 5-amino-3-(4-chlorobenzyl)-2-(methylthio)pyrimidine-4(3H)-one (70 mg, Yield: 100%) as pale yellow solid.

1H-NMR (δ ppm TMS/DMSO-d6): 2.42 (3H, s), 4.92 (2H, s), 5.22 (2H, s), 7.23 (2H, d, J=8.1 Hz), 7.32 (1H, s), 7.39 (2H, d, J=8.1 Hz), To a mixture of 5-amino-3-(4-chlorobenzyl)-2-(methylthio)pyrimidine-4(3H)-one (33.2 mg, 0.118 mmol) and THF (0.5 mL) were added sodium carbonate (15 mg, 0.14 mmol) and tetrahydro-2H-pyrane-4-carbonyl chloride (26 mg, 0.18 mmol) under ice-cooling, and the resulting mixture was stirred under ice-cooling for 2 hours. To the reaction mixture was added saturated aqueous sodium bicarbonate, and the mixture was extracted with ethyl acetate. The extract was washed by brine, dried over anhydrous sodium sulphate, and concentrated in vacuo to give 3-(4-chlorobenzyl)-2-methylthio-5-(tetrahydro-2H-pyrane-4-ylcarbonylamino) pyrimidine-4(3H)-one (48 mg, Yield: 100%) as pale yellow solid.

1H-NMR (δ ppm TMS/DMSO-d6): 1.54-1.70 (4H, m), 2.50 (3H, s), 2.83-2.92 (1H, m), 3.27-3.35 (2H, m), 3.84-3.91 (2H, m), 5.25 (2H, s), 7.27 (2H, d, J=7.8 Hz), 7.41 (2H, d, J=7.8 Hz), 8.70 (1H, s), 9.31 (1H, s).

To a mixture of 3-(4-chlorobenzyl)-2-methylthio-5-(tetrahydro-2H-pyrane-4-ylcarbonylamino)pyrimidine-4(3H)-one (46.4 mg, 0.118 mmol and dichloromethane (1 mL) was added m-chloroperbenzoic acid (30 mg, 0.13 mmol) under ice-cooling, and the resulting mixture was stirred under ice-cooling for 2 hours. To the reaction mixture was added 3-fluoro-4-isopropoxyaniline (30 mg, 0.18 mmol), and the resulting mixture was stirred at 50° C. for 2 hours. To the reaction mixture was added saturated aqueous sodium bicarbonate, and the mixture was extracted with dichloromethane. The extract was washed by brine, dried over anhydrous sodium sulphate, and concentrated in vacuo. The resulting residue was purified by reversed-phase HPLC (0.3% formic acid/acetonitrile) to give 2-(3-fluoro-4-isopropoxyphenylamino)-3-(4-chlorobenzyl)-5-(tetrahydro-2H-pyrane-4-yl carbonylamino)pyrimidine-4(3H)-one (31 mg, Yield: 51%) as pale yellow solid, 1H-NMR (δ ppm TMS/DMSO-d6): 1.26 (6H, d, J=5.8 Hz), 1.54-1.68 (4H, m), 2.71-2.81 (1H, m), 3.27-3.35 (2H, m), 3.83-3.90 (2H, m), 4.46-4.57 (1H, m), 5.43 (2H, s), 7.05-7.13 (2H, m), 7.22-7.45 (5H, m), 8.34 (1H, s), 8.76 (1H, s), 9.01 (1H, s).

EXAMPLE 31

Preparation of 1-(4-chlorobenzyl)-3-(2-methoxycarbonyl-2-methylpropyl)-6-(6-trifluoromethyl-2-pyridylamino)pyrimidine-2,4(1H,3H)-dion (I-108)

[Chemical Formula 153]

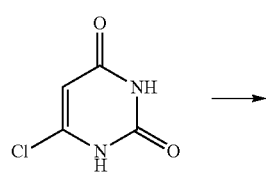

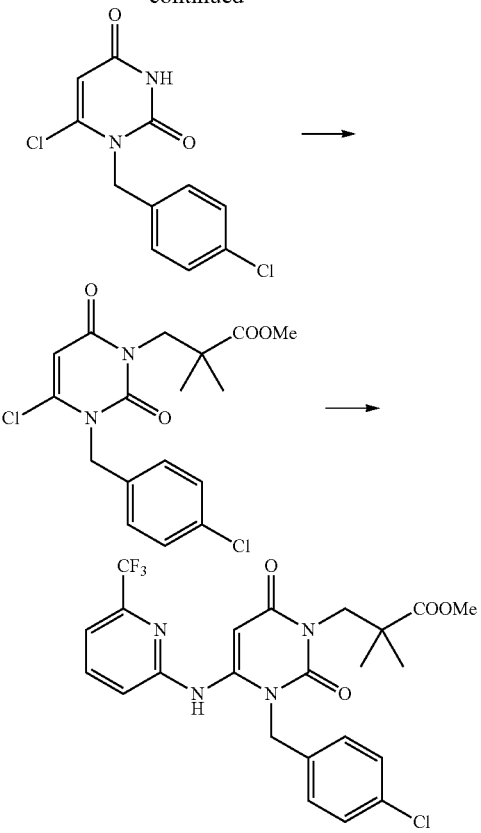

To a mixture of 6-chlorouracil (5.00 g, 34.1 mmol) and DMF (100 mL) were added 60% sodium hydride (1.64 g, 40.9 mmol) and lithium bromide (2.96 g, 34.18 mmol), and the resulting mixture was stirred at room temperature for 1 hour. To the reaction mixture was added 4-chlorobenzylbromide (7.71 g, 37.5 mmol), and the resulting mixture was stirred for additional 21 hours. To the reaction mixture was added water (100 mL), and the precipitated solid was filtered off. The solid was purified by silica gel column chromatography (ethyl acetate/hexane) and precipitated by methanol/ethyl acetate/hexane to give 6-chloro-1-(4-chlorobenzyl)pyrimidine-2,4 (1H,3H)-dion (3.87 g, Yield: 42%) as colorless solid, 1H-NMR (δ ppm TMS/DMSO-d6): 5.14 (2H, s), 5.96 (1H, s), 7.31 (2H, d, J=8.0 Hz), 7.43 (2H, d, J=8.0 Hz), 11.76 (1H, s).

To a mixture of 6-chloro-1-(4-chlorobenzyl)pyrimidine-2, 4(1H,3H)-dion (1.50 g, 5.53 mmol) and dioxane (30 mL) were added triphenylphosphine (2.90 g, 11.1 mmol), di-2-methoxyethylazodicarboxylate (1.81 g, 7.75 mmol) and 3-hydroxy-2,2-dimethyl-propanoic acid methyl ester (1.81 g, 7.75 mmol), and the resulting mixture was stirred at room temperature for 2 hours. To the reaction mixture were added water and ethyl acetate, and the mixture was washed by water. The organic layer was dried over anhydrous sodium sulphate, and concentrated in vacuo. The resulting residue was purified by silica gel column chromatography (ethyl acetate/hexane) to give 6-chloro-1-(4-chlorobenzyl)-3-(2-methoxycarbonyl-2-methylpropyl)pyrimidine-2,4(1H,3H)-dion (168 g, Yield: 79%) as colorless oil.

1H-NMR (δ ppm TMS/DMSO-d6): 1.12 (6H, s), 3.50 (3H, s), 3.99 (2H, 8), 5.19 (2H, s) 6.17 (1H, s), 7.32 (2H, d, J=8.0 Hz), 7.43 (2H, d, J=8.0 Hz).

To a mixture of 6-chloro-1-(4-chlorobenzyl)-3-(2-methoxycarbonyl-2-methylpropyl)pyrimidine-2,4(1H,3H)-dion (120 mg, 0.311 mmol) and dioxane (3 mL) were added 6-trifluoromethylpyridine-2-yl-amine (76 mg, 0.47 mmol), palladium acetate(II) (7.0 mg, 0.031 mmol), 4,5-bis(diphenylphosphino)-9,9-dimethylxanthene (27 mg, 0.047 mmol) and cesium carbonate (142 mg, 0.436 mmol), and the resulting mixture was heated at reflux for 1 hour. To the reaction mixture was added water, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give 1-(4-chlorobenzyl)-3-(2-methoxycarbonyl-2-methylpropyl)-6-(6-trifluoromethyl-2-pyrid ylamino)pyrimidine-2,4(1H,3H)-dion (110 mg, Yield: 69%) as colorless solid.

1H-NMR (δ ppm TMS/DMSO-d6): 1.11 (6H, s), 3.50 (3H, s), 4.01 (2H, s), 5.30 (2H, s), 6.10 (1H, s), 7.24 (2H, d, J=8.0 Hz), 7.35 (3H, m), 7.48 (1H, d, J=7.6 Hz), 7.96 (1H, m), 9.41 (1H, s).

EXAMPLE 32

Preparation of 1-(4-chlorobenzyl)-3-(2-hydroxycarbonyl-2-methylpropyl)-6-(6-trifluoromethyl-2-pyridylamino)pyrimidine-2,4(1H,3H)-dion (I-114)

[Chemical Formula 154]

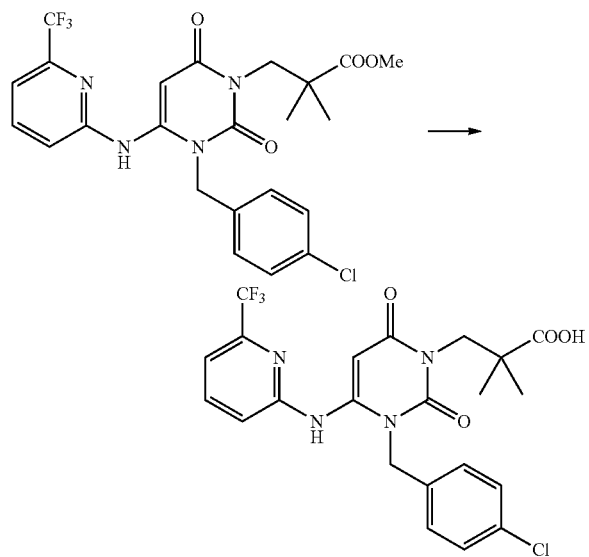

To a mixture of 1-(4-chlorobenzyl)-3-(2-methoxycarbonyl-2-methylpropyl)-6-(6-trifluoromethyl-2-pyridylamino)pyrimidine-2,4(1H,3H)-dion (105 mg, 0.206 mmol), methanol (0.6 mL), water (0.6 mL) and THF (0.6 mL) was added lithium hydroxide monohydrate (26 mg, 0.62 mmol), and the resulting mixture was stirred at 50° C. for 12 hours. The reaction mixture was purified by reversed-phase HPLC (0.3% formic acid/acetonitrile) to give 1-(4-chlorobenzyl)-3-(2-hydroxycarbonyl-2-methylpropyl)-6-(6-trifluoromethyl-2-pyrid ylamino)pyrimidine-2,4(1H,3H)-dion (63 mg, Yield: 62%) as colorless solid.

1H-NMR (δ ppm TMS/DMSO-d6): 1.08 (6H, s), 4.06 (2H, s), 5.32 (2H, s), 6.12 (1H, 3), 7.24 (2H, d, J=8.0 Hz), 7.34 (3H, m), 7.45 (1H, d, J=7.6 Hz), 7.94 (1H, m), 9.38 (1H, brs), 12.20 (1H, brs).

EXAMPLE 33

Preparation of 1-(4-chlorobenzyl)-6-(3-fluoro-4-isopropoxyphenylamino)-3-(methoxycarbonylmethyl)pyrimidine-2,4(1H,3H)-dion (I-104)

[Chemical Formula 155]

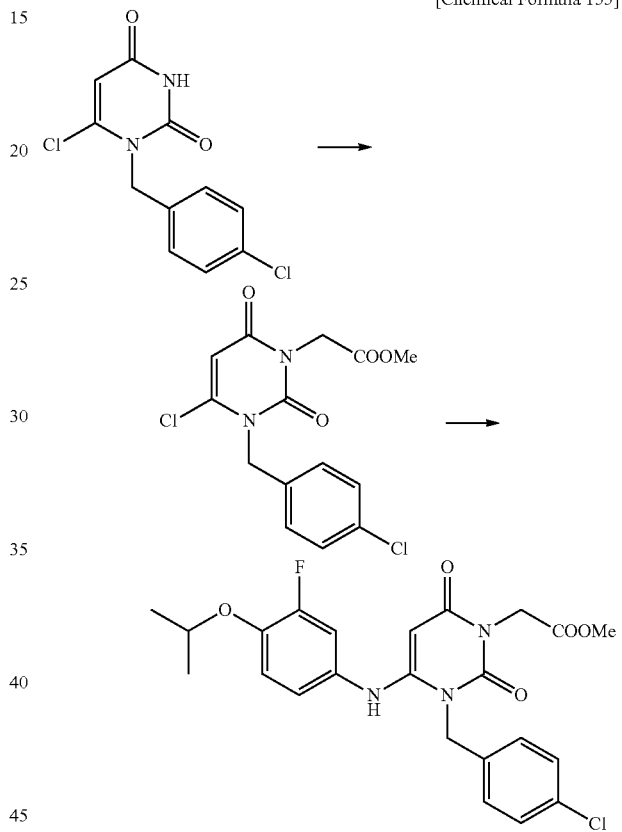

To a mixture of 6-chloro-1-(4-chlorobenzyl)pyrimidine-2,4(1H,3H)-dion (500 mg, 1.84 mmol) and DMF (5 mL) were added 60% sodium hydride (89 mg, 2.2 mmol) and methyl bromoacetate ester (0.21 mL, 2.2 mmol), and the resulting mixture was stirred at room temperature for 20 minutes. To the mixture was added 10% aqueous citric acid, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give 6-chloro-1-(4-chlorobenzyl)-3-(methoxycarbonylmethyl)pyrimidine-2,4(1H,3H)-dion (630 mg, Yield: 99%) as colorless oil.

1H-NMR (δ ppm TMS/DMSO-d6): 3.69 (3H, s), 3.99 (2H, s), 5.24 (2H, s), 6.27 (1H, s), 7.31 (2H, d, J=8.0 Hz), 7.45 (2H, d, J=8.0 Hz).

To a mixture of 6-chloro-1-(4-chlorobenzyl)-3-(methoxycarbonylmethyl)pyrimidine-2,4(1H,3H)-dion (600 mg, 1.75 mmol) and dioxane (12 mL) were added 3-fluoro-4-isopropoxyaniline (355 mg, 2.10 mmol), palladium acetate(II) (39 mg, 0.18 mmol), 4,5-bis(diphenylphosphino)-9,9-dimethylxanthene (152 mg, 0.262 mmol) and cesium carbonate (798 mg, 2.45 mmol), and the resulting mixture was heated at reflux for 1 hour. To the reaction mixture was added water, and the mixture was extracted with ethyl acetate. The extract was washed by brine, dried over anhydrous sodium sulphate, and concentrated in vacuo. The resulting residue was purified by silica gel column chromatography (ethyl acetate/hexane) to give 1-(4-chlorobenzyl)-6-(3-fluoro-4-isopropoxyphenylamino)-3-(methoxycarbonylmethyl)pyrimidine-2,4(1H,3H)-dion (690 mg, Yield: 83%) as yellow solid.

1H-NMR (δ ppm TMS/DMSO-d6): 1.28 (6H, d, J=6.0 Hz), 3.65 (3H, s), 4.53 (2H, s), 4.60 (2H, m), 5.29 (2H, s), 6.92 (1H, d, J=8.0 Hz), 7.09 (1H, m), 7.21 (1H, m), 7.30 (2H, d, J=8.0 Hz), 7.45 (2H, d, J=8.0 Hz), 8.70 (1H, s).

EXAMPLE 34

Preparation of 1-(4-chlorobenzyl)-6-(3-fluoro-4-isopropoxyphenylamino)-3-(hydroxycarbonylmethyl)pyrimidine-2,4(1H,3H)-dion (I-105)

[Chemical Formula 156]

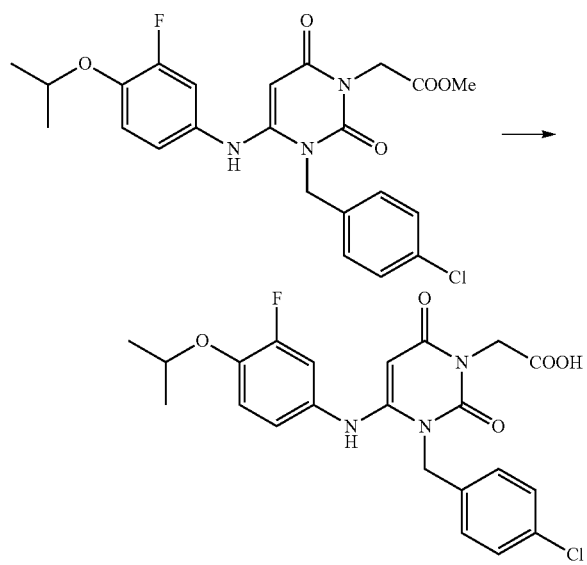

To a mixture of 1-(4-chlorobenzyl)-6-(3-fluoro-4-isopropoxyphenylamino)-3-(methoxycarbonylmethyl)pyrimidine-2,4(1H,3H)-dion (650 mg, 1.37 mmol), methanol (8 mL), water (4 mL) and THF (8 mL) was added lithium hydroxide monohydrate (172 mg, 4.10 mmol), and the resulting mixture was stirred at room temperature for 16 hours. To the mixture was added 10% aqueous citric acid, and the resulting mixture was extracted with ethyl acetate. The extract was washed by brine, dried over anhydrous sodium sulphate, and concentrated in vacuo. The resulting residue was precipitated by ethyl acetate and hexane to give 1-(4-chlorobenzyl)-6-(3-fluoro-4-isopropoxyphenylamino)-3-(hydroxycarbonylmethyl)pyrimidine-2,4(1H,3H)-dion (615 mg, Yield: 97%) as pale yellow solid.

1H-NMR (δ ppm TMS/DMSO-d6) 1.29 (6H, 1, J=6.0 Hz), 4.44 (2H, s), 4.60 (2H, s), 5.30 (2H, s), 6.93 (1H, d, J=8.0 Hz), 7.09 (1H, m), 7.21 (1H, m), 7.31 (2H, d, J=8.0 Hz), 7.44 (2H, d, J=8.0 Hz), 8.67 (1H, s), 12.85 (1H, brs).

EXAMPLE 35

Preparation of 1-(4-chlorobenzyl)-6-(3-fluoro-4-isopropoxyphenylamino)-3-(2-hydroxyethylcarbamoyl methyl)pyrimidine-2,4(1H,3H)-dion (I-112)

[Chemical Formula 157]

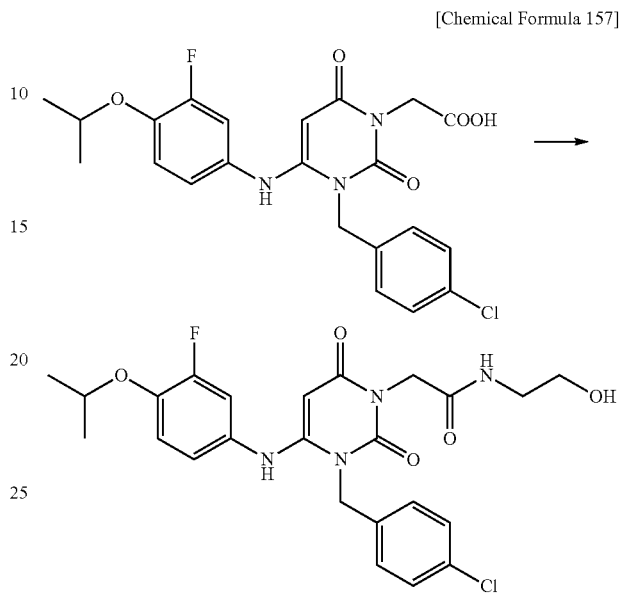

To a mixture of 1-(4-chlorobenzyl)-6-(3-fluoro-4-isopropoxyphenylamino)-3-(hydroxycarbonylmethyl)pyrimidine-2,4(1H,3H)-don (160 mg, 0.346 mmol) and DMF (3.2 mL) were added 2-aminoethanol (85 mg, 1.4 mmol), 1-hydroxybenzotriazole (52 mg, 0.38 mmol) and 1-(3-dimethylaminopropyl)-3-ethylcarbodiimide hydrochloride (100 mg, 0.52 mmol), and the resulting mixture was stirred at room temperature for 8 hours. To the reaction mixture was added 10% aqueous citric acid, and the resulting mixture was extracted with ethyl acetate. The extract was washed by brine, dried over anhydrous sodium sulphate, and concentrated in vacuo. The resulting residue was purified by reversed-phase HPLC (0.3% formic acid/acetonitrile) to give 1-(4-chlorobenzyl)-6-(3-fluoro-4-isopropoxyphenylamino)-3-(2-hydroxyethylcarbamoyl methyl)pyrimidine-2,4(1H,3H)-dion (96 mg, Yield: 55%) as colorless solid.

1H-NMR (δ ppm TMS/DMSO-d6): 1.28 (6H, d, J=6.0 Hz), 3.13 (2H, m), 4.38 (2H, s), 4.60 (2H, s), 5.28 (2H, s), 6.90 (1H, d, J=8.0 Hz), 7.05 (1H, m), 7.20 (1H, m), 7.31 (2H, d, J=8.0 Hz), 7.42 (2H, d, J=8.0 Hz), 8.03 (1H, s), 8.59 (1H, s).

EXAMPLE 36

Preparation of 1-(4-chlorobenzyl)-3-(2-methoxycarbonyl-2-methylpropyl)-6-(3-trifluoromethylbenzyl)pyrimidine-2,4(1H,3H)-dion (I-141)

[Chemical Formula 158]

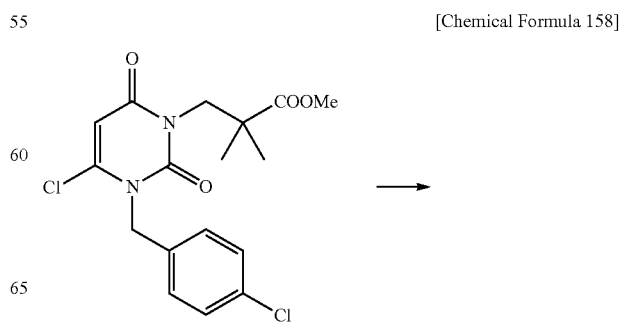

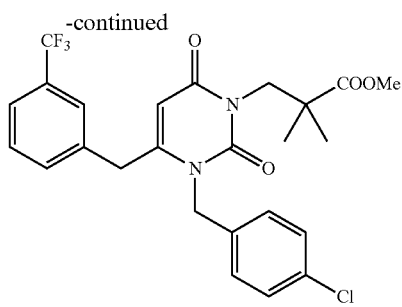

To a mixture of 6-chloro-1-(4-chlorobenzyl)-3-(methoxycarbonylmethyl)pyrimidine-2,4(1H,3H)-dion (250 mg, 0.649 mmol) and THF (5.5 mL) were added 3-trifluoromethylbenzyl zinc chloride (0.5 mol/L THF solution, 1.95 mL, 0.97 mmol), triphenylphosphine (17 mg, 0.065 mmol) and palladium acetate(II) (7.3 mg, 0.032 mmol), and the resulting mixture was heated at reflux for 1 hour. To the mixture was added 1 mol/L hydrochloric acid, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give 1-(4-chlorobenzyl)-3-(2-methoxycarbonyl-2-methylpropyl)-6-(3-trifluoromethylbenzyl)pyrimidine-2,4(1H,3H)-dion (272 mg, Yield: 82%) as colorless solid.

1H-NMR (δ ppm TMS/DMSO-d6): 1.10 (6H, s), 3.46 (3H, s), 4.00 (2H, s), 4.02 (2H, s), 5.06 (2H, s), 5.43 (1H, s), 7.10 (2H, d, J=8.0 Hz), 7.31 (2H, d, J=8.0 Hz), 7.54 (4H, m),

EXAMPLE 37

Preparation of 4-(3-chloro-4-isopropoxyphenylamino)-1-benzyl-5-(ethoxycarbonyl)pyridine-2(1H)-one (I-046)

[Chemical Formula 159]

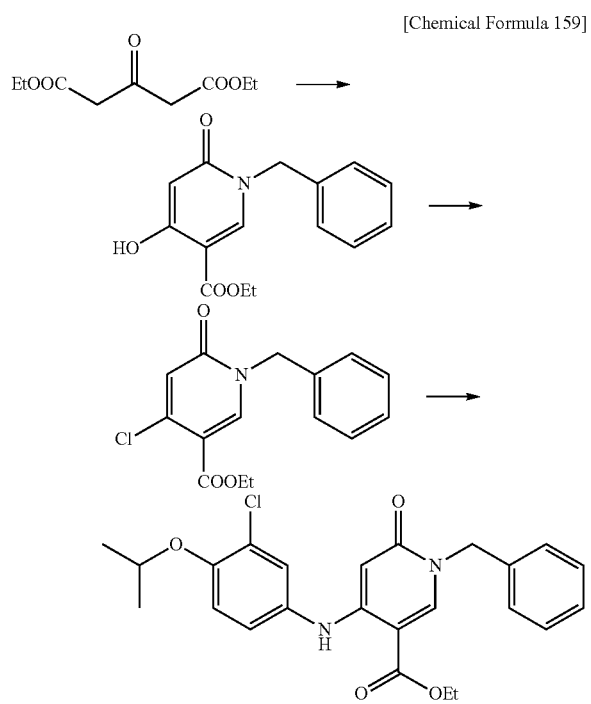

To a mixture of diethyl 1,3-acetonedicarboxylate (25.0 g, 124 mmol) and ethyl orthoformate (20.6 mL, 124 mmol) was added acetic anhydride (23.4 mL, 247 mmol), and the resulting mixture was heated at reflux for 15 hours. The reaction mixture was concentrated. To the residue was added benzylamine (16.2 mL, 148 mmol), and the mixture was stirred at room temperature for 2 hours and stirred at 90° C. for additional 20 hours. To the reaction mixture was added 1 mol/L hydrochloric acid, and the mixture was extracted with ethyl acetate. The extract was washed by brine, dried over anhydrous sodium sulphate, and concentrated in vacuo. The resulting residue was purified by silica gel column chromatography (ethyl acetate/hexane). The crude product was washed by diisopropyl ether to give 1-benzyl-5-ethoxycarbonyl-4-hydroxypyridine-2(1H)-one (13.8 g, Yield: 41%) as colorless solid.

1H-NMR (δ ppm TMS/CDCl3): 1.35 (3H, t, J=6.0 Hz), 4.34 (2H, q, J=6.0 Hz), 5.15 (2H, s), 5.99 (1H, s), 7.31 (5H, m), 8.10 (1H, s), 10.64 (1H, s).

A mixture of 1-benzyl-5-ethoxycarbonyl-4-hydroxypyridine-2(1H)-one (8.00 g, 29.3 mmol) and phosphorus oxychloride (27 ml) was stirred at 90° C. for 1 hour. To the reaction mixture was added saturated aqueous sodium bicarbonate, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give 4-chloro-1-benzyl-5-(ethoxycarbonyl-)pyridine-2(1H)-one (4.26 g, Yield: 50%) as colorless solid.

1H-NMR (δ ppm TMS/DMSO-d6): 1.29 (3H, t, J=6.8 Hz), 4.25 (2H, q, J=6.8 Hz), 5.22 (2H, s), 6.68 (1H, s), 7.32 (5H, m), 8.70 (1H, s).

To a mixture of 4-chloro-1-benzyl-5-(ethoxycarbonyl-)pyridine-2(1H)-one (2.00 g, 6.86 mmol) and dioxane (40 were added 3-chloro-4-isopropoxyaniline (1.91 g, 10.3 mmol), palladium acetate(II) (154 mg, 0.686 mmol), 4,5-bis(diphenylphosphino)-9,9-dimethylxanthene (595 mg, 1.03 mmol) and cesium carbonate (3.13 g, 9.60 mmol), and the resulting mixture was heated at reflux for 1 hour. The insoluble were removed by filtration and washed by ethyl acetate. The mother liquor was concentrated in vacuo. The resulting residue was purified by silica gel column chromatography (ethyl acetate/hexane) to give 4-(3-chloro-4-isopropoxyphenylamino)-1-benzyl-5-(ethoxycarbonyl)pyridine-2(1H)-one (2.37 g, Yield: 78%) as colorless solid.

1H-NMR (δ ppm TMS/DMSO-d6): 1.30 (9H, m), 4.28 (2H, q, J=6.8 Hz), 4.66 (1H, sept, J=6.0 Hz), 5.13 (2H, s), 5.41 (1H, s), 7.21 (1H, m), 7.27 (7H, m), 8.60 (1H, s), 9.12 (1H, s).

EXAMPLE 38

Preparation of 4-(3-chloro-4-isopropoxyphenylamino)-1-benzyl-5-(N-methoxy-N-methylcarbamoyl)pyridine-2(1H)-one (I-064)

[Chemical Formula 160]

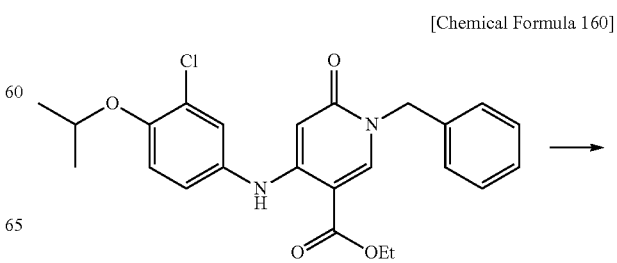

-continued

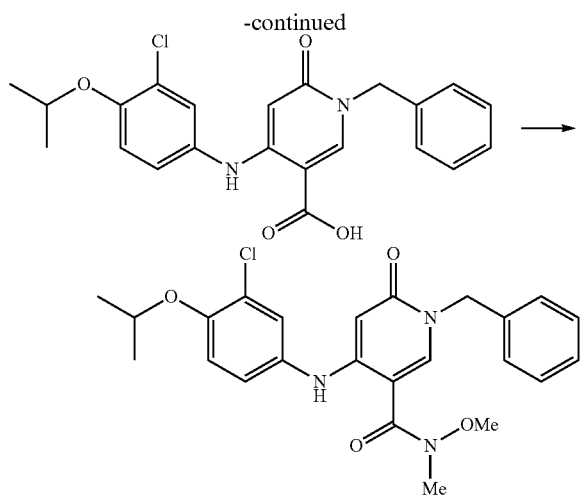

To a mixture of 4-(3-chloro-4-isopropoxyphenylamino)-1-benzyl-5-(ethoxycarbonyl)pyridine-2(1H)-one (2.36 g, 5.35 mmol), ethanol (16 mL), water (16 mL) and THF (16 mL) was added lithium hydroxide monohydrate (675 mg, 16.1 mmol), and the resulting mixture was stirred at 50° C. for 15 hours. To the reaction mixture was added 5% aqueous citric acid (100 mL), and the precipitated solid was filtered off. The resulting solid was precipitated by THF/ethyl acetate to give (3-chloro-4-isopropoxyphenylamino)-1-benzyl-5-hydroxycarbonylpyridine-2(1H) one (2.06 g, Yield: 93%) as colorless solid.

1H-NMR (δ ppm TMS/DMSO-d6): 1.30 (6H, d, J=6.0 Hz), 4.65 (1H, sept, J=6.0 Hz), 5.11 (2H, s), 5.43 (1H, s), 7.21 (1H, m), 7.30 (7H, m), 8.56 (1H, s), 9.48 (1H, s).

To a mixture of 4-(3-chloro-4-isopropoxyphenylamino)-1-benzyl-5-hydroxycarbonylpyridine-2(1H)-one (2.00 g, 4.34 mmol) and DMF (40 mL) were added O,N-dimethyl-hydroxylamine hydrochloride (945 mg, 9.69 mmol), 1-hydroxybenzotriazole (720 mg, 5.33 mmol), 1-(3-dimethylaminopropyl)-3-ethylcarbodiimide hydrochloride (1.39 g, 7.27 mmol) and triethylamine (1.34 mL, 9.69 mmol), and the resulting mixture was stirred at room temperature for 3 hours. To the reaction mixture was added water, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give 4-(3-chloro-4-isopropoxyphenylamino)-1-benzyl-5-(N-methoxy-N-methylcarbamoyl)pyridine-2(1H)-one (2.13 g, Yield: 96%) as colorless solid.

1H-NMR (δ ppm TMS/DMSO-d6): 1.30 (6H, d, J=6.0 Hz), 3.25 (3H, s), 3.54 (3H, s), 4.63 (1H, sept, J=6.0 Hz), 5.07 (2H, s), 5.56 (1H, s), 7.17 (1H, m), 7.30 (7H, m), 8.10 (1H, s), 8.33 (1H, s).

EXAMPLE 39

Preparation of 4-(3-chloro-4-isopropoxyphenylamino)-1-benzyl-5-(4-chlorobenzoyl)pyridine-2(1H)-one (I-065)

[Chemical Formula 161]

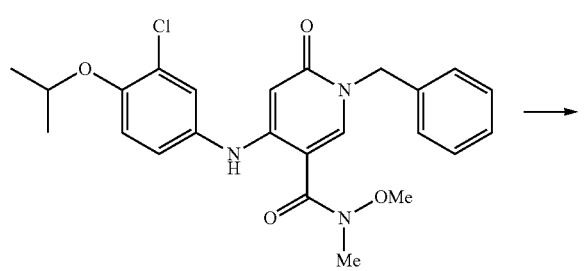

-continued

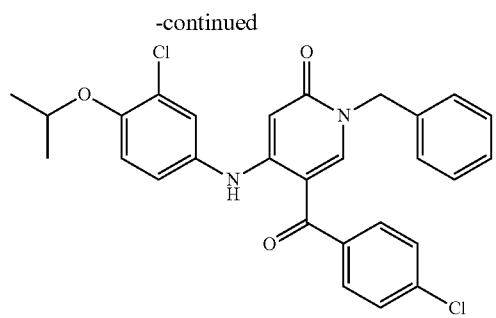

To a mixture of 4-(3-chloro-4-isopropoxyphenylamino)-1-benzyl-5-(N-methoxy-N-methylcarbamoyl)pyridine-2(1H)-one (800 mg, 1.76 mmol) and THF (24 mL) was added a solution of 4-chlorophenylmagnesiumbromide (1 mol/L diethyl ether solution, 13.2 mL, 13.2 mmol) under ice-cooling, and the resulting mixture was stirred at room temperature for 30 minutes. To the reaction mixture was added 2 mol/L hydrochloric acid (10 mL), and the mixture was extracted with ethyl acetate. The extract was washed by brine, dried over anhydrous sodium sulphate, and concentrated in vacuo. The resulting residue was purified by silica gel column chromatography (ethyl acetate/hexane) to give 4-(3-chloro-4-isopropoxyphenylamino)-1-benzyl-5-(4-chlorobenzoyl)pyridine-2(1H)-one (772 mg, Yield: 87%) as colorless solid.

1H-NMR (δ ppm TMS/DMSO-d6): 1.30 (6H, d, J=6.0 Hz), 4.64 (1H, sept, J=6.0 Hz), 5.06 (2H, s), 5.51 (1H, s), 7.29 (8H, m), 7.57 (2H, d, J=8.0 Hz), 7.62 (2H, d, J=8.0 Hz), 8.21 (1H, s), 9.55 (1H, s).

EXAMPLE 40

Preparation of 4-(3-chloro-4-isopropoxyphenylamino)-1-benzyl-5-(4-chloro-α-hydroxybenzyl)pyridine-2(1H)-one (I-068)

[Chemical Formula 162]

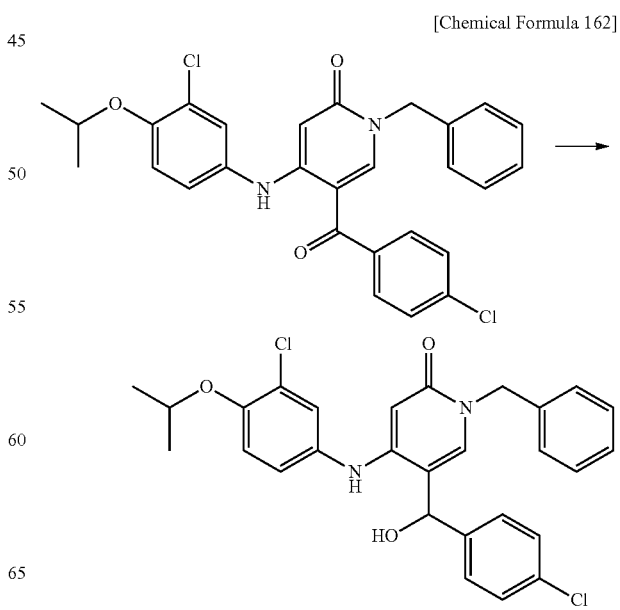

To a mixture of 4-(3-chloro-4-isopropoxyphenylamino)-1-benzyl-5-(4-chlorobenzoyl)pyridine-2(1H)-one (100 mg, 0.197 mmol) and ethanol (3 mL) was added sodium borohydride (15 mg, 0.39 mmol) under ice-cooling, and the resulting mixture was stirred under ice-cooling for 1 hour. To the reaction mixture was added 1 mol/L hydrochloric acid, and the mixture was extracted with ethyl acetate. The extract was washed by brine, dried over anhydrous sodium sulphate, and concentrated in vacuo to give 4-(3-chloro-4-isopropoxyphenylamino)-1-benzyl-5-(4-chloro-α-hydroxybenzyl)pyridine-2(1H)-one (100 mg, Yield: 100%) as colorless solid.

1H-NMR (δ ppm TMS/CDCl3): 1.36 (6H, d, J=6.0 Hz), 4.48 (1H, sept, J=6.0 Hz), 4.84 (2H, s), 5.63 (1H, s), 5.96 (1H, s), 6.55 (1H, s), 6.84 (2H, m), 7.10 (3H, m), 7.28 (7H, m), 7.50 (1H, s).

EXAMPLE 41

Preparation of 4-(3-chloro-4-isopropoxyphenylamino)-1-benzyl-5-(4-chlorobenzyl)pyridine-2(1H)-one (I-067)

[Chemical Formula 163]

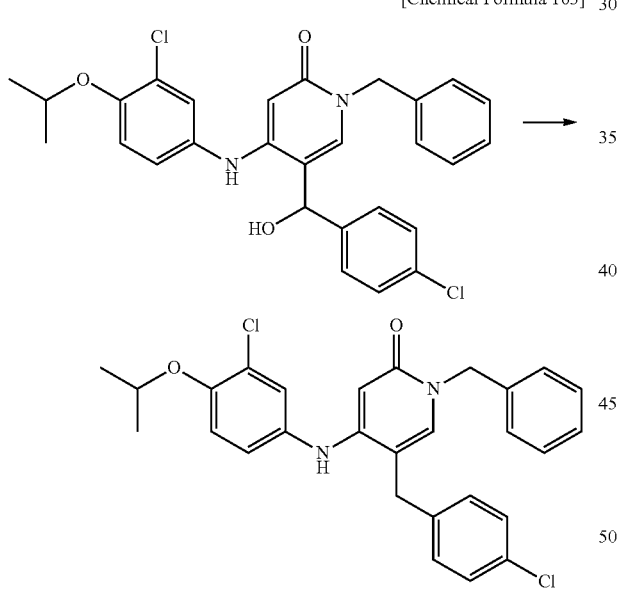

To a mixture of 4-(3-chloro-4-isopropoxyphenylamino)-1-benzyl-5-(4-chloro-α-hydroxybenzyl)pyridine-2(1H)-one (100 mg, 1.96 mmol) and trifluoroacetic acid (1.5 mL) was added triethylsilane (0.125 mL, 0.785 mmol), and the resulting mixture was stirred at 50° C. for 1 hour. The reaction mixture was concentrated. To the resulting residue was added saturated aqueous sodium bicarbonate, and the mixture was extracted with ethyl acetate. The extract was washed by brine, dried over anhydrous sodium sulphate, and concentrated in vacuo. The resulting residue was purified by silica gel column chromatography (ethyl acetate/hexane) to give 4-(3-chloro-4-isopropoxyphenylamino)-1-benzyl-5-(4-chlorobenzyl)pyridine-2(1H)-one (24 mg, Yield: 25%) as colorless solid.

1H-NMR (δ ppm TMS/DMSO-d6): 1.29 (6H, d, J=6.0 Hz), 3.34 (2H, s), 4.61 (1H, sept, J=6.0 Hz), 4.96 (2H, s), 5.49 (1H, s), 7.23 (12H, m), 7.66 (1H, s), 9.49 (1H, s).

EXAMPLE 42

Preparation of 1-(4-chlorobenzyl)-2-(3-fluoro-4-isopropoxyphenylamino)-5-(ethoxycarbonyl)pyrimidine-4(1H)-one (I-131)

[Chemical Formula 164]

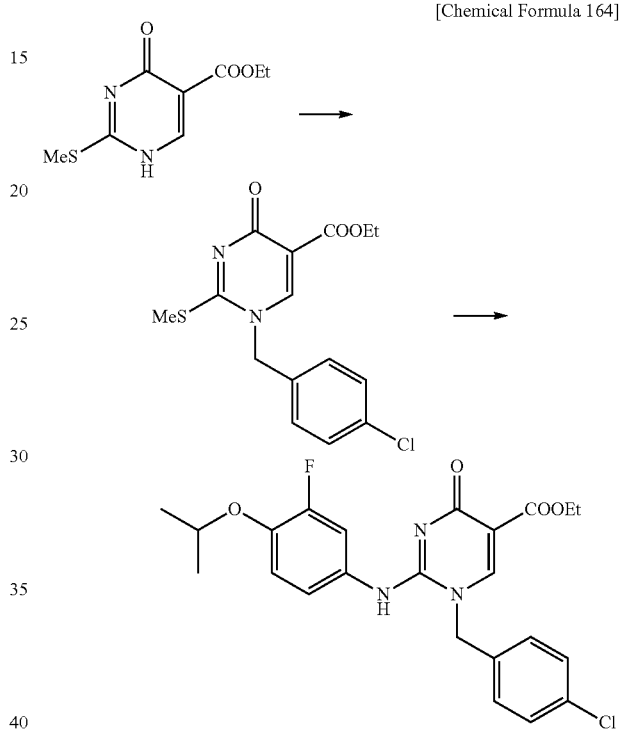

To a mixture of 2-methylthio-5-(ethoxycarbonyl)pyrimidine-4(1H)-one (2.00 g, 9.34 mmol) and dichloromethane (80 mL) were added diisopropylethylamine (2.45 mL, 14.0 mmol) and 4-chlorobenzylbromide (2.11 g, 10.3 mmol), and the resulting mixture was stirred at room temperature for 2 days. The reaction mixture was concentrated, and the precipitated solid was filtered off. The resulting solid was purified by silica gel column chromatography (ethyl acetate/hexane) to give 1-(4-chlorobenzyl)-2-methylthio-5-(ethoxycarbonyl)pyrimidine-4(1H)-one (1.85 g, Yield: 59%) as colorless solid.

1H-NMR (δ ppm TMS/DMSO-d6): 1.25 (3H, t, J=6.0 Hz), 2.45 (3H, s), 4.20 (2H, q, J=6.0 Hz), 5.28 (2H, s), 7.30 (2H, d, J=8.0 Hz), 7.47 (2H, d, J=8.0 Hz), 8.58 (1H, s).

A mixture of 1-(4-chlorobenzyl)-2-methylthio-5-(ethoxycarbonyl)pyrimidine-4(1H)-one (800 rag, 2.36 mmol), 3-fluoro-4-isopropoxyaniline (599 mg, 3.54 mmol), t-butanol (32 mL) and acetic acid (2.0 mL) was heated at reflux overnight. The precipitated solid was filtered off, and washed by ether to give 1-(4-chlorobenzyl)-2-(3-fluoro-4-isopropoxyphenylamino)-5-(ethoxycarbonyl)pyrimidine-4(1H)-one (792 mg, Yield: 73%) as colorless solid.

1H-NMR (δ ppm TMS/DMSO-d6): 1.25 (9H, m), 4.16 (2H, q, J=6.0 Hz), 4.47 (1H, m), 5.17 (2H, s), 6.48 (1H, m), 6.62 (1H, m), 7.03 (1H, 7.44 (4H, s), 8.64 (1H, s), 10.02 (1H, s).

EXAMPLE 43

Preparation of 1-(4-chlorobenzyl)-2-(3-fluoro-4-isopropoxyphenylamino)-5-(hydroxycarbonyl-)pyrimidine-4(1H)-one (I-140) and 1-(4-chlorobenzyl)-2-(3-fluoro-4-isopropoxyphenylamino)-5-[N-(2-hydroxyethyl)carbamoyl]pyrimidine-4(1H)-one (I-146)

[Chemical Formula 165]

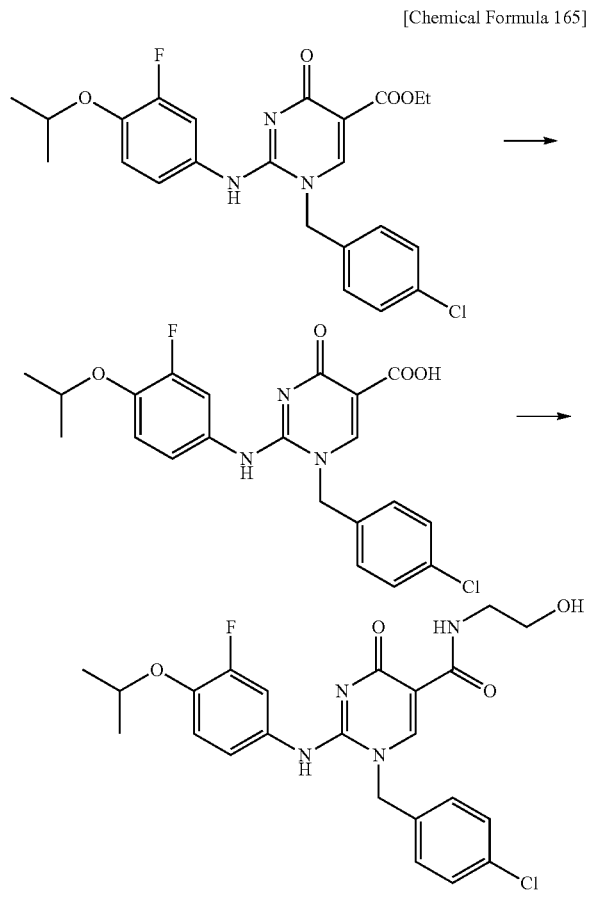

To a mixture of 1-(4-chlorobenzyl)-2-(3-fluoro-4-isopropoxyphenylamino)-5-(ethoxycarbonyl)pyrimidine-4(1H)-one (750 mg, 1.63 mmol), ethanol (5 water (5 mL) and THF (5 mL) was added lithium hydroxide monohydrate (205 mg, 4.89 mmol), and the resulting mixture was stirred at 40° C. for 12 hours. To the reaction mixture was added 10% aqueous citric acid, and the mixture was extracted with ethyl acetate. The extract was washed by brine, dried over anhydrous sodium sulphate, and concentrated in vacuo. The resulting residue was precipitated by dichloromethane and hexane to give 1-(4-chlorobenzyl)-2-(3-fluoro-4-isopropoxyphenylamino)-5-(hydroxycarbonyl)pyrimidine-4(1H)-one (700 mg, Yield: 99%) as colorless solid.

1H-NMR (δ ppm TMS/DMSO-d6): 1.27 (6H, d, J=6.0 Hz), 4.58 (1H, m), 5.49 (2H, s), 7.14 (2H, m), 7.39 (3H, m), 7.49 (2H, m), 8.72 (1H, s), 9.48 (1H, s).

To a mixture of 1-(4-chlorobenzyl)-2-(3-fluoro-4-isopropoxyphenylamino)-5-(hydroxycarbonyl)pyrimidine-4(1H)-one (80.0 rag, 0.185 mmol) and DMF (1.6 mL) were added 2-aminoethanol (22 mg, 0.37 mmol), 1-hydroxybenzotriazole (30 mg, 0.22 mmol) and 1-(3-dimethylaminopropyl)-3-ethylcarbodiimide hydrochloride (53 mg, 0.28 mmol), and the resulting mixture was stirred at room temperature for 2 days. To the reaction mixture was added water, and the resulting mixture was extracted with chloroform. The extract was concentrated in vacuo. The resulting residue was purified by reversed-phase HPLC (0.3% formic acid/acetonitrile) to give 1-(4-chlorobenzyl)-2-(3-fluoro-4-isopropoxyphenylamino)-5-[N-(2-hydroxyethyl)carbamoyl]pyrimidine-4(1H)-one (18 mg, Yield: 20%) as pale yellow solid.

1H-NMR (δ ppm TMS/CDCl3): 1.36 (6H, d, Hz), 3.53 (2H, m), 3.74 (2H, m), 4.47 (1H, sept, J=6.0 Hz), 5.08 (2H, s), 6.52 (1H, m), 6.59 (1H, m), 6.97 (1H, m), 7.36 (4H, s), 7.94 (1H, brs), 8.47 (1H, 8.82 (1H, s).

EXAMPLE 44

Preparation of 1-(4-chlorobenzyl)-7-(phenylamino)-3-(ethoxycarbonyl)quinoline-4(1H)-one (I-148)

[Chemical Formula 166]

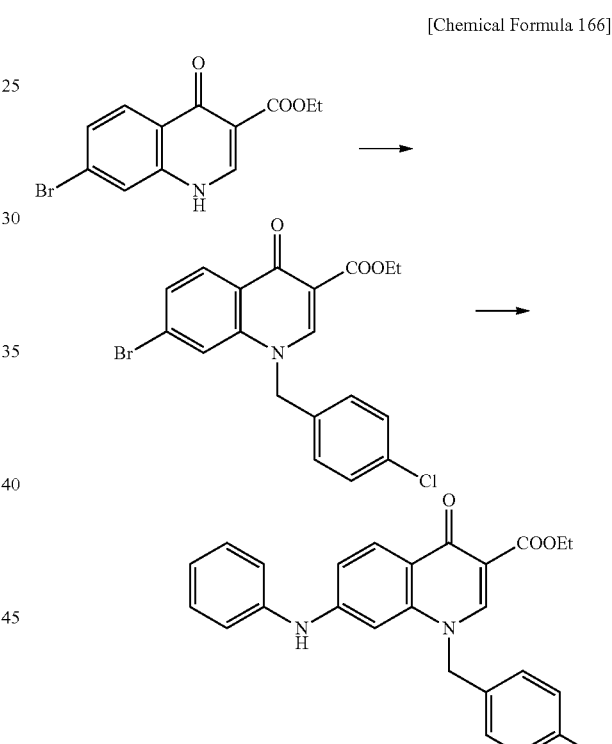

To a mixture of 7-promo-3-(ethoxycarbonyl)quinoline-4(1H)-one (250 mg, 0.844 mmol) and acetonitrile (5 mL) were added potassium carbonate (175 mg, 1.27 mmol) and 4-chlorobenzylbromide (208 mg, 1.01 mmol), and the resulting mixture was stirred at 100° C. for 5 hours. The insoluble were removed by filtration and washed by ethyl acetate. The mother liquor was concentrated in vacuo. The resulting residue was purified by silica gel column chromatography (ethyl acetate/hexane) to give 7-bromo-1-(4-chlorobenzyl)-3-(ethoxycarbonyl)quinoline-4(1H)-one (216 mg, Yield: 61%) as colorless solid.

1H-NMR (δ ppm TMS/DMSO-d6): 1.29 (3H, t, J=6.0 Hz), 4.24 (2H, q, J=6.0 Hz), 5.69 (2H, s), 7.28 (2H, d, J=8.0 Hz), 7.44 (2H, d, J=8.0 Hz), 7.61 (1H, d, J=8.0 Hz), 7.85 (1H, s), 8.14 (1H, d, J=8.0 Hz), 8.89 (1H, s).

To a mixture of 7-bromo-1-(4-chlorobenzyl)-3-(ethoxycarbonyl)quinoline-4(1H)-one (86.0 mg, 0.204 mmol) and dioxane (5 mL) were added aniline (29 mg, 0.31 mmol), palladium acetate(II) (4.6 mg, 0.020 mmol), 4,5-bis(diphenylphosphino)-9,9-dimethylxanthene (17 mg, 0.031 mmol) and cesium carbonate (93 mg, 0.29 mmol), and the resulting mixture was heated at reflux for 1 hour. To the reaction mixture was added water, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) and reversed-phase HPLC (0.3% formic acid/acetonitrile) to give 1-(4-chlorobenzyl)-7-(phenylamino)-3-(ethoxycarbonyl)quinoline-4 (1H)-one (24 mg, Yield: 27%) as colorless solid.

1H-NMR (δ ppm TMS/DMSO-d6): 1.29 (3H, t, J=6.0 Hz), 4.24 (2H, q, J=6.0 Hz), 5.52 (2H, s), 6.86 (3H, m), 6.99 (2H, m), 7.20 (4H, m), 7.48 (2H, d, J=8.0 Hz), 8.05 (1H, d, J=8.0 Hz), 8.80 (1H, s), 8.84 (1H, s).

EXAMPLE 45

Preparation of 1-(4-chlorobenzyl)-2-(4-isopropoxyphenylimino)-dihydro-pyrimidine-4,6-dion (I-322)

[Chemical Formula 167]

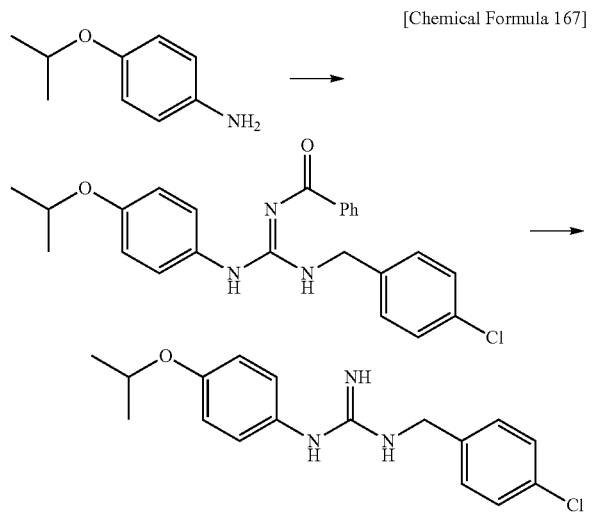

To a mixture of 4-isopropoxyaniline (15 g, 99 mmol) and acetonitrile (150 mL) was added gradually benzoylisothiocyanate (13.4 mL, 99 mmol) under ice-cooling, and the resulting mixture was stirred at room temperature for 50 minutes. To the reaction mixture were added gradually 4-chlorobenzylamine (12.1 mL, 99 mmol), triethylamine (13.8 mL, 99 mmol), and 1-ethyl-3-(3-dimethyl-aminopropyl) carbodiimide hydrochloride (20.9 g, 109 mmol) under ice-cooling, and the resulting mixture was stirred at room temperature for 2.5 hours. To the reaction mixture was added water (200 mL), and the mixture was extracted with toluene (300 mL). The extract was washed by brine (100 mL), dried over anhydrous magnesium sulfate, and concentrated in vacuo. The resulting residue was precipitated by toluene and hexane to give N-((4-chlorobenzylamino)(4-isopropoxyanilino)methylene) benzamide (38.1 g, Yield: 91%) as white powder.

1H-NMR (δ ppm TMS/CDCl₃): 1.34 (6H, d, J=6.0 Hz), 4.52 (1H, sept, J=6.0 Hz), 4.72 d, J=6.2 Hz), 5.09 (1H, brs), 6.87-6.92 (2H, m), 7.13-7.18 (2H, m), 7.24-7.31 (4H, m), 7.36-7.48 (3H, m), 8.21-8.25 (2H, m), 11.9 (1H, hrs).

To a mixture of N-((4-chlorobenzylamino)(4-isopropoxyanilino)methylene)benzamide (38.1 g, 90 alma and ethanol (380 mL) was added potassium hydroxide (17.9 g, 271 mmol), and the resulting mixture was stirred at 85° C. for 2.5 hours. To the reaction mixture was added water (380 mL), and the resulting mixture was stirred under ice-cooling for 30 minutes. The precipitated solid was filtered off, and washed by ethanol and water to give 1-(4-chlorobenzyl)-3-(4-isopropoxyphenyl) guanidine (25.8 g, Yield: 90%) as white powder.

1H-NMR (δ ppm TMS/CDCl₃): 1.34 (6H, d, J=6.0 Hz), 3.80 (1H, brs), 4.43 (2H, brs), 4.48 (1H, sept, J=6.0 Hz), 6.85 (4H, m), 7.30-7.36 (4H, m).

[Chemical Formula 168]

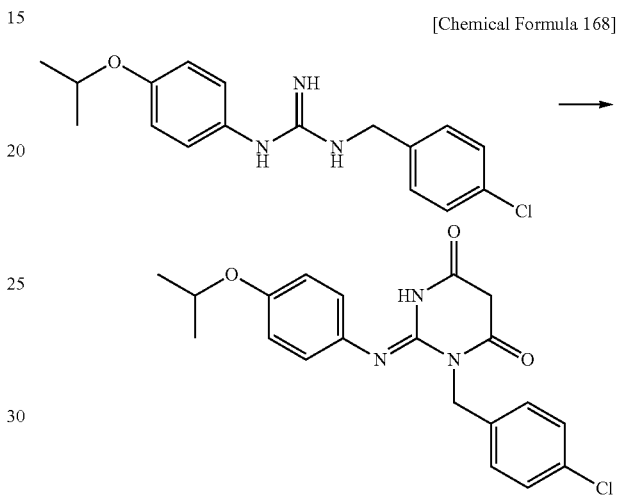

To a mixture of 1-(4-chlorobenzyl)-3-(4-isopropoxyphenyl)guanidine (2.0 g, 6.3 mmol), ethyl malonate (2.0 g, 12.6 mmol) and N-methyl-2-pyrrolidinone (20 mL) was added DBU (1.89 mL, 12.6 mmol), and the resulting mixture was stirred at 150° C. for 10 minutes under microwave irradiation. To the reaction mixture was added 2 mol/L hydrochloric acid (200 mL), and the mixture was extracted with ethyl acetate (300 mL). The extract was washed by water (200 mL) and brine (200 mL), dried over anhydrous magnesium sulfate, and concentrated in vacuo. The resulting residue was purified by HPLC to give 1-(4-chlorobenzyl)-2-(4-isopropoxyphenylimino)-dihydropyrimidine-4,6-dion (1.37 g, Yield: 56%) as yellow amorphous.

1H-NMR (δ ppm TMS/CDCl₃): 1.36 (6H, d, J=6.0 Hz), 3.62 (2H, s), 4.51 (1H, sept, J=6.0 Hz), 5.24 (2H, s), 6.67-6.74 (2H, m), 6.77-6.93 (2H, m), 7.23-7.32 (2H, m), 7.46-7.50 (2H, m), 7.77 (1H, brs).

EXAMPLE 46

Preparation of 1-(4-chlorobenzyl)-3-acetylamino-4-hydroxy-6-(4-isopropoxyphenylimino)-2,3-dihydro-pryimidine-4-one (I-339)

[Chemical Formula 169]

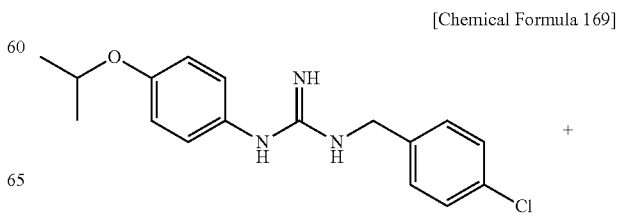

-continued

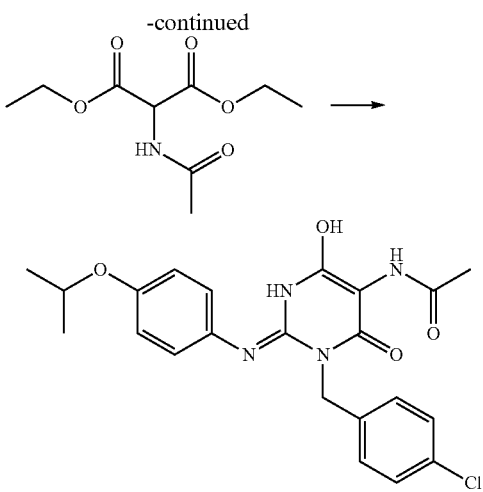

To a mixture of 1-(4-chlorobenzyl)-3-(4-isopropoxyphenyl)guanidine (300 mg, 0.944 mmol), 2-acetamideethyl malonate (410 mg, 1.89 mmol) and N-methyl-2-pyrrolidinone (3 mL) was added DBU (0.28 mL, 1.89 mmol), and the resulting mixture was stirred at 220° C. for 10 minutes under microwave irradiation. To the reaction mixture was added 2 mol/L hydrochloric acid (200 mL), and the resulting mixture was extracted with ethyl acetate (300 mL). The extract was washed by brine (200 mL), dried over anhydrous magnesium sulfate, and concentrated in vacuo. The resulting residue was purified by HPLC to give 1-(4-chlorobenzyl)-3-acetylamino-4-hydroxy-6-(4-isopropoxyphenylimino)-2,3-dihydro-pyrimidine-4-one (122 mg, Yield: 29%) as yellow solid.

1H-NMR (δ ppm TMS/DMSO-d6): 1.23 (6H, d, J=6.1 Hz), 1.92 (3H, s), 3.62 (2H, a), 4.54 (1H, sept, J=6.1 Hz), 5.32 (1H, s), 6.80-6.86 (2H, m), 7.17-7.26 (4H, m), 7.39-7.42 (2H, m), 8.66 (1H, brs), 8.72 (1H, brs), 11.0 (1H, brs).

EXAMPLE 47

Preparation of 1-(4-chlorobenzyl)-3-(2-methoxycarbonylethyl)carbamoyl-4-hydroxy-6-(4-isopropoxyphenylimino)-2,3-dihydro-pyrimidine-4-one (I-333)

[Chemical Formula 170]

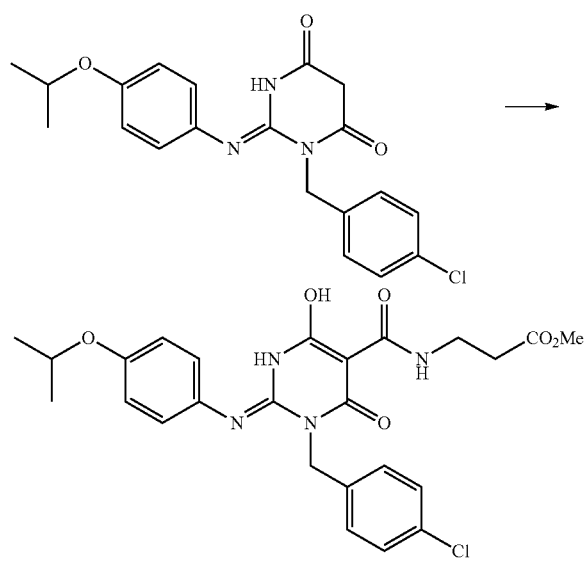

To a mixture of 1-(4-chlorobenzyl)-2-(4-isopropoxyphenylimino)-dihydropyrimidine-4,6-dion (300 mg, 0.778 mmol) and DMF (2 mL) were added 3-isocyanatopropionic acid methylester (502 mg, 3.89 mmol) and triethylamine (0.108 mL, 0.778 mmol), and the resulting mixture was stirred at 60° C. for 10 minutes. To the reaction mixture was added 1 mol/L hydrochloric acid (200 mL), and the resulting mixture was extracted with ethyl acetate (300 mL). The extract was washed by brine (200 mL), dried over anhydrous magnesium sulfate, and concentrated in vacuo. The resulting residue was purified by silica gel column chromatography (ethyl acetate/hexane) to give 1-(4-chlorobenzyl)-3-(2-methoxycarbonylethyl)carbamoyl-4-hydroxy-6-(4-isopropoxyphenylimino)-2,3-dihydropryimidine-4-one (145 mg, Yield: 36%) as white powder.

1H-NMR (δ ppm TMS/DMSO-d6): 1.25 (6H, d, J=5.9 Hz), 2.58 (2H, t, J=6.4 Hz), 3.50 (2H, m), 3.59 (3H, s), 4.58 (1H, sept, J=5.9 Hz), 5.32 (2H, s), 6.89 (2H, d, J=8.7 Hz), 7.16 (2H, d, J=8.7 Hz), 7.26 (2H, d, J=8.2 Hz), 7.42 (2H, d, Hz), 9.34 (1H, brs), 9.50 (1H, brs).

EXAMPLE 48

Preparation of 1-(4-chlorobenzyl)-3-(2-hydroxycarbonylethyl)carbamoyl-4-hydroxy-6-(4-isopropoxyphenylimino)-2,3-dihydropryimidine-4-one (I-336)

[Chemical Formula 171]

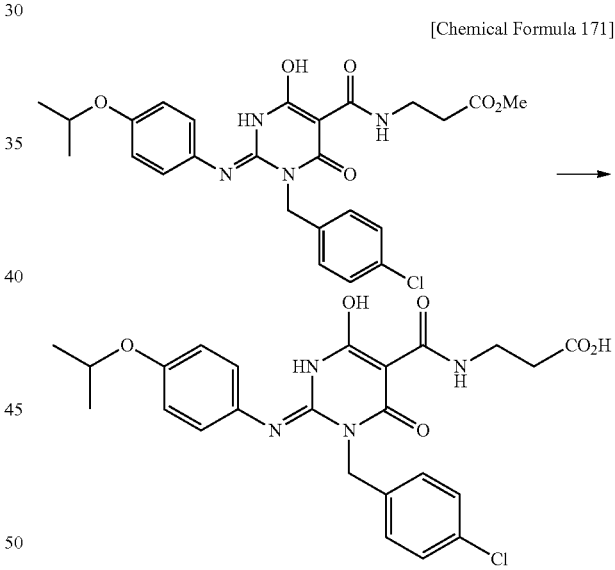

To a mixture of 1-(4-chlorobenzyl)-3-(2-methoxycarbonylethyl)carbamoyl-4-hydroxy-6-(4-isopropoxyphenylimino)-2,3-dihydro-pyrimidine-4-one (1.38 mg, 0.268 mmol), methanol (1 mL), water (1 mL) and THF (1 mL) was added 2 mol/L sodium hydroxide (0.402 mL), and the resulting mixture was stirred at room temperature for 30 minutes. To the mixture was added brine (100 mL) and 2 mol/L hydrochloric acid (1 mL), and the resulting mixture was extracted with ethyl acetate (300 mL). The extract was dried over anhydrous magnesium sulfate, and concentrated in vacuo. The resulting residue was recrystallized by ethyl acetate and hexane to give 1-(4-chlorobenzyl)-3-(2-hydroxycarbonylethyl)carbamoyl-4-hydroxy-6-(4-isopropoxyphenylimino)-2,3-dihydropryimidine-4-one (120 mg, Yield: 89%) as colorless solid.

1H-NMR (δ ppm TMS/DMSO-d6): 1.25 (6H, d, J=5.5 Hz), 2.50 (2H, m), 3.46 (2H, m), 4.57 (1H, sept, J=5.5 Hz), 5.32 (2H, s), 6.90 (2H, d, J=8.2 Hz), 7.16 (2H, d, J=8.2 Hz), 7.26 (2H, d, J=7.9 Hz), 7.42 (2H, d, J=8.9 Hz), 9.38 (1H, brs), 9.50 (H, brs), 12.4 (1H, brs), 16.1 (1H, brs).

EXAMPLE 49

Preparation of methyl 1-(4-chlorobenzyl)-2-(4-ethoxyphenylamino)-1H-benzo[d]imidazole-4-carboxylate (I-362)

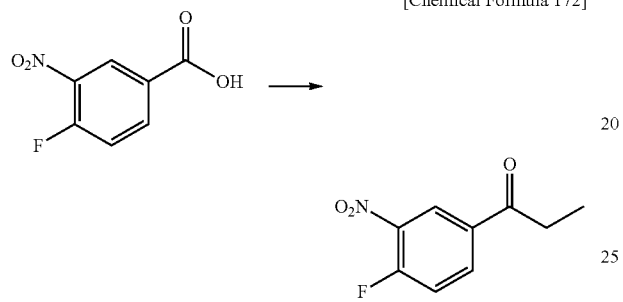

A mixture of 4-fluoro-3-nitrobenzoic acid (5 g, 27 mmol), concentrated sulphuric acid (0.144 mL, 2.7 mmol) and methanol (50 mL) was heated at reflux for 4 hours. The reaction mixture was concentrated. To the residue was added saturated aqueous sodium bicarbonate (200 mL), and the resulting mixture was extracted with ethyl acetate (200 mL). The extract was washed by brine (200 mL), dried over anhydrous sodium sulphate, and concentrated in vacuo. The resulting residue was purified by silica gel column chromatography (ethyl acetate/hexane) to give methyl(4-fluoro-3-nitro)benzoate (1.94 g, Yield: 36%) as white powder.

1H-NMR (δ ppm TMS/CDCl3): 3.98 (3H, s), 7.39 (1H, dd, J=10.1, 8.8 Hz), 8.33 (1H, ddd, J=8.8, 2.2, 1.1 Hz), 8.74 (1H, dd, J=7.1, 2.2 Hz).

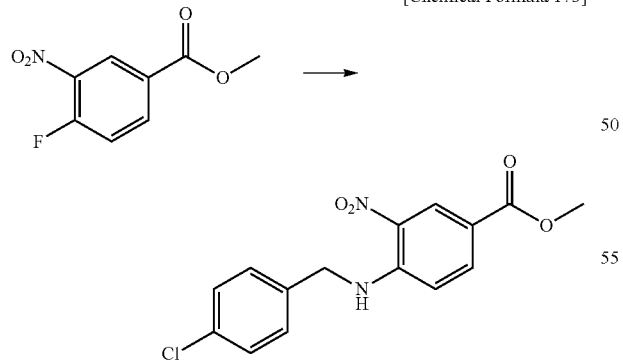

A mixture of methyl (4-fluoro-3-nitro)benzoate (1 g, 5.02 mmol), 4-chlorobenzylamine (747 mg, 5.27 mmol), N,N-diisopropylethylamine (0.965 ml, 5.52 mmol) and THF (20 mL) was stirred at room temperature for 5 hours. The reaction mixture was poured into water (50 mL), and the resulting mixture was extracted with ethyl acetate (50 mL). The extract was washed by brine (50 mL), dried over anhydrous sodium sulphate, and concentrated in vacuo to give methyl 4-(4-chlorobenzylamine)-3-nitrobenzoic acid ester (1.74 g, Yield: 100%) as yellow powder.

1H-NMR (δ ppm TMS/CDCl3): 3.90 (3H, s), 4.58 (2H, d, J=5.8 Hz), 6.80 (1H, d, J=9.1 Hz), 7.28 (2H, d, J=9.3 Hz), 7.36 (2H, d, J=9.3 Hz), 8.02 (1H, dd, J=6.5, 2.1 Hz), 8.69 (1H, brs), 8.91 (1H, d, J=2.1 Hz).

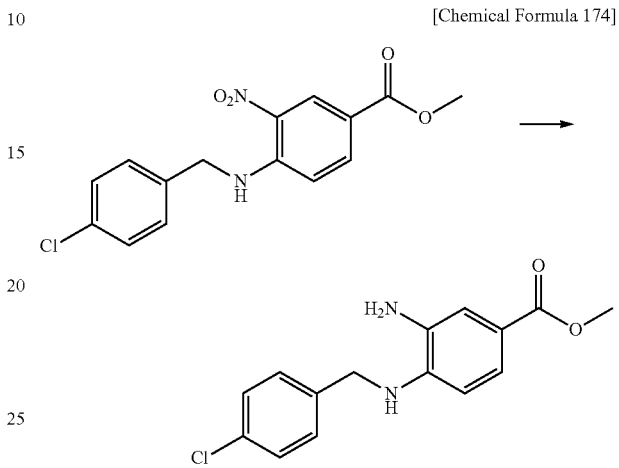

A mixture of methyl 4-(4-chlorobenzylamine)-3-nitrobenzoic acid ester (1 g, 3.12 mmol), 10% palladium on carbon (66 mg), and 50% methanol/ethyl acetate (20 mL) was stirred at room temperature for 1 hour under hydrogen atmosphere. Palladium on carbon was removed by filtration using Celite, and the residue was concentrated to give methyl 3-amino-4-(4-chlorobenzyl)aminobenzoate (809 mg, Yield: 89.2%) as grey powder.

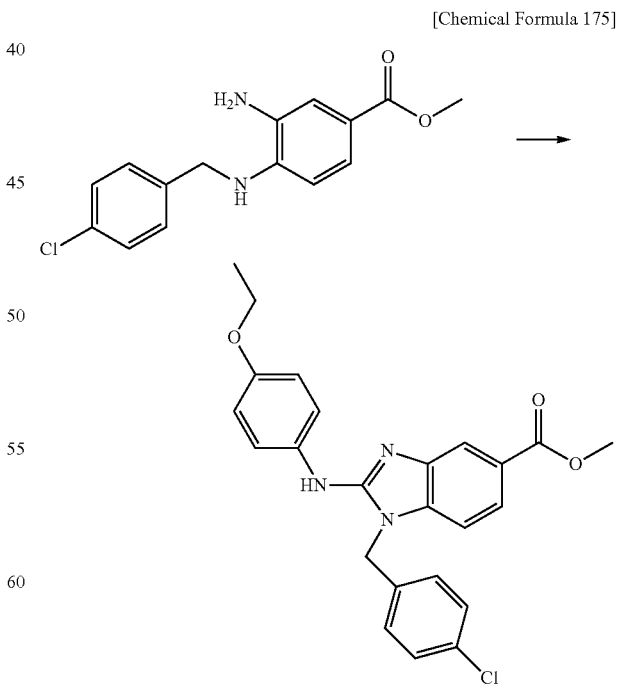

A mixture of methyl 3-amino-4-(4-chlorobenzyl)aminobenzoate (534 mg, 1.84 mmol), 1-ethoxy-4-isothiocyanatobenzene (362 mg, 2.02 mmol) and DMSO (5 mL) was stirred at room temperature for 0.5 hour. To the reaction mixture was added 1-(3-dimethylaminopropyl)-3-ethylcarbodiimide hydrochloride (704 mg, 3.67 mmol), the resulting mixture was stirred at 80° C. for 2 hours. The reaction mixture was poured into saturated aqueous sodium bicarbonate (10 mL), and the resulting mixture was extracted with ethyl acetate (10 mL). The extract was washed by brine (10 mL), dried over anhydrous sodium sulphate, and concentrated in vacuo. The resulting residue was purified by silica gel column chromatography (ethyl acetate/hexane). The resulting residue was precipitated by ethyl acetate and hexane to give methyl 1-(4-chlorobenzyl)-2-(4-ethoxyphenylamino)-1H-banze[d] imidazole-4-carboxylate (34.7 mg, Yield: 4.3%) as white powder.

1H-NMR (δ ppm TMS/CDCl3) 1.40 (3H, t, J=7.0 Hz), 3.92 (3H, s), 4.00 (2H, q, J=7.0 Hz), 5.19 (2H, s), 5.93 (1H, brs), 6.86 (2H, d, J=9.1 Hz), 7.09-7.14 (3H, m), 7.33-7.35 (4H, m), 7.88 (1H, d, J=8.24 Hz), 8.29 (1H, brs).

EXAMPLE 50

Preparation of 3-methyl-1-(4-methylbenzyl)-4-(4-phenoxyphenyl)iminoimidazolidine-2-one (I-363)

[Chemical Formula 176]

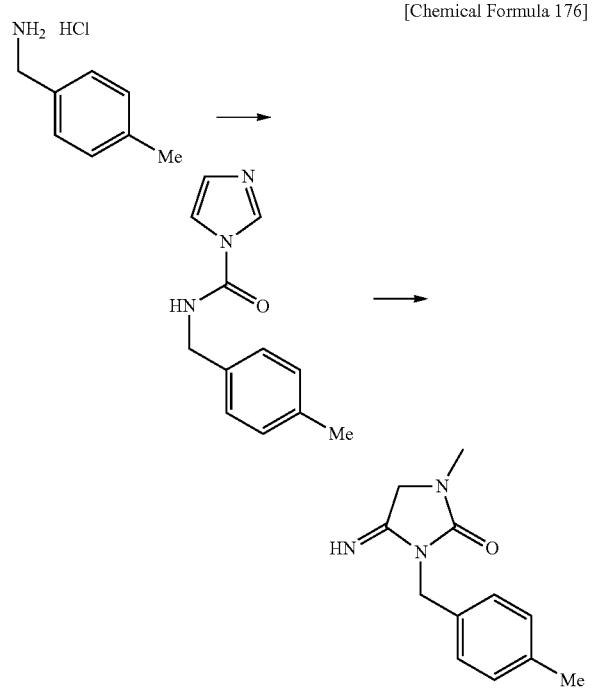

To a mixture of 4-methylbenzylamine hydrochloride (10 g, 83 mmol) and N,N-dimethylacetamide (50 mL) was added 1,1'-carbonyldiimidazole (14.05 g, 87 mmol) under ice-cooling. To the mixture was added DBU (18.66 mL, 124 mmol), and the resulting mixture was stirred at 0° C. for 30 minutes. To the reaction mixture was added 2-(methylamino)acetonitrile hydrochloride (10.55 g, 99 mmol) under ice-cooling. Further, to the mixture was added DBU (24.88 mL, 165 mmol) under ice-cooling, and the resulting mixture was stirred at room temperature for 45 minutes and stirred at 50° C. for additional 90 minutes. To the reaction mixture was added water (500 mL). The mixture was extracted with ethyl acetate (500 mL×2), washed by brine (500 mL), dried over anhydrous magnesium sulfate, and concentrated in vacuo. The resulting residue was purified by silica gel column chromatography (methanol/chloroform) to give 4-imino-3-methyl-1-(4-methylbenzyl)imidazolidine-2-one (9.43 g, Yield: 52%) as yellow solid.

1H-NMR (δ ppm TMS/CDCl$_3$): 2.31 (3H, s), 2.94 (3H, s), 3.93 (2H, s), 4.66 (2H, s), 6.90 (1H, br.s), 7.11 (2H, d, J=8.2 Hz), 7.27 (2H, d, J=8.2 Hz).

[Chemical Formula 177]

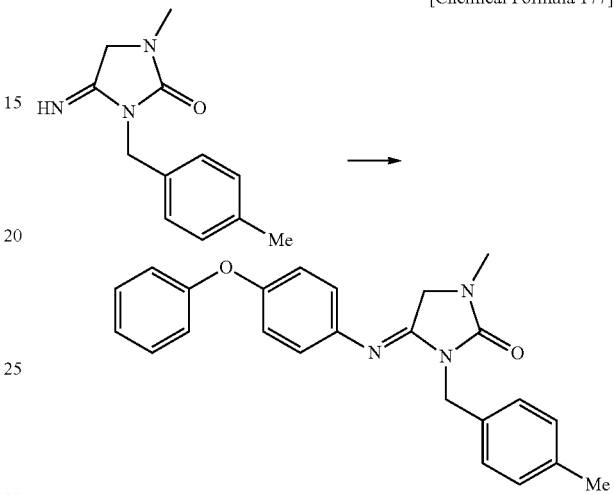

To a mixture of 4-imino-3-methyl-1-(4-methylbenzyl)imidazolidine-2-one (322 mg, 1.48 mmol), 4-bromo-diphenyl ether (443 mg, 1.78 mmol), 4,5-bis(diphenylphosphino)-9,9-dimethylxanthene (1.29 mg, 0.22 mmol), cesium carbonate (724 mg, 2.22 mmol) and dioxane (6.4 mL) was added palladium acetate (33.3 mg, 0.1 mmol) under nitrogen atmosphere, and the resulting mixture was heated at reflux for 3 hours. To the reaction mixture was added water (200 mL), and the mixture was extracted with ethyl acetate (300 mL). The extract was washed by brine (200 mL), dried over anhydrous magnesium sulfate, and concentrated in vacuo. The resulting residue was purified by high speed liquid chromatography (0.3% HCO$_2$H H$_2$O/MeCN 40-70%) to give (3-methyl-1-(4-methylbenzyl)-4-(4-phenoxyphenyl)iminoimidazolidine-2-one (17.2 mg, Yield: 3.0%) as yellow oil.

1H-NMR (δ ppm TMS/CDCl$_3$): 2.33 (3H, s), 2.89 (3H, s), 3.89 (2H, s), 4.78 (2H, a), 6.77-6.82 (2H, m), 6.93-7.14 (7H, m), 7.28-7.34 (4H, m).

EXAMPLE 51

Preparation of 3-(4-isopropoxyphenylamino)-6-methyl-4-(4-methylbenzyl)pyridazine (I-365)

[Chemical Formula 178]

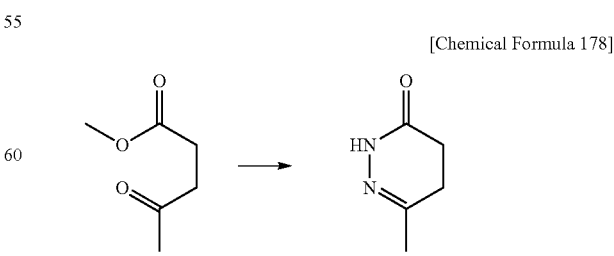

To a mixture of methyl levulinate (10 g, 77 mmol) and methanol (50 mL) was added hydrazine monohydrate (3.92 mL, 81 mmol), and the resulting mixture was stirred at room temperature for 15 minutes and stirred at 60° C. for additional 2 hours. Methanol was removed under reduced pressure, and toluene (100 mL) was added to the residue. The reaction mixture was concentrated to give 6-methyl-4,5-dihydropyridazine-3(2H)-one (8.49 g, Yield: 98.5%) as colorless solid.

1H-NMR (δ ppm TMS/CDCl$_3$): 2.05 (3H, 2.42-2.53 (4H, m), 8.50 (1H, br.s).

[Chemical Formula 179]

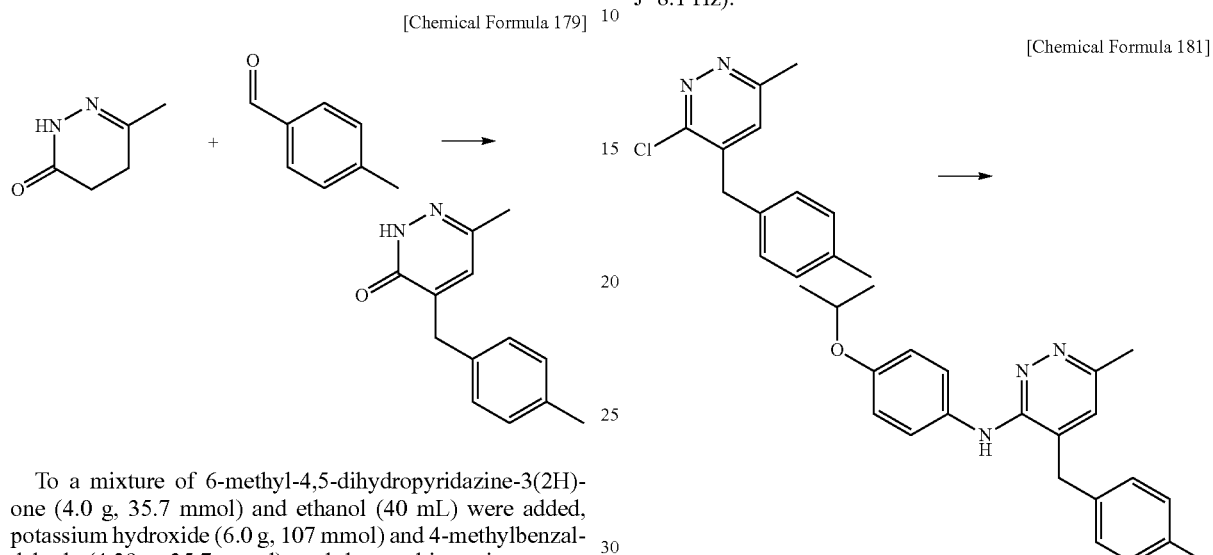

To a mixture of 6-methyl-4,5-dihydropyridazine-3(2H)-one (4.0 g, 35.7 mmol) and ethanol (40 mL) were added, potassium hydroxide (6.0 g, 107 mmol) and 4-methylbenzaldehyde (4.29 g, 35.7 mmol), and the resulting mixture was heated at reflux for 2 hours. The reaction mixture was poured into 2 mol/L hydrochloric acid (200 mL), and the mixture was extracted with ethyl acetate (300 mL). The extract was washed by brine (200 mL), dried over anhydrous magnesium sulfate, and concentrated in vacuo. To the residue was added a mixture of ethyl acetate and hexane, and the precipitated solid was filtered off to give 6-methyl-4-(4-methylbenzyl)pyridazine-3(2H)-one (3.74 g, Yield: 49%) as colorless solid.

1H-NMR (δ ppm TMS/CDCl$_3$): 2.22 (3M, s), 2.35 (3H, s), 3.85 (2H, s), 6.67 (1H, s), 7.11-7.17 (4H, m), 10.9 (1H, br.s).

[Chemical Formula 180]

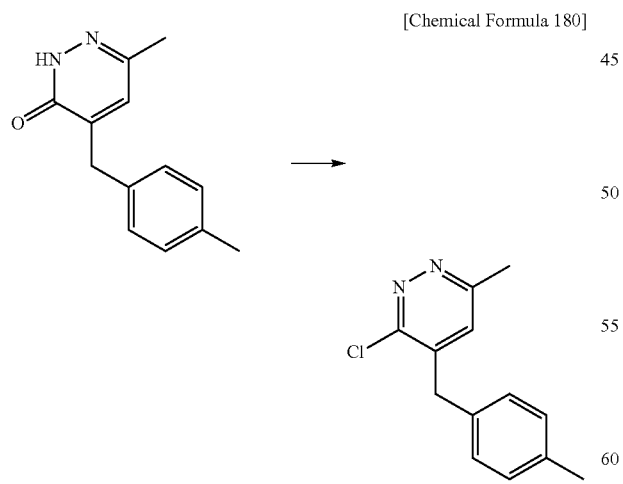

Phosphorus oxychloride (6.6 mL, 70 mmol) was added to 6-methyl-4-(4-methylbenzyl)pyridazine-3(2H)-one (1.5 g, 7.0 mmol), and the mixture was stirred at 1.00° C. for 1 hour. Phosphorus oxychloride was removed under reduced pressure. To the residue was added saturated aqueous sodium bicarbonate (200 mL), and the mixture was extracted with chloroform (300 mL). The extract was dried over anhydrous magnesium sulfate, and concentrated in vacuo. The resulting residue was purified by silica gel column chromatography (ethyl acetate/hexane) to give 3-chloro-6-methyl-4-(4-methylbenzyl)pyridazine (1.52 g, Yield: 93%) as pale yellow solid.

1H-NMR (δ ppm TMS/CDCl$_3$): 2.36 (3H, s), 2.59 (3H, s), 3.98 (2H, s), 6.91 (1H, s), 7.06 (2H, d, J=8.1 Hz), 7.16 (2H, d, J=8.1 Hz).

[Chemical Formula 181]

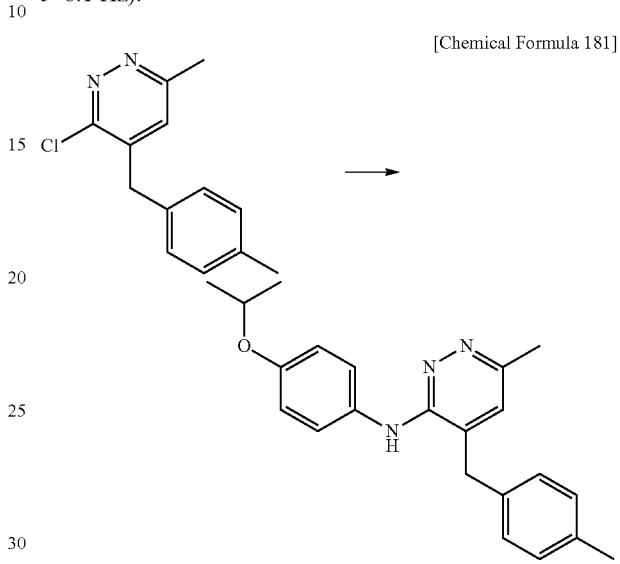

To a mixture of 3-chloro-6-methyl-4-(4-methylbenzyl)pyridazine (200 mg, 0.859 mmol), 4-isopropoxyaniline (169 mg, 1.12 mmol), 4,5-bis(diphenylphosphino)-9,9-dimethylxanthene (112 mg, 0.193 mmol), cesium carbonate (560 mg, 1.72 mmol) and dioxane (4 mL) was added palladium acetate (28.9 mg, 0.129 mmol) under nitrogen atmosphere, and the resulting mixture was heated at reflux for 1 hour. To the reaction mixture were added water (200 mL) and saturated aqueous ammonium chloride (5 mL). The resulting mixture was extracted with ethyl acetate (200 mL). The extract was washed by brine (200 mL), dried over anhydrous magnesium sulfate, and concentrated in vacuo. The resulting residue was purified by silica gel column chromatography (ethyl acetate/hexane) to give 3-(4-isopropoxyphenylamino)-6-methyl-4-(4-methylbenzyl)pyridazine (187 mg, Yield: 62.7%) as yellow amorphous.

1H-NMR (δ ppm TMS/CDCl$_3$): 1.31 (6H, d, J=6.1 Hz), 2.37 (3H, s), 2.56 (3H, s), 3.84 (2H, s), 4.46 (1H, sep, J=6.1 Hz), 5.96 (1H, s), 6.80 (2H, d, J=8.3 Hz), 7.08 (2H, d, J=7.9 Hz), 7.18 (2H, d, J=7.9 Hz), 7.34 (2H, d, J=8.3 Hz).

EXAMPLE 52

Preparation of 4-(4-chlorobenzyl)-6-(3-trifluoromethylphenylamino)-2H-1,4-benzoxazine-3(4H)-one (I-366)

[Chemical Formula 182]

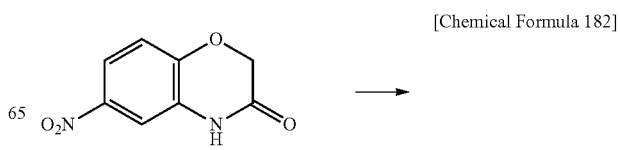

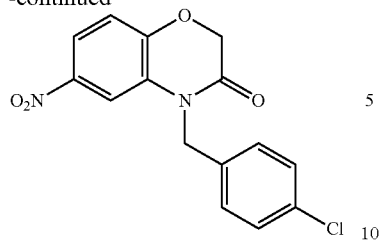

To a mixture of 6-nitro-2H-1,4-benzoxazine-3(4H)-one (3 g, 15.45 mmol), potassium carbonate (2.14 mg, 15.45 mmol) and DMF (30 mL) was added 4-chlorobenzyliodide (4.29 g, 17 mmol), and the resulting mixture was stirred at room temperature for 3 hours. To the reaction mixture were added water (300 mL) and 5% aqueous citric acid (50 mL), and the resulting mixture was extracted with ethyl acetate (200 mL). The extract was washed by brine (300 mL), dried over anhydrous sodium sulphate, and concentrated in vacuo. The resulting residue was recrystallized by ethyl acetate/hexane to give 4-(4-chlorobenzyl)-6-nitro-2H-1,4-benzoxazine-3(4H)-one (3.47 g, 70.5%) as pale brown solid.

1H-NMR (δ ppm TMS/CDCl$_3$): 4.85 (2H, s), 5.18 (2H, s), 7.07 (1H, d, J=8.7 Hz), 7.24 (2H, d, J=8.4 Hz), 7.33 (2H, d, J=8.4 Hz), 7.80 (1H, d, J=2.4 Hz), 7.90 (1H, dd, J=2.4, 8.7 Hz).

[Chemical Formula 183]

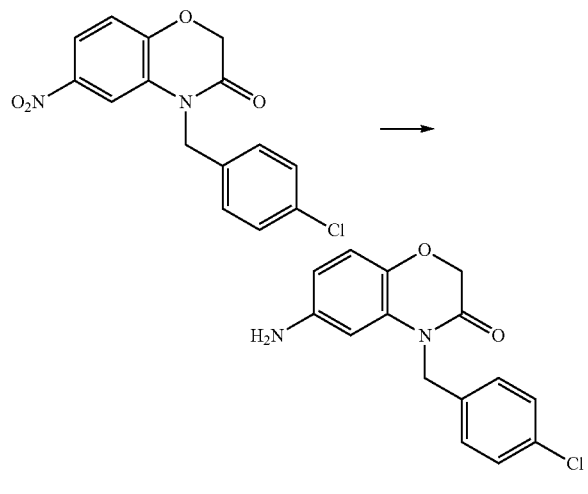

To a mixture of 4-(4-chlorobenzyl)-6-nitro-2H-1,4-benzoxazine-3(4H)-one (1 g, 3.14 mmol) and acetonitrile (20 mL) was added tin (II) chloride dihydrate (2.83 g, 12.55 mmol), and the resulting mixture was heated at reflux for 3 hours. The reaction mixture was poured into saturated aqueous sodium bicarbonate (300 mL), and the mixture was extracted with ethyl acetate (300 mL). The extract was washed by brine (300 mL), dried over anhydrous sodium sulphate, and concentrated in vacuo. The resulting residue was recrystallized by ethyl acetate/hexane to give 6-amino-4-(4-chlorobenzyl)-2H-1,4-benzoxazine-3(4H)-one (0.65 g, yield: 71.7%) as pale purple solid.

1H-NMR (δ ppm TMS/CDCl$_3$): 4.45 (2H, s), 4.63 (2H, s), 5.06 (2H, s), 6.16 (1H, d, J=2.7 Hz), 6.30 (1H, dd, J=2.7, 8.4 Hz), 6.81 (1H, d, J=3.7 Hz), 7.17 (2H, d, J=8.7 Hz), 7.30 (2H, d, J=8.4 Hz).

[Chemical Formula 184]

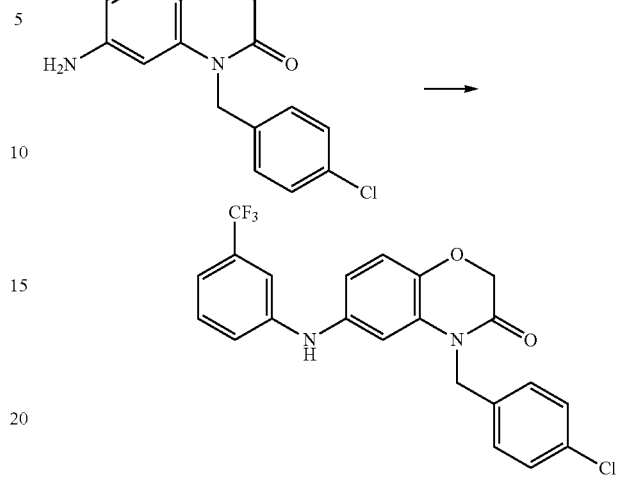

To a mixture of 6-amino-4-(4-chlorobenzyl)-2H-1,4-benzoxazine-3(4H)-one (100 mg, 0.346 mmol), palladium acetate (11.7 mg, 0.05 mmol), 4,5-bis(diphenylphosphino)-9,9-dimethylxanthene (45.1 mg, 0.08 mmol), cesium carbonate (226 mg, 0.69 mmol) and dioxane (2 mL) was added 1-bromo-3-trifluoromethylbenzene (0.048 mL, 0.346 mmol) under nitrogen atmosphere, and the resulting mixture was heated at reflux for 2 hours. To the reaction mixture were added water (20 mL) and 5% aqueous citric acid (4 mL), and the mixture was extracted with ethyl acetate (30 mL). The extract was washed by water (30 mL) and brine (30 mL), dried over anhydrous sodium sulphate, and concentrated in vacuo. The resulting residue was purified by silica gel column chromatography (ethyl acetate/hexane) to give 4-(4-chlorobenzyl) 6-(3-trifluoromethylphenylamino)-2H-1,4-benzoxazine-3(4H)-one (93 mg, Yield: 62.0%) as pale yellow solid.

1H-NMR (δ ppm TMS/CDCl$_3$): 4.72 (2H, s), 5.08 (2H, s), 5.62 (1H, s), 6.60 (1H, d, J=2.4 Hz), 6.70 (1H, dd, J=2.4, 8.7 Hz), 6.82 (1H, d, J=5.4 Hz), 6.96 (1H, d, J=8.7 Hz), 7.04-7.32 (7H, m).

EXAMPLE 53

Preparation of 1-(4-chlorobenzyl)-3-(ethoxycarbonylmethyl)-6-(4-isopropoxyphenylamino)-quinazoline-2,4-dion (I-367)

[Chemical Formula 185]

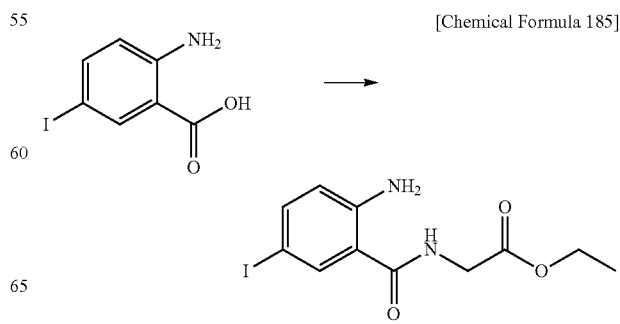

To a mixture of glycine ethyl ester hydrochloride (2.91 g, 20.9 mmol)) and DMF (50 mL) was added triethylamine (5.27 mL, 38 mmol), and the resulting mixture was stirred at room temperature for 10 minutes. To the mixture were added 2-amino-5-iodobenzoic acid (5 g, 19 mmol), 1-hydroxybenzotriazole hydrate (0.77 g, 5.7 mmol), and 1-(3-dimethylaminopropyl)-3-ethylcarbodiimide hydrochloride (5.47 g, 28.5 mmol), and the resulting mixture was stirred at room temperature for 1 hour. To the reaction mixture were added water (300 mL) and 5% aqueous citric acid (50 mL), and the resulting mixture was extracted with ethyl acetate (200 mL). The extract was washed by saturated aqueous sodium bicarbonate (300 mL), dried over anhydrous sodium sulphate, and concentrated in vacuo to give 2-amino-N-(ethoxycarbonylmethyl)-5-iodobenzamide (5.44 g, Yield: 82.2%) as pale yellow solid.

1H-NMR (δ ppm TMS/CDCl$_3$): 1.32 (3H, t, J=7.2 Hz), 4.17 (2H, d, J=4.8 Hz), 4.27 (2H, q, J=7.2 Hz), 5.30 (2H, s), 6.47 (1H, d, J=8.4 Hz), 6.49 (1H, s), 7.44 (1H, dd, J=1.2, 8.4 Hz), 7.66 (1H, d, J=1.8 Hz).

To a mixture of 3-(ethoxycarbonylmethyl)-6-iodoquinazoline-2,4-dion (1 g, 2.67 mmol), potassium carbonate (2.14 mg, 15.45 mmol) and DMF (10 mL) was added 4-chlorobenzyliodide (0.742 g, 2.94 mmol), and the resulting mixture was stirred at room temperature for 1 hour. To the reaction mixture were added water (200 mL) and 5% aqueous citric acid (30 mL), and the resulting mixture was extracted with ethyl acetate (200 mL). The extract was washed by saturated aqueous sodium bicarbonate (200 mL), dried over anhydrous sodium sulphate, and concentrated in vacuo. The resulting residue was recrystallized by ethyl acetate/hexane to give 1-(4-chlorobenzyl)-3-(ethoxycarbonylmethyl)-6-iodoquinazoline-2,4-dion (0.447 g, Yield: 33.5%) as pale brown solid.

1H-NMR (δ ppm TMS/CDCl$_3$): 1.30 (3H, t, J=6.9 Hz), 4.25 (2H, q, J=7.2 Hz), 4.87 (2H, s), 5.31 (2H, s), 6.83 (1H, d, J=8.7 Hz), 7.17 (2H, d, J=8.4 Hz), 7.31 (2H, d, J=8.4 Hz), 7.82 (1H, dd, J=1.8, 8.7 Hz), 8.53 (1H, d, J=2.4 Hz).

[Chemical Formula 186]

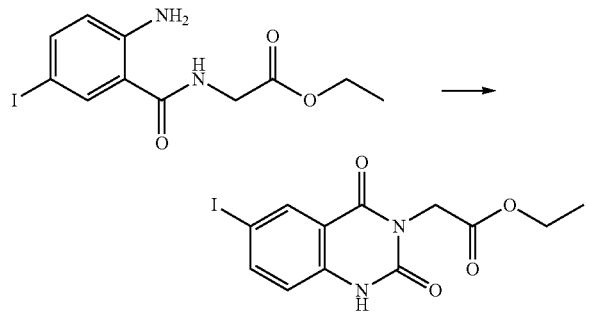

To a mixture of 2-amino-N-(ethoxycarbonylmethyl)-5-iodobenzamide (2 g, 5.74 mmol) and THF (20 mL) was added 1,1'-carbonyldiimidazole (1.85 g, 11.5 mmol), and the resulting mixture was stirred at 60° C. for 2 hours. To the reaction mixture were added water (100 mL) and 2 mol/L aqueous hydrochloric acid (40 mL), and the precipitated solid was filtered off to give 3-(ethoxycarbonylmethyl)-6-iodoquinazoline-2,4-dion (1.88 g, 87.5%) as pale yellow solid.

1H-NMR (δ ppm TMS/d$_6$ DMSO): 1.20 (3H, t, J=7.2 Hz), 4.14 (2H, q, J=7.2 Hz), 4.63 (2H, s), 7.05 (1H, d, J=8.7 Hz), 8.00 (1H, dd, J=1.8, 8.4 Hz), 8.18 (1H, d, J=5.1 Hz).

[Chemical Formula 187]

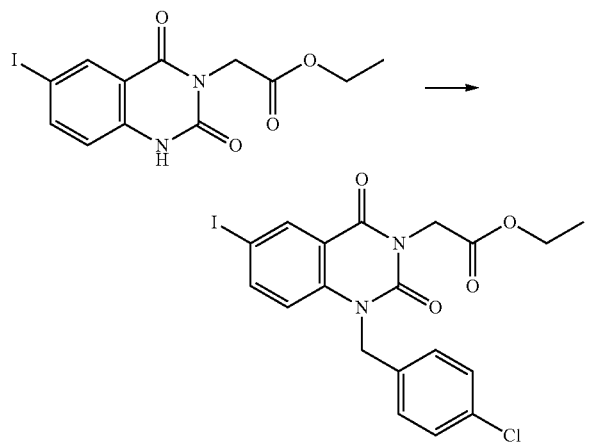

[Chemical Formula 188]

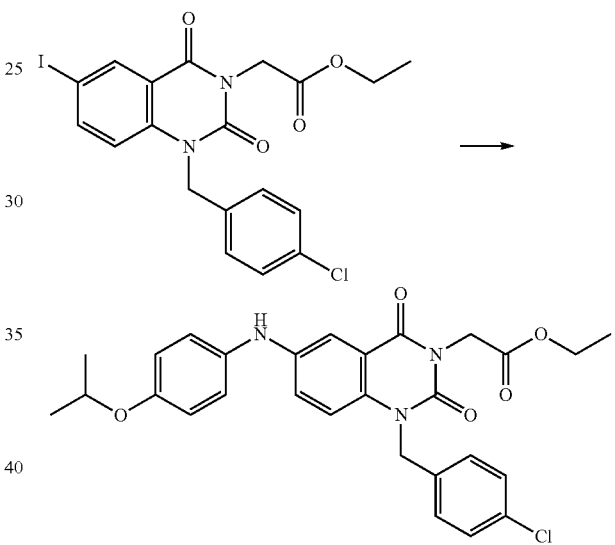

To a mixture of 1-(4-chlorobenzyl)-3-(ethoxycarbonylmethyl)-6-iodoquinazoline-2,4-dion (200 mg, 0.4 mmol), palladium acetate (13.5 mg, 0.06 mmol), 4,5-bis(diphenylphosphino)-9,9-dimethylxanthene (52.2 mg, 0.09 mmol), cesium carbonate (261 mg, 0.8 mmol) and dioxane mL) was added 4-isopropoxyaniline (0.071 ml, 0.48 mmol) under nitrogen atmosphere, and the resulting mixture was heated at reflux for 2 hours. The reaction mixture was poured into a mixture of water (1.00 mL) and 5% aqueous citric acid (10 mL), and the resulting mixture was extracted with ethyl acetate (100 mL). The extract was washed by water (100 mL), dried over anhydrous sodium sulphate, and concentrated in vacuo. The resulting residue was purified by silica gel column chromatography (ethyl acetate/hexane), and the residue was precipitated by hexane to give 1-(4-chlorobenzyl)-3-(ethoxycarbonylmethyl)-6-(4-isopropoxyphenylamino)-quinazoline-2,4-dion (7.7 mg, Yield: 3.7%) as yellow solid.

1H-NMR (δ ppm TMS/CDCl$_3$): 1.28 (3H, t, J=7.2 Hz), 1.33 (6H, d, J=6.0 Hz), 4.24 (2H, q, J=7.2 Hz), 4.74 (1H, m), 4.88 (2H, s), 5.29 (2H, s), 5.61 (1H, s), 6.84 (2H, d, J=8.7 Hz), 6.91 (1H, d, J=9.0 Hz), 7.01 (2H, d, J=8.7 Hz), 7.11 (1H, dd, J=3.0, 9.0 Hz), 7.19 (2H, d, J=8.7 Hz), 7.30 (2H, d, J=8.7 Hz), 7.68 (1H, d, J=2.7 Hz).

EXAMPLE 54

Preparation of 1,5-bis(4-chlorobenzyl)-4-(4-isopropoxyphenylamino)-6,7-dihydro-1,3,5-triazepine-2(5H)-one (I-368)

[Chemical Formula 189]

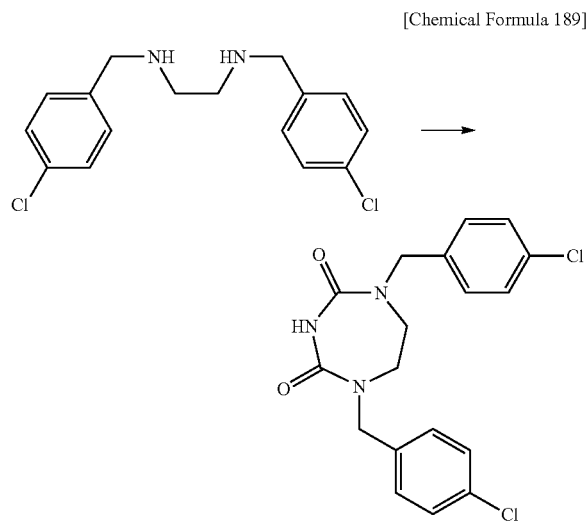

To a mixture of N,N'-bis(4-chlorobenzyl)ethylenediamine (5.47 g, 17.7 mmol) and xylene (124 mL) was added ethoxycarbonylisocyanate (1.834 mL, 17.7 mmol), and the resulting mixture was heated at reflux for 20 minutes. The reaction mixture was concentrated in vacuo. The resulting solid was washed by hexane to give 1,5-bis(4-chlorobenzyl)-1,3,5-triazepine-2,4-dion (5.34 g, Yield: 79.8%) as white solid.

1H-NMR (δ ppm TMS/d6-DMSO): 3.35 (4H, s), 4.46 (4H, s), 7.26 (4H, d, J=8.2 Hz), 7.38 (4H, d, J=7.8 Hz), 8.78 (1H, s).

[Chemical Formula 190]

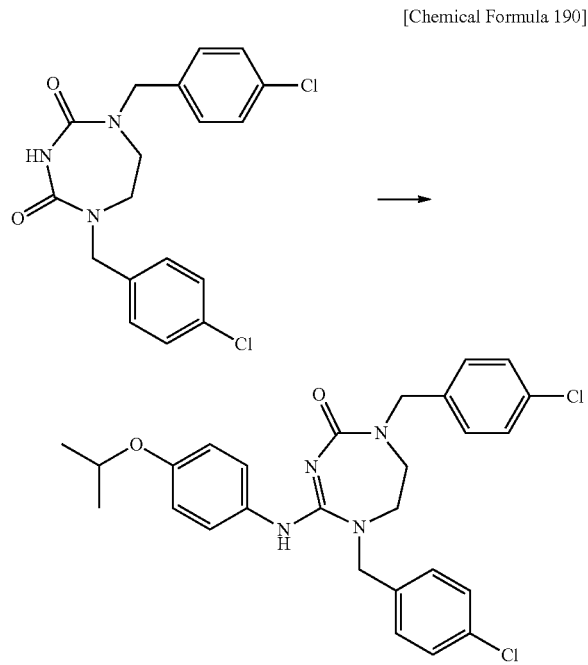

To a mixture of 1,5-bis(4-chlorobenzyl)-1,3,5-triazepine-2,4-dion (0.5 g, 1.32 mmol) and phosphorus oxychloride (2.46 mL, 26.4 mmol) was added dimethylaminopyridine (1.6 mg), and the resulting mixture was heated at reflux for 2 hours. The reaction mixture was concentrated in vacuo. To the resulting residue were added 4-isopropoxyaniline (0.196 mL, 1.32 mmol) and t-butanol (3 mL), and the resulting mixture was stirred at reflux for 2 hours. The reaction mixture was concentrated in vacuo. The resulting residue was purified by high speed liquid chromatography (0.3% $HCO_2HH_2O$/MeCN 40-70%), and the residue was precipitated by ethyl acetate/hexane to give 1,5-bis(4-chlorobenzyl-4-(4-isopropoxyphenylamino)-6,7-dihydro-1H-1,3,5-triazepine-2(5H)-one (70 mg, Yield: 10.3%) as pale yellow solid, 1H-NMR (δ ppm TMS/$CDCl_3$): 1.28 (3H, s), 1.33 (3H, s), 3.20 (2H, m), 3.40 (2H, m), 4.43 (1H, m), 4.49 (2H, s), 4.66 (2H, s), 6.47 (1H, br.s), 6.76 (2H, d, J=8.7 Hz), 6.87 (2H, 4, J=8.7 Hz), 7.18 (2H, d, J=8.5 Hz), 7.22-7.32 (6H, m).

The compounds used as intermediates are commercially available or can be synthesized by the method described in the following documents.
JP63112566
JP60112483
WO2006129609
Journal of Combinatorial Chemistry (2009), 11(6), 1050-1060.
Annah di Chimica, 1959, 49 2083-8.
J. Chem. Soc., Perkin Trans. 1, 1997, 2665-2672.
J. Chem. Soc., Perkin Trans. 1, 1997, 2673-2678.
J. Chem. Soc., Perkin Trans. 1, 1998, 3245-3252.
J. Org. Chem. 1987, 52, 3426-3434.
Tetrahedron (2004), 60(1), 211-217.
Journal of Fluorine Chemistry (2007), 128(7), 748-754.
Synlett, 2007, 2331-2336.
Liebigs Annalen der Chemie (1984), (6), 1193-204.
European Journal of Medicinal Chemistry (1988), 23(1), 53-62.
Journal of Heterocyclic Chemistry (1978), 15 (1), 77-80.
Bulletin of the Korean Chemical Society (2004), 25(7), 991-996
Chemische Berichte (1978), 111(3), 982-95
Journal of Medicinal Chemistry (2006), 49(2), 441-444.

The following compounds were synthesized according to the method described in the general synthetic procedures and Examples. The chemical structures of the compounds and the physical properties of them are described below.
(Method of Identification for the Compound)

LC/MS data of compound of the present invention were measured under any one of the following 3 conditions (Methods 1, 2 and 3), and a retention time and [M+H]⁺ are shown.
(Method 1)
Column: Xbridge C18 (5 μm, i.d. 4.6×50 mm) (Waters)
Flow rate: 3 mL/mm
UV detection wavelength: 254 nm
Mobile phase: [A] is 0.1% formic acid-containing aqueous solution, and [B] is 0.1% formic acid-containing acetonitrile solution
Gradient: Linear gradient of 10% to 100% solvent [B] for 3 minutes was performed, and 100% solvent [B] was maintained for 1 minute.
Column: Luna C18(2) (5 μm, i.d. 4.6×50 mm) (Phenomenex)
Flow rate: 3 mL/min
UV detection wavelength: 254 nm
Mobile phase: [A] is 0.1% formic acid-containing aqueous solution, and [B] is 0.1% formic acid-containing acetonitrile solution Gradient: Linear gradient of 10% to 100% solvent [B] for 3 minutes was performed, and 100% solvent [B] was maintained for 1 minute.

(Method 2)

Column: Shim-pack XR-ODS (2.2 μm, i.d. 50×3.0 mm) (Shimadzu)

Flow rate: 1.6 mL/min

UV detection wavelength: 254 nm

Mobile phase: [A] is 0.1% formic acid-containing aqueous solution, and [B] is 0.1% formic acid-containing acetonitrile solution Gradient: Linear gradient of 1.0% to 100% solvent [B] for 3 minutes was performed, and 100% solvent [B] was maintained for 1 minute.

(Method 3)

Column: Ascentis Express C18 (2.7 μm, i.d. 50×3.0 mm) (Agilent 1100)

Flow rate: 1.3 mL/min

UV detection wavelength: 254 nm

Mobile phase: [A] is 0.1% TFA-containing aqueous solution, and [B] is 0.1% TFA containing acetonitrile solution Gradient: Linear gradient of 3% to 97% solvent [B] for 2.9 minutes was performed, and 100% solvent [B] was maintained for 0.3 minute.

TABLE 7

| Structure | Compound No | Retention Time (min) | [M + H] | Method |
|---|---|---|---|---|
| 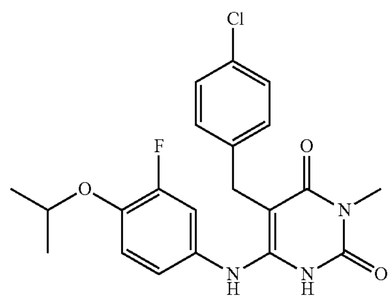 [SMILES: CC(C)Oc1ccc(Nc2[nH]c(=O)n(C)c(=O)c2Cc2ccc(Cl)cc2)cc1F] | I-001 | 2.24 | 418 | 2 |
| 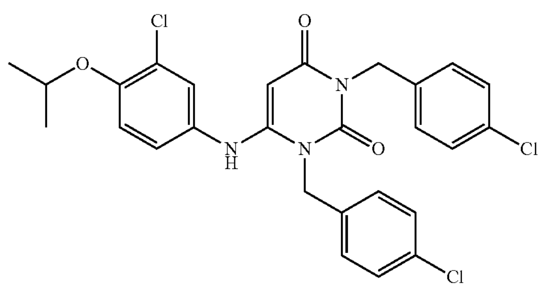 [SMILES: CC(C)Oc1ccc(Nc2cc(=O)n(Cc3ccc(Cl)cc3)c(=O)n2Cc2ccc(Cl)cc2)cc1Cl] | I-005 | 2.61 | 544 | 1 |
| 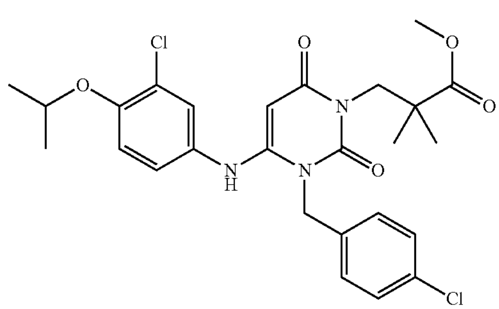 [SMILES: COC(=O)C(C)(C)Cn1c(=O)cc(Nc2ccc(OC(C)C)c(Cl)c2)n(Cc2ccc(Cl)cc2)c1=O] | I-010 | 2.38 | 534 | 1 |
| 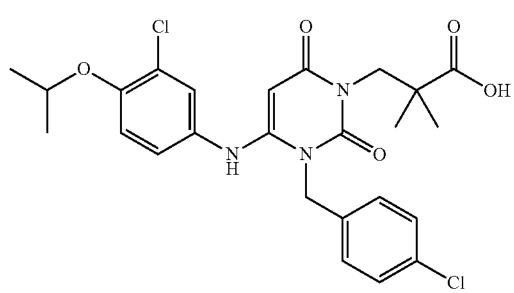 | I-012 | 2.10 | 520 | 1 |

TABLE 7-continued

| Structure | Compound No | Retention Time (min) | [M + H] | Method |
|---|---|---|---|---|
| 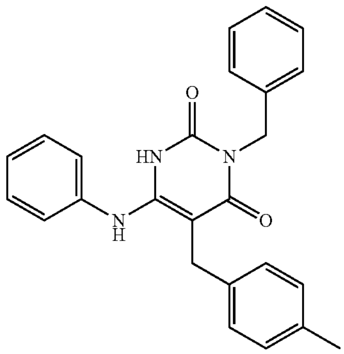 [SMILES: Cc1ccc(Cc2c(Nc3ccccc3)[nH]c(=O)n(Cc3ccccc3)c2=O)cc1] | I-013 | 2.05 | 398 | 1 |

TABLE 8

| Structure | Compound No | Retention Time (min) | [M + H] | Method |
|---|---|---|---|---|
| 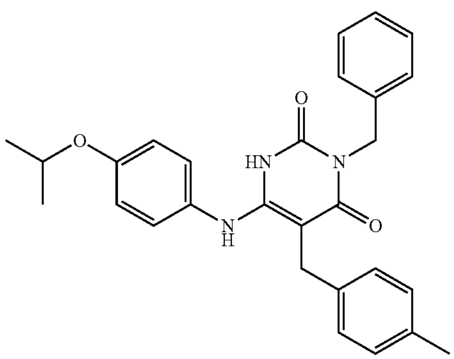 [SMILES: Cc1ccc(Cc2c(Nc3ccc(OC(C)C)cc3)[nH]c(=O)n(Cc3ccccc3)c2=O)cc1] | I-014 | 2.27 | 456 | 1 |
| 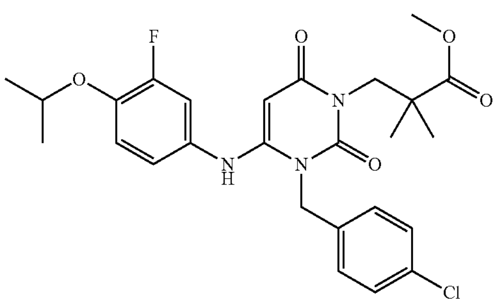 | I-020 | 2.28 | 518 | 1 |
| 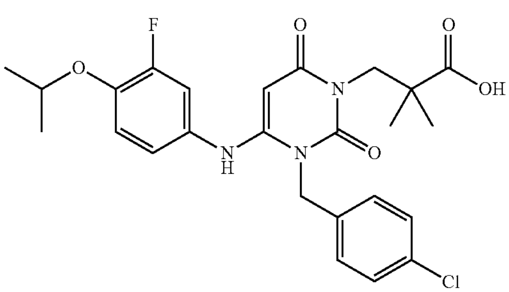 [SMILES: CC(C)Oc1ccc(Nc2cc(=O)n(CC(C)(C)C(=O)O)c(=O)n2Cc2ccc(Cl)cc2)cc1F] | I-021 | 2.01 | 504 | 1 |

TABLE 8-continued

| Structure | Compound No | Retention Time (min) | [M + H] | Method |
|---|---|---|---|---|
| 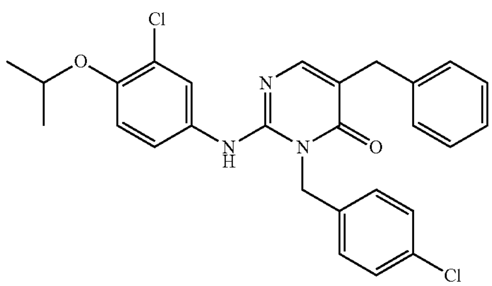 [SMILES: CC(C)Oc1ccc(Nc2ncc(Cc3ccccc3)c(=O)n2Cc2ccc(Cl)cc2)cc1Cl] | I-022 | 2.71 | 494 | 1 |
| 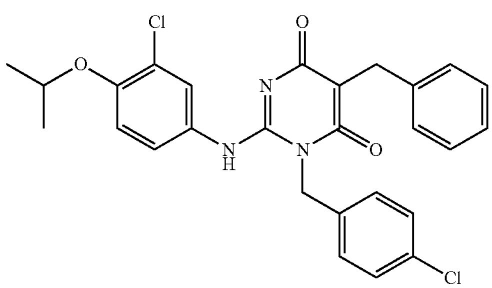 | I-023 | 2.47 | 494 | 1 |

TABLE 9

| Structure | Compound No | Retention Time (min) | [M + H] | Method |
|---|---|---|---|---|
| 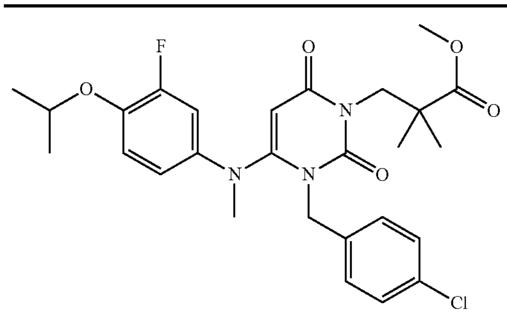 | I-027 | 2.49 | 532 | 1 |
| 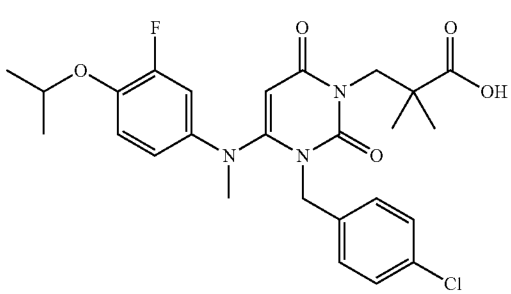 [SMILES: CC(C)Oc1ccc(N(C)c2cc(=O)n(CC(C)(C)C(=O)O)c(=O)n2Cc2ccc(Cl)cc2)cc1F] | I-028 | 2.20 | 518 | 1 |

TABLE 9-continued

| Structure | Compound No | Retention Time (min) | [M + H] | Method |
|---|---|---|---|---|
| 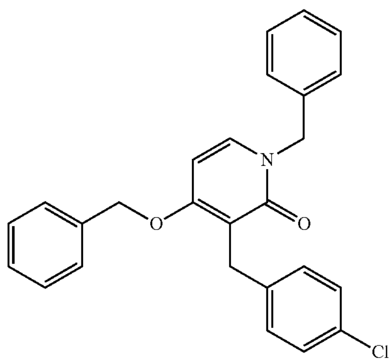 [SMILES: O=c1c(Cc2ccc(Cl)cc2)c(OCc2ccccc2)ccn1Cc1ccccc1] | I-042 | 2.64 | 416 | 2 |
| 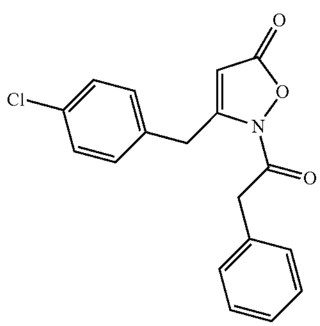 [SMILES: O=C(Cc1ccccc1)n1oc(=O)cc1Cc1ccc(Cl)cc1] | I-044 | 2.40 | 326 | 2 |
| 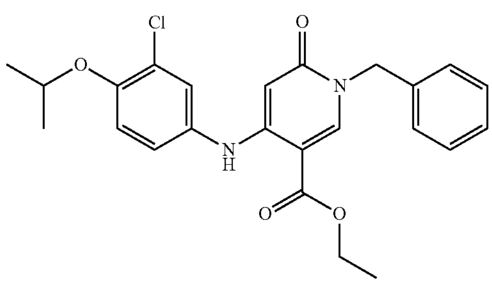 [SMILES: CCOC(=O)c1cn(Cc2ccccc2)c(=O)cc1Nc1ccc(OC(C)C)c(Cl)c1] | I-046 | 2.67 | 441 | 2 |

TABLE 10

| Structure | Compound No | Retention Time (min) | [M + H] | Method |
|---|---|---|---|---|
| 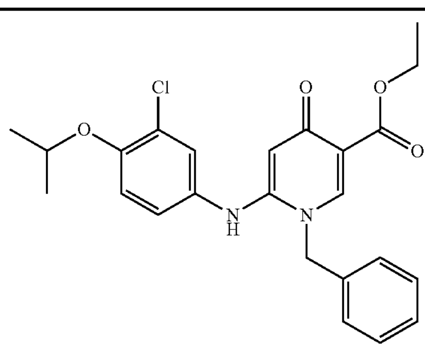 | I-049 | 1.86 | 441 | 1 |

TABLE 10-continued
| Structure | Compound No | Retention Time (min) | [M + H] | Method |
|---|---|---|---|---|
| 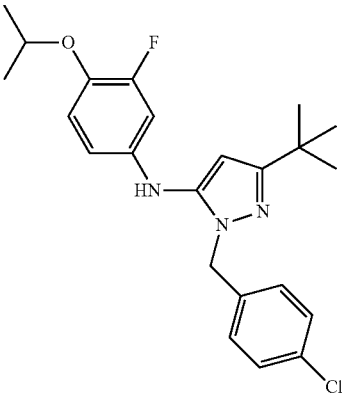 [SMILES: CC(C)Oc1ccc(Nc2cc(C(C)(C)C)nn2Cc2ccc(Cl)cc2)cc1F] | I-050 | 2.72 | 416 | 1 |
| 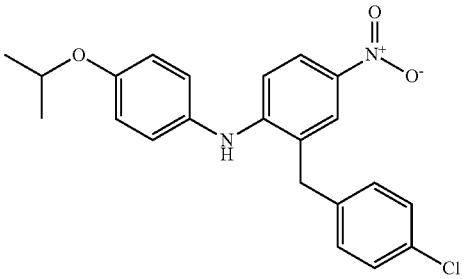 [SMILES: CC(C)Oc1ccc(Nc2ccc([N+](=O)[O-])cc2Cc2ccc(Cl)cc2)cc1] | I-052 | 2.93 | 397 | 2 |
| 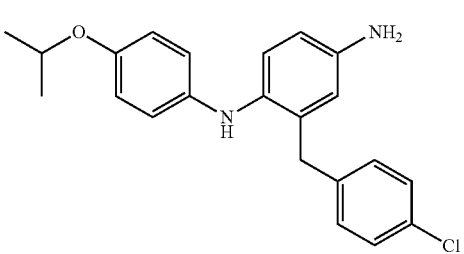 [SMILES: CC(C)Oc1ccc(Nc2ccc(N)cc2Cc2ccc(Cl)cc2)cc1] | I-053 | 1.97 | 367 | 2 |
| 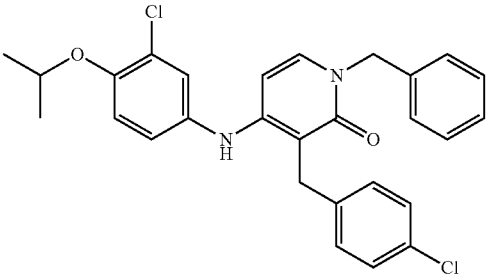 [SMILES: CC(C)Oc1ccc(Nc2ccn(Cc3ccccc3)c(=O)c2Cc2ccc(Cl)cc2)cc1Cl] | I-054 | 2.61 | 493 | 1 |

TABLE 11

| Structure | Compound No | Retention Time (min) | [M + H] | Method |
|---|---|---|---|---|
| (structure) | I-055 | 2.61 | 493 | 1 |
| (structure) | I-058 | 1.92 | 413 | 1 |
| (structure) | I-061 | 2.84 | 590 | 1 |
| (structure) | I-062 | 2.35 | 432 | 1 |

TABLE 11-continued
| Structure | Compound No | Retention Time (min) | [M + H] | Method |
|---|---|---|---|---|
| 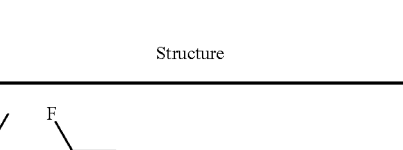 | I-063 | 2.93 | 432 | 1 |
TABLE 12
| Structure | Compound No | Retention Time (min) | [M + H] | Method |
|---|---|---|---|---|
| 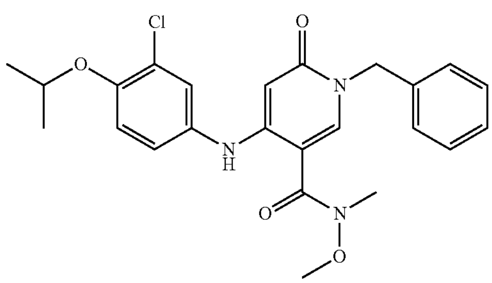 [SMILES: CON(C)C(=O)c1cn(Cc2ccccc2)c(=O)cc1Nc1ccc(OC(C)C)c(Cl)c1] | I-064 | 2.05 | 456 | 1 |
| 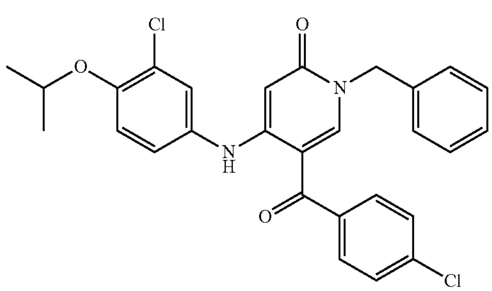 [SMILES: CC(C)Oc1ccc(Nc2cc(=O)n(Cc3ccccc3)cc2C(=O)c2ccc(Cl)cc2)cc1Cl] | I-065 | 2.70 | 507 | 1 |
| 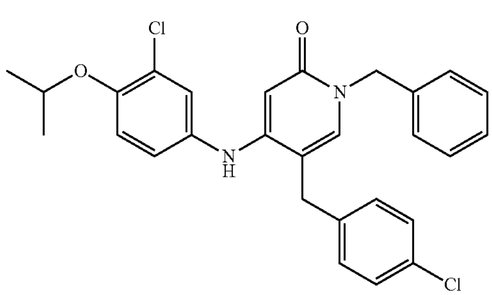 [SMILES: CC(C)Oc1ccc(Nc2cc(=O)n(Cc3ccccc3)cc2Cc2ccc(Cl)cc2)cc1Cl] | I-067 | 2.43 | 493 | 1 |

TABLE 12-continued

| Structure | Compound No | Retention Time (min) | [M + H] | Method |
|---|---|---|---|---|
| 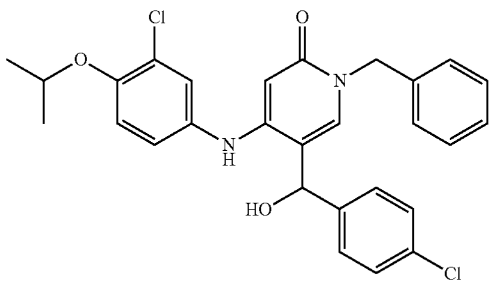 [SMILES: CC(C)Oc1ccc(Nc2cc(=O)n(Cc3ccccc3)cc2C(O)c2ccc(Cl)cc2)cc1Cl] | I-068 | 2.32 | 509 | 1 |
| 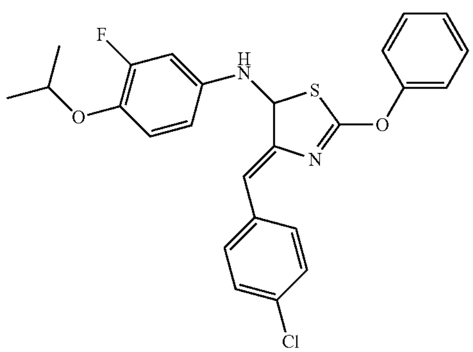 [SMILES: CC(C)Oc1ccc(NC2SC(Oc3ccccc3)=N/C2=C\c2ccc(Cl)cc2)cc1F] | I-069 | 2.81 | 469 | 1 |

TABLE 13

| Structure | Compound No | Retention Time (min) | [M + H] | Method |
|---|---|---|---|---|
| 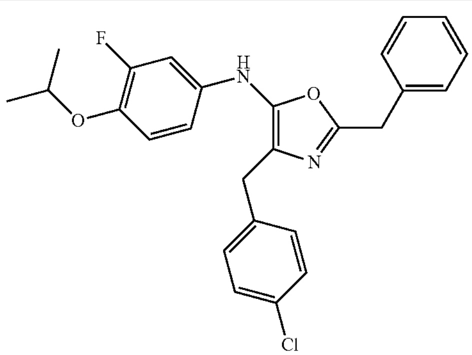 [SMILES: CC(C)Oc1ccc(Nc2oc(Cc3ccccc3)nc2Cc2ccc(Cl)cc2)cc1F] | I-070 | 2.68 | 451 | 1 |
| 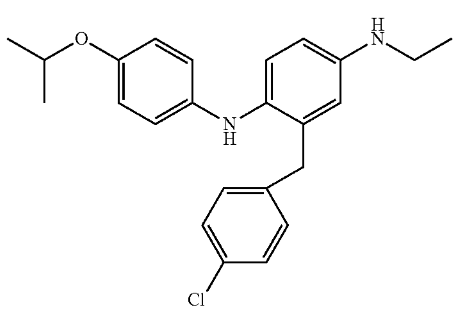 [SMILES: CCNc1ccc(Nc2ccc(OC(C)C)cc2)c(Cc2ccc(Cl)cc2)c1] | I-071 | 2.04 | 395 | 2 |

TABLE 13-continued

| Structure | Compound No | Retention Time (min) | [M + H] | Method |
|---|---|---|---|---|
| 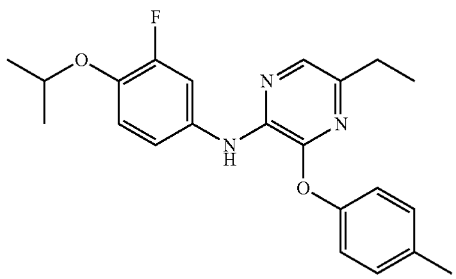 [SMILES: CCc1cnc(Nc2ccc(OC(C)C)c(F)c2)c(Oc2ccc(C)cc2)n1] | I-072 | 2.89 | 382 | 1 |
| 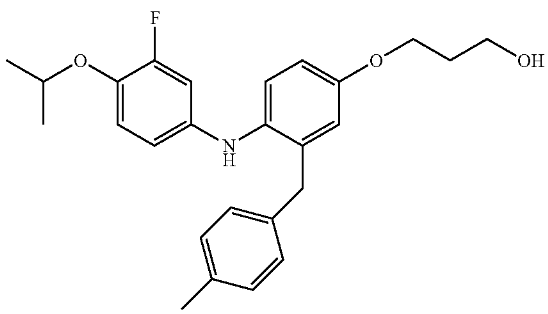 [SMILES: Cc1ccc(Cc2cc(OCCCO)ccc2Nc2ccc(OC(C)C)c(F)c2)cc1] | I-076 | 2.65 | 424 | 2 |
| 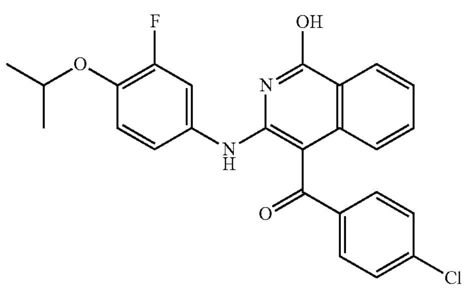 [SMILES: CC(C)Oc1ccc(Nc2nc(O)c3ccccc3c2C(=O)c2ccc(Cl)cc2)cc1F] | I-082 | 2.46 | 451 | 1 |

TABLE 14

| Structure | Compound No | Retention Time (min) | [M + H] | Method |
|---|---|---|---|---|
| 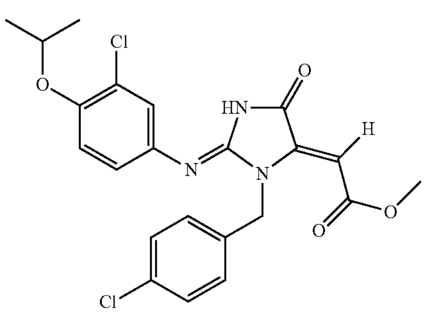 [SMILES: COC(=O)/C=C1/C(=O)N/C(=N\c2ccc(OC(C)C)c(Cl)c2)N1Cc1ccc(Cl)cc1] | I-085 | 2.61 | 462 | 1 |

TABLE 14-continued

| Structure | Compound No | Retention Time (min) | [M + H] | Method |
|---|---|---|---|---|
| 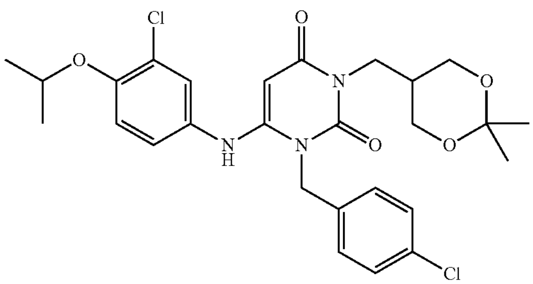 [SMILES: CC(C)Oc1ccc(Nc2cc(=O)n(CC3COC(C)(C)OC3)c(=O)n2Cc2ccc(Cl)cc2)cc1Cl] | I-094 | 2.28 | 548 | 1 |
| 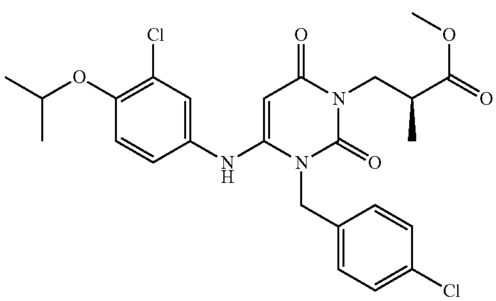 [SMILES: COC(=O)[C@@H](C)Cn1c(=O)cc(Nc2ccc(OC(C)C)c(Cl)c2)n(Cc2ccc(Cl)cc2)c1=O] | I-095 | 2.28 | 520 | 1 |
| 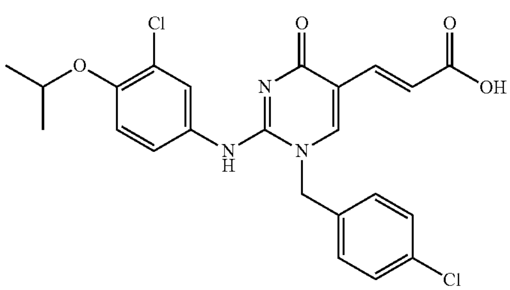 [SMILES: CC(C)Oc1ccc(Nc2nc(=O)c(/C=C/C(=O)O)cn2Cc2ccc(Cl)cc2)cc1Cl] | I-097 | 2.22 | 474 | 1 |
| 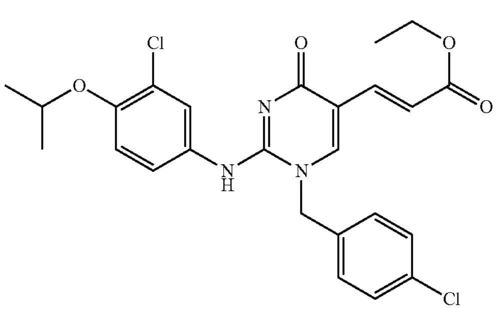 [SMILES: CCOC(=O)/C=C/c1cn(Cc2ccc(Cl)cc2)c(Nc2ccc(OC(C)C)c(Cl)c2)nc1=O] | I-098 | 2.57 | 502 | 1 |

TABLE 15

| Structure | Compound No | Retention Time (min) | [M + H] | Method |
|---|---|---|---|---|
| (structure) | I-099 | 1.90 | 508 | 1 |
| (structure) | I-100 | 2.07 | 506 | 1 |
| (structure) | I-103 | 2.24 | 520 | 1 |
| (structure) | I-104 | 2.10 | 476 | 1 |
| (structure) | I-105 | 1.86 | 462 | 1 |

TABLE 16

| Structure | Compound No | Retention Time (min) | [M + H] | Method |
|---|---|---|---|---|
| 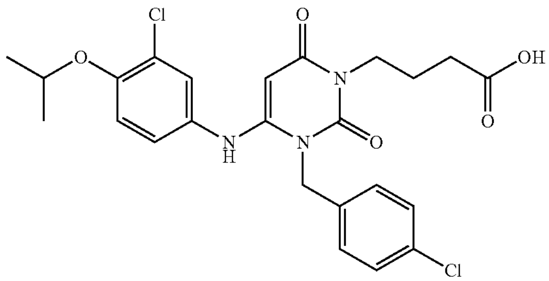 [SMILES: CC(C)Oc1ccc(Nc2cc(=O)n(CCCC(=O)O)c(=O)n2Cc2ccc(Cl)cc2)cc1Cl] | I-106 | 2.00 | 505 | 1 |
| 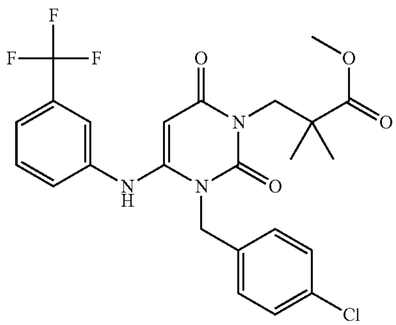 | I-107 | 2.27 | 510 | 1 |
| 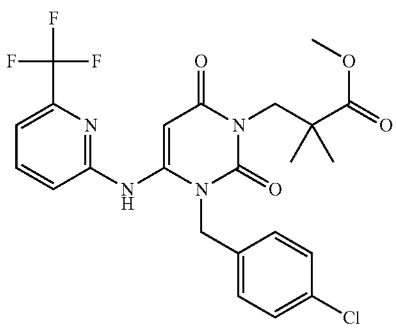 [SMILES: COC(=O)C(C)(C)Cn1c(=O)cc(Nc2cccc(C(F)(F)F)n2)n(Cc2ccc(Cl)cc2)c1=O] | I-108 | 2.21 | 511 | 1 |
| 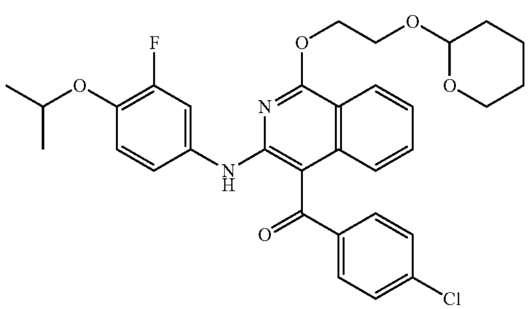 [SMILES: CC(C)Oc1ccc(Nc2nc(OCCOC3CCCCO3)c3ccccc3c2C(=O)c2ccc(Cl)cc2)cc1F] | I-109 | 3.19 | 579 | 1 |
| 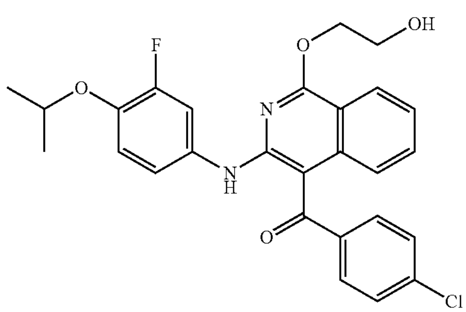 [SMILES: CC(C)Oc1ccc(Nc2nc(OCCO)c3ccccc3c2C(=O)c2ccc(Cl)cc2)cc1F] | I-110 | 2.71 | 495 | 1 |

TABLE 17

| Structure | Compound No | Retention Time (min) | [M + H] | Method |
|---|---|---|---|---|
| 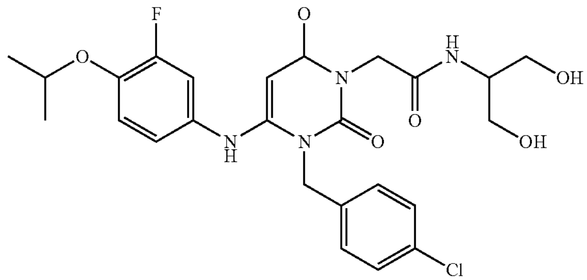 [SMILES: CC(C)Oc1ccc(NC2=CC(O)N(CC(=O)NC(CO)CO)C(=O)N2Cc2ccc(Cl)cc2)cc1F] | I-111 | 1.64 | 535 | 1 |
| 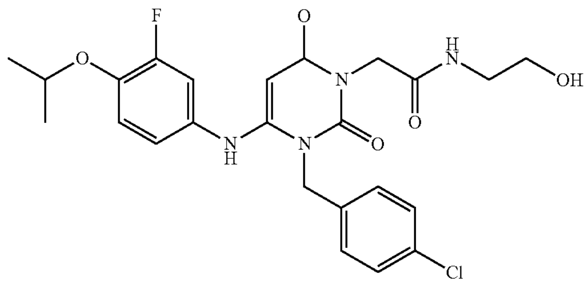 [SMILES: CC(C)Oc1ccc(NC2=CC(O)N(CC(=O)NCCO)C(=O)N2Cc2ccc(Cl)cc2)cc1F] | I-112 | 1.70 | 505 | 1 |
| 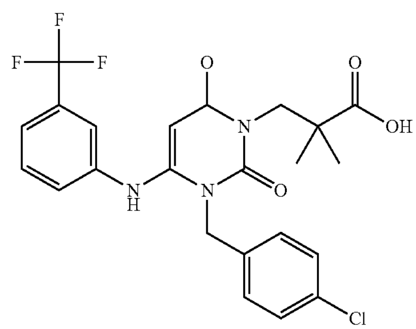 | I-113 | 1.99 | 496 | 1 |
| 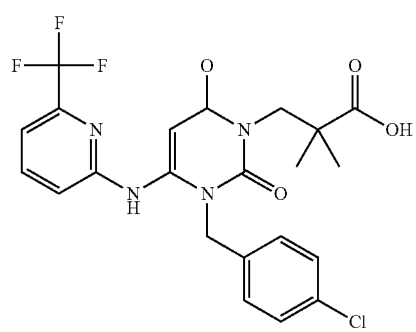 [SMILES: CC(C)(CN1C(=O)N(Cc2ccc(Cl)cc2)C(Nc2cccc(C(F)(F)F)n2)=CC1O)C(=O)O] | I-114 | 1.93 | 497 | 1 |
| 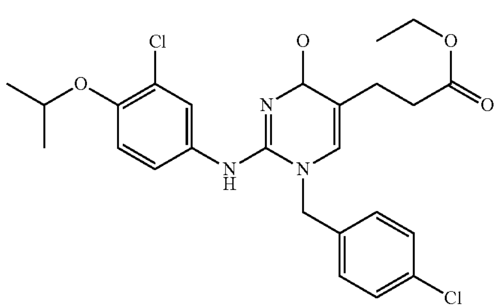 [SMILES: CCOC(=O)CCC1=CN(Cc2ccc(Cl)cc2)C(Nc2ccc(OC(C)C)c(Cl)c2)=NC1O] | I-115 | 2.27 | 504 | 1 |

TABLE 18

| Structure | Compound No | Retention Time (min) | [M + H] | Method |
|---|---|---|---|---|
| (structure) | I-116 | 1.89 | 506 | 1 |
| (structure) | I-117 | 1.91 | 476 | 1 |
| (structure) | I-118 | 2.37 | 437 | 1 |
| (structure) | I-120 | 2.19 | 511 | 1 |
| (structure) | I-123 | 2.20 | 413 | 1 |

TABLE 19

| Structure | Compound No | Retention Time (min) | [M + H] | Method |
|---|---|---|---|---|
| 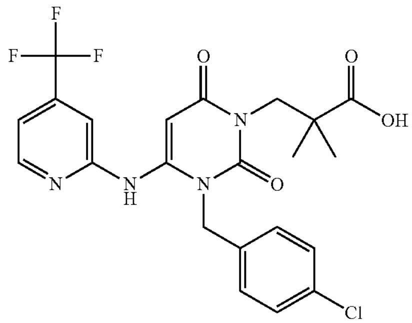 [SMILES: CC(C)(Cn1c(=O)cc(Nc2cc(C(F)(F)F)ccn2)n(Cc2ccc(Cl)cc2)c1=O)C(=O)O] | I-124 | 1.92 | 497 | 1 |
| 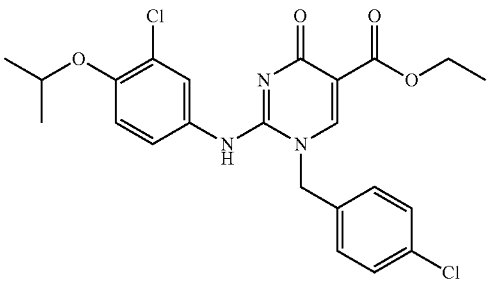 | I-125 | 2.37 | 476 | 1 |
| 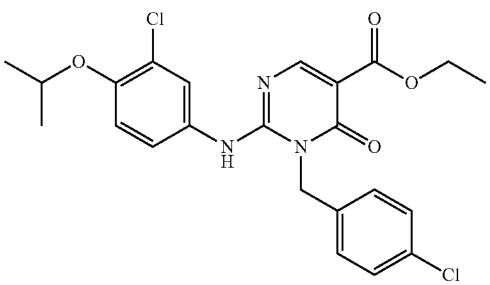 [SMILES: CCOC(=O)c1cnc(Nc2ccc(OC(C)C)c(Cl)c2)n(Cc2ccc(Cl)cc2)c1=O] | I-126 | 2.36 | 476 | 1 |
| 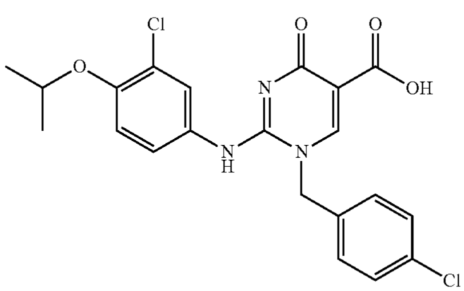 | I-127 | 2.11 | 448 | 1 |
| 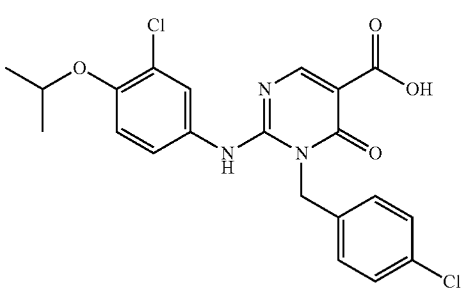 | I-129 | 2.26 | 448 | 1 |

TABLE 20

| Structure | Compound No | Retention Time (min) | [M + H] | Method |
|---|---|---|---|---|
| 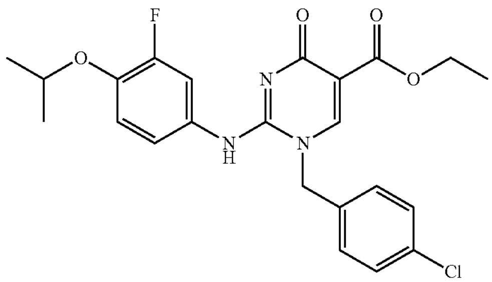 [SMILES: CCOC(=O)c1cn(Cc2ccc(Cl)cc2)c(Nc2ccc(OC(C)C)c(F)c2)nc1=O] | I-131 | 2.24 | 459 | 1 |
| 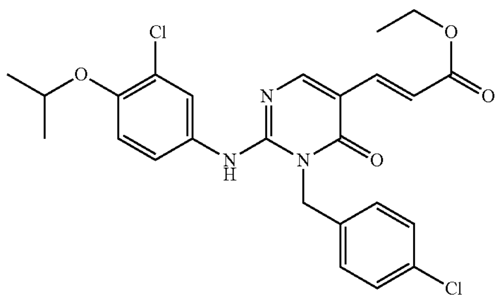 [SMILES: CCOC(=O)/C=C/c1cnc(Nc2ccc(OC(C)C)c(Cl)c2)n(Cc2ccc(Cl)cc2)c1=O] | I-132 | 2.59 | 502 | 1 |
| 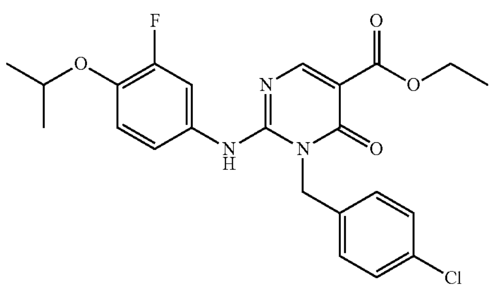 [SMILES: CCOC(=O)c1cnc(Nc2ccc(OC(C)C)c(F)c2)n(Cc2ccc(Cl)cc2)c1=O] | I-133 | 2.24 | 459 | 1 |
| 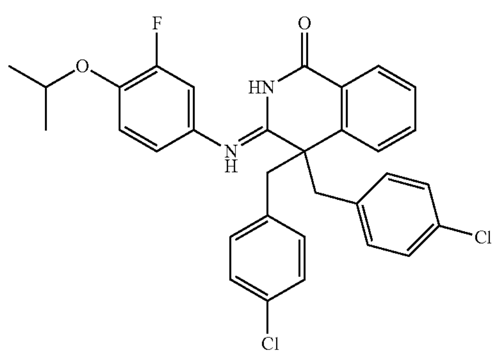 [SMILES: CC(C)Oc1ccc(/N=C2\NC(=O)c3ccccc3C2(Cc2ccc(Cl)cc2)Cc2ccc(Cl)cc2)cc1F] | I-135 | 2.91 | 561 | 1 |
| 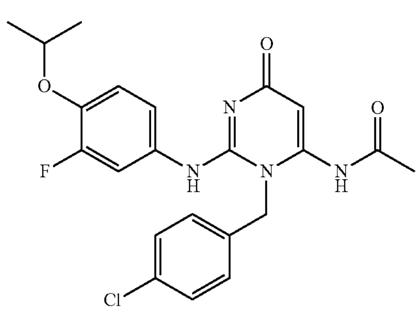 [SMILES: CC(=O)Nc1cc(=O)nc(Nc2ccc(OC(C)C)c(F)c2)n1Cc1ccc(Cl)cc1] | I-136 | 1.96 | 445 | 2 |

TABLE 21

| Structure | Compound No | Retention Time (min) | [M + H] | Method |
|---|---|---|---|---|
| 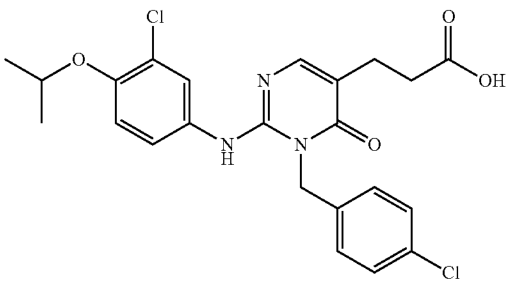 | I-137 | 2.08 | 476 | 1 |
| 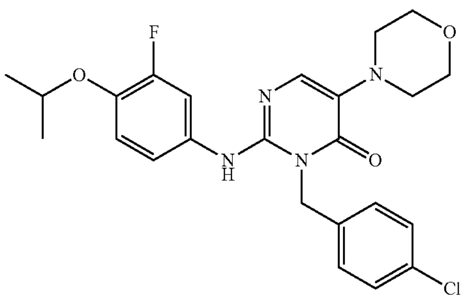 [SMILES: CC(C)Oc1ccc(Nc2ncc(N3CCOCC3)c(=O)n2Cc2ccc(Cl)cc2)cc1F] | I-138 | 2.09 | 473 | 1 |
| 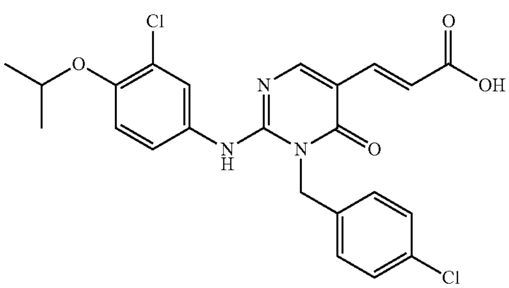 [SMILES: CC(C)Oc1ccc(Nc2ncc(/C=C/C(=O)O)c(=O)n2Cc2ccc(Cl)cc2)cc1Cl] | I-139 | 2.17 | 474 | 1 |
| 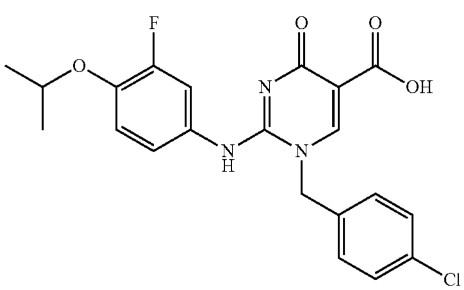 [SMILES: CC(C)Oc1ccc(Nc2nc(=O)c(C(=O)O)cn2Cc2ccc(Cl)cc2)cc1F] | I-140 | 1.99 | 432 | 1 |
| 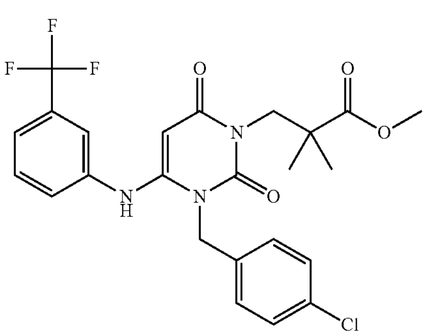 [SMILES: COC(=O)C(C)(C)Cn1c(=O)cc(Nc2cccc(C(F)(F)F)c2)n(Cc2ccc(Cl)cc2)c1=O] | I-141 | 2.44 | 509 | 1 |

TABLE 22

| Structure | Compound No | Retention Time (min) | [M + H] | Method |
|---|---|---|---|---|
| (structure) | I-142 | 2.16 | 432 | 1 |
| (structure) | I-146 | 1.84 | 475 | 1 |
| (structure) | I-147 | 2.15 | 495 | 1 |
| (structure) | I-148 | 1.99 | 433 | 1 |
| (structure) | I-149 | 2.03 | 490 | 1 |

TABLE 23

| Structure | Compound No | Retention Time (min) | [M + H] | Method |
|---|---|---|---|---|
| (structure) | I-150 | 1.75 | 505 | 1 |
| (structure) | I-151 | 1.66 | 489 | 1 |
| (structure) | I-152 | 1.88 | 475 | 1 |
| (structure) | I-153 | 1.78 | 505 | 1 |
| (structure) | I-154 | 3.01 | 455 | 1 |

TABLE 24

| Structure | Compound No | Retention Time (min) | [M + H] | Method |
|---|---|---|---|---|
| (I-155 structure) | I-155 | 2.37 | 453 | 1 |
| (I-156 structure) | I-156 | 1.75 | 489 | 1 |
| (I-157 structure) | I-157 | 2.49 | 486 | 1 |
| (I-158 structure) | I-158 | 2.57 | 503 | 1 |
| (I-159 structure) | I-159 | 1.98 | 473 | 1 |

TABLE 25

| Structure | Compound No | Retention Time (min) | [M + H] | Method |
|---|---|---|---|---|
| 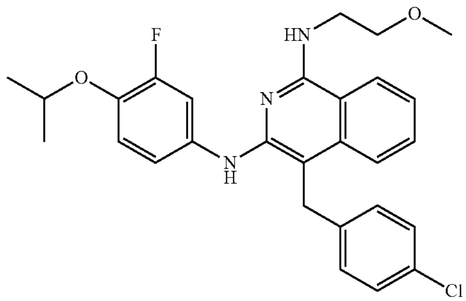 [SMILES: COCCNc1nc(Nc2ccc(OC(C)C)c(F)c2)c(Cc2ccc(Cl)cc2)c2ccccc12] | I-160 | 2.23 | 494 | 1 |
| 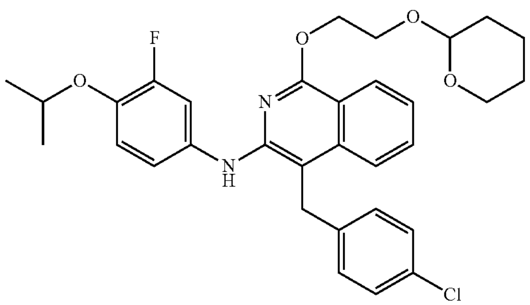 [SMILES: CC(C)Oc1ccc(Nc2nc(OCCOC3CCCCO3)c3ccccc3c2Cc2ccc(Cl)cc2)cc1F] | I-161 | 3.11 | 565 | 1 |
| 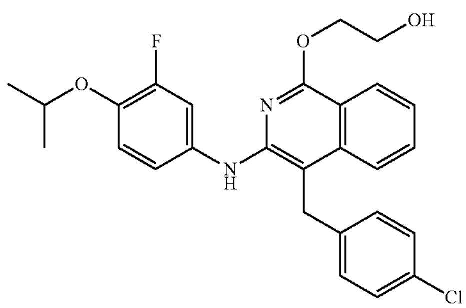 [SMILES: CC(C)Oc1ccc(Nc2nc(OCCO)c3ccccc3c2Cc2ccc(Cl)cc2)cc1F] | I-162 | 2.66 | 481 | 1 |
| 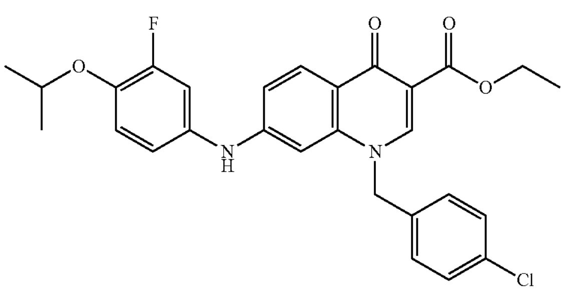 [SMILES: CCOC(=O)c1cn(Cc2ccc(Cl)cc2)c2cc(Nc3ccc(OC(C)C)c(F)c3)ccc2c1=O] | I-163 | 2.17 | 509 | 1 |
| 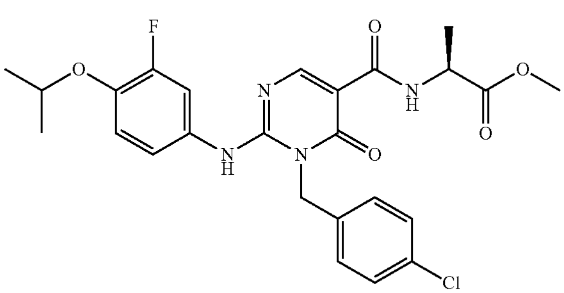 [SMILES: COC(=O)[C@H](C)NC(=O)c1cnc(Nc2ccc(OC(C)C)c(F)c2)n(Cc2ccc(Cl)cc2)c1=O] | I-164 | 2.26 | 517 | 1 |

TABLE 26

| Structure | Compound No | Retention Time (min) | [M + H] | Method |
|---|---|---|---|---|
| 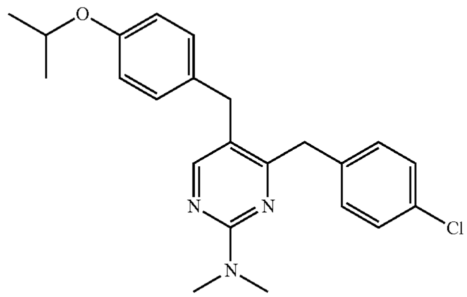 [SMILES: CC(C)Oc1ccc(Cc2cnc(N(C)C)nc2Cc2ccc(Cl)cc2)cc1] | I-165 | 2.20 | 396 | 3 |
| 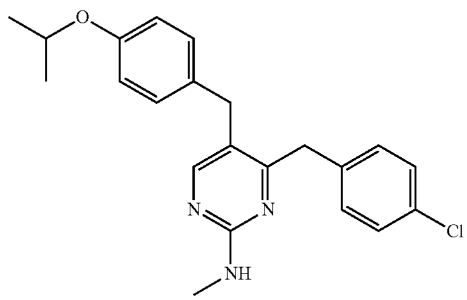 [SMILES: CNc1ncc(Cc2ccc(OC(C)C)cc2)c(Cc2ccc(Cl)cc2)n1] | I-166 | 2.07 | 382 | 3 |
| 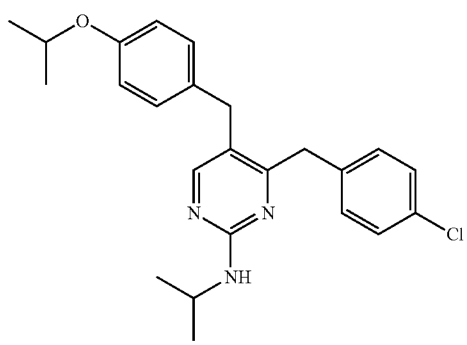 [SMILES: CC(C)Nc1ncc(Cc2ccc(OC(C)C)cc2)c(Cc2ccc(Cl)cc2)n1] | I-167 | 2.26 | 410 | 3 |
| 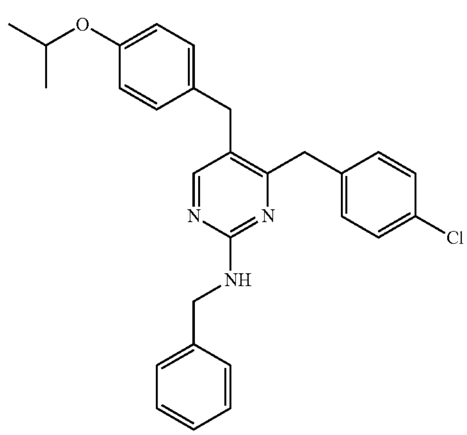 [SMILES: CC(C)Oc1ccc(Cc2cnc(NCc3ccccc3)nc2Cc2ccc(Cl)cc2)cc1] | I-168 | 2.42 | 458 | 3 |

TABLE 26-continued

| Structure | Compound No | Retention Time (min) | [M + H] | Method |
|---|---|---|---|---|
| 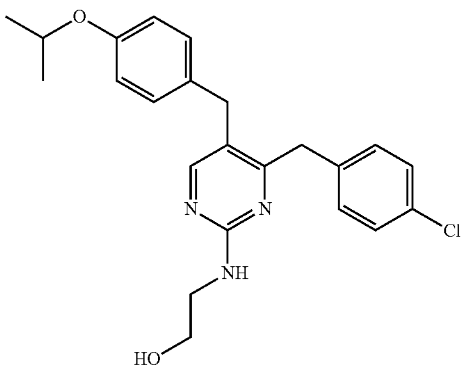 [SMILES: CC(C)Oc1ccc(Cc2cnc(NCCO)nc2Cc2ccc(Cl)cc2)cc1] | I-169 | 1.94 | 412 | 3 |

TABLE 27

| Structure | Compound No | Retention Time (min) | [M + H] | Method |
|---|---|---|---|---|
| 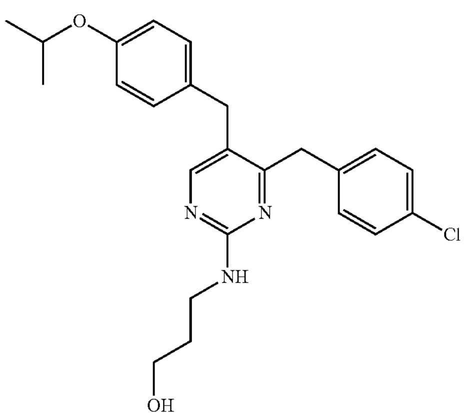 [SMILES: CC(C)Oc1ccc(Cc2cnc(NCCCO)nc2Cc2ccc(Cl)cc2)cc1] | I-170 | 1.97 | 426 | 3 |
| 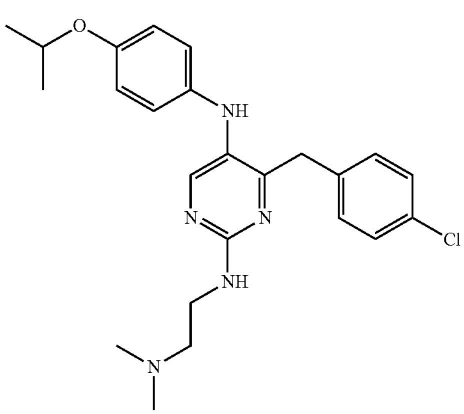 [SMILES: CC(C)Oc1ccc(Nc2cnc(NCCN(C)C)nc2Cc2ccc(Cl)cc2)cc1] | I-171 | 1.85 | 439 | 3 |

TABLE 27-continued

| Structure | Compound No | Retention Time (min) | [M + H] | Method |
|---|---|---|---|---|
| 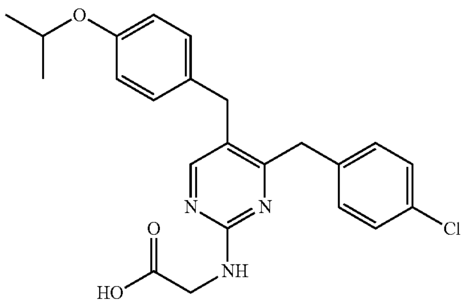 [SMILES: CC(C)Oc1ccc(Cc2cnc(NCC(=O)O)nc2Cc2ccc(Cl)cc2)cc1] | I-172 | 2.01 | 426 | 3 |
| 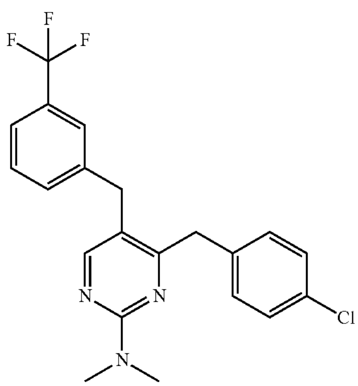 [SMILES: CN(C)c1ncc(Cc2cccc(C(F)(F)F)c2)c(Cc2ccc(Cl)cc2)n1] | I-173 | 2.22 | 406 | 3 |
| 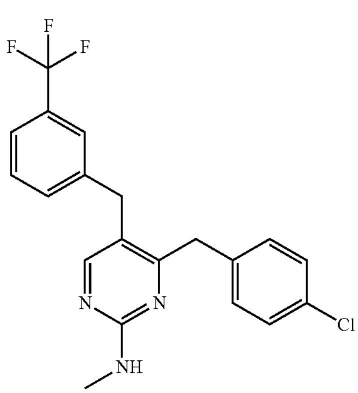 [SMILES: CNc1ncc(Cc2cccc(C(F)(F)F)c2)c(Cc2ccc(Cl)cc2)n1] | I-174 | 2.05 | 392 | 3 |

TABLE 28
| Structure | Compound No | Retention Time (min) | [M + H] | Method |
|---|---|---|---|---|
| 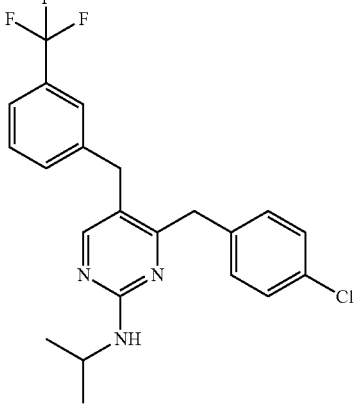 | I-175 | 2.20 | 420 | 3 |
| 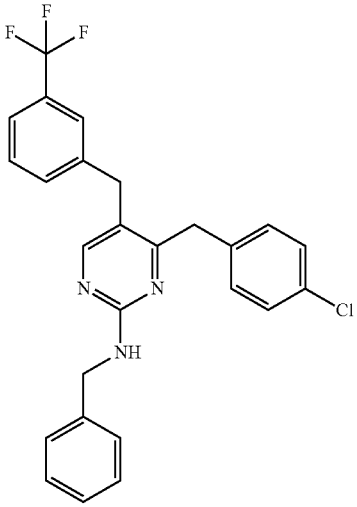 [SMILES: FC(F)(F)c1cccc(Cc2cnc(NCc3ccccc3)nc2Cc2ccc(Cl)cc2)c1] | I-176 | 2.42 | 468 | 3 |
| 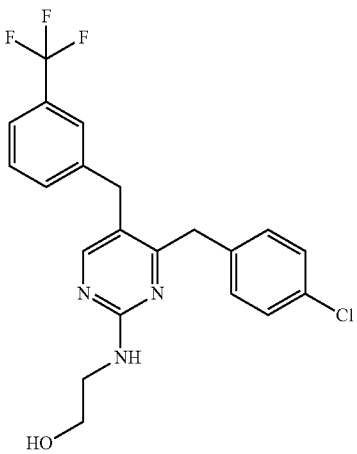 [SMILES: OCCNc1ncc(Cc2cccc(C(F)(F)F)c2)c(Cc2ccc(Cl)cc2)n1] | I-177 | 1.93 | 422 | 3 |

TABLE 28-continued

| Structure | Compound No | Retention Time (min) | [M + H] | Method |
|---|---|---|---|---|
| 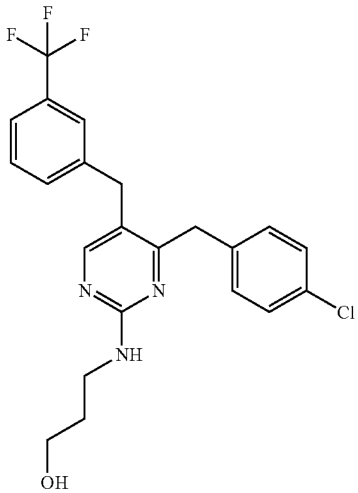 [SMILES: OCCCNc1ncc(Cc2cccc(C(F)(F)F)c2)c(Cc2ccc(Cl)cc2)n1] | I-178 | 1.94 | 436 | 3 |
| 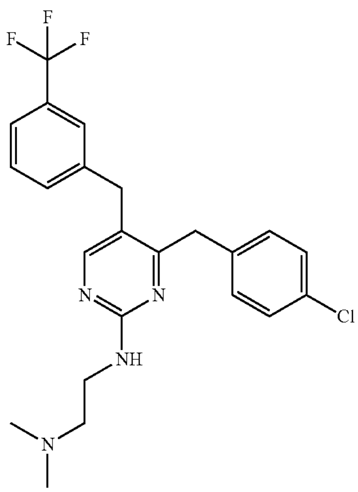 [SMILES: CN(C)CCNc1ncc(Cc2cccc(C(F)(F)F)c2)c(Cc2ccc(Cl)cc2)n1] | I-179 | 1.85 | 449 | 3 |

TABLE 29

| Structure | Compound No | Retention Time (min) | [M + H] | Method |
|---|---|---|---|---|
| 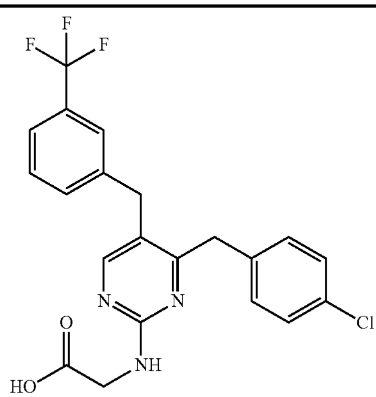 | I-180 | 2.03 | 436 | 3 |

TABLE 29-continued

| Structure | Compound No | Retention Time (min) | [M + H] | Method |
|---|---|---|---|---|
| 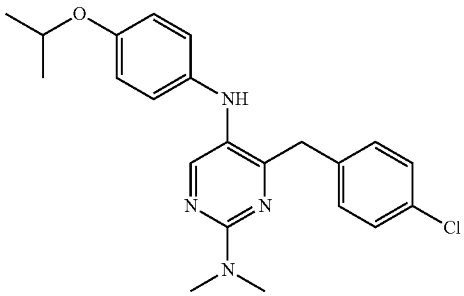 [SMILES: CC(C)Oc1ccc(Nc2cnc(N(C)C)nc2Cc2ccc(Cl)cc2)cc1] | I-181 | 2.19 | 397 | 3 |
| 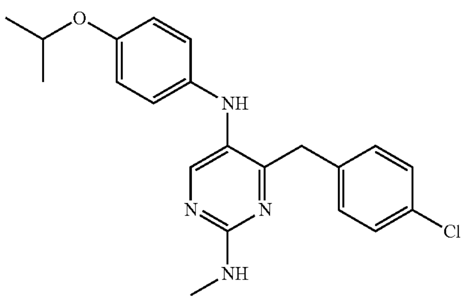 [SMILES: CNc1ncc(Nc2ccc(OC(C)C)cc2)c(Cc2ccc(Cl)cc2)n1] | I-182 | 2.01 | 383 | 3 |
| 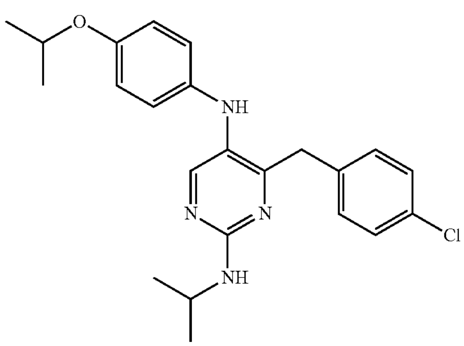 [SMILES: CC(C)Nc1ncc(Nc2ccc(OC(C)C)cc2)c(Cc2ccc(Cl)cc2)n1] | I-183 | 2.22 | 411 | 3 |
| 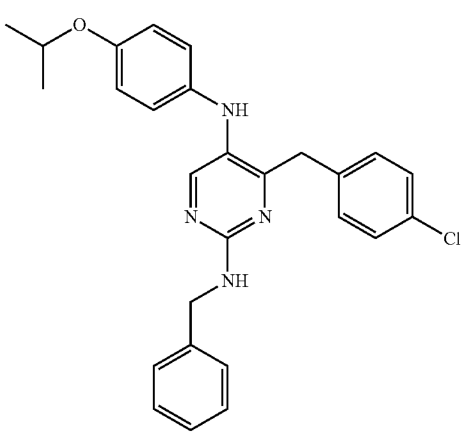 [SMILES: CC(C)Oc1ccc(Nc2cnc(NCc3ccccc3)nc2Cc2ccc(Cl)cc2)cc1] | I-184 | 2.39 | 459 | 3 |

TABLE 30

| Structure | Compound No | Retention Time (min) | [M + H] | Method |
|---|---|---|---|---|
| 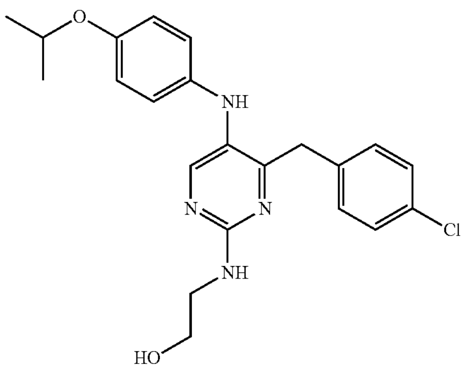 [SMILES: CC(C)Oc1ccc(Nc2cnc(NCCO)nc2Cc2ccc(Cl)cc2)cc1] | I-185 | 1.90 | 413 | 3 |
| 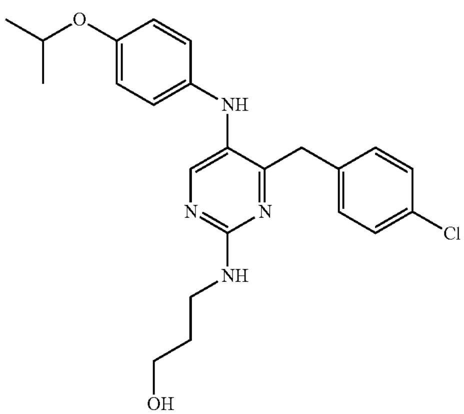 [SMILES: CC(C)Oc1ccc(Nc2cnc(NCCCO)nc2Cc2ccc(Cl)cc2)cc1] | I-186 | 1.91 | 427 | 3 |
| 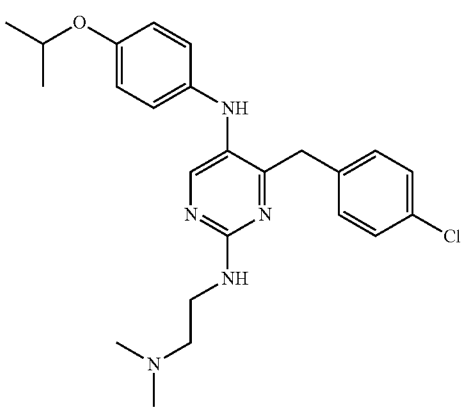 [SMILES: CC(C)Oc1ccc(Nc2cnc(NCCN(C)C)nc2Cc2ccc(Cl)cc2)cc1] | I-187 | 1.79 | 440 | 3 |
| 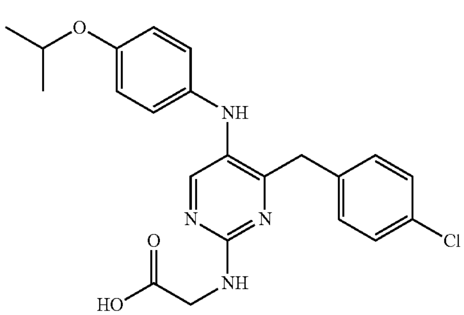 [SMILES: CC(C)Oc1ccc(Nc2cnc(NCC(=O)O)nc2Cc2ccc(Cl)cc2)cc1] | I-188 | 1.98 | 427 | 3 |

TABLE 30-continued
| Structure | Compound No | Retention Time (min) | [M + H] | Method |
|---|---|---|---|---|
| 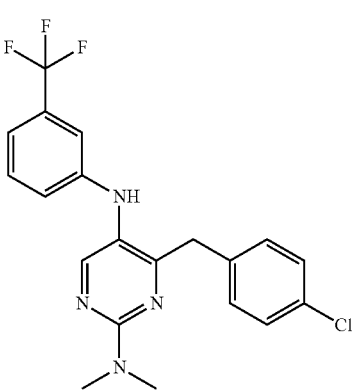 | I-189 | 2.38 | 407 | 3 |
TABLE 31
| Structure | Compound No | Retention Time (min) | [M + H] | Method |
|---|---|---|---|---|
| 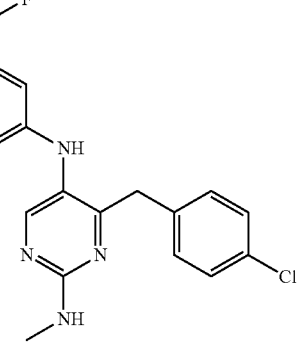 | I-190 | 2.13 | 393 | 3 |
| 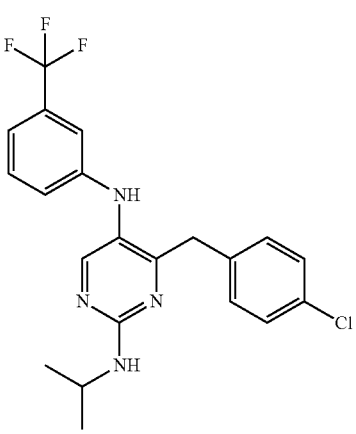 [SMILES: CC(C)Nc1ncc(Nc2cccc(C(F)(F)F)c2)c(Cc2ccc(Cl)cc2)n1] | I-191 | 2.34 | 421 | 3 |

TABLE 31-continued

| Structure | Compound No | Retention Time (min) | [M + H] | Method |
|---|---|---|---|---|
| 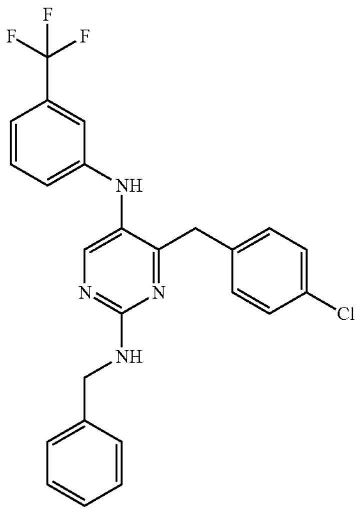 [SMILES: FC(F)(F)c1cccc(Nc2cnc(NCc3ccccc3)nc2Cc2ccc(Cl)cc2)c1] | I-192 | 2.54 | 469 | 3 |
| 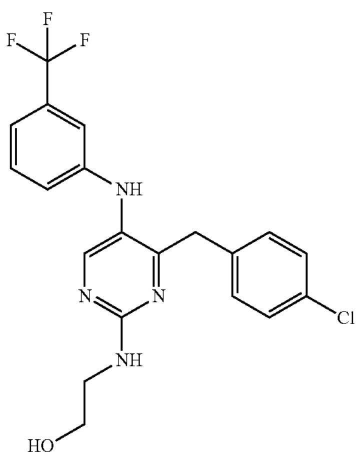 [SMILES: OCCNc1ncc(Nc2cccc(C(F)(F)F)c2)c(Cc2ccc(Cl)cc2)n1] | I-193 | 1.98 | 423 | 3 |
| 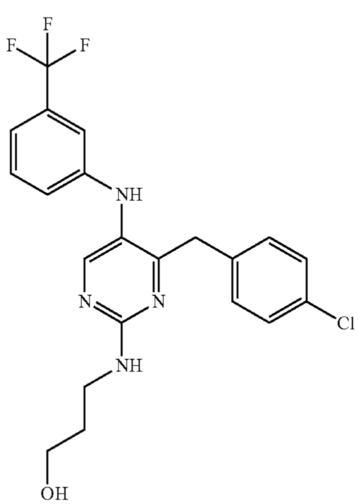 [SMILES: OCCCNc1ncc(Nc2cccc(C(F)(F)F)c2)c(Cc2ccc(Cl)cc2)n1] | I-194 | 1.99 | 437 | 3 |

TABLE 32

| Structure | Compound No | Retention Time (min) | [M + H] | Method |
|---|---|---|---|---|
| (structure) | I-195 | 1.97 | 450 | 3 |
| (structure) | I-196 | 2.11 | 437 | 3 |
| (structure) | I-197 | 2.25 | 517 | 1 |
| (structure) | I-198 | 2.20 | 481 | 1 |

TABLE 32-continued

| Structure | Compound No | Retention Time (min) | [M + H] | Method |
|---|---|---|---|---|
| (structure) | I-200 | 2.02 | 503 | 1 |

TABLE 33

| Structure | Compound No | Retention Time (min) | [M + H] | Method |
|---|---|---|---|---|
| (structure) | I-201 | 2.01 | 503 | 1 |
| (structure) | I-208 | 2.48 | 517 | 1 |
| (structure) | I-209 | 1.79 | 473 | 1 |

TABLE 33-continued

| Structure | Compound No | Retention Time (min) | [M + H] | Method |
|---|---|---|---|---|
| 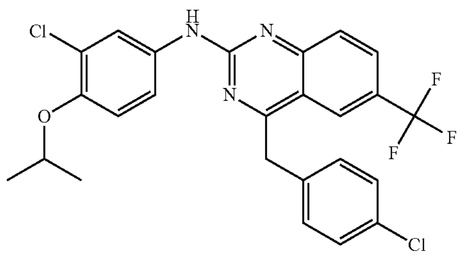 [SMILES: CC(C)Oc1ccc(Nc2nc(Cc3ccc(Cl)cc3)c3cc(C(F)(F)F)ccc3n2)cc1Cl] | I-210 | 3.03 | 506 | 1 |
| 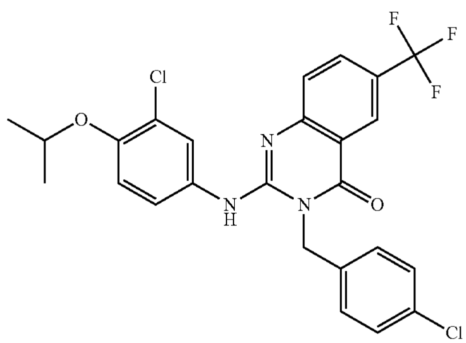 [SMILES: CC(C)Oc1ccc(Nc2nc3ccc(C(F)(F)F)cc3c(=O)n2Cc2ccc(Cl)cc2)cc1Cl] | I-211 | 2.95 | 522 | 1 |

TABLE 34

| Structure | Compound No | Retention Time (min) | [M + H] | Method |
|---|---|---|---|---|
| 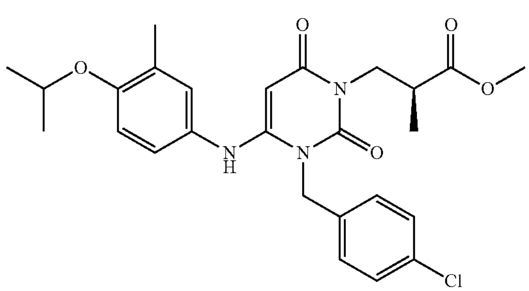 [SMILES: COC(=O)[C@@H](C)Cn1c(=O)cc(Nc2ccc(OC(C)C)c(C)c2)n(Cc2ccc(Cl)cc2)c1=O] | I-212 | 2.31 | 500 | 1 |
| 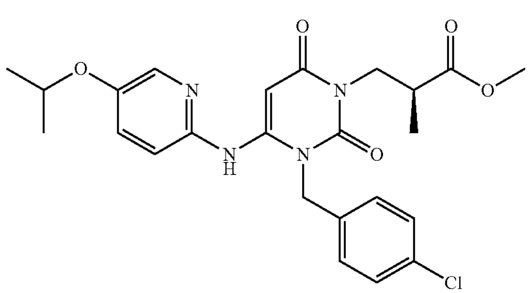 [SMILES: COC(=O)[C@@H](C)Cn1c(=O)cc(Nc2ccc(OC(C)C)cn2)n(Cc2ccc(Cl)cc2)c1=O] | I-213 | 2.02 | 487 | 1 |

TABLE 34-continued

| Structure | Compound No | Retention Time (min) | [M + H] | Method |
|---|---|---|---|---|
| 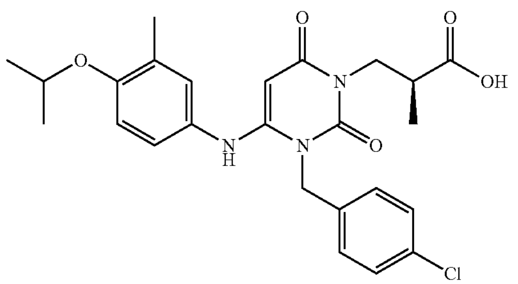 | I-215 | 2.08 | 486 | 1 |
| 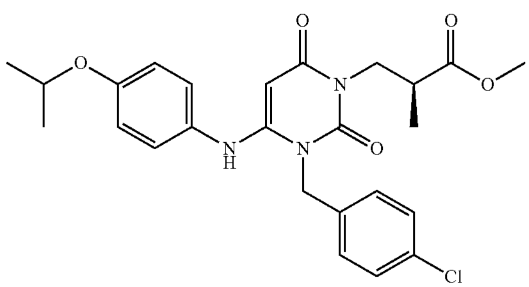 [SMILES: COC(=O)[C@@H](C)Cn1c(=O)cc(Nc2ccc(OC(C)C)cc2)n(Cc2ccc(Cl)cc2)c1=O] | I-216 | 2.15 | 486 | 1 |
| 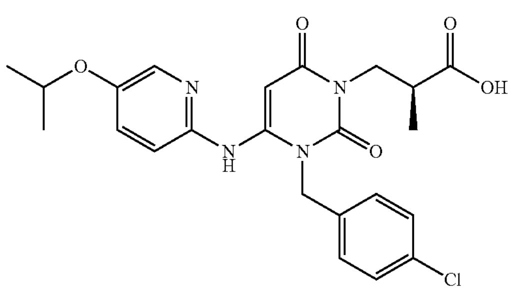 [SMILES: CC(C)Oc1ccc(Nc2cc(=O)n(C[C@H](C)C(=O)O)c(=O)n2Cc2ccc(Cl)cc2)cc1] | I-217 | 1.78 | 473 | 1 |

TABLE 35

| Structure | Compound No | Retention Time (min) | [M + H] | Method |
|---|---|---|---|---|
| 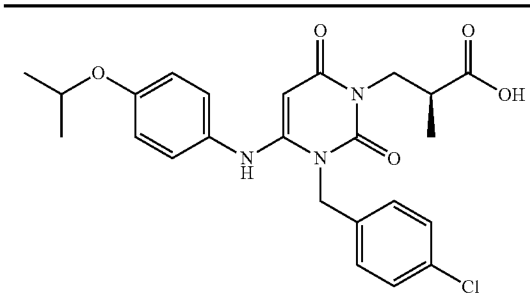 | I-218 | 1.92 | 472 | 1 |

TABLE 35-continued

| Structure | Compound No | Retention Time (min) | [M + H] | Method |
|---|---|---|---|---|
| (structure) | I-220 | 2.28 | 565 | 1 |
| (structure) | I-222 | 1.94 | 417 | 1 |
| (structure) | I-223 | 1.75 | 461 | 1 |
| (structure) | I-224 | 2.14 | 501 | 1 |

TABLE 36

| Structure | Compound No | Retention Time (min) | [M + H] | Method |
|---|---|---|---|---|
| (structure) | I-227 | 2.79 | 522 | 1 |
| (structure) | I-228 | 2.48 | 430 | 1 |
| (structure) | I-230 | 2.28 | 503 | 1 |
| (structure) | I-231 | 1.89 | 503 | 1 |
| (structure) | I-232 | 1.97 | 460 | 1 |

TABLE 37
| Structure | Compound No | Retention Time (min) | [M + H] | Method |
|---|---|---|---|---|
| 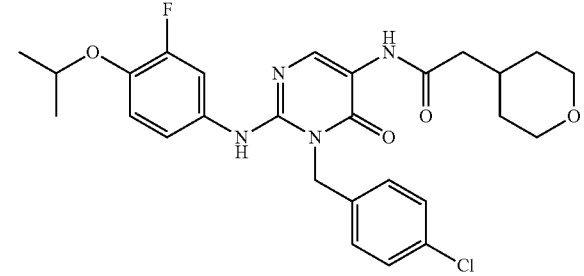 [SMILES: CC(C)Oc1ccc(Nc2ncc(NC(=O)CC3CCOCC3)c(=O)n2Cc2ccc(Cl)cc2)cc1F] | I-233 | 2.09 | 529 | 1 |
| 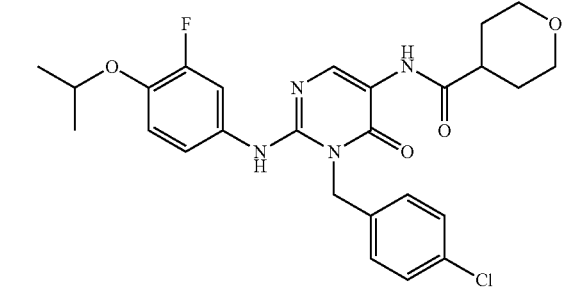 | I-234 | 2.07 | 515 | 1 |
| 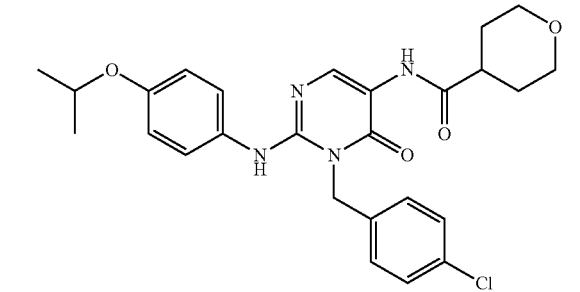 | I-235 | 1.97 | 497 | 1 |
| 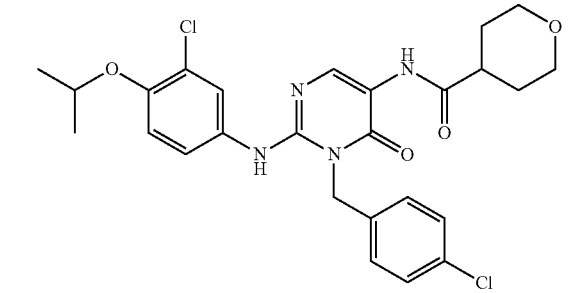 [SMILES: CC(C)Oc1ccc(Nc2ncc(NC(=O)C3CCOCC3)c(=O)n2Cc2ccc(Cl)cc2)cc1F] | I-236 | 2.18 | 531 | 1 |
| 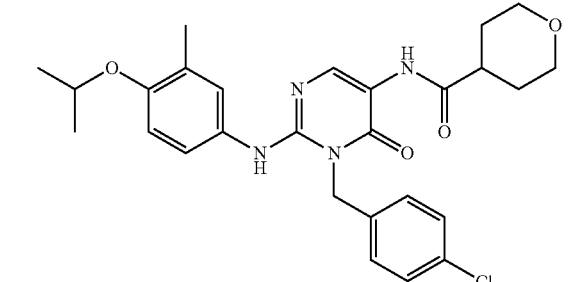 | I-237 | 2.13 | 511 | 1 |

TABLE 38

| Structure | Compound No | Retention Time (min) | [M + H] | Method |
|---|---|---|---|---|
| 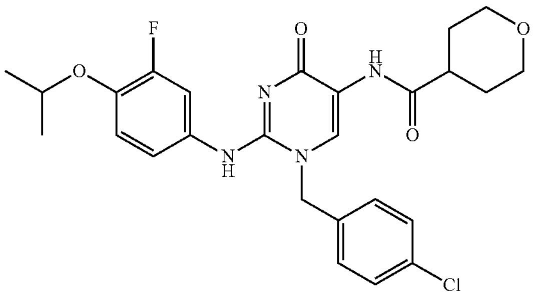 [SMILES: CC(C)Oc1ccc(Nc2nc(=O)c(NC(=O)C3CCOCC3)cn2Cc2ccc(Cl)cc2)cc1F] | I-238 | 1.81 | 515 | 1 |
| 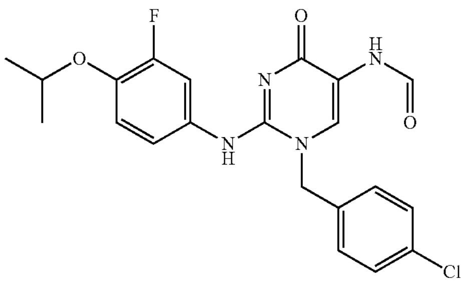 [SMILES: CC(C)Oc1ccc(Nc2nc(=O)c(NC=O)cn2Cc2ccc(Cl)cc2)cc1F] | I-239 | 1.72 | 431 | 1 |
| 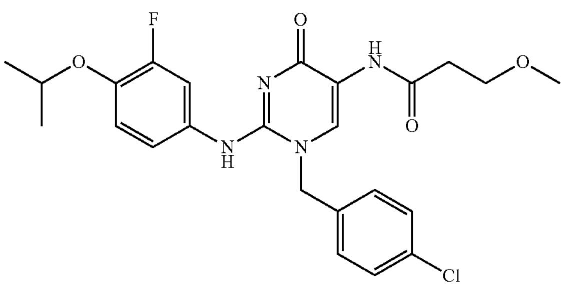 [SMILES: COCCC(=O)Nc1cn(Cc2ccc(Cl)cc2)c(Nc2ccc(OC(C)C)c(F)c2)nc1=O] | I-240 | 1.68 | 489 | 1 |
| 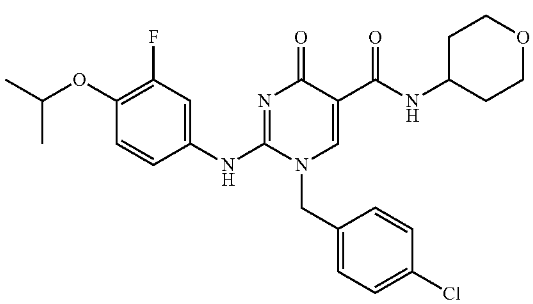 [SMILES: CC(C)Oc1ccc(Nc2nc(=O)c(C(=O)NC3CCOCC3)cn2Cc2ccc(Cl)cc2)cc1F] | I-241 | 1.89 | 515 | 1 |
| 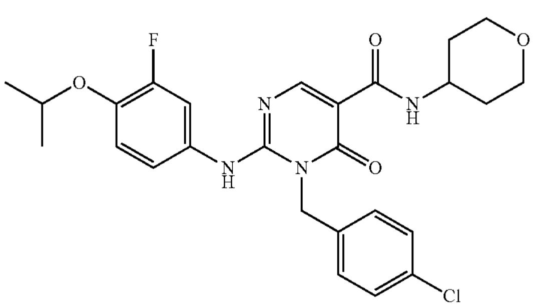 [SMILES: CC(C)Oc1ccc(Nc2ncc(C(=O)NC3CCOCC3)c(=O)n2Cc2ccc(Cl)cc2)cc1F] | I-242 | 1.94 | 515 | 1 |

TABLE 39

| Structure | Compound No | Retention Time (min) | [M + H] | Method |
|---|---|---|---|---|
| (structure) | I-243 | 1.62 | 403 | 1 |
| (structure) | I-244 | 1.40 | 548 | 1 |
| (structure) | I-245 | 1.74 | 550 | 1 |
| (structure) | I-246 | 1.80 | 445 | 1 |
| (structure) | I-247 | 2.06 | 473 | 1 |

TABLE 40
| Structure | Compound No | Retention Time (min) | [M + H] | Method |
|---|---|---|---|---|
| 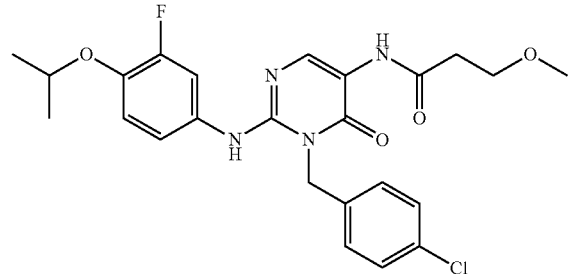 [SMILES: COCCC(=O)Nc1cnc(Nc2ccc(OC(C)C)c(F)c2)n(Cc2ccc(Cl)cc2)c1=O] | I-248 | 1.89 | 489 | 1 |
| 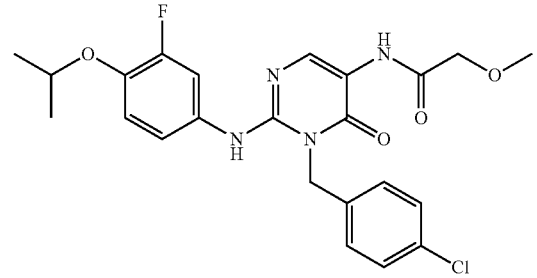 | I-249 | 1.97 | 475 | 1 |
| 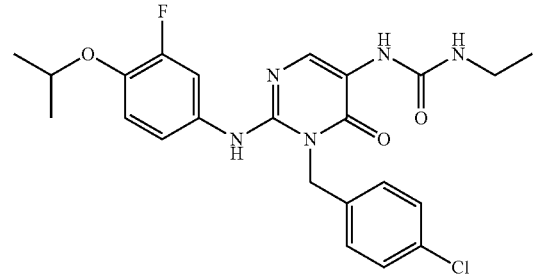 [SMILES: CCNC(=O)Nc1cnc(Nc2ccc(OC(C)C)c(F)c2)n(Cc2ccc(Cl)cc2)c1=O] | I-250 | 1.83 | 474 | 1 |
| 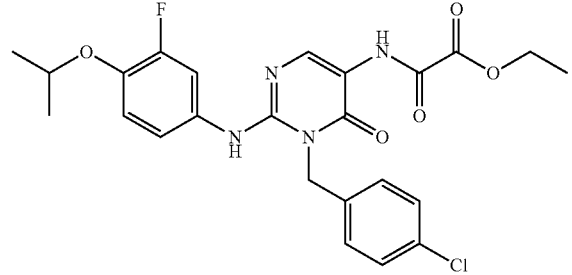 [SMILES: CCOC(=O)C(=O)Nc1cnc(Nc2ccc(OC(C)C)c(F)c2)n(Cc2ccc(Cl)cc2)c1=O] | I-251 | 2.11 | 503 | 1 |
| 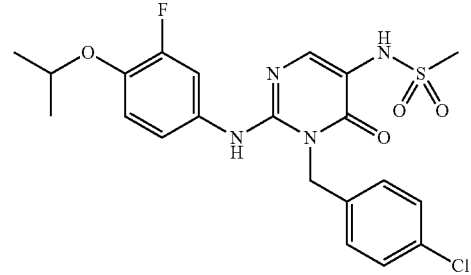 [SMILES: CC(C)Oc1ccc(Nc2ncc(NS(C)(=O)=O)c(=O)n2Cc2ccc(Cl)cc2)cc1F] | I-252 | 1.83 | 481 | 1 |

TABLE 41

| Structure | Compound No | Retention Time (min) | [M + H] | Method |
|---|---|---|---|---|
| (structure) | I-253 | 1.95 | 559 | 1 |
| (structure) | I-254 | 1.75 | 475 | 1 |
| (structure) | I-255 | 1.99 | 518 | 3 |
| (structure) | I-256 | 1.33 | 513 | 3 |
| (structure) | I-257 | 2.22 | 466 | 1 |

TABLE 42

| Structure | Compound No | Retention Time (min) | [M + H] | Method |
|---|---|---|---|---|
| 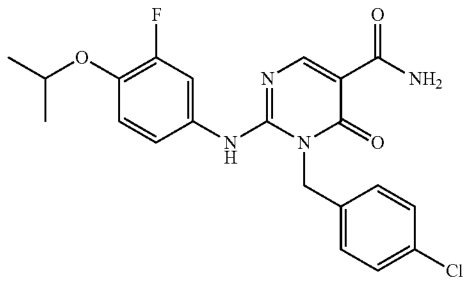 [SMILES: CC(C)Oc1ccc(Nc2ncc(C(N)=O)c(=O)n2Cc2ccc(Cl)cc2)cc1F] | I-258 | 1.80 | 431 | 1 |
| 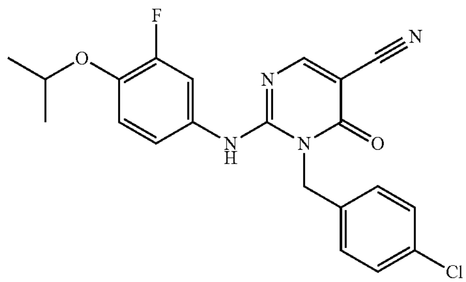 [SMILES: CC(C)Oc1ccc(Nc2ncc(C#N)c(=O)n2Cc2ccc(Cl)cc2)cc1F] | I-259 | 2.03 | 413 | 1 |
| 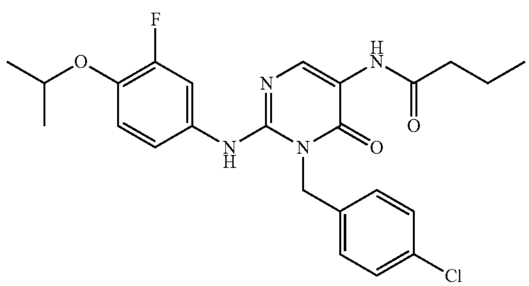 [SMILES: CCCC(=O)Nc1cnc(Nc2ccc(OC(C)C)c(F)c2)n(Cc2ccc(Cl)cc2)c1=O] | I-260 | 2.26 | 473 | 1 |
| 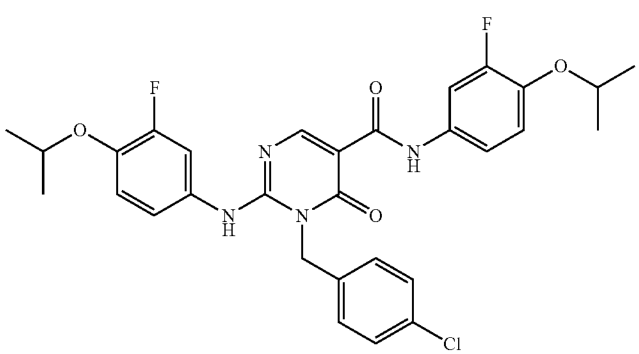 [SMILES: CC(C)Oc1ccc(NC(=O)c2cnc(Nc3ccc(OC(C)C)c(F)c3)n(Cc3ccc(Cl)cc3)c2=O)cc1F] | I-261 | 2.75 | 583 | 1 |
| 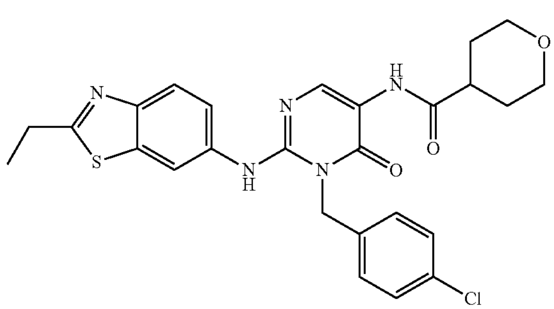 [SMILES: CCc1nc2ccc(Nc3ncc(NC(=O)C4CCOCC4)c(=O)n3Cc3ccc(Cl)cc3)cc2s1] | I-262 | 1.89 | 524 | 1 |

TABLE 43

| Structure | Compound No | Retention Time (min) | [M + H] | Method |
|---|---|---|---|---|
| 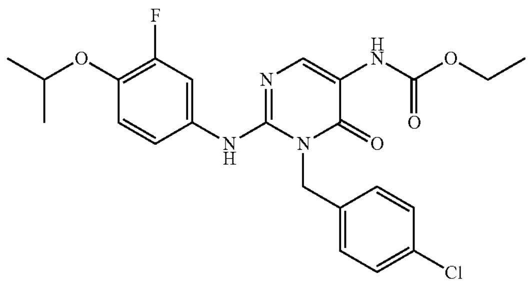 | I-263 | 2.30 | 474 | 1 |
| 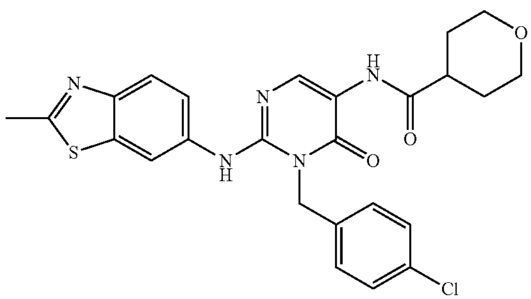 [SMILES: Cc1nc2ccc(Nc3ncc(NC(=O)C4CCOCC4)c(=O)n3Cc3ccc(Cl)cc3)cc2s1] | I-264 | 1.72 | 510 | 1 |
| 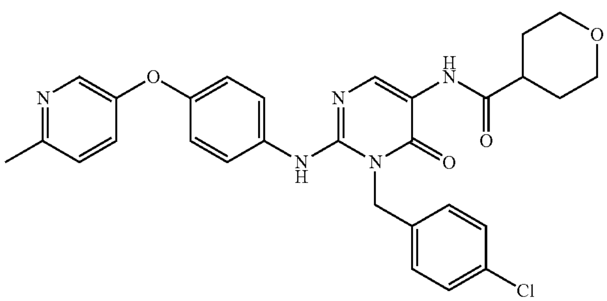 [SMILES: Cc1ccc(Oc2ccc(Nc3ncc(NC(=O)C4CCOCC4)c(=O)n3Cc3ccc(Cl)cc3)cc2)cn1] | I-265 | 1.40 | 546 | 1 |
| 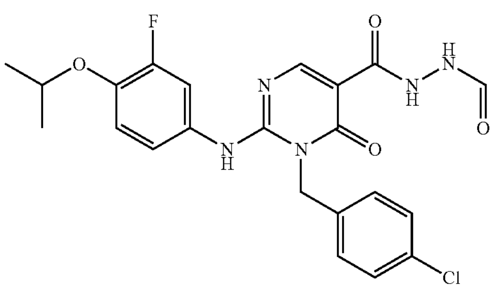 [SMILES: CC(C)Oc1ccc(Nc2ncc(C(=O)NNC=O)c(=O)n2Cc2ccc(Cl)cc2)cc1F] | I-266 | 1.86 | 474 | 1 |
| 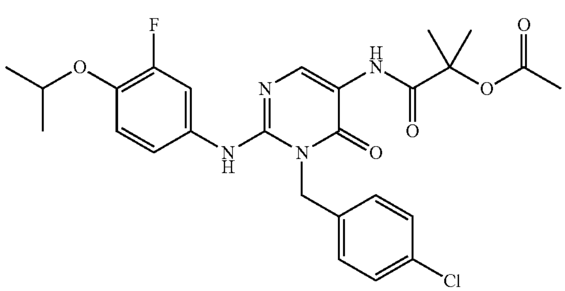 [SMILES: CC(=O)OC(C)(C)C(=O)Nc1cnc(Nc2ccc(OC(C)C)c(F)c2)n(Cc2ccc(Cl)cc2)c1=O] | I-267 | 2.31 | 531 | 1 |

TABLE 44

| Structure | Compound No | Retention Time (min) | [M + H] | Method |
|---|---|---|---|---|
| (structure) | I-268 | 2.10 | 489 | 1 |
| (structure) | I-269 | 1.84 | 475 | 1 |
| (structure) | I-270 | 1.92 | 556 | 1 |
| (structure) | I-271 | 2.31 | 546 | 1 |

TABLE 44-continued

| Structure | Compound No | Retention Time (min) | [M + H] | Method |
|---|---|---|---|---|
| (structure of I-272) | I-272 | 1.77 | 446 | 1 |

TABLE 45

| Structure | Compound No | Retention Time (min) | [M + H] | Method |
|---|---|---|---|---|
| (structure of I-273) | I-273 | 2.34 | 538 | 1 |
| (structure of I-274) | I-274 | 2.31 | 538 | 1 |
| (structure of I-275) | I-275 | 1.83 | 524 | 1 |

TABLE 45-continued

| Structure | Compound No | Retention Time (min) | [M + H] | Method |
|---|---|---|---|---|
| (structure) | I-276 | 1.83 | 524 | 1 |
| (structure) | I-277 | 1.80 | 446 | 1 |

TABLE 46

| Structure | Compound No | Retention Time (min) | [M + H] | Method |
|---|---|---|---|---|
| (structure) | I-278 | 1.98 | 516 | 1 |
| (structure) | I-279 | 1.89 | 538 | 1 |

TABLE 46-continued

| Structure | Compound No | Retention Time (min) | [M + H] | Method |
|---|---|---|---|---|
| 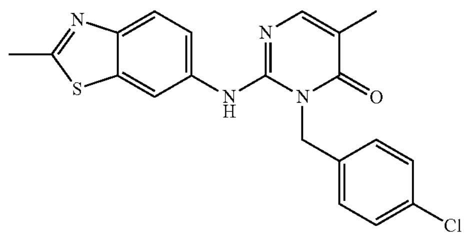 [SMILES: Cc1nc2ccc(Nc3ncc(C)c(=O)n3Cc3ccc(Cl)cc3)cc2s1] | I-280 | 1.83 | 397 | 1 |
| 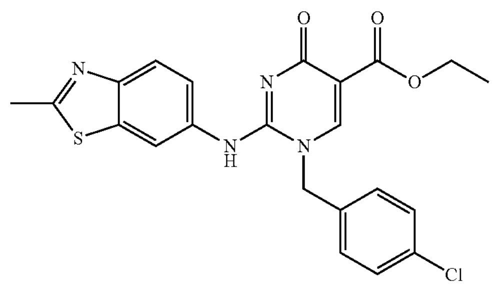 [SMILES: CCOC(=O)c1cn(Cc2ccc(Cl)cc2)c(Nc2ccc3nc(C)sc3c2)nc1=O] | I-282 | 1.91 | 455 | 1 |
| 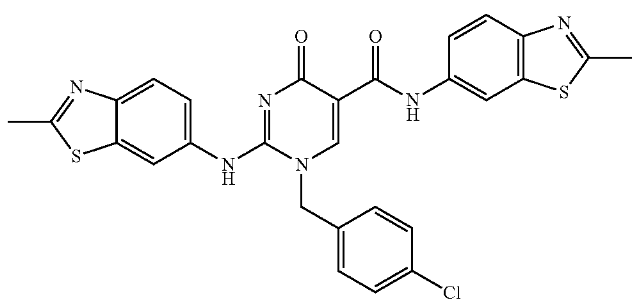 | I-284 | 2.39 | 573 | 1 |

TABLE 47

| Structure | Compound No | Retention Time (min) | [M + H] | Method |
|---|---|---|---|---|
| 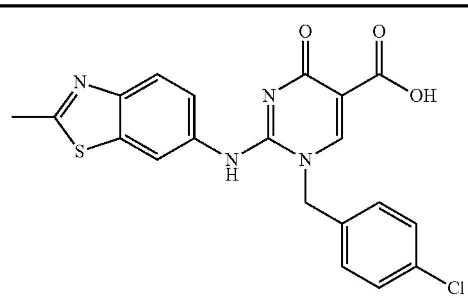 | I-285 | 1.67 | 427 | 1 |

TABLE 47-continued

| Structure | Compound No | Retention Time (min) | [M + H] | Method |
|---|---|---|---|---|
| 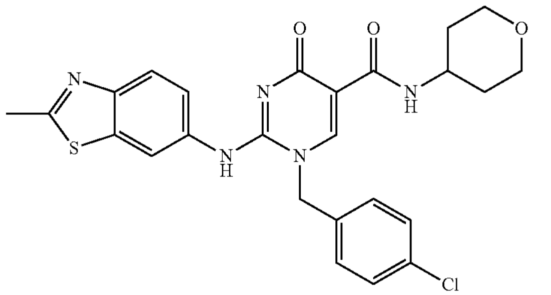 [SMILES: Cc1nc2ccc(Nc3nc(=O)c(C(=O)NC4CCOCC4)cn3Cc3ccc(Cl)cc3)cc2s1] | I-286 | 1.73 | 510 | 1 |
| 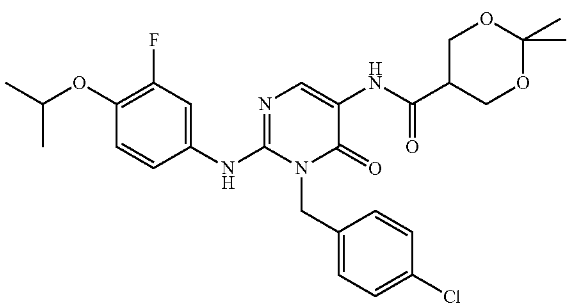 [SMILES: CC(C)Oc1ccc(Nc2ncc(NC(=O)C3COC(C)(C)OC3)c(=O)n2Cc2ccc(Cl)cc2)cc1F] | I-287 | 2.24 | 545 | 1 |
| 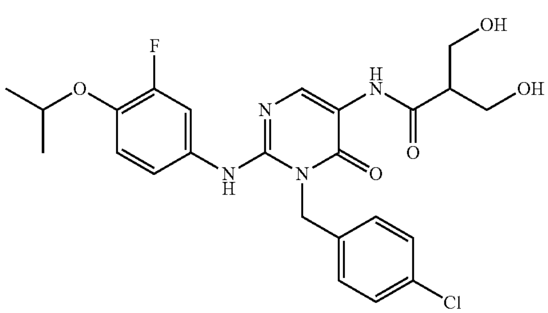 [SMILES: CC(C)Oc1ccc(Nc2ncc(NC(=O)C(CO)CO)c(=O)n2Cc2ccc(Cl)cc2)cc1F] | I-288 | 1.74 | 505 | 1 |
| 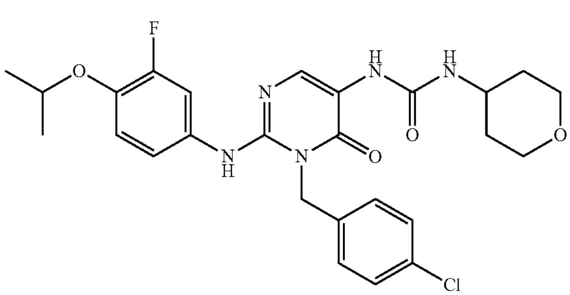 [SMILES: CC(C)Oc1ccc(Nc2ncc(NC(=O)NC3CCOCC3)c(=O)n2Cc2ccc(Cl)cc2)cc1F] | I-289 | 1.98 | 530 | 1 |

TABLE 48

| Structure | Compound No | Retention Time (min) | [M + H] | Method |
|---|---|---|---|---|
| (structure) | I-290 | 2.32 | 498 | 1 |
| (structure) | I-291 | 1.34 | 476 | 1 |
| (structure) | I-292 | 1.11 | 434 | 1 |
| (structure) | I-293 | 1.64 | 562 | 1 |
| (structure) | I-294 | 1.59 | 576 | 1 |

TABLE 49

| Structure | Compound No | Retention Time (min) | [M + H] | Method |
|---|---|---|---|---|
| 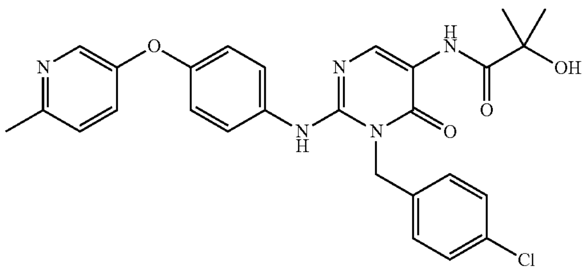 [SMILES: Cc1ccc(Oc2ccc(Nc3ncc(NC(=O)C(C)(C)O)c(=O)n3Cc3ccc(Cl)cc3)cc2)cn1] | I-295 | 1.42 | 520 | 1 |
| | I-298 | 1.15 | 536 | 1 |
| 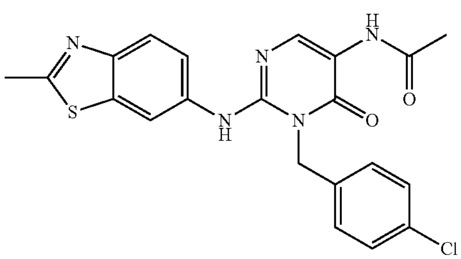 [SMILES: CC(=O)Nc1cnc(Nc2ccc3nc(C)sc3c2)n(Cc2ccc(Cl)cc2)c1=O] | I-297 | 1.61 | 440 | 1 |
| | I-298 | 2.16 | 496 | 1 |
| 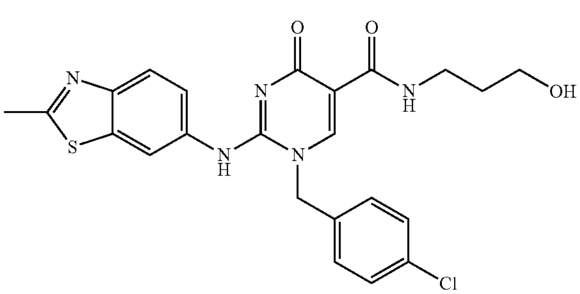 [SMILES: Cc1nc2ccc(Nc3nc(=O)c(C(=O)NCCCO)cn3Cc3ccc(Cl)cc3)cc2s1] | I-299 | 1.56 | 484 | 1 |

TABLE 50

| Structure | Compound No | Retention Time (min) | [M + H] | Method |
|---|---|---|---|---|
| 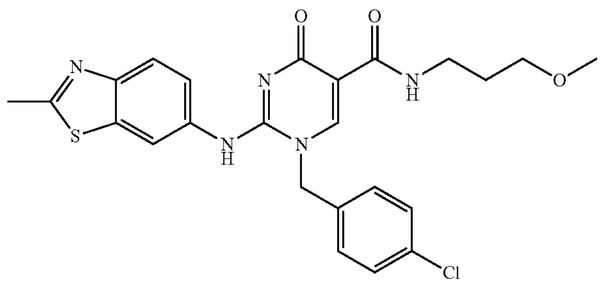 | I-300 | 1.77 | 498 | 1 |
| 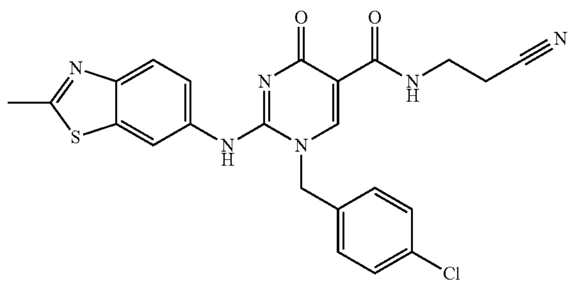 [SMILES: Cc1nc2ccc(Nc3nc(=O)c(C(=O)NCCC#N)cn3Cc3ccc(Cl)cc3)cc2s1] | I-301 | 1.72 | 479 | 1 |
| 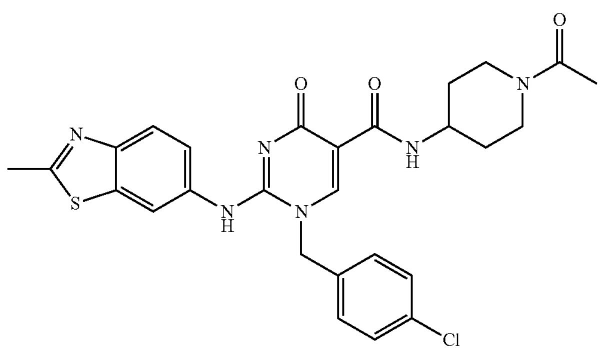 [SMILES: CC(=O)N1CCC(NC(=O)c2cn(Cc3ccc(Cl)cc3)c(Nc3ccc4nc(C)sc4c3)nc2=O)CC1] | I-302 | 1.61 | 551 | 1 |
| 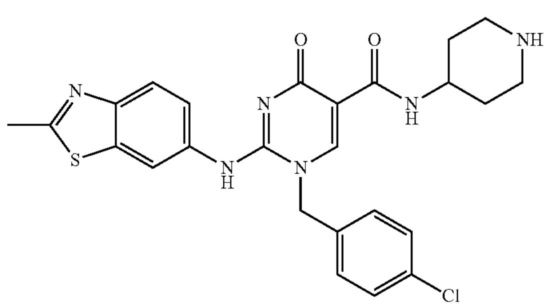 [SMILES: Cc1nc2ccc(Nc3nc(=O)c(C(=O)NC4CCNCC4)cn3Cc3ccc(Cl)cc3)cc2s1] | I-303 | 1.16 | 509 | 1 |
| 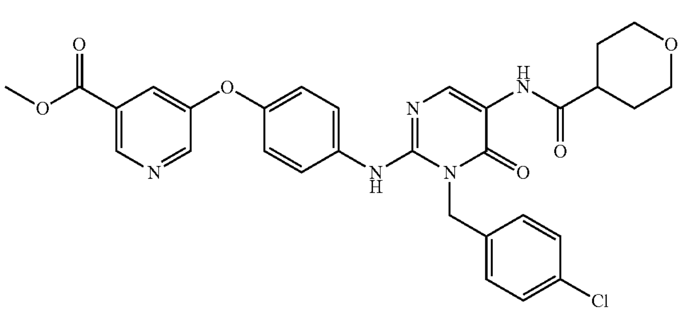 [SMILES: COC(=O)c1cncc(Oc2ccc(Nc3ncc(NC(=O)C4CCOCC4)c(=O)n3Cc3ccc(Cl)cc3)cc2)c1] | I-304 | 1.85 | 590 | 1 |

TABLE 51

| Structure | Compound No | Retention Time (min) | [M + H] | Method |
|---|---|---|---|---|
| 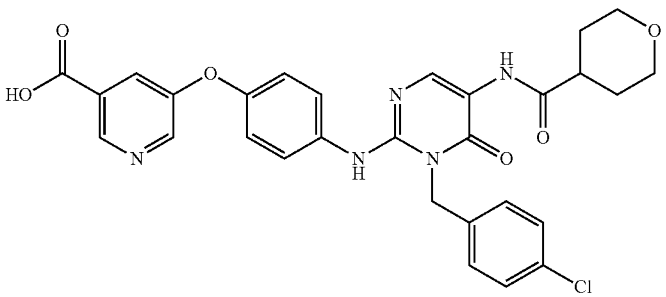 [SMILES: O=C(O)c1cncc(Oc2ccc(Nc3ncc(NC(=O)C4CCOCC4)c(=O)n3Cc3ccc(Cl)cc3)cc2)c1] | I-305 | 1.58 | 576 | 1 |
| 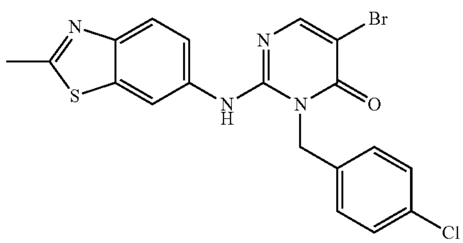 [SMILES: Cc1nc2ccc(Nc3ncc(Br)c(=O)n3Cc3ccc(Cl)cc3)cc2s1] | I-306 | 2.03 | 461 | 1 |
| 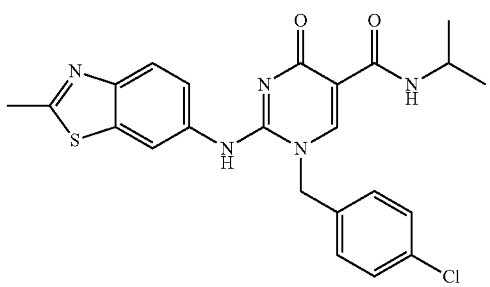 [SMILES: Cc1nc2ccc(Nc3nc(=O)c(C(=O)NC(C)C)cn3Cc3ccc(Cl)cc3)cc2s1] | I-307 | 1.91 | 468 | 1 |
| 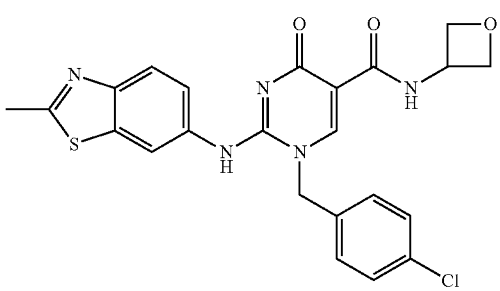 [SMILES: Cc1nc2ccc(Nc3nc(=O)c(C(=O)NC4COC4)cn3Cc3ccc(Cl)cc3)cc2s1] | I-308 | 1.62 | 482 | 1 |
| 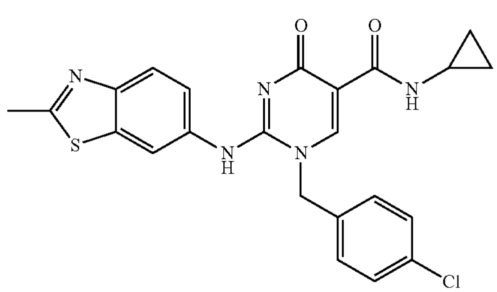 [SMILES: Cc1nc2ccc(Nc3nc(=O)c(C(=O)NC4CC4)cn3Cc3ccc(Cl)cc3)cc2s1] | I-309 | 1.80 | 466 | 1 |

TABLE 52
| Structure | Compound No | Retention Time (min) | [M + H] | Method |
|---|---|---|---|---|
| 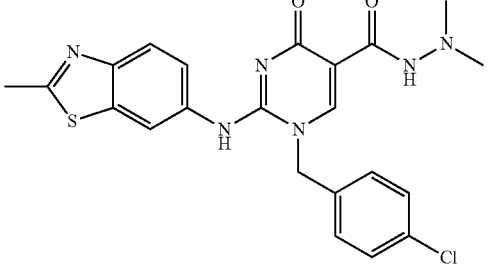 | I-310 | 1.54 | 469 | 1 |
| 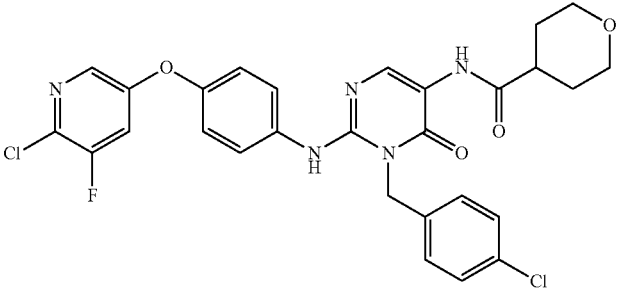 [SMILES: O=C(Nc1cnc(Nc2ccc(Oc3cnc(Cl)c(F)c3)cc2)n(Cc2ccc(Cl)cc2)c1=O)C1CCOCC1] | I-311 | 2.18 | 584 | 1 |
| 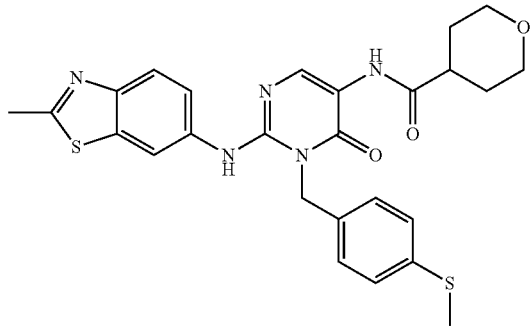 [SMILES: CSc1ccc(Cn2c(Nc3ccc4nc(C)sc4c3)ncc(NC(=O)C3CCOCC3)c2=O)cc1] | I-312 | 1.68 | 522 | 1 |
| 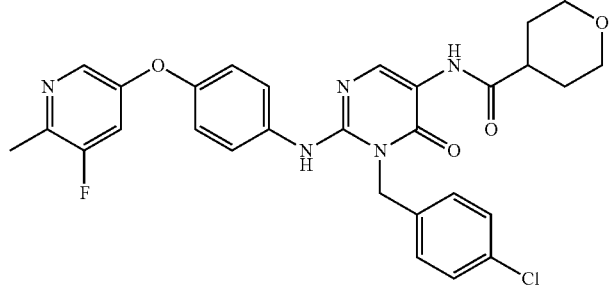 [SMILES: Cc1ncc(Oc2ccc(Nc3ncc(NC(=O)C4CCOCC4)c(=O)n3Cc3ccc(Cl)cc3)cc2)cc1F] | I-313 | 1.98 | 564 | 1 |
| 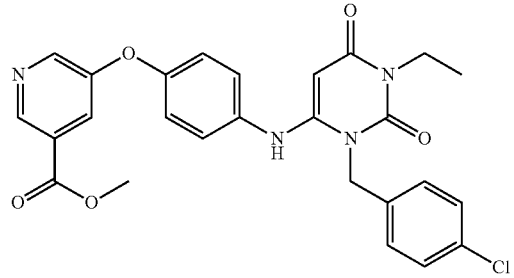 [SMILES: CCn1c(=O)cc(Nc2ccc(Oc3cncc(C(=O)OC)c3)cc2)n(Cc2ccc(Cl)cc2)c1=O] | I-314 | 1.95 | 507 | 1 |

TABLE 53

| Structure | Compound No | Retention Time (min) | [M + H] | Method |
|---|---|---|---|---|
| 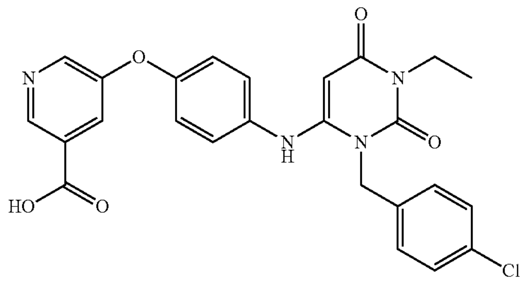 [SMILES: CCn1c(=O)cc(Nc2ccc(Oc3cncc(C(=O)O)c3)cc2)n(Cc2ccc(Cl)cc2)c1=O] | I-315 | 1.68 | 493 | 1 |
| 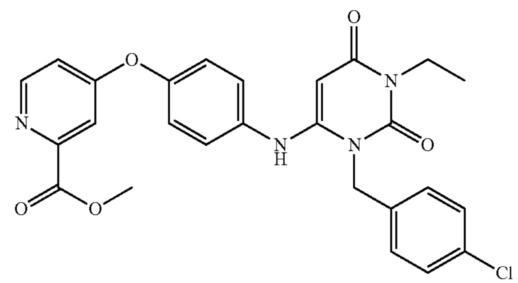 [SMILES: CCn1c(=O)cc(Nc2ccc(Oc3ccnc(C(=O)OC)c3)cc2)n(Cc2ccc(Cl)cc2)c1=O] | I-316 | 1.61 | 507 | 1 |
| 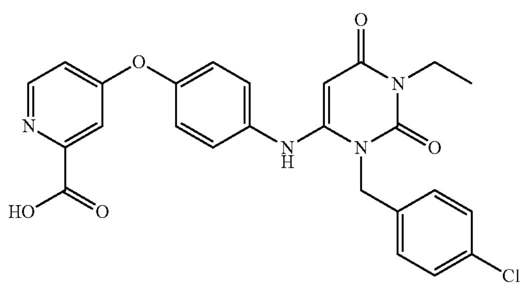 [SMILES: CCn1c(=O)cc(Nc2ccc(Oc3ccnc(C(=O)O)c3)cc2)n(Cc2ccc(Cl)cc2)c1=O] | I-317 | 1.39 | 493 | 1 |
| 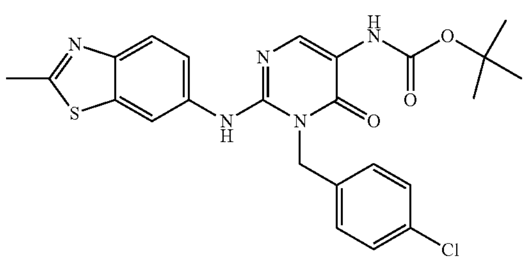 [SMILES: Cc1nc2ccc(Nc3ncc(NC(=O)OC(C)(C)C)c(=O)n3Cc3ccc(Cl)cc3)cc2s1] | I-318 | 2.32 | 498 | 1 |
| 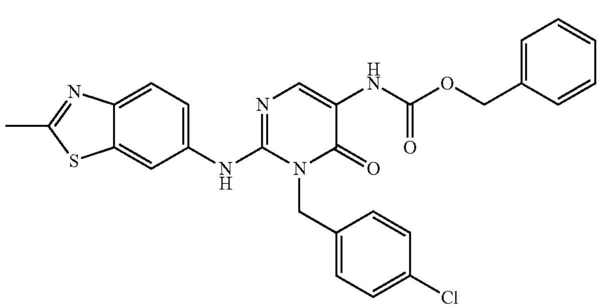 [SMILES: Cc1nc2ccc(Nc3ncc(NC(=O)OCc4ccccc4)c(=O)n3Cc3ccc(Cl)cc3)cc2s1] | I-319 | 2.27 | 532 | 1 |

TABLE 54

| Structure | Compound No | Retention Time (min) | [M + H] | Method |
|---|---|---|---|---|
| 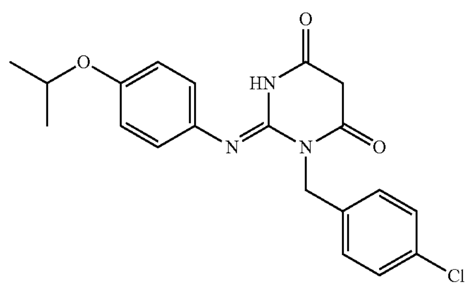 [SMILES: CC(C)Oc1ccc(/N=C2\NC(=O)CC(=O)N2Cc2ccc(Cl)cc2)cc1] | I-322 | 1.35 | 386 | 1 |
| 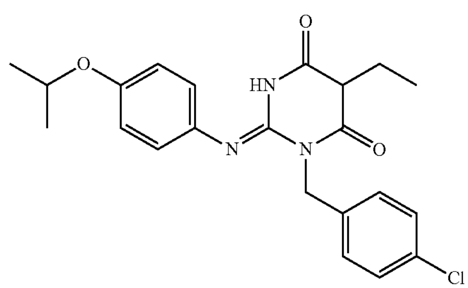 [SMILES: CCC1C(=O)N/C(=N\c2ccc(OC(C)C)cc2)N(Cc2ccc(Cl)cc2)C1=O] | I-323 | 1.81 | 386 | 1 |
| 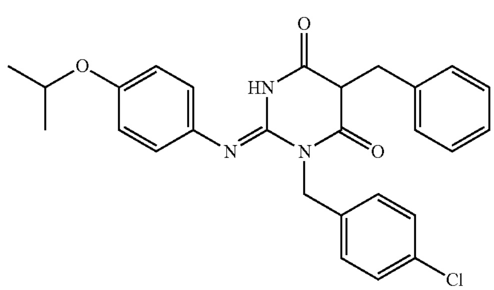 [SMILES: CC(C)Oc1ccc(/N=C2\NC(=O)C(Cc3ccccc3)C(=O)N2Cc2ccc(Cl)cc2)cc1] | I-324 | 1.51 | 444 | 1 |
| 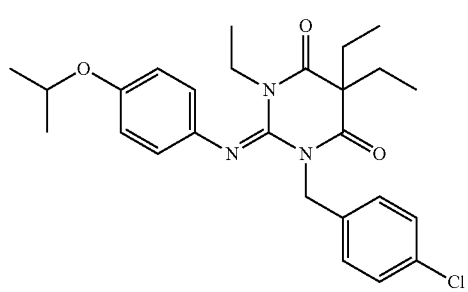 [SMILES: CCN1C(=O)C(CC)(CC)C(=O)N(Cc2ccc(Cl)cc2)/C1=N/c1ccc(OC(C)C)cc1] | I-325 | 2.92 | 470 | 1 |
| 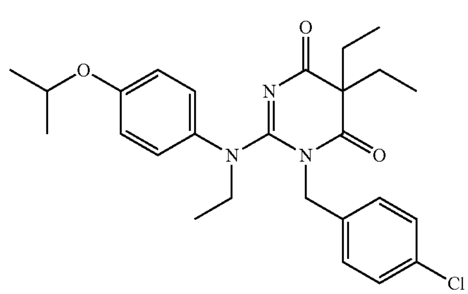 [SMILES: CCN(C1=NC(=O)C(CC)(CC)C(=O)N1Cc1ccc(Cl)cc1)c1ccc(OC(C)C)cc1] | I-326 | 2.8 | 470 | 1 |

TABLE 55

| Structure | Compound No | Retention Time (min) | [M + H] | Method |
|---|---|---|---|---|
| 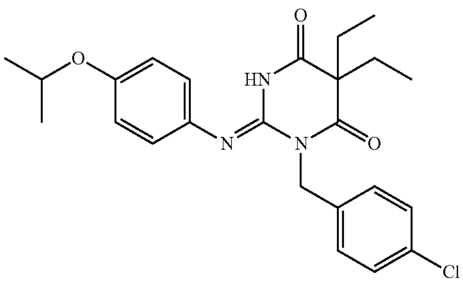 [SMILES: CCC1(CC)C(=O)N/C(=N\c2ccc(OC(C)C)cc2)N(Cc2ccc(Cl)cc2)C1=O] | I-327 | 2.53 | 440 | 1 |
| 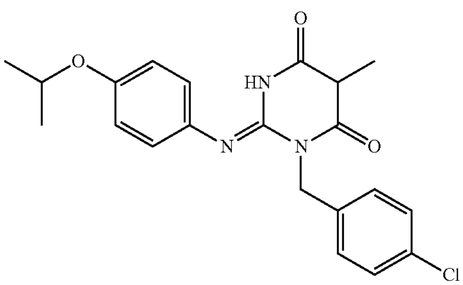 [SMILES: CC(C)Oc1ccc(/N=C2\NC(=O)C(C)C(=O)N2Cc2ccc(Cl)cc2)cc1] | I-328 | 1.94 | 400 | 1 |
| 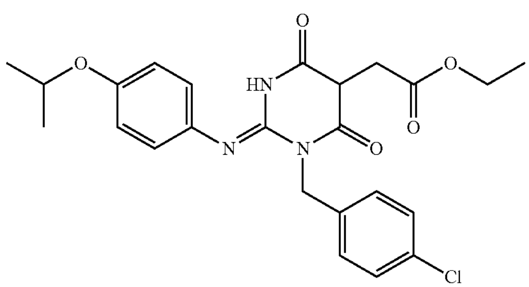 [SMILES: CCOC(=O)CC1C(=O)N/C(=N\c2ccc(OC(C)C)cc2)N(Cc2ccc(Cl)cc2)C1=O] | I-329 | 1.99 | 472 | 1 |
| 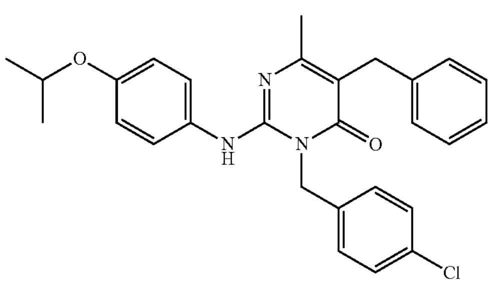 [SMILES: Cc1nc(Nc2ccc(OC(C)C)cc2)n(Cc2ccc(Cl)cc2)c(=O)c1Cc1ccccc1] | I-330 | 2.62 | 474 | 1 |
| 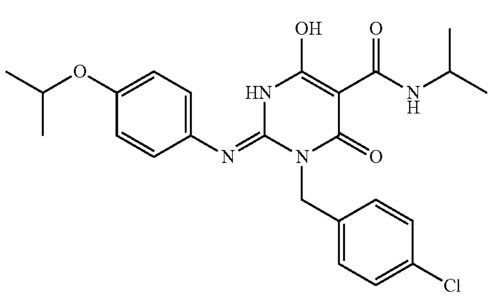 [SMILES: CC(C)NC(=O)c1c(O)[nH]/c(=N\c2ccc(OC(C)C)cc2)n(Cc2ccc(Cl)cc2)c1=O] | I-332 | 2.57 | 471 | 1 |

TABLE 56

| Structure | Compound No | Retention Time (min) | [M + H] | Method |
|---|---|---|---|---|
| 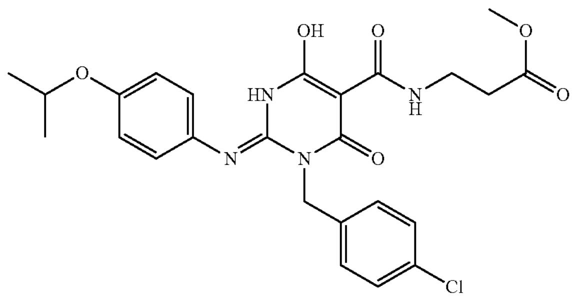 [SMILES: COC(=O)CCNC(=O)c1c(O)[nH]/c(=N\c2ccc(OC(C)C)cc2)n(Cc2ccc(Cl)cc2)c1=O] | I-333 | 2.56 | 515 | 2 |
| 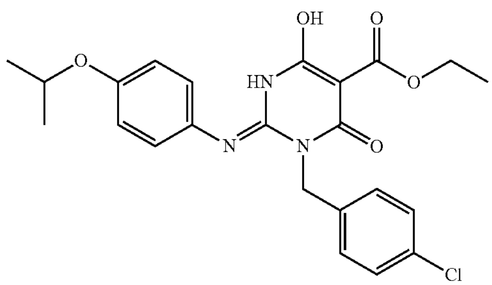 [SMILES: CCOC(=O)c1c(O)[nH]/c(=N\c2ccc(OC(C)C)cc2)n(Cc2ccc(Cl)cc2)c1=O] | I-334 | 2.51 | 458 | 2 |
| 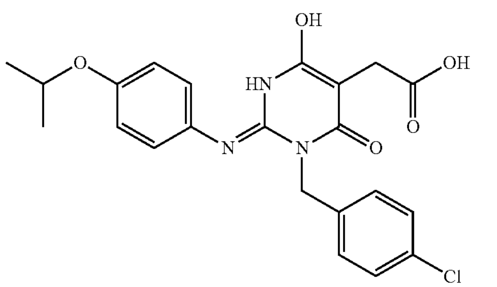 [SMILES: CC(C)Oc1ccc(/N=c2\[nH]c(O)c(CC(=O)O)c(=O)n2Cc2ccc(Cl)cc2)cc1] | I-335 | 1.70 | 444 | 1 |
| 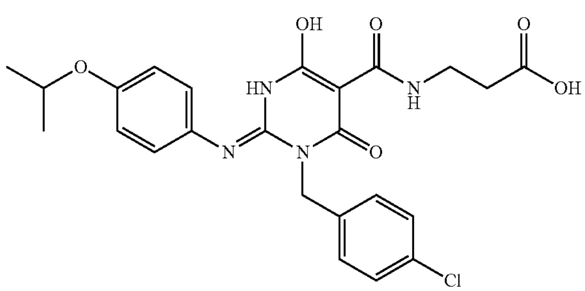 [SMILES: CC(C)Oc1ccc(/N=c2\[nH]c(O)c(C(=O)NCCC(=O)O)c(=O)n2Cc2ccc(Cl)cc2)cc1] | I-336 | 2.06 | 501 | 1 |
| 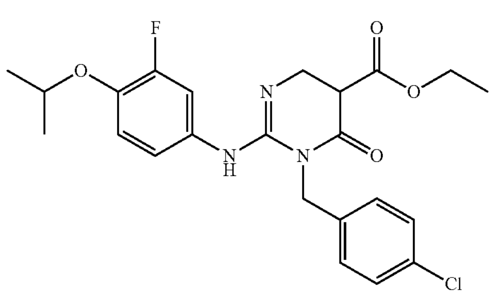 [SMILES: CCOC(=O)C1CN=C(Nc2ccc(OC(C)C)c(F)c2)N(Cc2ccc(Cl)cc2)C1=O] | I-337 | 2.04 | 462 | 1 |

TABLE 57

| Structure | Compound No | Retention Time (min) | [M + H] | Method |
|---|---|---|---|---|
| 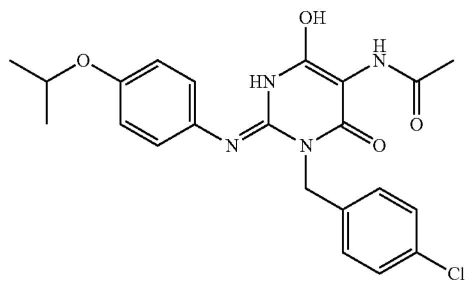 [SMILES: CC(=O)Nc1c(O)[nH]/c(=N\c2ccc(OC(C)C)cc2)n(Cc2ccc(Cl)cc2)c1=O] | I-339 | 1.60 | 443 | 1 |
| 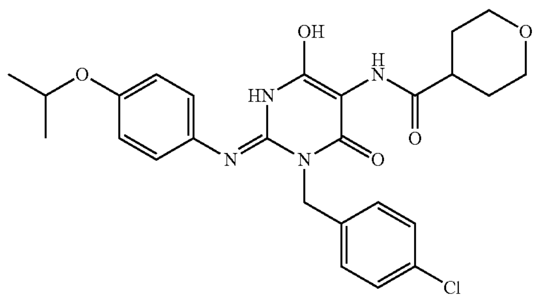 [SMILES: CC(C)Oc1ccc(/N=c2\[nH]c(O)c(NC(=O)C3CCOCC3)c(=O)n2Cc2ccc(Cl)cc2)cc1] | I-340 | 1.73 | 513 | 1 |
| 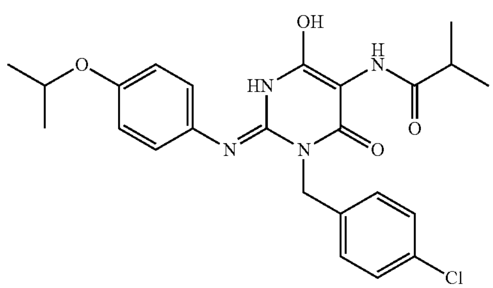 [SMILES: CC(C)Oc1ccc(/N=c2\[nH]c(O)c(NC(=O)C(C)C)c(=O)n2Cc2ccc(Cl)cc2)cc1] | I-341 | 1.99 | 471 | 1 |
| 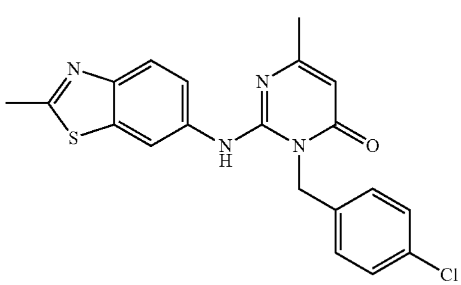 [SMILES: Cc1cc(=O)n(Cc2ccc(Cl)cc2)c(Nc2ccc3nc(C)sc3c2)n1] | I-343 | 1.85 | 397 | 1 |
| 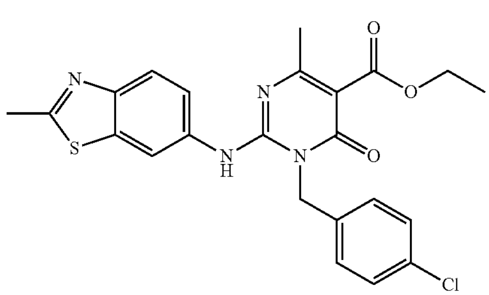 [SMILES: CCOC(=O)c1c(C)nc(Nc2ccc3nc(C)sc3c2)n(Cc2ccc(Cl)cc2)c1=O] | I-345 | 2.04 | 469 | 1 |

TABLE 58

| Structure | Compound No | Retention Time (min) | [M + H] | Method |
|---|---|---|---|---|
| 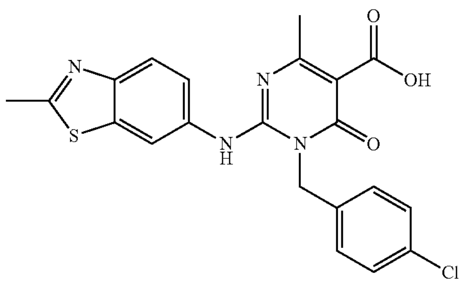 [SMILES: Cc1nc2ccc(Nc3nc(C)c(C(=O)O)c(=O)n3Cc3ccc(Cl)cc3)cc2s1] | I-346 | 1.95 | 441 | 1 |
| 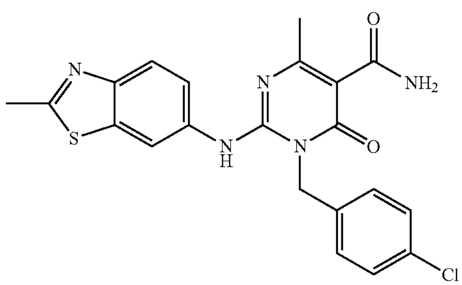 | I-347 | 1.67 | 440 | 1 |
| 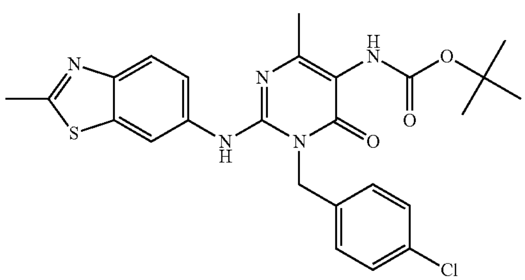 [SMILES: Cc1nc2ccc(Nc3nc(C)c(NC(=O)OC(C)(C)C)c(=O)n3Cc3ccc(Cl)cc3)cc2s1] | I-348 | 2.09 | 512 | 1 |
| 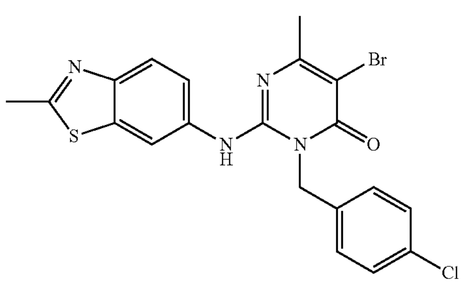 [SMILES: Cc1nc2ccc(Nc3nc(C)c(Br)c(=O)n3Cc3ccc(Cl)cc3)cc2s1] | I-349 | 2.19 | 475 | 1 |
| 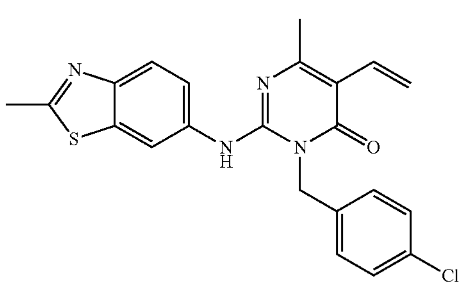 [SMILES: C=Cc1c(C)nc(Nc2ccc3nc(C)sc3c2)n(Cc2ccc(Cl)cc2)c1=O] | I-350 | 2.24 | 423 | 1 |

TABLE 59

| Structure | Compound No | Retention Time (min) | [M + H] | Method |
|---|---|---|---|---|
| (structure) | I-351 | 2.15 | 425 | 1 |
| (structure) | I-352 | 499 | 1.95 | 1 |
| (structure) | I-353 | 527 | 2.08 | 1 |
| (structure) | I-354 | 485 | 1.74 | 1 |
| (structure) | I-355 | 443 | 1.59 | 1 |

TABLE 60
| Structure | Compound No | Retention Time (min) | [M + H] | Method |
|---|---|---|---|---|
| 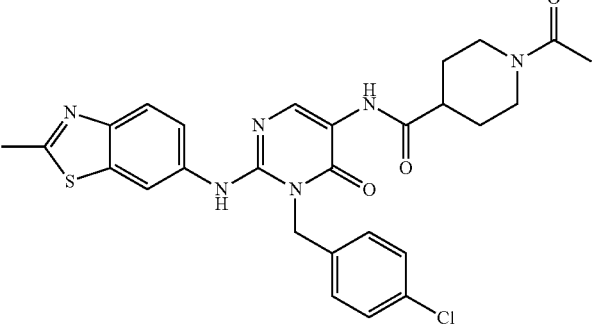 | I-358 | 551 | 1.69 | 1 |
| 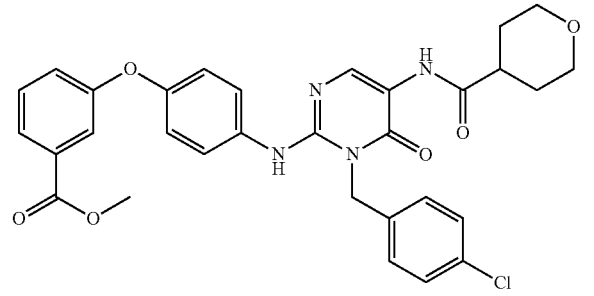 [SMILES: COC(=O)c1cccc(Oc2ccc(Nc3ncc(NC(=O)C4CCOCC4)c(=O)n3Cc3ccc(Cl)cc3)cc2)c1] | I-357 | 589 | 2.23 | 1 |
| 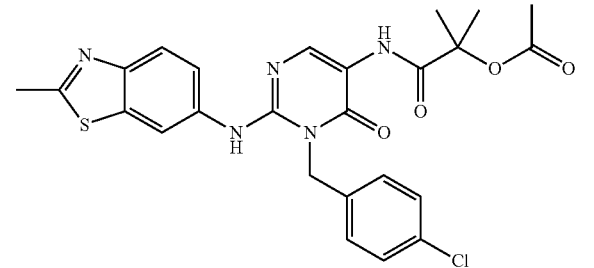 [SMILES: CC(=O)OC(C)(C)C(=O)Nc1cnc(Nc2ccc3nc(C)sc3c2)n(Cc2ccc(Cl)cc2)c1=O] | I-358 | 526 | 2.07 | 1 |
| 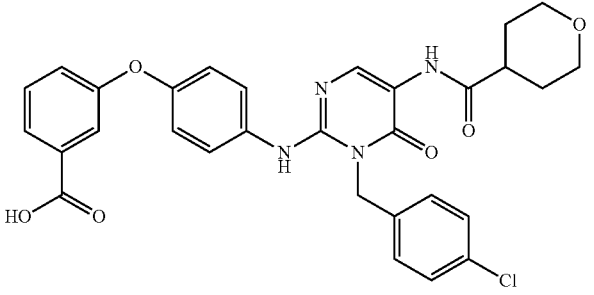 [SMILES: O=C(O)c1cccc(Oc2ccc(Nc3ncc(NC(=O)C4CCOCC4)c(=O)n3Cc3ccc(Cl)cc3)cc2)c1] | I-359 | 575 | 1.92 | 1 |
| 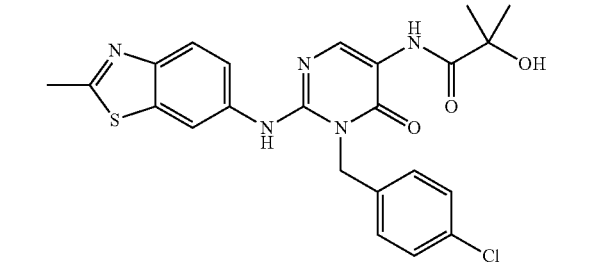 [SMILES: Cc1nc2ccc(Nc3ncc(NC(=O)C(C)(C)O)c(=O)n3Cc3ccc(Cl)cc3)cc2s1] | I-360 | 484 | 1.85 | 1 |

TABLE 61

| Structure | Compound No | Retention Time (min) | [M + H] | Method |
|---|---|---|---|---|
| (structure) | I-361 | 500 | 1.51 | 1 |
| (structure) | I-362 | 436 | 1.82 | 2 |
| (structure) | I-363 | 386 | 2.47 | 1 |
| (structure) | I-364 | 362 | 2.4 | 1 |
| (structure) | I-365 | 348 | 1.57 | 1 |

TABLE 62

| Structure | Compound No | Retention Time (min) | [M + H] | Method |
|---|---|---|---|---|
| 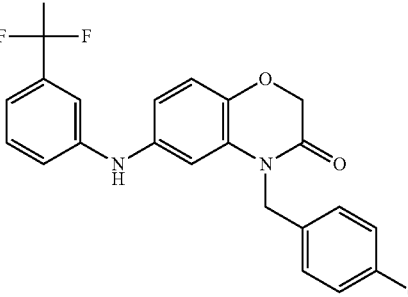 | I-366 | 433 | 2.69 | 2 |
| 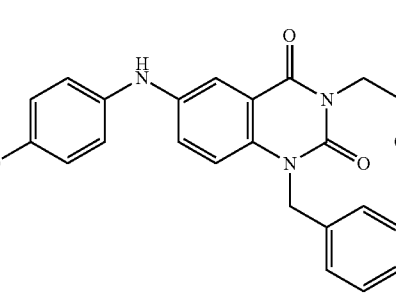 | I-367 | 522 | 2.74 | 2 |
| 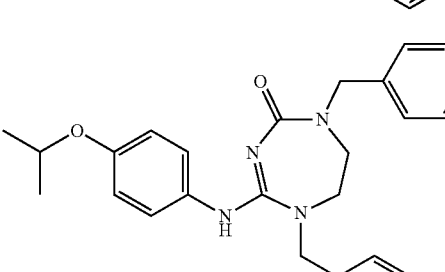 | I-368 | 511 | 1.85 | 1 |

TEST EXAMPLES

Stably expressing cell line (C6BU-1 cell transfected with human P2X$_3$ receptor gene (GenBank accession number Y07683) was used. The cells were seeded in a 96-well microtiter plate at a concentration of 8000 cells/well and cultured in the medium (8.3% fetal bovine serum, 8.3% horse serum, 1% antibiotic and antifungal in DMEM) for one day at 37° C. under 5% carbon dioxide atmosphere. The medium was replaced with 4 μM Fluo-3-AM solution (20 mM HEPES, 137 mM NaCl, 2.7 mM KCl, 0.9 in M MgCl$_2$, 5.0 mM CaCl$_2$, 5.6 D-glucose, 2.5 mM probenecid, 1.0% BSA, and 0.08% Pluronic F-127, pH 7.5) and incubated at 37° C. under 5% dioxide carbon atmosphere for one hour. The plate was washed with washing buffer (20 mM HEPES, 137 mM NaCl, 2.7 mM KCl, 0.9 mM MgCl$_2$, 5.0 mM CaCl$_2$, 5.6 mM D-glucose, 2.5 mM probenecid, pH 7.5), and each well was added with 40 μL of this buffer. The plate was placed in High-Throughput Screening System FDSS 3000 (Hamamatsu Photonics K.K.). Measurement of fluorescence intensity by FDSS 3000 was started, and 40 μL of DMSO solutions containing different concentrations of the test compound as prepared by dilution with dilution buffer (20 mM HEPES, 137 mM NaCl, 2.7 mM KCl, 0.9 mM MgCl$_3$, 5.0 mM CaCl$_2$, 5.6 D-glucose, 2.5 mM probenecid, 0.1% Pluronic F-127, pH7.5) were dispensed to each well through the built-in automatic dispenser. Five minutes after, 50 nM ATP solution (50 μL) prepared by dilution with the dilution buffer was dispensed through the built-in automatic dispenser, and the measurement of fluorescence intensity was continued for 3 min. For each well, the specific maximum fluorescence intensity was calculated as the ratio of the maximum fluorescence intensity after addition of the ATP solution to the fluorescence intensity at the starting of the measurement. The 50% inhibitory concentration (IC$_{50}$) was calculated under the assumption that the specific maximum fluorescence intensity without test compound is 0% inhibition, and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. IC$_{50}$ was calculated using Microsoft Excel (Microsoft. Corporation) and XLfit (idbs Ltd.)

The aforementioned in mM, μM and nM are each means mmol/L, μmol/L and nmol/L, respectively.

The data of the compounds of the present invention are as shown in the following Tables. In tables, μM means μmol/L.

TABLE 63

| Compound No. | IC50 (µM) | Compound No. | P2X3 IC50(µM) | Compound No. | P2X3 IC50(µM) |
|---|---|---|---|---|---|
| I-001 | 0.901 | I-201 | 0.229 | I-279 | 0.139 |
| I-005 | 0.238 | I-208 | 0.05 | I-280 | 0.237 |
| I-010 | 0.01 | I-209 | 0.397 | I-282 | 0.272 |
| I-012 | 0.006 | I-212 | 0.037 | I-286 | 0.008 |
| I-014 | 0.404 | I-213 | 0.427 | I-287 | 0.023 |
| I-020 | 0.028 | I-215 | 0.024 | I-288 | 0.017 |
| I-021 | 0.019 | I-216 | 0.105 | I-289 | 0.007 |
| I-022 | 0.147 | I-217 | 0.453 | I-290 | 0.023 |
| I-023 | 0.148 | I-218 | 0.055 | I-291 | 0.043 |
| I-046 | 0.395 | I-222 | 0.56 | I-292 | 0.433 |
| I-049 | 0.796 | I-223 | 0.724 | I-293 | 0.014 |
| I-061 | 0.748 | I-224 | 0.511 | I-294 | 0.009 |
| I-063 | 0.688 | I-227 | 0.974 | I-295 | 0.002 |
| I-065 | 0.128 | I-230 | 0.092 | I-296 | 0.007 |
| I-067 | 0.31 | I-231 | 0.226 | I-297 | 0.112 |
| I-068 | 0.105 | I-232 | 0.681 | I-298 | 0.008 |
| I-069 | 0.402 | I-233 | 0.049 | I-299 | 0.111 |
| I-070 | 0.635 | I-234 | 0.004 | I-300 | 0.164 |
| I-071 | 0.502 | I-235 | 0.011 | I-301 | 0.123 |
| I-072 | 0.749 | I-236 | 0.006 | I-302 | 0.087 |
| I-094 | 0.005 | I-237 | 0.013 | I-304 | 0.002 |
| I-095 | 0.016 | I-238 | 0.653 | I-305 | 0.004 |
| I-097 | 0.307 | I-239 | 0.515 | I-306 | 0.207 |
| I-098 | 0.233 | I-240 | 0.417 | I-307 | 0.040 |
| I-099 | 0.006 | I-241 | 0.031 | I-308 | 0.133 |
| I-100 | 0.009 | I-242 | 0.067 | I-309 | 0.061 |
| I-103 | 0.014 | I-243 | 0.676 | I-310 | 0.132 |
| I-104 | 0.096 | I-244 | 0.002 | I-311 | 0.004 |
| I-105 | 0.412 | I-245 | 0.0008 | I-312 | 0.011 |
| I-106 | 0.034 | I-246 | 0.106 | I-313 | 0.003 |
| I-107 | 0.051 | I-247 | 0.019 | I-314 | 0.035 |
| I-108 | 0.061 | I-248 | 0.024 | I-315 | 0.006 |
| I-110 | 0.405 | I-249 | 0.035 | I-316 | 0.009 |
| I-111 | 0.011 | I-250 | 0.007 | I-317 | 0.003 |
| I-112 | 0.014 | I-252 | 0.062 | I-318 | 0.009 |
| I-113 | 0.072 | I-253 | 0.536 | I-319 | 0.105 |
| I-114 | 0.16 | I-254 | 0.020 | I-323 | 0.207 |
| I-115 | 0.051 | I-255 | 0.054 | I-327 | 0.867 |
| I-116 | 0.315 | I-256 | 0.732 | I-330 | 0.350 |
| I-117 | 0.152 | I-257 | 0.319 | I-332 | 0.504 |
| I-125 | 0.243 | I-258 | 0.047 | I-333 | 0.115 |
| I-126 | 0.05 | I-259 | 0.436 | I-334 | 0.188 |
| I-129 | 0.49 | I-260 | 0.015 | I-339 | 0.518 |
| I-131 | 0.108 | I-262 | 0.003 | I-341 | 0.681 |
| I-132 | 0.206 | I-263 | 0.033 | I-343 | 0.694 |
| I-133 | 0.071 | I-264 | 0.004 | I-345 | 0.273 |
| I-137 | 0.219 | I-265 | 0.001 | I-347 | 0.182 |
| I-138 | 0.201 | I-266 | 0.055 | I-348 | 0.105 |
| I-139 | 0.331 | I-267 | 0.025 | I-349 | 0.280 |

TABLE 64

| Compound No. | IC50 (µM) | Compound No. | P2X3 IC50(µM) | Compound No. | P2X3 IC50(µM) |
|---|---|---|---|---|---|
| I-146 | 0.383 | I-268 | 0.004 | I-350 | 0.385 |
| I-148 | 0.324 | I-269 | 0.031 | I-351 | 0.146 |
| I-150 | 0.12 | I-270 | 0.010 | I-352 | 0.024 |
| I-152 | 0.096 | I-271 | 0.029 | I-353 | 0.009 |
| I-153 | 0.059 | I-272 | 0.104 | I-354 | 0.094 |
| I-156 | 0.509 | I-273 | 0.095 | I-355 | 0.057 |
| I-157 | 0.589 | I-274 | 0.066 | I-356 | 0.018 |
| I-158 | 0.02 | I-275 | 0.011 | I-357 | 0.003 |
| I-164 | 0.018 | I-276 | 0.032 | I-358 | 0.016 |
| I-190 | 0.99 | I-277 | 0.049 | I-359 | 0.002 |
| I-197 | 0.098 | I-278 | 0.016 | I-360 | 0.003 |
|  |  |  |  | I-361 | 0.010 |

Test Example 2

CYP3A4 Fluorescent MBI Test

The CYP3A4 fluorescent MBI test is a test of investigating enhancement of CYP3A4 inhibition of a compound by a metabolism reaction, and the test is performed using, as CYP3A4 enzyme expressed in *Escherichia coli* and employing, as an index, a reaction in which 7-benzyloxytrifluoromethylchmarin (BFC) is debenzylated by the CYP3A4 enzyme to produce a metabolite, 7-hydroxytrifluoromethylchmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration, 1.5625, 3.125, 6.25, 12.5, 25, 50 µmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile: 0.5 mol/L Tris (trishydroxyaminomethane)=4:1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index, After a predetermined time of a reaction, acetonitrile: 0.5 mol/L Tris (trishydroxyaminomethane)=4:1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between $IC_{50}$ values is 5 or more, this was defined as (+) and, when the difference is 3 µmol/L or less, this was defined as (−).

(Result)
I-100: (−)
I-305: (−)
I-315: (−)
I-354: (−)
I-359: (−)

Test Example 3

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation as typical substrate metabolism reactions of human main five (ATP enzyme forms (CYP1A2, 2C9, 2C19, 2D6, 3A4), an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; test drug concentration, 1.0. 5.0, 10, 20 μmol/L (four points).

Each five kinds of substrates, human hepatic microsome, or a test drug in 50 mmol/L Hepes buffer as a reaction solution was added to a 96-well plate at the composition as described above. NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

(Results)
I-100: five kinds >20 μmol/L
I-241: five kinds >20 μmol/L
I-305: five kinds >20 μmol/L
I-354: five kinds >20 μmol/L Test Example 4

FAT Test

20 μL of freezing-stored rat typhoid *bacillus* (*Salmonella typhimurium* TA98 strain, TA100 strain) is inoculated on 10 mL of a liquid nutrient medium (2.5% Oxoid nutrient broth No. 2), and this is cultured before shaking at 37° C. for 10 hours. 9 mL of a bacterial solution of the TA98 strain is centrifuged (2000×g, 10 minutes) to remove a culturing solution, the bacteria is suspended in 9 mL of a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), the suspension is added to 110 mL of an Exposure medium (Micro F buffer containing Biotin: 8 μg/mL, histidine: 0.2 μg/mL, glucose: 8 mg/mL), and the TA100 strain is added to 120 mL of the Exposure medium relative to 3.16 mL of the bacterial solution to prepare a test bacterial solution. Each 12 μL of a test substance DMSO solution (8 stage dilution from maximum dose 50 mg/mL at 2-fold ratio), DMSO as a negative control, 50 μg/mL of 4-nitroquinoline-1-oxide DMSO solution for the TA98 strain, 0.25 μg/mL of 2-(furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μl of the test bacterial solution and 90 μL of S9 mix under the metabolism activating condition) are mixed, and this is shaking-cultured at 37° C. for 90 minutes, 460 μL of the bacterial solution exposed to the test substance is mixed with 2300 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL is dispensed into microplate 48 wells/dose, and this is subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and is assessed by comparing with a negative control group.

Test Example 5

Solubility Test

The solubility of a compound was determined under a condition in which 1% DMSO was added. 10 mmol/L compound solution was prepared using DMSO, and then 6 μL of the compound solution was added to 594 μL of artificial intestinal juice in pH 8.8 (to 250 mL of 0.2 mol/L potassium dihydrogen phosphate reagent solution was added 118 mL of 0.2 mol/L NaOH reagent solution and water to provide a final volume of 1000 mL). After standing at 25 degrees Celsius for 16 hours, the mixed solution was filtrated with suction. The filtrate was diluted twice with methanol/water (1/1) and then a concentration in the filtration was measured with HPLC or LC/MS/MS by the absolute calibration method.

(Results)
I-100: >50 μmol/L
I-112: >50 μmol/L
I-117: >50 μmol/L
I-299: >50 μmol/L
I-305: >50 μmol/L
I-356: >50 μmol/L Test Example 6

Metabolism Stability Test

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile 1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%.

(Results) The remaining rate at the compound concentration 0.5 μmol/L are shown below.
I-100: 101%
I-131: 92%
I-241: 88%
I-289: 89%
I-315: 105%
I-359: 101%

Test Example 7 hERG Test

For the purpose of assessing risk of an electrocardiogram QT interval prolongation, effects on delayed rectifier K+ current ($I_{Kr}$), which plays an important role in the ventricular repolarization process, is studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), induced by depolarization pulse stimulation at +50 mV for 2 seconds and, further, repolarization pulse stimulation at −50 mV for 2 seconds is recorded. After the generated current is stabilized, extracellular solution (NaCl: 137 mmol/L, KCl: 4 mmol/L, $CaCl_2.2H_2O$: 1.8 mmol/L, $MgCl_2.6H_2O$: 1 mmol/L, glucose: 10 mmol/L, HEPES 4-(2-hydroxyethyl)-1-piperazineethanesulfonic acid): 10 mmol/L, pH=7.4) in which the test compound had been dissolved at an objective concentration (1.0 μmol/L) is applied to the cell under the room temperature condition for 10 minutes. From the recording $I_{Kr}$, an absolute value of the tail peak current is measured based on the current value at the resting membrane potential using an analysis software (DataXpress ver. 1. Molecular Devices Corporation). Further, the % inhibition relative to the tail peak current before application of the test substance is calculated, and compared with the vehicle-applied group (0.1% dimethyl sulfoxide solution) to assess influence of the test substance on $I_{Kr}$.

Test Example 8

Metabolic Stability Test

The test compound is reacted for a given period of time using cryopreserved rat hepatocytes that are prepared and the residual ratio is calculated based on the comparison between reacted and unreacted samples to evaluate the degree of hepatic metabolism.

The compound is reacted in the Williams E medium containing $1.0 \times 10^6$ cells/mL of cryopreserved rat hepatocytes at a temperature of 37° C. for 0, 1 or 2 hours. After reaction, 50 μL of reaction solution is added to and mixed with 100 μL of a solution containing methanol and acetonitrile in the proportion of one to one (v/v) and the mixture is centrifuged at 3000 rpm for 15 minutes. The test compound contained in the centrifugal supernatant is quantitated using a LC/MS/MS system and the residual ratio of the test compound after reaction is calculated regarding the amount of compound after the reaction for 0 minute as 100%.

Test Example 9

Bioavailability (BA) Test

Materials and Methods for Experiment of BA
(1) Animals: Mice or SD rats were used
(2) Breeding conditions: Mice or SD rats were allowed to freely take solid food and sterilized tap water.
(3) Dose and grouping: orally or intravenously administered at a predetermined dose; grouping was as follows (Dose depends on the compound)
Oral administration: 0.3 to 30 mg/kg (n=2 to 3)
Intravenous administration: 0.5 to 10 mg/kg (n=2 to 3)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein with a needle-equipped syringe
(6) Evaluation items: blood was collected over time, and the plasma concentration of drug was measured by LC/MS/MS
(7) Statistical analysis: regarding the transition of the plasma concentration of the present compound, the area under the plasma concentration-time curve (AUC) was calculated by non-linear least squares program WinNonlin (Registered trade name), and the bioavailability (BA) was calculated from the AUCs of the oral administration group and intravenous administration group
(Results)
I-021; 49.1%
I-100: 29.2%
I-215: 49.7%
I-286: 41.7%
I-313: 28.5%

Test Example 10

Protein Binding Test

The unbound fraction of the present compound in serum is measured using serum of various species.

The reactive conditions are as follows: Evaluation method, Equilibrium dialysis; Reaction time, 24 hours; Reaction temperature, 37° C.; Concentration of the present compound, 2 μg/mL The test solution is added to each serum and the mixture is agitated to prepare the serum samples at the concentration mentioned above. Each serum sample is added into one side of the cell and phosphate buffered saline (PBS) is added into the other side to perform equilibrium dialysis at 37° C. for 24 hours. Then, the concentration of the compounds in the samples that are obtained from both sides was measured by LC/MS/MS.

The ratio (%) of PBS concentration to serum concentration is expressed as unbound fraction.

Test Example 11

Evaluation of Rat $P2X_3$ Receptor Inhibitory Activity

Rat P2X3 receptor gene (GenBank accession number NM_031075) is expressed in C6BU-1 cell. The cells stably expressing rat $P2X_3$ are seeded in a 96-well microtiter plate at a concentration of 8000 cells/well and cultured in the medium (8.3% fetal bovine serum, 8.3% horse serum, 1% antibiotic and antifungal in DMEM) for one day at 37° C. under 5% carbon dioxide atmosphere. In transiently expressing system, the C6BU-1 cells are seeded in a 96-well microtiter plate at a concentration of 2500 cells/well and cultured in the medium for one day at 37° C. under 5% carbon dioxide atmosphere. The plasmid is transfected into the cells using transfection reagent FuGENE6 (Roche). The transfected cells are cultured in the medium for one day at 37° C. under 5% carbon dioxide atmosphere. The medium is replaced with 4 μM Firm-3-AM solution (pH 7.5) containing 20 mM HEPES, 137 mM NaCl, 2.7 mM KCl, 0.9 mM $MgCl_2$, 5.0 mM $CaCl_2$, 5.6 mM D-glucose, 2.5 mM probenecid, 10% BSA, and 0.08% Pluronic F-127, and incubated at 37° C. under 5% dioxide carbon atmosphere for one hour. The plate is washed with washing buffer (20 mmol/L HEPES, 137 mmol/L NaCl, 2.7 mmol/L, KCl, 0.9 mmol/L, $MgCl_2$, 5.0 mmol/L $CaCl_2$, 5.6 mmol/L D-glucose, 2.5 mmol/L probenecid, pH7.5), and each well is added with 40 μL of this buffer. The plate is placed in High-Throughput Screening System FDSS 3000 (Hamamatsu Photonics K.K.). Measurement of fluorescence intensity by FDSS 3000 is started, and 40 μL of DMSO solutions containing different concentrations of the test compound as prepared by dilution with dilution buffer (20 mmol/L HEPES, 137 mmol/L NaCl, 2.7 mmol/L, KCl, 0.9 mmol/L MgCl$_2$, 5.0 mmol/L CaCl$_2$, 5.6 mmol/L D-glucose, 2.5 namon probenecid, 0.1% Pluronic F-127, pH7.5) are dispensed to each well through the built-in automatic dispenser. Five minutes after, 50 mmol/L ATP solution (50 μL) prepared by dilution with the dilution buffer is dispensed through the built-in automatic dispenser, and the measurement of fluorescence intensity is continued for 3 min. For each well, the specific maximum fluorescence intensity is calculated as the ratio of the maximum fluorescence intensity after addition of the ATP solution to the fluorescence intensity at the starting of the measurement. The 50% inhibitory concentration (IC$_{50}$) is calculated under the assumption that the specific maximum fluorescence intensity without test compound is 0% inhibition and that the specific maximum fluorescence intensity when the dilution buffer is added in place of ATP solution is 100% inhibition, to evaluate the inhibitory activity of the test compound. FDSS software (Hamamatsu Photonics K.K.) is used for calculation of the specific maximum fluorescence intensity. IC$_{50}$ is calculated using Microsoft Excel (Microsoft Corporation) and XLfit (idbs Ltd.).

Test Example 12

Evaluation of rat P2X$_3$ Receptor Inhibitory Activity in the Presence of Rat Serum Albumin (RSA)

Rat P2X3 receptor gene (GenBank accession number NM_031075) is expressed in C6BU-1 cell. The cells stably expressing rat P2X$_3$ are seeded in a 96-well microtiter plate at a concentration of 8000 cells/well and cultured in the medium (8.3% fetal bovine serum, 8.3% horse serum, 1% antibiotic and antifungal in DMEM) for one day at 37° C. under 5% carbon dioxide atmosphere. In transiently expressing system, the C6BU-1 cells are seeded in a 96-well microtiter plate at a concentration of 2500 cells/well and cultured in the medium for one day at 37° C. under 5% carbon dioxide atmosphere. The plasmid is transfected into the cells using transfection reagent FuGENE6 (Roche). The transfected cells are cultured in the medium for one day at 37° C. under 5% carbon dioxide atmosphere. The medium is replaced with 4 μM Fluo-3-AM solution (pH7.5) containing 20 mmol/L HEPES, 137 mmol/L NaCl, 2.7 mmol/L 0.9 mmol/L MgCl$_2$, 5.0 mmol/L CaCl$_2$, 5.6 mmol/L D-glucose, 2.5 mmol/L probenecid, 10% BSA, and 0.08% Pluronic F-127, and incubated at 37° C. under 5% carbon dioxide atmosphere for one hour. The plate is washed with washing buffer (20 mmol/L HEPES, 137 mmol/L NaCl, 2.7 mmol/L KCl, 0.9 mmol/L MgCl$_2$, 5.0 mmol/L CaCl$_2$, 5.6 mmol/L D-glucose, 2.5 mmol/L probenecid, pH7.5), and each well is added with 40 μL of this buffer. The plate is placed in High-Throughput Screening System FDSS 3000 (Hamamatsu Photonics K.K.). Measurement of fluorescence intensity by FDSS 3000 is started, and 40 μL of DMSO solutions containing 1% RSA (final concentrations) and different concentrations of the test compound as prepared by dilution with dilution buffer (20 mmol/L HEPES, 137 mmol/L NaCl, 2.7 mmol/L KCl, 0.9 mmol/L MgCl$_2$, 5.0 mmol/L CaCl$_2$, 5.6 mmol/L D-glucose, 2.5 mmol/L probenecid, 0.1% Pluronic F-127, pH7.5) are dispensed to each well through the built-in automatic dispenser. Five minutes after, 50 mmol/L ATP solution (50 μL) prepared by dilution with the dilution buffer is dispensed through the built-in automatic dispenser, and the measurement of fluorescence intensity is continued for 3 min. For each well, the specific maximum fluorescence intensity is calculated as the ratio of the maximum fluorescence intensity after addition of the ATP solution to the fluorescence intensity at the starting of the measurement. The 50% inhibitory concentration (IC$_{50}$) is calculated under the assumption that the specific maximum fluorescence intensity without test compound is 0% inhibition and that the specific maximum fluorescence intensity when the dilution buffer is added in place of ATP solution is 100% inhibition, to evaluate the inhibitory activity of the test compound. FDSS software (Hamamatsu Photonics K.K.) is used for calculation of the specific maximum fluorescence intensity. IC$_{50}$ is calculated using Microsoft Excel (Microsoft Corporation) and XLfit (Ribs Ltd.).

Test Example 13

Evaluation of the Urinary Function in a Rat Model of Cystitis Surgery for Cystometry A rat is fixed in the supine position after being given anesthesia through the inhalation of 2% isoflurane (Anesthetic background: Nitrous oxide:Oxygen=7:3). A midline incision is made in its abdomen to expose the bladder. A cannula (made by processing a polyethylene tube (PE-50: Becton Dickinson)) is inserted through a small incision on top of the bladder and fixed to create a bladder fistula. The other end of the cannula is led through the hypodermal tissue to the back, and the muscular coat and skin are sutured. The cannula, which is led to the back, is protected with a stainless spring in the middle and connected to the cannula swivel.

Acetic Acid Infusion

Two days after the surgery, 0.3% acetic acid is infused into the bladder through the indwelled cannula at a rate of 4 mL/hr for 30 minutes to induce cystitis.

Cystometry Measurement

Three days after the acetic acid infusion, the other end of the cannula inserted into the bladder is connected to a T shape stopcock and then the intravesical pressure is recorded continuously using a pressure amplifier while infusing warmed normal saline solution at a rate of 3.0 mL/hr from one side and through a pressure transducer on the other side. The baseline of the intravesical pressure is measured (for approximately 40 minutes) after a measurement for stable duration (for approximately 20 minutes). After that, a vehicle, positive control compound or test compounds are administered, and the value after administration is measured for approximately 120 minutes. At the same time, the voided urine is received on scales under the cage to measure the variation in weight simultaneously.

Data Adoption Criteria

Based on the voiding interval, normal animals whose voiding interval is 10 minutes or longer are adopted and those whose voiding interval is shorter than that are excluded. In cystitis rat model, those whose voiding interval is less than half the average value of the normal animals are adopted as animals with cystitis and those whose voiding interval is longer than that were excluded.

Collection of Residual Urine

After the completion of the measurement, the infusion of normal saline solution is stopped immediately after urination to collect the residual urine under pentobarbital sodium anesthesia. The collected residual urine is transferred to the voided urine receiver and recorded on the chart.

Analysis Items

Intravesical pressure one to two hours after the start of the measurement (pressure during rest and pressure during urination), voiding interval, voided volume per urination, and residual urine volume Preparation Example 1

A granule containing the following ingredient is prepared.

| Ingredient | |
| --- | --- |
| Compound of the formula (I) | 10 mg |
| Lactose | 700 mg |
| Corn starch | 274 mg |
| HPC-L | 16 mg |

The compound of the formula (I) and lactose are passed through a 60 mesh sieve. Corn starch is passed through a 120 mesh sieve. These are mixed with a V-type mixing machine. An aqueous solution of HPC-L (low viscosity hydroxypropylcellulose) is added to a mixture powder, and this is kneaded, granulated (extrusion granulation, pore diameter 0.5 to 1 mm), and dried. The resulting dry granule is sieved with a vibration sieve (12/60 mesh) to obtain a granule.

Preparation Example 2

A powder for filling into a capsule containing the following ingredients is prepared.

| Ingredient | |
| --- | --- |
| Compound of the formula (I) | 15 mg |
| Lactose | 90 mg |
| Corn starch | 42 mg |
| HPC-L | 3 mg |

The compound of the formula (I), and lactose are passed through a 60 mesh sieve. Corn starch is passed through a 120 mesh sieve. These are mixed, a HPC-L solution is added to the mixed powder, this is kneaded, granulated, and dried. The resulting dry granule is adjusted in a size, and 150 mg of it is filled into a No. 4 hard gelatin capsule.

Preparation Example 3

A tablet containing the following ingredients is prepared.

| Ingredient | |
| --- | --- |
| Compound of the formula (I) | 10 mg |
| Lactose | 90 mg |
| Microcrystaline cellulose | 30 mg |
| CMC-Na | 15 mg |
| Magnesium stearate | 5 mg |

The compound of the formula (Ia), lactose, microcrystalline cellulose, CMC-Na (carboxymethylcellulose sodium salt) are passed through a 60 mesh sieve, and mixed. Magnesium stearate is mixed into a mixture powder to obtain a mixture powder for tabletting. The present mixed powder is directly compressed to obtain a 150 mg tablet.

Formulation Example 4

The following ingredients are warmed, mixed, and sterilized to obtain an injectable.

| Ingredient | |
| --- | --- |
| Compound of the formula (I) | 3 mg |
| Nonionic surfactant | 15 mg |
| Purified water for injection | 1 ml |

Formulation Example 5

A cataplasm containing the following ingredients is prepared. Ingredient Compound of the formula (I) 50 mg
aqueous-based (5% ethanol/5% butylene glycol/90% purified water) 950 mg
glycerin
kaoline
aqueous polyvinyl alcohol The compound of the formula (I) is added to aqueous-based. The mixture is irradiated by ultrasonic for 15 minutes and then is sufficiently stirred to obtain a solution. 5 part of glycerin, 1 part of kaoline and 5 part of aqueous polyvinyl alcohol are homogeneously mixed and 1 part of the resulting solution is added to the above solution including the compound of the formula (I). The obtained solution is mixed and to give a paste form and the resulting paste is applied to an non-woven fabric. The resulting composition is covered by polyester film to give a cataplasm.

The compounds described in the present specification showed inhibiting activity on $P2X_3$ receptor and analgesic activity. Furthermore, as the compounds of the invention are effective on $P2X_3$ subtype, the compounds are also considered to have inhibiting activity on $P2X_{2/3}$ receptor, which comprises $P2X_3$ subtype.

[Industrial Applicability]

The compounds of the present invention have antagonistic effect on $P2X_3$ and/or $P2X_{2/3}$ receptor and are useful in the treatment of diseases or conditions associated with a $P2X_3$ and/or $P2X_{2/3}$ receptor, such as chronic pain, overactive bladder, etc.

The invention claimed is:

1. A pharmaceutical composition having a $P2X_3$ and/or $P2X_{2/3}$ receptor antagonistic effect comprising a compound of the formula (I):

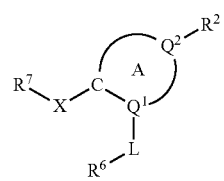

(I)

wherein ring A is a substituted or unsubstituted dihydropyridine ring, or a substituted or unsubstituted dihydropyrimidine ring;

C is a carbon atom;

—X— is —N($R^{16}$);

$R^{16}$ is hydrogen, substituted or unsubstituted alkyl, substituted or unsubstituted alkenyl, substituted or unsubstituted alkynyl, or substituted or unsubstituted acyl;

$R^7$ is substituted or unsubstituted 5 or 6-membered heteroaryl or substituted or unsubstituted 6 to 10-membered aryl;

$Q^1$ is a nitrogen atom; and $Q^2$ is a carbon atom;

-L- is —$(CR^{9a}R^{9b})n^1$—;

$R^{9a}$ and $R^{9b}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy, or $R^{9c}$ and $R^{9d}$ attached to the same carbon atom, and/or $R^{9a}$ and $R^{9b}$ attached to the same carbon atom are taken together to form oxo or thioxo;

$n^1$ is an integer of 1 to 4;

$R^6$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; and $R^2$ is hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino;

or its pharmaceutically acceptable salt or a solvate thereof.

2. The pharmaceutical composition having a P2X$_3$ and/or P2X$_{2/3}$ receptor antagonistic effect according to claim 1, comprising the compound wherein ring A is a substituted or unsubstituted dihydropyrimidine ring, or its pharmaceutically acceptable salt or a solvate thereof.

3. The pharmaceutical composition having a P2X$_3$ and/or P2X$_{2/3}$ receptor antagonistic effect according to claim 1 comprising the compound wherein ring A is a ring optionally substituted with oxo or thioxo, or its pharmaceutically acceptable salt or a solvate thereof.

4. The pharmaceutical composition having a P2X$_3$ and/or P2X$_{2/3}$ receptor antagonistic effect according to claim 1 comprising the compound wherein —X— is —NH—; $R^7$ is substituted or unsubstituted 6-membered heteroaryl or substituted or unsubstituted phenyl; -L- is —(CR$^{9a}$R$^{9b}$)—; or its pharmaceutically acceptable salt or a solvate thereof.

5. The pharmaceutical composition having a P2X$_3$ and/or P2X$_{2/3}$ receptor antagonistic effect according to claim 1 comprising the compound wherein $R^2$ is a group of the formula: —NH—C(=O)—(CR$^{8a}$R$^{8b}$)n-R$^9$; or a group of the formula: —(CR$^{8a}$R$^{8b}$)m-R$^9$;

n is an integer of 0 to 4; $R^{8a}$ and $R^{8b}$ are each independently hydrogen, halogen, hydroxy, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, m is an integer of 1 to 6;

or its pharmaceutically acceptable salt or a solvate thereof.

6. The pharmaceutical composition having a P2X$_3$ and/or P2X$_{2/3}$ receptor antagonistic effect according to claim 1 comprising the compound of the formula:

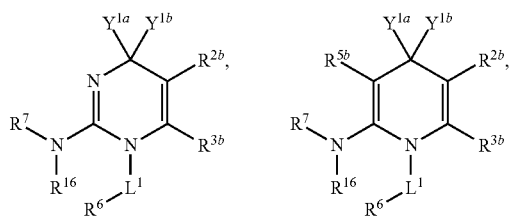

or

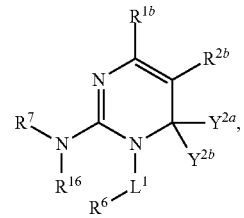

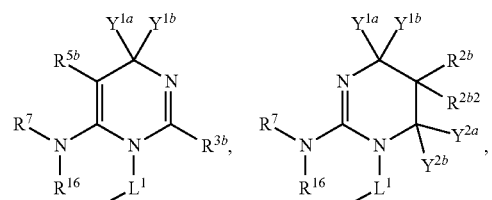

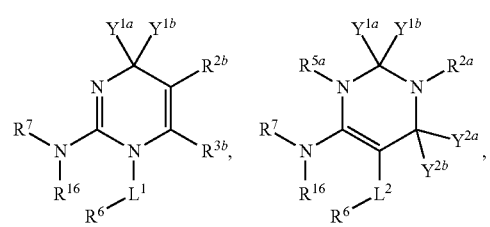

-continued

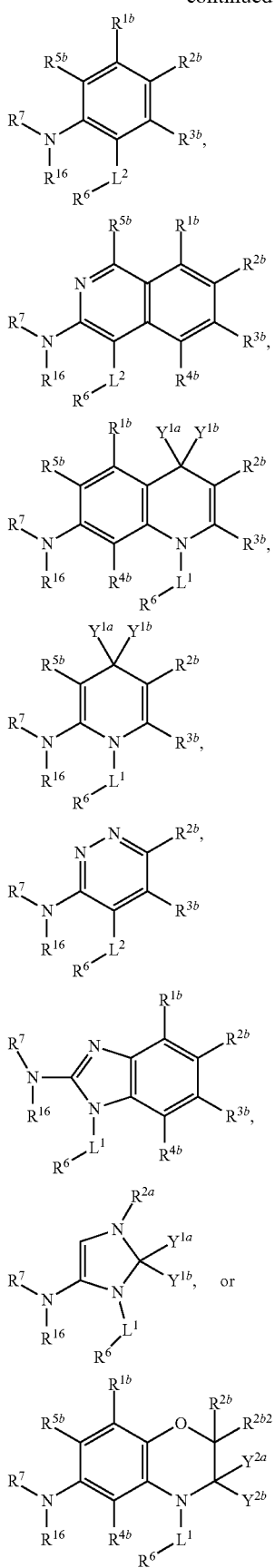

wherein
$Y^{1a}$, $Y^{1b}$, $Y^{2a}$, $Y^{2b}$, $R^{1b}$, $R^{2b}$, and $R^{5b}$ are each independently hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, or $Y^{1a}$ and $Y^{1b}$, and/or $Y^{2a}$ and $Y^{2b}$ are taken together to form oxo or thioxo;

$R^{2a}$ and $R^{5a}$ are each independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, or substituted or unsubstituted sulfamoyl;

$R^7$ is a group of the formula:

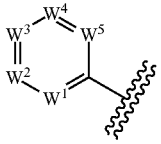

wherein
$=W^1-W^2=W^3-W^4=W^5-$ is a group selected from the following (a) to (h):
(a): $=C(H)-C(R^{10a})=C(R^{10b})-C(R^{10c})=C(H)-$;
(b): $=N-C(R^{10a})=C(R^{10b})-C(R^{10c})=C(H)-$;
(c): $=C(H)-N=C(R^{10b})-C(R^{10c})=C(H)-$;

(d): =C(H)—C(R^{10a})=N—C(R^{10c})=C(H)—;
(e): =C(H)—C(R^{10a})=C(R^{10b})—N=C(H)—;
(f): =N—C(R^{10a})=C(R^{10b})—C(R^{10c})=N—;
(g): =C(H)—C(R^{10a})=N—C(R^{10c})=C(H)—; and
(h): =C(H)—N=C(R^{10b})—N=C(H)—;
R^{10a}, R^{10b} and R^{10c} are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or R^{10a} and R^{10b}, or R^{10b} and R^{10c} together with ring atoms to which they are attached form a non-aromatic carbocyclic ring, a non-aromatic heterocyclic ring, an aromatic carbocyclic ring, or an aromatic heterocyclic ring;

R^{16} is hydrogen, substituted or unsubstituted acyl, substituted or unsubstituted alkyl, substituted or unsubstituted alkenyl, or substituted or unsubstituted alkynyl;

L^1 is —CR^{9a}R^{9b}—;

R^{9a}, and R^{9b} are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy;

or its pharmaceutically acceptable salt or a solvate thereof.

7. The pharmaceutical composition having a P2X$_3$ and/or P2X$_{2/3}$ receptor antagonistic effect according to claim 6 comprising the compound of the formula:

or its pharmaceutically acceptable salt or a solvate thereof.

8. The pharmaceutical composition having a P2X$_3$ and/or P2X$_{2/3}$ receptor antagonistic effect according to claim 6 comprising the compound of the formula:

or

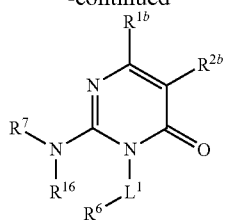

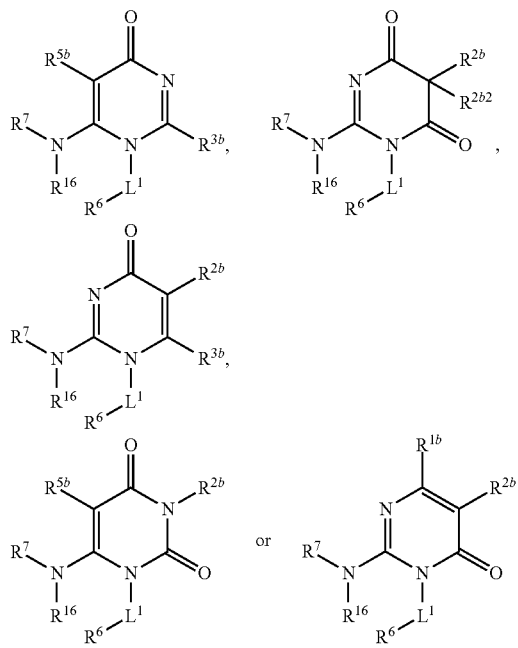

or its pharmaceutically acceptable salt or a solvate thereof.

9. The pharmaceutical composition having a P2X$_3$ and/or P2X$_{2/3}$ receptor antagonistic effect according to any one of claims 1, and 6 to 8 comprising the compound wherein R$^6$ is a group of the formula:

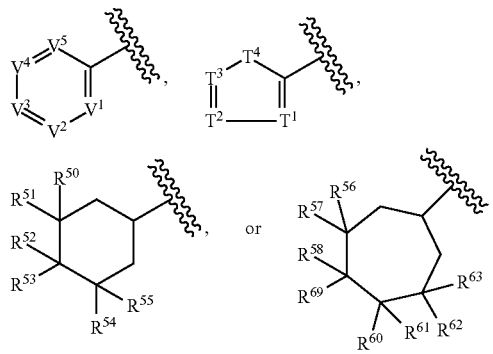

wherein =V$^1$-V$^2$=V$^3$-V$^4$=V$^5$- is a group selected from the following (i) to (p):

(i): =C(H)—C(R$^A$)=C(R$^B$)—C(R$^C$)=C(H)—;
(j): =N—C(R$^A$)=C(R$^B$)—C(R$^C$)=C(H)—;
(k): =C(H)—N=C(R$^B$)—C(R$^C$)=C(H)—;
(l): =C(H)—C(R$^A$)=N—C(R$^C$)=C(H)—;
(m): =C(H)—C(R$^A$)=C(R$^B$)—N=C(H)—;
(n): =N—C(R$^A$)=C(R$^B$)—C(R$^C$)=N—;
(o): =C(H)—C(R$^A$)=N—C(R$^C$)=C(H)—; and
(p): =C(H)—N=C(R$^B$)—N=C(H)—;

R$^A$, R$^B$ and R$^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or R$^A$ and R$^B$, or R$^B$ and R$^C$ together with ring atoms to which they are attached form a non-aromatic carbocyclic ring, a non-aromatic heterocyclic ring, an aromatic carbocyclic ring, or an aromatic heterocyclic ring;

=T$^1$-T$^2$=T$^3$-T$^4$- is a group selected from the following (q) to (t):

(q): =C(H)—C(R$^D$)=C(R$^E$)—S—;
(r): =C(H)—C(R$^D$)=C(R$^E$)—O—;
(s): =N—C(R$^D$)=C(R$^E$)—S—; and
(t): =N—C(R$^D$)=C(R$^E$)—O—;

R$^D$ and R$^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or R$^A$ and R$^B$, or R$^B$ and R$^C$ together with ring atoms to which they are attached form a non-aromatic carbocyclic ring, a non-aromatic heterocyclic ring, an aromatic carbocyclic ring, or an aromatic heterocyclic ring; and R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, and R$^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or its pharmaceutically acceptable salt or a solvate thereof.

10. A compound of the formula (I):

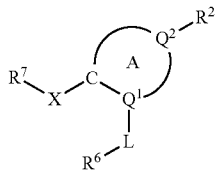
(I)

wherein ring A is a substituted or unsubstituted dihydropyridine ring, or a substituted or unsubstituted dihydropyrimidine ring, C is a carbon atom;

—X— is —N($R^{16}$)—;

$R^{16}$ is hydrogen, substituted or unsubstituted alkyl, substituted or unsubstituted alkenyl, or substituted or unsubstituted alkynyl, or substituted or unsubstituted acyl;

$R^7$ is a group of the formula:

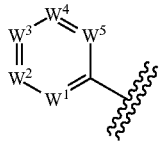

wherein

=$W^1$-$W^2$=$W^3$-$W^4$=$W^5$- is a group selected from the following (a) to (h):

(a): =C(H)—C($R^{10a}$)=C($R^{10b}$)—C($R^{10c}$)=C(H)—;
(b): =N—C($R^{10a}$)=C($R^{10b}$)—C($R^{10c}$)=C(H)—;
(c): =C(H)—N=C($R^{10b}$)—C($R^{10c}$)=C(H)—;
(d): =C(H)—C($R^{10a}$)=N—C($R^{10c}$)=C(H)—;
(e): =C(H)—C($R^{10a}$)=C($R^{10b}$)—N=C(H)—;
(f): =N—C($R^{10a}$)=C($R^{10b}$)—C($R^{10c}$)=N—;
(g): =C(H)—C($R^{10a}$)=N—C($R^{10c}$)=C(H)—; and
(h): =C(H)—N=C($R^{10b}$)—N=C(H)—;

$R^{10a}$, $R^{10b}$ and $R^{10c}$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, provided that groups of (a) to (h) have at least one substituent;

$Q^1$ is a nitrogen atom; and
$Q^2$ is a carbon atom;
-L- is —C$R^{9c}R^{9d}$—;

$R^{9a}$, and $R^{9b}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy; and $R^6$ is a group of the formula:

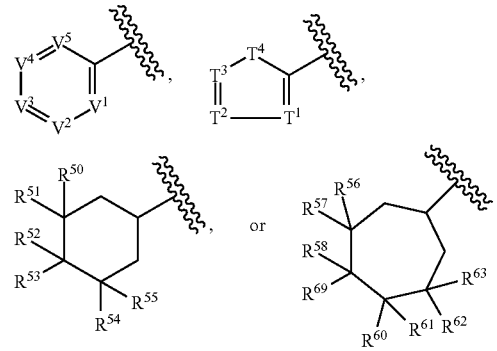

wherein =$V^1$-$V^2$=$V^3$-$V^4$=$V^5$- is a group selected from the following (i) to (p):

(i): =C(H)—C($R^A$)=C($R^B$)—C($R^C$)=C(H)—;
(j): =N—C($R^A$)=C($R^B$)—C($R^C$)=C(H)—;
(k): =C(H)—N=C($R^B$)—C($R^C$)=C(H)—;
(l): =C(H)—C($R^A$)=N—C($R^C$)=C(H)—;
(m): =C(H)—C($R^A$)=C($R^B$)—N=C(H)—;
(n): =N—C($R^A$)=C($R^B$)—C($R^C$)=N—;
(o): =C(H)—C($R^A$)=N—C($R^C$)=C(H)—; and
(p): =C(H)—N=C($R^B$)—N=C(H)—;

$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring, provided that groups of (i) to (p) have at least one substituent;

=$T^1$-$T^2$=$T^3$-$T^4$- is a group selected from the following (q) to (t):

(q): =C(H)—C($R^D$)=C($R^E$)—S—;
(r): =C(H)—C($R^D$)=C($R^E$)—O—;

(s): =N—C(R$^D$)=C(R$^E$)—S—; and
(t): =N—C(R$^D$)=C(R$^E$)—O—;
R$^D$ and R$^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy;
or R$^A$ and R$^B$, or R$^B$ and R$^C$ together with ring atoms to which they are attached form a non-aromatic carbocyclic ring, a non-aromatic heterocyclic ring, an aromatic carbocyclic ring, or an aromatic heterocyclic ring;
R$^{50}$, R$^{51}$, R$^{52}$, R$^{53}$, R$^{54}$, R$^{55}$, R56, R57, R58, R59, R60, R61, R62, and R63 are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy; and
R$^2$ is hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, provided that
(ii) a compound wherein

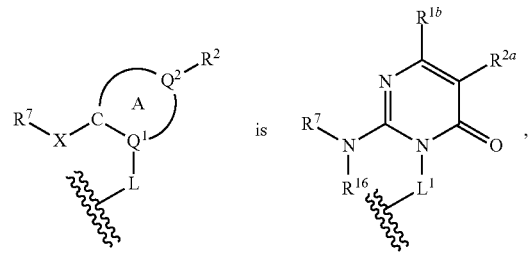

is

R$^{16}$ is hydrogen, and
(α) R$^{1b}$ is unsubstituted alkyl, and R$^{2b}$ is substituted or unsubstituted arylmethyl or substituted or unsubstituted heteroarylmethyl, or
(β) R$^{1b}$ is trifluoromethyl, and R$^{2b}$ is hydrogen,
(v) a compound wherein
R$^7$ is phenyl substituted with —C(=O)CH(Me)CH$_2$C(=O)OMe,

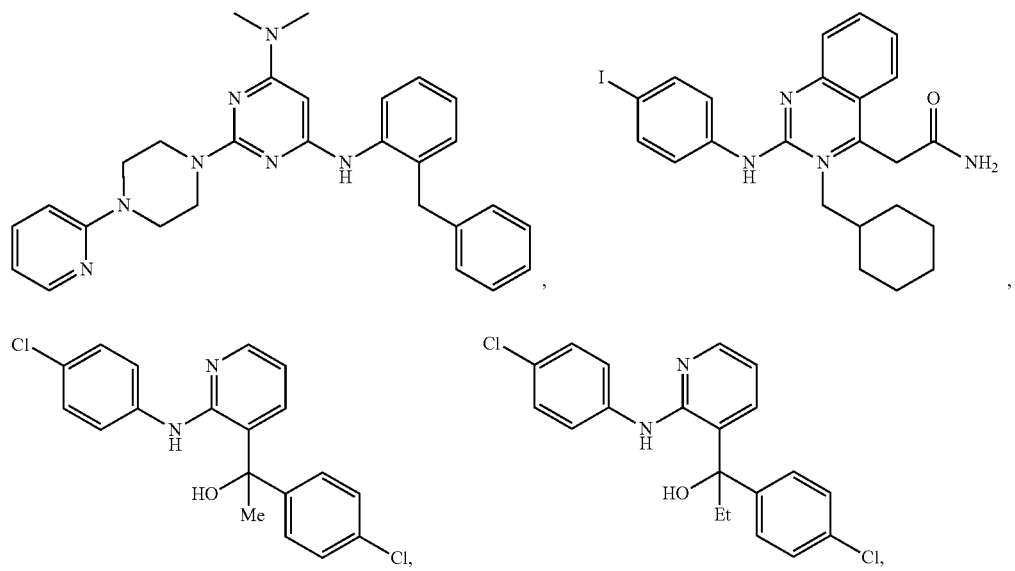

-continued
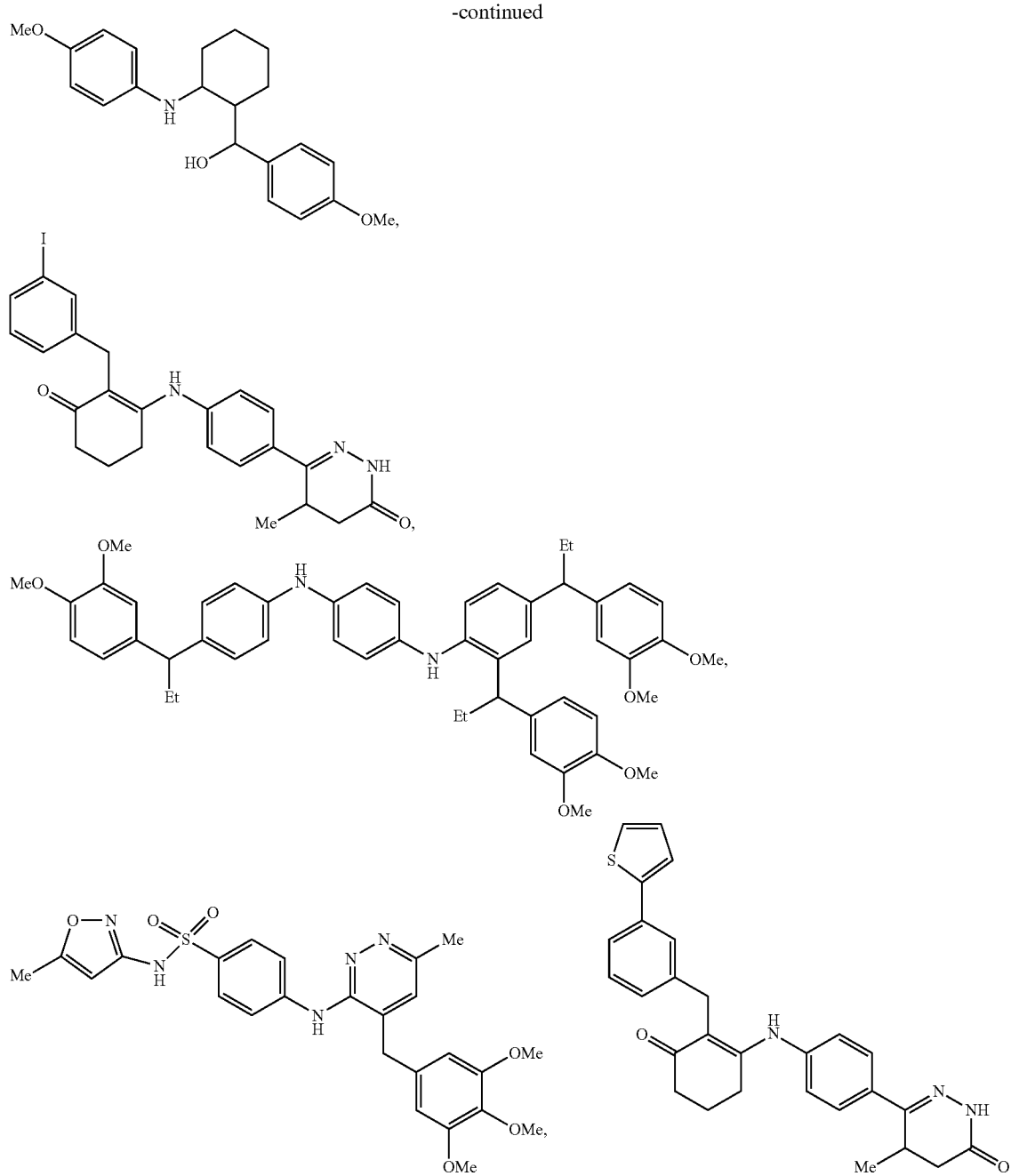
are excluded,
or its pharmaceutically acceptable salt or a solvate thereof.
11. The compound according to claim 10, wherein the compound is:
-continued
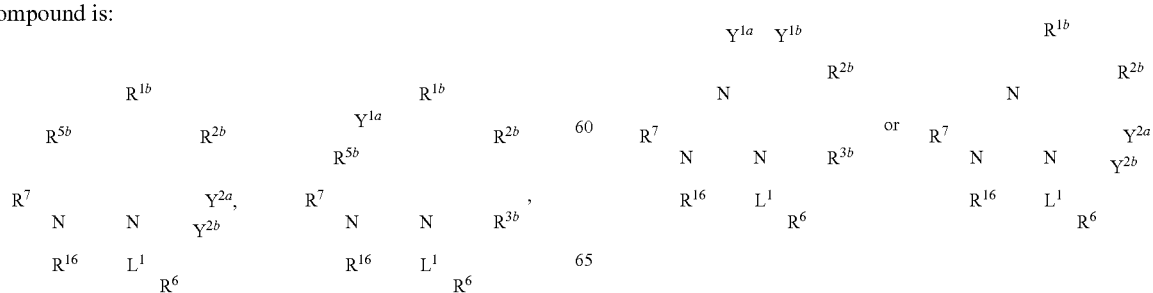

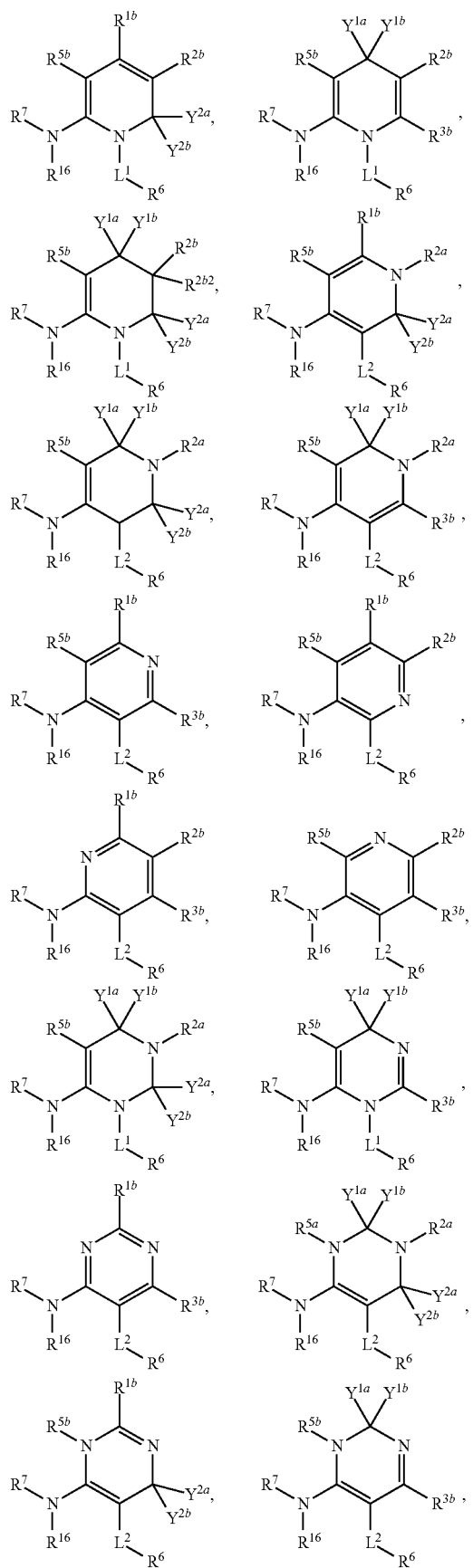

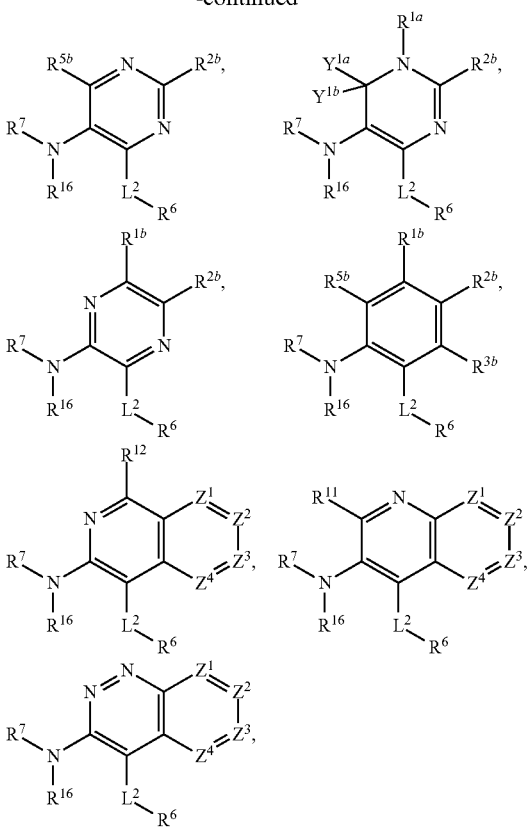

wherein
$Y^{1a}$, $Y^{1b}$, $Y^{2a}$, $Y^{2b}$, $R^{1b}$, $R^{2b}$, and $R^{5b}$ are each independently hydrogen, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, substituted or unsubstituted cycloalkylthio, substituted or unsubstituted cycloalkenylthio, substituted or unsubstituted non-aromatic heterocyclylthio, substituted or unsubstituted arylthio, substituted or unsubstituted heteroarylthio, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, substituted or unsubstituted acyl, substituted or unsubstituted carbamoyl, substituted or unsubstituted sulfamoyl, or substituted or unsubstituted amino, or $Y^{1a}$ and $Y^{1b}$, and/or $Y^{2a}$ and $Y^{2b}$ are taken together to form oxo or thioxo;

-$L^1$- is —$CR^{9c}R^{9d}$—;

or its pharmaceutically acceptable salt or a solvate thereof.

12. The compound according to claim 11, wherein the compound is:

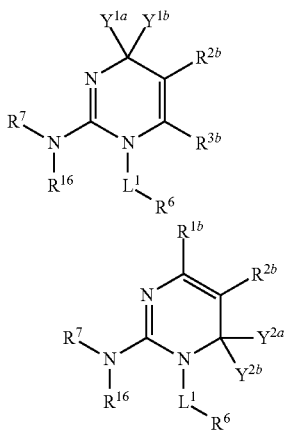

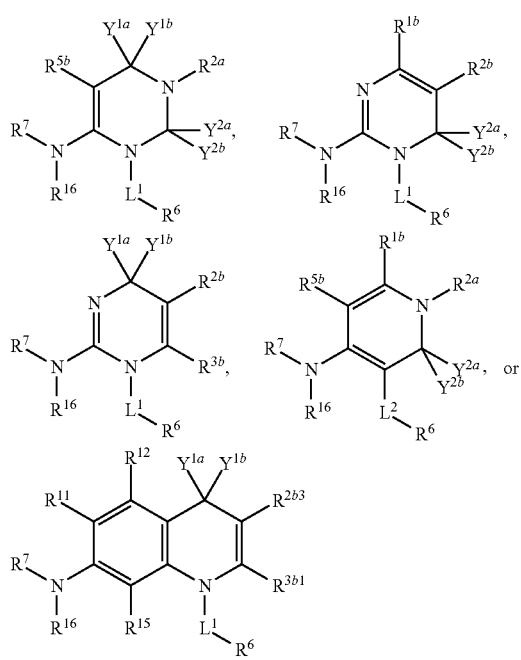

or its pharmaceutically acceptable salt or a solvate thereof.

13. The compound according to claim 11, wherein the compound is:

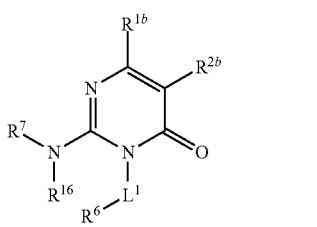

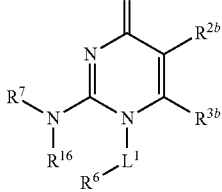

or its pharmaceutically acceptable salt or a solvate thereof.

14. The compound according to claim 10 or 11, wherein $R^{10a}$ and $R^{10c}$ are each independently hydrogen, halogen, or haloalkyl; and $R^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyloxy, provided that at least one of $R^{10a}$ and $R^{10c}$ is halogen or haloalkyl in groups of (d) and (g); or $R^{10a}$ and $R^{10b}$, or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, or its pharmaceutically acceptable salt or a solvate thereof.

15. The compound according to claim 10, wherein ring A is a ring optionally substituted with oxo or thioxo, or its pharmaceutically acceptable salt or a solvate thereof.

16. The compound according to claim 11 or 12, wherein $Y^{1a}$ and $Y^{1b}$, and $Y^{2a}$ and $Y^{2b}$ are each independently taken together to form oxo, or its pharmaceutically acceptable salt or a solvate thereof.

17. The compound according to claim 10 or 11, wherein $R^{16}$ is hydrogen, or its pharmaceutically acceptable salt or a solvate thereof.

18. The compound according to claim 10 or 11, wherein $R^2$ or $R^{2b}$ is a group of the formula: —NH—C(=O)—($CR^{8a}R^{8b}$)n-$R^9$; or a group of the formula: —($CR^{8a}R^{8b}$)m-$R^9$;

n is an integer of 0 to 4; $R^{8a}$ and $R^{8b}$ are each independently hydrogen, halogen, hydroxy, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl, m is an integer of 1 to 6 or its pharmaceutically acceptable salt or a solvate thereof.

19. A compound of the formula:

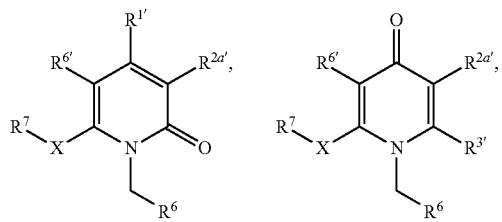

-continued

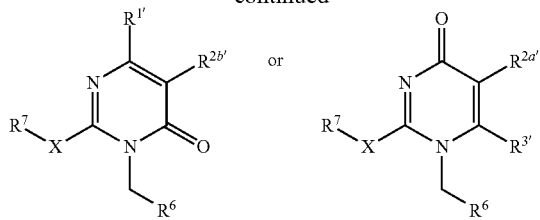

wherein
$R^{1'}$, $R^{3'}$ and $R^{5'}$ are each independently hydrogen or halogen;
$R^{2a'}$ is a group of the formula: —NH—C(=O)—$(CR^{8a}R^{8b})$n-$R^9$; or a group of the formula: —$(CR^{8a}R^{8b})$m-$R^9$;
n is an integer of 0 to 4; $R^{8a}$ and $R^{8b}$ are each independently hydrogen, halogen, hydroxy, or substituted or unsubstituted alkyl; $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, or substituted or unsubstituted guanidyl,
m is an integer of 1 to 6;
$R^{2b'}$ is C1-C6 alkyl or the group of the formula: —$(CR^{8a}R^{8b})$m-$R^9$; m is an integer of 1 to 6;
—X— is —NH— or —$CH_2$—; and
$R^7$ is a group of the formula:

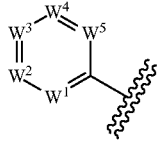

wherein =$W^1$-$W^2$=$W^3$-$W^4$=$W^5$- is
(a): =C(H)—C($R^{10a}$)=C($R^{10b}$)—C($R^{10c}$)=C(H)—;
(b): =N—C($R^{10a}$)=C($R^{10b}$)—C($R^{10c}$)=C(H)—;
(c): =C(H)—N=C($R^{10b}$)—C($R^{10c}$)=C(H)—;
(d): =C(H)—C($R^{10a}$)=N—C($R^{10c}$)=C(H)—;
(e): =C(H)—C($R^{10a}$)=C($R^{10b}$)—N=C(H)—;
(f): =N—C($R^{10a}$)=C($R^{10b}$)—C($R^C$)=N—;
(g): =C(H)—C($R^{10a}$)=N—C($R^{10c}$)=C(H)—; and
(h): =C(H)—N=C($R^{10b}$)—N=C(H)—;
$R^{10a}$ and $R^{10c}$ are each independently hydrogen, halogen, or haloalkyl; and
$R^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyloxy, provided that at least one of $R^{10a}$ and $R^{10c}$ is halogen or haloalkyl in groups of (d) and (g); or
$R^{10a}$ and $R^{10b}$, or $R^{10c}$ together with ring atoms to which they are attached form a non-aromatic carbocyclic ring, a non-aromatic heterocyclic ring, an aromatic carbocyclic ring, or an aromatic heterocyclic ring, $R^6$ is a group of the formula:

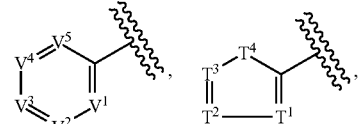

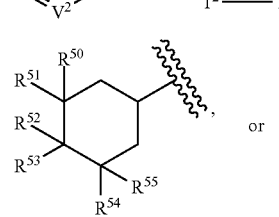

wherein =$V^1$-$V^2$=$V^3$-$V^4$=$V^5$- is a group selected from the following (i) to (p):
(i): =C(H)—C($R^A$)=C($R^B$)—($R^C$)=C(H)—;
(j): =N—C($R^A$)=C($R^B$)—C($R^C$)=C(H)—;
(k): =C(H)—N=C($R^B$)—C($R^C$)=C(H)—;
(l): =C(H)—C($R^A$)=N—C($R^C$)=C(H)—;
(m): =C(H)—C($R^A$)=C($R^B$)—N=C(H)—;
(n): =N—C($R^A$)=C($R^B$)—C($R^C$)=N—;
(o): =C(H)—C($R^A$)=N—C($R^C$)=C(H)—; and
(p): =C(H)—N=C($R^B$)—N=C(H)—;
$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring, provided that groups of (i) to (p) have at least one substituent;
=$T^1$-$T^2$=$T^3$-$T^4$- is a group selected from the following (q) to (t):
(q): =C(H)—C($R^D$)=C($R^E$)—S—;
(r): =C(H)—C($R^D$)=C($R^E$)—O—;
(s): =N—C($R^D$)=C($R^E$)—S—; and
(t): =N—C($R^D$)=C($R^E$)—O—;
$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring; and $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy;

or its pharmaceutically acceptable salt or a solvate thereof.

20. The compound according to any one of claims 10, 11, and 19, wherein n is 1 to 3, and $R^9$ is hydroxy, carboxy, cyano, substituted or unsubstituted aikyloxy, substituted or unsubstituted alkyloxycarbonyl, substituted or unsubstituted carbamoyl, substituted or unsubstituted sulfamoyl, or subsfituted or unsubstituted amino, or its pharmaceutically acceptable salt or a solvate thereof.

21. The compound according to any one of claims 10 11, and 19, wherein $R^A$, $R^B$, $R^C$, $R^D$, $R^E$, $R^{50}$, $R^{51}$, $R^{52}$, $R^{53}$, $R^{54}$, $R^{55}$, $R^{56}$, $R^{57}$, $R^{56}$, $R^{59}$, $R^{69}$, $R^{61}$, $R^{62}$, and $R^{63}$ are each independently hydrogen, halogen, alkyl, or alkyloxy, or its pharmaceutically acceptable salt or a solvate thereof.

22. The compound according to claim 21, wherein $R^6$ is phenyl, thienyl, cyclohexyl, or cycloheptyl: and $R^A$, $R^B$, $R^C$, $R^D$, $R^E$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently hydrogen, halogen, alkyl, or alkyloxy, or its pharmaceutically acceptable salt or a solvate thereof.

23. The compound according to claim 19 wherein —X— is —NH—, or its pharmaceutically acceptable salt or a solvate thereof.

24. The compound according to any one of claims 10 11, and 19, wherein $R^7$ is a group of the formula

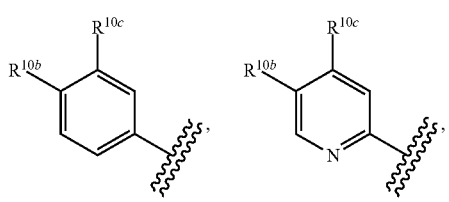

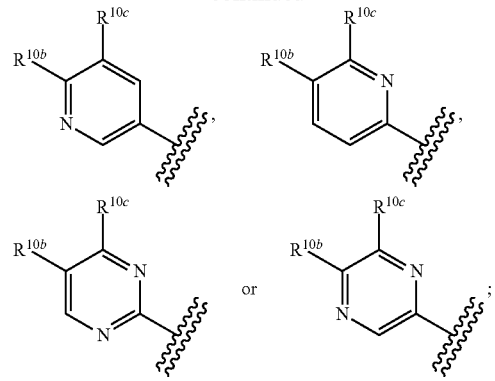

wherein $R^{10b}$ is substituted or unsubstituted alkyl, substituted or unsubstituted alkyloxy, substituted or unsubstituted aryloxy, or substituted or unsubstituted heteroaryloxy, or substituted or unsubstituted nitrogen-containing non-aromatic heterocyclyloxy; and $R^{10c}$ is hydrogen, halogen, or haloalkyl; or $R^{10b}$ and $R^{10c}$ together with ring atoms to which they are attached form a non-aromatic carbocyclic ring, a non-aromatic heterocyclic ring, an aromatic carbocyclic ring, or an aromatic heterocyclic ring, or its pharmaceutically acceptable salt or a solvate thereof.

25. The compound according to claim 24, wherein $R^7$ is a group of the formula:

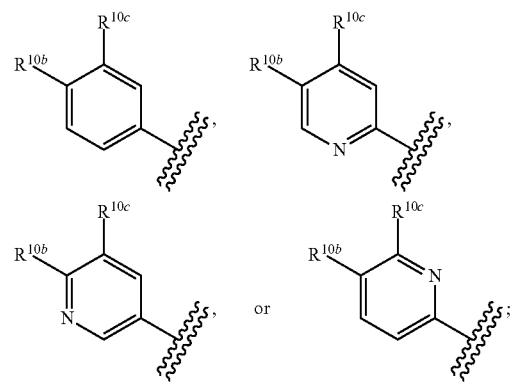

or its pharmaceutically acceptable salt or a solvate thereof.

26. A pharmaceutical composition comprising the compound according to claim 10, or its pharmaceutically acceptable salt or a solvate thereof.

27. A method for treating and/or preventing a disease related to $P2X_3$ and/or $P2X_{2/3}$ receptor comprising administering the compound according to claim 10, or its pharmaceutically acceptable salt, or a solvate thereof.

28. The pharmaceutical composition having a $P2X_3$ and/or $P2X_{2/3}$ receptor antagonistic effect according to claim 1 comprising the compound wherein ring A is a ring substituted with oxo, —X— is —NH—;

$R^7$ is substituted or unsubstituted 6-membered heteroaryl or substituted or unsubstituted phenyl;

-L- is —$(CR^{9a}R^{9b})$—;

or its pharmaceutically acceptable salt or a solvate thereof.

29. The pharmaceutical composition having a $P2X_3$ and/or $P2X_{2/3}$ receptor antagonistic effect according to claim 28 comprising the compound wherein $R^6$ is a group of the formula:

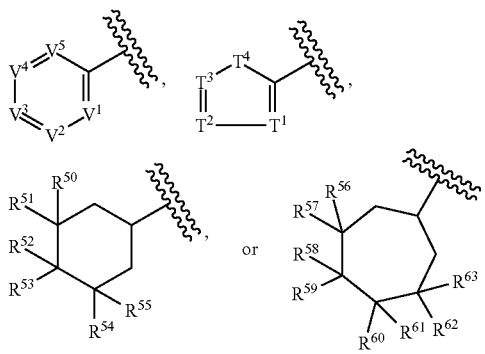

wherein =V¹-V²=V³-V⁴=V⁵- is a group selected from the following (i) to (p):
- (i): =C(H)—C(R^A)=C(R)—C(R^C)=C(H)—;
- (j): =N—C(R^A)=C(R^B)—C(R^C)=C(H)—;
- (k): =C(H)—N=C(R^B)—C(R^C)=C(H)—;
- (l): =C(H)—C(R^A)=N—C(R^C)=C(H)—;
- (m): =C(H)—C(R^A)=C(R^B)—N=C(H)—;
- (n): =N—C(R^A)=C(R^B)—C(R^C)=N—;
- (o): =C(H)—C(R^A)=N—C(R^C)=C(H)—; and
- (p): =C(H)—N=C(R^B)—N=C(H)—;

$R^A$, $R^B$ and $R^C$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyi, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyioxy, substituted or unsubstituted aryloxy, or substituted or unsubstituted heteroaryloxy; or $R^A$ and $R^B$, or $R^B$ and $R^C$ together ith ring atoms to which they are attached form a non-aromatic carbocyclic ring, a non-aromatic heterocyclic ring, an aromatic carbocyclic ring, or an aromatic heterocyclic ring;

=T¹-T²=T³-T⁴- is a group selected from the following (q) to (t):
- (q): =C(H)—C(R^D)=C(R^E)—S—;
- (r): =C(H)—C(R^D)=C(R^E)—O—;
- (s): =N—C(R^D)=C(R^E)—S—; and
- (t): =N—C(RD)=C(R^E)—O—;

$R^D$ and $R^E$ are each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted aikenyloxycarbonyl, substituted or unsubstituted alkynyloxycarbonyl, substituted or unsubstituted carbamoyl, substituted or unsubstituted amino, substituted or unsubstituted suifamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryi, substituted or unsubstituted cycloalkyloxy, substituted or unsubstituted cycloalkenyloxy, substituted or unsubstituted non-aromatic heterocyclyloxy, substituted or unsubstituted aryioxy, or substituted or unsubstituted heteroaryloxy; or $R^A$ and $R^B$, or $R^B$ and $R^C$ together with ring atoms to which they are attached form a non-aromatic carbocyclic ring, a non-aromatic heterocyclic ring, an aromatic carbocyclic ring, or an aromatic heterocyclic ring; and $R50$, $R^{51}$, $R^{52}$, $R^{53}$, $R^{54}$, $R^{55}$, $R^{56}$, $R^{57}$, $R^{58}$, $R^{59}$, $R^{61}$, $R^{62}$, and $R^{63}$ are each independently hydrogen, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or its pharmaceutically acceptable salt or a solvate thereof.

30. The pharmaceutical composition having a P2X₃ and/or P2X_{2/3} receptor antagonist effect according to claim 29 comprising the compound wherein $R^2$ is a group of the formula: —NH—C(=O)—$(CR^{8a}R^{8b})$n-$R^9$; or a group of the formula:—$(CR^{8a}R^{8b})$m-$R^9$;

n is an integer of 0 to 4; $R^{8a}$ and $R^{8b}$ are each independently hydrogen, halogen, hydroxy, or substituted or unsubstituted alkyl; and $R^9$ is hydroxy, carboxy, sulfo, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyi, substituted or unsubstituted amino, or substituted or unsubstituted guanidyl, m is an integer of 1 to 6;

or its pharmaceutically acceptable salt or a solvate thereof.

31. The compound according to claim 11, wherein the compound is:

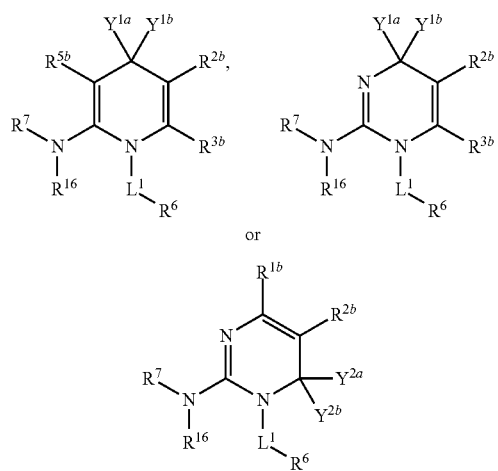

wherein $Y^{1a}$ and $Y^{1b}$, and $Y^{2a}$ and $Y^{2b}$ are each independently taken together to form oxo, R$^{16}$ is hydrogen, R$^6$ is phenyl, thienyl, cyclohexyl, or cycloheptyl; and R$^A$, R$^B$, R$^C$, R$^D$, R$^E$, R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, and R$^{63}$ are each independently hydrogen, halogen, alkyl, or alkyloxy.

32. The compound according to claim 31, wherein R$^{10a}$ and R$^{10c}$ are each independently hydrogen, halogen, or haloalkyl; and R$^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyloxy, provided that at least one of R$^{10a}$ and R$^{10c}$ is halogen or haloalkyl in groups of (d) and (g); or R$^{10a}$ and R$^{10b}$, or R$^{10b}$ and R$^{10c}$ together with ring atoms to which they are attached form a non-aromatic carbocyclic ring, a non-aromatic heterocyclic ring, an aromatic carbocyclic ring, or an aromatic heterocyclic ring, or its pharmaceutically acceptable salt or a solvate thereof.

33. The compound according to claim 31, wherein R$^7$ is a group of the formula:

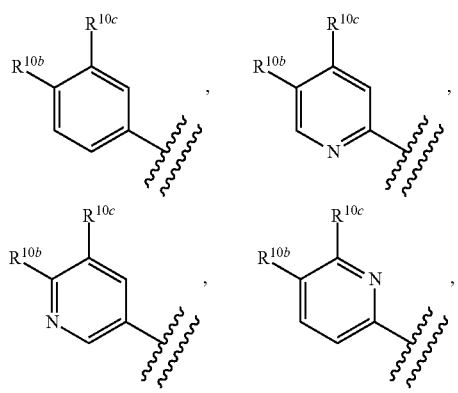

-continued

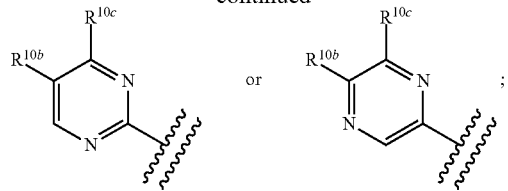

wherein R$^{10b}$ is substituted or unsubstituted alkyl, substituted or unsubstituted alkyloxy, substituted or unsubstituted aryloxy, substituted or unsubstituted heteroaryloxy, or substituted or unsubstituted nitrogen-containing non-aromatic heterocyclyloxy; and R$^{10c}$ is hydrogen, halogen, or haloalkyl; or R$^{10b}$ and R$^{10c}$ together with ring atoms to which they are attached form a non-aromatic carbocyclic ring, a non-aromatic heterocyclic ring, an aromatic carbocyclic ring, or an aromatic heterocyclic ring, or its pharmaceutically acceptable salt or a solvate thereof.

34. The compound according to claim 32 or 33, wherein R$^2$ or R$^{2b}$ is a group of the formula; —NH—C(=O)—(CR$^{8a}$R$^{8b}$)n-R$^9$; or a group of the formula: —(CR$^{8a}$R$^{8b}$)m-R$^9$;

n is an integer of 0 to 4; R$^{8a}$ and R$^{8b}$ are each independently hydrogen, halogen, hydroxy, or substituted or unsubstituted alkyl; and R$^9$ is hydroxy, carboxy, sulfa, cyano, a substituted or unsubstituted non-aromatic heterocyclic group, substituted or unsubstituted heteroaryl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfarnoyl, substituted or unsubstituted amino, or substituted or unsubstituted guanidyl, m is an integer of 1 to 6; or its pharmaceutically acceptable salt or a solvate thereof.

\* \* \* \* \*